(12) United States Patent
Einat et al.

(10) Patent No.: US 7,259,253 B2
(45) Date of Patent: Aug. 21, 2007

(54) GENES ASSOCIATED WITH MECHANICAL STRESS, EXPRESSION PRODUCTS THEREFROM, AND USES THEREOF

(75) Inventors: Paz Einat, Ness Ziona (IL); Orit Segev, Rehovot (IL); Rami Skaliter, Ness Ziona (IL); Elena Feinstein, Rehovot (IL); Alexander Faerman, Bnei Aiish (IL); Aviva Samach, D.N. Emek Soreq (IL)

(73) Assignee: Quark Biotech, Inc., Fremont, CA (US)

( * ) Notice: Subject to any disclaimer, the term of this patent is extended or adjusted under 35 U.S.C. 154(b) by 323 days.

(21) Appl. No.: 10/454,351

(22) Filed: Jun. 4, 2003

(65) Prior Publication Data

US 2004/0053301 A1    Mar. 18, 2004

Related U.S. Application Data

(63) Continuation-in-part of application No. PCT/US01/46400, filed on Dec. 4, 2001, and a continuation-in-part of application No. 09/312,216, filed on May 14, 1999, now abandoned.

(51) Int. Cl.
*C07H 21/02* (2006.01)
*C07H 21/04* (2006.01)
*C12Q 1/68* (2006.01)

(52) U.S. Cl. .................. 536/23.1; 536/24.3; 435/6
(58) Field of Classification Search ............ 536/23.1, 536/24.3; 435/6
See application file for complete search history.

(56) References Cited

U.S. PATENT DOCUMENTS

| | | | | |
|---|---|---|---|---|
| 4,912,207 A | * | 3/1990 | Majerus et al. | 536/23.51 |
| 5,002,876 A | * | 3/1991 | Sreekrishna et al. | 435/69.5 |
| 5,445,941 A | | 8/1995 | Yang | |
| 5,599,708 A | | 2/1997 | Mundy et al. | |
| 5,759,781 A | * | 6/1998 | Ward et al. | 435/6 |
| 5,763,416 A | | 6/1998 | Bonadio et al. | |
| 5,861,249 A | | 1/1999 | Beach et al. | |
| 5,882,925 A | | 3/1999 | Falb | |
| 6,369,027 B1 | | 4/2002 | Boyle et al. | |

FOREIGN PATENT DOCUMENTS

| WO | WO 94/00472 | * 1/1994 |
|---|---|---|
| WO | WO 99/60164 | 11/1999 |

OTHER PUBLICATIONS

Thye Promega Catalog p. 92, (1993/1994).*

Abersold et al, "Quantitative proteome analysis: methods and applications," *Ann N.Y. Acad Sci.* 919:33-47 (2000).

Asahina et al, "Human Osteogenic Protein-1 Induces Both Chondroblastic and Osteoblastic Differentiation of Osteoprogenitor Cells Derived From Newborn Rat Calvaria," *J Cell Biol.* 123(4):921-933 (1993).

Dahl et al, "Effects of normal mouse serum on the IL-3-induced proliferation of bone marrow cells," *Blood* 73(3):700-705 (1989).

Fanciullini et al, "Cloning of a novel human RNA polymerase II subunit downregulated by doxorubicin: new potential mechanisms of drug related toxicity," *Letters* 384(1):48-52 (1996).

Fukui et al, "Molecular Cloning of the Human Histamine H1 Receptor Gene," *Biochem Biophys Res Commun* 201:894-901 (1994).

Joensuu et al, "A Sequence-Ready Map of the Usher Syndrome Type III Critical Region on Chromosome 3q," *Genomics*, 63(3):409-416 (2000).

Mason et al, "Mechanically Regulated Expression of a Neural Glutamate Transporter in Bone: A Role for Excitatory Amino Acids as Osteotropic Agents," *Bone* 20(3):199-205 (1997).

Nagase et al "Prediction of the coding sequences of unidentified human genes. V. The coding sequences of 40 new genes (KIAA0161-KIAA0200) deduced by analysis of cDNA clones from human cell line KG-1," *DNA Res* 3(1):17-24 (1996).

Ngo, J.T. et al, "Computational Complexity Protein Structure Prediction, and the Levinthal Paradox," in *The Protein Folding Problem and Tertiary Structure Prediction*. Merz, Jr. K. et al. Eds. Berkhauser, Boston. p. 491-495 (1994).

Schena et al, "Parallel human genome analysis: microarray-based expression monitoring of 1000 genes," *Proc Natl Acad Sci* 93(20):10614-10619 (1996).

Seki et al, "Characterization of cDNA clones in size-fractionated cDNA libraries from human brain,".*DNA Research* 4:345-349 (1997).

AA087194: mk22e03.r1 Soares mouse pNMF19.5 *Mus musculus* cDNA clone IMAGE:493660 5', MRNA sequence; submitted 1996].

* cited by examiner

*Primary Examiner*—Ethan Whisenant
(74) *Attorney, Agent, or Firm*—Browdy and Neimark, PLLC

(57) ABSTRACT

The disclosure relates to human and mechanical stress induced genes, in particular gene 608, and functional equivalents, probes therefor, tests to identify such genes, polypeptide expression products of such genes, antibodies to the polypeptides, uses for such genes, expression products and antibodies, e.g., in diagnosis (for instance risk determination), treatment, prevention, or control, of osteoporosis or fractures; and to diagnostic, treatment, prevention, or control methods or processes, as well as compositions therefor and methods or processes for making and using such compositions, and receptors therefor and methods or processes for obtaining and using such receptors.

18 Claims, 89 Drawing Sheets

Figure 1

```
CGAGAGACGACAGAAGGTTACGGCTGCGAGAAGACGACAGAAGGGTCCAGAAAAA
GGAAAGTGCTGGAGGGGAGTGGGGACAAAAGCAGCGACCAAGTGAATGTCACTTC
AGTGACTGAGGCCAGGCAAAACGCGCGGGAAGGATTTTGTGTAGCTTGGGACCCTT
TCATAGACACTGATGACACGTTTACGCAAAATAGAAATTTGAGGAGAAACGCCTGG
GCCTTCGGAAAGGAGTGATTGATTAGTACTTGCAAGTTTAGGTGACTTTAAGGAGAA
CTAACTAATGTATACTATTGAGGGAGGAGGAAGAGCATTACAGAGTTTCCAGCAGC
AGCAGGAAAGCTTTGGTTAATTTGGAAATGGATGATAGCATTAAAATAACAGAAGC
GCCTCCAGGTCTCTGAAGCTTCAGTCCCCAGCTGAAAGCCAGAAAAGACTAAGCC
CACTAAGCCTTTTGATCCCTTTGGAAGCAAAGAACTTTCCTTCCCTGGGGTGAAGAC
TCTCCTCAGAAGATTTCCTGTCTCTGCCTATGTTACAAGAGGAATCAAAACCAAGAC
AGAAGAGCTCAGGATGCAGGTGAGAGGCAGGGAAGTCAGCGGCTTGTTGATCTCCC
TCACTGCTGTCTGCCTGGTGGTCACCCCTGGGAGCAGGGCCTGTCCTCGCCGCTGTG
CCTGCTATGTGCCCACAGAGGTGCACTGTACATTTCGGTACCTGACCTCCATCCCAG
ATGGCATCCCGGCCAATGTGGAACGAATAAATTTAGGATATAACAGCCTTACTAGAT
TGACAGAAAACGACTTTGATGGCCTGAGCAAACTGGAGTTACTCATGCTGCACAGT
AATGGCATTCACAGAGTCAGTGACAAGACCTTCTCGGGCTTGCAGTCCTTGCAGGTC
TTAAAAATGAGCTATAACAAAGTCCAAATCATTCGGAAGGATACTTTCTACGGACTC
GGGAGCTTGGTCCGGTTGCACCTGGATCACAACAACATTGAATTCATCAACCCTGAG
GCCTTTTATGGACTTACCTCGCTCCGCTTGGTACATTTAGAAGGAAACCGGCTCACA
AAGCTCCATCCAGACACATTTGTCTCATTAAGCTATCTCCAGATATTTAAAACCTCTT
TCATTAAGTACCTGTTCTTGTCTGATAACTTCCTGACCTCCCTCCCAAAAGAAATGGT
CTCCTACATGCCAAACCTAGAAAGCCTGTATTTGCATGGAAACCCATGGACCTGTGA
CTGCCATTTAAAGTGGTTGTCTGAGTGGATGCAGGGAAACCCAGATATAATAAAAT
GCAAGAAAGACAGAAGCTCTTCCAGTCCTCAGCAATGTCCCCTTTGCATGAACCCCA
GGATCTCTAAAGGCAGACCCTTTGCTATGGTACCATCTGGAGCTTTCCTATGTACAA
AGCCAACCATTGATCCATCACTGAAGTCAAAGAGCCTGGTTACTCAGGAGGACAAT
GGATCTGCCTCCACCTCACCTCAAGATTTCATAGAACCCTTTGGCTCCTTGTCTTTGA
ACATGACANANNTNTCTGGAAATAAGGCCGACATGGTCTGTAGTATCCAAAAGCCA
TCAAGGACATCACCAACTGCATTCACTGAAGAAATGACTACATCATGCTAAATGC
GTCATTTTCCACAAATCTTGTGTGCAGTGTAGATTATAATCACATCCAGCCAGTGTG
GCAACTTCTGGCTTTATACAGTGACTCTCCTCTGATACTAGAAAGGAAGCCCCAGCT
TACCGAGACTCCTTCACTGTCTTCTAGATATAAACAGGTGGCTCTTAGGCCTGAAGA
CATTTTACCAGCATAGAGGCTGATGTCAGAGCAGACCCTTTTGGTTCCAACAAGA
AAAAATTGTCTTGCAGCTGAACAGAACTGCCACCACACTTAGCACATTACAGATCCA
GTTTTCCACTGATGCTCAAATCGCTTTACCAAGGGCGGAGATGAGAGCGGAGAGAC
TCAAATGGACCATGATCCTGATGATGAACAATCCCAAACTGGAACGCACTGTCCTGG
TTGGCGGCACTATTGCCCTGAGCTGTCCAGGCAAAGGCGACCCTTCACCTCACTTGG
AATGGCTTCTAGCTGATGGGAGTAAAGTGAGAGCCCCTTACGTTAGCGAGGATGGG
```

Figure 1 (Cont.)

CGAATCCTAATAGACAAAAATGGGAAGTTGGAACTGCAGATGGCTGACAGCTTTGA
TGCAGGTCTTTACCACTGCATAAGCACCAATGATGCAGATGCGGATGTTCTCACATA
CAGGATAACTGTGGTAGAGCCCTATGGAGAAAGCACACATGACAGTGGAGTCCAGC
ACACAGTGGTTACGGGTGAGACGCTCGACCTTCCATGCCTTTCCACGGGTGTTCCAG
ATGCTTCTATTAGCTGGATTCTTCCAGGGAACACTGTGTTCTCTCAGCCATCAAGAG
ACAGGCAAATTCTTAACAATGGGACCTTAAGAATATTACAGGTTACGCCAAAAGAT
CAAGGTCATTACCAATGTGTGGCTGCCAACCCATCAGGGGCCGACTTTTCAGTTTT
AAAGTTTCAGTTCAAAAGAAAGGCCAAAGGATGGTTGAGCATGACAGGGAGGCAG
GTGGATCTGGACTTGGAGAACCCAACTCCAGTGTTTCCCTTAAGCAGCCAGCATCTT
TGAAACTCTCTGCATCAGCTTTGACAGGGTCAGAGGCTGGAAAACAAGTCTCCGGTG
TACATAGGAAGAACAAACATAGAGACTTAATACATCGGCGGCGTGGGGATTCCACG
CTCCGGCGATTCAGGGAGCATAGGAGGCAGCTCCCTCTCTCTGCTCGGAGAATTGAC
CCGCAACGCTGGGCAGCACTTCTAGAAAAAGCCAAAAAGAATTCTGTGCCAAAAAA
GCAAGAAAATACCACAGTAAAGCCAGTGCCACTGGCTGTTCCCCTCGTGGAACTCA
CTGACGAGGAAAAGGATGCCTCTGGCATGATTCCTCCAGATGAAGAATTCATGGTTC
TGAAAACTAAGGCTTCTGGTGTCCCAGGAAGGTCACCAACTGCTGACTCTGGACCAG
TAAATCATGGTTTTATGACGAGTATAGCTTCTGGCACAGAAGTCTCAACTGTGAATC
CACAAACACTACAATCTGAGCACCTTCCTGATTTCAAATTATTTAGTGTAACAAACG
GTACAGCTGTGACAAAGAGTATGAACCCATCCATAGCAAGCAAAATAGAAGATACA
ACCAACCAAAACCCAATCATTATCTTTCCATCAGTAGCTGAAATTCGAGATTCTGCT
CAGGCAGGAAGAGCATCTTCCCAAAGTGCACACCCTGTAACAGGGGGAAACATGGC
TACCTATGGCCATACCAACACATATAGTAGCTTTACCAGCAAAGCCAGTACAGTCTT
GCAGCCAATAAATCCAACAGAAAGTTATGGACCTCAGATACCTATTACAGGAGTCA
GCAGACCTAGCAGTAGTGACATCTCTTCTCACACTACTGCAGACCCTAGCTTCTCCA
GTCACCCTTCAGGTTCACACACCACTGCCTCGTCTTTATTTCACATTCCTAGAAACAA
CAATACAGGTAACTTCCCCTTGTCCAGGCACTTGGGAAGAGAGAGGACAATTTGGA
GCAGAGGGAGAGTTAAAAACCCACATAGAACCCCAGTTCTCCGACGGCATAGACAC
AGGACTGTGAGGCCAGCAATCAAGGGACCTGCTAACAAAAATGTGAGCCAAGTTCC
AGCCACAGAGTACCCTGGGATGTGCCACACATGTCCTTCCGCAGAGGGGCTCACAG
TGGCTACTGCAGCACTGTCAGTTCCAAGTTCATCCCACAGTGCCCTCCCCAAAACTA
ATAATGTTGGGGTCATAGCAGAAGAGTCTACCACTGTGGTCAAGAAACCACTGTTAC
TATTTAAGGACAAACAAAATGTAGATATTGAGATAATAACAACCACTACAAAATAT
TCCGGAGGGGAAAGTAACCACGTGATTCCTACGGAAGCAAGCATGACTTCTGCTCC
AACATCTGTATCCCTGGGGAAATCTCCTGTAGACAATAGTGGTCACCTGAGCATGCC
TGGGACCATCCAAACTGGGAAAGATTCAGTGGAAACAACACCACTTCCCAGCCCCC
TCAGCACACCCTCAATACCAACAAGCACAAAATTCTCAAAGAGGAAAACTCCCTTG
CACCAGATCTTTGTAAATAACCAGAAGAAGGAGGGGATGTTAAAGAATCCATATCA
ATTCGGTTTACAAAAGAACCCAGCCGCAAAGCTTCCCAAAATAGCTCCTCTTTTACC
CACAGGTCAGAGTTCCCCCTCAGATTCTACAACTCTCTTGACAAGTCCGCCACCAGC
TCTGTCTACAACAATGGCTGCCACTCAGAACAAGGGCACTGAAGTAGTATCAGGTG

Figure 1 (Cont.)

```
CCAGAAGTCTCTCAGCAGGGAAGAAGCAGCCCTTCACCAACTCCTCTCCAGTGCTTC
CTAGCACCATAAGCAAGAGATCTAATACATTAAACTTCTTGTCAACGGAAACCCCCA
CAGTGACAAGTCCTACTGCTACTGCATCTGTCATTATGTCTGAAACCCAACGAACAA
GATCCAAAGAAGCAAAAGACCAAATAAAGGGGCCTCGGAAGAACAGAAACAACGC
AAACACCACCCCCAGGCAGGTTTCTGGCTATAGTGCATACTCAGCTCTAACAACAGC
TGATACCCCCTTGGCTTTCAGTCATTCCCCACGACAAGATGATGGTGGAAATGTAAG
TGCAGTTGCTTATCACTCAACAACCTCTCTTCTGGCCATAACTGAACTGTTTGAGAA
GTACACCCAGACTTTGGGAAATACAACAGCTTTGGAAACAACGTTGTTGAGCAAAT
CACAGGAGAGTACCACAGTGAAAAGAGCCTCAGACACACCACCACCACTCCTCAGC
AGTGGGGCGCCCCAGTGCCCACTCCTTCCCCACCTCCTTTTACTAAGGGTGTGGTT
ACAGACAGCAAAGTCACATCAGCTTTCCAGATGACGTCAAATAGAGTGGTCACCAT
ATATGAATCTTCAAGGCACAATACAGATCTGCAGCAACCCTCAGCAGAGGCTAGCC
CCAATCCTGAGATCATAACTGGAACCACTGACTCTCCCTCTAATCTGTTTCCATCCAC
TTCTGTGCCAGCACTAAGGGTAGATAAACCACAGAATTCTAAATGGAAGCCCTCTCC
CTGGCCAGAACACAAATATCAGCTCAAGTCATACTCCGAAACCATTGAGAAGGGCA
AAAGGCCAGCAGTAAGCATGTCCCCCACCTCAGCCTTCCAGAGGCCAGCACTCAT
GCCTCACACTGGAATACACAGAAGCATGCAGAAAAGAGTGTTTTTGATAAGAAACC
TGGTCAAAACCCAACTTCCAAACATCTGCCTTACGTCTCTCTACCTAAGACTCTATTG
AAAAAGCCAAGAATAATTGGAGGAAAGGCTGCAAGCTTTACAGTTCCAGCTAATTC
AGACGTTTTCTTCCTTGTGAGGCTGTTGGAGACCCACTGCCCATCATCCACTGGACC
AGAGTTTCATCAGGANTTGAAATATCCCAAGGGACACAGAAAAGCCGGTTCCACGT
GCTTCCCAATGGCACCTTGTCCATCCAGAGGGTCAGTATTCAGGACCGTGGACAGTA
CCTGTGCTCTGCATTTAATCCACTGGGCGTAGACCATTTTCATGTCTCTTTGTCTGTG
GTTTTTTACCCGGCAAGGATTTTGGACAGACATGTCAAGGAGATCACAGTTCACTTT
GGAAGTACTGTGGAACTAAAGTGCAGAGTGGAGGGTATGCCGAGGCCTACGGTTTC
CTGGATACTTGCAAACCAAACGGTGGTCTCAGAAACGGCCAAGGGAAGCAGAAAGG
TCTGGGTAACACCTGATGGAACATTGATCATCTATAATCTGAGTCTTTATGATCGTG
GTTTTTACAAGTGTGTGGCCAGCAACCCATCTGGCCAGGATTCACTGTTGGTTAAGA
TACAAGTCATCACAGCTCCCCCTGTCATTATAGAGCAAAAGAGGCAAGCCATCGTTG
GGGTTTTAGGTGGAAGTTTGAAACTGCCCTGCACTGCAAAAGGAACTCCCCAGCCTA
GTGTTCACTGGGTCCTTTATGATGGGACTGAACTAAAACCATTGCAGTTGACTCATT
CCAGATTTTTCTTGTATCCAAATGGAACTCTGTATATAAGAAGCATCGCTCCTTCAGT
GAGGGGCACTTATGAGTGCATTGCCACCAGCTCCTCAGGCTCAGAGAGAAGGGTAG
TGATTCTTACTGTGGAAGAGGGAGAGACAATCCCCAGGATAGAAACTGCCTCTCAG
AAATGGACTGAGGTGAATTTGGGTGAGAAATTACTACTGAACTGCTCAGCTACTGG
GGATCCAAAGCCTAGAATAATCTGGAGGCTGCCATCCAAGGCTGTCATCGACCAGT
GGCACAGAATGGGCAGCCGAATCCACGTCTACCCAAATGGATCCTTGGTGGTTGGG
TCAGTGACGGAAAAAGACGCTGGTGACTACTTATGTGTGGCAAGAAACAAAATGGG
AGATGACCTAGTCCTGATGCATGTCCGCCTGAGATTGACACCTGCCAAAATTGAACA
GAAGCAGTATTTTAAGAAGCAAGTGCTCCATGGGAAAGATTTCCAAGTTGACTGCA
```

Figure 1 (Cont.)

```
AGGCCTCTGGCTCCCCTGTGCCTGAGGTATCCTGGAGTTTGCCTGATGGGACAGTGC
TCAACAATGTAGCCCAAGCTGATGACAGTGGCTATAGGACCAAGAGGTACACCCTT
TTCCACAATGGAACCTTGTATTTCAACAACGTTGGGATGGCAGAGGAAGGAGATTAT
ATCTGCTCTGCCCAGAACACCTTAGGGAAAGATGAGATGAAAGTCCACCTAACAGT
TCTAACAGCCATCCCACGGATAAGGCAAAGCTACAAGACCACCATGAGGCTCAGGG
CTGGAGAAACAGCTGTCCTTGACTGCGAGGTCACTGGGGAACCGAAGCCCAATGTA
TTTTGGTTGCTGCCTTCCAACAATGTCATTTCATTCTCCAATGACAGGTTCACATTTC
ATGCCAATAGAACTTTGTCCATCCATAAAGTGAAACCACTTGACTCTGGGGACTATG
TGTGCGTAGCTCAGAATCCTAGTGGGGATGACACTAAGACATACAAACTGGACATT
GTCTCTAAACCTCCATTAATCAATGGCCTGTATGCAAACAAGACTGTTATTAAAGCC
ACAGCCATTCGGCACTCCAAAAAATACTTTGACTGCAGAGCAGATGGGATCCCATCT
TCCCAGGTCACGTGGATTATGCCAGGCAATATTTTCCTCCCAGCTCCATACTTTGGA
AGCAGAGTCACGGTCCATCCAAATGGAACCTTGGAGATGAGGAACATCCGGCTTTC
TGACTCTGCGGACTTCACCTGTGTGGTTCGGAGCGAGGGAGGAGAGAGTGTGTTGGT
AGTGCAGTTAGAAGTCCTAGAAATGCTGAGAAGACCAACATTCAGAAACCCATTCA
ACGAAAAAGTCATCGCCCAAGCTGGCAAGCCCGTAGCACTGAACTGCTCTGTGGAT
GGGAACCCCCCACCTGAAATTACCTGGATCTTACCTGACGGCACACAGTTTGCTAAC
AGACCACACAATTCCCCGTATCTGATGGCAGGCAATGGCTCTCTCATCCTTTACAAA
GCAACTCGGAACAAGTCAGGGAAGTATCGCTGTGCAGCCAGGAATAAGGTTGGCTA
CATCGAGAAACTCATCCTGTTAGAGATTGGGCAGAAGCCAGTCATTCTGACATACGA
ACCAGGGATGGTGAAGAGCGTCAGTGGGGAACCGTTATCACTGCATTGTGTGTCTG
ATGGGATCCCCAAGCCAAATGTCAAGTGGACTACACCGGGTGGCCATGTAATCGAC
AGGCCTCAAGTGGATGGAAAATACATACTGCATGAAAATGGCACGCTGGTCATCAA
AGCAACAACAGCTCACGACCAAGGAAATTATATCTGTAGGGCTCAAAACAGTGTTG
GCCAGGCAGTTATTAGCGTGTCAGTGATGGTTGTGGCCTACCCTCCCCGAATCATAA
ACTACCTACCCAGGAACATGCTCAGGAGGACAGGGGAAGCCATGCAGCTCCACTGT
GTGGCCTTGGGAATCCCCAAGCCAAAAGTCACCTGGGAGACGCCAAGACACTCCCT
GCTCTCAAAAGCAACAGCAAGAAAACCCCATAGAAGTGAGATGCTTCACCCACAAG
GTACGCTGGTCATTCAGAATCTCCAAACCTCGGATTCCGGAGTCTATAAGTGCAGAG
CTCAGAACCTACTTGGGACTGATTACGCAACAACTTACATCCAGGTACTCTGACAGG
AAGGGGGAGACTAAAATTCAACAGAAGTCCACATCCACAGGGTTTATTTTTTGGAA
GAAGTTTAATCAAAGGCAGCCATAGGCATGTAAATGAGTCTGAATACATTTACAGT
ATTAAATTTACAATGGACATGCGATGAGACTTGTAAATGAAAGCATTGTGAACTGA
AACCGAGTCTCTGTGGATCTCAAAGCAAACTCTTAACTTAAGGCACTTTGATTTTGC
CAACAAATAATAACAAACATTAAGAGAAAAAATGATCCACTACGAAATAACAAAC
GGCTAATGCACCTGAATTCTCAGTAAAAGACCTTTCTCTCGCTAACAGTTGCCAGC
TGCCTCGTGTCTGTTTCCTACCAATGTCACAAACATCGCACACAGGGTGAATGGAGT
CAACGGGAAAGATTAAGTTTGCGGTCTGTGTAAATCTCAATGTACAAATATTCTGTC
NCTGGTTTATAAACATTTTGATAAAACCGAAAAAAAAAAAAAAAAAAAAAAAAA
AAAA (SEQ ID NO: 1)
``` pcDNA3.1-806 construct

Figure 3

MQVRGREVSGLLISLTAVCLVVTPGSRACPRRCACYVPTEVHCTFRYLTSIPDGIPANVE
RINLGYNSLTRLTENDFDGLSKLELLMLHSNGIHRVSDKTFSGLQSLQVLKMSYNKVQII
RKDTFYGLGSLVRLHLDHNNIEFINPEAFYGLTSLRLVHLEGNRLTKLHPDTFVSLSYLQI
FKTSFIKYLFLSDNFLTSLPKEMVSYMPNLESLYLHGNPWTCDCHLKWLSEWMQGNPDI
IKCKKDRSSSSPQQCPLCMNPRISKGRPFAMVPSGAFLCTKPTIDPSLKSKSLVTQEDNGS
ASTSPQDFIEPFGSLSLNMTXXSGNKADMVCSIQKPSRTSPTAFTEENDYIMLNASFSTNL
VCSVDYNHIQPVWQLLALYSDSPLILERKPQLTETPSLSSRYKQVALRPEDIFTSIEADVR
ADPFWFQQEKIVLQLNRTATTLSTLQIQFSTDAQIALPRAEMRAERLKWTMILMMNNPK
LERTVLVGGTIALSCPGKGDPSPHLEWLLADGSKVRAPYVSEDGRILIDKNGKLELQMA
DSFDAGLYHCISTNDADADVLTYRITVVEPYGESTHDSGVQHTVVTGETLDLPCLSTGV
PDASISWILPGNTVFSQPSRDRQILNNGTLRILQVTPKDQGHYQCVAANPSGADFSSFKV
SVQKKGQRMVEHDREAGGSGLGEPNSSVSLKQPASLKLSASALTGSEAGKQVSGVHRK
NKHRDLIHRRRGDSTLRRFREHRRQLPLSARRIDPQRWAALLEKAKKNSVPKKQENTTV
KPVPLAVPLVELTDEEKDASGMIPPDEEFMVLKTKASGVPGRSPTADSGPVNHGFMTSI
ASGTEVSTVNPQTLQSEHLPDFKLFSVTNGTAVTKSMNPSIASKIEDTTNQNPIIIFPSVAE
IRDSAQAGRASSQSAHPVTGGNMATYGHTNTYSSFTSKASTVLQPINPTESYGPQIPITGV
SRPSSSDISSHTTADPSFSSHPSGSHTTASSLFHIIPRNNNTGNFPLSRHLGRERTIWSRGRV
KNPHRTPVLRRHRHRTVRPAIKGPANKNVSQVPATEYPGMCHTCPSAEGLTVATAALS
VPSSSHSALPKTNNVGVIAEESTTVVKKPLLLFKDKQNVDIEIITTTKYSGGESNHVIPTE
ASMTSAPTSVSLGKSPVDNSGHLSMPGTIQTGKDSVETTPLPSPLSTPSIPTSTKFSKRKTP
LHQIFVNNQKKEGMLKNPYQFGLQKNPAAKLPKIAPLLPTGQSSPSDSTTLLTSPPPALST
TMAATQNKGTEVVSGARSLSAGKKQPFTNSSPVLPSTISKRSNTLNFLSTETPTVTSPTAT
ASVIMSETQRTRSKEAKDQIKGPRKNRNNANTTPRQVSGYSAYSALTTADTPLAFSHSP
RQDDGGNVSAVAYHSTTSLLAITELFEKYTQTLGNTTALETTLLSKSQESTTVKRASDTP
PPLLSSGAPPVPTPSPPPFTKGVVTDSKVTSAFQMTSNRVVTIYESSRHNTDLQQPSAEAS
PNPEIITGTTDSPSNLFPSTSVPALRVDKPQNSKWKPSPWPEHKYQLKSYSETIEKGKRPA
VSMSPHLSLPEASTHASHWNTQKHAEKSVFDKKPGQNPTSKHLPYVSLPKTLLKKPRIIG
GKAASFTVPANSDVFLPCEAVGDPLPIIHWTRVSSGXEISQGTQKSRFHVLPNGTLSIQRV
SIQDRGQYLCSAFNPLGVDHFHVSLSVVFYPARILDRHVKEITVHFGSTVELKCRVEGMP
RPTVSWILANQTVVSETAKGSRKVWVTPDGTLIIYNLSLYDRGFYKCVASNPSGQDSLL
VKIQVITAPPVIIEQKRQAIVGVLGGSLKLPCTAKGTPQPSVHWVLYDGTELKPLQLTHS
RFFLYPNGTLYIRSIAPSVRGTYECIATSSSGSERRVVILTVEEGETIPRIETASQKWTEVN
LGEKLLLNCSATGDPKPRIIWRLPSKAVIDQWHRMGSRIHVYPNGSLVVGSVTEKDAGD
YLCVARNKMGDDLVLMHVRLRLTPAKIEQKQYFKKQVLHGKDFQVDCKASGSPVPEV
SWSLPDGTVLNNVAQADDSGYRTKRYTLFHNGTLYFNNVGMAEEGDYICSAQNTLGK
DEMKVHLTVLTAIPRIRQSYKTTMRLRAGETAVLDCEVTGEPKPNVFWLLPSNNVISFS
NDRFTFHANRTLSIHKVKPLDSGDYVCVAQNPSGDDTKTYKLDIVSKPPLINGLYANKT
VIKATAIRHSKKYFDCRADGIPSSQVTWIMPGNIFLPAPYFGSRVTVHPNGTLEMRNIRLS

Figure 3 (Cont.)

DSADFTCVVRSEGGESVLVVQLEVLEMLRRPTFRNPFNEKVIAQAGKPVALNCSVDGNP
PPEITWILPDGTQFANRPHNSPYLMAGNGSLILYKATRNKSGKYRCAARNKVGYIEKLIL
LEIGQKPVILTYEPGMVKSVSGEPLSLHCVSDGIPKPNVKWTTPGGHVIDRPQVDGKYIL
HENGTLVIKATTAHDQGNYICRAQNSVGQAVISVSVMVVAYPPRIINYLPRNMLRRTGE
AMQLHCVALGIPKPKVTWETPRHSLLSKATARKPHRSEMLHPQGTLVIQNLQTSDSGVY
KCRAQNLLGTDYATTYIQVL (SEQ ID NO: 2)

Figure 4

| Exon/Intron No. | Exon start | Exon end | Exon length | Intron length |
|---|---|---|---|---|
| 1 | 1 | 542 | 542 | 2356 |
| 2 | 2898 | 3094 | 197 | 1334 |
| 3 | 4428 | 4557 | 130 | 3068 |
| 4 | 7625 | 8019 | 394 | |

Figure 6

Human 608 exon & intron map

| Exon/Intron No. | Exon start | Exon end | Exon length | Intron length | Remarks |
|---|---|---|---|---|---|
| 1 | 1 | 208 | 208 | 69 | no valid splice site found upstream this exon1 |
| 2 | 277 | 429 | 153 | 18 | |
| 3 | 447 | 485 | 39 | 1561 | |
| 4 | 2046 | 2244 | 199 | 1351 | |
| 5 | 3595 | 3724 | 130 | 3254 | |
| 6 | 6978 | 7359 | 382 | 4123 | |
| 7 | 11482 | 14903 | 3422 | 38 | |
| 8 | 14941 | 15307 | 367 | 51 | |
| 9 | 15358 | 15825 | 468 | 1039 | |
| 10 | 16864 | ~17760 | ~897 | ? | last exon might be incomplete! |
| 11 | ? (1) | 2317 | ~2317 | 25 | Exon is not complete and start site is not known |
| 12 | 2342 | 2397 | 56 | - | |

Figure 7

```
ATGAAGGTAAAAGGCAGAGGAATCACCTGCTTGCTGGTCTCCTTTGCTGTGATCTGCCTGGTCGCCACC
CCTGGGGGCAAGGCCTGTCCTCGCCGCTGTGCCTGTTATATGCCTACGGAGGTACACTGCACATTTCGG
TACCTGACTTCCATCCCAGACAGCATCCCGCCCAATGTGGAACGCATCAATTTAGGATACAACAGCTTG
GTTAGATTGATGGAAACAGATTTTTCTGGCCTGACCAAACTGGAGTTACTCATGCTTCACAGCAATGGC
ATTCACACAATCCCTGACAAGACCTTCTCAGATTTGCAGGCCTTGCAGGTCTTAAAAATGAGCTATAAT
AAAGTCCGAAAACTTCAGAAAGATACTTTTTATGGCCTCAGGAGCTTGACACGATTGCACATGGACCAC
AACAATATTGAGTTTATAAACCCAGAGGTTTTTTATGGGCTCAACTTTCTCCGCCTGGTGCACTTGGAA
GGAAATCAGCTCACTAAGCTCCACCCAGATACATTTGTCTCTTTGAGCTACCTCCAGATATTTAAAATC
TCTTTCATTAAGTTCCTATACTTGTCTGATAACTTCCTGACCTCCCTCCCTCAAGAGATGGTCTCCTAT
ATGCCTGACCTAGACAGCCTTTACCTGCATGGAAACCCATGGACCTGTGATTGCCATTTAAAGTGGTTG
TCTGACTGGATACAGCCAGATGTAATAAAATGCAAAAAAGATAGAAGTCCCTCTAGTGCTCAGCAGTGT
CCACTTTGCATGAACCCTAGGACTTCTAAAGGCAAGCCGTTAGCTATGGTCTCAGCTGCAGCTTTCCAG
TGTGCCAAGCCAACCATTGACTCATCCCTGAAATCAAAGAGCCTGACTATTCTGGAAGACAGTAGTTCT
GCTTTCATCTCTCCCCAAGGTTTCATGGCACCCTTTGGCTCCCTCACTTTGAATATGACAGATCAGTCT
GGAAATGAAGCTAACATGGTCTGCAGTATTCAAAAGCCCTCAAGGACATCACCCATTGCATTCACTGAA
GAAAATGACTACATCGTGCTAAATACTTCATTTTCAACATTTTTGGTGTGCAACATAGATTACGGTCAC
ATTCAGCCAGTGTGGCAAATTTTGGCTTTGTACAGTGATTCTCCTCTGATACTAGAAAGGAGCCACTTG
CTTAGTGAAACACCGCAGCTCTATTACAAATATAAACAGGTGGCTCCTAAGCCTGAAGACATTTTTACC
AACATAGAGGCAGATCTCAGAGCAGATCCCTCTTGGTTAATGCAAGACCAAATTTCCTTGCAGCTGAAC
AGAACTGCCACCACATTCAGTACATTACAGATCCAGTACTCCAGTGATGCTCAAATCACTTTACCAAGA
GCAGAGATGAGGCCAGTGAAACACAAATGGACTATGATTTCAAGGGATAACAATACTAAGCTGGAACAT
ACTGTCTTGGTAGGTGGAACCGTTGGCCTGAACTGCCCAGGCCAAGGAGACCCCACCCCACACGTGGAT
TGGCTTCTAGCTGATGGAAGTAAAGTGAGAGCCCCTTATGTCAGTGAGGATGGACGGATCCTAATAGAC
AAAAGTGGAAAATTGGAACTCCAGATGGCTGATAGTTTTGACACAGGCGTATATCACTGTATAAGCAGC
AATTATGATGATGCAGATATTCTCACCTATAGGATAACTGTGGTAGAACCTTTGGTCGAAGCCTATCAG
GAAAATGGGATTCATCACACAGTTTTCATTGGTGAAACACTTGATCTTCCATGCCATTCTACTGGTATC
CCAGATGCCTCTATTAGCTGGGTTATTCCAGGAAACAATGTGCTCTATCAGTCATCAAGAGACAAGAAA
GTTCTAAACAATGGCACATTAAGAATATTACAGGTCACCCCGAAAGACCAAGGTTATTATCGCTGTGTG
GCAGCCAACCCATCAGGGGTTGATTTTTTGATTTTCCAAGTTTCAGTCAAGATGAAAGGACAAAGGCCC
TTGGAGCATGATGGAGAAACAGAGGGATCTGGACTTGATGAGTCCAATCCTATTGCTCATCTTAAGGAG
CCACCAGGTGCACAACTCCGTACATCTGCTCTGATGGAGGCTGAGGTTGGAAAACACACCTCAAGCACA
AGTAAGAGGCACAACTATCGGGAATTAACACTCCAGCGACGTGGAGATTCAACACATCGACGTTTTAGG
GAGAATAGGAGGCATTTCCCTCCCTCTGCTAGGAGAATTGACCCACAACATTGGGCGGCACTGTTGGAG
AAAGCTAAAAAGAATGCTATGCCAGACAAGCGAGAAAATACCACAGTGAGCCCACCCCCAGTGGTCACC
CAACTCCCAAACATACCTGGTGAAGAAGACGATTCCTCAGGCATGCTCGCTCTACATGAGGAATTTATG
GTCCCGGCCACTAAAGCTTTGAACCTTCCAGCAAGGACAGTGACTGCTGACTCCAGAACAATATCTGAT
AGTCCTATGACAAACATAAATTATGGCACAGAATTCTCTCCTGTTGTGAATTCACAAATACTACCACCT
GAAGAACCCACAGATTTCAAACTGTCTCTACTGCTATTAAAACTACAGCCATGTCAAAGAATATAAACCCA
ACCATGTCAAGCCAAATACAAGGCACAACCAATCAACATTCATCCACTGTCTTTCCACTGCTACTTGGA
GCAACTGAATTTCAGGACTCTGACCAGATGGGAAGAGGAAGAGAGCATTTCCAAAGTAGACCCCCAATA
ACAGTAAGGACTATGATCAAAGATGTCAATGTCAAAATGCTTAGTAGCACCACCAACAAACTATTATTA
GAGTCAGTAAATACCACAAATAGTCATCAGACATCTGTAAGAGAAGTGAGTGAACCCAGGCACAATCAC
TTCTATTCTCACACTACTCAAATACTTAGCACCTCCACGTTCCCTTCAGATCCACACACAGCTGCTCAT
TCTCAGTTTCCGATCCCTAGAAATAGTACAGTTAACATCCCGCTGTTCAGACGCTTTGGGAGGCAGAGG
AAAATTGGCGGAAGGGGGCGGATTATCAGCCCATATAGAACTCCAGTTCTGCGACGGCATAGATACAGC
ATTTTCAGGTCAACAACCAGAGGTTCTTCTGAAAAAAGCACTACTGCATTCTCAGCCACAGTGCTCAAT
GTGACATGTCTGTCCTGTCTTCCCAGGGAGAGGCTCACCACTGCCACAGCAGCATTGTCTTTTCCAAGT
GCTGCTCCCATCACCTTCCCCAAAGCTGACATTGCTAGAGTCCCATCAGAAGAGTCTACAACTCTAGTC
CAGATCCACTATTACTACTTGAGAACAAACCCAGTGTAGAGAAAACAACACCCACAATAAAATATTTC
AGGACTGAAATTTCCCAAGTGACTCCAACTGGTGCAGTCATGACATATGCTCCAACATCCATACCCATG
GAAAAAACTCACAAAGTAAACGCCAGTTACCCACGTGTGTCTAGCACCAATGAAGCTAAAAGAGATTCA
GTGATTACATCGTCACTTTCAGGTGCTATCACCAAGCCACCAATGACTATTATAGCCATTACAAGGTTT
TCAAGAAGGAAAATTCCCTGGCAACAGAACTTTGTAAATAACCATAACCCAAAAGGCAGATTAAGGAAT
CAACATAAAGTTAGTTTACAAAAAAGCACAGCTGTGATGCTTCCTAAAACATCTCCTGCTTTACCACAG
AGACAAAGTTCCCCTTTCCATTTCACCACACTTTCAACAAGTGTGATGCAAATTCCATCTAATACCTTG
ACTACCGCTCACCACACTACGACCAAAACACACAATCCTGGAAGTCTTCCAACAAAGAAGGAGCTTCCC
TTCCCACCCCTTAACCCTATGCTTCCTAGTATTATAAGCAAAGACTCAAGTACAAAAGCATCATATCA
ACGCAAACAGCAATACCAGCAACAACTCCTACCTTCCCTGCATCTGTCATCACTTATGAAACCCAAACA
GAGAGATCTAGAGCACAAACAATACAAAGAGAACAGGAGCCTCAAAAGAAGAACAGGACTGACCCAAAC
ATCTCTCCAGACCAGAGTTCTGGCTTCACTACACCCACTGCTATGACACCTCCTGCTCTGGCATTCACT
```

Figure 7 (Cont.)

```
CATTCCCCACCAGAAAACACAACTGGGATTTCAAGCACAATCAGTTTTCATTCAAGAACTCTTAATCTG
ACAGATGTGATTGAAGAACTAGCCCAAGCAAGTACTCAGACTTTGAAGAGCACAATTGCTTCTGAAACA
ACTTTGTCCAGCAAATCACACCAGAGTACCACAACTAGGAAAGCATCATTAGACACTCCCATACCACCA
TTCTTGAGCAGCAGTGCTACTCTAATGCCAGTTCCCATCTCCCCTCCCTTTACTCAGAGAGCAGTTACT
GACACACGTGGCGACTCCCATTTCCGGCTTATGACAAATACAGTGGTCAAGCTGCACGAATCCTCAAGG
CACAATCTCCAAATGCCAAGTTCACAATTGGAACCACTCACTTCATCTACCTCTAATCTGTTACATTCT
ACTCCCATGCCAGCACTAACAACAGTTAAATCACAGAATTCCAAATTAACTCCATCTCCCTGGGCAGAA
TACCAATTTTGGCACAAACCATACTCAGACATTGCTGAAAAAGGCAAAAAGCCAGAAGTAAGCATGTTG
GCTACTACAGGCCTGTCCGAGGCCACCACTCTTGTTTCAGATTGGGATGGACAGAAGAACACAAAGAAG
AGTGACTTTGATAAGAAACCAGTTCAAGAAGCAACAACTTCCAAACTCCTTCCCTTTGACTCTTTGTCT
AGGTATATATTTGAAAAGCCCAGGATAGTTGGAGGAAAAGCTGCAAGTTTTACTATTCCAGCTAACTCA
GATGCCTTTCTTCCCTGTGAAGCTGTTGGAAATCCCCTGCCCACCATTCATTGGACCAGAGTTTCAGGA
CTTGATTTATCTAGAGGAAACCAGAATAGCAGGGTCCAGGTTCTCCCCAATGGTACCCTGTCCATCCAG
AGGGTGGAAATTCAGGACCGCGGACAGTACTTGTGTTCCGCATCCAATCTGTTTGGCACAGACCACCTT
CATGTCACCTTGTCTGTGGTTTCCTATCCTCCCAGGATCCTGGAGAGACGTACCAAAGAGATCACAGTT
CATTCCGGAAGCACTGTGGAACTGAAGTGCAGAGCAGAAGGTAGGCCAAGCCCTACAGTTACCTGGATT
CTTGCAAACCAAACAGTTGTCTCAGAATCATCCCAGGGAAGTAGGCAGGCTGTGGTGACGGTTGACGGA
ACATTGGTCCTCCACAATCTCAGTATTTATGACCGTGGCTTTTACAAATGTGTGGCCAGCAACCCAGGT
GGCCAGGATTCACTGCTGGTTAAAATACAAGTCATTGCAGCACCACCTGTTATTCTAGAGCAAAGGAGG
CAAGTCATTGTAGGCACTTGGGGTGAAAGTTTAAAACTGCCCTGTACTGCAAAAGGAACTCCTCAGCCC
AGCGTTTACTGGGTCCTCTCTGATGGCACTGAAGTGAAACCATTACAGTTTACCAATTCCAAGTTGTTC
TTATTTTCAAATGGGACTTTGTATATAAGAAACCTAGCCTCTTCAGACAGGGGCACTTATGAATGCATT
GCTACCAGTTCCACTGGTTCGGAGCGAAGAGTAGTAATGCTTACAATGGAAGAGCGAGTGACCAGCCCC
AGGATAGAAGCTGCATCCCAGAAAAGGACTGAAGTGAATTTTGGGGACAAATTACTACTGAACTGCTCA
GCCACTGGGGAGCCCAAACCCCAAATAATGTGGAGGTTACCATCCAAGGCTGTGGTCGACCAGTGGAGC
TGGATCCACGTCTACCCTAATGGATCCCTGTTTATTGGATCAGTAACAGAAAAAGACAGTGGTGTCTAC
TTGTGTGTGGCAAGAAACAAAATGGGGGATGATCTGATACTGATGCATGTTAGCCTAAGACTGAAACCT
GCCAAAATTGACCACAAGCAGTATTTTAGAAAGCAAGTGCTCCATGGGAAAGATTTCCAAGTAGATTGC
AAAGCTTCCGGCTCCCCAGTGCCAGAGATATCTTGGAGTTTGCCTGATGGAACCATGATCAACAATGCA
ATGCAAGCCGATGACAGTGGCCACAGGACTAGGAGATATACCCTTTTCAACAATGGAACTTTATACTTC
AACAAAGTTGGGGTAGCGGAGGAAGGAGATTATACTTGCTATGCCCAGAACACCCTAGGGAAAGATGAA
ATGAAGGTCCACTTAACAGTTATAACAGCTGCTCCCCGGATAAGGCAGAGTAACAAAACCAACAAGAGA
ATCAAAGCTGGAGACACAGCTGTCCTTGACTGTGAGGTCACTGGGGATCCCAAACCAAAAATATTTTGG
TTGCTGCCTTCCAATGACATGATTTCCTTCTCCATTGATAGGTACACATTTCATGCCAATGGGTCTTTG
ACCATCAACAAAGTGAAACTGCTCGATTCTGGAGAGTACGTATGTGTAGCCCGAAATCCCAGTGGGGAT
GACACCAAAATGTACAAACTGGATGTGGTCTCTAAACCTCCATTAATCAATGGTCTGTATACAAACAGA
ACTGTTATTAAAGCCACAGCTGTGAGACATTCCAAAAAACACTTTGACTGCAGAGCTGAAGGGACACCA
TCTCCTGAAGTCATGTGGATCATGCCAGACAATATTTTCCTCACAGCCCCATACTATGGAAGCAGAATC
ACAGTCCATAAAAATGGAACCTTGGAAATTAGGAATGTGAGGCTTTCAGATTCAGCCGACTTTATCTGT
GTGGCCCGAAATGAAGGTGGAGAGAGCGTGTTGGTAGTACAGTTAGAAGTACTGGAAATGCTGAGAAGA
CCGACATTTAGAAATCCATTTAATGAAAAATAGTTGCCCAGCTGGGAAAGTCCACAGCATTGAATTGC
TCTGTTGATGGTAACCCACCACCTGAAATAATCTGGATTTTACCAAATGGCACACGATTTTCCAATGGA
CCACAAAGTTATCAGTATCTGATAGCAAGCAATGGTTCTTTTATCATTTCTAAAACAACTCGGGAGGAT
GCAGGAAAATATCGCTGTGCAGCTAGGAATAAAGTTGGCTATATTGAGAAATTAGTCATATTAGAAATT
GGCCAGAAGCCAGTTATTCTTACCTATGCACCAGGGACAGTAAAAGGCATCAGTGGAGAATCTCTATCA
CTGCATTGTGTGTCTGATGGAATCCCTAAGCCAAATATCAAATGGACTATGCCAAGTGGTTATGTAGTA
GACAGGCCTCAAATTAATGGGAAATACATATTGCATGACAATGGCACCTTAGTCATTAAAGAAGCAACA
GCTTATGACAGAGGAAACTATATCTGTAAGGCTCAAAATAGTGTTGGTCATACACTGATTACTGTTCCA
GTAATGATTGTAGCCTACCCTCCCCGAATTACAAATCGTCCACCCAGGAGTATTGTCACCAGGACAGGG
GCAGCCTTTCAGCTCCACTGTGTGGCCTTGGGAGTTCCCAAGCCAGAAATCACATGGGAGATGCCTGAC
CACTCCCTTCTCTCAACGGCAAGTAAAGAGAGGACACATGGAAGTGAGCAGCTTCACTTACAAGGTACC
CTAGTCATTCAGAATCCCCAAACCTCCGATTCTGGGATATACAAATGCACAGCAAAGAACCCACTTGGT
AGTGATTATGCAGCAACGTATATTCAAGTAATCTGA
```

Figure 8 A

| Region | | | Region Length | % identity | % positives | % gaps |
|---|---|---|---|---|---|---|
| General | Rat | Human | | | | |
| 1-655 | 1-655 | 1-653 | 655 | 76 | 86 | 0 |
| 656-726 | 656-726 | 654-724 | 71 | 46 | 62 | 0 |
| 727-779 | 727-779 | 725-777 | 53 | 77 | 86 | 0 |
| 780-1634 | 780-1617 | 778-1612 | 655 | 38 | 53 | 4 |
| 1635-end | 1618-end | 1613-end | 980 | 74 | 85 | 0 |
| | Total | Alignment | 2614 | 62 | 74 | 1 |

Figure 8 B

| Region | | Length | % identity | % positives | % gaps |
|---|---|---|---|---|---|
| Rat | Mouse | | | | |
| 1-238 | 1-238 | 238 | 91 | 92 | 1 |

Figure 8 C

| Region | | | Region Length | % identity |
|---|---|---|---|---|
| General | Rat | Human | | |
| 1-1965 | 1-1965 | 1-1965 | 1965 | 83 |
| 1966-2178 | 1966-2178 | 1966-2178 | 213 | 86 |
| 2179-2337 | 2179-2337 | 2179-2337 | 159 | 86 |
| 2338-4893 | 2338-4893 | 2338-4863 | 2565 | 63 |
| 4894-7833 | 4852-7791 | 4864-7761 | 2940 | 80 |
| | Total | Alignment | 7842 | 80 |

Figure 8 D

| Region | | | Region Length | % identity |
|---|---|---|---|---|
| General | Rat | Mouse | | |
| 1-720 | 1-718 | 1-720 | 720 | 93 |

Figure 9

MQKRGREVSCLLISLTAICLVVTPGSRVCPRRCACYVPTEVHCTFRDLTSIPDGPANVER
VNLGYNSLTRLTENDFSGLSRLELLMLHSNGIHRVSDKTFSGLQSLQVLKMSYNKVQIIE
KDTLYGLRSLTRLHLDHNNIEFINPEAFYGLTLLRLVHLEGNRLTKLHPDTFVSLSYLQIF
KTSFIKXLYLYDNFTSLPKEMVSSMPNLESLYLHGNPWTCDCHLKWLSEWMQGNP
(SEQ ID NO: 15)

Figure 10

MKVKGRGITCLLVSFAVICLVATPGGKACPRRCACYMPTEVHCTFRYLTSIPDSIPPNVE
RINLGYNSLVRLMETDFSGLTKLELLMLHSNGIHTIPDKTFSDLQALQVLKMSYNKVRK
LQKDTFYGLRSLTRLHMDHNNIEFINPEVFYGLNFLRLVHLEGNQLTKLHPDTFVSLSYL
QIFKISFIKFLYLSDNFLTSLPQEMSYMPDLDSLLYLHGNPWTCDCHLRWLSDWIQPDVI
KCKKDRSPSSAQQCPLCMNPRTSKGKPLAMVSAAAFQCAKPTIDSSLKSKSLTILEDSSS
AFISPQGFMAPFGSLTLNMTDQSGNEANMVCSIQKPSRTSPIAFTEENDYIVLNTSFSTFL
VCNIDYGHIQPVWQILALYSDSPLILERSHLLSETPQLYYKYKQVAPKPEDIFTNIEADLR
ADPSWLMQDQISLQLNRTATTFSTLQIQYSSDAQITLPRAEMRPVKHKWTMISRDNNTK
LEHTVLVGGTVGLNCPGQGDPTPHVDWLLADGSKVRAPYVSEDGRILIDKSGKLELQM
ADSFDTGVYHCISSNYDDADILTYRITVVEPLVEAYQENGIHHTVFIGETLDLPCHSTGIP
DASISWVIPGNNVLYQSSRDKKVLNNGTLRILQVTPKDQGYYRCVAANPSGVDFLIFQV
SVKMKGQRPLEHDGETEGSGLDESNPIAHLKEPPGAQLRTSALMEAEVGKHTSSTSKRH
NYRELTLQRRGDSTHRRFRENRRHFPPSARRIDPQHWAALLEKAKKNAMPDKRENTTV
SPPPVVTQLPNIPGEEDDSSGMLALHEEFMVPATKALNLPARTVTADSRTISDSPMTNIN
YGTEFSPVVNSQILPPEEPTDFKLSTAILTTAMSKNINPTMSSQIQGTTNQHSSTVFPLLLG
ATEFQDSDQMGRGREHFQSRPPITVRTMIKDVNVKMLSSTTNKLLLESVNSHQTSVREV
SEPRHNHFYSHTTQILSTSTFPSDPHTAAHSQFPIPRNSTVNIPLFRRFGRQRKIGGRGRIIS
PYRTPVLRRHRYSIFRSTTRGSSEKSTTAFSATVLNVTCLSCLPRELTTATAALSFPSAAPI
TFPKADIARVPSEESTTLVQNPLLLLENKPSVEKTTPTIKYFRTEISQVTPTGAVMTYAPT
SIPMEKTHKVNASYPRVSSTNEAKRDSVITSSLSGAITKPPMTIIAITRFSRRKIPWQQNFV
NNHNPKGRLRNQHKVSLQKSTAVMLPKTSPALPQRQSSPFHFRRLSTSVMQIPSNTLTT
AHHTTTKTHNPGSLPTKKELPFPPLNPMLPSIISKDSSTKSIISTQTAIPATTPTFPASVITYE
TQTERSRAQTIQREQEPQKKNRTDPNISPDQSSGFTTPTAMTPPALAFTHSPPENTTGISST
ISFHSRTLNLTDVIEELAQASTQTLKSTIASETTLSSKSHQSTTTRKASLDTPIPPFLSSSAT
LMPVPISPPFTQRAVTDTRGDSHFRLMTNTVVKLHESSRHNLQMPSSQLEPLTSSTSNLL
HSTPMPALTTVKSQNSKLTPSPWAEQFWHKPYSDIAEKGKKPEVSMLATTGLSEATTLV
SDWDGQKNTKKSDFDKKPVQEATTSKLLPFDSLSRYIFEKPRIVGGKAASFTIPANSDAF
LPCEAVGNPLPTIHWTRVSGLDLSRGNQNSRVQVLPNGTLSIQRVEIQDRFQYLCSASNL
FGTDHLHVTLSVVSYPPRILERRTKEITVHSGSTVELKCRAEGRPSPTVTWILANQTVVSE
SSQGSRQAVVTVDGTLVLHNLSIYDRGFYKCVASNPGGQDSLLVKIQVIAAPPVILEQRR
QVIVGTWGESLKLPCTAKGTPQPSVYWVLSDGTEVKPLQFTNSKLFLFSNGTLYIRNLAS

Figure 10(Cont.)

SDRFTYECIATSSTGSERRVVMLTMEERVTSPRIEAASQKRTEVNFGDKLLLNCSATGEP
KPQIMRLPSKAVVDQGSWIHYPNGSLFIGVTEKDSGVYLCVARNKMGDDLILMHVSLR
LKPAKIDHKQYFRKQVLHGKDFQVDCKASGSPVPEISWSLPDGTMINNAMQADDSGHR
TRRYRLFNNGTLYFNKVGVAEEGDYTCYAQNTLGKDEMKVHLTVITAAPRIRQSNKTN
KRIKAGDTAAVLDCEVTGDPKPKIFWLLPSNDMISFSIDRYTFHANGSLTINKVKLLDSG
EYVCVARNPSGDDTKMYKLDVVSKPPLINGLYTNRTVIKATAVRHSKKHFDCRAEGTP
SPEVMWIMPDNIFLTAPYYGSRITVHKNGTLEIRNVRLSADFICVARNEGGESVLVVQLE
VLEMLRRPTFRNPRNPFNEKIVAQLGKSTALNCVSVDGNPPPEIIWILPNGTRFSNGPQSY
QYLIASNGSFIISKTTREDAGKYRCAARNKVGYIEKLVILEIGQKPVILTYAPGTVKGISGE
SLSLHCVSDGIPKPNIKWTMPSGYVVDRPQINGKYILHDNGTLVIKEATAYDRGNYICKA
QNSVGHTLITVPVMIVAYPPRITNRPPRSIVTRTGAAFQLHCVALGVPKPEITWEMPDHS
LLSTASKERTHGSEQLHLQGTLVIQNPQTSDSGIYKCTAKNPLGSDYAATYIQVI (SEQ ID
NO: 16)

Northern blots, RT-PCR

Cell lines & primary cells

| | | |
|---|---|---|
| C6 | Rat glioma | - |
| C2C12 | Myoblasts | - |
| STO | Fibroblasts | - |
| Bone marrow | Stromal cells | - (+) |
| PC-3 | prostatic carcinoma | - |
| SAOS-2 | osteosarcoma | - |
| U2OS | osteosarcoma | + |
| Articular cartilage | chondrocytes | - |
| ROS | osteosarcoma | - |
| Calvaria | Osteoblasts | + |
| C3H10T1/2 | mesenchyme | - (+) |
| MC3T3-E1 | preosteoblastic | - (+) |

Figure 19A
Figure 19B
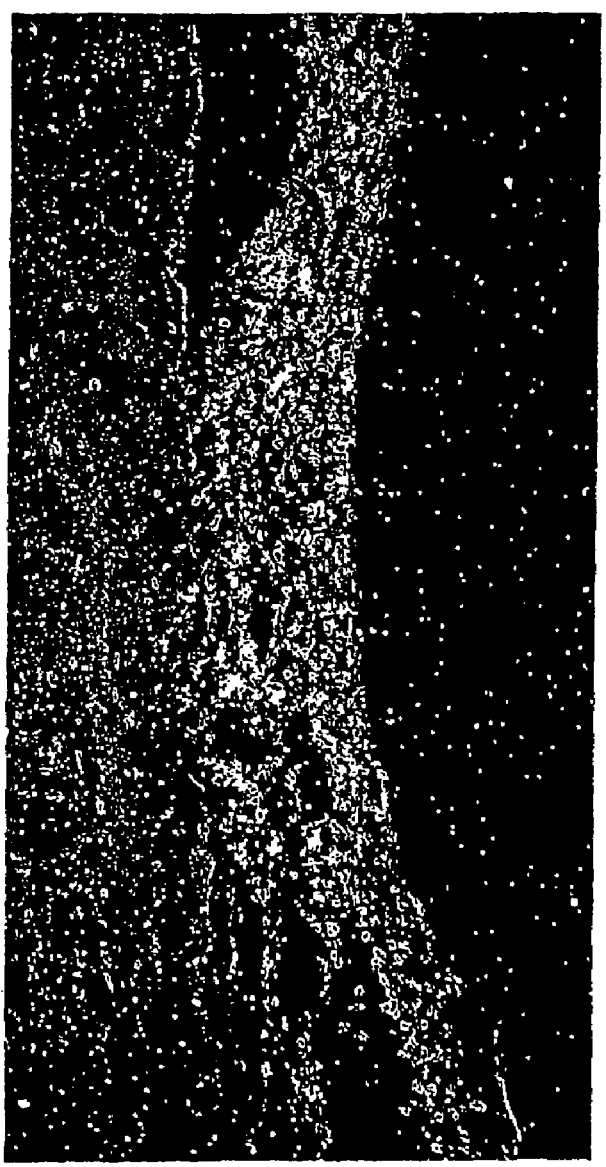

Figure 26

TAAGCCTTTTGCTCCCGTTGGAAGCAAAGAACGTTCCTTCAATCAGGTGAAGGCTCT
CCTCAGAAGATTTCATGTCTCAGCTTATGTTACAAGAGGATTCAAAAGCAAGACAGA
AGAGCTCAGGTATAGCCAACTCTTTTGTTAAATACAGTATGAGGCTTAAGTGTACGG
CAACTCATGTGGTATTCATTTGCGGCTCTCTTCTCTTATAACTAACTCTTAAGGTGCA
TATAGTCTCTTCTGTTTCCCAGCTACCTTGCACCATCTTTGTTTATCTAATAATAGCA
AGCTCATCTGCTTTTTAATCATCACGCAGAGAGTATTCAAAAATATTCAGTGATGTA
ACAGTGACAGTGTAGGCATAGAAGTAATCATTAGTAAATCTTAATATGGGTTAAACT
CATTCATAACAGCTCCAGGTTGG (SEQ ID NO:19)

TTTGGAACCAACCCAGATGCCCCTCAACAGAGAAATGGGCCAGAAAATGTGGTCCA
TTTATCCAATGGAATACTACTCAACTTATTAAAAACAACGACTTTCATAAAATTTTA
GGCAAATGNATGGTCTGNAGGATCTTGAGTGAGGTAACCCAATCACAAAGAACAC
TCATGGTATGCACTCACTGATAAGTGGCTATTTGTCTATGGAGTGATTAAAAGGGA
AGAAGACACATAGCTTTTTGTGTGTATAATATTAAGATGGAAATTTGCCAGTGCTGT
TTGGCTTATGAGTGAATCTTGTTTCAGTGGATTACCGGAAGAAAATAATAAGTGAAC
TGTAGGAAGAAGTAGTTAATCAAGGTGACAAAGTATCCTGACACATTGGGAAAAGA
CCACAGTCCAGGAAACTGAGTCTTAAGGATTCATATTAACTCCAGTTCCCATGTGC
AGCTCTGAGACTTTGGCAGATCAGACACTTAACTTCACCAGCTTCCTACACAGAGCA
GTTACTATCCTTGCCTTCACACATGGAGTGTGCCATTAAGTGCCTGAACATGAGTCT
GACTTGTTAATAATCTTTAAAATCCAATTGTGTGTAAAGTATGTGACCAAAGAGCAT
GGTCATGCTATTAACCTTTGATGTTCTATGGACTCTTAATTTTATGGTAGAAATGTCA
ACAAGCTTGTGGAGGCTGGAAGATACAAGGCTTAAGAGGATGGCCTTTCAGTTTTG
AAAGTAATTCAGTATGTGTTCTGGCATCCCTTTTCCTAAAGCAATTTAACCCCCCAA
GTAGGCATAATTTTAATGCTTACTTCATCAGAATATATCTAATTGACTCTTCTAAAAA
GACTTTGGTATGCATAGGATCTAAATGTAAATGTGATTTACTGACATAATAAATAGG
AGAAACTGAGCTAGAATAGGTATAAAATATGTGCTGGCTTTCTAATAGGTCTTATAG
GTTATATAAGAGGTGGGAAAGGAATATTTGAAACATCTAGAAGTAAAATGATCCTG
AGTAGCGATCCTGGGAAAATACGTACTCTAACACACTGCAATCATCTCTCTGTGGTT
TGCTGGAGCTGAGGTCTGGAAGGCTCGACCTTGGTTAGAAATAACCTACCGAATAC
AGAGCTATGACGTTAGTCTGGAAGGAGCTTTGGAAGAATGACAAGCTGTAGCTGCC
CAGAACATACTAGATGCCATATTTCCAAGGCAAGTGTCCACATGCGGACATCTTAAG
AATATGGTTGTCTCTGCAGTGCTAAGGACCTTGTTCGTGCCACACAGGTCTCCAGGG
TTAGTGCTAACTCTGACTGCTTGACTCTTTAATTCTCCCTTGATCATTAATGACTAGA
AATCACTTGGTGATTAGCAACTGGATATGGAATATTACTTAATTTGTACCGAAGCCA
GGCCACCTCAGCTTTGGCAGCTCCATTCATTCTGTGGAGCCCAGTCACGTGGGTTTG
AATCAACTGTACTGTTTCTACTTACAAGACGCATTACCTGAGATGAGTCATTTTTCTT
CACAAGTCTTTTTAGAAGAGTCAATTAGACATATTCTGATGAAGTAAGCATATAAAG

Figure 26 (Cont.)

TGAGAGCAGCATGAATGTGTTCCATGTATGCTCATGGATGCTATTATAATGTGGAAA
TAAACTGACTTTAAAAAAAAAAGCTTATGATACTTGTCACAGAGTAAATCTTCCATA
AATATCATCTGCATTTATAAATTATTTTCATAATCCATCAATTAAAAACCTTTAGAAA
TTTTGTTAACACAAAGATCCCTAGGCCCCTGCCCTAGGATGGTCTGTATGGTGGGCC
TGAGAGATGGAGCTTAAGAACTTACTTGCTCCAGGAGCACATCTTCAGAACATCTGC
CTCAAAACATTTATCCCAAATGCTCATCAAAGGCTCACTCACATGTGCTTCAACCAC
AGGGATTAAACAGTCATTTTAGTCACATTTCTCAAACGGTGGAAGCCTGCTAGAGGA
ACAGGATGTATCAGGATAACATCCAACCTTACAAAAGGATGTCATAACCCTCACCA
CAACAAACAACAACGACAACAAACCCATAAAAATTATCACGGCAAATGAACTAAGC
CATATGCAGAAAAGTATTATATGTTCTCATTGTGGGTGTTTTCCTTAATAGTCAA
ATATGCAGAATATAGACAAAGATGGTTTATGCAAGTGGGGATGGCGAAGGATACTT
GTAGATTAGAGGACACAAAGCAACAACTACAGAGTGAAGTAATCCAGAGACTTAAT
GTATAATATGAGGACTGTATTTAATAATTCTATTTAAGATACACAGCAAACGAGTGT
ATCTTACTAACACACACTTACATAGAGAGAATAAAGTGATAGATACGTTTGTTTT
ATCTTCATGTAGCTGATAATTTCATATTGTACACCTCAAACATAGATAACCAACAAA
GAGGAAGAGGATAGGTGCCTCTCCCAGGGCGGAAGAGTACATTCGAAAGTCAGACA
CCATTGTGTAGATGTACCACATGGAGGAGCTAGAGAAAGTAGCCAAGGAGCTAAAG
GGATCTGCAACCCTATAGGTGGAACAACATTATGAGCTAACCAGTACCCCGGAGCT
CTTGACTCTAGCTGCATATATATCAAAAGATGGCCTAATCGGCCATCACTGGAAAGA
GAGGCCATTGGACTTGCAAACTTTATATGCCCCAGTACAGGGGAATACCAGGGCCA
AAAAGGGGGAGTGGGTGGGCAGGGGAGTGGGGGTGGGTGGATATGGGGACTTTT
GGTATAGCATTGGAAATGTAAATGAGTTAAATACCTAATAAAAAATGGAAAAAAA
AAAAAAAAAAAAAAAAAGGAAGGTCAGACACCTCACTTCACTGCTATCTCAACTTG
CAAACAGAAGGGGAGTCACAAACCCAGGACAAACCACAGTGATTGAAGCGTCTTTG
AATGTTATTGCTGTTGTTGTTACCACCATCATTAGCATATATTCATTGTGAAAACTTA
CGGGGTCTATGACATGTTTTTTATTCAAGTATATCACATGCTGTCAGCATATTTGGC
ACCACTACCAGCCCCAGCCCCCTTTGCCCCGCCCCAACACACACACACACACACAC
ACACACACACACACACACACACACACACACACACACACCTTTACCTTCTCCTGGGCA
TCATCTGCTCACTCACCCACCCAAGCTTAATCCTTTTCCTTCCCTGCAATAGTACCTC
TCCTATTTTTATGTCTAGGTTCCCCCTCCCCCTGTTAGGAGATGGGAGAGGTCACGA
AAGAAAGGAATTTGTAGCCCTTGAGCCAGCCCGGGCCACAGAGCCTGCCACCAGAC
AGGAAAAGCCCAGGGCTTACCAGCACAGGAGGAGCAAACTCGCAGGCGAGCCTGG
GTTGGCGCTGGTGGTCCCGGGTCGATGGCCCGCCCATTCCCAGAAGCCGAGGCTATA
GCTGCGTCACCTGCCCCGCCCTCCTCCCGAGTGAAGACCCCTAGAGGCTGAGCAGAC
CCCAAAGGCGGTGCAATTCCATTGGCCCAAGGCAGAGGTGAGCGGCTGCTAATCCC
CTCGGGAAGTGAAGGGACCCAGAGAGTCTGGTAGATGTGGGAGCTGGGGTTCAGGG
CGAGACAGAGGGTGGGATGGGCAGAAGGGTCCAGGAAAGGAAAGTACTGGAGGGG
AGTTGGGACAAAAGCAGCGACCAAGGGAACATCGCTTCAGTGACTGAAGCCAGGCA
AAAGGAGCGGGAAGGATTATATGTAGCCTGGGACGCTTTCATAAACACTGATGACG
TGTTTGTGCAAAGCAAGCAATTTGAGGAGAAACGCCTGGGACGTCGGAAAGAAGGA

Figure 26 (Cont.)

```
GTGATCGATTAGTACTTGTAAGTTTAGGTGAGTTTGAGAACTAACTAACCTATACTA
TTGAGGGAGAAGGAAGAGCATTCCAGCAGCAGCAGCAGCAGCAGCAATCAGATAA
AGGAAAGCTTTGGTTAGTTTGGAAATGTATGATACCATTAAAATAACAGAAGCGCCT
CCAGTTCTCTGAAGAGTCAGTCCCCCAGCTAGTGAAGACTAAGCCTACTAAGCCTTT
TGCTCCCGTTGGAAGCAAAGAACGTTCCTTCAATCAGGTGAAGGCTCTCCTCAGAAG
ATTTCCTGTCTCTGCTTATGTTACAAGAGGATTCAAAAGCAAGACAGAAGAGCTCAG
GTATTGCCAACTCTTTTGTTAAATACAGTTTGAGGCTTAAGTGTACGGGAACTCATG
TGGTATTCATTTACGGCTCTCTTCTCTTATAACTAACTCTTAAGGTGCATATAGTCTC
TTCTGTTTCCCAGCTACCTTGTACCATCTTTGTTTATCTAATAATAGCAAGCTCATCT
GCTTTTTAATCATCACGCAGAGAGTATTCAAAAATATTCAGTGATGTAACAGTGACA
GTGTAGGCATAGAAGTAATCATTAGTAAATCTTAATTTGGGTTAAACTCATTCATAA
CAGCTCCAGGTTGGGAGGGATCACTGAGCCTTCGCCACGTGCGGGTTAAAGATATTT
TCTAACAAGAGAAGCAGAATTCTTCCTTGGCCATGCTCCCCATCACTGTGTCAGTAA
GCAGAGGGGTGTTTCCAAGCAGAGAAAGAGCAGACAGTGTTATGCCTGCAAAGTCA
GAGACTCAGCCCTCCCAGCTGGTCAGTTACTGTCCTCCCGGTCATTAGTTGGCTCTG
AAAAGGCCCATGTGTCCTTATTGGCAAGGACTTGCAGACATGCTAGAAAGAAATTT
GACCTTTTTTTCTAGTGGGTTATTACAGCTGTAAAAGTATTTTGGAAGGTTAAGCCA
AATAAATAAAACACATATTAAATAATACAATGTTACAAAAATTGATCATATAAAGA
AGTACATTCATAAATGCAATGTGAAAAATATATATAATTTTTATCTATTTACTGGTGC
AAAGTTTTCTAAATTGCACATGTACTATTTTTATATTTATAAAAATATTTTTAAAATG
TATATAAAAGTGTAAAAGGCTCTTGGTCAAACAAGAGAGTTAAATTTACAAACTTTA
ATTGTCCCGATAACATTATTATGATCTCTAATGACAGGGATCCTGCTTTTCATTGGGA
AATGAGAAGCTATGAAGATATGTTTACAATAATAAGCCCATTTAGTGATAAAGTCCA
ATGGGAAGCTAGCACACACTGGTTTATAAAGAGAACAGTTTCCTGAGTCTATGCAA
GTTTACACTCTAGGGAATAAGAGTTCCTCTTTCTCCAGATTTCACTAGCATTTGTTGT
CATCATTTATCTTCTTGATGATGAGCATTATAAGTGGAATAAGATAGGATCTCAAAG
GAATGTCAATTTGGATGCCCTGAACAATCTTTCAGGTCTTTCTTTCAGTTCACTAGTC
TATTCATTTATTGGATAATTGGGGGGATGGTGGTAATTTTTTTGCAGTTCTTATGGAA
TTCCAAAAAACAAAAAACAAACCAACCAACCAAAAACCTCTGAAACTAGAACTACC
AATCCATTACTGGGTATGTAACAAAGAGAAATCTGCACAGAATTTATTGCTACATTG
TTCATTATTCACGACAGCCAAGAATGTGGAACCAACTTACGTAGCCGTCAAAATATG
AACGGATAAAGAAAATGTGGAAATGTGTACAACAGAGTCCCATGTGGCCATAAAAG
AGTGAAATCATGACATATGCAGGAAATGGATGCAACTGGAAATCAATTGGGCTAAT
CAAAACAAGACAGACTCAAAAAGGAAACACCGTGTAGCTTCTCTGACAAACAGAAG
CTAGATTTACACTTGTACGTGCGCATGTGTGTTTAGAATTTTATTTAGTTATACACTA
TTCTAATCTGTGAGTGTGTATAAAGGCATGCATGTAAAGCAAAAACAAGCTAGCTG
GGGTGGGTAGGAGAGAAAGCAATGAGAGGAGTTAATAAGAACGAAGCATAGTAAC
ATAGGTGCCAGGATGAAATGCATTAATTTGTATGCTAACTAAACCACAGACAGGAG
GCACACGTTCAAACCAGGGTGAAATCCCAGCACAGAGAAGGGGAAGTAGACACAA
AGTTTCGCCACTAACCAAGAAGCCATTTGCAGTTGCTGCCTGCTGGGAAGGGGCGTT
```

Figure 26 (Cont.)

```
CCAGTTTTCTCCAGTCTGACACTGTGTATAACAACCAGTTGACAATACAAAGTTGGC
ATGATGGATGGTTTTTGTGCTATTTTTCATTTTTTTTCTTACTGTTTTGTTGTTGTGGT
GGTTGTTGTGGTGGTGGCTGTGGTTTTCATTTGTTTCTTTTGAGAGAGAGAAGGAAC
ATGAAATTGGGTGGGTAGGAAGCTGGAAACGATCTGGAAGAAGTTGGGGAAAGAG
AAAAATTGTATGGAGCATATTTAAACAAACAAACAAACAAAAGGTTCATTTT
GCCACAAAAAGGTGTGAATTAAATTAACCAGTTACGACTCTTAAAGAAAATATTCCC
AATTATTCCCAGAGTTGCTATGTATGCTGTGCCTAGGACTTTGCTTGAACTGGCCCTA
TAACTCTGGTGTGGTGTCTTTTCAGGATGCAGAAGAGAGGCAGGGAAGTCAGCTGCT
TGCTGATCTCCCTCACTGCCATCTGCCTGGTGGTCACCCCTGGGAGCAGGGTCTGTC
CTCGCCGATGTGCCTGCTATGTGCCCACAGAGGTGCACTGTACATTTCGGGACCTGA
CCTCCATCCCAGACGGGCATCCCAGCCAATGTGGAACGAGTCAATTTAGGGTGTGTG
GACCTTGCCTGATCTCCTTCTCAGAGAGGGACCACTGATTTTCCTGGTACTTTGCCCC
CCAAACACCTGTGATTACTTTTAATAGTTTCTTCTAAAATGGGTTCATACAAACCTT
ATATTGTGGAGACAATGAACATTTTATCCCAATAGTCTTTTACTAGAACTTGAAGCC
CCTCTTAGTTGTTTGGGAGCCTCATAATTATGGGGCAGCTTTATTCTGAATGAATTTT
AAATGAAAAGATACAGTTTCTGTTAACAATCATTATGATACCAAGGAAGAGGAAT
TGTCATTGAATATTTTAAAAAAGCATTTCTTTTGCAATTTATAAATACCCATTACAAA
ATGGCTTACTTAAAATACTTGCCTTACTAAATCTGACAAATTATGGTGATATTTTGAA
GGTTTATGAAAATTTGTTTATGTGTATAAATGCACAAGAAATGGGATATGCCATCAC
CTATGTGCCATTAGTGAGCATGTACAGTATGCCAAACACTATTGTTCACGTTTGGAG
GAAGTAATGGGGGTGGGGGAGCAACAAGGGTTATAACCGTATACCCAGTGCCTTGG
AAGCGATTGCAAACAGTAAAGACTGACATTGTGTTCTCCTATGAGGGAGGGGCCTT
GGGCTGAGCACTTTGCAATGAGCATTTGCTCATTGTGCTGGCAGGTTTTATGATAAC
TTGACCCAAGCTAGAGTCACTGGAGAGGAAGGAACTTCAACTGAGAACATGCCTGA
AGAAGATCAGATTATAGGCAGGCCTGTGGGCATTTTCTTAATTAGTGATTCATGGG
GCAGGGCCCAGTCCATTGTTCGTGGTACCATTTCTCAGGCACTATTAAAAAAAAAAA
AACAGGCTGAGCAAGTGTCAAGGAGCAAGTCAGTGAGCAGCAGCCCTAATGATCTC
TGCATCAGCTCCTGCCTCCAGGTTCCTACCCTATTTGAGTTCCTGTCCTAGCTCCCTA
CAGTGATGAACAATGATGTGGAAGTATAAGCCAAATAAATCCTTTCTTCCCCAACTT
GCTGTTGGTCATGATGTTTCATCACAGTGATAATAGTCCTCATGAAGATGCTGGTGT
TTATAACACCTTTGGACTAAATTCTGTTATCTATAGCTGAGGAAAATGGAGCATAGA
AAGTCTCCAGACTACACCAGAGTGTAATCTGGGCCTGAGCTTAGAATCACACCCAC
GTGCACTCCACTGCCGGGGCTTCTTAACCGGAACACAGTTGTAAAAGGGAATTTTCT
GTTTGTTTCCATTTTGACATGTGGACTTTAATTGACGATTCATCTGAAGCTGAAAATG
ATTTTTTTTCCAGGTATAACAGCCTCACTAGATTGACAGAAAATGACTTTTCTGGCCT
GAGCAGACTGGAGTTACTCATGCTGCACAGCAATGGCATTCACAGAGTCAGTGACA
AGACCTTCTCGGGCTTGCAGTCCTTGCAGGTGAGATAGGTAGAGGGTGATGGAGGC
TGAGAAGAGAGGTGCAACTGTGGGTTATACCCAAAGCTGCTGATTCCCGTGGGAG
ACATTCTATAAGCATTCTATAAACTAGAGGCAGATATCAAGGAAGGATTTCAATTGT
AATGCAATTTTATGAGAAAATTTGAATATTAAGAAAATGCTGGGGAAAATGCTTAC
```

Figure 26 (Cont.)

```
ACAATTGCGAGGACCTAATTTAGGATCTCCAATAGCCACATAAAAAGCACAGCATG
GCGGCAGACACCTGCAATTCCTGTCCCTGGAAGCACCTGTTCAGAATCCCAGAGACT
CATTGGCCAAACACTCTATTCAATCAATGAAGTCCATATTCAGTGACAAAACTTGAC
TCAGAAACTAATGTGGAAAGCATCAGGAAGACAGCCAACATCTGGTCTCTACTCAT
GCATGAATAAGGGATCCCAGAGAGAAGGGAAGAAAAAGGAAGGAAGGAAGGAAG
GAAGGAAGGAAGGAAGGAAGGAAGGAAGGAAGGAAGAGAGGGAGGAAAGGAGGG
AGGGAAGGAAGGAAAGGGAAAGGAAAAAAGAGATGGGGAGGGAGGGAAGGAAAG
GAAAGGGGGAGAAAGAAGAGAAGAAAGGAAAATAAATAAATTTTCAGGGATTATT
ACACCTTTAAATTTTATCCATAAAAGGTCATTTCCACCTGTTTGTCTGGAAGTAGAGT
GGGATCCCTTATATAAGGGCAGTCTTTAACATAGTAGCATTTTATAAACCATTACAA
ATTTTGAGTTTTCTCTACTTTTTATCCTCTACCATCTTCAAACTGAAACTACAATTATT
CCCACAAATGAAGAAAATGCTGTAAGAGTTTTCACACACCGAAGTGGGAAACTTAA
GGATTAGACAAGTCTAACAATGAGAATGGGGAGAACAAAAAGAGACTGCACAGGG
AGCCCTTTCTCTGCTTATAATCTTGACACTTGAGAAGCTAATTGACGCTGCATGACTA
CTCAACTCTTTAAGCAAACAATGCTGTTGTTCATGAAAAGCACAATAAAGTACATAT
GTCCCATAATATTCATCAAAATTTGCATGCAGCACATAATAGCAATCAAAGCAATAA
CACCCACTGTTCACAGAGACTTTAAACATGAAACTGGAACTATGTCTAGTGTTTTGA
CTTAGGGTACATAGTATGCTGTGTCTGTATGTACCAATGTTGATTTAGGTCATCAGA
CAGCATTTGGAACATGTATCTTCAGGAGGAATCATTCATGTATCCTGCATGAAATTC
TCCACCTATGTTTATTCTCTTAGCCAGGTTTTTCTCTGATGGAGAAACATTGGGTTTG
AGGTTTTACTCCCAGGTAACATTTAGGGAAAAGCTGTCTATGTTCTCAGTTTGGCTTT
TATTTATGAGGGATGTTGGTATTCCAGAAAATTCTCTTTTGAAGAGATTACAATTTA
GGTCAAAACAGAAAAATATGTAAAAAGTTATTGTTTTTATTAGTATTTCATGTTCTTT
TCTTTTTTAAAAATGGTATGCTTAGAACTAATTAAGATTAGATTAGATTAGATTAGA
AAATAATCAGAGAGGGATTTGATGAATGCTAAAGCATCATGAAAAATTCAAAATTT
TTTGCTTCTAATTCAGAATCAATTAAATTCATATTACTATAAAAGACAGCACGCCAG
ATGTGTGCCAGCTGAGGAGTGGATAAACTGTGTAACGTGAGTGCTATGTAGAAACA
GAAAGGAGTGAAGGGTTGATGTGCGCTGCAACATCTTGAAAACATTCGGCTACATG
ATGGAAGCCAGGCACAAAAAGCCACATATTGCATGGTTATGTTTATATGAAATGTTT
AAAATACATGGATTCTTAGCAAACAGAGTAAGATGTTACTTAGGGTCAGGAAAAGA
TTAAAAAAAAAAAAACTATTGATGTGGAATGATCTTAATTTGGGGAAAAGACAATT
TCCTAAGACGAAATAGTTGAGGTAGATATAGTTATATCCCTGTGGATATTGTAATAA
ACCAGCATGCTGTGCTCTGAGAAGGGCCTAATGAAGGGGCAGGAGGAAGTGAAATG
AGATGGTAGAAAGGAAAGTCATATACCATGGCTTCTCTCGTGGGTGGAATCTAGAT
ATGTTAATATATTGACATAAAGGAAGGAATTGTTTAGGGAAGGATCAAAACCAACA
GGAGTGAGGGAGACAATAGGAACCAATGAGAGGCAAAGTTCATGGTCAATGTGTGT
GGAGACACCATAATAAAACTCCTTTTTTGTTTGCTAACTAAAACCACTAAAATCTAA
AAACAAAACATTTTTGCACAAGAATTATTTATTATTCAATAAAGATGTTTAAATGGG
GGAAGTTGAAGTTCATTGATAGTCTCATAAATCTTAAATGTATTTAAACTGCTTTTTA
CGTTTTTTATTATTAATTACTCTTGCTGTCATTATTATCATCATCATTATCGTCATCAT
```

Figure 26 (Cont.)

CATCACTAATGCTTTTCACCATACACAAATGTAGGCAGAAGAGTGTAATCCACTTAG
TGAGGCAATCTTGGAGAGGGAAAGGAAGCGGATGCGGGGCAGAGGCACACAGGAG
GACAGTGAGAGGGAAATGAACAAGAAAAAATGTGGACACATGCACAAAAATTCCA
TAGTCCACTACATTACTTTGTATTCTAATATTAAGAAAATAATAAACCCATTTCTGTG
CACTTATCACCCAGGCTCAACAGTTATCTTGGCCACAGATCCTGTCTCACTGCATCCT
GTCCACCTGAGTCCACTTAGCGTTCTGAATCCAATCCAGGGCATGATGCTTACTCCT
ACACAGAACTAAAGATTAAAGAGAGTTTAAAAGTAACCATGACATCTCTCTGTTCCT
TTAGCGATAAGTTCTTAATATTTATGGCTGCTTGTGTATGTTCTAATTTCTCTAATATT
GTCACATTTAGTTGGCAACTACTTTGTTTGAATTGAGTTGGAGTTAAGGTCCCATAG
GATTAATCTCAACATATTTCTATATTTATAAACTTTTCTCTCTTTGTGAAAGTTCCTTT
GAGAAAACAAATATGCCCATATCTTTCTTTACAGGTCTTAAAAATGAGCTATAACAA
AGTCCAAATAATTGAGAAGGATACTTTGTATGGACTCAGGAGCTTGACCCGGTTGCA
CCTGGATCACAACAACATTGAGTTTATCAACCCCGAGGCGTTTTACGGACTCACCTT
GCTCCGCTTGGTACATCTAGAAGGAAACCGGCTGACAAAGCTCCATCCAGACACAT
TTGTCTCTTTGAGCTATCTCCAGATATTTAAAACCTCCTTCATTAAGNACCTGTACTT
GTATGATAACTTCATTGACCTCCCTCCCAAAAGAAATGGTCTCCTCTATGCCAAACC
TAGAAAGCCTTTACTTGCATGGAAACCCATGGACCTGTGACTGCCATTTAAAGTGGT
TGTCCGAGTGGATGCAGGGAAACCCAGGTAACTATCTTGTTTGTTTGTTTCTTTTTTT
ATARKACGTATTTTCCTCAATTTCATTTAGAATGATATCCCAAAAGTCCCCCATAACC
TCCCCCCCACTTCCCTACCTACCCATTCCCATTTTTTGGCCCTGGCATTCCCCTGTACT
GGGGCATATAAAGTTTGCGTGTCCAATGGACCTCTCTTTCCAGTGATGGCCAACTAG
GCCATCTTTTGATACATATGCAGCTAGAGTCAAGAGCTCTGGGGTACTGGTTAGTTC
ATAATGTTGTTGCACCTACAGGGTTGAA (SEQ ID NO:20)

Figure 27

MPKRAHWGALSVVLILLWGHPRVALACPHPCACYVPSEVHCTFRSLASVPAGIARHVE
RINLGFNSIQALSETSFAGLTKLELLMIHGNEIPSIPDGALRDLSSLQVFKFSYNKLRVITG
QTLQGLSNLMRLHIDHNKIEFIHPQAFNGLTSLRLLHLEGNLLHQLHPSTFSTFTFLDYFR
LSTIRHLYLAENMVRTLPASMLRNMPLLENLYLQGNPWTCDCEMRWFLEWDAKSRGIL
KCKKDKAYEGGQLCAMCFSPKKLYKHEIHKLKDMTCLKPSIESPLRQNRSRSIEEEQEQ
EEDGGSQLILEKFQLPQWSISLNMTDEHGNMVNLVCDIKKPMDVYKIHLNQTDPPDIDIN
ATVALDFECPMTRENYEKLWKLIAYYSEVPVKLHRELMLSKDPRVSYQYRQDADEEAL
YYTGVRAQILAEPEWVMQPSIDIQLNRRQSTAKKVLLSYYTQYSQTISTKDTRQARGRS
WVMIEPSGAVQRDQTVLEGGPCQLSCNVKASESPSIFWVLPDGSILKAPMDDPDSKFSIL
SSGWLRIKSMEPSDSGLYQCIAQVRDEMDRMVYRVLVQSPSTQPAEKDTVTIGKNPGES
VTLPCNALAIPEAHLSWILPNRRIINDLANTSHVYMLPNGTLSIPKVQVSDSGYYRCVAV
NQQGADHFTVGITVTKKGSGLPSKRGRRPGAKALSRVREDIVEDEGGSGMGDEENTSR
RLLHPKDQEVFLKTKDDAINGDKKAKKGRRKLKLWKHSEKEPETNVAEGRRVFESRRR
INMANKQINPERWADILAKVRGKNLPKGTEVPPLIKTTSPPSLSLEVTPPFPAVSPPSASP
VQTVTSAEESSADVPLLGEEEHVLGTISSASMGLEHNHNGVILVEPEVTSTPLEEVVDDL
SEKTEEITSTEGDLKGTAAPTLISEPYEPSPTLHTLDTVYEKPTHEETATEGWSAADVGSS
PEPTSSEYEPPLDAVSLAESEPMQYFDPDLETKSQPDEDKMKEDTFAHLTPTPTIWVNDS
STSQLFEDSTIGEPGVPGQSHLQGLTDNIHLVKSSLSTQDTLLIKKGMKEMSQTLQGGNM
LEGDPTHSRSSESEGQESKSITLPDSTLGIMSSMSPVKKPAETTVGTLLDKDTTTVTTTPR
QKVAPSSTMSTHPSRRRPNGRRRLRPNKFRHRHKQTPPTTFAPSETFSTQPTQAPDIKISS
QVESSLVPTAWVDNTVNTPKQLEMEKNAEPTSKGTPRRKHGKRPNKHRYTPSTVSSRA
SGSKPSPSPENKHRNIVTPSSETILLPRTVSLKTEGPYDSLDYMTTTRKIYSSYPKVQETLP
VTYKPTSDGKEIKDDVATNVDKHKSDILVTGESITNAIPTSRSLVSTMGEFKEESSPVGFP
GTPTWNPSRTAQPGRLQTDIPVTTSGENLTDPPLLKELEDVDFTSEFLSSLTVSTPFHQEE
AGSSTTLSSIKVEVASSQAETTTLDQDHLETTVAILLSETRPQNHTPTAARMKEPASSSPS
TILMSLGQTTTTKPALPSPRISQASRDSKENVFLNYVGNPETEATPVNNEGTQHMSGPNE
LSTPSSDRDAFNLSTKLELEKQVFGSRSLPRGPDSQRQDGRVHASHQLTRVPAKPILPTA
TVRLPEMSTQSASRYFVTSQSPRHWTNKPEITTYPSGALPENKQFTTPRLSSTTPLPLHM
SKPSIPSKFTDRRTDQFNGYSKVFGNNNIPEARNPVGKPPSPRIPHYSNGRLPFFTNKTLSF
PQLGVTRRPQIPTSPAPVMRERKVIPGSYNRIHSHSTFHLDFGPPAPPLLHTPQTTGSPSTN
LQNIPMVSSTQSSISFITSSVQSSGSFHQSSSKFFAGGPPASKFWSLGEKPQILTKSPQTVSV
TAETDTVFPCEATGKPKPFVTWTKVSTGALMTPNTRIQRFEVLKNGTLVIRKVQVQDRG
QYMCTASNLHGLDRMVVLLSVTVQQPQILASHYQDVTVYLGDTIAMECLAKGTPAPQI
SWIFPDRRVWQTVSPVESRITLHENRTLSIKEASFSDRGVYKCVASNAAGADSLAIRLHV
AALPPVIHQEKLENISLPPGLSIHIHCTAKAAPLPSVRWVLGDGTQIRPSQFLHGNLFVFP
NGTLYIRNLAPKDSGRYECVAANLVGSARRTVQLNVQRAAANARITGTSPRRTDVRYG
GTLKLDCSASGDPWPRILWRLPSKRMIDALFSFDSRIKVFANGTLVVKSVTDK

Figure 27 (Cont.)

DAGDYLCVARNKVGDDYVVLKVDVVMKPAKIEHKEENDHKVFYGGDLKVDCVATGL
PNPEISWSLPDGSLVNSFMQSDDSGGRTKRYVVFNNGTLYFNEVGMREEGDYTCFAEN
QVGKDEMRVRVKVVTAPATIRNKTYLAVQVPYGDVVTVACEAKGEPMPKVTWLSPTN
KVIPTSSEKYQIYQDGTLLIQKAQRSDSGNYTCLVRNSAGEDRKTVWIHVNVQPPKING
NPNPITTVREIAAGGSRKLIDCKAEGIPTPRVLWAFPEGVVLPAPYYGNRITVHGNGSLDI
RSLRKSDSVQLVCMARNEGGEARLIVQLTVLEPMEKPIFHDPISEKITAMAGHTISLNCS
AAGTPTPSLVWVLPNGTDLQSGQQLQRFYHKADGMLHISGLSSVDAGAYRCVARNAA
GHTERLVSLKVGLKPEANKQYHNLVSIINGETLKLPCTPPGAGQGRFSWTLPNGMHLEG
PQTLGRVSLLDNGTLTVREASVFDRGTYVCRMETEYGPSVTSIPVIVIAYPPRITSEPTPVI
YTRPGNTVKLNCMAMGIPKADITWELPDKSHLKAGVQARLYGNRFLHPQGSLTIQHAT
QRDAGFYKCMAKNILGSDSKTTYIHVF (SEQ ID NO: 21)

Figure 28

ATGCCCAAGC GCGCGCACTG GGGGGCCCTC TCCGTGGTGC TGATCCTGCT
TTGGGGCCAT CCGCGAGTGG CGCTGGCCTG CCCGCATCCT TGTGCCTGCT
ACGTCCCCAG CGAGGTCCAC TGCACGTTCC GATCCCTGGC TTCCGTGCCC
GCTGGCATTG CTAGACACGT GGAAAGAATC AATTTGGGGT TAATAGCAT
ACAGGCCCTG TCAGAAACCT CATTTGCAGG ACTGACCAAG TTGGAGCTAC
TTATGATTCA CGGCAATGAG ATCCCAAGCA TCCCCGATGG AGCTTTAAGA
GACCTCAGCT CTCTTCAGGT TTTCAAGTTC AGCTACAACA AGCTGAGAGT
GATCACAGGA CAGACCCTCC AGGGTCTCTC TAACTTAATG AGGCTGCACA
TTGACCACAA CAAGATCGAG TTTATCCACC CTCAAGCTTT CAACGGCTTA
ACGTCTCTGA GGCTACTCCA TTTGGAAGGA AATCTCCTCC ACCAGCTGCA
CCCCAGCACC TTCTCCACGT TCACATTTTT GGATTATTTC AGACTCTCCA
CCATAAGGCA CCTCTACTTA GCAGAGAACA TGGTTAGAAC TCTTCCTGCC
AGCATGCTTC GGAACATGCC GCTTCTGGAG AATCTTTACT TGCAGGGAAA
TCCGTGGACC TGCGATTGTG AGATGAGATG GTTTTTGGAA TGGGATGCAA
AATCCAGAGG AATTCTGAAG TGTAAAAAGG ACAAAGCTTA TGAAGGCGGT
CAGTTGTGTG CAATGTGCTT CAGTCCAAAG AAGTTGTACA ACATGAGAT
ACACAAGCTG AAGGACATGA CTTGTCTGAA GCCTTCAATA GAGTCCCCTC
TGAGACAGAA CAGGAGCAGG AGTATTGAGG AGGAGCAAGA ACAGGAAGAG
GATGGTGGCA GCCAGCTCAT CCTGGAGAAA TTCCAACTGC CCCAGTGGAG
CATCTCTTTG AATATGACCG ACGAGCACGG GAACATGGTG AACTTGGTCT
GTGACATCAA GAAACCAATG GATGTGTACA AGATTCACTT GAACCAAACG
GATCCTCCAG ATATTGACAT AAATGCAACA GTTGCCTTGG ACTTTGAGTG
TCCAATGACC CGAGAAAACT ATGAAAAGCT ATGGAAATTG ATAGCATACT
ACAGTGAAGT TCCCGTGAAG CTACACAGAG AGCTCATGCT CAGCAAAGAC
CCCAGAGTCA GCTACCAGTA CAGGCAGGAT GCTGATGAGG AAGCTCTTTA
CTACACAGGT GTGAGAGCCC AGATTCTTGC AGAACCAGAA TGGGTCATGC
AGCCATCCAT AGATATCCAG CTGAACCGAC GTCAGAGTAC GGCCAAGAAG
GTGCTACTTT CCTACTACAC CCAGTATTCT CAAACAATAT CCACCAAAGA
TACAAGGCAG GCTCGGGGCA GAAGCTGGGT AATGATTGAG CCTAGTGGAG
CTGTGCAAAG AGATCAGACT GTCCTGGAAG GGGGTCCATG CCAGTTGAGC
TGCAACGTGA AGCTTCTGA GAGTCCATCT ATCTTCTGGG TGCTTCCAGA
TGGCTCCATC CTGAAAGCGC CCATGGATGA CCCAGACAGC AAGTTCTCCA
TTCTCAGCAG TGGCTGGCTG AGGATCAAGT CCATGGAGCC ATCTGACTCA
GGCTTGTACC AGTGCATTGC TCAAGTGAGG GATGAAATGG ACCGCATGGT
ATATAGGGTA CTTGTGCAGT CTCCCTCCAC TCAGCCAGCC GAGAAAGACA
CAGTGACAAT TGGCAAGAAC CCAGGGGAGT CGGTGACATT GCCTTGCAAT
GCTTTAGCAA TACCCGAAGC CCACCTTAGC TGGATTCTTC CAAACAGAAG
GATAATTAAT GATTTGGCTA ACACATCACA TGTATACATG TTGCCAAATG
GAACTCTTTC CATCCCAAAG GTCCAAGTCA GTGATAGTGG

Figure 28 (Cont.)

TTACTACAGA TGTGTGGCTG TCAACCAGCA AGGGGCAGAC CATTTTACGG
TGGGAATCAC AGTGACCAAG AAAGGGTCTG GCTTGCCATC CAAAAGAGGC
AGACGCCCAG GTGCAAAGGC TCTTTCCAGA GTCAGAGAAG ACATCGTGGA
GGATGAAGGG GGCTCGGGCA TGGGAGATGA AGAGAACACT TCAAGGAGAC
TTCTGCATCC AAAGGACCAA GAGGTGTTCC TCAAAACAAA GGATGATGCC
ATCAATGGAG ACAAGAAAGC CAAGAAGGG AGAAGAAAGC TGAAACTCTG
GAAGCATTCG GAAAAGAAC CAGAGACCAA TGTTGCAGAA GGTCGCAGAG
TGTTTGAATC TAGACGAAGG ATAAACATGG CAAACAAACA GATTAATCCG
GAGCGCTGGG CTGATATTTT AGCCAAAGTC CGTGGGAAAA ATCTCCTAA
GGGCACAGAA GTACCCCGT TGATTAAAAC CACAAGTCCT CCATCCTTGA
GCCTAGAAGT CACACCACCT TTTCCTGCTG TTTCTCCCCC CTCAGCATCT
CCTGTGCAGA CAGTAACCAG TGCTGAAGAA TCCTCAGCAG ATGTACCTCT
ACTTGGTGAA GAAGAGCACG TTTGGGTAC CATTTCCTCA GCCAGCATGG
GGCTAGAACA CAACCACAAT GGAGTTATTC TTGTTGAACC TGAAGTAACA
AGCACACCTC TGGAGGAAGT TGTTGATGAC CTTTCTGAGA AGACTGAGGA
GATAACTTCC ACTGAAGGAG ACCTGAAGGG GACAGCAGCC CCTACACTTA
TATCTGAGCC TTATGAACCA TCTCCTACTC TGCACACATT AGACACAGTC
TATGAAAAGC CCACCCATGA AGAGACGGCA ACAGAGGGTT GGTCTGCAGC
AGATGTTGGA TCGTCACCAG AGCCCACATC CAGTGAGTAT GAGCCTCCAT
TGGATGCTGT CTCCTTGGCT GAGTCTGAGC CCATGCAATA CTTTGACCCA
GATTTGGAGA CTAAGTCACA ACCAGATGAG GATAAGATGA AAGAAGACAC
CTTTGCACAC CTTACTCCAA CCCCCACCAT CTGGGTTAAT GACTCCAGTA
CATCACAGTT ATTTGAGGAT TCTACTATAG GGGAACCAGG TGTCCCAGGC
CAATCACATC TACAAGGACT GACAGACAAC ATCCACCTTG TGAAAAGTAG
TCTAAGCACT CAAGACACCT TACTGATTAA AAAGGGTATG AAAGAGATGT
CTCAGACACT ACAGGGAGGA AATATGCTAG AGGGAGACCC CACACACTCC
AGAAGTTCTG AGAGTGAGGG CCAAGAGAGC AAATCCATCA CTTTGCCTGA
CTCCACACTG GGTATAATGA GCAGTATGTC TCCAGTTAAG AAGCCTGCGG
AAACCACAGT TGGTACCCTC CTAGACAAAG ACACCACAAC AGTAACAACA
ACACCAAGGC AAAAGTTGC TCCGTCATCC ACCATGAGCA CTCACCCTTC
TCGAAGGAGA CCCAACGGGA GAAGGAGATT ACGCCCCAAC AAATTCCGCC
ACCGGCACAA GCAAACCCCA CCCACAACTT TGCCCCATC AGAGACTTTT
TCTACTCAAC CAACTCAAGC ACCTGACATT AAGATTTCAA GTCAAGTGGA
GAGTTCTCTG GTTCCTACAG CTTGGGTGGA TAACACAGTT AATACCCCCA
AACAGTTGGA AATGGAGAAG AATGCAGAAC CCACATCCAA GGGAACACCA
CGGAGAAAAC ACGGGAAGAG GCCAAACAAA CATCGATATA CCCCTTCTAC
AGTGAGCTCA AGAGCGTCCG GATCCAAGCC CAGCCCTTCT CCAGAAAATA
AACATAGAAA CATTGTTACT CCCAGTTCAG AAACTATACT TTTGCCTAGA
ACTGTTTCTC TGAAAACTGA GGGCCCTTAT GATTCCTTAG ATTACATGAC
AACCACCAGA AAAATATATT CATCTTACCC TAAAGTCCAA GAGACACTTC
CAGTCACATA

Figure 28 (Cont.)

TAAACCCACA TCAGATGGAA AAGAAATTAA GGATGATGTT GCCACAAATG
TTGACAAACA TAAAAGTGAC ATTTTAGTCA CTGGTGAATC AATTACTAAT
GCCATACCAA CTTCTCGCTC CTTGGTCTCC ACTATGGGAG AATTTAAGGA
AGAATCCTCT CCTGTAGGCT TTCCAGGAAC TCCAACCTGG AATCCCTCAA
GGACGGCCCA GCCTGGGAGG CTACAGACAG ACATACCTGT TACCACTTCT
GGGGAAAATC TTACAGACCC TCCCCTTCTT AAAGAGCTTG AGGATGTGGA
TTTCACTTCC GAGTTTTTGT CCTCTTTGAC AGTCTCCACA CCATTTCACC
AGGAAGAAGC TGGTTCTTCC ACAACTCTCT CAAGCATAAA AGTGGAGGTG
GCTTCAAGTC AGGCAGAAAC CACCACCCTT GATCAAGATC ATCTTGAAAC
CACTGTGGCT ATTCTCCTTT CTGAAACTAG ACCACAGAAT CACACCCCTA
CTGCTGCCCG GATGAAGGAG CCAGCATCCT CGTCCCCATC ACAATTCTC
ATGTCTTTGG GACAAACCAC CACCACTAAG CCAGCACTTC CCAGTCCAAG
AATATCTCAA GCATCTAGAG ATTCCAAGGA AAATGTTTTC TTGAATTATG
TGGGGAATCC AGAAACAGAA GCAACCCCAG TCAACAATGA AGGAACACAG
CATATGTCAG GGCCAAATGA ATTATCAACA CCCTCTTCCG ACCGGGATGC
ATTTAACTTG TCTACAAAGC TGGAATTGGA AAAGCAAGTA TTTGGTAGTA
GGAGTCTACC ACGTGGCCCA GATAGCCAAC GCCAGGATGG AAGAGTTCAT
GCTTCTCATC AACTAACCAG AGTCCCTGCC AAACCCATCC TACCAACAGC
AACAGTGAGG CTACCTGAAA TGTCCACACA AAGCGCTTCC AGATACTTTG
TAACTTCCCA GTCACCTCGT CACTGGACCA ACAAACCGGA AATAACTACA
TATCCTTCTG GGGCTTTGCC AGAGAACAAA CAGTTTACAA CTCCAAGATT
ATCAAGTACA ACAATTCCTC TCCCATTGCA CATGTCCAAA CCCAGCATTC
CTAGTAAGTT TACTGACCGA AGAACTGACC AATTCAATGG TTACTCCAAA
GTGTTTGGAA ATAACAACAT CCCTGAGGCA AGAAACCCAG TTGGAAAGCC
TCCCAGTCCA AGAATTCCTC ATTATTCCAA TGGAAGACTC CCTTTCTTTA
CCAACAAGAC TCTTTCTTTT CCACAGTTGG GAGTCACCCG GAGACCCCAG
ATACCCACTT CTCCTGCCCC AGTAATGAGA GAGAGAAAAG TTATTCCAGG
TTCCTACAAC AGGATACATT CCCATAGCAC CTTCCATCTG GACTTTGGCC
CTCCGGCACC TCCGTTGTTG CACACTCCGC AGACCACGGG ATCACCCTCA
ACTAACTTAC AGAATATCCC TATGGTCTCT TCCACCCAGA GTTCTATCTC
CTTTATAACA TCTTCTGTCC AGTCCTCAGG AAGCTTCCAC CAGAGCAGCT
CAAAGTTCTT TGCAGGAGGA CCTCCTGCAT CCAAATTCTG GTCTCTTGGG
GAAAAGCCCC AAATCCTCAC CAAGTCCCCA CAGACTGTGT CCGTCACCGC
TGAGACAGAC ACTGTGTTCC CCTGTGAGGC AACAGGAAAA CCAAAGCCTT
TCGTTACTTG GACAAAGGTT TCCACAGGAG CTCTTATGAC TCCGAATACC
AGGATACAAC GGTTTGAGGT TCTCAAGAAC GGTACCTTAG TGATACGGAA
GGTTCAAGTA CAAGATCGAG GCCAGTATAT GTGCACCGCC AGCAACCTGC
ACGGCCTGGA CAGGATGGTG GTCTTGCTTT CGGTCACCGT GCAGCAACCT
CAAATCCTAG CCTCCCACTA CCAGGACGTC ACTGTCTACC TGGGAGACAC
CATTGCAATG GAGTGTCTGG CCAAAGGGAC CCCAGCCCCC CAAATTTCCT
GGATCTTCCC TGACAGGAGG GTGTGGCAAA CTGTGTCCCC

Figure 28 (Cont.)

```
CGTGGAGAGC CGCATCACCC TGCACGAAAA CCGGACCCTT TCCATCAAGG
AGGCGTCCTT CTCAGACAGA GGCGTCTATA AGTGCGTGGC CAGCAATGCA
GCCGGGGCGG ACAGCCTGGC CATCCGCCTG CACGTGGCGG CACTGCCCCC
CGTTATCCAC CAGGAGAAGC TGGAGAACAT CTCGCTGCCC CCGGGGCTCA
GCATTCACAT TCACTGCACT GCCAAGGCTG CGCCCCTGCC CAGCGTGCGC
TGGGTGCTCG GGACGGTAC CCAGATCCGC CCTCGCAGT TCCTCCACGG
GAACTTGTTT GTTTTCCCCA ACGGGACGCT CTACATCCGC AACCTCGCGC
CCAAGGACAG CGGGCGCTAT GAGTGCGTGG CCGCCAACCT GGTAGGCTCC
GCGCGCAGGA CGGTGCAGCT GAACGTGCAG CGTGCAGCAG CCAACGCGCG
CATCACGGGC ACCTCCCCGC GGAGGACGGA CGTCAGGTAC GGAGGAACCC
TCAAGCTGGA CTGCAGCGCC TCGGGGACC CCTGGCCGCG CATCCTCTGG
AGGCTGCCGT CCAAGAGGAT GATCGACGCG CTCTTCAGTT TTGATAGCAG
AATCAAGGTG TTTGCCAATG GGACCCTGGT GGTGAAATCA GTGACGGACA
AAGATGCCGG AGATTACCTG TGCGTAGCTC GAAATAAGGT TGGTGATGAC
TACGTGGTGC TCAAAGTGGA TGTGGTGATG AAACCGGCCA AGATTGAACA
CAAGGAGGAG AACGACCACA AAGTCTTCTA CGGGGGTGAC CTGAAAGTGG
ACTGTGTGGC CACCGGGCTT CCCAATCCCG AGATCTCCTG GAGCCTCCCA
GACGGGAGTC TGGTGAACTC CTTCATGCAG TCGGATGACA GCGGTGGACG
CACCAAGCGC TATGTCGTCT TCAACAATGG GACACTCTAC TTTAACGAAG
TGGGGATGAG GGAGGAAGGA GACTACACCT GCTTTGCTGA AAATCAGGTC
GGGAAGGACG AGATGAGAGT CAGAGTCAAG GTGGTGACAG CGCCCGCCAC
CATCCGGAAC AAGACTTACT TGGCGGTTCA GGTGCCCTAT GGAGACGTGG
TCACTGTAGC CTGTGAGGCC AAAGGAGAAC CCATGCCCAA GGTGACTTGG
TTGTCCCCAA CCAACAAGGT GATCCCCACC TCCTCTGAGA AGTATCAGAT
ATACCAAGAT GGCACTCTCC TTATTCAGAA AGCCCAGCGT TCTGACAGCG
GCAACTACAC CTGCCTGGTC AGGAACAGCG CGGGAGAGGA TAGGAAGACG
GTGTGGATTC ACGTCAACGT CCAGCCACCC AAGATCAACG GTAACCCCAA
CCCCATCACC ACCGTGCGGG AGATAGCAGC CGGGGGCAGT CGGAAACTGA
TTGACTGCAA AGCTGAAGGC ATCCCCACCC CGAGGGTGTT ATGGGCTTTT
CCCGAGGGTG TGGTTCTGCC AGCTCCATAC TATGGAAACC GGATCACTGT
CCATGGCAAC GGTTCCCTGG ACATCAGGAG TTTGAGGAAG AGCGACTCCG
TCCAGCTGGT ATGCATGGCA CGCAACGAGG GAGGGGAGGC GAGGTTGATC
GTGCAGCTCA CTGTCCTGGA GCCCATGGAG AAACCCATCT CCACGACCC
GATCAGCGAG AAGATCACGG CCATGGCGGG CCACACCATC AGCCTCAACT
GCTCTGCCGC GGGGACCCCG ACACCCAGCC TGGTGTGGGT CCTTCCCAAT
GGCACCGATC TGCAGAGTGG ACAGCAGCTG CAGCGCTTCT ACCACAAGGC
TGACGGCATG CTACACATTA GCGGTCTCTC CTCGGTGGAC GCTGGGGCCT
ACCGCTGCGT GGCCCGCAAT GCCGCTGGCC ACACGGAGAG GCTGGTCTCC
CTGAAGGTGG GACTGAAGCC AGAAGCAAAC AAGCAGTATC ATAACCTGGT
CAGCATCATC AATGGTGAGA CCCTGAAGCT CCCCTGCACC CCTCCCGGGG
CTGGGCAGGG ACGTTTCTCC TGGACGCTCC CCAATGGCAT GCATCTGGAG
```

Figure 28 (Cont.)

```
GGCCCCCAAA CCCTGGGACG CGTTTCTCTT CTGGACAATG GCACCCTCAC
GGTTCGTGAG GCCTCGGTGT TGACAGGGG TACCTATGTA TGCAGGATGG
AGACGGAGTA CGGCCCTTCG GTCACCAGCA TCCCCGTGAT TGTGATCGCC
TATCCTCCCC GGATCACCAG CGAGCCCACC CCGGTCATCT ACACCCGGCC
CGGGAACACC GTGAAACTGA ACTGCATGGC TATGGGATT CCCAAAGCTG
ACATCACGTG GGAGTTACCG GATAAGTCGC ATCTGAAGGC AGGGGTTCAG
GCTCGTCTGT ATGGAAACAG ATTTCTTCAC CCCCAGGGAT CACTGACCAT
CCAGCATGCC ACACAGAGAG ATGCCGGCTT CTACAAGTGC ATGGCAAAAA
ACATTCTCGG CAGTGACTCC AAAACAACTT ACATCCACGT CTTCTGAAAT
GTGGATTCCA GAATGATTGC TTAGGAACTG ACAACAAAGC GGGGTTTGTA
AGGGAAGCCA GGTTGGGGAA TAGGAGCTCT TAAATAATGT GTCACAGTGC
ATGGTGGCCT CTGGTGGGTT TCAAGTTGAG GTTGATCTTG ATCTACAATT
GTTGGGAAAA GGAAGCAATG CAGACACGAG AAGGAGGGCT CAGCCTTGCT
GAGACACTTT CTTTTGTGTT TACATCATGC CAGGGGCTTC ATTCAGGGTG
TCTGTGCTCT GACTGCAATT TTTCTTCTTT TGCAAATGCC ACTCGACTGC
CTTCATAAGC GTCCATAGGA TATCTGAGGA ACATTCATCA AAAATAAGCC
ATAGACATGA ACAACACCTC ACTACCCCAT TGAAGACGCA TCACCTAGTT
AACCTGCTGC AGTTTTTACA TGATAGACTT TGTTCCAGAT TGACAAGTCA
TCTTTCAGTT ATTTCCTCTG TGACTTCAAA ACTCCAGCTT GCCCAATAAG
GATTTAGAAC CAGAGTGACT GATATATATA TATATATTTT AATTCAGAGT
TACATACATA CAGCTACCAT TTTATATGAA AAAAGAAAAA CATTTCTTCC
TGGAACTCAC TTTTTATATA ATGTTTTATA TATATATTTT TTCCTTTCAA
ATCAGACGAT GAGACTAGAA GGAGAAATAC TTTCTGTCTT ATTAAAATTA
ATAAATTATT GGTCTTTACA AGACTTGGAT ACATTACAGC AGACATGGAA
ATATAATTTT AAAAAATTTC TCTCCAACCT CCTTCAAATT CAGTCACCAC
TGTTATATTA CCTTCTCCAG GAACCCTCCA GTGGGGAAGG CTGCGATATT
AGATTTCCTT GTATGCAAAG TTTTTGTTGA AAGCTGTGCT CAGAGGAGGT
GAGAGGAGAG GAAGGAGAAA ACTGCATCAT AACTTTACAG AATTGAATCT
AGAGTCTTCC CCGAAAAGCC CAGAAACTTC TCTGCAGTAT CTGGCTTGTC
CATCTGGTCT AAGGTGGCTG CTTCTTCCCC AGCCATGAGT CAGTTTGTGC
CCATGAATAA TACACGACCT GTTATTTCCA TGACTGCTTT ACTGTATTTT
TAAGGTCAAT ATACTGTACA TTTGATAATA AAATAATATT CTCCCAAAAA AAAAA
```

Figure 29

```
ATGAAGGTAAAAGGCAGAGGAATCACCTGCTTGCTGGTCTCCTTTGCTGTGATCTGCCTGGTCGCCACC
CCTGGGGGCAAGGCCTGTCCTCGCCGCTGTGCCTGTTATATGCCTACGGAGGTACACTGCACATTTCGG
TACCTGACTTCCATCCCAGACAGCATCCCGCCCAATGTGGAACGCATCAATTTAGGATACAACAGCTTG
GTTAGATTGATGGAAACAGATTTTTCTGGCCTGACCAAACTGGAGTTACTCATGCTTCACAGCAATGGC
ATTCACACAATCCCTGACAAGACCTTCTCAGATTTGCAGGCCTTGCAGGTCTTAAAAATGAGCTATAAT
AAAGTCCGAAAACTTCAGAAAGATACTTTTTATGGCCTCAGGAGCTTGACACGATTGCACATGGACCAC
AACAATATTGAGTTTATAAACCCAGAGGTTTTTTATGGGCTCAACTTTCTCCGCCTGGTGCACTTGGAA
GGAAATCAGCTCACTAAGCTCCACCCAGATACATTTGTCTCTTTGAGCTACCTCCAGATATTTAAAATC
TCTTTCATTAAGTTCCTATACTTGTCTGATAACTTCCTGACCTCCCTCCCTCAAGAGATGGTCTCCTAT
ATGCCTGACCTAGACAGCCTTTACCTGCATGGAAACCCATGGACCTGTGATTGCCATTTAAAGTGGTTG
TCTGACTGGATACAGGAGAAGCCAGATGTAATAAAATGCAAAAAAGATAGAAGTCCCTCTAGTGCTCAG
CAGTGTCCACTTTGCATGAACCCTAGGACTTCTAAAGGCAAGCCGTTAGCTATGGTCTCAGCTGCAGCT
TTCCAGTGTGCCAAGCCAACCATTGACTCATCCCTGAAATCAAAGAGCCTGACTATTCTGGAAGACAGT
AGTTCTGCTTTCATCTCTCCCCAAGGTTTCATGGCACCCTTTGGCTCCCTCACTTTGAATATGACAGAT
CAGTCTGGAAATGAAGCTAACATGGTCTGCAGTATTCAAAAGCCCTCAAGGACATCACCCATTGCATTC
ACTGAAGAAATGACTACATCGTGCTAAATACTTCATTTTCAACATTTTTGGTGTGCAACATAGATTAC
GGTCACATTCAGCCACTCTGGCAAATTTTGGCTTTGTACAGTGATTCTCCTCTGATACTAGAAAGGAGC
CACTTGCTTAGTGAAACACCGCAGCTCTATTACAAATATAAACAGGTGGCTCCTAAGCCTGAAGACATT
TTTACCAACATAGAGGCAGATCTCAGAGCAGATCCCTCTTGGTTAATGCAAGACCAAATTTCCTTGCAG
CTGAACAGAACTGCCACCACATTCAGTACATTACAGATCCAGTACTCCAGTGATGCTCAAATCACTTTA
CCAAGAGCAGAGATGAGGCCAGTGAAACACAAATGGACTATGATTTCAAGGGATAACAATACTAAGCTG
GAACATACTGTCTTGGTAGGTGGAACCGTTGGCCTGAACTGCCCAGGCCAAGGAGACCCCACCCCACAC
GTGGATTGGCTTCTAGCTGATGAAGTAAAGTGAGAGCCCCTTATGTCAGTGAGGATGGACGGATCCTA
ATAGACAAAAGTGGAAAATTGGAACTCCAGATGGCTGATAGTTTTGACACAGGCGTATATCACTGTATA
AGCAGCAATTATGATGATGCAGATATTCTCACCTATAGGATAACTGTGGTAGAACCTTTGGTCGAAGCC
TATCAGGAAATGGGATTCATCACACAGTTTTCATTGGTGAAACACTTGATCTTCCATGCCATTCTACT
GGTATCCCAGATGCCTCTATTAGCTGGGTTATTCCAGGAAACAATGTGCTCTATCAGTCATCAAGAGAC
AAGAAAGTTCTAAACAATGGCACATTAAGAATATTACAGGTCACCCCGAAAGACCAAGGTTATTATCGC
TGTGTGGCAGCCAACCCATCAGGGGTTGATTTTTTGATTTTCCAAGTTTCAGTCAAGATGAAAGGACAA
AGGCCCTTGGAGCATGATGGAGAAACAGAGGGATCTGGACTTGATGAGTCCAATCCTATTGCTCATCTT
AAGGAGCCACCAGGTGCACAACTCCGTACATCTGCTCTGATGGAGGCTGAGGTTGGAAAACACACCTCA
AGCACAAGTAAGAGGCACAACTATCGGAATTAACACTCCAGCGACGTGGAGATTCAACACATCGACGT
TTTAGGGAGAATAGGAGGCATTTCCCTCCCTCTGCTAGGAGAATTGACCCACAACATTGGGCGGCACTG
TTGGAGAAAGCTAAAAAGAATGCTATGCCAGACAAGCGAGAAAATACCACAGTGAGCCCACCCCCAGTG
GTCACCCAACTCCCAAACATACCTGGTGAAGAAGACGATTCCTCAGGCATGCTCGCTCTACATGAGGAA
TTTATGGTCCCGGCCACTAAAGCTTTGAACCTTCCAGCAAGGACAGTGACTGCTGACTCCAGAACAATA
TCTGATAGTCCTATGACAAACATAAATTATGGCACAGAATTCTCTCCTGTTGTGAATTCACAAATACTA
CCACCTGAAGAACCCACAGATTTCAAACTGTCTACTGCTATTAAAACTACAGCCATGTCAAAGAATATA
AACCCAACCATGTCAAGCCAAATACAAGGCACAACCAATCAACATTCATCCACTGTCTTTCCACTGCTA
CTTGGAGCAACTGAATTTCAGGACTCTGACCAGATGGGAAGAGGAAGAGAGCATTTCCAAAGTAGACCC
CCAATAACAGTAAGGACTATGATCAAAGATGTCAATGTCAAATGCTTAGTAGCACCACCAACAAACTA
TTATTAGAGTCAGTAAATACCACAAATAGTCATCAGACATCTGTAAGAGAAGTGAGTGAACCCAGGCAC
AATCACTTCTATTCTCACACTACTCAAATACTTAGCACCTCCACGTTCCCTTCAGATCCACACACAGCT
GCTCATTCTCAGTTTCCGATCCCTAGAAATAGTACAGTTAACATCCCGCTGTTCAGACGCTTTGGGAGG
CAGAGGAAAATTGGCGGAAGGGGCGGATTATCAGCCCATATAGAACTCCAGTTCTGCGACGGCATAGA
TACAGCATTTTCAGGTCAACAACCAGAGGTTCTTCTGAAAAAAGCACTACTGCATTCTCAGCCAGAGTG
CTCAATGTGACATGTCTGTCCTGTCTTCCCAGGGAGAGGCTCACCACTGCCACAGCAGCATTGTCTTTT
CCAAGTGCTGCTCCCATCACCTTCCCCAAAGCTGACATTGCTAGAGTCCCATCAGAAGAGTCTACAACT
CTAGTCCAGAATCCACTATTACTACTTGAGAACAAACCCAGTGTAGAGAAAACAACACCCACAATAAAA
TATTTCAGGACTGAAATTTCCCAAGTGACTCCAACTGGTGCAGTCATGACATATGCTCCAACATCCATA
CCCATGGAAAAAACTCACAAAGTAAACGCCAGTTACCCACGTGTGTCTAGCACCAATGAAGCTAAAAGA
GATTCAGTGATTACATCGTCACTTTCAGGTGCTATCACCAAGCCACCAATGACTATTATAGCCATTACA
AGGTTTTCAAGAAGGAAAATTCCCTGGCAACAGAACTTTGTAAATAACCATAACCCAAAAGGCAGATTA
AGGAATCAACATAAAGTTAGTTTACAAAAAAGCACAGCTGTGATGCTTCCTAAAACATCTCCTGCTTTA
CCACAGAGACAAAGTTCCCCTTTCCATTTCACCACACTTTCAACAAGTGTGATGCAAATTCCATCTAAT
ACCTTGACTACCGCTCACCACACTACGACCAAAACACACAATCCTGGAAGTCTTCCAACAAAGAAGGAG
CTTCCCTTCCCACCCCTTAACCCTATGCTTCCTAGTATTATAAGCAAAGACTCAAGTACAAAAGCATC
ATATCAACGCAAACAGCAATACCAGCAACAACTCCTACCTTCCCTGCATCTGTCATCACTTATGAAACC
CAAACAGAGAGATCTAGAGCACAAACAATACAAAGAGAACAGGAGCCTCAAAAGAAGAACAGGACTGAC
CCAAACATCTCTCCAGACCAGAGTTCTGGCTTCACTACACCCACTGCTATGACACCTCCTGCTCTGGCA
```

Figure 29 (Cont.)

```
TTCACTCATTCCCCACCAGAAAACACAACTGGGATTTCAAGCACAATCAGTTTTCATTCAAGAACTCTT
AATCTGACAGATGTGATTGAAGAACTAGCCCAAGCAAGTACTCAGACTTTGAAGAGCACAATTGCTTCT
GAAACAACTTTGTCCAGCAAATCACACCAGAGTACCACAACTAGGAAAGCATCATTAGACACTCCCATA
CCACCATTCTTGAGCAGCAGTGCTACTCTAATGCCAGTTCCCATCTCCCCTCCCTTTACTCAGAGAGCA
GTTACTGACACACGTGGCGACTCCCATTTCCGGCTTATGACAAATACAGTGGTCAAGCTGCACGAATCC
TCAAGGCACAATCTCCAAATGCCAAGTTCACAATTGGAACCACTCACTTCATCTACCTCTAATCTGTTA
CATTCTACTCCCATGCCAGCACTAACAACAGTTAAATCACAGAATTCCAAATTAACTCCATCTCCCTGG
GCAGAATACCAATTTTGGCACAAACCATACTCAGACATTGCTGAAAAAGGCAAAAAGCCAGAAGTAAGC
ATGTTGGCTACTACAGGCCTGTCCGAGGCCACCACTCTTGTTTCAGATTGGGATGGACAGAAGAACACA
AAGAAGAGTGACTTTGATAAGAAACCAGTTCAAGAAGCAACAACTTCCAAACTCCTTCCCTTTGACTCT
TTGTCTAGGTATATATTTGAAAAGCCCAGGATAGTTGGAGGAAAAGCTGCAAGTTTTACTATTCCAGCT
AACTCAGATGCCTTTCTTCCCTGTGAAGCTGTTGGAAATCCCCTGCCCACCATTCATTGGACCAGAGTT
TCAGGACTTGATTTATCTAGAGGAAACCAGAATAGCAGGGTCCAGGTTCTCCCCAATGGTACCCTGTCC
ATCCAGAGGGTGGAAATTCAGGACCGCGGACAGTACTTGTGTTCCGCATCCAATCTGTTTGGCACAGAC
CACCTTCATGTCACCTTGTCTGTGGTTTCCTATCCTCCCAGGATCCTGGAGAGACGTACCAAAGAGATC
ACAGTTCATTCCGGAAGCACTGTGGAACTGAAGTGCAGAGCAGAAGGTAGGCCAAGCCCTACAGTTACC
TGGATTCTTGCAAACCAAACAGTTGTCTCAGAATCATCCCAGGGAAGTAGGCAGGCTGTGGTGACGGTT
GACGGAACATTGGTCCTCCACAATCTCAGTATTTATGACCGTGGCTTTTACAAATGTGTGGCCAGCAAC
CCAGGTGGCCAGGATTCACTGCTGGTTAAAATACAAGTCATTGCAGCACCACCTGTTATTCTAGAGCAA
AGGAGGCAAGTCATTGTAGGCACTTGGGGTGAAAGTTTAAAACTGCCCTGTACTGCAAAAGGAACTCCT
CAGCCCAGCGTTTACTGGGTCCTCTCTGATGGCACTGAAGTGAAACCATTACAGTTTACCAATTCCAAG
TTGTTCTTATTTTCAAATGGACTTTGTATATAAGAAACCTAGCCTCTTCAGACAGGGGCACTTATGAA
TGCATTGCTACCAGTTCCACTGGTTCGGAGCGAAGAGTAGTAATGCTTACAATGGAAGAGCGAGTGACC
AGCCCCAGGATAGAAGCTGCATCCCAGAAAAGGACTGAAGTGAATTTTGGGGACAAATTACTACTGAAC
TGCTCAGCCACTGGGGAGCCCAAACCCCAAATAATGTGGAGGTTACCATCCAAGGCTGTGGTCGACCAG
TGGAGCTGGATCCACGTCTACCCTAATGGATCCCTGTTTATTGGATCAGTAACAGAAAAAGACAGTGGT
GTCTACTTGTGTGTGGCAAGAAACAAAATGGGGATGATCTGATACTGATGCATGTTAGCCTAAGACTG
AAACCTGCCAAAATTGACCACAAGCAGTATTTTAGAAAGCAAGTGCTCCATGGGAAAGATTTCCAAGTA
GATTGCAAAGCTTCCGGCTCCCCAGTGCCAGAGATATCTTGGAGTTTGCCTGATGGAACCATGATCAAC
AATGCAATGCAAGCCGATGACAGTGGCCACAGGACTAGGAGATATACCCTTTTCAACAATGGAACTTTA
TACTTCAACAAAGTTGGGGTAGCGGAGGAAGGAGATTATACTTGCTATGCCCAGAACACCCTAGGGAAA
GATGAAATGAAGGTCCACTTAACAGTTATAACAGCTGCTCCCCGGATAAGGCAGAGTAACAAAACCAAC
AAGAGAATCAAAGCTGGAGACACAGCTGTCCTTGACTGTGAGGTCACTGGGGATCCCAAACCAAAAATA
TTTTGGTTGCTGCCTTCCAATGACATGATTTCCTTCTCCATTGATAGGTACACATTTCATGCCAATGGG
TCTTTGACCATCAACAAAGTGAAACTGCTCGATTCTGGAGAGTACGTATGTGTAGCCCGAAATCCCAGT
GGGGATGACACCAAAATGTACAAACTGGATGTGGTCTCTAAACCTCCATTAATCAATGGTCTGTATACA
AACAGAACTGTTATTAAAGCCACAGCTGTGAGACATTCCAAAAAACACTTTGACTGCAGAGCTGAAGGG
ACACCATCTCCTGAAGTCATGTGGATCATGCCAGACAATATTTTCCTCACAGCCCCATACTATGGAAGC
AGAATCACAGTCCATAAAAATGGAACCTTGGAAATTAGGAATGTGAGGCTTTCAGATTCAGCCGACTTT
ATCTGTGTGGCCCGAAATGAAGGTGGAGAGAGCGTGTTGGTAGTACAGTTAGAAGTACTGGAAATGCTG
AGAAGACCGACATTTAGAAATCCATTTAATGAAAAAATAGTTGCCCAGCTGGGAAAGTCCACAGCATTG
AATTGCTCTGTTGATGGTAACCCACCACCTGAAATAATCTGGATTTTACCAAATGGCACACGATTTTCC
AATGGACCACAAAGTTATCAGTATCTGATAGCAAGCAATGGTTCTTTTATCATTTCTAAAACAACTCGG
GAGGATGCAGGAAAATATCGCTGTGCAGCTAGGAATAAAGTTGGCTATATTGAGAAATTAGTCATATTA
GAAATTGGCCAGAAGCCAGTTATTCTTACCTATGCACCAGGGACAGTAAAAGGCATCAGTGGAGAATCT
CTATCACTGCATTGTGTGTCTGATGAATCCCTAAGCCAAATATCAAATGGACTATGCCAAGTGGTTAT
GTAGTAGACAGGCCTCAAATTAATGGGAAATACATATTGCATGACAATGGCACCTTAGTCATTAAAGAA
GCAACAGCTTATGACAGAGGAAACTATATCTGTAAGGCTCAAAATAGTGTTGGTCATACACTGATTACT
GTTCCAGTAATGATTGTAGCCTACCCTCCCCGAATTACAAATCGTCCACCCAGGAGTATTGTCACCAGG
ACAGGGGCAGCCTTTCAGCTCCACTGTGTGGCCTTGGGAGTTCCCAAGCCAGAAATCACATGGGAGATG
CCTGACCACTCCCTTCTCTCAACGGCAAGTAAAGAGAGGACACATGGAAGTGAGCAGCTTCACTTACAA
GGTACCCTAGTCATTCAGAATCCCCAAACCTCCGATTCTGGGATATACAAATGCACAGCAAAGAACCCA
CTTGGTAGTGATTATGCAGCAACGTATATTCAAGTAATCTGA
```

Figure 30

```
ORIGIN
   1   MKVKGRGITC  LLVSFAVICL  VATPGGKACP  RRCACYMPTE  VHCTFRYLTS
  51   IPDSIPPNVE  RINLGYNSLV  RLMETDFSGL  TKLELLMLHS  NGIHTIPDKT
 101   FSDLQALQVL  KMSYNKVRKL  QKDTFYGLRS  LTRLHMDHNN  IEFINPEVFY
 151   GLNFLRLVHL  EGNQLTKLHP  DTFVSLSYLQ  IFKISFIKFL  YLSDNFLTSL
 201   PQEMVSYMPD  LDSLYLHGNP  WTCDCHLKWL  SDWIQEKPDV  IKCKKDRSPS
 251   SAQQCPLCMN  PRTSKGKPLA  MVSAAAFQCA  KPTIDSSLKS  KSLTILEDSS
 301   SAFISPQGFM  APFGSLTLNM  TDQSGNEANM  VCSIQKPSRT  SPIAFTEEND
 351   YIVLNTSFST  FLVCNIDYGH  IQPVWQILAL  YSDSPLILER  SHLLSETPQL
 401   YYKYKQVAPK  PEDIFTNIEA  DLRADPSWLM  QDQISLQLNR  TATTFSTLQI
 451   QYSSDAQITL  PRAEMRPVKH  KWTMISRDNN  TKLEHTVLVG  GTVGLNCPGQ
 501   GDPTPHVDWL  LADGSKVRAP  YVSEDGRILI  DKSGKLELQM  ADSFDTGVYH
 551   CISSNYDDAD  ILTYRITVVE  PLVEAYQENG  IHHTVFIGET  LDLPCHSTGI
 601   PDASISWVIP  GNNVLYQSSR  DKKVLNNGTL  RILQVTPKDQ  GYYRCVAANP
 651   SGVDFLIFQV  SVKMKGQRPL  EHDGETEGSG  LDESNPIAHL  KEPPGAQLRT
 701   SALMEAEVGK  HTSSTSKRHN  YRELTLQRRG  DSTHRRFREN  RRHFPPSARR
 751   IDPQHWAALL  EKAKKNAMPD  KRENTTVSPP  PVVTQLPNIP  GEEDDSSGML
 801   ALHEEFMVPA  TKALNLPART  VTADSRTISD  SPMTNINYGT  EFSPVVNSQI
 851   LPPEEPTDFK  LSTAIKTTAM  SKNINPTMSS  QIQGTTNQHS  STVFPLLLGA
 901   TEFQDSDQMG  RGREHFQSRP  PITVRTMIKD  VNVKMLSSTT  NKLLLESVNT
 951   TNSHQTSVRE  VSEPRHNHFY  SHTTQILSTS  TFPSDPHTAA  HSQFPIPRNS
1001   TVNIPLFRRF  GRQRKIGGRG  RIISPYRTPV  LRRHRYSIPR  STTRGSSEKS
1051   TTAFSATVLN  VTCLSCLPRE  RLTTATAALS  FPSAAPITPP  KADIARVPSE
1101   ESTTLVQNPL  LLLENKPSVE  KTTPTIKYFR  TEISQVTPTG  AVMTYAPTSI
1151   PMEKTHKVNA  SYPRVSSTNE  AKRDSVITSS  LSGAITKPPM  TIIAITRFSR
1201   RKIPWQQNFV  NNHNPKGRLR  NQHKVSLQKS  TAVMLPKTSP  ALPQRQSSPF
1251   HFTTLSTSVM  QIPSNTLTTA  HHTTTKTHNP  GSLPTKKELP  FPPLNPMLPS
1301   IISKDSSTKS  IISTQTAIPA  TTPTFPASVI  TYETQTERSR  AQTIQREQEP
1351   QKKNRTDPNI  SPDQSSGFTT  PTAMTPPALA  FTHSPPENTT  GISSTISFHS
1401   RTLNLTDVIE  ELAQASTQTL  KSTIASETTL  SSKSHQSTTT  RKASLDTPIP
1451   PFLSSSATIM  PVPISPPFTQ  RAVTDTRGDS  HFRLMTNTVV  KLHESSRHNL
1501   QMPSSQLEPL  TSSTSNLLHS  TPMPALTTVK  SQNSKLTPSP  WAEYQFWHKP
1551   YSDIAEKGKK  PEVSMLATTG  LSEATTLVSD  WDGQKNTKKS  DFDKKPVQEA
1601   TTSKLLPFDS  LSRYIFEKPR  IVGGKAASFT  IPANSDAFLP  CEAVGNPLPT
1651   IHWTRVSGLD  LSRGNQNSRV  QVLPNGTLSI  QRVEIQDRGQ  YLCSASNLFG
1701   TDHLHVTLSV  VSYPPRILER  RTKEITVHSG  STVELKCRAE  GRPSPTVTWI
1751   LANQTVVSES  SQGSRQAVVT  VDGTLVLHNL  SIYDRGFYKC  VASNPGGQDS
1801   LLVKIQVIAA  PPVILEQRRQ  VIVGTWGESL  KLPCTAKGTP  QPSVYWVLSD
1851   GTEVKPLQFT  NSKLFLFSNG  TLYIRNLASS  DRGTYECIAT  SSTGSERRVV
1901   MLTMEERVTS  PRIEAASQKR  TEVNFGDKLL  LNCSATGEPK  PQIMWRLPSK
1951   AVVDQWSWIH  VYPNGSLFIG  SVTEKDSGVY  LCVARNKMGD  DLILMHVSLR
2001   LKPAKIDHKQ  YFRKQVLHGK  DFQVDCKASG  SPVPEISWSL  PDGTMINNAM
2051   QADDSGHRTR  RYTLFNNGTL  YFNKVGVAEE  GDYTCYAQNT  LGKDEMKVHL
2101   TVITAAPRIR  QSNKTNKRIK  AGDTAVLDCE  VTGDPKPKIF  WLLPSNDMIS
2151   FSIDRYTFHA  NGSLTINKVK  LLDSGEYVCV  ARNPSGDDTK  MYKLDVVSKP
2201   PLINGLYTNR  TVIKATAVRH  SKKHFDCRAE  GTPSPEVMWI  MPDNIFLTAP
2251   YYGSRITVHK  NGTLEIRNVR  LSDSADFICV  ARNEGGESVL  VVQLEVLEML
2301   RRPTFRNPFN  EKIVAQLGKS  TALNCSVDGN  PPPEIIWILP  NGTRFSNGPQ
2351   SYQYLIASNG  SFIISKTTRE  DAGKYRCAAR  NKVGYIEKLV  ILEIGQKPVI
2401   LTYAPGTVKG  ISGESLSLHC  VSDGIPKPNI  KWTMPSGYVV  DRPQINGKYI
2451   LHDNGTLVIK  EATAYDRGNY  ICKAQNSVGH  TLITVPVMIV  AYPPRITNRP
2501   PRSIVTRTGA  AFQLHCVALG  VPKPEITWEM  PDHSLLSTAS  KERTHGSEQL
2551   HLQGTLVIQN  PQTSDSGIYK  CTAKNPLGSD  YAATYIQVI*
```

Figure 31

OCP rat amino acid sequence

>608-663Nterm Rat Protein (663 aa)

```
MQVRGREVSGLLISLTAVCLVVTPGSRACPRRCACYVPTEVHCTFRYLTSIPDGIPANVE
RINLGYNSLTRLTENDFDGLSKLELLMLHSNGIHRVSDKTFSGLQSLQVLKMSYNKVQII
RKDTFYGLGSLVRLHLDHNNIEFINPEAFYGLTSLRLVHLEGNRLTKLHPDTFVSLSYLQ
IFKTSFIKYLFLSDNFLTSLPKEMVSYMPNLESLYLHGNPWTCDCHLKWLSEWMQGNPDI
IKCKKDRSSSSPQQCPLCMNPRISKGRPFAMVPSGAFLCTKPTIDPSLKSKSLVTQEDNG
SASTSPQDFIEPFGSLSLNMTXXSGNKADMVCSIQKPSRTSPTAFTEENDYIMLNASFST
NLVCSVDYNHIQPVWQLLALYSDSPLILERKPQLTETPSLSSRYKQVALRPEDIFTSIEA
DVRADPFWFQQEKIVLQLNRTATTLSTLQIQFSTDAQIALPRAEMRAERLKWTMILMMNN
PKLERTVLVGGTIALSCPGKGDPSPHLEWLLADGSKVRAPYVSEDGRILIDKNGKLELQM
ADSFDAGLYHCISTNDADADVLTYRITVVEPYGESTHDSGVQHTVVTGETLDLPCLSTGV
PDASISWILPGNTVFSQPSRDRQILNNGTLRILQVTPKDQGHYQCVAANPSGADFSSFKV
SVQ
```

Figure 34

```
   1 GCGGCCGCCA CACCCGCCAC CAGTTCGCCA TGAAGGTAAA AGGCAGAGGA ATCACCTGCT
  61 TGCTGGTCTC CTTTGCTGTG ATCTGCCTGG TCGCCACCCC TGGGGGCAAG GCCTGTCCTC
 121 GCCGCTGTGC CTGTTATATG CCTACGGAGG TACACTGCAC ATTTCGGTAC CTGACTTCCA
 181 TCCCAGACAG CATCCCGCCC AATGTGGAAC GCATCAATTT AGGATACAAC AGCTTGGTTA
 241 GATTGATGGA AACAGATTTT TCTGGCCTGA CCAAACTGGA GTTACTCATG CTTCACAGCA
 301 ATGGCATTCA CACAATCCCT GACAAGACCT TCTCAGATTT GCAGGCCTTG CAGGTCTTAA
 361 AAATGAGCTA TAATAAAGTC CGAAAACTTC AGAAAGATAC TTTTTATGGC CTCAGGAGCT
 421 TGACACGATT GCACATGGAC CACAACAATA TTGAGTTTAT AAACCCAGAG GTTTTTTATG
 481 GGCTCAACTT TCTCCGCCTG GTGCACTTGG AAGGAAATCA GCTCACTAAG CTCCACCCAG
 541 ATACATTTGT CTCTTTGAGC TACCTCCAGA TATTTAAAAT CTCTTTCATT AAGTTCCTAT
 601 ACTTGTCTGA TAACTTCCTG ACCTCCCTCC CTCAAGAGAT GGTCTCCTAT ATGCCTGACC
 661 TAGACAGCCT TTACCTGCAT GGAAACCCAT GGACCTGTGA TTGCCATTTA AAGTGGTTGT
 721 CTGACTGGAT ACAGGAGAAG CCAGATGTAA TAAAATGCAA AAAAGATAGA AGTCCCTCTA
 781 GTGCTCAGCA GTGTCCACTT TGCATGAACC CTAGGACTTC TAAAGGCAAG CCGTTAGCTA
 841 TGGTCTCAGC TGCAGCTTTC CAGTGTGCCA AGCCAACCAT TGACTCATCC CTGAAATCAA
 901 AGAGCCTGAC TATTCTGGAA GACAGTAGTT CTGCTTTCAT CTCTCCCCAA GGTTTCATGG
 961 CACCCTTTGG CTCCCTCACT TTGAATATGA CAGATCAGTC TGGAAATGAA GCTAACATGG
1021 TCTGCAGTAT TCAAAAGCCC TCAAGGACAT CACCCATTGC ATTCACTGAA GAAAATGACT
1081 ACATCGTGCT AAATACTTCA TTTTCAACAT TTTTGGTGTG CAACATAGAT TACGGTCACA
1141 TTCAGCCAGT GTGGCAAATT TGGCTTTGT ACAGTGATTC TCCTCTGATA CTAGAAAGGA
1201 GCCACTTGCT TAGTGAAACA CCGCAGCTCT ATTACAAATA TAAACAGGTG GCTCCTAAGC
1261 CTGAAGACAT TTTTACCAAC ATAGAGGCAG ATCTCAGAGC AGATCCCTCT TGGTTAATGC
1321 AAGACCAAAT TTCCTTGCAG CTGAACAGAA CTGCCACCAC ATTCAGTACA TTACAGATCC
1381 AGTACTCCAG TGATGCTCAA ATCACTTTAC CAAGAGCAGA GATGAGGCCA GTGAAACACA
1441 AATGGACTAT GATTTCAAGG GATAACAATA CTAAGCTGGA ACATACTGTC TTGGTAGGTG
1501 GAACCGTTGG CCTGAACTGC CCAGGCAAG GAGACCCCAC CCACACGTG GATTGGCTTC
1561 TAGCTGATGG AAGTAAAGTG AGAGCCCCTT ATGTCAGTGA GGATGGACGG ATCCTAATAG
1621 ACAAAAGTGG AAAATTGGAA CTCCAGATGG CTGATAGTTT TGACACAGGC GTATATCACT
1681 GTATAAGCAG CAATTATGAT GATGCAGATA TTCTCACCTA TAGGATAACT GTGGTAGAAC
1741 CTTTGGTCGA AGCCATCAG GAAAATGGGA TTCATCACAC AGTTTTCATT GGTGAAACAC
1801 TTGATCTTCC ATGCCATTCT ACTGGTATCC CAGATGCCTC TATTAGCTGG GTTATTCCAG
1861 GAAACAATGT GCTCTATCAG TCATCAAGAG ACAAGAAAGT TCTAAACAAT GGCACATTAA
1921 GAATATTACA GGTCACCCCG AAAGACCAAG GTTATTATCG CTGTGTGGCA GCCAACCCAT
1981 CAGGGGTTGA TTTTTTGATT TTCCAAGTTT CAGTCAAGAT GAAAGGACAA AGGCCCTTGG
2041 AGCATGATGG AGAAACAGAG GGATCTGGAC TTGATGAGTC CAATCCTATT GCTCATCTTA
2101 AGGAGCCACC AGGTGCACAA CTCCGTACAT CTGCTCTGAT GGAGGCTGAG GTTGGAAAAC
2161 ACACCTCAAG CACAAGTAAG AGGCACAACT ATCGGGAATT AACACTCCAG CGACGTGGAG
2221 ATTCAACACA TCGACGTTTT AGGGAGAATA GGAGGCATTT CCCTCCCTCT GCTAGGAGAA
2281 TTGACCCACA ACATTGGGCG GCACTGTTGG AGAAAGCTAA AAAGAATGCT ATGCCAGACA
2341 AGCGAGAAAA TACCACAGTG AGCCCACCCC CAGTGGTCAC CCAACTCCCA AACATACCTG
2401 GTGAAGAAGA CGATTCCTCA GGCATGCTCG CTCTACATGA GGAATTTATG GTCCCGGCCA
2461 CTAAAGCTT
```

Figure 36

```
   1  AAGCTTTGAA CCTTCCAGCA AGGACAGTGA CTGCTGACTC CAGAACAATA TCTGATAGTC
  61  CTATGACAAA CATAAATTAT GGCACAGAAT TCTCTCCTGT TGTGAATTCA CAAATACTAC
 121  CACCTGAAGA ACCCACAGAT TTCAAACTGT CTACTGCTAT TAAAACTACA GCCATGTCAA
 181  AGAATATAAA CCCAACCATG TCAAGCCAAA TACAAGGCAC AACCAATCAA CATTCATCCA
 241  CTGTCTTTCC ACTGCTACTT GGAGCAACTG AATTTCAGGA CTCTGACCAG ATGGGAAGAG
 301  GAAGAGAGCA TTTCCAAAGT AGACCCCAA TAACAGTAAG GACTATGATC AAAGATGTCA
 361  ATGTCAAAAT GCTTAGTAGC ACCACCAACA AACTATTATT AGAGTCAGTA ATACCACAA
 421  ATAGTCATCA GACATCTGTA AGAGAAGTGA GTGAACCCAG GCACAATCAC TTCTATTCTC
 481  ACACTACTCA AATACTTAGC ACCTCCACGT TCCCTTCAGA TCCACACACA GCTGCTCATT
 541  CTCAGTTTCC GATCCCTAGA AATAGTACAG TTAACATCCC GCTGTTCAGA CGCTTTGGGA
 601  GGCAGAGGAA AATTGGCGGA AGGGGGCGGA TTATCAGCCC ATATAGAACT CCAGTTCTGC
 661  GACGGCATAG ATACAGCATT TTCAGGTCAA CAACCAGAGG TTCTTCTGAA AAAAGCACTA
 721  CTGCATTCTC AGCCACAGTG CTCAATGTGA CATGTCTGTC CTGTCTTCCC AGGGAGAGGC
 781  TCACCACTGC CACAGCAGCA TTGTCTTTTC CAAGTGCTGC TCCCATCACC TTCCCCAAAG
 841  CTGACATTGC TAGAGTCCCA TCAGAAGAGT CTACAACTCT AGTCCAGAAT CCACTATTAC
 901  TACTTGAGAA CAAACCCAGT GTAGAGAAAA CAACACCCAC AATAAAATAT TTCAGGACTG
 961  AAATTTCCCA AGTGACTCCA ACTGGTGCAG TCATGACATA TGCTCGAACA TCCATACCCA
1021  TGGAAAAAAC TCACAAAGTA AACGCCAGTT ACCCACGTGT GTCTAGCACC AATGAAGCTA
1081  AAAGAGATTC AGTGATTACA TCGTCACTTT CAGGTGCTAT CACCAAGCCA CCAATGACTA
1141  TTATAGCCAT TACAAGGTTT TCAAGAAGGA AAATTCCCTG GCAACAGAAC TTTGTAAATA
1201  ACCATAACCC AAAAGGCAGA TTAAGGAATC AACATAAAGT TAGTTTACAA AAAAGCACAG
1261  CTGTGATGCT TCCTAAAACA TCTCCTGCTT TACCCAGAGA CAAAGTCTCC CCTTTCCATT
1321  TCACCACACT TTCAACAAGT GTGATGCAAA TTCCATCTAA TACCTTGACT ACCGCTCACC
1381  ACACTACGAC CAAAACACAC AATCCTGGAA GTCTTCCAAC AAAGAAGGAG CTTCCCTTCC
1441  CACCCCTTAA CCCTATGCTT CCTAGTATTA TAAGCAAAGA CTCAAGTACA AAAAGCATCA
1501  TATCAACGCA AACAGCAATA CCAGCAACAA CTCCTACCTT CCCTGCATCT GTCATCACTT
1561  ATGAAACCCA AACAGAGAGA TCTAGAGCAC AAACAATACA AAGAGAACAG GAGCCTCAAA
1621  AGAAGAACAG GACTGACCCA AACATCTCTC CAGACCAGAG TTCTGGCTTC ACTACACCCA
1681  CTGCTATGAC ACCTCCTGTT CTAACCACAG CCGAAACTTC AGTCAAGCCC AGTGTCTCTG
1741  CATTCACTCA TTCCCCACCA GAAAACACAA CTGGGATTTC AAGCACAATC AGTTTTCATT
1801  CAAGAACTCT TAATCTGACA GATGTGATTG AAGAACTAGC CAAGCAAGT ACTCAGACTT
1861  TGAAGAGCAC AATTGCTTCT GAAACAACTT TGTCCAGCAA ATCACACCAG AGTACCACAA
1921  CTAGGAAAGC AATCATTAGA CACTCAACCA TACCACCATT CTTGAGCAGC AGTGCTACTC
1981  TAATGCCAGT TCCCATCTCC CCTCCCTTTA CTCAGAGAGC AGTTACTGAC AACGTGGCGA
2041  CTCCCATTTC CGGGCTTATG ACAAATACAG TGGTCAAGCT GCACGAATCC TCAAGGCACA
2101  ATGCTAAACC ACAGCAATTA GTAGCAGAGG TTGCAACATC CCCCAAGGTT CACCCAAATG
2161  CCAAGTTCAC AATTGGAACC ACTCACTTCA TCTACTCTAA TCTGTTACAT TCTACTCCCA
2221  TGCCAGCACT AACAACAGTT AAATCACAGA ATTCTAAATT AACTCCATCT CCCTGGGCAG
2281  AAAACCAATT TTGGCACAAA CCATACTCAG AAATTGCTGA AAAAGGCAAA AAGCCAGAAG
2341  TAAGCATGTT GGCTACTACA GGCCTGTCCG AGGCCACCAC TCTTGTTTCA GATTGGGATG
2401  GACAGAAGAA CACAAAGAAG AGTGACTTTG ATAAGAAACC AGTTCAAGAA GCAACAACTT
2461  CCAAACTCCT TCCCTTTGAC TCTTTGTCTA GGTATATATT TGAAAAGCCC AGGATAGTTG
2521  GAGGAAAAGC TGCAAGTTTT ACTATTCCAG CTAACTCAGA TGCCTTTCTT CCCTGTGAAG
2581  CTGTTGGAAA TCCCCTGCCC ACCATTCATT GGACCAGAGT CCCATCAGGA CTTGATTTAT
2641  CTAAGAGGAA ACAGAATAGC AGGGTCCAGG TTCTGTTCCGC ATCCAATCTG TTTGGCACAG
2701  GGGTGGAAAT TCAGGACCGC GGACAGTACT TGTGTTCCTCC CAGGATCCTG GAGAGACGTA
2761  ACCACCTTCA TGTCACCTTG TCTGTGGTTT CCTATCCTCC CAGGATCCTG GAGAGACGTA
2821  CCAAAGAGAT CACAGTTCAT TCCGGAAGCA CTGTGGAACT GAAGTGCAGA GCAGAAGGTA
2881  GGCCAAGCCC TACAGTTACC TGGATTCTTG CAAACCAAAC AGTTGTCTCA GAATCATCCC
2941  AGGGAAGTAG GCAGGCTGTG GTGACGGTTG ACGGAACGGT GGTCCTCCAC AATCTCAGTA
3001  TTTATGACCG TGGCTTTTAC AAATGTGTGG CCAGCAACCC AGGTGGCAAGG GATTCACTGC
3061  TGGTTAAAAT ACAAGTCATT GCAGCACCAC CTGTTATTCT AGAGCAAAGG AGGCAAGTCA
3121  TTGTAGGCAC TTGGGGTGAA AGTTTAAAAC TGCCCTGTAC TGCAAAAGGA ACTCCTCAGC
```

Figure 36 (Cont.)

```
3181 CCAGCGTTTA CTGGGTCCTC TCTGATGGCA CTGAAGTGAA ACCATTACAG TTTACCAATT
3241 CCAAGTTGTT CTTATTTTCA AATGGGACTT TGTATATAAG AAACCTAGCC TCTTCAGACA
3301 GGGGCACTTA TGAATGCATT GCTACCAGTT CCACTGGTTC GGAGCGAAGA GTAGTAATGC
3361 TTACAATGGA AGAGCGAGTG ACCAGCCCCA GGATAGAAGC TGCATCCCAG AAAAGGACTG
3421 AAGTGAATTT TGGGGACAAA TTACTACTGA ACTGCTCAGC CACTGGGGAG CCCAAACCCC
3481 AAATAATGTG GAGGTTACCA TCCAAGGCTG TGGTCGAC
```

Figure 38

```
   1 GTCGACCAGC AGCATAGAGT GGGCAGCTGG ATCCACGTCT ACCCTAATGG ATCCCTGTTT
  61 ATTGGATCAG TAACAGAAAA AGACAGTGGT GTCTACTTGT GTGTGGCAAG AAACAAAATG
 121 GGGGATGATC TGATACTGAT GCATGTTAGC CTAAGACTGA AACCTGCCAA AATTGACCAC
 181 AAGCAGTATT TTAGAAAGCA AGTGCTCCAT GGGAAAGATT TCCAAGTAGA TTGCAAAGCT
 241 TCCGGCTCCC CAGTGCCAGA GATATCTTGG AGTTTGCCTG ATGAACCAT GATCAACAAT
 301 GCAATGCAAG CCGATGACAG TGGCCACAGG ACTAGGAGAT ATACCCTTTT CAACAATGGA
 361 ACTTTATACT TCAACAAAGT TGGGGTAGCG GAGGAAGGAG ATTATACTTG CTATGCCCAG
 421 AACACCCTAG GGAAAGATGA AATGAAGGTC CACTTAACAG TTATAACAGC TGCTCCCCGG
 481 ATAAGGCAGA GTAACAAAAC CAACAAGAGA ATCAAAGCTG GAGACACAGC TGTCCTTGAC
 541 TGTGAGGTCA CTGGGGATCC CAAACCAAAA ATATTTGGT TGCTGCCTTC CAATGACATG
 601 ATTTCCTTCT CCATTGATAG GTACACATTT CATGCCAATG GGTCTTTGAC CATCAACAAA
 651 GTGAAACTGC TCGATTCTGG AGAGTACGTA TGTGTAGCCC GAAATCCCAG TGGGGATGAC
 721 ACCAAAATGT ACAAACTGGA TGTGGTCTCT AAACCTCCAT TAATCAATGG TCTGTATACA
 781 AATAGAACTG TTATTAAAGC CACAGCTGTG AGACATTCCA AAAAACACTT TGACTGCAGA
 841 GCTGAAGGGA CACCATCTCC TGAAGTCATG TGGACCATGC CAGACAATAT TTTCCTCACA
 901 GCCCCATACT ATGGAAGCAG AATCACAGTC CATAAAAATG GAACCTTGGA AATTAGGAAT
 961 GTGAGGCTTT CAGATTCAGC CGACTTTATC TGTGTGGCCC GAAATGAAGG TGGAGAGAGC
1021 GTGTTGGTAG TACAGTTAGA AGTACTGGAA ATGCCACAG GACCGACATT TAGAAATCCA
1081 TTTAATGAAA AAATAGTTGC CCAGCTGGGA AAGTCCACAG CATTGAATTG CTCTGTTGAT
1141 GGTAACCCAC CACCTGAAAT AATCTGGATT TTACCAAATG GCACACGATT TTCCAATGGA
1201 CCACAAAGTT ATCAGTATCT GATAGCAAGC AATGGTTCTT TTATCATTTC TAAAACAACT
1261 CGGGAGGATG CAGGAAAATA TCGCTGTGCA GCTAGGAATA AAGTTGGCTA TATTGAGAAA
1321 TTAGTCATAT TAGAAATTGG CCAGAAGCCA GTTATTCTTA CCTATGCACC AGGGACAGTA
1381 AAAGGCATCA GTGGAGAATC TCTATCACTG CATTGTGTGT CTGATGGAAT CCCTAAGCCA
1441 AATATCAAAT GGACTATGCC AAGTGGTTAT GTAGTAGACA GGCCTCAAAT TAATGGGAAA
1501 TACATATTGC ATGACAATGG CACCTTAGTC ATTAAAGAAG CAACAGCTTA TGACAGAGGA
1561 AACTATATCT GTAAGGCTCA AAATAGTGTT GGTCATACAC TGATTACTGT TCCAGTAATG
1621 ATTGTAGCCT ACCCTCCCCG AATTACAAAT CGTCCACCCA GGAGTATTGT CACCAGGACA
1681 GGGGCAGCCT TTCAGCTCCA CTGTGTGGCC TTGGGAGTTC CCAAGCCAGA AATCACATGG
1741 GAGATGCCTG ACCACTCCCT TCTCTCAACG GCAAGTAAAG AGAGGACACA TGGAAGTGAG
1801 CAGCTTCACT TACAAGGTAC CCTAGTCATT CAGAATCCCC AAACCTCCGA TTCTGGGATA
1861 TACAAATGCA CAGCAAAGAA CCCACTTGGT AGTGATTATG CAGCAACGTA TATTCAAGTA
1921 ATCCACCACC ACCACCACCA TTGAACTAGT
```

Figure 39

```
   1  atgcccaagc gcgcgcactg gggggccctc tctgtggtgc tgatcctgct ttggggtcat
  61  ccgcgagtgg cgctggcctg ccctcatcct tgtgcctgct acgtccccag cgaggtccac
 121  tgcacgttcc gatccctggc ttctgtgccc gctggcattg ctaaacatgt ggaagaatc
 181  aatttggggt ttggaattct gaagtgtaaa aaggacaaag cttatgaagg cggtcagttg
 241  tgtgcaatgt gcttcagtcc aaagaagttg tacaaacatg agattcacaa gctgaaggac
 301  ctgacttgtc tgaagccttc catagagtct cctctgagac agaacaggag caggagtatt
 361  gaggaggagc aaaaacaaga agagaatggt gacagccagc tcatcctgga gaaaatccaa
 421  cttccccagt ggagcatctc tttgaatatg actgatgagc acgggaacct ggtgaacttg
 481  gtgtgtgaca tcaagaaacc aatggatgtg tacaaaattc acttgaacca aacagatcct
 541  ccagatattg acataaatgc aatggttgcc ttggactttg agtatccaat gacccaggaa
 601  aactatgaaa atctatggaa attgatagca tactacagtg aagttcccat gaagctacac
 661  agagagctca tgctcagcaa acaccccaga gtcagctacc agtacaggca agatgccgat
 721  gaagaagctc tttactacac aggtgtgaga gcccagattc ttgcagaacc agaatggatc
 781  atgcagccat ccatagatat ccagctgaac cgacctcaga gtacggccaa gaaggtgcta
 841  ctttcctact acaaccagta ttctcaaaca atagccacca aagatacaag gcaggctcgg
 901  ggcagaagct gggtaatgat tgagcctagt agagctgtgc aaaaagatca gactgtcctg
 961  gaaggggtc gatgccagtt gagctgcaat gtgaaagctt ctgagagtcc atctatcttc
1021  tgggtgcttc agatggctc catcctgaaa gtgcctgtgg atgacccaga cagcaagttc
1081  tccattctca gcagtggctg gctgaggatc aagtccatgg agccatctga ctcgggcttg
1141  taccagtgca ttgctcaagt gaggggatga aatggaccgca tggtatatag ggtacttgtg
1201  cagtctccct ccactcagcc agccgagaaa gacacagtga caattggcaa gaacccaggg
1261  gagccagtga tgttgccttg caatgcttta gctatacccg aagcccacct tagctggatt
1321  cttccaaaca gaaggataat taatgatttg gctaacacat cacatgtata catgctgcca
1381  aatggaactc tttccatccc aaaggtccaa gtcagtgaca gtggttacca cagatgtgtg
1441  gctgtcaacc agcatggggc agaccatatc acggtgggaa tcacagtgac aagaaaggt
1501  tctggctcgc catccaaaag aggcagatgg ccaggtccaa aggctctttc cagagtgaga
1561  gaagacatcg tggaggatga aggggtctca ggcacgggag atgaagagaa cacttcaagg
1621  agacttctac atccaaagca ccaagaggcg ttcctcaaaa caaaggatga tgccatcaat
1681  ggagataaga aagccaagaa agggagaaga aagctgaaac tctggaagca ttcagaaaaa
1741  gaaccagaga ccagtgttgc agaagatctc agagtgtttg aatcaagacg aaggataaac
1801  gtggcaaaca acagattaa tccggagcac tgggctgata ttttagccaa agtctttggg
1861  aaaaatctcc ctacaggcac agaagtatcc caattatta aaaccacaag ttctccattc
1921  ttgagcctag tagtcacacc acctttgcct gctgtttctc ccccttggc atctccaata
1981  cagacagcaa caagtgctga agaatcctca gcagatgtac ctctactcag cgaaggaaag
2041  cacatttga gtaccatttc ctcagccagc atgggactag aacaccacaa caatggagtt
2101  attcttgttg aacctgaagt aacaagcaca cctctggaag aagttgttga tgagtattcc
2161  aagaagactg aggagatgac ttccactgaa ggcgacctga gggactgc agcctctaca
2221  cttatatctg agccttatga acaatctcct actctacaca cttagacac agtctatgaa
2281  gagcccaccc atgaagagac ggaaacagag ggttggtctg cagcagatgt tggatcctca
2341  ccagatccca catccagtga gtatgagctt ccattggttg ttgtctcctt ggctgagtct
2401  aagcctgtgc aatactttga cccagatttg gagactaatt cacaaccaca tgaggataac
2461  ataaaagaat acagttttgc acaccttact ccaaccgcca tcatctggtt taatgactct
2521  agtacatcac tgtcatttga ggattctact gtaggggaac aaggtgtccc aggcaaatca
2581  catctacaag gaccgacaga gaacatccag cttgtgaaaa gtagttttag cactcaagac
2641  accttattga ttaaaaaagg tatgaaagag atgtctcaga cactacaggg aggaaatatg
2701  ctagagggag accctacaca ctccagaagt tctgagaatg agggccaaga gagcaaatcc
2761  atcactttac ctgactccac actgggtata acgagcagta cgtctccagt taagaagcct
2821  gcggaaacca cagttgtcac cctgctacac aaagacacca acagaaac aactccaagg
2881  caaaaagtgg cttcatcatc caccatgagc actcacctt tcgaaggag acccaatggg
2941  agaaaattac accctcacaa attccaccac cggcacaagc aaacccacc cacaacttt
3001  gctccattag agacttttc tactcaacca actcaagcaa ctgacattaa gatttcaaat
3061  caaatggaga gttctctggt tcctacatct tgggagatta acacagttaa taccccaaa
3121  cagctggaaa tggagaagaa tgtagagctc atatcaaagg gaactccacg gagaaaacac
```

Figure 39 (Cont.)

```
3181  gggaagaggc caaacaaaca tcgatatacc ccttctacag tgagttcaag agcatctgca
3241  tccaagccca gcccttctcc agaaaataaa catagaaaca ttgttactcc cagttcagaa
3301  actacacttt tgcctagaaa tgtttctctg aaaactgagg gcgtttatga ttccttagat
3361  tacacgacaa ccaccagaaa aatacattca tctcaccata aagtccaaga cacacttcca
3421  gtcatgtata aacccacatc agatggaaaa gaaattcagg atgatgttgc cacaaatgtt
3481  gacaaacata aaagtgacat tttagtccct ggtgagtcaa ttacaaatgt cacacaaact
3541  tctcgctcct tggtctccac tatgggagaa tttaaggaag aatcctctcc tgtgggcttt
3601  ccaggaattc caacctggaa tccctcaagg aaagctcagc ctgggaggct acagacagac
3661  atacatgtta ccacttctgg ggaaacccct acagaccctc cccttgttaa cgagcttgag
3721  gatgtggatt ttacttctga gttttgtcc tctgtgacag tctccacacc atttcaccag
3781  gaagaagctg gtttttccac aattctctca agcataaaag tggagatggc ttcaagtcag
3841  gtagaaacta ccaccttgg tcaagatcat catgaaacca ctgtggctat tctccactct
3901  gaaactagac cacagaatca catccttact gctgcctgga tgaaggagcc agcatctttg
3961  tcccctccca tgattctcct gtctttggga caaccacca ccactaagcc agaacttctc
4021  agtccaagaa catctcaaat atgtaaagat tccaaggaaa atgtttttctt gaattacatg
4081  gggaatccag aaacagaagc aaccccagtg aaaatgaag gaacacagcg tatgtcaggg
4141  ccaatgaat tatcaacacc atcttctgac cacgatgcat ttaacttgtc tacaaagcta
4201  gaattggaaa agcaagtatt tgatagtagg agtctaacac gtgcccaga tagccaccac
4261  caggatggaa gagttcatgc ttctcatcaa ctaaccagaa tccctgccaa acccatccta
4321  ccaacaggaa cagtgaggct gcctgaaatg tccacacaaa gcacttccag atactttgta
4381  actttccagc cacctcatca cgggaccaac aaaccagaaa taactacata tccttctagg
4441  gctttgccag agagcaaaca gtttacaact ccaagagtag caagtacaac tcctctccta
4501  tcacacatgt ccaaacccag catttctagt aagtttgctg acctaagaac tgaccaatcc
4561  aatggctcct acaaagtgtt tggaaatagc aacatccctg aggcaagaaa ctcagttgga
4621  aagcctctca gtccaagaat ttatcattat tccaatggaa gactccccttt ctttaccaac
4681  aggactcttt ctttttcaca gttgggagtc acccggagac ccagataacc ctcttctcct
4741  gtcccagtaa tgagagagag aaaagttaat ccaggttcct acaataggat atattcccat
4801  agcaccttcc atctggactt tggccttcca gcacctccac tgttgcacac tccatggacc
4861  atggtatcac ccccaactaa cttacagaat atccctatgg tctcatccac ccagagttct
4921  gtctcctta taacatcttc tgtccagtcc tcaggaagca tccaccaaag cggctcaaag
4981  ttctttgcag gaggaccgcc tgcatccaaa ttctggcctc ttggggaaaa gccccaaatc
5041  ctcaccaagt ccccacagac tgtgtctgtc actgctgaaa cggacgctgt gttccgtgt
5101  gaggcaatag gaaaaccaaa gcctttcgtt acttggacaa aagtttccac aggagttctt
5161  atgactccga ataccaggat acaacggttt gaggttctca agaacggtac cttagtgata
5221  aggaagtttc aagtgcaaga tcgaggccag tatatgtgca ccgccagcaa cctgtacggc
5281  ctggacagga tggtggtctt tctctgggtc accgtgcagc aacctcaaat cctagcctcc
5341  cactaccagg acgtcaccgt ctacctggga gacaccatta caatgagtg tctggcgaaa
5401  gggacccag ccccccaaat ttcctggatc ttccgtgaca ggagggtgtg gcaaactctg
5461  tcctcgtgg agggccggat caccctgcac caaaaccgga cccttttccat caaggaggcg
5521  tccttctcag acagaggcgt ctataagtgc gtggccagca acgcaaccg ggcggacagc
5581  gtgtccatcc gcctacacgt ggcggcactg cccccatta tccaccagga gaagctggag
5641  aacatctcgc tgccccgggg gctcagcatt cacattcact gcactgccaa agctgcgccc
5701  ctgccagcg tgtctgggt gctcggggat ggtacccaaa tccgcccctc gcatttcctc
5761  caccggaact tgtttgtttt ccccaacggg acgctctaca tctgcaacct cgcgcccaag
5821  gacagcgggc gctatgagtg cgtggccgcc aacctgatcg gctccgcgcg cagtacggtg
5881  cagctgaacg tgcagcgcgc agcagcgaac gcgcgcatca cgggcacctc ctcgcagagg
5941  acggacgtca ggtacggagg gaccctcaag ctggactgca gcgcctcggg ggatccctgg
6001  ccgcgcatcc tctggaggct gccgtccaag aggacgatcg acgcgctttt cagttttgat
6061  agtagaatca aggtgtttgc caacaggacc ctggtggtga aatcaatgac agacaaagac
6121  gccggagatt acctgtgtgt agctcgaaat aaggttggtg atgactggt ggtgctcaag
6181  gtggatgtga tgatgaaacc ggccaagatt gaacacaagg aggagaacga ccacaaagtc
6241  ttctacaggg gtgacctgaa agtggactgt gtggccactg gacttcccaa tcccgagatc
6301  tcctggagcc tcctggatgg gagtctggtg aactccttca tgcagtcaga tgacagtggt
6361  ggacgcacca agcactatgt ggtcttcaac aatggggacac tctacttcag tgaagtgggg
6421  atgaggagg aaggagacta cacctgcttt gctgaaaatc aggttgggaa ggatgagatg
6481  agagtcagag tcaagatggt gacacctgcc accatctgga caagactta cttggcagtt
6541  caggtaccct atggagatgt ggtcactgta acctgtgagg ccaaggaga accatgccc
```

Figure 39 (Cont.)

```
6601  aaggtgactt ggttgtcccc agccaacagg gtgatcccca cctcctctga gaagtatcag
6661  atataccaat atggcactct ccttattcag aaagcccagt gctctgacag cggcaactac
6721  acctgcctgg tcaggaacag tgccggagag gataggaaga cagtgtggat tcacgtcaac
6781  ctccagccac ccaagatcaa tggtaacccc aacccatca ccaccgtgtg ggagatagca
6841  gccggggca gtcggaaact gattgactgc aaagctgaag gcatcccac cccgagggtg
6901  ttatgggctt tcccgaggg tgtggttctg ccagatccat actatggaaa ccggatcact
6961  gtccatggca acggttccct ggacatcagg agtttgagga gagcgactc cgtccagctg
7021  gtatgcatgg cacgcaacga gggaggggag gcgaggttga tcgtgcagct cactgtcctg
7081  gagcccatgg agaaacccat cttccacgac ccgatcagcg agaagatcac ggccatggcg
7141  ggccacacca tcagcctcaa ctgctctgcc gcggggaccc tgacacccag cctggtgtgg
7201  gtccttccca atggcaccga tctgcagagt ggacagcagc tgcagcgctt ctaccacaag
7261  gctgacggca tgctacacat tagcggtctc tcctcggtgg acgccggggc ctaccgctgc
7321  gtggcccgca atgccgcggg ccacacggag aggctggtct ccctgaaggt gggactgaag
7381  ccagaagcaa acaagcagta tcataacctg gtcagcatca tcaatggtga gaccctgaag
7441  ctcccctgca ccctcctgc agctgggcag ggacatttct cctggacact cccaatggc
7501  atgcatctgg agggccccca aaccctggga cgcgtttctc ttctggacaa tggcaccctc
7561  acggttcgtg aggcctcggt gtttgacagg ggtacctatg tatgcaggat ggagacggcg
7621  tacggccctt cggtcaccag catcccgtg attgtgatcg cctatcctcc ccggatcacc
7681  agcgagccta ccccagtcat ctacacccgt cccgggaaca ccgtgaaact gaactgcatg
7741  gctatgggga ttcccaaagg tgacatcacg tgggagttac cggataagtt gcatctgaag
7801  gcagggggttc aggctcgtct gtatggaaac agatttcttc accccaggg atcactgacc
7861  atccagcagg ccagacggag agacgctggc ttctacaagt gcacggcaaa aaacattctc
7921  agcagtgact ccaaaacaac ttatatccat gtcttctgaa atgtggattc cagaatgatt
7981  gctcaggaac tgacaacaaa gcggggtttg taagggaagc caggctgggg aatcagagct
8041  cttaaataat gtgtcacagt gcatggtggc ccccggtggg attcaagttg aggttgatct
8101  tgatctacaa ttgttgggaa aaggaagcaa tacagacatg agtaaaaggg ctcagcctca
8161  ctgagaactt tcttttgtgt ttacatcatg ccaggggctt cattcagggt gtctgtgctc
8221  tgactgtaat tttattttt ttgcaaatgt cattcgactg cctgcgtaag tgtccatagg
8281  atatctgagg aacattcacc gaaataagc catagacatg aacaacacct cactccccca
8341  ttgaagatgc atcgtctagt taacctgctg cagttttttac atgatagact ttgttccaga
8401  ttgacaagtc atctttcagt tatttcctct atcacttcaa aactccagct tgcccaataa
8461  ggatttagaa ctagagtgat tgttatatat ataatatata tattttaatt cagagttaca
8521  tacatacagc taccattta tatgaaaaaa acatttcttc ctggaaccca cttttatgt
8581  aattttttta tataaatatt tttcctttca aatcagatga tgagactaga aggagaaata
8641  ctttctgtct cattaaaatt aataaatgat tggtctttac aagacttgga tacattacag
8701  cagacatgga aatagaattt taaacaattc ctctccaacc tccttcaaat tcagtcgcta
8761  ctgttatgtt actttctcca gcaaccctgc actggggaag gctgtgatat tagatttcct
8821  tgtatgcaaa gttttgttg aaagctgtgc tcagcggagg tgagaggaga ggaggagaaa
8881  actgcatcat atctttccag aattgaatct agagtcttcc ctggaaagcc cagaaacttc
8941  tctgcagtat ctgacttgtc catctggtct aaggtggctg cttcttccgc aaccatgagt
9001  tagtctgtgt ccatgaataa tacaagatct gttatttcca tgactgcttt actgtaattt
9061  tagggtcaat atactgtaca tttgataata aatatattc tcccaaaaa
```

Figure 40

```
   1  mpkrahwgal svvlillwgh prvalacphp cacyvpsevh ctfrslasvp agiakhveri
  61  nlgfgilkck kdkayeggql camcfspkkl ykheihklkd ltclkpsies plrqnrsrsi
 121  eeeqkqeeng dsqlilekiq lpqwsislnm tdehgnlvnl vcdikkpmdv ykihlnqtdp
 181  pdidinamva ldfeypmtqe nyenlwklia yysevpmklh relmlskhpr vsyqyrqdad
 241  eealyytgvr agilaepewi mqpsidiqln rpqstakkvl lsyynqysqt iatkdtrqar
 301  grswvmieps ravqkdqtvl eggrcqlscn vkasespsif wvlpdgsilk vpvddpdskf
 361  silssgwlri ksmepsdsgl yqciaqvrde mdrmvyrvlv qspstqpaek dtvtigknpg
 421  epvmlpcnal aipeahlswi lpnrriindl antshvymlp ngtlsipkvq vsdsgyhrcv
 481  avnqhgadhi tvgitvtkkg sgspskrgrw pgpkalsrvr edivedegvs gtgdeentsr
 541  rllhpkhqea flktkddain gdkkakkgrr klklwkhsek epetsvaedl rvfesrrrin
 601  vankqinpeh wadilakvfg knlptgtevs piikttsspf lslvvtpplp avspplaspi
 661  qtatsaeess advpllsegk hilstissas mglehhnngv ilvepevtst pleevvdeys
 721  kkteemtste gdlkgtaast lisepyeqsp tlhtldtvye eptheetete gwsaadvgss
 781  pdptsseyel plvvvslaes kpvqyfdpdl etnsqphedn ikeysfahlt ptaiiwfnds
 841  stslsfedst vgeqgvpgks hlqgpteniq lvkssfstqd tllikkgmke msqtlqggnm
 901  legdpthsrs seneggesks itlpdstlgi tsstspvkkp aettvvtllh kdtttettpr
 961  qkvassstms thpsrrrpng rklhphkfhh rhkqtppttf apletfstqp tqatdikisn
1021  qmesslvpts weintvntpk qlemeknvel iskgtprrkh gkrpnkhryt pstvssrasa
1081  skpspspenk hrnivtpsse ttllprnvsl ktegvydsld yttttrkihs shhkvqdtlp
1141  vmykptsdgk eiqddvatnv dkhksdilvp gesitnvtqt srslvstmge fkeesspvgf
1201  pgiptwnpsr kaqpgrlqtd ihvttsgetp tdpplvnele dvdftsefls svtvstpfhq
1261  eeagfstils sikvemassq vetttlgqdh hettvailhs etrpqnhilt aawmkepasl
1321  sppmillslg qttttkpell sprtsqickd skenvflnym gnpeteatpv knegtqrmsg
1381  pnelstpssd hdafnlstkl elekqvfdsr sltrgpdshh qdgrvhashq ltripakpil
1441  ptgtvrlpem stqstsryfv tfqpphhgtn kpeittypsr alpeskqftt prvasttpll
1501  shmskpsiss kfadlrtdqs ngsykvfgns nipearnsvg kplspriyhy sngrlpfftn
1561  rtlsfsqlgv trrpqipssp vpvmrerkvn pgsynriysh stfhldfglp appllhtpwt
1621  mvspptnlqn ipmvsstqss vsfitssvqs sgsihqsgsk ffaggppask fwplgekpqi
1681  ltkspqtvsv taetdavfpc eaigkpkpfv twtkvstgvl mtpntriqrf evlkngtlvi
1741  rkfqvqdrgq ymctasnlyg ldrmvvflwv tvqqpqilas hyqdvtvylg dtitmeclak
1801  gtpapqiswi frdrrvwqtl ssvegritlh qnrtlsikea sfsdrgvykc vasnatrads
1861  vsirlhvaal ppiihqekle nislppglsi hihctakaap lpsvlwvlgd gtqirpshfl
1921  hrnlfvfpng tlyicnlapk dsgryecvaa nligsarstv qlnvqraaan aritgtssqr
1981  tdvryggtlk ldcsasgdpw prilwrlpsk rtidalfsfd srikvfanrt lvvksmtdkd
2041  agdylcvarn kvgddcvvlk vdvmmkpaki ehkeendhkv fyrgdlkvdc vatglpnpei
2101  swslldgslv nsfmqsddsg grtkhyvvfn ngtlyfsevg mreegdytcf aenqvgkdem
2161  rvrvkmvtpa tiwnktylav qvpygdvvtv tceakgepmp kvtwlspanr viptssekyq
2221  iyqygtlliq kaqcsdsgny tclvrnsage drktvwihvn lqppkingnp npittvweia
2281  aggsrklidc kaegiptprv lwafpegvvl pdpyygnrit vhgngsldir slrksdsvql
2341  vcmarnegge arlivqltvl epmekpifhd pisekitama ghtislncsa agtltpslvw
2401  vlpngtdlqs gqqlqrfyhk adgmlhisgl ssvdagayrc varnaaghte rlvslkvglk
2461  peankqyhnl vsiingetlk lpctppaagq ghfswtlpng mhlegpqtlg rvslldngtl
2521  tvreasvfdr gtyvcrmeta ygpsvtsipv iviaypprit septpviytr pgntvklncm
2581  amgipkgdit welpdklhlk agvqarlygn rflhpqgslt iqqarrrdag fykctaknil
2641  ssdskttyih vf
```

Figure 41 (Cont.)

```
hAdlican FL    1041 ihlvksslstqdtllikkgmkemsqtlqggnmlegdpthsrssesegqesksitlpdstlgimssmspvkkpaettvgtl
hadlican2 FL    869 iqlvkssfstqdtllikkgmkemsqtlqggnmlegdpthsrssenegqesksitlpdstlgitsstspvkkpaettvvtl
hLOC96359 si      1 ----------------------------------------------------------------------------
hLOC90792 si      1 ---------------------------------------------------------------------------- hAdlican FL    1121 ldkdtttvtttprqkvapsstmsthpsrrrpngrrrlrpnkfrhrhkqtppttfapsetfstqptqapdikissqvessl
hadlican2 FL    949 lhkdttt-ettprqkvasssstmsthpsrrrpng-rklhphkfhhrhkqtppttfapletfstqptqatdikisnqmessl
hLOC96359 si      1 ----------------------------------------------------------------------------
hLOC90792 si      1 ---------------------------------------------------------------------------- hAdlican FL    1201 vptawvdntvntpkqlemeknaeptskgtprrkhgkrpnkhrytpstvssrasgskpspspenkhrnivtpssetillpr
hadlican2 FL   1027 vptsweintvntpkqlemeknveliskgtprrkhgkrpnkhrytpstvssrasaskpspspenkhrnivtpssettllpr
hLOC96359 si      1 ----------------------------------------------------------------------------
hLOC90792 si      1 ---------------------------------------------------------------------------- hAdlican FL    1281 tvslktegpydsldymttrkiyssypkvqetlpvtykptsdgkeikddvatnvdkhksdilvtgesitnaiptsrslvs
hadlican2 FL   1107 nvslktegvydsldyttttrkihsshhkvqdtlpvmykptsdgkeiqddvatnvdkhksdilvpgesitnvtqtsrslvs
hLOC96359 si      1 ----------------------------------------------------------------------------
hLOC90792 si      1 ---------------------------------------------------------------------------- hAdlican FL    1361 tmgefkeesspvgfpgtptwnpsrtaqpgrlqtdipvttsgenltdppllkeledvdftseflssltvstpfhqeeagss
hadlican2 FL   1187 tmgefkeesspvgfpgiptwnpsrkaqpgrlqtdihvttsgetptdpplvneledvdftseflssvtvstpfhqeeagfs
hLOC96359 si      1 ----------------------------------------------------------------------------
hLOC90792 si      1 ---------------------------------------------------------------------------- hAdlican FL    1441 ttlssikvevassqaettldqdhlettvaillsetrpqnhtptaarmkepassspstilmslgqttttkpalpsprisq
hadlican2 FL   1267 tilssikvemassqvetttlgqdhhettvailhsetrpqnhiltaawmkepaslsppmillslgqttttkpellsprtsq
hLOC96359 si      1 ----------------------------------------------------------------------------
hLOC90792 si      1 ---------------------------------------------------------------------------- hAdlican FL    1521 asrdskenvflnyvgnpeteatpvnnegtqhmsgpnelstpssdrdafnlstklelekqvfgsrslprgpdsqrqdgrvh
hadlican2 FL   1347 ickdskenvflnymgnpeteatpvknegtqrmsgpnelstpssdhdafnlstklelekqvfdsrsltrgpdshhqdgrvh
hLOC96359 si      1 ----------------------------------------------------------------------------
hLOC90792 si      1 ---------------------------------------------------------------------------- hAdlican FL    1601 ashqltrvpakpilptatvrlpemstqsasryfvtsqsprhwtnkpeittypsgalpenkgfttprlssttiplplbmsk
hadlican2 FL   1427 ashqltripakpilptgtvrlpemstqstsryfvtfqpphhgtnkpeittypsralpeskgfttprvastt-pllshmsk
hLOC96359 si      1 ----------------------------------------------------------------------------
hLOC90792 si      1 ---------------------------------------------------------------------------- hAdlican FL    1681 psipskftdrrtdqfngyskvfgnnnipeatnpvgkppspriphysngrlpfftnktlsfpqlgvtrrpqiptspapvmr
hadlican2 FL   1506 psisskfadlrtdqsngsykvfgnsnipeatnsvgkplspriyhysngrlpfftnrtlsfsqlgvtrrpqipsspvpvmr
hLOC96359 si      1 ----------------------------------------------------------------------------
hLOC90792 si      1 ---------------------------------------------------------------------------- hAdlican FL    1761 erkvipgsynrihshstfhldfgppappllhtpqttgspstnlqnipmvsstqssisfitssvqssgsfhqssskffagg
hadlican2 FL   1586 erkvnpgsynriyshstfhldfglpappllhtpwtmvspptnlqnipmvsstqssvsfitssvqsagsihqsgskffagg
hLOC96359 si      1 ----------------------------------------------------------------------------
hLOC90792 si      1 ---------------------------------------------------------------------------- hAdlican FL    1841 ppaskfwslgekpqiltkspqtvsvtaetdtvfpceatgkpkpfvtwtkvstgalmtpntriqrfevlkngtlvirkvqv
hadlican2 FL   1666 ppaskfwplgekpqiltkspqtvsvtaetdavfpceaigkpkpfvtwtkvstgvlmtpntriqrfevlkngtlvirkfqv
hLOC96359 si      1 ----------------------------------------------------------------------------
hLOC90792 si      1 ---------------------------------------------------------------------------- hAdlican FL    1921 qdrgqymctasnlhgldmvvllsvtvqqpqilashyqdvtvylgdtiameclakgtpapqiswifpdrrvwqtvspves
hadlican2 FL   1746 qdrgqymctasnlygldrmvvflwvtvqqpqilashyqdvtvylgdtitmeclakgtpapqiswifrdrrvwqtlssveg
hLOC96359 si      1 ----------------------------------------------------------------------------
hLOC90792 si      1 ---------------------------------------------------------------------------- hAdlican FL    2001 ritlhenrtlsikeasfsdrgvykcvasnaagadslairlhvaalppvihqeklenislppglsihihctakaaplpsvr
hadlican2 FL   1826 ritlhqnrtlsikeasfsdrgvykcvasnatradsvsirlhvaalppiihqeklenislppglsihihctakaaplpsvl
hLOC96359 si      1 ----------------------------------------------------------------------------
hLOC90792 si      1 ---------------------------------------------------------------------------- hAdlican FL    2081 wvlgdgtqirpsqflhgnlfvfpngtlyirnlapkdsgryecvaanlvgsarrtvqlnvqraaanaritgtsprrtdvry
hadlican2 FL   1906 wvlgdgtqitpshflhrnlfvfpngtlyicnlapkdsgryecvaanlvgsarstvqlnvqraaanaritgtssgrtdvry
hLOC96359 si      1 ----------------------------------------------------------------------------
hLOC90792 si      1 ---------------------------------------------------------------------------- hAdlican FL    2161 ggtlkldcsasgdpwprilwrlpskrmidalfsfdsrikvfangtlvvksvtdkdagdylcvarnkvgddyvvlkvdvvm
```

Figure 41 (Cont.)

```
hAdlican2 FL   1986 ggtlkldcsasgdpwprilwrlpskrtidalfsfdsrikvfanrtlvvksmtdkdagdylcvarnkvgddcvvlkvdvmm
hLOC96359 si      1 ----------------------------------------------------------------------------
hLOC90792 si      1 --------------------------------------------------mtdkdagdylcvarnkvgddcvvlkvdvmm hAdlican  FL   2241 kpakiehkeendhkvfyggdlkvdcvatglpnpeiswslpdgslvnsfmqsddsggrtkryvvfnngtlyfnevgmreeg
hAdlican2 FL   2066 kpakiehkeendhkvfyrgdlkvdcvatglpnpeiswslldgslvnsfmqsddsggrtkhyvvfnngtlyfsevgmreeg
hLOC96359 si      1 ------------------------------------mqsddsggrtkhyvvfnngtlyfsevgmreeg
hLOC90792 si     31 kpakiehkeendhkvfyrgdlkvdcvatglpnpeiswslldgslvnsfmqsddsggrtkhyvvfnngtlyfsevgmreeg hAdlican  FL   2321 dytcfaenqvgkdemrvrvkvvtapatirnktylavqvpygdvvtvaceakgepmpkvtwlsptnkviptssekyqiyqd
hAdlican2 FL   2146 dytcfaenqvgkdemrvrvkmvt-patiwnktylavqvpygdvvtvtceakgepmpkvtwlspanrviptssekyqiyqy
hLOC96359 si     33 dytcfaenqvgkdemrvrvkmvt-patiwnktylavqvpygdvvtvtceakgepmpkvtwlspanrviptssekyqiyqy
hLOC90792 si    111 dytcfaenqvgkdemrvrvkmvt-patiwnktylavqvpygdvvtvtceakgepmpkvtwlspanrviptssekyqiyqy hAdlican  FL   2401 gtlliqkaqrsdsgnytclvrnsagedrktvwihvnvqppkingnpnpittvreiaaggsrklidckaegiptprvlwaf
hAdlican2 FL   2225 gtlliqkaqcsdsgnytclvrnsagedrktvwihvnlqppkingnpnpittvweiaaggsrklidckaegiptprvlwaf
hLOC96359 si    112 gtlliqkaqcsdsgnytclvrnsagedrktvwihvnlqppkingnpnpittvweiaaggsrklidckaegiptprvlwaf
hLOC90792 si    190 gtlliqkaqcsdsgnytclvrnsagedrktvwihvnlqppkingnpnpittvweiaaggsrklidckaegiptprvlwaf hAdlican  FL   2481 pegvvlpapyygnritvhgngsldirslrksdsvqlvcmarneggearlivqltvlepmekpifhdpisekitamaghti
hAdlican2 FL   2305 pegvvlpdpyygnritvhgngsldirslrksdsvqlvcmarneggearlivqltvlepmekpifhdpisekitamaghti
hLOC96359 si    192 pegvvlpdpyygnritvhgngsldirslrksdsvqlvcmarneggearlivqltvlepmekpifhdpisekitamaghti
hLOC90792 si    270 pegvvlpdpyygnritvhgngsldirslrksdsvqlvcmarneggearlivqltvlepmekpifhdpisekitamaghti hAdlican  FL   2561 slncsaagtptpslvwvlpngtdlqsgqqlqrfyhkadgmlhisglssvdagayrcvarnaaghterlvslkvglkpean
hAdlican2 FL   2385 slncsaagtltpslvwvlpngtdlqsgqqlqrfyhkadgmlhisglssvdagayrcvarnaaghterlvslkvglkpean
hLOC96359 si    272 slncsaagtltpslvwvlpngtdlqsgqqlqrfyhkadgmlhisglssvdagayrcvarnaaghterlvslkvglkpean
hLOC90792 si    350 slncsaagtltpslvwvlpngtdlqsgqqlqrfyhkadgmlhisglssvdagayrcvarnaaghterlvslkvglkpean hAdlican  FL   2641 kqyhnlvsiingetlklpctppgagqgrfswtlpngmhlegpqtlgrvslldngtltvreasvfdrgtyvcrmeteygps
hAdlican2 FL   2465 kqyhnlvsiingetlklpctppaagqghfswtlpngmhlegpqtlgrvslldngtltvreasvfdrgtyvcrmetaygps
hLOC96359 si    352 kqyhnlvsiingetlklpctppaagqghfswtlpngmhlegpqtlgrvslldngtltvreasvfdrgtyvcrmetaygps
hLOC90792 si    430 kqyhnlvsiingetlklpctppaagqghfswtlpngmhlegpqtlgrvslldngtltvreasvfdrgtyvcrmetaygps hAdlican  FL   2721 vtsipviviayppritseptpviytrpgntvklncmamgipkaditwelpdkshlkagvqarlygnrflhpqgsltiqba
hAdlican2 FL   2545 vtsipviviayppritseptpviytrpgntvklncmamgipkgditwelpdklhlkagvqarlygnrflhpqgsltiqqa
hLOC96359 si    432 vtsipviviayppritseptpviytrpgntvklncmamgipkgditwelpdklhlkagvqarlygnrflhpqgsltiqqa
hLOC90792 si    510 vtsipviviayppritseptpviytrpgntvklncmamgipkgditwelpdklhlkagvqarlygnrflhpqgsltiqqa hAdlican  FL   2801 tqrdagfykcmaknilgsdskttyihvf
hAdlican2 FL   2625 rrrdagfykctaknilssdskttyihvf
hLOC96359 si    512 rrrdagfykctaknilssdskttyihvf
hLOC90792 si    590 rrrdagfykctaknilssdskttyihvf
```

Figure 42

| | | | | | | |
|---|---|---|---|---|---|---|
| atgaaggtaa | aaggcagagg | aatcacctgc | ttgctggtct | cctttgctgt | gatctgcctg | 60 |
| gtcgccaccc | ctgggggcaa | ggcctgtcct | cgccgctgtg | cctgttatat | gcctacggag | 120 |
| gtacactgca | catttcggta | cctgacttcc | atcccagaca | gcatcccgcc | caatgtggaa | 180 |
| cgcatcaatt | taggatacaa | cagcttggtt | agattgatgg | aaacagattt | ttctggcctg | 240 |
| accaaactgg | agttactcat | gcttcacagc | aatggcattc | acacaatccc | tgacaagacc | 300 |
| ttctcagatt | tgcaggcctt | gcaggtctta | aaaatgagct | ataataaagt | ccgaaaactt | 360 |
| cagaaagata | cttttttatgg | cctcaggagc | ttgacacgat | tgcacatgga | ccacaacaat | 420 |
| attgagttta | taaacccaga | ggttttttat | gggctcaact | ttctccgcct | ggtgcacttg | 480 |
| gaaggaaatc | agctcactaa | gctccaccca | gatacatttg | tctctttgag | ctacctccag | 540 |
| atatttaaaa | tctctttcat | taagttccta | tacttgtctg | ataacttcct | gacctccctc | 600 |
| cctcaagaga | tggtctccta | tatgcctgac | ctagacagcc | tttacctgca | tggaaaccca | 660 |
| tggacctgtg | attgccattt | aaagtggttg | tctgactgga | tacaggagaa | gccagatgta | 720 |
| ataaaatgca | aaaagatag | aagtccctct | agtgctcagc | agtgtccact | ttgcatgaac | 780 |
| cctaggactt | ctaaaggcaa | gccgttagct | atggtctcag | ctgcagcttt | ccagtgtgcc | 840 |
| aagccaacca | ttgactcatc | cctgaaatca | aagagcctga | ctattctgga | agacagtagt | 900 |
| tctgctttca | tctctccca | aggtttcatg | gcacccttg | gctccctcac | tttgaatatg | 960 |
| acagatcagt | ctggaaatga | agctaacatg | gtctgcagta | ttcaaaagcc | ctcaaggaca | 1020 |
| tcacccattg | cattcactga | agaaaatgac | tacatcgtgc | taaatacttc | attttcaaca | 1080 |
| tttttggtgt | gcaacataga | ttacggtcac | attcagccag | tgtggcaaat | tttggctttg | 1140 |
| tacagtgatt | ctcctctgat | actagaaagg | agccacttgc | ttagtgaaac | accgcagctc | 1200 |
| tattacaaat | ataaacaggt | ggctcctaag | cctgaagaca | ttttttaccaa | catagaggca | 1260 |
| gatctcagag | cagatccctc | ttggttaatg | caagaccaaa | tttccttgca | gctgaacaga | 1320 |
| actgccacca | cattcagtac | attacagatc | cagtactcca | gtgatgctca | aatcactta | 1380 |
| ccaagagcag | agatgaggcc | agtgaaacac | aaatggacta | tgatttcaag | ggataacaat | 1440 |
| actaagctgg | aacatactgt | cttggtaggt | ggaaccgttg | gcctgaactg | cccaggccaa | 1500 |
| ggagacccca | ccccacacgt | ggattggctt | ctagctgatg | gaagtaaagt | gagagcccct | 1560 |
| tatgtcagtg | aggatggacg | gatcctaata | gacaaagtg | gaaaattgga | actccagatg | 1620 |
| gctgatagtt | ttgacacagg | cgtatatcac | tgtataagca | gcaattatga | tgatgcagat | 1680 |
| attctcacct | ataggataac | tgtggtagaa | cctttggtcg | aagcctatca | ggaaaatggg | 1740 |
| attcatcaca | cagttttcat | tggtgaaaca | cttgatcttc | catgccattc | tactggtatc | 1800 |
| ccagatgcct | ctattagctg | ggttattcca | ggaaacaatg | tgctctatca | gtcatcaaga | 1860 |
| gacaagaaag | ttctaaacaa | tggcacatta | agaatattac | aggtcacccc | gaaagaccaa | 1920 |
| ggttattatc | gctgtgtggc | agccaaccca | tcaggggttg | attttttgat | tttccaagtt | 1980 |
| tcagtcaaga | tgaaaggaca | aaggcccttg | gagcatgatg | gagaaacaga | gggatctgga | 2040 |
| cttgatgagt | ccaatcctat | tgctcatctt | aaggagccac | caggtgcaca | actccgtaca | 2100 |
| tctgctctga | tggaggctga | ggttggaaaa | cacacctcaa | gcacaagtaa | gaggcacaac | 2160 |
| tatcgggaat | taacactcca | gcgacgtgga | gattcaacac | atcgacgttt | tagggagaat | 2220 |
| aggaggcatt | tccctccctc | tgctaggaga | attgacccac | aacattgggc | ggcactgttg | 2280 |
| gagaaagcta | aaaagaatgc | tatgccagac | aagcgagaaa | ataccacagt | gagcccaccc | 2340 |
| ccagtggtca | cccaactccc | aaacatacct | ggtgaagaag | acgattcctc | aggcatgctc | 2400 |
| gctctacatg | aggaatttat | ggtcccggcc | actaaagctt | tgaaccttcc | agcaaggaca | 2460 |
| gtgactgctg | actccagaac | aatatctgat | agtcctatga | caaacataaa | ttatggcaca | 2520 |
| gaattctctc | ctgttgtgaa | ttcacaaata | ctaccacctg | aagaacccac | agatttcaaa | 2580 |
| ctgtctactg | ctattaaaac | tacagccatg | tcaaagaata | taaacccaac | catgtcaagc | 2640 |
| caaatacaag | gcacaaccaa | tcaacattca | tccactgtct | ttccactgct | acttggagca | 2700 |
| actgaatttc | aggactctga | ccagatggga | agaggaagag | agcatttcca | aagtagaccc | 2760 |
| ccaataacag | taaggactat | gatcaaagat | gtcaatgtca | aaatgcttag | tagcaccacc | 2820 |
| aacaaactat | tattagagtc | agtaaatacc | acaaatagtc | atcagacatc | tgtaagagaa | 2880 |
| gtgagtgaac | ccaggcacaa | tcacttctat | tctcacacta | ctcaaatact | tagcacctcc | 2940 |
| acgttccctt | cagatccaca | cacagctgct | cattctcagt | ttccgatccc | tagaaatagt | 3000 |
| acagttaaca | tcccgctgtt | cagacgcttt | gggaggcaga | ggaaaattgg | cggaaggggg | 3060 |
| cggattatca | gcccatatag | aactccagtt | ctgcgacggc | atagatacag | catttttcagg | 3120 |

Figure 42 (Cont.)

```
tcaacaacca gaggttcttc tgaaaaaagc actactgcat tctcagccac agtgctcaat    3180
gtgacatgtc tgtcctgtct tcccagggag aggctcacca ctgccacagc agcattgtct    3240
tttccaagtg ctgctcccat caccttcccc aaagctgaca ttgctagagt cccatcagaa    3300
gagtctacaa ctctagtcca gaatccacta ttactacttg agaacaaacc cagtgtagag    3360
aaaacaacac ccacaataaa atatttcagg actgaaattt cccaagtgac tccaactggt    3420
gcagtcatga catatgctcc aacatccata cccatggaaa aaactcacaa agtaaacgcc    3480
agttacccac gtgtgtctag caccaatgaa gctaaagag attcagtgat tacatcgtca     3540
ctttcaggtg ctatcaccaa gccaccaatg actattatag ccattacaag gttttcaaga    3600
aggaaaattc cctggcaaca gaactttgta ataaccata acccaaaagg cagattaagg     3660
aatcaacata agttagttt acaaaaaagc acagctgtga tgcttcctaa aacatctcct     3720
gctttaccca gagacaaagt ctcccctttc catttcacca cactttcaac aagtgtgatg    3780
caaattccat ctaataccatt gactaccgct caccacacta cgaccaaaac acacaatcct   3840
ggaagtcttc caacaaagaa ggagcttccc ttcccacccc ttaaccctat gcttcctagt    3900
attataagca aagactcaag tacaaaaagc atcatatcaa cgcaaacagc aataccagca    3960
acaactccta ccttccctgc atctgtcatc acttatgaaa cccaaacaga gagatctaga    4020
gcacaaacaa tacaaagaga acaggagcct caaagaaga acaggactga cccaaacatc     4080
tctccagacc agagttctgg cttcactaca cccactgcta tgacacctcc tgttctaacc    4140
acagccgaaa cttcagtcaa gccagtgtc tctgcattca ctcattcccc accagaaaac    4200
acaactggga tttcaagcac aatcagtttt cattcaagaa ctcttaatct gacagatgtg    4260
attgaagaac tagcccaagc aagtactcag acttttgaaga gcacaattgc ttctgaaaca   4320
actttgtcca gcaaatcaca ccagagtacc acaactagga aagcaatcat tagacactca    4380
accataccac cattcttgag cagcagtgct actctaatgc cagttcccat ctcccctccc    4440
tttactcaga gagcagttac tgacaacgtg gcgactccca tttccgggct tatgacaaat    4500
acagtggtca agctgcacga atcctcaagg cacaatgcta aaccacagca attagtagca    4560
gaggttgcaa catcccccaa ggttcaccca aatgccaagt tcacaattgg aaccactcac    4620
ttcatctact ctaatctgtt acattcact cccatgccag cactaacaac agttaaatca     4680
cagaattcta aattaactcc atctccctgg gcagaaaacc aattttggca caaaccatac    4740
tcagaaattg ctgaaaaagg caaaaagcca gaagtaagca tgttggctac tacaggcctg    4800
tccgaggcca ccactcttgt ttcagattgg gatggacaga agaacacaaa gaagagtgac    4860
tttgataaga aaccagttca agaagcaaca acttccaaac tccttccctt tgactctttg    4920
tctaggtata tatttgaaaa gcccaggata gttggaggaa aagctgcaag ttttactatt    4980
ccagctaact cagatgcctt tcttccctgt gaagctgttg gaaatcccct gcccaccatt    5040
cattggacca gagtcccatc aggacttgat ttatctaaga ggaaacagaa tagcagggtc    5100
caggttctcc ccaatggtac cctgtccatc cagagggtgg aaattcagga ccgcggacag    5160
tacttgtgtt ccgcatccaa tctgtttggc acagaccacc ttcatgtcac cttgtctgtg    5220
gttcctatc ctccaggat cctggagaga cgtaccaaag agatcacagt tcattccgga     5280
agcactgtgg aactgaagtg cagagcagaa ggtaggccaa gccctacagt tacctggatt    5340
cttgcaaacc aaacagttgt ctcagaatca tcccagggaa gtaggcaggc tgtggtgacg    5400
gttgacggaa cattggtcct ccacaatctc agtatttatg accgtggctt ttacaaatgt    5460
gtggccagca cccaggtgg ccaggattca ctgctggtta aaatacaagt cattgcagca    5520
ccacctgtta ttctagagca aaggaggcaa gtcattgtag gcacttgggg tgaaagttta    5580
aaactgccct gtactgcaaa aggaactcct cagcccagcg tttactgggt cctctctgat    5640
ggcactgaag tgaaaccatt acagtttacc aattccaagt tgttcttatt ttcaaatggg    5700
actttgtata taagaaacct agcctcttca gacaggggca cttatgaatg cattgctacc    5760
agttccactg gttcggagcg aagagtagta atgcttacaa tggaagagcg agtgaccagc    5820
cccaggatag aagctgcatc ccagaaaagg actgaagtga attttgggga caaattacta    5880
ctgaactgct cagccactgg ggagcccaaa ccccaaataa tgtggaggtt accatccaag    5940
gctgtggtcg accagcagca tagagtgggc agctggatcc acgtctaccc taatggatcc    6000
ctgtttattg gatcagtaac agaaaaagac agtggtgtct acttgtgtgt ggcaagaaac    6060
aaaatggggg atgatctgat actgatgcat gttagcctaa gactgaaacc tgccaaaatt    6120
gaccacaagc agtattttag aaagcaagtg ctccatggga agatttcca agtagattgc    6180
aaagcttccg gctccccagt gccagagata tcttggagtt tgcctgatgg aaccatgatc    6240
aacaatgcaa tgcaagccga tgacagtggc cacaggacta ggagatatac cctttcaac   6300
aatggaactt tatacttcaa caaagtgggg tagcggagg aaggagatta tacttgctat    6360
gcccagaaca ccctagggaa agatgaaatg aaggtccact taacagttat aacagctgct    6420
cccggataa ggcagagtaa caaaccaac aagagaatca aagctggaga cacagctgtc     6480
```

Figure 42 (Cont.)

```
cttgactgtg aggtcactgg ggatcccaaa ccaaaaatat tttggttgct gccttccaat 6540
gacatgattt ccttctccat tgataggtac acatttcatg ccaatgggtc tttgaccatc 6600
aacaaagtga aactgctcga ttctggagag tacgtatgtg tagcccgaaa tcccagtggg 6660
gatgacacca aaatgtacaa actggatgtg gtctctaaac ctccattaat caatggtctg 6720
tatacaaaca gaactgttat taaagccaca gctgtgagac attccaaaaa acactttgac 6780
tgcagagctg aagggacacc atctcctgaa gtcatgtgga tcatgccaga caatattttc 6840
ctcacagccc catactatgg aagcagaatc acagtccata aaaatggaac cttggaaatt 6900
aggaatgtga ggctttcaga ttcagccgac tttatctgtg tggcccgaaa tgaaggtgga 6960
gagagcgtgt tggtagtaca gttagaagta ctggaaatgc tgagaagacc gacatttaga 7020
aatccattta atgaaaaaat agttgcccag ctgggaaagt ccacagcatt gaattgctct 7080
gttgatggta acccaccacc tgaaataatc tggattttac caaatggcac acgatttttcc 7140
aatggaccac aaagttatca gtatctgata gcaagcaatg gttcttttat catttctaaa 7200
acaactcggg aggatgcagg aaaatatcgc tgtgcagcta ggaataaagt tggctatatt 7260
gagaaattag tcatattaga aattggccag aagccagtta ttcttaccta tgcaccaggg 7320
acagtaaaag gcatcagtgg agaatctcta tcactgcatt gtgtgtctga tggaatccct 7380
aagccaaata tcaaatggac tatgccaagt ggttatgtag tagacaggcc tcaaattaat 7440
gggaaataca tattgcatga caatggcacc ttagtcatta agaagcaac agcttatgac 7500
agaggaaact atatctgtaa ggctcaaaat agtgttggtc atacactgat tactgttcca 7560
gtaatgattg tagcctaccc tccccgaatt acaaatcgtc cacccaggag tattgtcacc 7620
aggacagggg cagcctttca gctccactgt gtggccttgg gagttcccaa gccagaaatc 7680
acatgggaga tgcctgacca ctcccttctc tcaacggcaa gtaaagagag gacacatgga 7740
agtgagcagc ttcacttaca aggtacccta gtcattcaga atccccaaac ctccgattct 7800
gggatataca aatgcacagc aaagaaccca cttggtagtg attatgcagc aacgtatatt 7860
caagtaatct ga                                                        7872
```

Figure 43

```
Met Lys Val Lys Gly Arg Gly Ile Thr Cys Leu Leu Val Ser Phe Ala
1               5                   10                  15

Val Ile Cys Leu Val Ala Thr Pro Gly Gly Lys Ala Cys Pro Arg Arg
            20                  25                  30

Cys Ala Cys Tyr Met Pro Thr Glu Val His Cys Thr Phe Arg Tyr Leu
        35                  40                  45

Thr Ser Ile Pro Asp Ser Ile Pro Pro Asn Val Glu Arg Ile Asn Leu
    50              55                  60

Gly Tyr Asn Ser Leu Val Arg Leu Met Glu Thr Asp Phe Ser Gly Leu
65              70                  75                      80

Thr Lys Leu Glu Leu Leu Met Leu His Ser Asn Gly Ile His Thr Ile
                85                  90                  95

Pro Asp Lys Thr Phe Ser Asp Leu Gln Ala Leu Gln Val Leu Lys Met
                100                 105                 110

Ser Tyr Asn Lys Val Arg Lys Leu Gln Lys Asp Thr Phe Tyr Gly Leu
            115                 120                 125

Arg Ser Leu Thr Arg Leu His Met Asp His Asn Asn Ile Glu Phe Ile
    130                 135                 140

Asn Pro Glu Val Phe Tyr Gly Leu Asn Phe Leu Arg Leu Val His Leu
145                 150                 155                 160

Glu Gly Asn Gln Leu Thr Lys Leu His Pro Asp Thr Phe Val Ser Leu
                165                 170                 175

Ser Tyr Leu Gln Ile Phe Lys Ile Ser Phe Ile Lys Phe Leu Tyr Leu
            180                 185                 190

Ser Asp Asn Phe Leu Thr Ser Leu Pro Gln Glu Met Val Ser Tyr Met
        195                 200                 205

Pro Asp Leu Asp Ser Leu Tyr Leu His Gly Asn Pro Trp Thr Cys Asp
    210                 215                 220

Cys His Leu Lys Trp Leu Ser Asp Trp Ile Gln Glu Lys Pro Asp Val
225                 230                 235                 240

Ile Lys Cys Lys Lys Asp Arg Ser Pro Ser Ser Ala Gln Gln Cys Pro
            245                 250                 255

Leu Cys Met Asn Pro Arg Thr Ser Lys Gly Lys Pro Leu Ala Met Val
            260                 265                 270
```

Figure 43 (Cont.)

```
Ser Ala Ala Ala Phe Gln Cys Ala Lys Pro Thr Ile Asp Ser Ser Leu
        275                 280                 285

Lys Ser Lys Ser Leu Thr Ile Leu Glu Asp Ser Ser Ser Ala Phe Ile
        290                 295                 300

Ser Pro Gln Gly Phe Met Ala Pro Phe Gly Ser Leu Thr Leu Asn Met
305                 310                 315                 320

Thr Asp Gln Ser Gly Asn Glu Ala Asn Met Val Cys Ser Ile Gln Lys
                325                 330                 335

Pro Ser Arg Thr Ser Pro Ile Ala Phe Thr Glu Glu Asn Asp Tyr Ile
                340                 345                 350

Val Leu Asn Thr Ser Phe Ser Thr Phe Leu Val Cys Asn Ile Asp Tyr
        355                 360                 365

Gly His Ile Gln Pro Val Trp Gln Ile Leu Ala Leu Tyr Ser Asp Ser
        370                 375                 380

Pro Leu Ile Leu Glu Arg Ser His Leu Leu Ser Glu Thr Pro Gln Leu
385                 390                 395                 400

Tyr Tyr Lys Tyr Lys Gln Val Ala Pro Lys Pro Glu Asp Ile Phe Thr
                405                 410                 415

Asn Ile Glu Ala Asp Leu Arg Ala Asp Pro Ser Trp Leu Met Gln Asp
                420                 425                 430

Gln Ile Ser Leu Gln Leu Asn Arg Thr Ala Thr Thr Phe Ser Thr Leu
        435                 440                 445

Gln Ile Gln Tyr Ser Ser Asp Ala Gln Ile Thr Leu Pro Arg Ala Glu
        450                 455                 460

Met Arg Pro Val Lys His Lys Trp Thr Met Ile Ser Arg Asp Asn Asn
465                 470                 475                 480

Thr Lys Leu Glu His Thr Val Leu Val Gly Gly Thr Val Gly Leu Asn
                485                 490                 495

Cys Pro Gly Gln Gly Asp Pro Thr Pro His Val Asp Trp Leu Leu Ala
                500                 505                 510

Asp Gly Ser Lys Val Arg Ala Pro Tyr Val Ser Glu Asp Gly Arg Ile
        515                 520                 525

Leu Ile Asp Lys Ser Gly Lys Leu Glu Leu Gln Met Ala Asp Ser Phe
        530                 535                 540

Asp Thr Gly Val Tyr His Cys Ile Ser Ser Asn Tyr Asp Asp Ala Asp
545                 550                 555                 560

Ile Leu Thr Tyr Arg Ile Thr Val Val Glu Pro Leu Val Glu Ala Tyr
```

Figure 43 (Cont.)

```
              565                       570                       575
Gln Glu Asn Gly Ile His His Thr Val Phe Ile Gly Glu Thr Leu Asp
            580                   585                   590

Leu Pro Cys His Ser Thr Gly Ile Pro Asp Ala Ser Ile Ser Trp Val
        595                   600                   605

Ile Pro Gly Asn Asn Val Leu Tyr Gln Ser Ser Arg Asp Lys Lys Val
    610                   615                   620

Leu Asn Asn Gly Thr Leu Arg Ile Leu Gln Val Thr Pro Lys Asp Gln
625                   630                   635                   640

Gly Tyr Tyr Arg Cys Val Ala Ala Asn Pro Ser Gly Val Asp Phe Leu
                645                   650                   655

Ile Phe Gln Val Ser Val Lys Met Lys Gly Gln Arg Pro Leu Glu His
            660                   665                   670

Asp Gly Glu Thr Glu Gly Ser Gly Leu Asp Glu Ser Asn Pro Ile Ala
        675                   680                   685

His Leu Lys Glu Pro Pro Gly Ala Gln Leu Arg Thr Ser Ala Leu Met
    690                   695                   700

Glu Ala Glu Val Gly Lys His Thr Ser Ser Thr Ser Lys Arg His Asn
705                   710                   715                   720

Tyr Arg Glu Leu Thr Leu Gln Arg Arg Gly Asp Ser Thr His Arg Arg
                725                   730                   735

Phe Arg Glu Asn Arg Arg His Phe Pro Pro Ser Ala Arg Arg Ile Asp
            740                   745                   750

Pro Gln His Trp Ala Ala Leu Leu Glu Lys Ala Lys Lys Asn Ala Met
        755                   760                   765

Pro Asp Lys Arg Glu Asn Thr Thr Val Ser Pro Pro Pro Val Val Thr
    770                   775                   780

Gln Leu Pro Asn Ile Pro Gly Glu Glu Asp Asp Ser Ser Gly Met Leu
785                   790                   795                   800

Ala Leu His Glu Glu Phe Met Val Pro Ala Thr Lys Ala Leu Asn Leu
                805                   810                   815

Pro Ala Arg Thr Val Thr Ala Asp Ser Arg Thr Ile Ser Asp Ser Pro
            820                   825                   830

Met Thr Asn Ile Asn Tyr Gly Thr Glu Phe Ser Pro Val Val Asn Ser
        835                   840                   845

Gln Ile Leu Pro Pro Glu Glu Pro Thr Asp Phe Lys Leu Ser Thr Ala
    850                   855                   860
```

Figure 43 (Cont.)

```
Ile Lys Thr Thr Ala Met Ser Lys Asn Ile Asn Pro Thr Met Ser Ser
865                 870                 875                 880

Gln Ile Gln Gly Thr Thr Asn Gln His Ser Ser Thr Val Phe Pro Leu
                885                 890                 895

Leu Leu Gly Ala Thr Glu Phe Gln Asp Ser Asp Gln Met Gly Arg Gly
                900                 905                 910

Arg Glu His Phe Gln Ser Arg Pro Pro Ile Thr Val Arg Thr Met Ile
        915                 920                 925

Lys Asp Val Asn Val Lys Met Leu Ser Ser Thr Thr Asn Lys Leu Leu
    930                 935                 940

Leu Glu Ser Val Asn Thr Thr Asn Ser His Gln Thr Ser Val Arg Glu
945                 950                 955                 960

Val Ser Glu Pro Arg His Asn His Phe Tyr Ser His Thr Thr Gln Ile
                965                 970                 975

Leu Ser Thr Ser Thr Phe Pro Ser Asp Pro His Thr Ala Ala His Ser
                980                 985                 990

Gln Phe Pro Ile Pro Arg Asn Ser Thr Val Asn Ile Pro Leu Phe Arg
                995                 1000                1005

Arg Phe Gly Arg Gln Arg Lys Ile Gly Gly Arg Gly Arg Ile Ile
    1010                1015                1020

Ser Pro Tyr Arg Thr Pro Val Leu Arg Arg His Arg Tyr Ser Ile
    1025                1030                1035

Phe Arg Ser Thr Thr Arg Gly Ser Ser Glu Lys Ser Thr Thr Ala
    1040                1045                1050

Phe Ser Ala Thr Val Leu Asn Val Thr Cys Leu Ser Cys Leu Pro
    1055                1060                1065

Arg Glu Arg Leu Thr Thr Ala Thr Ala Ala Leu Ser Phe Pro Ser
    1070                1075                1080

Ala Ala Pro Ile Thr Phe Pro Lys Ala Asp Ile Ala Arg Val Pro
    1085                1090                1095

Ser Glu Glu Ser Thr Thr Leu Val Gln Asn Pro Leu Leu Leu Leu
    1100                1105                1110

Glu Asn Lys Pro Ser Val Glu Lys Thr Thr Pro Thr Ile Lys Tyr
    1115                1120                1125

Phe Arg Thr Glu Ile Ser Gln Val Thr Pro Thr Gly Ala Val Met
    1130                1135                1140

Thr Tyr Ala Pro Thr Ser Ile Pro Met Glu Lys Thr His Lys Val
    1145                1150                1155
```

Figure 43 (Cont.)

```
Asn Ala Ser Tyr Pro Arg Val Ser Ser Thr Asn Glu Ala Lys Arg
    1160            1165                1170
Asp Ser Val Ile Thr Ser Ser Leu Ser Gly Ala Ile Thr Lys Pro
    1175            1180                1185
Pro Met Thr Ile Ile Ala Ile Thr Arg Phe Ser Arg Arg Lys Ile
    1190            1195                1200
Pro Trp Gln Gln Asn Phe Val Asn Asn His Asn Pro Lys Gly Arg
    1205            1210                1215
Leu Arg Asn Gln His Lys Val Ser Leu Gln Lys Ser Thr Ala Val
    1220            1225                1230
Met Leu Pro Lys Thr Ser Pro Ala Leu Pro Arg Asp Lys Val Ser
    1235            1240                1245
Pro Phe His Phe Thr Thr Leu Ser Thr Ser Val Met Gln Ile Pro
    1250            1255                1260
Ser Asn Thr Leu Thr Thr Ala His His Thr Thr Thr Lys Thr His
    1265            1270                1275
Asn Pro Gly Ser Leu Pro Thr Lys Lys Glu Leu Pro Phe Pro Pro
    1280            1285                1290
Leu Asn Pro Met Leu Pro Ser Ile Ile Ser Lys Asp Ser Ser Thr
    1295            1300                1305
Lys Ser Ile Ile Ser Thr Gln Thr Ala Ile Pro Ala Thr Thr Pro
    1310            1315                1320
Thr Phe Pro Ala Ser Val Ile Thr Tyr Glu Thr Gln Thr Glu Arg
    1325            1330                1335
Ser Arg Ala Gln Thr Ile Gln Arg Glu Gln Glu Pro Gln Lys Lys
    1340            1345                1350
Asn Arg Thr Asp Pro Asn Ile Ser Pro Asp Gln Ser Ser Gly Phe
    1355            1360                1365
Thr Thr Pro Thr Ala Met Thr Pro Pro Val Leu Thr Thr Ala Glu
    1370            1375                1380
Thr Ser Val Lys Pro Ser Val Ser Ala Phe Thr His Ser Pro Pro
    1385            1390                1395
Glu Asn Thr Thr Gly Ile Ser Ser Thr Ile Ser Phe His Ser Arg
    1400            1405                1410
Thr Leu Asn Leu Thr Asp Val Ile Glu Glu Leu Ala Gln Ala Ser
    1415            1420                1425
Thr Gln Thr Leu Lys Ser Thr Ile Ala Ser Glu Thr Thr Leu Ser
```

Figure 43 (Cont.)

```
      1430                      1435                      1440
Ser Lys Ser His Gln Ser Thr Thr Thr Arg Lys Ala Ile Ile Arg
    1445                      1450                      1455
His Ser Thr Ile Pro Pro Phe Leu Ser Ser Ser Ala Thr Leu Met
    1460                      1465                      1470
Pro Val Pro Ile Ser Pro Pro Phe Thr Gln Arg Ala Val Thr Asp
    1475                      1480                      1485
Asn Val Ala Thr Pro Ile Ser Gly Leu Met Thr Asn Thr Val Val
    1490                      1495                      1500
Lys Leu His Glu Ser Ser Arg His Asn Ala Lys Pro Gln Gln Leu
    1505                      1510                      1515
Val Ala Glu Val Ala Thr Ser Pro Lys Val His Pro Asn Ala Lys
    1520                      1525                      1530
Phe Thr Ile Gly Thr Thr His Phe Ile Tyr Ser Asn Leu Leu His
    1535                      1540                      1545
Ser Thr Pro Met Pro Ala Leu Thr Thr Val Lys Ser Gln Asn Ser
    1550                      1555                      1560
Lys Leu Thr Pro Ser Pro Trp Ala Glu Asn Gln Phe Trp His Lys
    1565                      1570                      1575
Pro Tyr Ser Glu Ile Ala Glu Lys Gly Lys Lys Pro Glu Val Ser
    1580                      1585                      1590
Met Leu Ala Thr Thr Gly Leu Ser Glu Ala Thr Thr Leu Val Ser
    1595                      1600                      1605
Asp Trp Asp Gly Gln Lys Asn Thr Lys Lys Ser Asp Phe Asp Lys
    1610                      1615                      1620
Lys Pro Val Gln Glu Ala Thr Thr Ser Lys Leu Leu Pro Phe Asp
    1625                      1630                      1635
Ser Leu Ser Arg Tyr Ile Phe Glu Lys Pro Arg Ile Val Gly Gly
    1640                      1645                      1650
Lys Ala Ala Ser Phe Thr Ile Pro Ala Asn Ser Asp Ala Phe Leu
    1655                      1660                      1665
Pro Cys Glu Ala Val Gly Asn Pro Leu Pro Thr Ile His Trp Thr
    1670                      1675                      1680
Arg Val Pro Ser Gly Leu Asp Leu Ser Lys Arg Lys Gln Asn Ser
    1685                      1690                      1695
Arg Val Gln Val Leu Pro Asn Gly Thr Leu Ser Ile Gln Arg Val
    1700                      1705                      1710
```

Figure 43 (Cont.)

Glu Ile Gln Asp Arg Gly Gln Tyr Leu Cys Ser Ala Ser Asn Leu
    1715            1720            1725

Phe Gly Thr Asp His Leu His Val Thr Leu Ser Val Val Ser Tyr
    1730            1735            1740

Pro Pro Arg Ile Leu Glu Arg Arg Thr Lys Glu Ile Thr Val His
    1745            1750            1755

Ser Gly Ser Thr Val Glu Leu Lys Cys Arg Ala Glu Gly Arg Pro
    1760            1765            1770

Ser Pro Thr Val Thr Trp Ile Leu Ala Asn Gln Thr Val Val Ser
    1775            1780            1785

Glu Ser Ser Gln Gly Ser Arg Gln Ala Val Val Thr Val Asp Gly
    1790            1795            1800

Thr Leu Val Leu His Asn Leu Ser Ile Tyr Asp Arg Gly Phe Tyr
    1805            1810            1815

Lys Cys Val Ala Ser Asn Pro Gly Gly Gln Asp Ser Leu Leu Val
    1820            1825            1830

Lys Ile Gln Val Ile Ala Ala Pro Pro Val Ile Leu Glu Gln Arg
    1835            1840            1845

Arg Gln Val Ile Val Gly Thr Trp Gly Glu Ser Leu Lys Leu Pro
    1850            1855            1860

Cys Thr Ala Lys Gly Thr Pro Gln Pro Ser Val Tyr Trp Val Leu
    1865            1870            1875

Ser Asp Gly Thr Glu Val Lys Pro Leu Gln Phe Thr Asn Ser Lys
    1880            1885            1890

Leu Phe Leu Phe Ser Asn Gly Thr Leu Tyr Ile Arg Asn Leu Ala
    1895            1900            1905

Ser Ser Asp Arg Gly Thr Tyr Glu Cys Ile Ala Thr Ser Ser Thr
    1910            1915            1920

Gly Ser Glu Arg Arg Val Val Met Leu Thr Met Glu Glu Arg Val
    1925            1930            1935

Thr Ser Pro Arg Ile Glu Ala Ala Ser Gln Lys Arg Thr Glu Val
    1940            1945            1950

Asn Phe Gly Asp Lys Leu Leu Leu Asn Cys Ser Ala Thr Gly Glu
    1955            1960            1965

Pro Lys Pro Gln Ile Met Trp Arg Leu Pro Ser Lys Ala Val Val
    1970            1975            1980

Asp Gln Gln His Arg Val Gly Ser Trp Ile His Val Tyr Pro Asn
    1985            1990            1995

Figure 43 (Cont.)

```
Gly Ser Leu Phe Ile Gly Ser Val Thr Glu Lys Asp Ser Gly Val
    2000              2005              2010

Tyr Leu Cys Val Ala Arg Asn Lys Met Gly Asp Asp Leu Ile Leu
    2015              2020              2025

Met His Val Ser Leu Arg Leu Lys Pro Ala Lys Ile Asp His Lys
    2030              2035              2040

Gln Tyr Phe Arg Lys Gln Val Leu His Gly Lys Asp Phe Gln Val
    2045              2050              2055

Asp Cys Lys Ala Ser Gly Ser Pro Val Pro Glu Ile Ser Trp Ser
    2060              2065              2070

Leu Pro Asp Gly Thr Met Ile Asn Asn Ala Met Gln Ala Asp Asp
    2075              2080              2085

Ser Gly His Arg Thr Arg Arg Tyr Thr Leu Phe Asn Asn Gly Thr
    2090              2095              2100

Leu Tyr Phe Asn Lys Val Val Ala Glu Glu Gly Asp Tyr Thr
    2105              2110              2115

Cys Tyr Ala Gln Asn Thr Leu Gly Lys Asp Glu Met Lys Val His
    2120              2125              2130

Leu Thr Val Ile Thr Ala Ala Pro Arg Ile Arg Gln Ser Asn Lys
    2135              2140              2145

Thr Asn Lys Arg Ile Lys Ala Gly Asp Thr Ala Val Leu Asp Cys
    2150              2155              2160

Glu Val Thr Gly Asp Pro Lys Pro Lys Ile Phe Trp Leu Leu Pro
    2165              2170              2175

Ser Asn Asp Met Ile Ser Phe Ser Ile Asp Arg Tyr Thr Phe His
    2180              2185              2190

Ala Asn Gly Ser Leu Thr Ile Asn Lys Val Lys Leu Leu Asp Ser
    2195              2200              2205

Gly Glu Tyr Val Cys Val Ala Arg Asn Pro Ser Gly Asp Asp Thr
    2210              2215              2220

Lys Met Tyr Lys Leu Asp Val Val Ser Lys Pro Pro Leu Ile Asn
    2225              2230              2235

Gly Leu Tyr Thr Asn Arg Thr Val Ile Lys Ala Thr Ala Val Arg
    2240              2245              2250

His Ser Lys Lys His Phe Asp Cys Arg Ala Glu Gly Thr Pro Ser
    2255              2260              2265

Pro Glu Val Met Trp Ile Met Pro Asp Asn Ile Phe Leu Thr Ala
    2270              2275              2280
```

Figure 43 (Cont.)

```
Pro Tyr Tyr Gly Ser Arg Ile Thr Val His Lys Asn Gly Thr Leu
    2285              2290              2295
Glu Ile Arg Asn Val Arg Leu Ser Asp Ser Ala Asp Phe Ile Cys
    2300              2305              2310
Val Ala Arg Asn Glu Gly Gly Glu Ser Val Leu Val Val Gln Leu
    2315              2320              2325
Glu Val Leu Glu Met Leu Arg Arg Pro Thr Phe Arg Asn Pro Phe
    2330              2335              2340
Asn Glu Lys Ile Val Ala Gln Leu Gly Lys Ser Thr Ala Leu Asn
    2345              2350              2355
Cys Ser Val Asp Gly Asn Pro Pro Pro Glu Ile Ile Trp Ile Leu
    2360              2365              2370
Pro Asn Gly Thr Arg Phe Ser Asn Gly Pro Gln Ser Tyr Gln Tyr
    2375              2380              2385
Leu Ile Ala Ser Asn Gly Ser Phe Ile Ile Ser Lys Thr Thr Arg
    2390              2395              2400
Glu Asp Ala Gly Lys Tyr Arg Cys Ala Ala Arg Asn Lys Val Gly
    2405              2410              2415
Tyr Ile Glu Lys Leu Val Ile Leu Glu Ile Gly Gln Lys Pro Val
    2420              2425              2430
Ile Leu Thr Tyr Ala Pro Gly Thr Val Lys Gly Ile Ser Gly Glu
    2435              2440              2445
Ser Leu Ser Leu His Cys Val Ser Asp Gly Ile Pro Lys Pro Asn
    2450              2455              2460
Ile Lys Trp Thr Met Pro Ser Gly Tyr Val Val Asp Arg Pro Gln
    2465              2470              2475
Ile Asn Gly Lys Tyr Ile Leu His Asp Asn Gly Thr Leu Val Ile
    2480              2485              2490
Lys Glu Ala Thr Ala Tyr Asp Arg Gly Asn Tyr Ile Cys Lys Ala
    2495              2500              2505
Gln Asn Ser Val Gly His Thr Leu Ile Thr Val Pro Val Met Ile
    2510              2515              2520
Val Ala Tyr Pro Pro Arg Ile Thr Asn Arg Pro Pro Arg Ser Ile
    2525              2530              2535
Val Thr Arg Thr Gly Ala Ala Phe Gln Leu His Cys Val Ala Leu
    2540              2545              2550
Gly Val Pro Lys Pro Glu Ile Thr Trp Glu Met Pro Asp His Ser
    2555              2560              2565
```

Figure 43 (Cont.)

Leu Leu Ser Thr Ala Ser Lys Glu Arg Thr His Gly Ser Glu Gln
　　 2570　　　　　　 2575　　　　　　　 2580

Leu His Leu Gln Gly Thr Leu Val Ile Gln Asn Pro Gln Thr Ser
　　 2585　　　　　　 2590　　　　　　　 2595

Asp Ser Gly Ile Tyr Lys Cys Thr Ala Lys Asn Pro Leu Gly Ser
　　 2600　　　　　　 2605　　　　　　　 2610

Asp Tyr Ala Ala Thr Tyr Ile Gln Val Ile
　　 2615　　　　　　 2620

Figure 44

```
CGAGAGACGA CAGAAGGTTA CGGCTGCGAG AAGACGACAG AAGGGTCCAG AAAAAGGAAA GTGCTGGAGG  70
GGAGTGGGGA CAAAAGCAGC GACCAAGTGA ATGTCACTTC AGTGACTGAG GCCAGGCAAA ACGCGCGGGA 140
AGGATTTTGT GTAGCTTGGG ACCCTTTCAT AGACACTGAT GACACGTTTA CGCAAAATAG AAATTTGAGG 210
AGAAACGCCT GGGCCTTCGG AAAGGAGTGA TTGATTAGTA CTTGCAAGTT TAGGTGACTT TAAGGAGAAC 280
TAACTAATGT ATACTATTGA GGGAGGAGGA AGAGCATTAC AGAGTTTCCA GCAGCAGCAG GAAAGCTTTG 350
GTTAATTTGG AAATGGATGA TAGCATTAAA ATAACAGAAG CGCCTCCAGG TCTCTGAAGC TTCAGTCCCC 420
CAGCTGAAAG CCAGAAAAGA CTAAGCCCAC TAAGCCTTTT GATCCCTTTG GAAGCAAAGA ACTTTCCTTC 490
CCTGGGGTGA AGACTCTCCT CAGAAGATTT CCTGTCTCTG CCTATGTTAC AAGAGGAATC AAAACCAAGA 560
CAGAAGAGCT CAGGATGCAG GTGAGAGGCA GGGAAGTCAG CGGCTTCTTG ATCTCCCTCA CTGCTGTCTG 630
CCTGGTGGTC ACCCCTGGGA GCAGGGCCTG TCCTCGCCGC TGTGCCTGCT ATGTGCCCAC AGAGGTGCAC 700
TGTACATTTC GGTACCTGAC CTCCATCCCA GATGGCATCC CGGCCAATGT GGAACGAATA AATTTAGGAT 770
ATAACAGCCT TACTAGATTG ACAGAAAACG ACTTTGATGG CCTGAGCAAA CTGGAGTTAC TCATGCTGCA 840
CAGTAATGGC ATTCACAGAG TCAGTGACAA GACCTTCTCG GGCTTGCAGT CCTTGCAGGT CTTAAAAATG 910
AGCTATAACA AAGTCCAAAT CATTCGGAAG GATACTTTCT ACGGACTCGG GAGCTTGGTC CGGTTGCACC 980
TGGATCACAA CAACATTGAA TTCATCAACC CTGAGGCCTT TTATGGACTT ACCTCGCTCC GCTTGGTACA 1050
TTTAGAAGGA AACCGGCTCA CAAAGCTCCA TCCAGACACA TTTGTCTCAT TAAGCTATCT CCAGATATTT 1120
AAAACCTCTT TCATTAAGTA CCTGTTCTTG TCTGATAACT TCCTGACCTC CCTCCCAAAA GAAATGGTCT 1190
CCTACATGCC AAACCTAGAA AGCCTGTATT TGCATGGAAA CCCATGGACC TGTGACTGCC ATTTAAAGTG 1260
GTTGTCTGAG TGGATGCAGG GAAACCCAGA TATAATAAAA TGCAAGAAAG ACAGAAGCTC TTCCAGTCCT 1330
CAGCAATGTC CCCTTTGCAT GAACCCCAGG ATCTCTAAAG GGAGACCCTT TGCTATGGTA CCATCTGGAG 1400
CTTTCCTATG TACAAAGCCA ACCATTGATC CATCACTGAA GTCAAAGAGC CTGGTTACTC AGGAGGACAA 1470
TGGATCTGCC TCCACCTCAC CTCAAGATTT CATAGAACCC TTTGGCTCCT TGTCTTTGAA CATGACAGAC 1540
CTGTCTGGAA ATAAGGCCGA CATGGTCTGT AGTATCCAAA AGCCATCAAG GACATCACCA ACTGCATTCA 1610
CTGAAGAAAA TGACTACATC ATGCTAAATG CGTCATTTTC CACAAATCTT GTGTGCAGTG TAGATTATAA 1680
TCACATCCAG CCAGTGTGGC AACTTCTGGC TTTATACAGT GACTCTCCTC TGATACTAGA AAGGAAGCCC 1750
CAGCTTACCG AGACTCCTTC ACTGTCTTCT AGATATAAAC AGGTGGCTCT TAGCCTGAA GACATTTTTA 1820
CCAGCATAGA GGCTGATGTC AGAGCAGACC CTTTTTGGTT CCAACAAGAA AAAATTGTCT TGCAGCTGAA 1890
CAGAACTGCC ACCACACTTA GCACATTACA GATCCAGTTT TCCACTGATG CTCAAATCGC TTTACCAAGG 1960
GCGGAGATGA GAGCGGAGAG ACTCAAATGG ACCATGATCC TGATGATGAA CAATCCCAAA CTGGAACGCA 2030
CTGTCCTGGT TGGCGGCACT ATTGCCCTGA GCTGTCCAGG CAAAGGCGAC CCTTCACCTC ACTTGGAATG 2100
```

Figure 44 (Cont.)

```
GCTTCTAGCT GATGGGAGTA AAGTGAGAGC CCCTTACGTT AGCGAGGATG GGCGAATCCT AATAGACAAA 2170
AATGGGAAGT TGGAACTGCA GATGGCTGAC AGCTTTGATG CAGGTCTTTA CCACTGCATA AGCACCAATG 2240
ATGCAGATGC GGATGTTCTC ACATACAGGA TAACTGTGGT AGAGCCCTAT GGAGAAAGCA CACATGACAG 2310
TGGAGTCCAG CACACAGTGG TTACGGGTGA GACGCTCGAC CTTCCATGCC TTTCCACGGG TGTTCCAGAT 2380
GCTTCTATTA GCTGGATTCT TCCAGGGAAC ACTGTGTTCT CTCAGCCATC AAGAGACAGG CAAATTCTTA 2450
ACAATGGGAC CTTAAGAATA TTACAGGTTA CGCCAAAAGA TCAAGGTCAT TACCAATGTG TGGCTGCCAA 2520
CCCATCAGGG GCCGACTTTT CCAGTTTTAA AGTTTCAGTT CAAAAGAAAG GCCAAAGGAT GGTTGAGCAT 2590
GACAGGGAGG CAGGTGGATC TGGACTTGGA GAACCCAACT CCAGTGTTTC CCTTAAGCAG CCAGCATCTT 2660
TGAAACTCTC TGCATCAGCT TTGACAGGGT CAGAGGCTGG AAAACAAGTC TCCGGTGTAC ATAGGAAGAA 2730
CAAACATAGA GACTTAATAC ATCGGCGGCG TGGGGATTCC ACGCTCCGGC GATTCAGGGA GCATAGGAGG 2800
CAGCTCCCTC TCTCTGCTCG GAGAATTGAC CCGCAACGCT GGGCAGCACT TCTAGAAAAA GCCAAAAAGA 2870
ATTCTGTGCC AAAAAAGCAA GAAAATACCA CAGTAAAGCC AGTGCCACTG GCTGTTCCCC TCGTGGAACT 2940
CACTGACGAG GAAAAGGATG CCTCTGGCAT GATTCCTCCA GATGAAGAAT TCATGGTTCT GAAAACTAAG 3010
GCTTCTGGTG TCCCAGGAAG GTCACCAACT GCTGACTCTG GACCAGTAAA TCATGGTTTT ATGACGAGTA 3080
TAGCTTCTGG CACAGAAGTC TCAACTGTGA ATCCACAAAC ACTACAATCT GAGCACCTTC CTGATTTCAA 3150
ATTATTTAGT GTAACAAACG GTACAGCTGT GACAAGAGT ATGAACCCAT CCATAGCAAG CAAAATAGAA 3220
GATACAACCA ACCAAAACCC AATCATTATC TTTCCATCAG TAGCTGAAAT TCGAGATTCT GCTCAGGCAG 3290
GAAGAGCATC TTCCCAAAGT GCACACCCTG TAACAGGGGG AAACATGGCT ACCTATGGCC ATACCAACAC 3360
ATATAGTAGC TTTACCAGCA AAGCCAGTAC AGTCTTGCAG CCAATAAATC CAACAGAAAG TTATGGACCT 3430
CAGATACCTA TTACAGGAGT CAGCAGACCT AGCAGTAGTG ACATCTCTTC TCACACTACT GCAGACCCTA 3500
GCTTCTCCAG TCACCCTTCA GGTTCACACA CCACTGCCTC GTCTTTATTT CACATTCCTA GAAACAACAA 3570
TACAGGTAAC TTCCCCTTGT CCAGGCACTT GGGAAGAGAG AGGACAATTT GGAGCAGAGG GAGAGTTAAA 3640
AACCCACATA GAACCCCAGT TCTCCGACGG CATAGACACA GGACTGTGAG GCCAGCAATC AAGGGACCTG 3710
CTAACAAAAA TGTGAGCCAA GTTCCAGCCA CAGAGTACCC TGGGATGTGC CACACATGTC CTTCCGCAGA 3780
GGGGCTCACA GTGGCTACTG CAGCACTGTC AGTTCCAAGT TCATCCCACA GTGCCCTCCC CAAAACTAAT 3850
AATGTTGGGG TCATAGCAGA AGAGTCTACC ACTGTGGTCA AGAAACCACT GTTACTATTT AAGGACAAAC 3920
AAAATGTAGA TATTGAGATA ATAACAACCA CTACAAAATA TTCCGGAGGG GAAAGTAACC ACGTGATTCC 3990
TACGGAAGCA AGCATGACTT CTGCTCCAAC ATCTGTATCC CTGGGGAAAT CTCCTGTAGA CAATAGTGGT 4060
CACCTGAGCA TGCCTGGGAC CATCCAAACT GGGAAAGATT CAGTGGAAAC AACACCACTT CCCAGCCCCC 4130
TCAGCACACC CTCAATACCA ACAAGCACAA AATTCTCAAA GAGGAAAACT CCCTTGCACC AGATCTTTGT 4200
AAATAACCAG AAGAAGGAGG GGATGTTAAA GAATCCATAT CAATTCGGTT TACAAAAGAA CCCAGCCGCA 4270
```

Figure 44 (Cont.)

```
AAGCTTCCCA AAATAGCTCC TCTTTTACCC ACAGGTCAGA GTTCCCCCTC AGATTCTACA ACTCTCTTGA   4340
CAAGTCCGCC ACCAGCTCTG TCTACAACAA TGGCTGCCAC TCAGAACAAG GGCACTGAAG TAGTATCAGG   4410
TGCCAGAAGT CTCTCAGCAG GGAAGAAGCA GCCCTTCACC AACTCCTCTC CAGTGCTTCC TAGCACCATA   4480
AGCAAGAGAT CTAATACATT AAACTTCTTG TCAACGGAAA CCCCCACAGT GACAAGTCCT ACTGCTACTG   4550
CATCTGTCAT TATGTCTGAA ACCCAACGAA CAAGATCCAA AGAAGCAAAA GACCAAATAA AGGGGCCTCG   4620
GAAGAACAGA AACAACGCAA ACACCACCCC CAGGCAGGTT TCTGGCTATA GTGCATACTC AGCTCTAACA   4690
ACAGCTGATA CCCCCTTGGC TTTCAGTCAT TCCCCACGAC AAGATGATGG TGGAAATGTA AGTGCAGTTG   4760
CTTATCACTC AACAACCTCT CTTCTGGCCA TAACTGAACT GTTGAGAAG TACACCCAGA CTTTGGGAAA   4830
TACAACAGCT TTGGAAACAA CGTTGTTGAG CAAATCACAG GAGAGTACCA CAGTGAAAAG AGCCTCAGAC   4900
ACACCACCAC CACTCCTCAG CAGTGGGGCG CCCCCAGTGC CCACTCCTTC CCCACCTCCT TTTACTAAGG   4970
GTGTGGTTAC AGACAGCAAA GTCACATCAG CTTTCCAGAT GACGTCAAAT AGAGTGGTCA CCATATATGA   5040
ATCTTCAAGG CACAATACAG ATCTGCAGCA ACCCTCAGCA GAGGCTAGCC CCAATCCTGA GATCATAACT   5110
GGAACCACTG ACTCTCCCTC TAATCTGTTT CCATCCACTT CTGTGCCAGC ACTAAGGGTA GATAAACCAC   5180
AGAATTCTAA ATGGAAGCCC TCTCCCTGGC CAGAACACAA ATATCAGCTC AAGTCATACT CCGAAACCAT   5250
TGAGAAGGGC AAAAGGCCAG CAGTAAGCAT GTCCCCCCAC CTCAGCCTTC CAGAGGCCAG CACTCATGCC   5320
TCACACTGGA ATACACAGAA GCATGCAGAA AAGAGTGTTT TTGATAAGAA ACCTGGTCAA AACCCAACTT   5390
CCAAACATCT GCCTTACGTC TCTCTACCTA AGACTCTATT GAAAAAGCCA AGAATAATTG GAGGAAAGGC   5460
TGCAAGCTTT ACAGTTCCAG CTAATTCAGA CGTTTTTCTT CCTTGTGAGG CTGTTGGAGA CCCACTGCCC   5530
ATCATCCACT GGACCAGAGT TTCATCAGGA CTTGAAATAT CCCAAGGGAC ACAGAAAAGC CGGTTCCACG   5600
TGCTTCCCAA TGGCACCTTG TCCATCCAGA GGGTCAGTAT TCAGGACCGT GGACAGTACC TGTGCTCTGC   5670
ATTTAATCCA CTGGGCGTAG ACCATTTTCA TGTCTCTTTG TCTGTGGTTT TTTACCCGGC AAGGATTTTG   5740
GACAGACATG TCAAGGAGAT CACAGTTCAC TTTGGAAGTA CTGTGGAACT AAAGTGCAGA GTGGAGGGTA   5810
TGCCGAGGCC TACGGTTTCC TGGATACTTG CAAACCAAAC GGTGGTCTCA GAAACGGCCA AGGGAAGCAG   5880
AAAGGTCTGG GTAACACCTG ATGGAACATT GATCATCTAT AATCTGAGTC TTTATGATCG TGGTTTTTAC   5950
AAGTGTGTGG CCAGCAACCC ATCTGGCCAG GATTCACTGT TGGTTAAGAT ACAAGTCATC ACAGCTCCCC   6020
CTGTCATTAT AGAGCAAAAG AGGCAAGCCA TCGTTGGGGT TTTAGGTGCA AGTTTGAAAC TGCCCTGCAC   6090
TGCAAAAGGA ACTCCCCAGC CTAGTGTTCA CTGGGTCCTT TATGATGGGA CTGAACTAAA ACCATTGCAG   6160
TTGACTCATT CCAGATTTTT CTTGTATCCA AATGGAACTC TGTATATAAG AAGCATCGCT CCTTCAGTGA   6230
GGGGCACTTA TGAGTGCATT GCCACCAGCT CCTCAGGCTC AGAGAGAAGG GTAGTGATTC TTACTGTGGA   6300
AGAGGGAGAG ACAATCCCCA GGATAGAAAC TGCCTCTCAG AAATGGACTG AGGTGAATTT GGGTGAGAAA   6370
TTACTACTGA ACTGCTCAGC TACTGGGGAT CCAAAGCCTA GAATAATCTG GAGGCTGCCA TCCAAGGCTG   6440
```

Figure 44 (Cont.)

| | | | | | | |
|---|---|---|---|---|---|---|
| TCATCGACCA | GTGGCACAGA | ATGGGCAGCC | GAATCCACGT | CTACCCAAAT | GGATCCTTGG | TGGTTGGGTC | 6510 |
| AGTGACGGAA | AAAGACGCTG | GTGACTACTT | ATGTGTGGCA | AGAAACAAAA | TGGGAGATGA | CCTAGTCCTG | 6580 |
| ATGCATGTCC | GCCTGAGATT | GACACCTGCC | AAAATTGAAC | AGAAGCAGTA | TTTTAAGAAG | CAAGTGCTCC | 6650 |
| ATGGGAAAGA | TTTCCAAGTT | GACTGCAAGG | CCTCTGGCTC | CCCTGTGCCT | GAGGTATCCT | GGAGTTTGCC | 6720 |
| TGATGGGACA | GTGCTCAACA | ATGTAGCCCA | AGCTGATGAC | AGTGGCTATA | GGACCAAGAG | GTACACCCTT | 6790 |
| TTCCACAATG | GAACCTTGTA | TTTCAACAAC | GTTGGGATGG | CAGAGGAAGG | AGATTATATC | TGCTCTGCCC | 6860 |
| AGAACACCTT | AGGGAAAGAT | GAGATGAAAG | TCCACCTAAC | AGTTCTAACA | GCCATCCCAC | GGATAAGGCA | 6930 |
| AAGCTACAAG | ACCACCATGA | GGCTCAGGGC | TGGAGAAACA | GCTGTCCTTG | ACTGCGAGGT | CACTGGGGAA | 7000 |
| CCGAAGCCCA | ATGTATTTTG | GTTGCTGCCT | TCCAACAATG | TCATTTCATT | CTCCAATGAC | AGGTTCACAT | 7070 |
| TTCATGCCAA | TAGAACTTTG | TCCATCCATA | AAGTGAAACC | ACTTGACTCT | GGGGACTATG | TGTGCGTAGC | 7140 |
| TCAGAATCCT | AGTGGGGATG | ACACTAAGAC | ATACAAACTG | GACATTGTCT | CTAAACCTCC | ATTAATCAAT | 7210 |
| GGCCTGTATG | CAAACAAGAC | TGTTATTAAA | GCCACAGCCA | TTCGGCACTC | CAAAAAATAC | TTTGACTGCA | 7280 |
| GAGCAGATGG | GATCCCATCT | TCCCAGGTCA | CGTGGATTAT | GCCAGGCAAT | ATTTTCCTCC | CAGCTCCATA | 7350 |
| CTTTGGAAGC | ACAGTCACGG | TCCATCCAAA | TGGAACCTTG | GAGATGAGGA | ACATCCGGCT | TTCTGACTCT | 7420 |
| GCGGACTTCA | CCTGTGTGGT | TCGGAGCGAG | GGAGGAGAGA | GTGTGTTGGT | AGTGCAGTTA | GAAGTCCTAG | 7490 |
| AAATGCTGAG | AAGACCAACA | TTCAGAAACC | CATTCAACGA | AAAAGTCATC | GCCCAAGCTG | GCAAGCCCGT | 7560 |
| AGCACTGAAC | TGCTCTGTGG | ATGGGAACCC | CCCACCTGAA | ATTACCTGGA | TCTTACCTGA | CGGCACACAG | 7630 |
| TTTGCTAACA | GACCACACAA | TTCCCCGTAT | CTGATGGCAG | GCAATGGCTC | TCTCATCCTT | TACAAAGCAA | 7700 |
| CTCGGAACAA | GTCAGGGAAG | TATCGCTGTG | CAGCCAGGAA | TAAGGTTGGC | TACATCGAGA | AACTCATCCT | 7770 |
| GTTAGAGATT | GGGCAGAAGC | CAGTCATTCT | GACATACGAA | CCAGGGATGG | TGAAGAGCGT | CAGTGGGGAA | 7840 |
| CCGTTATCAC | TGCATTGTGT | GTCTGATGGG | ATCCCCAAGC | CAAATGTCAA | GTGGACTACA | CCGGGTGGCC | 7910 |
| ATGTAATCGA | CAGGCCTCAA | GTGGATGGAA | AATACATACT | GCATGAAAAT | GGCACCCTGG | TCATCAAAGC | 7980 |
| AACAACAGCT | CACGACCAAG | GAAATTATAT | CTGTAGGGCT | CAAAACAGTG | TTGGCCAGGC | AGTTATTAGC | 8050 |
| GTGTCAGTGA | TGGTTGTGGC | CTACCCTCCC | CGAATCATAA | ACTACCTACC | CAGGAACATG | CTCAGGAGGA | 8120 |
| CAGGGGAAGC | CATGCAGCTC | CACTGTGTGG | CCTTGGGAAT | CCCCAAGCCA | AAAGTCACCT | GGGAGACGCC | 8190 |
| AAGACACTCC | CTGCTCTCAA | AAGCAACAGC | AAGAAAACCC | CATAGAAGTG | AGATGCTTCA | CCCACAAGGT | 8260 |
| ACGCTGGTCA | TTCAGAATCT | CCAAACCTCG | GATTCCGGAG | TCTATAAGTG | CAGAGCTCAG | AACCTACTTG | 8330 |
| GGACTGATTA | CGCAACAACT | TACATCCAGG | TACTCTGACA | GGAAGGGGGA | GACTAAAATT | CAACAGAAGT | 8400 |
| CCACATCCAC | AGGGTTTATT | TTTTGGAAGA | AGTTTAATCA | AAGGCAGCCA | TAGGCATGTA | AATGAGTCTG | 8470 |
| AATACATTTA | CAGTATTAAA | TTTACAATGG | ACATGCGATG | AGACTTGTAA | ATGAAAGCAT | TGTGAACTGA | 8540 |
| AACCGAGTCT | CTGTGGATCT | CAAAGCAAAC | TCTTAACTTA | AGGCACTTTG | ATTTTGCCAA | CAAATAATAA | 8610 |

Figure 44 (Cont.)

```
CAAACATTAA GAGAAAAAAA TGATCCACTA CGAAATAACA AACGGCTAAT GCACCTGAAT TCTCAGTAAA   8680
AAGACCTTTC TCTCGCTAAC AGTTGCCAGC TGCCTCGTGT CTGTTTCCTA CCAATGTCAC AAACATCGCA   8750
CACAGGGTGA ATGGAGTCAA CGGGAAAGAT TAAGTTTGCG GTCTGTGTAA ATCTCAATGT ACAAATATTC   8820
TGTCNCTGGT TTATAAACAT TTTGATAAAA CCGAAAAAAA AAAAAAAAA AAAAAAAAA AAA   8883
```

Figure 45

| | | | | | | | | | | | | | | |
|---|---|---|---|---|---|---|---|---|---|---|---|---|---|---|
|Met|Gln|Val|Arg|Gly|Arg|Glu|Val|Ser|Gly|Leu|Leu|Ile|Ser|Leu|Thr|
|1| | |5| | | | |10| | | | |15| | |

Ala Val Cys Leu Val Val Thr Pro Gly Ser Arg Ala Cys Pro Arg Arg
            20             25               30

Cys Ala Cys Tyr Val Pro Thr Glu Val His Cys Thr Phe Arg Tyr Leu
     35                40                 45

Thr Ser Ile Pro Asp Gly Ile Pro Ala Asn Val Glu Arg Ile Asn Leu
    50               55             60

Gly Tyr Asn Ser Leu Thr Arg Leu Thr Glu Asn Asp Phe Asp Gly Leu
65               70            75              80

Ser Lys Leu Glu Leu Leu Met Leu His Ser Asn Gly Ile His Arg Val
         85              90              95

Ser Asp Lys Thr Phe Ser Gly Leu Gln Ser Leu Gln Val Leu Lys Met
       100            105           110

Ser Tyr Asn Lys Val Gln Ile Ile Arg Lys Asp Thr Phe Tyr Gly Leu
     115             120           125

Gly Ser Leu Val Arg Leu His Leu Asp His Asn Asn Ile Glu Phe Ile
   130              135            140

Asn Pro Glu Ala Phe Tyr Gly Leu Thr Ser Leu Arg Leu Val His Leu
145           150          155             160

Glu Gly Asn Arg Leu Thr Lys Leu His Pro Asp Thr Phe Val Ser Leu
        165          170           175

Ser Tyr Leu Gln Ile Phe Lys Thr Ser Phe Ile Lys Tyr Leu Phe Leu
       180          185           190

Ser Asp Asn Phe Leu Thr Ser Leu Pro Lys Glu Met Val Ser Tyr Met
    195           200           205

Pro Asn Leu Glu Ser Leu Tyr Leu His Gly Asn Pro Trp Thr Cys Asp
210               215          220

Cys His Leu Lys Trp Leu Ser Glu Trp Met Gln Gly Asn Pro Asp Ile
225           230          235            240

Ile Lys Cys Lys Lys Asp Arg Ser Ser Ser Pro Gln Gln Cys Pro
          245          250          255

Leu Cys Met Asn Pro Arg Ile Ser Lys Gly Arg Pro Phe Ala Met Val
       260          265           270

Pro Ser Gly Ala Phe Leu Cys Thr Lys Pro Thr Ile Asp Pro Ser Leu
   275            280           285

Figure 45 (Cont.)

```
Lys Ser Lys Ser Leu Val Thr Gln Glu Asp Asn Gly Ser Ala Ser Thr
    290             295             300
Ser Pro Gln Asp Phe Ile Glu Pro Phe Gly Ser Leu Ser Leu Asn Met
305             310             315                 320
Thr Asp Leu Ser Gly Asn Lys Ala Asp Met Val Cys Ser Ile Gln Lys
            325             330                 335
Pro Ser Arg Thr Ser Pro Thr Ala Phe Thr Glu Glu Asn Asp Tyr Ile
            340             345             350
Met Leu Asn Ala Ser Phe Ser Thr Asn Leu Val Cys Ser Val Asp Tyr
        355             360             365
Asn His Ile Gln Pro Val Trp Gln Leu Leu Ala Leu Tyr Ser Asp Ser
    370             375             380
Pro Leu Ile Leu Glu Arg Lys Pro Gln Leu Thr Glu Thr Pro Ser Leu
385             390             395                 400
Ser Ser Arg Tyr Lys Gln Val Ala Leu Arg Pro Glu Asp Ile Phe Thr
            405             410             415
Ser Ile Glu Ala Asp Val Arg Ala Asp Pro Phe Trp Phe Gln Gln Glu
            420             425             430
Lys Ile Val Leu Gln Leu Asn Arg Thr Ala Thr Thr Leu Ser Thr Leu
            435             440             445
Gln Ile Gln Phe Ser Thr Asp Ala Gln Ile Ala Leu Pro Arg Ala Glu
    450             455             460
Met Arg Ala Glu Arg Leu Lys Trp Thr Met Ile Leu Met Met Asn Asn
465             470             475                 480
Pro Lys Leu Glu Arg Thr Val Leu Val Gly Gly Thr Ile Ala Leu Ser
            485             490             495
Cys Pro Gly Lys Gly Asp Pro Ser Pro His Leu Glu Trp Leu Leu Ala
            500             505             510
Asp Gly Ser Lys Val Arg Ala Pro Tyr Val Ser Glu Asp Gly Arg Ile
        515             520             525
Leu Ile Asp Lys Asn Gly Lys Leu Glu Leu Gln Met Ala Asp Ser Phe
        530             535             540
Asp Ala Gly Leu Tyr His Cys Ile Ser Thr Asn Asp Ala Asp Ala Asp
545             550             555                 560
Val Leu Thr Tyr Arg Ile Thr Val Val Glu Pro Tyr Gly Glu Ser Thr
            565             570             575
His Asp Ser Gly Val Gln His Thr Val Val Thr Gly Glu Thr Leu Asp
            580             585             590
```

Figure 45 (Cont.)

```
Leu Pro Cys Leu Ser Thr Gly Val Pro Asp Ala Ser Ile Ser Trp Ile
        595                 600                 605

Leu Pro Gly Asn Thr Val Phe Ser Gln Pro Ser Arg Asp Arg Gln Ile
        610                 615                 620

Leu Asn Asn Gly Thr Leu Arg Ile Leu Gln Val Thr Pro Lys Asp Gln
625                 630                 635                 640

Gly His Tyr Gln Cys Val Ala Ala Asn Pro Ser Gly Ala Asp Phe Ser
                645                 650                 655

Ser Phe Lys Val Ser Val Gln Lys Lys Gly Gln Arg Met Val Glu His
                660                 665                 670

Asp Arg Glu Ala Gly Gly Ser Gly Leu Gly Glu Pro Asn Ser Ser Val
        675                 680                 685

Ser Leu Lys Gln Pro Ala Ser Leu Lys Leu Ser Ala Ser Ala Leu Thr
        690                 695                 700

Gly Ser Glu Ala Gly Lys Gln Val Ser Gly Val His Arg Lys Asn Lys
705                 710                 715                 720

His Arg Asp Leu Ile His Arg Arg Arg Gly Asp Ser Thr Leu Arg Arg
                725                 730                 735

Phe Arg Glu His Arg Arg Gln Leu Pro Leu Ser Ala Arg Arg Ile Asp
                740                 745                 750

Pro Gln Arg Trp Ala Ala Leu Leu Glu Lys Ala Lys Lys Asn Ser Val
        755                 760                 765

Pro Lys Lys Gln Glu Asn Thr Thr Val Lys Pro Val Pro Leu Ala Val
        770                 775                 780

Pro Leu Val Glu Leu Thr Asp Glu Glu Lys Asp Ala Ser Gly Met Ile
785                 790                 795                 800

Pro Pro Asp Glu Glu Phe Met Val Leu Lys Thr Lys Ala Ser Gly Val
                805                 810                 815

Pro Gly Arg Ser Pro Thr Ala Asp Ser Gly Pro Val Asn His Gly Phe
                820                 825                 830

Met Thr Ser Ile Ala Ser Gly Thr Glu Val Ser Thr Val Asn Pro Gln
        835                 840                 845

Thr Leu Gln Ser Glu His Leu Pro Asp Phe Lys Leu Phe Ser Val Thr
        850                 855                 860

Asn Gly Thr Ala Val Thr Lys Ser Met Asn Pro Ser Ile Ala Ser Lys
865                 870                 875                 880

Ile Glu Asp Thr Thr Asn Gln Asn Pro Ile Ile Phe Pro Ser Val
                885                 890                 895
```

Figure 45 (Cont.)

```
Ala Glu Ile Arg Asp Ser Ala Gln Ala Gly Arg Ala Ser Ser Gln Ser
            900                 905                 910

Ala His Pro Val Thr Gly Gly Asn Met Ala Thr Tyr Gly His Thr Asn
        915                 920                 925

Thr Tyr Ser Ser Phe Thr Ser Lys Ala Ser Thr Val Leu Gln Pro Ile
    930                 935                 940

Asn Pro Thr Glu Ser Tyr Gly Pro Gln Ile Pro Ile Thr Gly Val Ser
945                 950                 955                 960

Arg Pro Ser Ser Ser Asp Ile Ser Ser His Thr Thr Ala Asp Pro Ser
            965                 970                 975

Phe Ser Ser His Pro Ser Gly Ser His Thr Thr Ala Ser Ser Leu Phe
            980                 985                 990

His Ile Pro Arg Asn Asn Asn Thr Gly Asn Phe Pro Leu Ser Arg His
        995                 1000                1005

Leu Gly Arg Glu Arg Thr Ile Trp Ser Arg Gly Arg Val Lys Asn
    1010                1015                1020

Pro His Arg Thr Pro Val Leu Arg Arg His Arg His Arg Thr Val
    1025                1030                1035

Arg Pro Ala Ile Lys Gly Pro Ala Asn Lys Asn Val  Ser Gln Val
    1040                1045                1050

Pro Ala Thr Glu Tyr Pro Gly Met Cys His Thr Cys Pro Ser Ala
    1055                1060                1065

Glu Gly Leu Thr Val Ala Thr Ala Ala Leu Ser Val Pro Ser Ser
    1070                1075                1080

Ser His Ser Ala Leu Pro Lys Thr Asn Asn Val Gly Val Ile Ala
    1085                1090                1095

Glu Glu Ser Thr Thr Val Val Lys Lys Pro Leu Leu Leu Phe Lys
    1100                1105                1110

Asp Lys Gln Asn Val Asp Ile Glu Ile Ile Thr Thr Thr Thr Lys
    1115                1120                1125

Tyr Ser Gly Gly Glu Ser Asn His Val Ile Pro Thr Glu Ala Ser
    1130                1135                1140

Met Thr Ser Ala Pro Thr Ser Val Ser Leu Gly Lys Ser Pro Val
    1145                1150                1155

Asp Asn Ser Gly His Leu Ser Met Pro Gly Thr Ile Gln Thr Gly
    1160                1165                1170
```

Figure 45 (Cont.)

```
Lys Asp Ser Val Glu Thr Thr Pro Leu Pro Ser Pro Leu Ser Thr
    1175            1180            1185

Pro Ser Ile Pro Thr Ser Thr Lys Phe Ser Lys Arg Lys Thr Pro
    1190            1195            1200

Leu His Gln Ile Phe Val Asn Asn Gln Lys Lys Glu Gly Met Leu
    1205            1210            1215

Lys Asn Pro Tyr Gln Phe Gly Leu Gln Lys Asn Pro Ala Ala Lys
    1220            1225            1230

Leu Pro Lys Ile Ala Pro Leu Leu Pro Thr Gly Gln Ser Ser Pro
    1235            1240            1245

Ser Asp Ser Thr Thr Leu Leu Thr Ser Pro Pro Pro Ala Leu Ser
    1250            1255            1260

Thr Thr Met Ala Ala Thr Gln Asn Lys Gly Thr Glu Val Val Ser
    1265            1270            1275

Gly Ala Arg Ser Leu Ser Ala Gly Lys Lys Gln Pro Phe Thr Asn
    1280            1285            1290

Ser Ser Pro Val Leu Pro Ser Thr Ile Ser Lys Arg Ser Asn Thr
    1295            1300            1305

Leu Asn Phe Leu Ser Thr Glu Thr Pro Thr Val Thr Ser Pro Thr
    1310            1315            1320

Ala Thr Ala Ser Val Ile Met Ser Glu Thr Gln Arg Thr Arg Ser
    1325            1330            1335

Lys Glu Ala Lys Asp Gln Ile Lys Gly Pro Arg Lys Asn Arg Asn
    1340            1345            1350

Asn Ala Asn Thr Thr Pro Arg Gln Val Ser Gly Tyr Ser Ala Tyr
    1355            1360            1365

Ser Ala Leu Thr Thr Ala Asp Thr Pro Leu Ala Phe Ser His Ser
    1370            1375            1380

Pro Arg Gln Asp Asp Gly Gly Asn Val Ser Ala Val Ala Tyr His
    1385            1390            1395

Ser Thr Thr Ser Leu Leu Ala Ile Thr Glu Leu Phe Glu Lys Tyr
    1400            1405            1410

Thr Gln Thr Leu Gly Asn Thr Thr Ala Leu Glu Thr Thr Leu Leu
    1415            1420            1425

Ser Lys Ser Gln Glu Ser Thr Thr Val Lys Arg Ala Ser Asp Thr
    1430            1435            1440

Pro Pro Pro Leu Leu Ser Ser Gly Ala Pro Pro Val Pro Thr Pro
    1445            1450            1455
```

Figure 45 (Cont.)

```
Ser Pro Pro Pro Phe Thr Lys Gly Val Val Thr Asp Ser Lys Val
    1460            1465            1470

Thr Ser Ala Phe Gln Met Thr Ser Asn Arg Val Val Thr Ile Tyr
    1475            1480            1485

Glu Ser Ser Arg His Asn Thr Asp Leu Gln Gln Pro Ser Ala Glu
    1490            1495            1500

Ala Ser Pro Asn Pro Glu Ile Ile Thr Gly Thr Thr Asp Ser Pro
    1505            1510            1515

Ser Asn Leu Phe Pro Ser Thr Ser Val Pro Ala Leu Arg Val Asp
    1520            1525            1530

Lys Pro Gln Asn Ser Lys Trp Lys Pro Ser Pro Trp Pro Glu His
    1535            1540            1545

Lys Tyr Gln Leu Lys Ser Tyr Ser Glu Thr Ile Glu Lys Gly Lys
    1550            1555            1560

Arg Pro Ala Val Ser Met Ser Pro His Leu Ser Leu Pro Glu Ala
    1565            1570            1575

Ser Thr His Ala Ser His Trp Asn Thr Gln Lys His Ala Glu Lys
    1580            1585            1590

Ser Val Phe Asp Lys Lys Pro Gly Gln Asn Pro Thr Ser Lys His
    1595            1600            1605

Leu Pro Tyr Val Ser Leu Pro Lys Thr Leu Leu Lys Lys Pro Arg
    1610            1615            1620

Ile Ile Gly Gly Lys Ala Ala Ser Phe Thr Val Pro Ala Asn Ser
    1625            1630            1635

Asp Val Phe Leu Pro Cys Glu Ala Val Gly Asp Pro Leu Pro Ile
    1640            1645            1650

Ile His Trp Thr Arg Val Ser Ser Gly Leu Glu Ile Ser Gln Gly
    1655            1660            1665

Thr Gln Lys Ser Arg Phe His Val Leu Pro Asn Gly Thr Leu Ser
    1670            1675            1680

Ile Gln Arg Val Ser Ile Gln Asp Arg Gly Gln Tyr Leu Cys Ser
    1685            1690            1695

Ala Phe Asn Pro Leu Gly Val Asp His Phe His Val Ser Leu Ser
    1700            1705            1710

Val Val Phe Tyr Pro Ala Arg Ile Leu Asp Arg His Val Lys Glu
    1715            1720            1725

Ile Thr Val His Phe Gly Ser Thr Val Glu Leu Lys Cys Arg Val
    1730            1735            1740
```

Figure 45 (Cont.)

```
Glu Gly Met Pro Arg Pro Thr Val Ser Trp Ile Leu Ala Asn Gln
    1745            1750                1755
Thr Val Val Ser Glu Thr Ala Lys Gly Ser Arg Lys Val Trp Val
    1760            1765                1770
Thr Pro Asp Gly Thr Leu Ile Ile Tyr Asn Leu Ser Leu Tyr Asp
    1775            1780                1785
Arg Gly Phe Tyr Lys Cys Val Ala Ser Asn Pro Ser Gly Gln Asp
    1790            1795                1800
Ser Leu Leu Val Lys Ile Gln Val Ile Thr Ala Pro Pro Val Ile
    1805            1810                1815
Ile Glu Gln Lys Arg Gln Ala Ile Val Gly Val Leu Gly Gly Ser
    1820            1825                1830
Leu Lys Leu Pro Cys Thr Ala Lys Gly Thr Pro Gln Pro Ser Val
    1835            1840                1845
His Trp Val Leu Tyr Asp Gly Thr Glu Leu Lys Pro Leu Gln Leu
    1850            1855                1860
Thr His Ser Arg Phe Phe Leu Tyr Pro Asn Gly Thr Leu Tyr Ile
    1865            1870                1875
Arg Ser Ile Ala Pro Ser Val Arg Gly Thr Tyr Glu Cys Ile Ala
    1880            1885                1890
Thr Ser Ser Ser Gly Ser Glu Arg Arg Val Val Ile Leu Thr Val
    1895            1900                1905
Glu Glu Gly Glu Thr Ile Pro Arg Ile Glu Thr Ala Ser Gln Lys
    1910            1915                1920
Trp Thr Glu Val Asn Leu Gly Glu Lys Leu Leu Leu Asn Cys Ser
    1925            1930                1935
Ala Thr Gly Asp Pro Lys Pro Arg Ile Ile Trp Arg Leu Pro Ser
    1940            1945                1950
Lys Ala Val Ile Asp Gln Trp His Arg Met Gly Ser Arg Ile His
    1955            1960                1965
Val Tyr Pro Asn Gly Ser Leu Val Val Gly Ser Val Thr Glu Lys
    1970            1975                1980
Asp Ala Gly Asp Tyr Leu Cys Val Ala Arg Asn Lys Met Gly Asp
    1985            1990                1995
Asp Leu Val Leu Met His Val Arg Leu Arg Leu Thr Pro Ala Lys
    2000            2005                2010
Ile Glu Gln Lys Gln Tyr Phe Lys Lys Gln Val Leu His Gly Lys
    2015            2020                2025
```

Figure 45 (Cont.)

```
Asp Phe Gln Val Asp Cys Lys Ala Ser Gly Ser Pro Val Pro Glu
    2030            2035                2040

Val Ser Trp Ser Leu Pro Asp Gly Thr Val Leu Asn Asn Val Ala
    2045            2050                2055

Gln Ala Asp Asp Ser Gly Tyr Arg Thr Lys Arg Tyr Thr Leu Phe
    2060            2065                2070

His Asn Gly Thr Leu Tyr Phe Asn Asn Val Gly Met Ala Glu Glu
    2075            2080                2085

Gly Asp Tyr Ile Cys Ser Ala Gln Asn Thr Leu Gly Lys Asp Glu
    2090            2095                2100

Met Lys Val His Leu Thr Val Leu Thr Ala Ile Pro Arg Ile Arg
    2105            2110                2115

Gln Ser Tyr Lys Thr Thr Met Arg Leu Arg Ala Gly Glu Thr Ala
    2120            2125                2130

Val Leu Asp Cys Glu Val Thr Gly Glu Pro Lys Pro Asn Val Phe
    2135            2140                2145

Trp Leu Leu Pro Ser Asn Asn Val Ile Ser Phe Ser Asn Asp Arg
    2150            2155                2160

Phe Thr Phe His Ala Asn Arg Thr Leu Ser Ile His Lys Val Lys
    2165            2170                2175

Pro Leu Asp Ser Gly Asp Tyr Val Cys Val Ala Gln Asn Pro Ser
    2180            2185                2190

Gly Asp Asp Thr Lys Thr Tyr Lys Leu Asp Ile Val Ser Lys Pro
    2195            2200                2205

Pro Leu Ile Asn Gly Leu Tyr Ala Asn Lys Thr Val Ile Lys Ala
    2210            2215                2220

Thr Ala Ile Arg His Ser Lys Lys Tyr Phe Asp Cys Arg Ala Asp
    2225            2230                2235

Gly Ile Pro Ser Ser Gln Val Thr Trp Ile Met Pro Gly Asn Ile
    2240            2245                2250

Phe Leu Pro Ala Pro Tyr Phe Gly Ser Arg Val Thr Val His Pro
    2255            2260                2265

Asn Gly Thr Leu Glu Met Arg Asn Ile Arg Leu Ser Asp Ser Ala
    2270            2275                2280

Asp Phe Thr Cys Val Val Arg Ser Glu Gly Gly Glu Ser Val Leu
    2285            2290                2295

Val Val Gln Leu Glu Val Leu Glu Met Leu Arg Arg Pro Thr Phe
    2300            2305                2310
```

Figure 45 (Cont.)

```
Arg Asn Pro Phe Asn Glu Lys Val Ile Ala Gln Ala Gly Lys Pro
    2315            2320            2325

Val Ala Leu Asn Cys Ser Val Asp Gly Asn Pro Pro Pro Glu Ile
    2330            2335            2340

Thr Trp Ile Leu Pro Asp Gly Thr Gln Phe Ala Asn Arg Pro His
    2345            2350            2355

Asn Ser Pro Tyr Leu Met Ala Gly Asn Gly Ser Leu Ile Leu Tyr
    2360            2365            2370

Lys Ala Thr Arg Asn Lys Ser Gly Lys Tyr Arg Cys Ala Ala Arg
    2375            2380            2385

Asn Lys Val Gly Tyr Ile Glu Lys Leu Ile Leu Leu Glu Ile Gly
    2390            2395            2400

Gln Lys Pro Val Ile Leu Thr Tyr Glu Pro Gly Met Val Lys Ser
    2405            2410            2415

Val Ser Gly Glu Pro Leu Ser Leu His Cys Val Ser Asp Gly Ile
    2420            2425            2430

Pro Lys Pro Asn Val Lys Trp Thr Thr Pro Gly Gly His Val Ile
    2435            2440            2445

Asp Arg Pro Gln Val Asp Gly Lys Tyr Ile Leu His Glu Asn Gly
    2450            2455            2460

Thr Leu Val Ile Lys Ala Thr Thr Ala His Asp Gln Gly Asn Tyr
    2465            2470            2475

Ile Cys Arg Ala Gln Asn Ser Val Gly Gln Ala Val Ile Ser Val
    2480            2485            2490

Ser Val Met Val Val Ala Tyr Pro Pro Arg Ile Ile Asn Tyr Leu
    2495            2500            2505

Pro Arg Asn Met Leu Arg Arg Thr Gly Glu Ala Met Gln Leu His
    2510            2515            2520

Cys Val Ala Leu Gly Ile Pro Lys Pro Lys Val Thr Trp Glu Thr
    2525            2530            2535

Pro Arg His Ser Leu Leu Ser Lys Ala Thr Ala Arg Lys Pro His
    2540            2545            2550

Arg Ser Glu Met Leu His Pro Gln Gly Thr Leu Val Ile Gln Asn
    2555            2560            2565

Leu Gln Thr Ser Asp Ser Gly Val Tyr Lys Cys Arg Ala Gln Asn
    2570            2575            2580

Leu Leu Gly Thr Asp Tyr Ala Thr Thr Tyr Ile Gln Val Leu
    2585            2590            2595
```

GENES ASSOCIATED WITH MECHANICAL STRESS, EXPRESSION PRODUCTS THEREFROM, AND USES THEREOF

CROSS-REFERENCE TO RELATED APPLICATIONS

The present application is a continuation-in-part of International Application No. PCT/US01/46400, filed Dec. 4, 2001, the entire contents of which are hereby incorporated by reference, and also a continuation-in-part of U.S. patent application Ser. No. 09/312,216, filed May 14, 1999, now abandoned the entire contents of which are also hereby incorporated by reference. Each document or reference cited in those applications is hereby expressly incorporated herein by reference. Documents or references are also cited in the following text, and these documents or references ("herein-cited documents or references"), as well as each document or reference cited in each of the herein-cited documents or references, are hereby expressly incorporated herein by reference.

FIELD OF THE INVENTION

This invention relates to mechanical stress induced genes and their functional equivalents, probes therefor, tests to identify such genes, expression products of such genes, uses for such genes and expression products, e.g., in diagnosis (for instance risk determination), treatment, prevention, or control, of osteoporosis or factors or processes which lead to osteoporosis, osteopenia, osteopetrosis, osteosclerosis, osteoarthritis, periodontosis and bone fractures; and, to diagnosis, treatment, prevention, or control methods or processes, as well as compositions therefor and methods or processes for making and using such compositions, and receptors for such expression products and methods or processes for obtaining and using such receptors.

BACKGROUND OF THE INVENTION

Bone is composed of a collagen-rich organic matrix impregnated with mineral, largely calcium and phosphate. Two major forms of bone exist, compact cortical bone forms the external envelopes of the skeleton and trabecular or medullary bone forms plates that traverse the internal cavities of the skeleton. The responses of these two forms to metabolic influences and their susceptibility to fracture differ.

Bone undergoes continuous remodeling (turnover, renewal) throughout life. Mechanical and electrical forces, hormones and local regulatory factors influence remodeling. Bone is renewed by two opposing activities that are coupled in time and space. Parfitt (1979) Calcif. Tis. Int. 28:1-5. These activities, resorption and formation, are contained within a temporary anatomic structure known as a bone-remodeling unit. Parfitt (1981) Res. Staff Physic. Dec.:60-72. Within a given bone-remodeling unit, old bone is resorbed by osteoclasts. The resorbed cavity created by osteoclasts is subsequently filled with new bone by osteoblasts, synthesizing bone organic matrix.

Peak bone mass is mainly genetically determined, though dietary factors and physical activity can have positive effects. Peak bone mass is attained at the point when skeletal growth ceases, after which time bone loss starts.

In contrast to the positive balance that occurs during growth, in osteoporosis, the resorbed cavity is not completely refilled by bone. Parfitt (1988), Osteoporosis: Etiology, Diagnosis, and Management (Riggs and Melton, eds.) Raven Press, New York, pp. 74-93. Osteoporosis, or porous bone, is a progressive and chronic disease characterized by low bone mass and structural deterioration of bone tissue, leading to bone fragility and an increased susceptibility to fractures of the hip, spine, and wrist (diminishing bone strength).

Bone loss occurs without symptoms. The Consensus Development Conference ((1993) Am. J. Med. 94:646-650) defined osteoporosis as "a systemic skeletal disease characterized by low bone mass and microarchitectural deterioration of bone tissue, with a consequent increase in bone fragility and susceptibility to fracture."

Common types of osteoporosis include postmenopausal osteoporosis; and senile osteoporosis, which generally occurs in later life, e.g., 70+ years. See, e.g., U.S. Pat. No. 5,691,153. Osteoporosis is estimated to affect more than 25 million people in the United States (Rosen (1997) Calcif. Tis. Int. 60:225-228); and, at least one estimate asserts that osteoporosis affects 1 in 3 women. Keen et al. (1997) Drugs Aging 11:333-337. Moreover, life expectancy has increased, and in the western world, 17% of women are now over 50 years of age: a woman can expect to live one third of her life after menopause. Thus, some estimate that 1 out of every 2 women and 1 out of 5 men will eventually develop osteoporosis; and, that 75 million people in the U.S., Japan and Europe have osteoporosis. The World Summit of Osteoporosis Societies estimates that more than 200 million people worldwide are afflicted with the disease. The actual incidence of the disease is difficult to estimate since the condition is often asymptomatic until a bone fracture occurs. It is believed that there are over 1.5 million osteoporosis-associated bone fractures per year in the U.S. Of these, 300,000 are hip fractures that usually require hospitalization and surgery and may result in lengthy or permanent disability or even death. See a minireview by Spangler et al. "The Genetic Component of Osteoporosis" (1997) Cambridge Scientific Abstracts".

Osteoporosis is also a major health problem in virtually all societies. Eisman (1996); Wark (1996) Maturitas 23:193-207; and U.S. Pat. No. 5,834,200. There is a 20-30% mortality rate related to hip fractures in elderly women (U.S. Pat. No. 5,691,153); and, such a patient with a hip fracture has a 10-15% greater chance of dying than others of the same age. Further, although men suffer fewer hip injuries than women, men are 25% more likely than women to die within one year of the injury. See Spangler et al., supra. Also, about 20% of the patients who lived inependently before a hip fracture remain confined in a long-term health care facility one year later. The treatment of osteoporosis and related fractures costs over $10 billion annually.

Osteoporosis treatment helps stop further bone loss and fractures. Common therapeutics include HRT (hormone replacement therapy), bisphosphonates, e.g., alendronate (Fosamax), estrogen and estrogen receptor modulators, progestin, calcitonin, and vitamin D. While there may be numerous factors that determine whether any particular person will develop osteoporosis, a step towards prevention, control or treatment of osteoporosis is determining whether one is at risk for osteoporosis. Genetic factors also play an important role in the pathogenesis of osteoporosis. Ralston (1997); see also Keen et al. (1997); Eisman (1996); Rosen (1997); Cole (1998); Johnston et al. (1995) Bone 17(2 Suppl)19S-22S; Gong et al. (1996) Am. J. Hum. Genet. 59:146-151; and Wasnich (1996) Bone 18(3 Suppl):179S-183S. Some attribute 50-60% of total bone variation (bone mineral density: "BMD"), depending upon the bone area, to genetic effects. Livshits et al. (1996) Hum. Biol. 68:540-554. However, up to 85%-90% of the variance in bone mineral density may be genetically determined.

Studies have shown from family histories, twin studies, and racial factors, that there may be a predisposition for osteoporosis. Jouanny et al. (1995) Arthritis Rheum. 38:61-67; Garnero et al. (1996) J. Clin. Endrocrinol. Metab. 81:140-146;Cummings (1996) Bone 18(3 Suppl):165S-167S; and Lonzer et al. (1996) Clin. Pediatr. 35:185-189. Several candidate genes may be involved in this, most probably multigenic, process.

Cytokines are powerful regulators of bone resorption and formation under control of estrogen/testosterone, parathyroid hormone and 1,25(OH)2D3. Some cytokines primarily enhance osteoclastic bone resorption e.g. IL-1 (interleukin-1), TNF (tumor necrosis factor) and IL-6 (interleukin-6); while others primarily stimulate bone formation e.g. TGF-β (transforming growth factor-β), IGF (insulin-like growth factor) and PDGF (platelet derived growth factor).

There is need for clinical and epidemiological research for the prevention and treatment of osteoporosis for gaining greater knowledge of factors controlling bone cell activity and regulation of bone mineral and matrix formation and remodeling.

Bone develops via a number of processes. Mesenchymal cells can differentiate directly into bone, as occurs in the flat bones of the craniofacial skeleton; this process is termed intramembranous ossification. Alternatively, cartilage provides a template for bone morphogenesis, as occurs in the majority of human bones. The cartilage template is replaced by bone in a process known as endochondral ossification. Reddi (1981) Collagen Rel. Res. 1:209-226. Bone is also continuously modeled during growth and development and remodeled throughout the life of the organism in response to physical and chemical signals. Development and maintenance of cartilage and bone tissue during embryogenesis and throughout the lifetime of vertebrates is very complex. It is widely accepted that a multitude of factors, from systemic hormones to local regulatory factors such as the members of the TGF-β superfamily, cytokines and prostaglandins, act in concert to regulate the continuous processes of bone formation and bone resorption. Disturbance of the balance between osteoblastic bone deposition and osteoclastic bone resorption is responsible for many skeletal diseases.

Diseases of bone loss are a major public health problem especially for women in all Western communities. The most common cause of osteopenia is osteoporosis; other causes include osteomalacia and bone disease related to hyperparathyroidism. Osteopenia has been defined as the appearance of decreased bone mineral content on radiography, but the term more appropriately refers to a phase in the continuum from decreased bone mass to fractures and infirmity.

It is estimated that 30 million Americans are at risk for osteoporosis, the most common among these diseases, and there are probably 100 million people similarly at risk worldwide. Melton (1995) Bone Min. Res. 10:175. These numbers are growing as the proportion of the elderly in the world population increases. Despite recent successes with drugs that inhibit bone resorption, there is a clear need for specific anabolic agents that will considerably increase bone formation in people who have already suffered substantial bone loss. There are no such drugs currently approved.

Mechanical stimulation induces new bone formation in vivo and increases osteoblastic differentiation and metabolic activity in culture. Mechanotransduction in bone tissue involves several steps: 1) mechanochemical transduction of the signal; 2) cell-to-cell signaling; and 3) increased number and activity of osteoblasts. Cell-to-cell signaling after mechanical stimulus involves prostaglandins, especially those produced by COX-2, and nitric oxide. Prostaglandins induce new bone formation by promoting both proliferation and differentiation of osteoprogenitor cells.

OBJECTS AND SUMMARY OF THE INVENTION

In a search for agents that enhance osteoblast proliferation/differentiation and bone formation, mechanical force was employed as an osteogenesis inducer and a proprietary gene discovery methodology was carried out to detect genes that are specifically expressed in very early osteo-, chondro-progenitor cells.

The present invention provides human mechanical stress induced genes and their functional equivalents, expression products of such genes, uses for such genes and expression products for treatment, prevention, control, of osteoporosis or factors or processes which are involved in bone diseases including, but not limited to, osteoporosis, osteopenia, osteopetrosis, osteosclerosis, osteoarthritis, periodontosis and bone fracture. The invention further provides diagnostic, treatment, prevention, control methods or processes as well as compositions.

The invention additionally provides an isolated nucleic acid molecule, and the complement thereof, encoding the protein 608 or a functional portion thereof or a polypeptide, which is at least substantially homologous thereto. The invention encompasses an isolated nucleic acid molecule encoding human protein 608 (or "OCP") or a functional portion thereof.

The invention further encompasses a method for preventing, treating or controlling osteoporosis or low bone density or other factors associated with, causing or contributing to bone diseases including, but not limited to, osteopenia, osteopetrosis, osteosclerosis, osteoarthritis, periodontosis or symptoms thereof, or other conditions involving mechanical stress or a lack thereof, by administering to a subject in need thereof, a polypeptide or portion thereof provided herein; and accordingly, the invention comprehends uses of polypeptides in preparing a medicament or therapy for such prevention, treatment or control.

The invention also comprehends a method for preventing, treating or controlling osteoporosis or low bone density or other factors causing or contributing to osteoporosis or symptoms thereof or other conditions involving mechanical stress or a lack thereof, by administering a composition comprising a gene or functional portion thereof, the expression product of that gene or a functional portion thereof, an antibody or portion thereof elicited by such an expression product or portion thereof, and, the invention thus further comprehends uses of such genes, expression products, antibodies, portions thereof, in the preparation of a medicament or therapy for such control, prevention or treatment.

Analogously with the OCP-related description above, the invention further encompasses methods of use of Adlican and a novel polypeptide Adlican-2 as described herein for any use of OCP. The Adlican gene, or Adlican-2 gene, or functional portions thereof, can likewise be used for any purpose described herein for an OCP gene. The invention further encompasses compositions comprising a physiologically acceptable excipient and at least one of Adlican, the Adlican gene and antibodies specific to Adlican, and at least one of Adlican-2, the Adlican-2 gene and antibodies specific to Adlican-2.

The invention additionally provides receptors for expression products of human mechanical stress induced genes and their functional equivalents, such as OCP and Adlican, and methods or processes for obtaining and using such receptors. The invention also provides methods of using such receptors in assays, for instance for identifying proteins or polypeptides that bind to, associate with or block the receptors, and for testing the effects of such polypeptides. These and other embodiments are disclosed or are obvious from and encompassed by, the Detailed Description which follows the Brief Description of the Figures below.

BRIEF DESCRIPTION OF THE FIGURES

The following Detailed Description, given by way of example, but not intended to limit the invention to specific embodiments described, may be understood in conjunction with the accompanying Figures, in which FIG. 1 shows the rat 608 cDNA sequence (SEQ ID NO:1).

FIG. 3 shows the OCP rat protein amino acid sequence (SEQ ID NO:2).

FIG. 4 shows the mouse OCP exon and intron map.

FIG. 6 shows the human OCP exon and intron list.

FIG. 7 shows the OCP human cDNA sequence (predicted coding region) (nucleotides 1-7796 of SEQ ID NO:6).

FIGS. 8A-8D show the percent identity between FIG. 8A. rat protein/human protein; FIG. 8B. rat protein/mouse protein; FIG. 8C. rat cDNA/human cDNA; and FIG. 8D. rat cDNA/mouse cDNA, based on the OCP human cDNA sequence of FIG. 7.

FIG. 9 shows the partial mouse OCP protein amino acid sequence (236 aa) (SEQ ID NO:15).

FIG. 10 shows the OCP human protein amino acid sequence (2587 aa) (SEQ ID NO:16), based on the OCP human cDNA sequence of FIG. 7.

FIGS. 19A-B show photomicrographs of the highly vascularized endosteal tissue. This was developed in reaction to the wire insertion (area 3 on FIG. 16), FIG. 19A. brightfield and FIG. 19B. darkfield. This tissue contains many cells expressing the OCP gene.

FIG. 26 shows the sequences of the primer (SEQ ID NO:19) and QB3 (CMF608) (SEQ ID NO:20).

FIG. 27 shows the Adlican amino acid sequence (SEQ ID NO: 21).

FIG. 28 shows the Adlican DNA sequence (SEQ ID NO: 22).

FIG. 29 shows the predicted DNA sequence of the coding region-ORF of human OCP (SEQ ID NO: 23).

FIG. 30 shows the predicted amino acid sequence corresponding to the predicted coding region-ORF of human OCP (SEQ ID NO: 24).

FIG. 31 shows the sequence of the N-terminal 663 amino acid fragment derived from the OCP rat protein (SEQ ID NO: 25).

FIG. 34 shows the physical sequence of the 5' fragment (A) cloned into pBluescript KS to NotI (5') and HindIII (3') sites. Fragment A is comprised of the 5' region (2440 bp) of the complete human OCP sequence and includes, in addition, at the 5' end, 21 nucleotides of the β-actin "Kozak" region (SEQ ID NO:26).

FIG. 36 shows the physical sequence of the middle fragment (B) cloned into pBluescript KS to HindIII (5') and SalI (3') sites. Fragment B is comprised of the central region (3518 bp) of the complete human OCP sequence (SEQ ID NO:27).

FIG. 38 shows the physical sequence of the 3' fragment (C) cloned into pMCS SV(A) to SalI (5') and SpeI (3') sites. Fragment C is comprised of the 3' region (1923 bp, not including the 3 bp stop codon) of the complete human OCP sequence and includes, at the 3' end, 18 nucleotides coding for 6 Histidine residues (SEQ ID NO:28). Also cloned fragment C contains a silent mutation (C>T transition) compared to the predicted sequence of human OCP ORF. This transition does not change the identity of the encoded amino acid residue.

FIG. 39 shows the predicted DNA sequence of Adlican-2 (SEQ ID NO:29). Bases 1555 and 5638 are presented as "g" but could be any other base.

FIG. 40 shows the predicted amino acid sequence of human Adlican-2 (SEQ ID NO:30).

FIG. 41 shows the amino acid sequence alignment of (i) human Adlican (SEQ ID NO: 21), (ii) human Adlican-2 full amino acid predicted sequence, as determined by the inventors (SEQ ID NO 30), (iii) deduced sequence (hLOC96359) of human Adlican-2 fragment of 539 amino acid residues as found in the database (residues 2036-2652 of SEQ ID NO 30), and (iv) deduced sequence (hLOC90792) of human Adlican-2-fragment of 617 amino acid residues as found in the database (residues 2114-2652 of SEQ ID NO 30).

FIG. 42 shows the complete physical DNA sequence of the coding region (ORF) of human OCP (SEQ ID NO: 31).

FIG. 43 shows the predicted amino acid sequence corresponding to the complete physical DNA sequence of the coding region (ORF) of human OCP (SEQ ID NO:32).

FIG. 44 shows the full rat 608 cDNA sequence (SEQ ID NO:33). This sequence is virtually identical to SEQ ID NO:1, but five unknown nucleotides (designated "n" in SEQ ID NO:1) have been identified. The ORF is from position 575 to 8368.

FIG. 45 shows the OCP rat protein amino acid sequence corresponding to the above ORF sequence (SEQ ID NO:34). Three previously unknown amino acids have been identified, as compared to SEQ ID NO:2, where these amino acids are designated "Xaa".

DETAILED DESCRIPTION OF THE INVENTION

Figure 2:
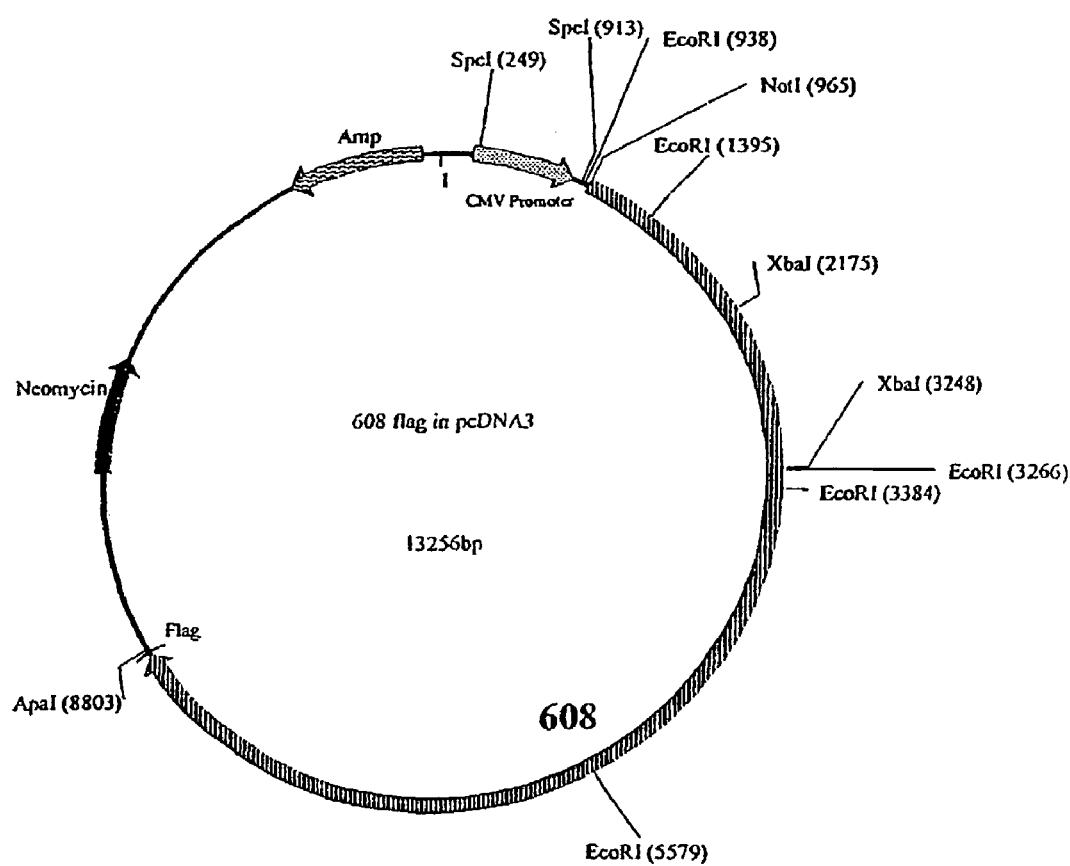
FIG. 2 shows the pcDNA3.1-608 construct.
Figure 5:
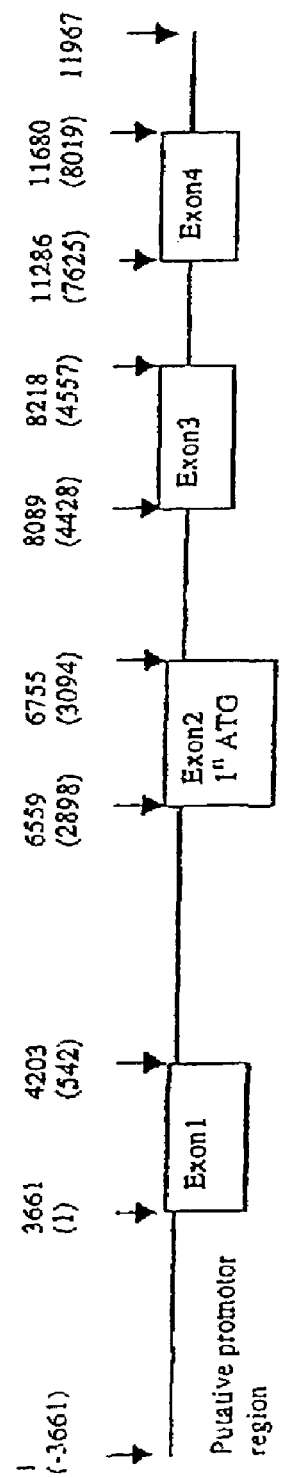
FIG. 5 shows the OCP map of exon-intron borders.
Figures 11A, 11B:
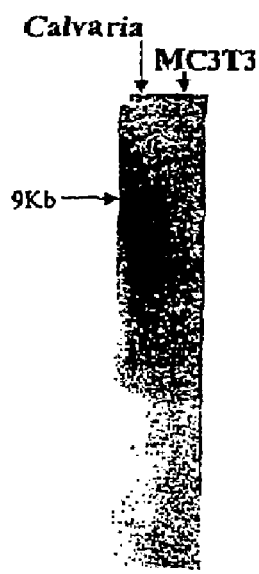
FIGS. 11A-11B show a list of expression patterns of OCP in primary cells and various other cell lines. A. Northern blot of poly A+ RNA RT-PCR from rat primary calvaria cells and MC3T3 cells is shown. The main 8.9 kb transcript is present only in calvaria cells. RT-PCR assays with specific OCP primers were performed on total RNA from various lines as indicated on the right side of the figure. In all assays similar amounts of GapDH RT-PCR products were detected in all RNA samples. In addition, B. no GapDH products were detected in any RNA samples, when RT was omitted. (−) represents no expression of OCP, while (+) represents expression. When (− +) are indicated, the expression of OCP is induced only upon specific conditions.

The present invention is related to the discovery of a novel gene, 608 ("OCP"), the expression of which is upregulated by mechanical stress on primary calvaria cells. Several functional features identify OCP as a most specific early marker of osteo- or chondro-progenitor cells as well as an inducer of osteoblast proliferation and differentiation.

As used herein, the same gene of the invention may be referred to either as "608" or "OCP." RNA refers to RNA isolated from cell cultures, cultured tissues or cells or tissues isolated from organisms which are stimulated, differentiated, exposed to a chemical compound, infected with a pathogen, or otherwise stimulated. As used herein, translation is defined as the synthesis of protein encoded by an mRNA template.

As used herein, stimulation of translation, transcription, stability or transportation of unknown target mRNA or stimulating element, includes chemically, pathogenically, physically, or otherwise inducing or repressing an mRNA population encoded by genes derived from native tissues and/or cells under pathological and/or stress conditions. In other words, stimulating the expression of an mRNA with a stress inducing element or "stressor" includes, but is not limited to, the application of an external cue, stimulus, or stimuli that stimulates or initiates translation of an mRNA stored as untranslated mRNA in the cells from the sample. The stressor may cause an increase in stability of certain mRNAs, or induce the transport of specific mRNAs from the nucleus to the cytoplasm. The stressor may also induce specific gene transcription. In addition to stimulating translation of mRNA from genes in native cells/tissues, stimulation can include induction and/or repression of genes under pathological and/or stress conditions. The method utilizes a stimulus or stressor to identify unknown target genes regulated at the various possible levels by the stress inducing element or stressor.

More in particular, with respect to nucleic acid molecules (rat 608 and human 608 genes) and polypeptides expressed from them, the invention further comprehends isolated and/or purified nucleic acid molecules and isolated and/or purified polypeptides having at least about 70%, preferably at least about 75% or about 77% homology ("substantially homologous"); advantageously at least about 80% or about 83%, such as at least about 85% or about 87% homology ("significantly homologous"); for instance at least about 90% or about 93% homology ("highly homologous"); more advantageously at least about 95%, e.g., at least about 97%, about 98%, about 99% or even about 100% homology ("very highly homologous" to "100% (homologous"); or from about 84-100% homology considered "highly conserved". The invention also comprehends that these nucleic acid molecules and polypeptides can be used in the same fashion as the herein or aforementioned nucleic acid molecules and polypeptides.

Nucleotide sequence homology can be determined using the "Align" program of Myers and Miller, ((1988) CABIOS 4:11-17) and available at NCBI. Alternatively or additionally, the term "homology" for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, AGTCAGTC has a sequence similarity of 75% to AATCAATC ($N_{ref}=8$; $N_{dif}=2$).

Alternatively or additionally, "homology" with respect to sequences can refer to the number of positions with identical nucleotides or amino acid residues divided by the number of nucleotides or amino acid residues in the shorter of the two sequences wherein alignment of the two sequences can be determined in accordance with the Wilbur and Lipman algorithm ((1983) Proc. Natl. Acad. Sci. USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc., CA). When RNA sequences are said to be similar, or have a degree of sequence identity or homology with DNA sequences, thymidine (T) in the DNA sequence is considered equal to uracil (U) in the RNA sequence. RNA sequences within the scope of the invention can be derived from DNA sequences or their complements, by substituting thymidine (T) in the DNA sequence with uracil (U).

Additionally or alternatively, amino acid sequence similarity or identity or homology can be determined, for instance, using the BlastP program (Altschul et al. Nucl. Acids Res. 25:3389-3402) and available at NCBI. The following references provide algorithms for comparing the relative homology of amino acid residues of two proteins, and additionally, or alternatively, with respect to the foregoing, the teachings in these references can be used for determining percent homology. Smith et al. (1981) Adv. Appl. Math. 2:482-489; Smith et al. (1983) Nucl. Acids Res. 11:2205-2220; Devereux et al. (1984) Nucl. Acids Res. 12:387-395; Feng et al. (1987) J. Molec. Evol. 25:351-360; Higgins et al. (1989) CABIOS 5:151-153; and Thompson et al. (1994) Nucl. Acids Res. 22:4673-480.

As to uses, the inventive genes and expression products as well as genes identified by the herein disclosed methods and expression products thereof and the compositions comprising Adlican or the Adlican gene (including "functional" variations of such expression products, and truncated portions of herein defined genes such as portions of herein defined genes which encode a functional portion of an expression product) are useful in treating, preventing or controlling or diagnosing mechanical stress conditions or absence or reduced mechanical stress conditions.

As described herein, Adlican, including functional portions thereof, can be used in all methods suitable for OCP. The sequence homology between Adlican and human OCP provides this novel use of the Adlican protein. Adlican is provided, for instance, in AF245505.1:1.8487. Adlican is named for "Adhesion protein with Leucine-rich repeats has immunoglobulin domains related to perleCAN"; and shows elevated expression in cartilage from osteoarthritis patients.

The Adlican gene, or functional portions thereof, can likewise be used for any purpose described herein for an OCP gene. The invention further encompasses compositions comprising a physiologically acceptable excipient and at least one of Adlican, the Adlican gene and antibodies specific to Adlican.

OCP expression is related to proliferation and differentiation of osteoblasts and chondrocytes. The expression product of OCP, or cells or vectors expressing OCP may cause cells to selectively proliferate and differentiate and thereby increase or alter bone density. Detecting levels of OCP mRNA or expression and comparing it to "normal" non-osteopathic levels may allow one to detect subjects at risk for osteoporosis or lower levels of osteoblasts and chondrocytes.

The medicament or treatment can be any conventional medicament or treatment for osteoporosis. Alternatively, or additionally, the medicament or treatment can be the particular protein of the gene detected in the inventive methods, or that which inhibits that protein, e.g., binds to it. Similarly, additionally, or alternatively, the medicament or treatment can be a vector which expresses the protein of the gene detected in the inventive methods or that which inhibits expression of that gene; again, for instance, that which can bind to it and/or otherwise prevents its transcription or translation. The selection of administering a protein or that which expresses it, or of administering that which inhibits the protein or the gene expression, can be done without undue experimentation, e.g., based on down-regulation or up-regulation as determined by inventive methods (e.g., in the osteoporosis model).

In the practice of the invention, one can employ general methods in molecular biology. Standard molecular biology techniques known in the art and not specifically described are generally followed as in Sambrook et al. (1989, 1992) Molecular Cloning: A Laboratory Manual, Cold Spring Harbor Laboratory, New York; and Ausubel et al. (1989) Current Protocols in Molecular Biology, John Wiley and Sons, Baltimore, Md.

PCR comprising the methods of the invention is performed in a reaction mixture comprising an amount, typically between <10 ng-200 ng template nucleic acid; 50-100 pmoles each oligonucleotide primer; 1-1.25 mM each deoxynucleotide triphosphate; a buffer solution appropriate for the polymerase used to catalyze the amplification reaction; and 0.5-2 Units of a polymerase, most preferably a thermostable polymerase (e.g., Taq polymerase or Tth polymerase).

Antibodies may be used in various aspects of the invention, e.g., in detection or treatment or prevention methods. Antibodies can be monoclonal, polyclonal or recombinant for use in the immunoassays or other methods of analysis necessary for the practice of the invention. By the term "antibody" as used in the present invention is meant both poly- and mono-clonal complete antibodies as well as fragments thereof, such as Fab, $F(ab')_2$, and Fv, which are capable of binding the epitopic determinant. These antibody fragments retain the ability to selectively bind with its antigen or receptor and are exemplified as follows, inter alia:

(1) Fab, the fragment which contains a monovalent antigen-binding fragment of an antibody molecule can be produced by digestion of whole antibody with the enzyme papain to yield a light chain and a portion of the heavy chain;

(2) $(Fab')_2$, the fragment of the antibody that can be obtained by treating whole antibody with the enzyme pepsin without subsequent reduction; F(ab'$_2$) is a dimer of two Fab fragments held together by two disulfide bonds;

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule.

Conveniently, the antibodies may be prepared against the immunogen or antigenic portion thereof for example a synthetic peptide based on the sequence, or prepared recombinantly by cloning techniques or the natural gene product and/or portions thereof may be isolated and used as the immunogen. The genes are identified as set forth in the present invention and the gene product identified. Immunogens can be used to produce antibodies by standard antibody production technology well known to those skilled in the art as described generally in Harlow and Lane (1988) Antibodies: A Laboratory Manual, Cold Spring Harbor Laboratory, Cold Spring Harbor, N.Y.; and Borrebaeck (1992) Antibody Engineering—A Practical Guide, W. H. Freeman and Co. Antibody fragments, as mentioned above, include Fab, F(ab')2, Fv and scFv prepared by methods known to those skilled in the art. Bird et al. (1988) Science 242:423-426. Any peptide having sufficient flexibility and length can be used as an scFv linker. Usually the linker is selected to have little to no immunogenicity. Linker sequences can also provide additional functions, such as a means for attaching a drug or a solid support.

For producing polyclonal antibodies, a host, such as a rabbit or goat, is immunized with the immunogen or an immunogenic fragment thereof, generally with an adjuvant and, if necessary, coupled to a carrier; and antibodies to the immunogen are collected from the sera of the immunized animal. The sera can be adsorbed against related immunogens so that no cross-reactive antibodies remain in the sera rendering the polyclonal antibody monospecific.

For producing monoclonal antibodies (mAbs), an appropriate donor, generally a mouse, is hyperimmunized with the immunogen and splenic antibody producing cells are isolated. These cells are fused to an immortal cell, such as a myeloma cell, to provide an immortal fused cell hybrid that secretes the antibody. The cells are then cultured, in bulk, and the mAbs are harvested from the culture media for use. Hybridoma cell lines provide a constant, inexpensive source of chemically identical antibodies and preparations of such antibodies can be easily standardized. Methods for producing mAbs are well known to those of ordinary skill in the art. See, e.g. U.S. Pat. No. 4,196,265.

For producing recombinant antibodies, mRNAs from antibody producing B lymphocytes of animals, or hybridomas are reverse-transcribed to obtain cDNAs. See generally, Huston et al. (1991) Met. Enzymol. 203:46-88; Johnson and Bird (1991) Met. Enzymol. 203:88-99; and Mernaugh and Mernaugh (1995) In, Molecular Methods in Plant Pathology (Singh and Singh eds.) CRC Press Inc. Boca Raton, Fla., pp. 359-365). Antibody cDNA, which can be full or partial length, is amplified and cloned into a phage or a plasmid. The cDNA can be a partial length of heavy and light chain cDNAs, separated or connected by a linker. The antibody, or antibody fragment, is expressed using a suitable expression system to obtain recombinant antibody. Antibody cDNA can also be obtained by screening pertinent expression libraries.

Antibodies can be bound to a solid support substrate or conjugated with a detectable moiety or be both bound and conjugated as is well known in the art. For a general discussion of conjugation of fluorescent or enzymatic moieties see, Johnston and Thorpe (1982) Immunochemistry in Practice, Blackwell Scientific Publications, Oxford. The binding of antibodies to a solid support substrate is also well known in the art. See for a general discussion, Harlow and Lane (1988); and Borrebaeck (1992). The detectable moieties contemplated with the present invention include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{13}$C and iodination.

Antibodies can also be used as an active agent in a therapeutic composition and such antibodies can be humanized, for instance, to enhance their effects. See, Huls et al. Nature Biotech. 17:1999. "Humanized" antibodies are antibodies in which at least part of the sequence has been altered from its initial form to render it more like human immunoglobulins. In one version, the H chain and L chain C regions are replaced with human sequence. In another version, the CDR regions comprise amino acid sequences from the antibody of interest, while the V framework regions have also been converted human sequences. See, for example, EP 0329400. In a third version, V regions are humanized by designing consensus sequences of human and mouse V regions, and converting residues outside the CDRs that are different between the consensus sequences. The invention encompasses humanized mAbs.

The expression product from the gene or portions thereof can be useful for generating antibodies such as monoclonal or polyclonal antibodies which are useful for diagnostic purposes or to block activity of expression products or portions thereof or of genes or a portion thereof, e.g., as therapeutics.

Note that some antibodies to the mouse or rat 608 polypeptide may also bind the human 608 polypeptide. A preferred set of antibodies encompassed by this invention are antibodies which bind human 608 polypeptide but which do not bind rat 608 polypeptide. Another preferred set of antibodies encompassed by this invention are antibodies which bind human 608 polypeptide but which do not bind mouse 608 polypeptide.

The genes of the present invention or portions thereof, e.g., a portion thereof which expresses a protein which function the same as or analogously to the full length protein, or genes identified by the methods herein can be expressed recombinantly, e.g., in *Escherichia coli* or in another vector or plasmid for either in vivo expression or in vitro expression. The methods for making and/or administering a vector or recombinant or plasmid for expression of gene products of genes of the invention or identified by the invention or a portion thereof either in vivo or in vitro can be any desired method, e.g., a method which is by or analogous to the methods disclosed in: U.S. Pat. Nos. 4,603,112; 4,769,330; 5,174,993; 5,505,941; 5,338,683; 5,494,807; 4,394,448; 4,722,848; 4,745,051; 4,769,331; 5,591,639; 5,589,466; 4,945,050; 5,677,178; 5,591,439; 5,552,143; and 5,580,859; U.S. patent application Ser. No. 920,197, filed Oct. 16, 1986; WO 94/16716; WO 96/39491; WO91/11525; WO 98/33510; WO 90/01543; EP 0 370 573; EP 265785; Paoletti (1996) Proc. Natl. Acad. Sci. USA 93:11349-11353; Moss (1996) Proc. Natl. Acad. Sci. USA 93:11341-11348; Richardson (Ed) (1995) Methods in Molecular Biology 39, "Baculovirus Expression Protocols," Humana Press Inc.; Smith et al. (1983) Mol. Cell. Biol.

3:2156-2165; Pennock et al. (1984) Mol. Cell. Biol. 4:399-406; Roizman Proc. Natl. Acad. Sci. USA 93:11307-11312; Andreansky et al. Proc. Natl. Acad. Sci. USA 93:11313-11318; Robertson et al. Proc. Natl. Acad. Sci. USA 93:11334-11340; Frolov et al. Proc. Natl. Acad. Sci. USA 93:11371-11377; Kitson et al. (1991) J. Virol. 65:3068-3075; Grunhaus et al. (1992) Sem. Virol. 3:237-52; Ballay et al. (1993) EMBO J. 4:3861-65; Graham (1990) Tibtech 8:85-87; Prevec et al. J. Gen. Virol. 70:429-434; Felgner et al. (1994) J. Biol. Chem. 269:2550-2561; (1993) Science 259:1745-49; McClements et al. (1996) Proc. Natl. Acad. Sci. USA 93:11414-11420; Ju et al. (1998) Diabetologia 41:736-739; and Robinson et al. (1997) Sem. Immunol. 9:271-283.

The expression product generated by vectors or recombinants can also be isolated and/or purified from infected or transfected cells; for instance, to prepare compositions for administration to patients. However, in certain instances, it may be advantageous to not isolate and/or purify an expression product from a cell; for instance, when the cell or portions thereof enhance the effect of the polypeptide.

As used herein, "treatment" refers to clinical intervention in an attempt to alter the natural course of the individual or cell being treated, and may be performed either for prophylaxis or during the course of clinical pathology. Desirable effects of the treatment include preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis.

An inventive vector or recombinant expressing a gene or a portion thereof identified herein or from a method herein can be administered in any suitable amount to achieve expression at a suitable dosage level, e.g., a dosage level analogous to the herein mentioned dosage levels (wherein the gene product is directly present). The inventive vector or recombinant nucleotide can be administered to a patient or infected or transfected into cells in an amount of about at least $10^3$ pfu; more preferably about $10^4$ pfu to about $10^{10}$ pfu, e.g., about $10^5$ pfu to about $10^9$ pfu, for instance about $10^6$ pfu to about $10^8$ pfu. In plasmid compositions, the dosage should be a sufficient amount of plasmid to elicit a response analogous to compositions wherein gene product or a portion thereof is directly present; or to have expression analogous to dosages in such compositions; or to have expression analogous to expression obtained in vivo by recombinant compositions. For instance, suitable quantities of plasmid DNA in plasmid compositions can be 1 µg to 100 mg, preferably 0.1 to 10 mg, e.g., 500 µg, but lower levels such as 0.1 to 2 mg or preferably 1-10 µg may be employed. Documents cited herein regarding DNA plasmid vectors can be consulted for the skilled artisan to ascertain other suitable dosages for DNA plasmid vector compositions of the invention, without undue experimentation.

Compositions for administering vectors can be as in or analogous to such compositions in documents cited herein or as in or analogous to compositions herein described, e.g., pharmaceutical or therapeutic compositions and the like.

Thus, the invention comprehends in vivo gene expression which is sometimes termed "gene therapy." Gene therapy can refer to the transfer of genetic material (e.g. DNA or RNA) of interest into a host subject or patient to treat or prevent a genetic or acquired disease, condition or phenotype. The particular gene that is to be used or which has been identified as the target gene is identified as set forth herein. The genetic material of interest encodes a product (e.g. a protein, polypeptide, peptide or functional RNA) the production in vivo of which is desired. For example, the genetic material of interest can encode a hormone, receptor, enzyme, polypeptide or peptide of therapeutic value. For a review see, in general, the text "Gene Therapy" (Advances in Pharmacology 40, Academic Press, 1997).

Two basic approaches to gene therapy have evolved: (1) ex vivo; and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, homologous recombination, etc.) and, an expression system as needed and then the modified cells are expanded in culture and returned to the host/patient. These genetically reimplanted cells have been shown to produce the transfected gene product in situ. In in vivo gene therapy, target cells are not removed from the subject; rather, the gene to be transferred is introduced into the cells of the recipient organism in situ, that is within the recipient. Alternatively, if the host gene is defective, the gene is repaired in situ. Culver (1998) Antisense DNA & RNA Based Therapeutics, February, 1998, Coronado, Calif. These genetically altered cells have been shown to produce the transfected gene product in situ.

The gene expression vehicle is capable of delivery/transfer of heterologous nucleic acid into a host cell. The expression vehicle may include elements to control targeting, expression and transcription of the nucleic acid in a cell-selective manner as is known in the art. It should be noted that often the 5'UTR and/or 3'UTR of the gene may be replaced by the 5' UTR and/or 3'UTR of the expression vehicle. Therefore, as used herein, the expression vehicle may, as needed, not include the 5'UTR and/or 3'UTR shown in sequences herein and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any non-translated DNA sequence that works contiguously with the coding sequence (in cis) to change the basal transcription level dictated by the promoter. The expression vehicle can also include a selection gene as described herein.

Vectors can be introduced into cells or tissues by any one of a variety of known methods within the art. Such methods can be found generally described in Sambrook et al. (1989, 1992); Ausubel et al. (1989); Chang et al. (1995) Somatic Gene Therapy, CRC Press, Ann Arbor, Mich.; Vega et al. (1995) Gene Targeting, CRC Press, Ann Arbor, Mich.; Vectors: A Survey of Molecular Cloning Vectors and Their Uses, Butterworths, Boston Mass. (1988); and Gilboa et al. (1986) BioTech. 4:504-512, as well as other documents cited herein and include, for example, stable or transient transfection, lipofection, electroporation and infection with recombinant viral vectors. In addition, see U.S. Pat. No. 4,866,042 for vectors involving the central nervous system; and also U.S. Pat. Nos. 5,464,764 and 5,487,992 for positive-negative selection methods.

Introduction of nucleic acids by infection offers advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed cell culture. Viral vectors can also be modified with specific receptors or ligands to alter target specificity through receptor-mediated events.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

In particular, use of the 608 gene (or a functional fragment thereof) for treatment of osteoporosis, and/or osteoarthritis, and/or osteopetrosis, and/or osteosarcoma, and/or fracture healing is envisaged using gene therapy methods. As described above, a plasmid or DNA vector expressing the gene could be injected directly to the target tissue; alternatively a virus bearing a plasmid or DNA vector expressing the gene could be injected directly to the target tissue. Another embodiment is that cells transfected with a plasmid or DNA vector expressing the gene could be injected directly to the target tissue. These transfected cells should preferably be the patient's own cells for example mesenchymal stem cells drawn from the bone marrow.

Delivery of gene products (products from herein defined genes: genes identified herein or by inventive methods or portions thereof) and/or antibodies or portions thereof and/or agonists or antagonists (collectively or individually "therapeutics"), and compositions comprising the same, as well as of compositions comprising a vector expressing gene products, can be done without undue experimentation from this disclosure and the knowledge in the art.

The pharmaceutically "effective amount" for purposes herein is thus determined by such considerations as are known in the art. The amount must be effective to achieve improvement including but not limited to improved survival rate or more rapid recovery, or improvement or amelioration or elimination of symptoms and other indicators, e.g., of osteoporosis, for instance, improvement in bone density, as are selected as appropriate measures by those skilled in the art.

It is noted that humans are treated generally longer than the mice or other experimental animals exemplified herein. Human treatment has a length proportional to the length of the disease process and drug effectiveness. The doses may be single doses or multiple doses over a period of several days, but single doses are preferred. Thus, one can scale up from animal experiments, e.g., rats, mice, and the like, to humans, by techniques from this disclosure and the knowledge in the art.

The present invention provides an isolated nucleic acid molecule containing nucleotides having a sequence set forth in at least one of SEQ ID NO:1, SEQ ID NO:3, SEQ ID NO: 6, SEQ ID NO: 20, SEQ ID NO: 22, SEQ ID NO: 23, SEQ ID NO: 29 or SEQ ID NO: 31 or as inserted in a plasmid designated pCm-H-608-663-N-term, deposited under ATCC Accession No. PTA-3638, supplements thereof and a polynucleotide having a sequence that differs from SEQ ID NO:1, SEQ ID NO:3, SEQ ID NO: 6, SEQ ID NO: 20, SEQ ID NO: 22, SEQ ID NO: 23, SEQ ID NO: 26, SEQ ID NO: 27, SEQ ID NO: 28, SEQ ID NO: 29 or SEQ ID NO: 31 or as inserted in a plasmid designated pCm-H-608-663-N-term, deposited under ATCC Accession No. PTA-3638 due to the degeneracy of the genetic code or a sequence which hybridizes under stringent conditions to a sequence in a plasmid designated pCm-H608-663-N-term or a functional portion thereof or a polynucleotide which is at least substantially homologous thereto. In a preferred embodiment, the nucleic acid molecule comprises a polynucleotide having at least 15 nucleotides from SEQ ID NO:1, SEQ ID NO:3, SEQ ID NO: 6, SEQ ID NO: 20, SEQ ID NO: 22, SEQ ID NO: 23, SEQ ID NO: 29 or SEQ ID NO: 31 or as inserted in a plasmid designated pCm-H-608-663-N-term, deposited under ATCC Accession No. PTA-3638, preferably at least 50 nucleotides and more preferably at least 100 nucleotides.

The present invention further provides an isolated nucleic acid molecule containing nucleotides having a sequence set forth in at least one of SEQ ID NO:26, SEQ ID NO:27, SEQ ID NO: 28, or SEQ ID NO:26 and SEQ ID NO:27 or SEQ ID NO:26 and SEQ ID NO:27 and SEQ ID NO: 28 or as inserted in a plasmid designated pKS H608 5'-2.4Kb bAc#1 (deposited on Nov. 21, 2001 under the terms of the Budapest Treaty with the American Type Culture Collection (ATCC), P.O. Box 1549, Manassas, Va. 20108, USA, under ATCC accession number PTA-3878), pKS H608 m.FRG.3.5Kb#34 (deposited on Nov. 21, 2001 under the terms of the Budapest Treaty with the American Type Culture Collection (ATCC), P.O. Box 1549, Manassas, Va. 20108, USA, under ATCC accession number PTA-3876) or pM H608 3'-1.9Kb HSTG#3.3 (deposited on Nov. 21, 2001 under the terms of the Budapest Treaty with the American Type Culture Collection (ATCC), P.O. Box 1549, Manassas, Va. 20108, USA, under ATCC accession number PTA-3877), supplements thereof and a polynucleotide having a sequence that differs from SEQ ID NO:26, SEQ ID NO:27, SEQ ID NO: 28, or SEQ ID NO:26 and SEQ ID NO:27 or SEQ ID NO:26 and SEQ ID NO:27 and SEQ ID NO: 28 or as inserted in a plasmid designated pKS H608 5'-2.4Kb bAc#1, pKS H608 m.FRG.3.5Kb#34 or pM H608 3'-1.9Kb HSTG#3.3 due to the degeneracy of the genetic code or a sequence which hybridizes under stringent conditions to a sequence in a plasmid designated pKS H608 5'-2.4Kb bAc#1, pKS H608 m.FRG.3.5Kb#34 or pM H608 3'-1.9Kb HSTG#3.3 or a functional portion thereof or a polynucleotide which is at least substantially homologous thereto. In a preferred embodiment, the nucleic acid molecule comprises a polynucleotide having at least 15 nucleotides from SEQ ID NO:26, SEQ ID NO:27, SEQ ID NO: 28, or SEQ ID NO:26 and SEQ ID NO:27 or SEQ ID NO:26 and SEQ ID NO:27 and SEQ ID NO: 28 or as inserted in a plasmid designated pKS H608 5'-2.4Kb bAc#1, pKS H608 m.FRG.3.5Kb#34 or pM H608 3'-1.9Kb HSTG#3.3, preferably at least 50 nucleotides and more preferably at least 100 nucleotides.

The present invention also provides a composition of the isolated nucleic acid molecule, a vector comprising the isolated nucleic acid molecule, a composition containing said vector and a method for preventing, treating or controlling bone diseases including, but not limited to, osteoporosis, osteopenia, osteopetrosis, osteosclerosis, osteoarthritis, periodontosis, bone fractures or low bone density or other conditions involving mechanical stress or a lack thereof in a subject, comprising administering the inventive composition, or the inventive vector, and a method for preparing a polypeptide comprising expressing the isolated nucleic acid molecule or comprising expressing the polypeptide from the vector.

The present invention further provides a method for preventing, treating or controlling osteoporosis, osteopenia, osteopetrosis, osteosclerosis, osteoarthritis, periodontosis, bone fractures or low bone density or other factors causing or contributing to osteoporosis or symptoms thereof or other conditions involving mechanical stress or a lack thereof in a subject, comprising administering an isolated nucleic acid molecule or functional portion thereof or a polypeptide comprising an expression product of the gene or functional portion of the polypeptide or an antibody to the polypeptide or a functional portion of the antibody. In one embodiment of the invention, the isolated nucleic acid molecule encodes a 10 kD to 100 kD N-terminal cleavage product of the OCP protein. Preferably, the N-terminal cleavage product comprises of a polypeptide of about 25 kD. More preferably the N-terminal cleavage product comprises a polypeptide of about 70-80 kD, most preferably about 1-663 amino acids or about 1-741 amino acids of the OCP protein.

The present invention provides an isolated polypeptide encoded by the inventive polynucleotide. In one embodiment of the invention, the polypeptide is identified as human 608 protein, rat 608 protein, human Adlican-2 protein or a functional portion thereof or a polypeptide which is at least substantially homologous thereto. More particularly this invention is directed to an isolated polypeptide wherein the functional portion comprises consecutive amino acids having a sequence set forth in SEQ ID NO:2, SEQ ID NO:16, SEQ ID NO: 24, SEQ ID NO: 25, SEQ ID NO: 30, SEQ ID NO: 32 or SEQ ID NO: 34. Particular fragments of the polypeptide are about the first 663 amino acids or about the first 741 amino acids of the sequence set forth in SEQ ID NO:2, SEQ ID NO:16, SEQ ID NO: 24, SEQ ID NO: 25, SEQ ID NO: 30, SEQ ID NO: 32 or SEQ ID NO: 34. Other particular fragments of the human 608 protein include amino acids 1-500, 501-1000, 1001-1500, 1501-2000, 2001-2500, and 2051-2623 of the sequence set forth in SEQ ID NO: 32. Further particular fragments of the human 608 protein include amino acids 250-749, 750-129, 1250-1749, 1750-2249 and 2250-2623 of the sequence set forth in SEQ ID NO: 32. Nucleic acid molecules (polynucleotides) encoding these particular fragments are also envisaged as aspects of the invention. Similar particular polypeptide fragments of the Adlican-2 protein (SEQ ID NO: 30), and similar particular polynucleotide fragments of the Adlican-2 nucleic acid (SEQ ID NO: 29) are also envisaged as aspects of the invention.

The present invention also provides a composition comprising one or of isolated polypeptides, an antibody specific for the polypeptide or a functional portion thereof, a composition comprising the antibody or a functional portion thereof, and a method for treating or preventing osteoporosis, or fracture healing, bone elongation, or periodontosis in a subject, comprising administering to the subject a N-terminal polypeptide having a molecular weight of between 10 kD and 100 kD, preferably about 25 kD to about 70-80 kD.

The present invention provides for a method of treating or preventing osteoarthritis, osteopetrosis, or osteosclerosis, comprising administering to a subject an effective amount of a chemical or a neutralizing mAbs that inhibit the activity of the N-terminal polypeptide having a molecular weight of between 10 kD and 30 kD, preferably about 25 kD.

As used herein, the term "subject," "patient," "host" include, but are not limited to human, bovine, pig, mouse, rat, goat, sheep and horse.

Those skilled in the art will recognize that the components of the compositions should be selected to be chemically inert with respect to the gene product and optional adjuvant or additive. This will present no problem to those skilled in chemical and pharmaceutical principles, or problems can be readily avoided by reference to standard texts or by simple experiments (not involving undue experimentation), from this disclosure and the documents cited herein.

The present invention provides receptors of the expression products of human mechanical stress induced genes and their functional equivalents, such as OCP and Adlican, and methods or processes for obtaining and using such receptors. The receptors of the present invention are those to which the expression products of mechanical stress induced genes and their functional equivalents bind or associate as determined by conventional assays, as well as in vivo. For example, binding of the polypeptides of the instant invention to receptors can be determined in vitro, using candidate receptor molecules that are associated with lipid membranes. See, e.g., Watson, J. et al., Development of FlashPlate® technology to measure ($^{35}$S) GTP gamma S binding to Chinese hamster ovary cell membranes expressing the cloned human 5-HT1B receptor, Journal of Biomolecular Screening. Summer, 1998; 3 (2) 101-105; Komesli-Sylviane et al., Chimeric extracellular domain of type II transforming growth factor (TGF)-beta receptor fused to the Fc region of human immunoglobulin as a TGF-beta antagonist, European Journal of Biochemistry. June, 1998; 254 (3) 505-513. See, generally, Darnell et al., Molecular Cell Biology, 644-646, Scientific American Books, New York (1986). Scanning electron microscopy ("SEM"), x-ray crystallography and reactions using labelled polypeptides are examples of conventional means for determining whether polypeptides have bound or associated with a receptor molecule. For instance, X-ray crystallography can provide detailed structural information to determine whether and to what extent binding or association has occurred. See, e.g., U.S. Pat. No. 6,037,117; U.S. Pat. No. 6,128,582 and U.S. Pat. No. 6,153,579. Further, crystallography, including X-ray crystallography, provides three-dimensional structures that show whether a candidate polypeptide ligand can or would bind or associate with a target molecule, such as a receptor. See, e.g., WO 99/45379; U.S. Pat. Nos. 6,087,478 and 6,110,672. Such binding or association shows that the receptor molecule is the receptor for the candidate polypeptide.

With the disclosures in the present specification of the inventive genes, expression products and uses thereof, those skilled in the art can obtain by conventional methods the receptors for the inventive expression products. The conventional means for obtaining the receptors include raising monoclonal antibodies (Mabs) to candidate receptors, purifying the receptors from a tissue sample by use of an affinity column, treatment with a buffer, and collection of the eluate receptor molecules. Other means of isolating and purifying the receptors are conventional in the art, for instance isolation and purification by dialysis, salting out, and electrophoretic (e.g. SDS-PAGE) and chromatographic (e.g. ion-exchange and gel-filtration, in additional to affinity) techniques. Such methods can be found generally described in Stryer, Biochemistry, 44-50, W. H. Freeman & Co., New York (3d ed. 1988); Darnell et al., Molecular Cell Biology, 77-80 (1986); Alberts et al., Molecular Biology of the Cell, 167-172, 193 Garland Publishing, New York (2d ed. 1989).

Sequencing of the isolated receptor involves methods known in the art, for instance directly sequencing a short N-terminal sequence of the receptor, constructing a nucleic-acid probe, isolating the receptor gene, and determining the entire amino-acid sequence of the receptor from the nucleic-acid sequence. Alternatively, the entire receptor protein can be sequenced directly. Automated Edman degradation is one conventional method used to partially or entirely sequence a receptor protein, facilitated by chemical or enzymatic cleavage. Automated sequenators, such as an ABI-494 Procise Sequencer (Applied Biosystems) can be used. See, generally, Stryer, Biochemistry, 50-58 (3d ed. 1988).

The invention provides methods for using such receptors in assays, for instance for identifying proteins or polypeptides that bind to, associate with or block the inventive receptors, determining binding constants and degree of binding, and for testing the effects of such polypeptides, for instance utilising membrane receptor preparations. See Watson (1998); Komesli-Sylviane (1998). For instance, Flash-Plate ® (Perkin-Elmer, Mass., USA) technology can be used with the present invention to determine whether and to what degree candidate polypeptides bind to and are functional with respect to a receptor of the invention.

Diagnostics:

The gene and polypeptides of the invention can be employed as a diagnostic in several ways as follows:
1. Diagnosis of osteoarthritis by detection of 608 protein or parts of it, or detection of 608 RNA in synovial fluid.
2. Diagnosis of osteoporosis by detection of 608 protein or fragments thereof, or detection of 608 RNA, preferably in a blood sample.
3. Diagnosis of a fracture by detection of 608 protein or fragments thereof, or detection of 608 RNA, preferably in a blood sample.
4. Diagnosis of susceptibility to osteoporosis, and/or osteoarthritis, and/or osteopetrosis, and/or osteosarcoma associated with mutated 608 by PCR or RT PCR of DNA or RNA respectively. DNA and/or RNA from bodily fluids or from a tissue, and preferably DNA from blood are tested.
5. Diagnosis of a disease associated with mutated 608 by PCR or RT PCR of DNA or RNA respectively. DNA and/or RNA from bodily fluids or from a tissue and preferably DNA from blood are tested The diagnostic methods to be utilized are described in more detail as follows.

In diagnosis, the sample is taken from a bodily fluid or from a tissue, preferably bone or cartilage tissue; the bodily fluid is selected from the group of fluid consisting of blood, lymph fluid, ascites, serous fluid, pleural effusion, sputum, cerebrospinal fluid, lacrimal fluid, synovial fluid, saliva, stool, sperm and urine, preferably blood or urine. Measurement of level of the 608 polypeptide may be determined by a method selected from the group consisting of immunohistochemistry, western blotting, ELISA, antibody microarray hybridization and targeted molecular imaging; antibodies have been described above. Such methods are well-known in the art, for example for immunohistochemistry: M. A. Hayat (2002) Microscopy, Immunohistochemistry and Antigen Retrieval Methods: For Light and Electron Microscopy, Kluwer Academic Publishers; Brown C (1998): "Antigen retrieval methods for immunohistochemistry", *Toxicol Pathol;* 26(6): 830-1); for western blotting: Laemmeli UK(1970): "Cleavage of structural proteins during the assembley of the head of a bacteriophage T4", *Nature;* 227: 680-685; and Egger & Bienz(1994) "Protein (western) blotting", *Mol Biotechnol;* 1(3): 289-305); for ELISA: Onorato et al.(1998) "Immunohistochemical and ELISA assays for biomarkers of oxidative stress in aging and disease", *Ann NY Acad Sci* 20; 854: 277-90); for antibody microarray hybridization :Huang(2001) "Detection of multiple proteins in an antibody-based protein microarray system, *Immunol Methods* 1; 255 (1-2): 1-13); and for targeted molecular imaging: Thomas (2001). Targeted Molecular Imaging in Oncology, Kim et al (Eds)., Springer Verlag, inter alia.

Measurement of level of 608 polynucleotide may be determined by a method selected from: RT-PCR analysis, in-situ hybridization, polynucleotide microarray and Northern blotting. Such methods are well-known in the art, for example for in-situ hybridization Andreeff & Pinkel (Editors) (1999), "Introduction to Fluorescence In Situ Hybridization: Principles and Clinical Applications", John Wiley & Sons Inc.; and for Northern blotting Trayhurn (1996) "Northern blotting", *Proc Nutr Soc;* 55(1B): 583-9 and Shifman & Stein (1995) "A reliable and sensitive method for non-radioactive Northern blot analysis of nerve growth factor mRNA from brain tissues", *Journal of Neuroscience Methods;* 59: 205-208 inter alia.

A better understanding of the present invention and of its many advantages will be had from the following examples, given by way of illustration and as a further description of the invention.

EXPERIMENTAL DETAILS

Example 1

608 Gene Expression by In Situ Hybridization

The 608 gene expression pattern was studied by in situ hybridization on sections of bones from ovariectomized and sham-operated rats. Female Wistar rats weighing 300-350 g were subjected to ovariectomy under general anesthesia. Control rats were operated on in the same way but ovaries were not excised as a sham operation.

Three weeks after the operation, rats were sacrificed and tibia were excised together with the knee joint. Bones were fixed for three days in 4% paraformaldehyde and then decalcified for four days in a solution containing 5% formic acid and 10% formalin. Decalcified bones were postfixed in 10% formalin for three days and embedded into paraffin.

The ectopic bone formation model was employed to study the bone development 608 gene expression pattern. Rat bone marrow cells were seeded into cylinders of demineralized bone matrix prepared from rat tibiae. Cylinders were implanted subcutaneously into adult rats. After three weeks, rats were sacrificed and implants were decalcified and embedded into paraffin as described above for tibial bones.

The 6 μm sections were prepared and hybridized in situ. After hybridization, sections were dipped into nuclear track emulsion and exposed for three weeks at 4° C. Autoradiographs were developed, stained with hematoxylin-eosin and studied under microscopy using brightfield and darkfield illumination.

For further assessment of cell and tissue specificity of 608 gene expression, an in situ hybridization study was performed on sections of multitissue block containing multiple samples of adult rat tissues. The 608 expression developmental pattern was studied on sagittal sections of mouse embryos of 12.5, 14.5 and 16.5 days postconception (dpc) stages.

Microscopic study of hybridized sections of long bones revealed a peculiar pattern of 608 probe hybridization. The hybridization signal can be seen mainly in fibroblast-like cells found in several locations throughout the sections. Prominent accumulations of these cells can be seen in the area of periosteal modeling in metaphysis, and also in regions of active remodeling of compact bone in diaphysis: at the boundary between bone marrow and endosteal osteoblasts and in periosteum; also in close contact with osteoblasts. Perivascular connective tissue filling Volkmann's canals in compact bone in diaphysis and epiphysis also contains 608-expressing cells. No hybridization was found within cancellous bone and in bone marrow. This hybridization pattern suggests that cells expressing 608 are associated with areas of remodeling of preexisting bone and are not involved in primary endochondral ossification.

At the growth plate level, 608 expressing cells can be seen in the perichondral fibrous ring of LaCroix. Some investigators regard this fibrous tissue as the aggregation of residual mesenchymal cells able to differentiate into both osteoblasts and chondrocytes. In this respect it is noteworthy that single cells expressing 608 can be seen in epiphyseal cartilage. These 608-expressing cells are rounded cells within the lateral segment of epiphysis (sometimes in close vicinity to the LaCroix ring) and flattened cells covering the articulate surface. Most cells in articulate cartilage and all chondrocytes on the growth plate do not show 608 expression. Ovariectomy did not alter the intensity and pattern of 608 expression in bone tissue.

In ectopic bone sections, 608 hybridization signal can be seen in some fibroblast-like cells either scattered within unmineralized connective tissue matrix or concentrated at the boundary between this tissue and osteoblasts of immature bone.

608 gene expression patterns revealed by in situ hybridization in bone and cartilage indicate that its expression marks some skeletal tissue elements able to differentiate into two skeletal cell types—osteoblasts and chondrocytes. The terminal differentiation of these cells appears to be accompanied by down-regulation of 608 expression. The latter observation is supported by peculiar temporal pattern of 608 expression in primary cultures of osteogenic cells isolated from calvaria bones of rat fetuses. In these cultures, expression was revealed by in situ hybridization in the vast majority of cells after one and two weeks of incubation in vitro. Three and four week old cultures showing signs of ossification contained no 608 expressing cells. Significantly, no hybridization signal was found on sections of multitissue block hybridized to 608 probe suggesting high specificity of this gene expression for the skeletal tissue in adult organisms.

An in situ hybridization study of embryonic sections demonstrated that, at 12.5 dpc, a weak hybridization signal can be discerned in some mesenchymal cells in several locations throughout the embryonic body. The most prominent signal is found in the head in loose mesenchymal tissue surrounding the olfactory epithelium and underlying the surface epithelium of nose tip. Other mesenchymal cells in the head also show a hybridization signal: non-cartilaginous part of basisphenoid bone primordium and mesenchyme surrounding the dental laminae (tooth primordia) in the mandible.

In the trunk, expression can be detected in less developed vertebrae primordia in the thoraco-lumbar region. The hybridization signal here marks the condensed portion of sclerotomes. Another area of the trunk showing a hybridization signal is comprised of a thin layer of mesenchymal cells in the anterior part of the thoracic body wall.

At later stages of development, 14.5 and 16.5 dpc, probe 608 gave no hybridization signal. Thus, it appears that during embryonic development the 608 gene is transiently expressed by at least some mesenchymal and skeleton-forming cells. This expression is down-regulated at later stages of development. More detailed study of late embryonic and postnatal stages of development reveals the timing of appearance of cells expressing 608 in bone tissue.

Further experiments to study the expression of the OCP gene in embryonic development were performed as follows. The targeting vector used to produce OCP knockout mice included a "knock-in" of the β-galactosidase (LacZ) reporter gene into the OCP gene. The LacZ gene was fused to the first exon of the OCP gene—a non-coding exon. Thus, expression of LacZ is expected to depend on the OCP regulatory elements and to mark the cells expressing OCP.

Analysis of LacZ staining was performed during embryonic development on OCP knockout mice. The expression pattern revealed by this analysis reflects the activation of the OCP gene promoter, which results in expression of the knocked-in LacZ gene. This data in general supports the pattern detected by the in-situ hybridization described above.

At 10.5 dpc expression is seen in the apical ectodermal ridge (AER), in the forelimbs only. This specialized region, together with the zone of polarizing activity (ZPA), directs and coordinates the development of the limb bud.

At 12.5 dpc expression in AER is maintained in the forelimbs and appears also in hindlimbs. In addition, it appears in precartilagenous condensations of the ribs, in mesenchymal tissue in the face, in mesenchymal tissue rostral to the forelimb, a region of future muscle development, and in the tip of the genital tubercle.

At 14.5 dpc there is broader expression, in the head region, limbs, ribs, and back. Although no expression at 14.5 dpc was detected in the in situ RNA hybridization experiments described above, expression was detected in this experiment, probably because the lacZ staining is a more sensitive detection method.

To summarize:
1. There is an interesting pattern of expression of gene OCP in embryonic development: in tissues originating from different germ layers (ectoderm and mesoderm), in critical regions of pattern formation (AER), and an apparently regulated pattern during cartilage and bone development.
2. In mesodermal tissues, the gene is expressed mainly in skeletal lineages, but also in some myoblasts and some dermal cells as well.
3. Ectodermal expression appears in the head mesenchyme, derived from neural crest cells, and cells in the apical ectodermal ridge.

The 608 expression pattern during embryonic development is closely coupled with regions of bone and cartilage development. This expression pattern strongly suggests a role for 608 in bone metabolism.

Example 2

Isolation of Rat OCP

Primary rat calvaria cells grown on elastic membranes that were stretched for 20 minutes provided a model system for a stimulator of bone formation following mechanical force. Gene expression patterns were compared before and after the application of mechanical force.

OCP expression was upregulated approximately 3-fold by mechanical force. This was detected both by microarray analysis and by Northern blot analysis using poly (A)+ RNA from rat calvaria cells before and after the mechanical stress. In rat calvaria primary cells and in rat bone extract this gene was expressed as a main RNA species of approximately 8.9 kb and a minor RNA transcript of approximately 9 kb. The hybridization signal was not detected in any other rat RNA from various tissue sources, including testis, colon, intestine, kidney, stomach, thymus, lung, uterus, heart, brain, liver, eye, and lymph node.

The partial OCP rat cDNA clone (4007 bp long) isolated from a rat calvaria cDNA phage library was found to contain a 3356 bp open reading frame closed at the 3' end. Comparison to public mouse databases revealed no sequence homologues. A complete OCP rat cDNA clone was isolated from the rat calvaria cDNA library by a combination of 5' RACE technique (Clontech), RT-PCR of 5' cDNA fragments, and ligation of the latter products to the original 3' clone. The full rat cDNA clone that was generated (shown in FIG. 1—SEQ ID NO:1) was sequenced, and no mutations were found. The full sequence stretch is 8883 bp long and contains an ORF (nt 575-8366) for a 2597 amino acid residue protein. FIG. 3—SEQ ID NO:2. The cDNA does not contain a polyadenylation site, but contains a 3' poly A stretch.

608 encodes a large protein that appears to be a part of the extra-cellular matrix. The gene may be actively involved in supporting osteoblast differentiation. Another option is that it is expressed in regions were remodeling takes place. Such an hypothesis is also compatible with a role in directing osteoclast action and thus it may be a target for inhibition by small molecules.

In normal bone formation, activation of osteoblasts leads to secretion of various factors that attract osteoclast precursors or mature osteoclasts to the sites of bone formation to initiate the process of bone resorption. In normal bone formation both functions are balanced. Imbalance to any side causes either osteitis deformans (osteoblast function overwhelms) or osteoporosis (osteoclast function overwhelms).

Among known osteoblast activators—mechanical force stimulation—is actually applied in the present model. As proof of principle, increased expression of several genes known to respond to mechanical stress by transcriptional upregulation were found. They include tenascin, endothelin and possibly trombospondin.

Example 3

Full-Length OCP cDNA Construction and Expression

TNT (transcription—translation) assays were performed according to the manufacturer's instructions (Promega— TNT coupled reticulocyte lysate systems), using specific fragments taken from various regions of the gene. In all assays a clear translation product was observed. The following fragments were tested:

| Frag. | Location | TNT products Fragment size (bp) | Translation product size (kD) | Promoter |
|---|---|---|---|---|
| 1 | 134-2147 | 2013 | 73 | T7 |
| 2 | 3912-5014 | 1102 | 40 | " |
| 3 | 574-1513 | 939 | 34 | " |

Example 4

The Mouse OCP Gene

Two mouse genomic Bac clones containing the mouse OCP gene promoter region and part of the coding region were identified, based on their partial homology to the 5'UTR region of the rat-608 cDNA. These clones (23-261L4 and 23-241H7 with ~200 Kb average insert length) were bought from TIGR.

Specific primers for the amplification of a part of the mouse-OCP promoter region were designed and used for PCR screening of a mouse genomic phage library (performed by Lexicon Genetics Inc. for the Applicants). One phage clone containing part of the genomic region of the mouse 608 gene was detected and completely sequenced. The length of this clone was reported to be 11,963 bp. Parts of the physical "Lexicon" clone were re-sequenced by the inventors and corrections were made. The resequenced clone is 11,967 bp long. Exon-location prediction (FIG. 4) was performed based on the alignment of the mouse genomic and the rat cDNA sequences.

Example 5

The Human OCP Gene

On the nucleotide level, the rat OCP cDNA sequence is homologous to the human genomic DNA sequence located on chromosome 3. Based on the homology and bioinformatic analysis (FIG. 6), a putative cDNA sequence was generated. FIG. 7. The highest similarity is evident between nt 1-1965 (1-655 a.a); 2179-2337 (727-779 a.a); and 4894-7833 (1635 a.a.-end) as presented in the table shown in FIG. 8. On the protein level, no homologues were found in the data bank.

Example 6

The Deduced OCP Protein

The deduced OCP protein was generated following the alignment of the rat, mouse and human cDNA sequences and the equivalent rat, mouse and human amino acid sequences, respectively. The following alignments were made: (a) alignment of rat, human, and mouse OCP cDNA coding regions (rat cDNA: SEQ ID NO:7; human 5+3 corrected: SEQ ID NO:8; and mus cDNA 5: SEQ ID NO:9)

(b) alignment of rat, human and mouse OCP proteins (rat: SEQ ID NO: 10; human 5+3 corrected: SEQ ID NO:11; and mouse 5 corrected: SEQ ID NO:12) and (c) alignment of rat and human OCP proteins (rat: SEQ ID NO:13; and human 5+3 corrected: SEQ ID NO:14).

The deduced OCP protein (FIG. 10): contains the following features a. a cleavable, well-defined N-terminal signal peptide (aa 1-28);

b. a leucine-rich repeat region (aa 28-280). This region can be divided into N-terminal and C-terminal domains of leucine-rich repeats (aa 28-61 and 219-280, respectively). Between them, there are six leucine-rich repeat outliers (aa 74-96, 98-120, 122-144, 146-168, 178-200, 202-224). Leucine rich repeats are usually found in extracellular portions of a number of proteins with diverse functions. These repeats are thought to be involved in protein-protein interactions. Each leucine-rich repeat is composed of β-sheet and α-helix. Such units form elongated non-globular structures;

c. twelve immunoglobulin C-2 type repeats at amino acid positions 488-558, 586-652, 1635-1704, 1732-1801, 1829-1898, 1928-1997, 2025-2100, 2128-2194, 2233-2294, 2324-2392, 2419-2487, 2515-2586. Thus, two Ig-like repeats are found immediately downstream of a leucine-rich region, while the remaining 10 repeats are clustered at the protein's C-terminus. Immunoglobulin C-2 type repeats are involved in protein—protein interaction and are usually found in extracellular protein portions;

d. no transmembrane domain; and 5 nuclear localization domains (NLS) at: 724, 747, 1026, 1346 and 1618.

These observations indicate that OCP belongs to the Ig superfamily. OCP is a serine-rich protein (10.3% versus av. 6.3%), with a central nuclear prediction domain and an N-terminal extracellular prediction domain.

Example 7

Bone Fracture Healing

Expression of 608 RNA is bone-specific. Moreover, it seems to be specific to bone progenitors (as judged by their location in bone and involvement in normal bone modeling and remodeling processes) that do not yet express the known bone-specific markers. To further prove the relevance of 608-expressing cells to osteogenic lineage, the patterns of 608 expression in the animal model of bone fracture healing that imply the activation of bone formation processes were studied.

The sequence of physiological events following bone fracture is now relatively well understood. Healing takes place in three phases—inflammatory, reparative and remodeling. In each phase certain cells predominate and specific histological and biochemical events are observed. Although these phases are referred to separately, it is well known that events described in one phase persist into the next and events apparent in a subsequent phase begin before this particular phase predominates. These events have been described over the years in investigative reports and review articles. Ham (1969) In, Histology, 6th ed. Philadelphia, Lippincott, p. 441; and Urist and Johnson (1943) J. Bone Joint Surg. 25:375.

During the first phase immediately following fracture (the inflammatory phase), wide-spread vasodilatation and exudation of plasma lead to the acute edema visible in the region of a fresh fracture. Acute inflammatory cells migrate to the region, as do polymorphonuclear leukocytes and then macrophages. The cells that participate directly in fracture repair during the second phase (the reparative phase), are of mesenchymal origin and are pluripotent. These cells form collagen, cartilage and bone. Some cells are derived from the cambium layer of the periosteum and form the earliest bone. Endosteal cells also participate. However, the majority of cells directly taking part in fracture healing enter the fracture site with the granulation tissue that invades the region from surrounding vessels. Trueta (1963) J. Bone Joint Surg. 45:402. Note that the entire vascular bed of an extremity enlarges shortly after the fracture has occurred but the osteogenic response is limited largely to the zones surrounding the fracture itself. Wray (1963) Angiol. 14:134.

The invading cells produce tissue known as "callus" (made up of fibrous tissue, cartilage, and young, immature fibrous bone), rapidly enveloping the ends of the bone, with a resulting gradual increase in stability of the fracture fragments. Cartilage thus formed will eventually be resorbed by a process that is indistinguishable except for its lack of organization from endochondral bone formation. Bone will be formed by those cells having an adequate oxygen supply and subjected to the relevant mechanical stimuli.

Early in the repair process, cartilage formation predominates and glycosaminoglycans are found in high concentrations. Later, bone formation is more obvious. As this phase of repair takes place, the bone ends gradually become enveloped in a mass of callus containing increasing amounts of bone. In the middle of the reparative phase the remodeling phase begins, with resorption of portions of the callus and the laying down of trabecular bone along lines of stress. Finally, exercise increases the rate of bone repair. Heikkinen et al. Scand J. Clin. Lab. Invest. 25 (suppl 113):32. In situ hybridization results have shown that OCP expression is confined to very specific regions where bone and cartilage formation is initiated.

Figure 16:
FIG. 16 shows a low power photomicrograph of fractured bone one week after the operation. Note that well-developed woven bone and fibrocartilagenous callus formed at the fracture site. Bone marrow tissue was mainly destroyed by insertion of the wire used for the fracture immobilization. Marked areas are presented at higher magnification in the following figures.
Figure 17A:
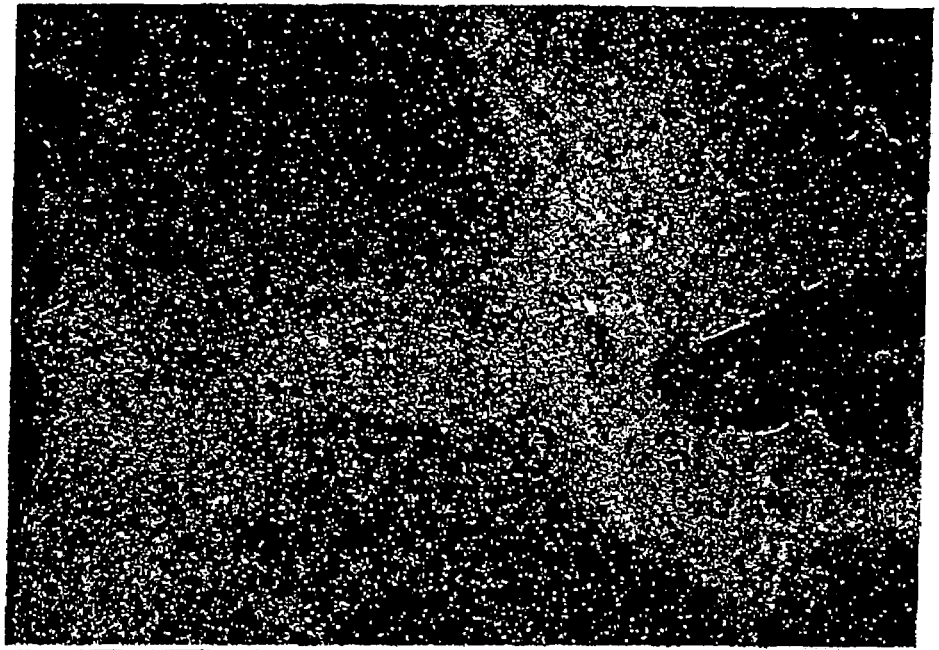
FIGS. 17A-17B show photomicrographs of the central part of callus, FIG. 17A. brightfield and FIG. 17B. darkfield. Cells expressing the OCP gene con be seen in the fibrous part of the callus. There was no hybridization signal from chondrocytes.
Figure 17:
Figure 18A:
FIGS. 18A-18B show photomicrographs of the callus area marked by 2 in FIG. 16, FIG. 18A. brightfield and FIG. 18B. darkfield. Cells expressing the OCP gene can be seen in a highly vascularized subperiosteal area bordering the cartilagenous part of the callus.
Figure 18B:
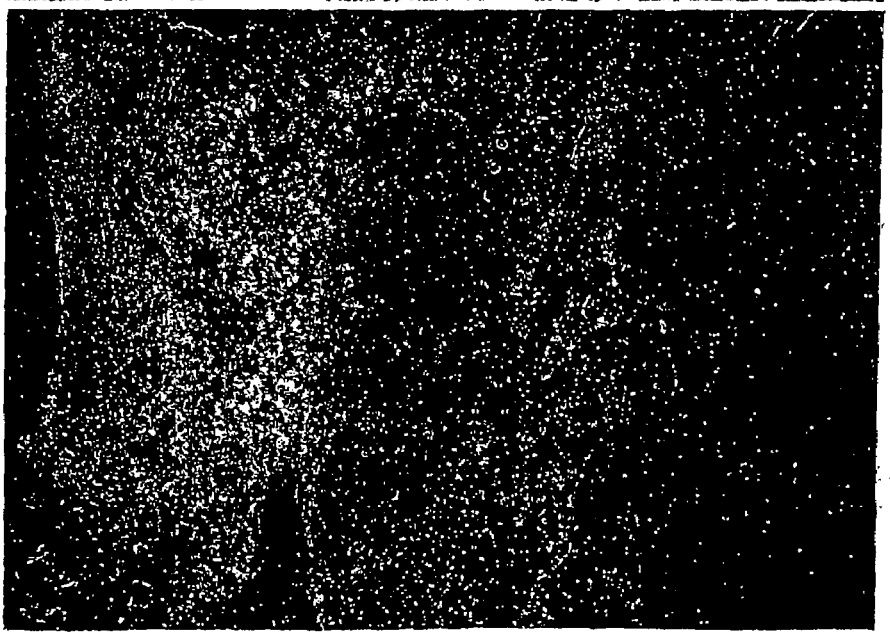
Figure 20:
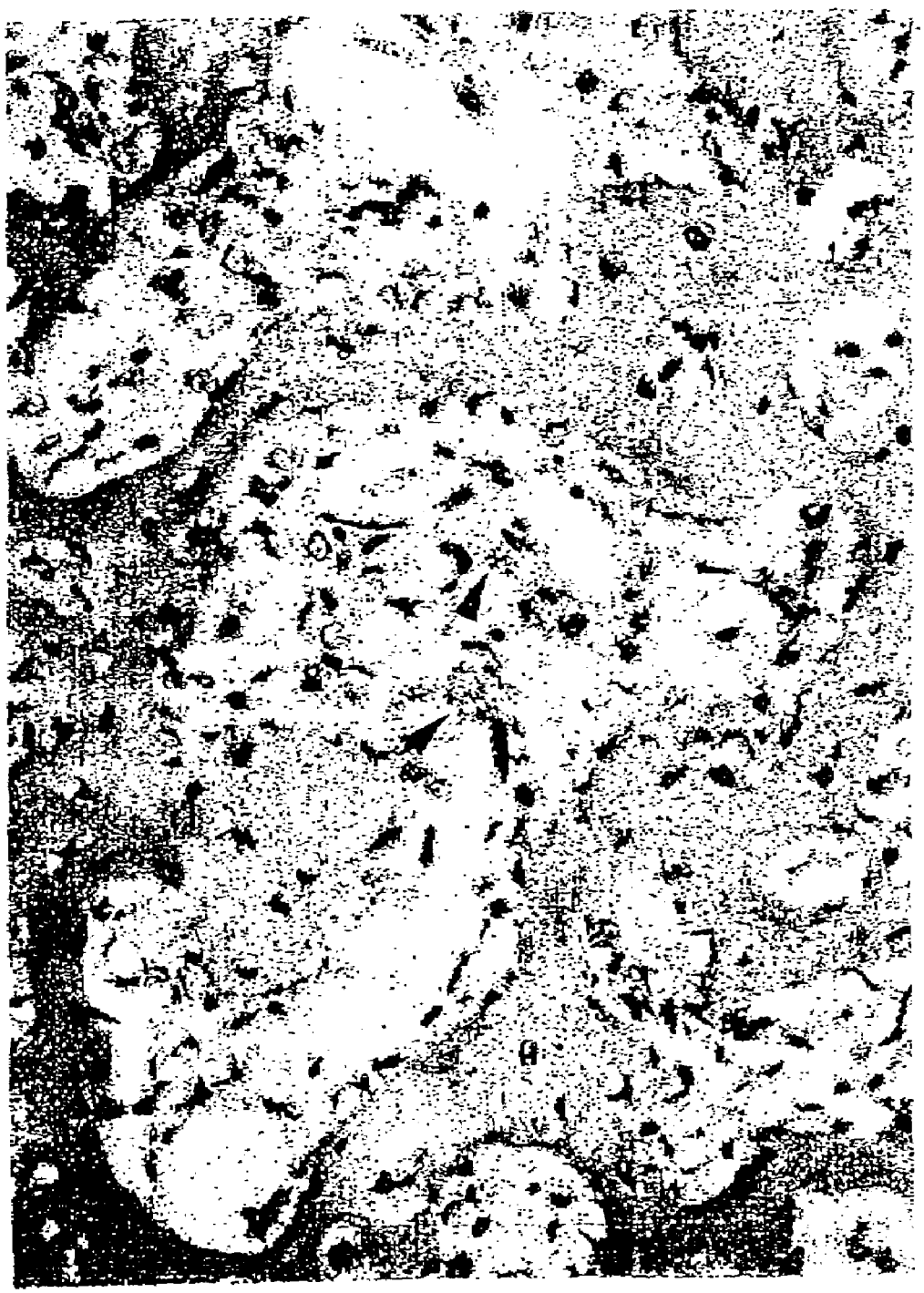
FIG. 20 shows a high power photomicrograph of perivascular cells. The perivascular cells express the 608 gene within lacuna of woven bone arrowheads.
Figure 21:
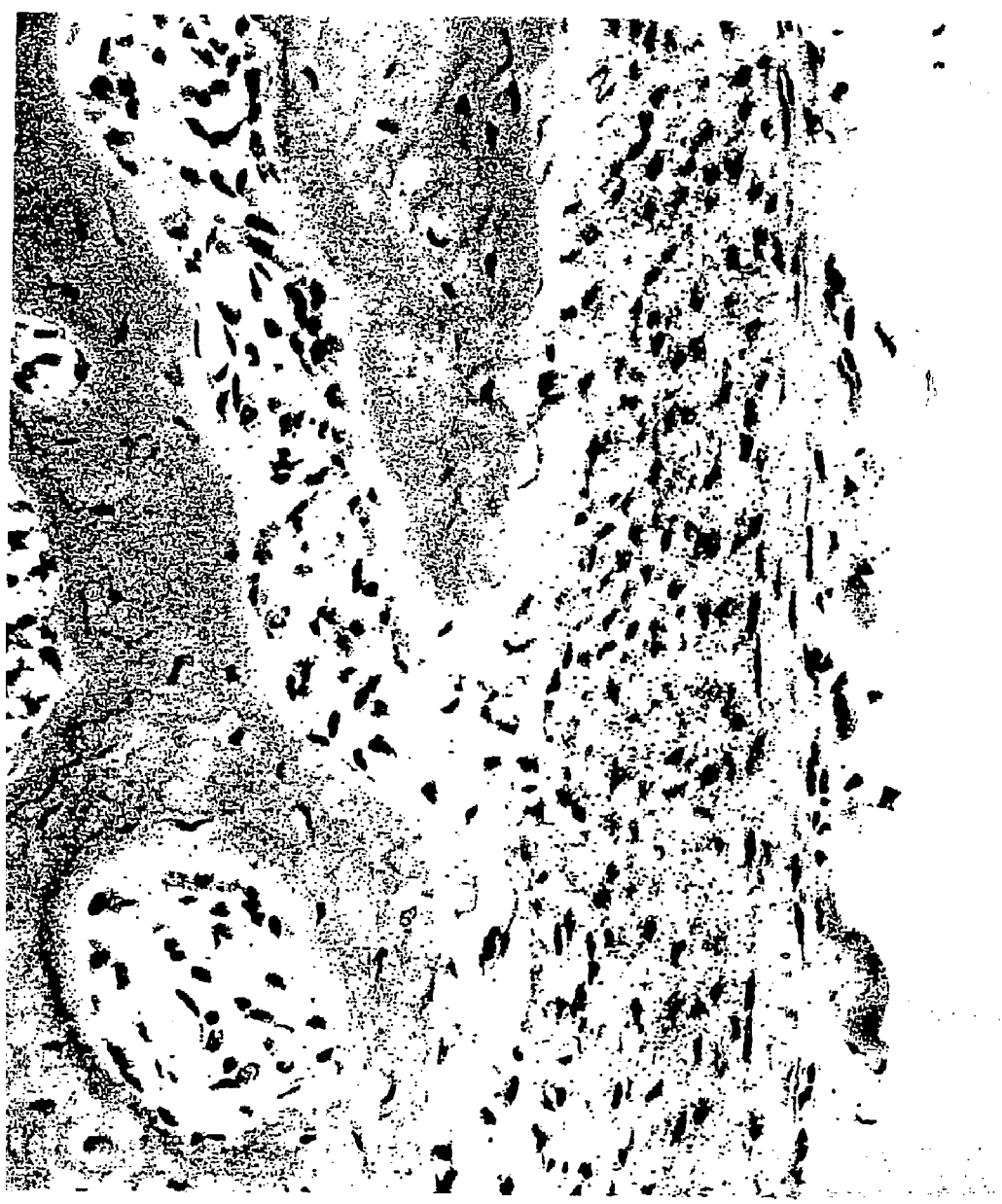
FIG. 21 shows a high power photomicrograph of periosteum covering the woven bone. Multiple cells display expression of the 608 gene in periosteum. Arrowheads point to two 608 expressing cells within the woven bone.
Figure 22A:
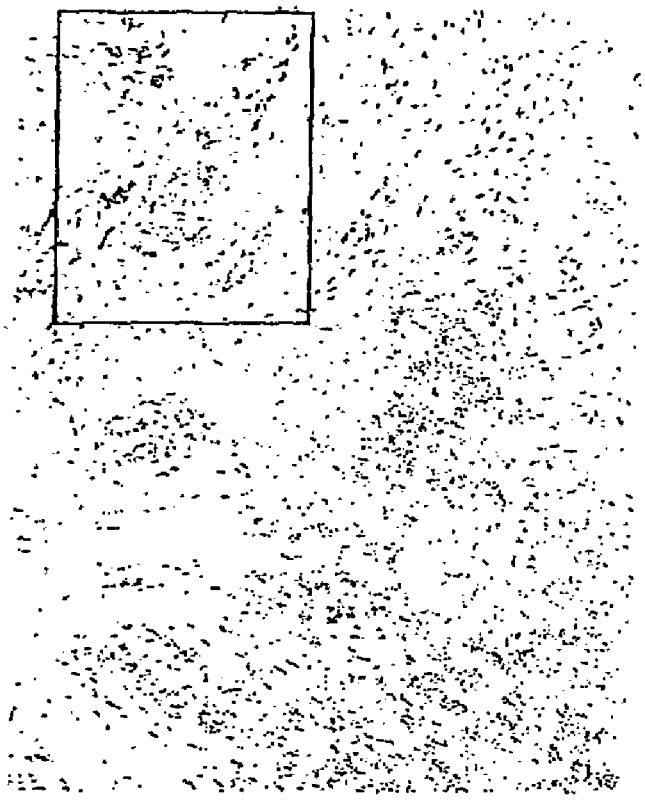
FIGS. 22A-22B show FIG. 22A. brightfield and FIG. 22B. darkfield photomicrographs of a section of fractured bone healed for 4 weeks. Multiple cells in periosteal tissue area of active remodeling of the cancellous bone covering the callus show a hybridization signal.
Figure 22B:
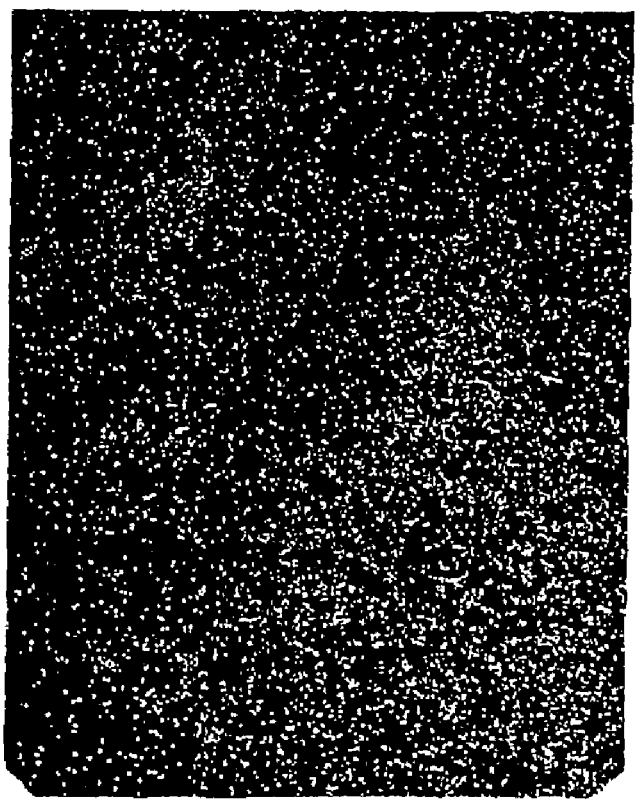
Figure 23:
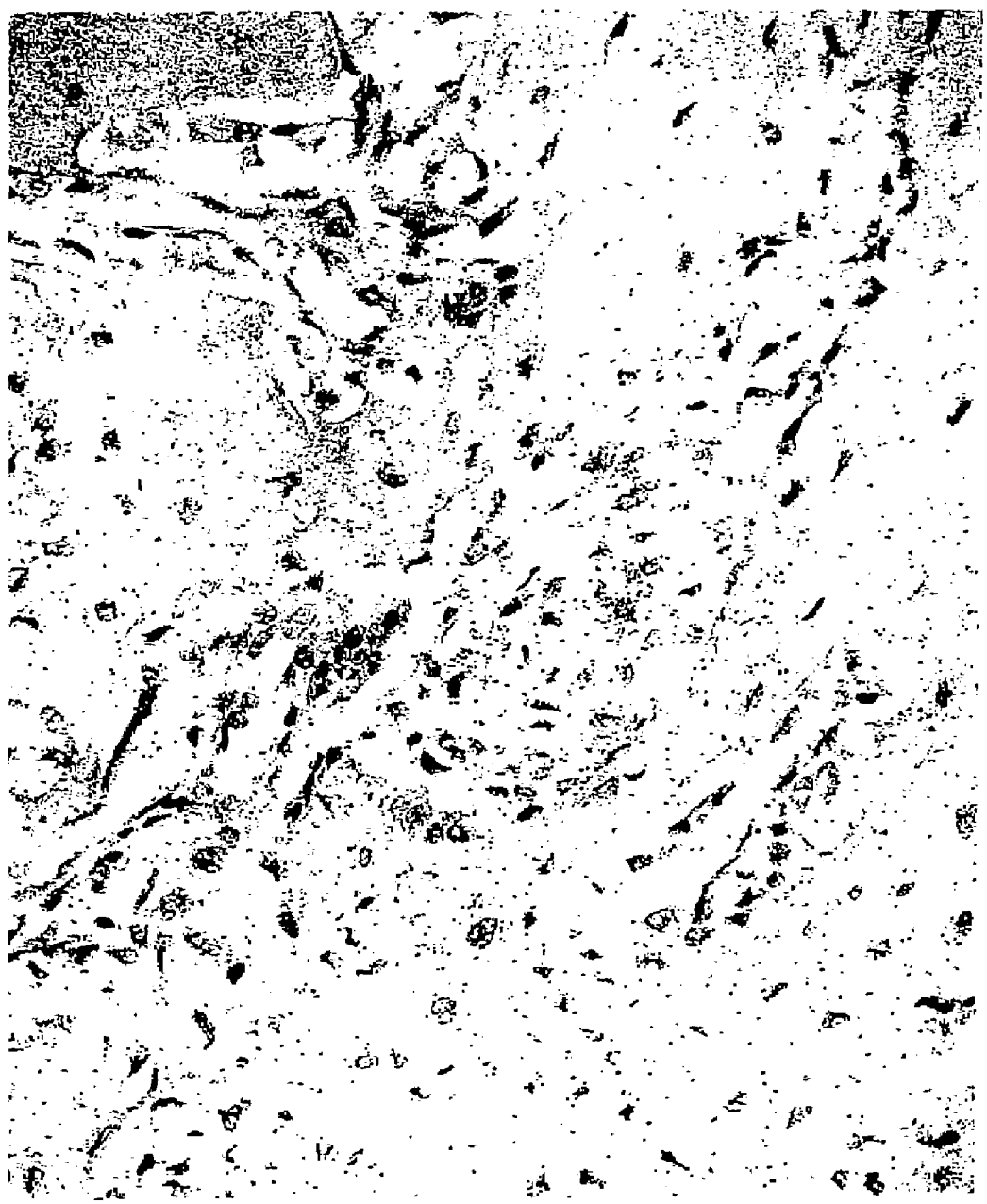
FIG. 23 shows the boxed area of FIG. 22 presented at higher magnification. Several OCP-expressing cells are concentrated in vascular tissue that fills the cavities resulting from osteoclast activity (marked by asterisks).

In order to find out if OCP expression is induced in an animal model of bone fracture healing, a standard midshaft fracture was created in rat femur by means of a blunt guillotine, driven by a dropped weight. Bonnarens et al. (1984) Orthop. Res. 2:97-101. One, 2, 3 and 4 week-fractured bones were excised, fixed in buffered formalin, decalcified in EDTA solution and embedded in paraffin. All sections were hybridized with the OCP probe. The in-situ hybridization results show that a strong hybridization signal was apparent during the first and second weeks of fracture healing in the highly vascularized areas of the connective tissue within the callus (FIGS. 16-18), the endosteum (FIG. 19), the woven bone (FIG. 20) and the periosteum FIG. 21). The periosteum is regarded as a source of undifferentiated progenitors participating in callus formation at the site of bone fracture. The hybridization signal disappeared slowly during further differentiation stages of fracture healing (three and four weeks) and was retained only in the vascularized connective tissue. 22 displays brightfield (left) and darkfield (right) photomicrographs of a section of fractured bone healed for 4 weeks. In these later healing stages, the mature callus tissue was found to be comprised mainly by cancellous bone undergoing remodeling into compact bone, with little if any cartilage or woven bone present. The volume of the vascularized periosteal tissue is decreased but multiple cells in the periosteal tissue area of active remodeling of the cancellous bone covering the callus, show hybridization signal. This tissue covers the center, of the callus and is also entrapped within the bone. See FIGS. 22 and 23. The box in FIG. 22 is enlarged in FIG. 23. As in the earlier stages, no hybridization signal was found in chondrocytes and osteoblasts. FIGS. 17 and 23. Several OCP expressing cells are concentrated in the vascular tissue that fills the cavities resulting from osteoclast activity (marked by asterisks).

Fractures in the young heal rapidly, while adult bone fractures heal slowly. The cause is a slower recruitment of specific chondro-/osteo-progenitors for the reparative process in the adult bone. Denervation retards fracture healing by diminishing the stress across the fracture site, while mechanical stress increases the rate of repair probably by increasing the proliferation and differentiation of specific bone progenitor cells and as a result, accelerates the rate of bone formation. The above results confirm our conclusions (see also hereunder) that OCP is most probably involved in induction of cortical and trabecular bone formation and remodeling, endochondral bone growth during development, and bone repair processes. In addition, there is strong evidence that OCP expression is tightly regulated, and induced during the earliest stages of bone fracture repair when osteo-/chondro-progenitor cells are recruited. This observation suggests that OCP plays a role in this process.

Taking into account the pattern of 608 expression during the process of bone fracture healing, it seems a reasonable hypothesis that 608-positive precursor cells are involved not only in remodeling of intact bone but also in the repair processes of the fractured bone as well.

Example 8

OCP Transcriptional Regulation

In order to clone the longest possible fragment which will contain the OCP regulatory region/s, bacs L4 and H7 were restricted with three different enzymes: BamHI, Bgl II and SauIIIA. The resulting fragments were cloned into the BamHI site of pKS. Ligation mixes were transformed into bacteria (E. coli—DH5α) and 1720 colonies were plated onto nitrocellulose filters which were screened with $^{32}$P-labeled PCR fragment spanning the mouse-OCP-exon1. Positive colonies were isolated.

Two identical clones, 14C10 and 15E11, contained the largest inserts (BamHI-derived ~13 Kb inserts). The 14C10 clone is longer than the OCP "Lexicon" clone by ~8 Kb at the 5'end.

a. Cloning of Mouse OCP Promoter and UTR Upstream to the Reporter Gene—EGFP

The 1.4 Kb genomic region of the mouse OCP gene, flanked by BamHI site (nuc 5098 of the "Lexicon" clone which is the start site of clone p14C10) and the first ATG codon (first nucleotide of exon 2), was synthesized by genomic PCR using the "Lexicon" clone as template and pre-designed primers: 5'primer (For1) located upstream to the BamHI site (nucleotides 4587-4611 of the Lexicon clone) and 3' primer (Rev 2) located immediately upstream to the first ATG (nucleotides 6560-6540 of the Lexicon clone) and tailed by a NotI site. The PCR product was cut by BamHI and NotI and the resulting 1.4 Kb fragment was ligated to pMCSIE into BamHI/NotI sites upstream to the EGFP reporter gene. The resulting clone was designated pMCSIEm608prm1.4.

Clone p14C10 was cut by XbaI and BamHI and the excised 4.088 Kb fragment was ligated into the BamHI and XbaI sites of pMCSIEm608prm1.4, upstream to the 1.4 Kb insert. The resulting clone was designated pMCSIEm608prm5.5 and contains 5552 nucleotides of the mouse 608 promoter and UTR upstream to EGFP. The insert of pMCSIEm608prm5.5 clone was completely sequenced.

The whole 13 Kb insert of p14C10 was excised by BamHI and ligated upstream to the 1.4 Kb insert of pMCSIEm608prm1.4 into the BamHI site. The resulting construct, pMCSIEm608prm14.5 contains a 14.5 Kb fragment of the mouse-OCP promoter and UTR upstream to EGFP.

b. Cloning Mouse OCP Promoter and UTR Upstream to the Reporter Gene—Luciferase

Both inserts of pMCSIEm608prm5.5 and of pMCSIEm608prm14.5 were also cloned upstream to luciferase, in Promega's pGL3-Basic vector. The 5.5 Kb insert of pMCSIEm608prm5.5 was excised by EcoRV and XbaI and ligated to SmaI and NheI sites of pGL3-Basic vector. The resulting clone is designated pGL3basicm608prm5.5.

Plasmid pMCSIEm608prm14.5 was restricted by NotI and the cohesive ends of the linearized plasmid were filled and turned into blunt ends. The 14.5 Kb insert was then excised by cutting the linear plasmid by SalI. The purified 14.5 Kb fragment was ligated to the XhoI and HindIII (filled in) sites of pGL3-basic upstream to the luciferase gene to create the construct designated pGL3basicm608prm14.5. SEQ ID NO:18 depicts 4610 bp that have been sequenced.

c. Analysis of TF Binding DNA Elements Common to Mouse and Human OCP

Known transcription factor (TF) binding DNA elements were analyzed for similarity upstream of human and mouse OCP ATG using the DiAlign program of Genomatix GmbH. The genomic pieces used are the proprietary mouse genomic OCP and reverse complement of AC024886 92001 to 111090. The locations of the ATG in these DNA pieces are:
575 on rat cDNA
*6521 on mouse genomic
*3381 on the piece extracted from human genomic DNA AC0024886 14 elements were extracted in this procedure and analyzed for transcription binding motifs using the MatInspector.

Some of the main "master gene" binding sites are the osteoblast-/chondrocyte-specific Cbaf1 factor; the chondrocyte-specific SOX 9 factor; the myoblast-specific Myo-D and Myo-F factors; the brain- and bone-specific WT1; Egr 3 and Egr 2 factors (Egr superfamily); the vitamin D-responsive (VDR) factor; the adipocyte-specific PPAR factor; and the ubiquitous activator SP1.

Example 9

Expression Pattern and Regulation of Gene 608:
Expression of Gene 608 in Regard to Other
Osteogenic Lineage Markers Expression of gene 608 was tested in primary cells and in cell lines with regard to expression of various markers of osteogenic and chondrogenic lineages. The results of this analysis are summarized in the following table and showed that expression of 608 is restricted to committed early osteoprogenitor cells.

| Cells | 608 | Collagen I | Collagen II | Alk. Phos. | Osteocalcin | Cbfa1 | Osteopontin |
|---|---|---|---|---|---|---|---|
| STO (fibroblasts) | - | - | + | - | + | + | + |
| ROS (osteosarcoma) | - | - | - | + | + | +/- | + |
| MC3T3 (pre-osteoblasts) | + | - | - | + | + | + | + |
| C2C12 (pre-myoblasts) | - | - | - | - | + | - | + |
| C6 (glioma) | - | | | - | | | |
| Calvaria mouse | + | | | + | | | |
| Calvaria rat | + | | | + | | | |
| C3H10T1/2 (mesenchymal stem cells) | - | - | + | - | + | - | + |

Example 10

OCP Expression is Mechanically Induced in MC3T3 E1 Cells

Figure 12:
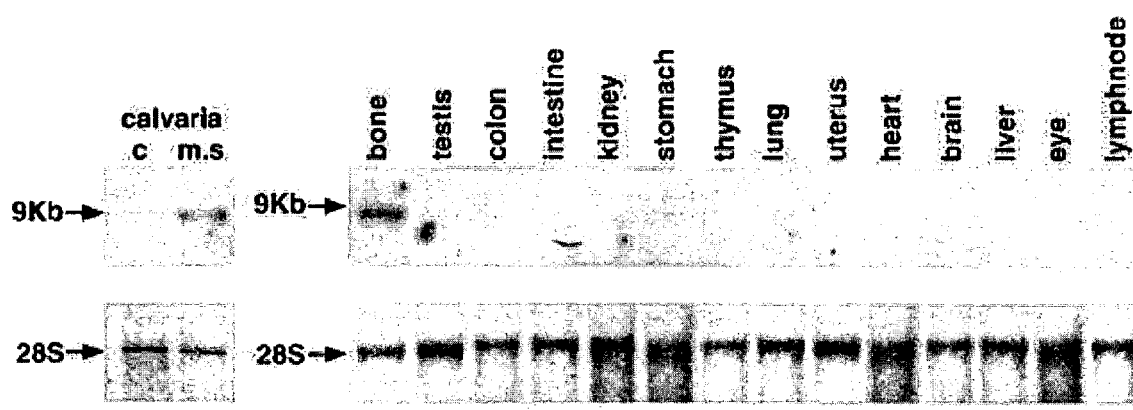
FIG. 12 shows responsiveness of CMF608 expression to mechanical stimulation by Northern blot analysis using polyA RNA from primary rat calvaria cells before and after mechanical stress (m.s.)—see left of Figure. In these cells, CMF608 is transcribed as a single RNA species of approximately 9 Kb. On tissue blot, CMF608-specific 9 Kb mRNA transcript was hardly detectable in any other tissue type except for the bone (B)—see right of Figure.
Figure 13:
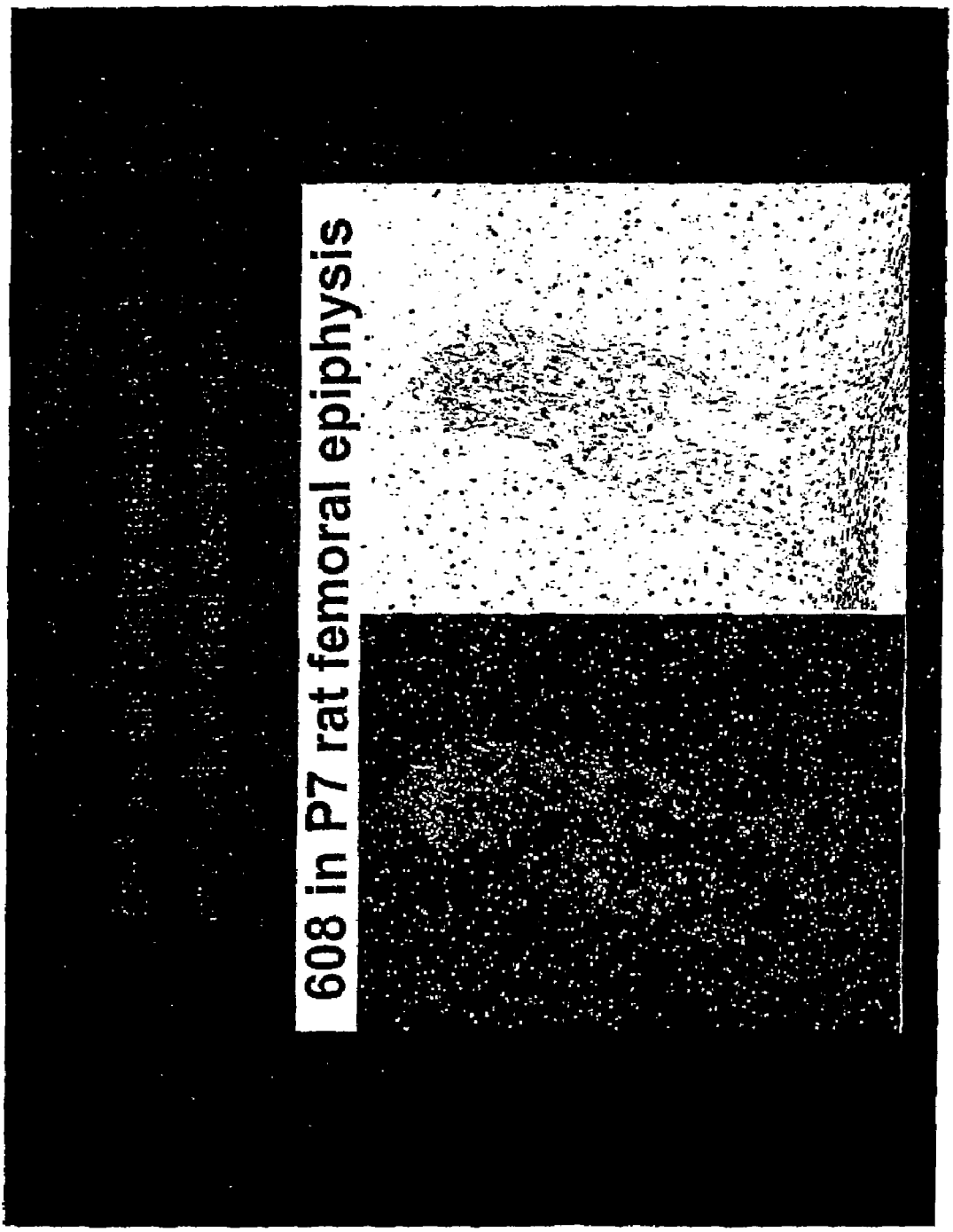
FIG. 13 shows that OCP is an early marker of endochondral ossification in P7 rat femoral epiphysis.
Figure 14:
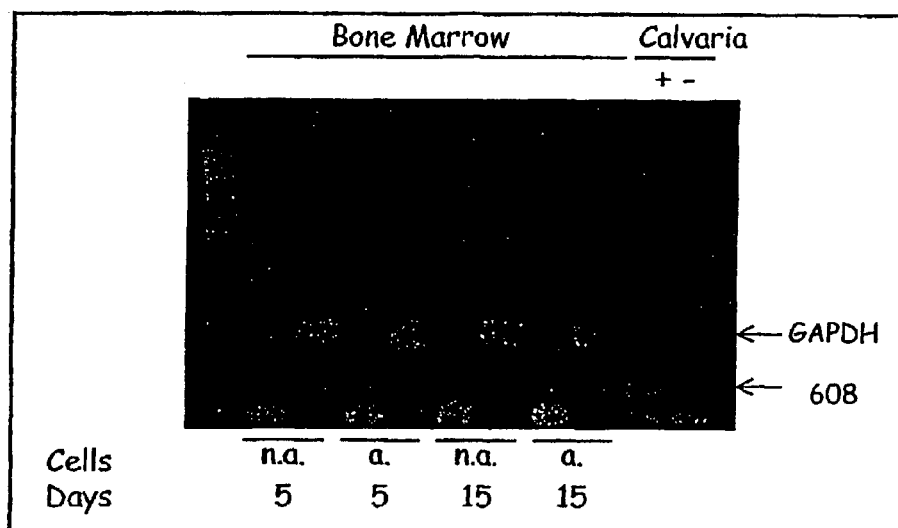
FIG. 14 shows that OCP is induced during osteoblastic differentiation of bone marrow stroma cells and is a specific marker of early osteoblastic differentiation in bone marrow.
Figure 15:
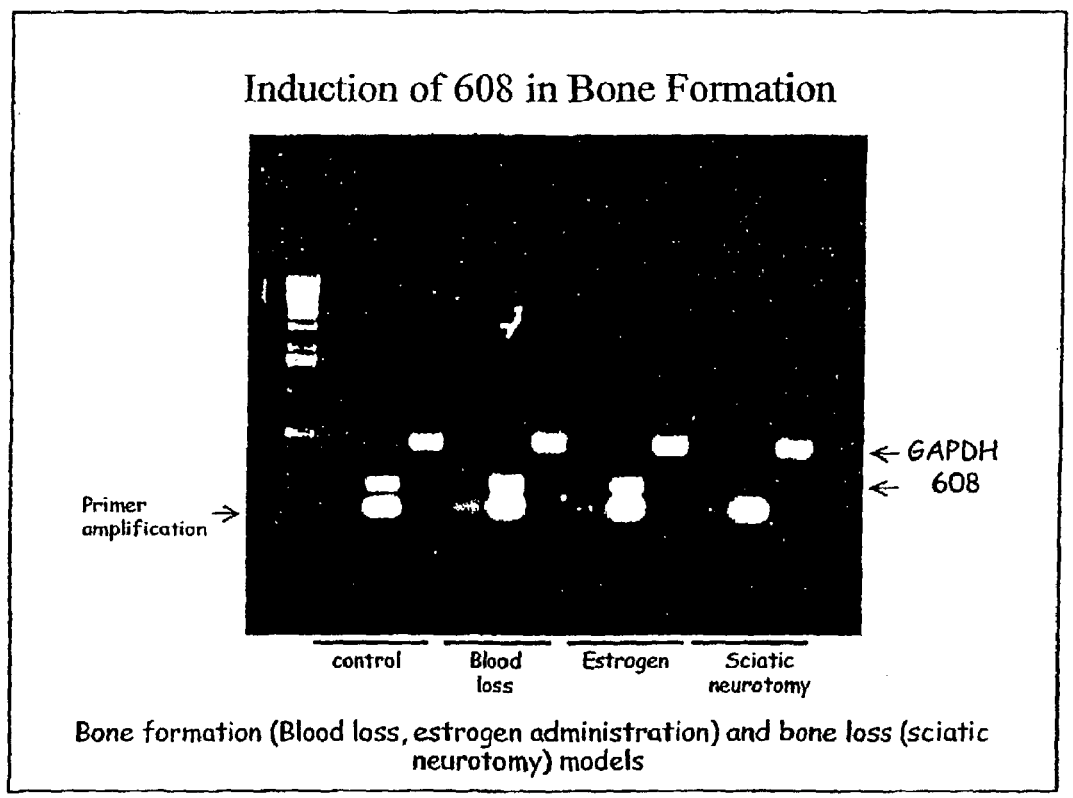
FIG. 15 shows in vivo regulation of OCP expression in bone marrow formation by various treatments. The results shown are representative of three experiments using total cellular RNA from treated two-month old mice. The different treatments are indicated. The RT-PCR products are marked. Control mice did not undergo any treatment. In each treatment group the left lane represents negative control without the addition of RT, the central lane represents the OCP RT-PCR product and the right lane represents the GapDH RT-PCR product. Bone formation is shown with blood loss and estrogen administration; bone loss is shown with sciatic neurotomy models.

OCP transcription was detected by RT-PCR in mouse calvaria cells, U2OS cells (human osteosarcoma cell line), and human embryonal bone. FIG. 14. OCP was initially discovered as being upregulated during mechanical stress in calvaria cells. In the present invention, we demonstrate that the influence of mechanical stress on OCP expression can be reproduced in another cell system using a different type of mechanical stimulation. In serum-deprived MC3T3-E1 pre-osteoblastic cells, mechanical stimulation caused by mild (287×g) centrifugation markedly induced OCP mRNA accumulation. FIG. 15. Other osteoblastic marker genes (osteopontin, ALP (staining—not shown) and Cbfa1) were transcriptionally augmented by this procedure. FIG. 15. The RT-PCR product of a non-osteoblastic marker gene (GAPDH) was used as a control to compare RNA levels between samples. No increased expression was noticed when the latter primers were used. No expression was detected in non-osteoblastic cells (FIG. 14), suggesting that OCP expression is specifically induced in osteogenesis. Responsiveness of CMF608 expression to mechanical stimulation was confirmed by Northern blot analysis using polyA RNA from primary rat calvaria cells before and after mechanical stress (FIG. 12.).

Example 11

OCP Induction During Endochondral Growth—In Situ Hybridization Analysis

Our previous results demonstrated that OCP is expressed during adult mice bone modeling and remodeling. The expression was restricted to the following regions:
1 perichondrium
2 periosteum
3 active remodeling and modeling regions
4 perivascular connective tissue
5 articular cartilage covering cells
6 embryo-condensed mesenchymal cells—head, vertebrae and trunk
7 ectopic bone formation No previous observations suggest any role for OCP in bone development or initiation of endochondral ossification (longitudinal growth of long bones). Thus, the expression pattern of OCP by in situ hybridization on sections of bones from 1 week old mice was analyzed. At this stage of bone development, osteogenesis starts within the epiphysis (secondary ossification center). The hind limb skeleton of 1 week old rat pups (femur together with tibia) was fixed in buffered formalin and longitudinal sections of decalcified tissue were processed for in situ hybridization according to standard in-house protocol. Autoradiographs were developed, stained with hematoxylin-eosin and studied under microscope using brightfield and darkfield illumination.

A strong fluorescence signal was observed all over the second ossification center using OCP probes. FIG. 17 In addition, the hybridization signal delineates periosteal and perichondrial tissue in a way similar to that found earlier in adult bones. Surrounding mature chondrocytes displayed no signal. A very faint signal was observed using the osteocalcin probe which is a marker of mature osteoblasts.

In conclusion, OCP is expressed in osteoprogenitor cells that initiate endochondral ossification during bone development.

Example 12

In vivo Regulation by Stimuli Either Promoting or Suppressing Bone Formation: Estrogen Administration, Blood Loss and Sciatic Neurotomy Osteogenic cells are believed to derive from precursor cells present in the marrow stroma and along the bone surface. Blood loss, a condition that stimulates hemopoietic stem cells, activates osteoprogenitor cells in the bone marrow and initiates a systemic osteogenic response. High-dose estrogen administration also increases de novo medullary bone formation possibly via stimulation of generation of osteoblasts from bone marrow osteoprogenitor cells. In contrast, skeletal unweighting, whether due to space-flight, prolonged bed-rest, paralysis or cast immobilization leads to bone loss in humans and laboratory animal models. To detect alteration in OCP expression pattern following the above procedures, the following experiments were performed on two month old mice:
  estrogen administration (500 μg/animal/week),
  bleeding (withdrawing approximately 1.6% body weight),
  unilateral (right limb) sciatic neurotomy,
  control groups for each treatment Total RNA was extracted from long bones after two-day treatment and RT-PCR using OCP-specific primers was performed. The results demonstrate that OCP expression was highly enhanced following blood loss and estrogen administration, while down-regulation was observed following sciatic neurotomy. FIG. 19.

By having a unique cell marker (OCP) we can show that the above procedures induce or reduce bone formation by increasing ordecreasing the number of osteoprogenitor cells. The above results suggest once more that OCP is a major member of a group of "bone specific genes" that regulate the accumulation of bone specific precursor cells.

Example 13

OCP Induction During Osteoblastic Differentiation of Bone Marrow Stroma Cells

Bone formation should be augmented in trabecular bone and cortical bone in osteoporotic patients. We have previously detected OCP expression in periosteum and endosteum (surrounding the cortical bone) but no signal was apparent in bone marrow cells. The latter cells normally differentiate to mature osteoblasts embedded in the trabecular and cortical bone matrix.

To further assess OCP expression in bone marrow progenitor cells, the inventors extracted total RNA from mouse and rat bone marrow immediately after obtaining it and after cultivation for up to 15 days in culture. No OCP-specific RT-PCR product was detected with RNA from freshly obtained bone marrow (both in adherent and non-adherent) cells. However, a faint signal was found after 5 days in culture, and it was further enhanced when RNA from cells grown for 15 days in culture was used. ALP (alkaline phosphatase) expression (an osteoblastic marker) was also found to be enhanced after 15 days. At both time points, adherent and non-adherent cells were reseeded, and RNA extractions were prepared 5 and 15 days later. A stronger RT-PCR product was observed with RNA extracted from originally adherent cells, suggesting the existence of less mature progenitors in the non-adherent population of bone marrow cells. The RT-PCR product of a non-osteoblastic marker gene (GAP-DH) was used as a control to compare RNA levels between samples.

In conclusion, bone marrow progenitor cells do not express OCP, but differentiate to more committed cells that do express this gene.

Example 14

OCP Role in Osteogenesis In Vitro

Figure 24:
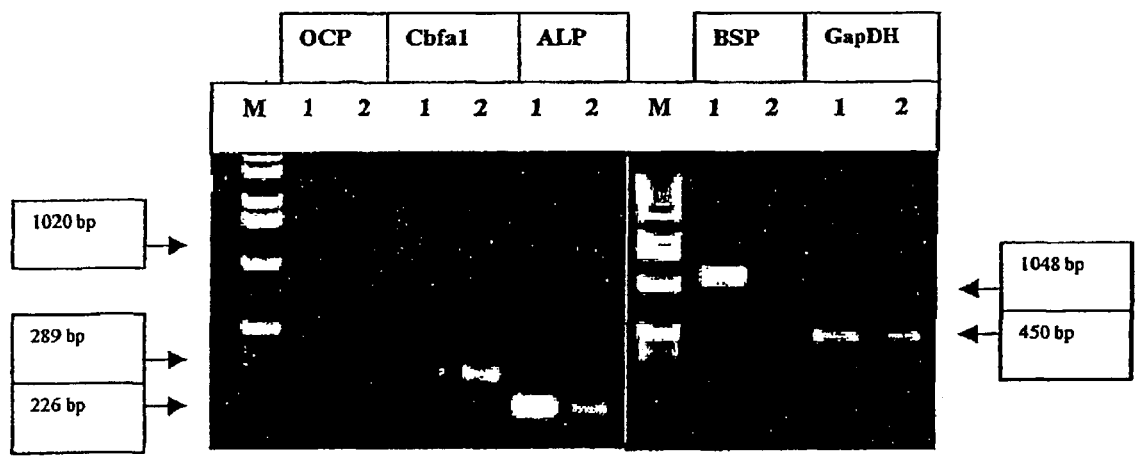
FIG. 24 shows increased osteoblast differentiation in OCP-transfected ROS cells. RT-PCR assays were with OCP, Cbfa1, ALP, BSP and GapDH specific primers as indicated above. The results shown are representative of two experiments using total cellular RNA from: (1) the stable OCP-expressed ROS cell line; and (2) the control ROS cell line (stable transfection with pCDNA). The OCP RT-PCR product is 1020 bp, the Cbaf1 product is 289 bp, the ALP product is 226 bp, the BSP product is 1048 bp and the GapDH (control) product is 450 bp long. M represents protein markers.
Figure 25:
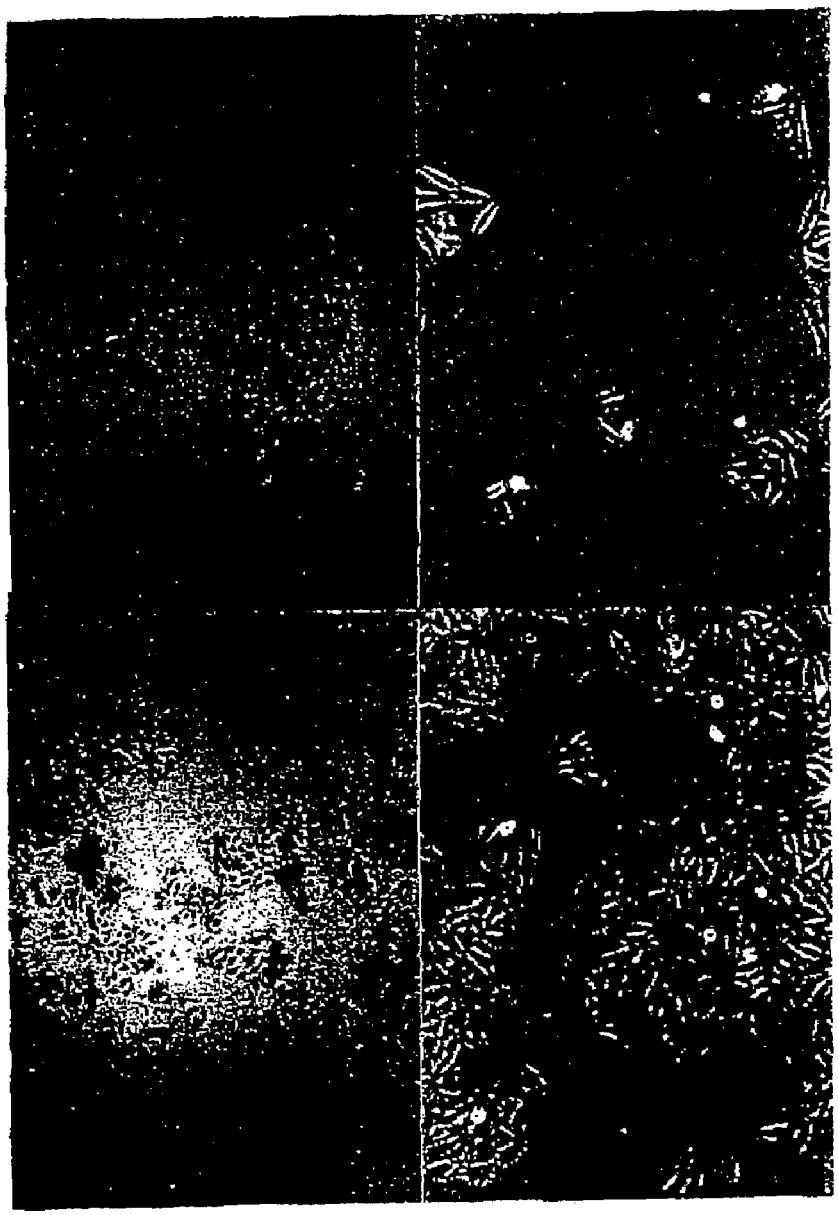
FIG. 25 shows increased osteoblast proliferation in OCP-transfected ROS cells.
Figure 32:
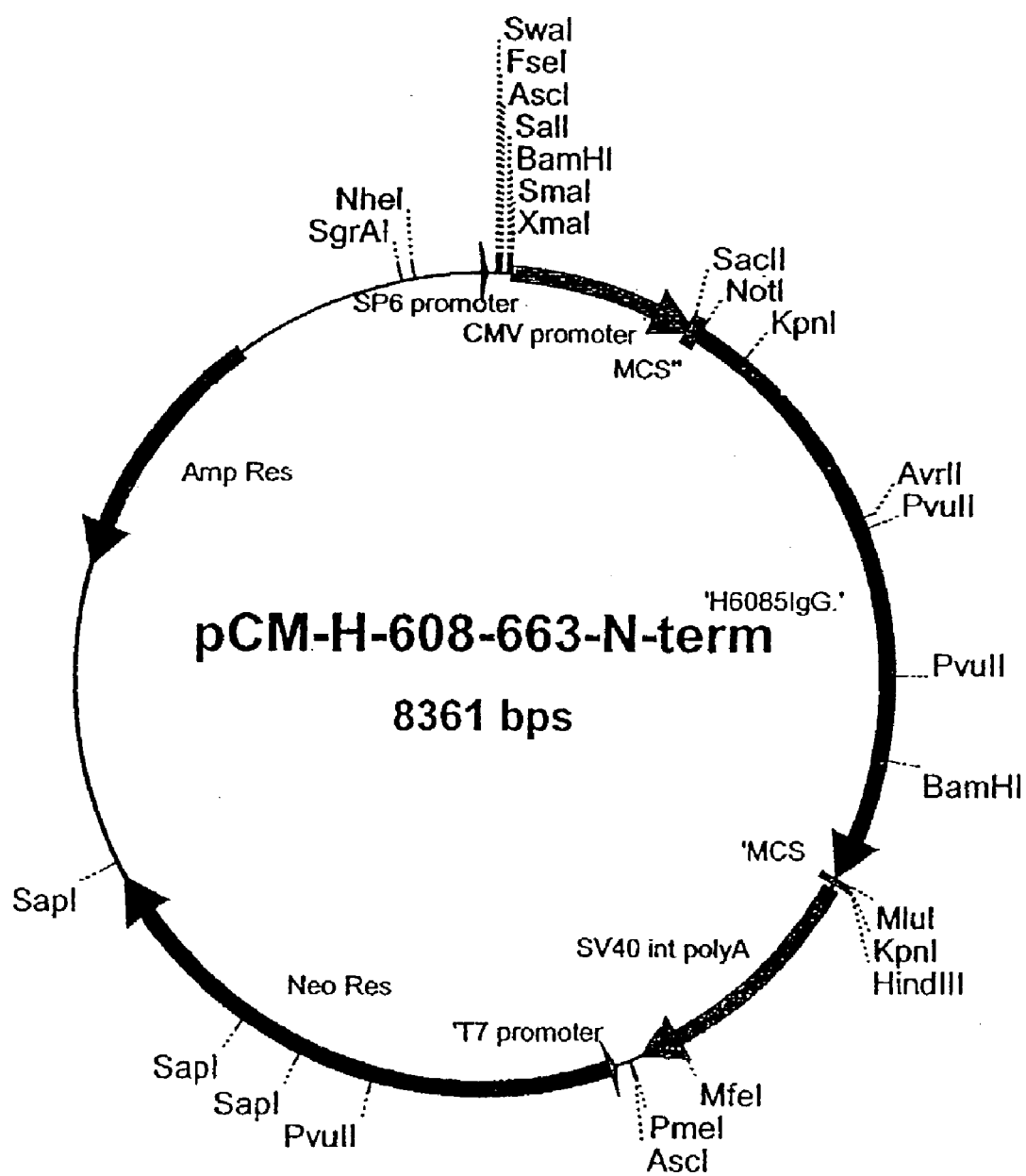
FIG. 32 shows the pCM-H-608-663-N-term construct map.
Figure 33:
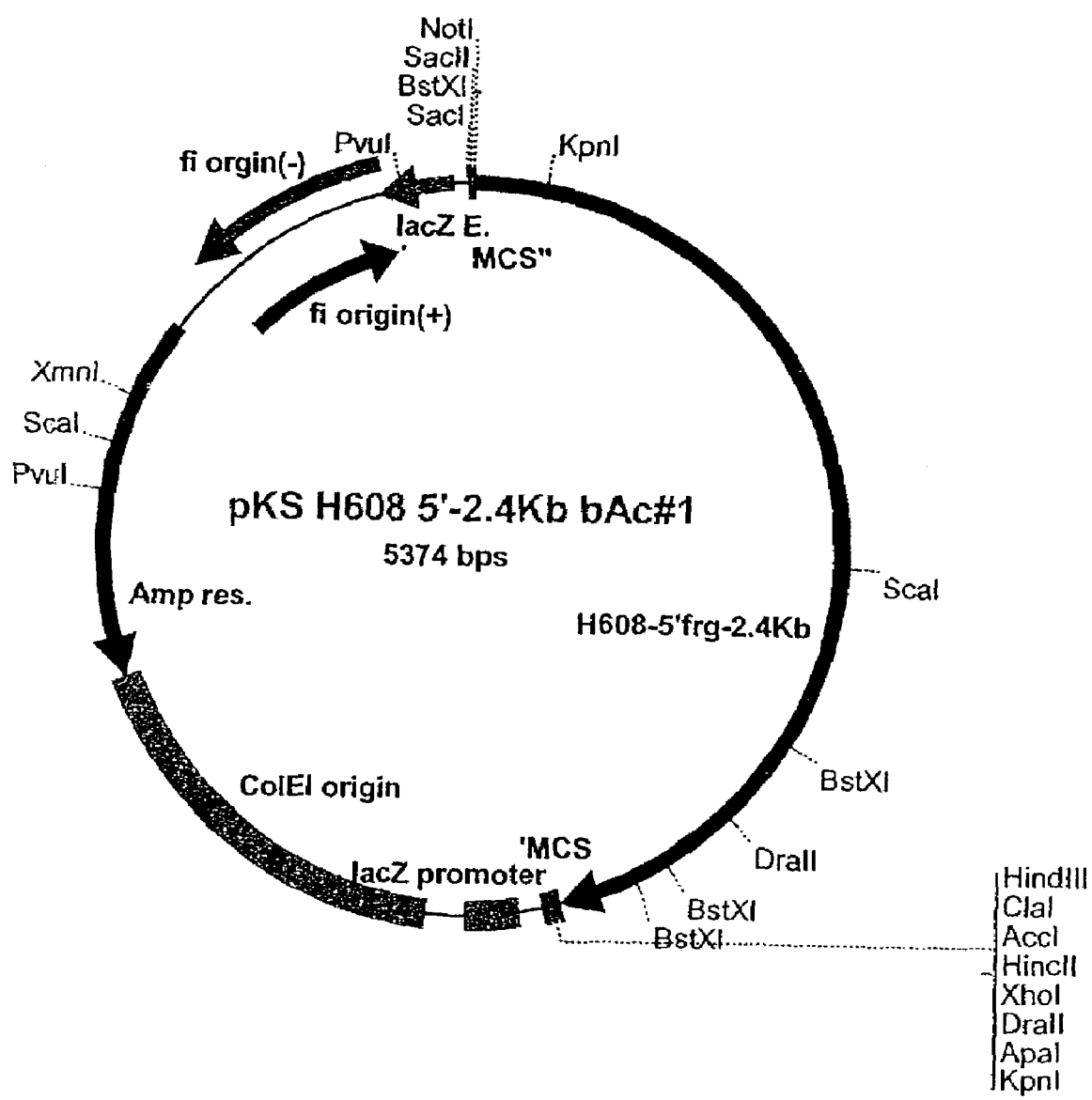
FIG. 33 shows the structure of the pKS H608 5'-2.4 Kb bAc#1 construct (deposited on Nov. 21, 2001 under the terms of the Budapest Treaty with the American Type Culture Collection (ATCC), P.O. Box 1549, Manassas, Va. 20108, USA, under ATCC accession number PTA-3878).
Figure 35:
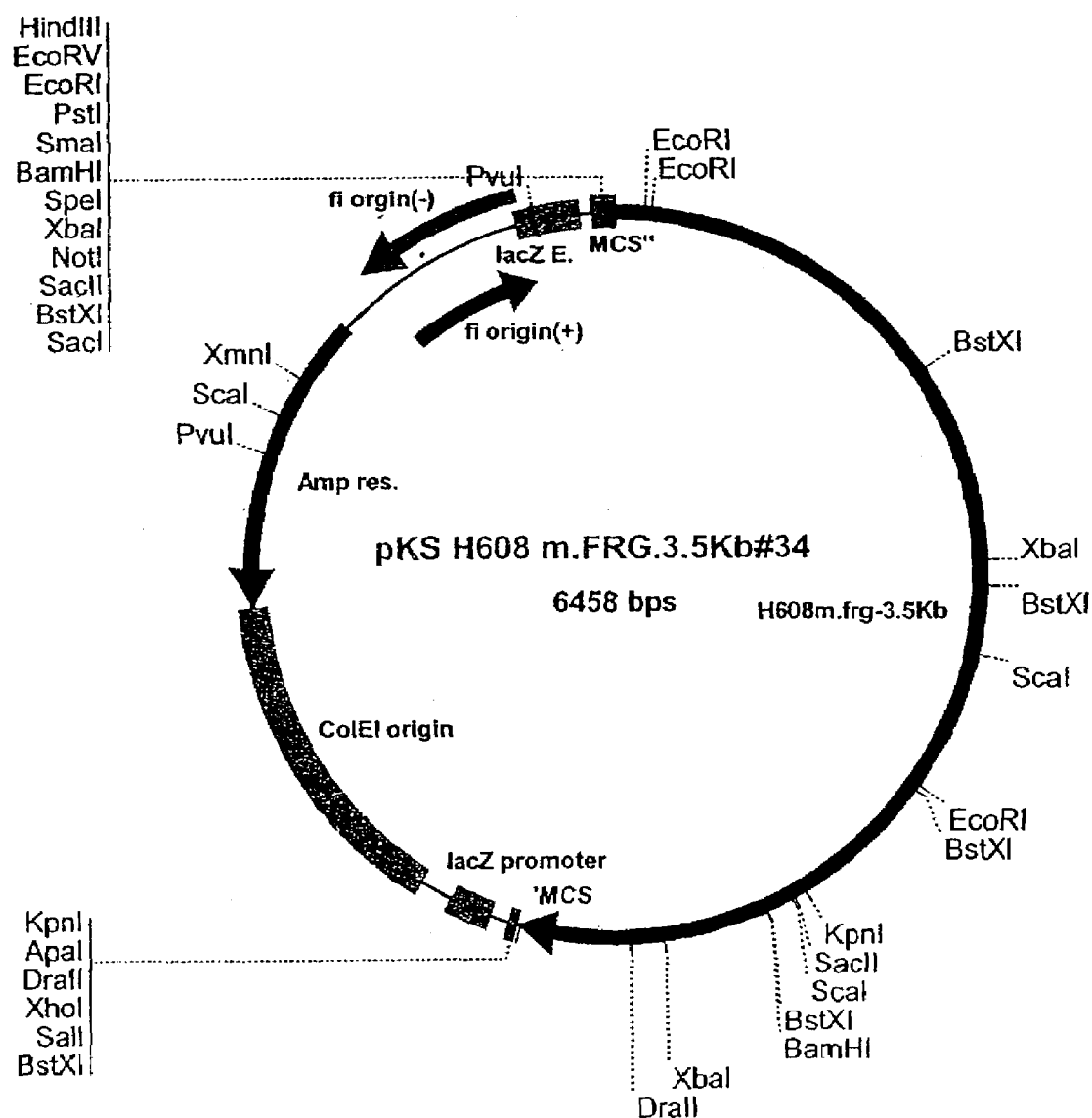
FIG. 35 shows the structure of the pKS H608 m.FRG.3.5Kb#34 construct (deposited on Nov. 21, 2001 under the terms of the Budapest Treaty with the American Type Culture Collection (ATCC), P.O. Box 1549, Manassas, Va. 20108, USA, under ATCC accession number PTA-3876).
Figure 37:
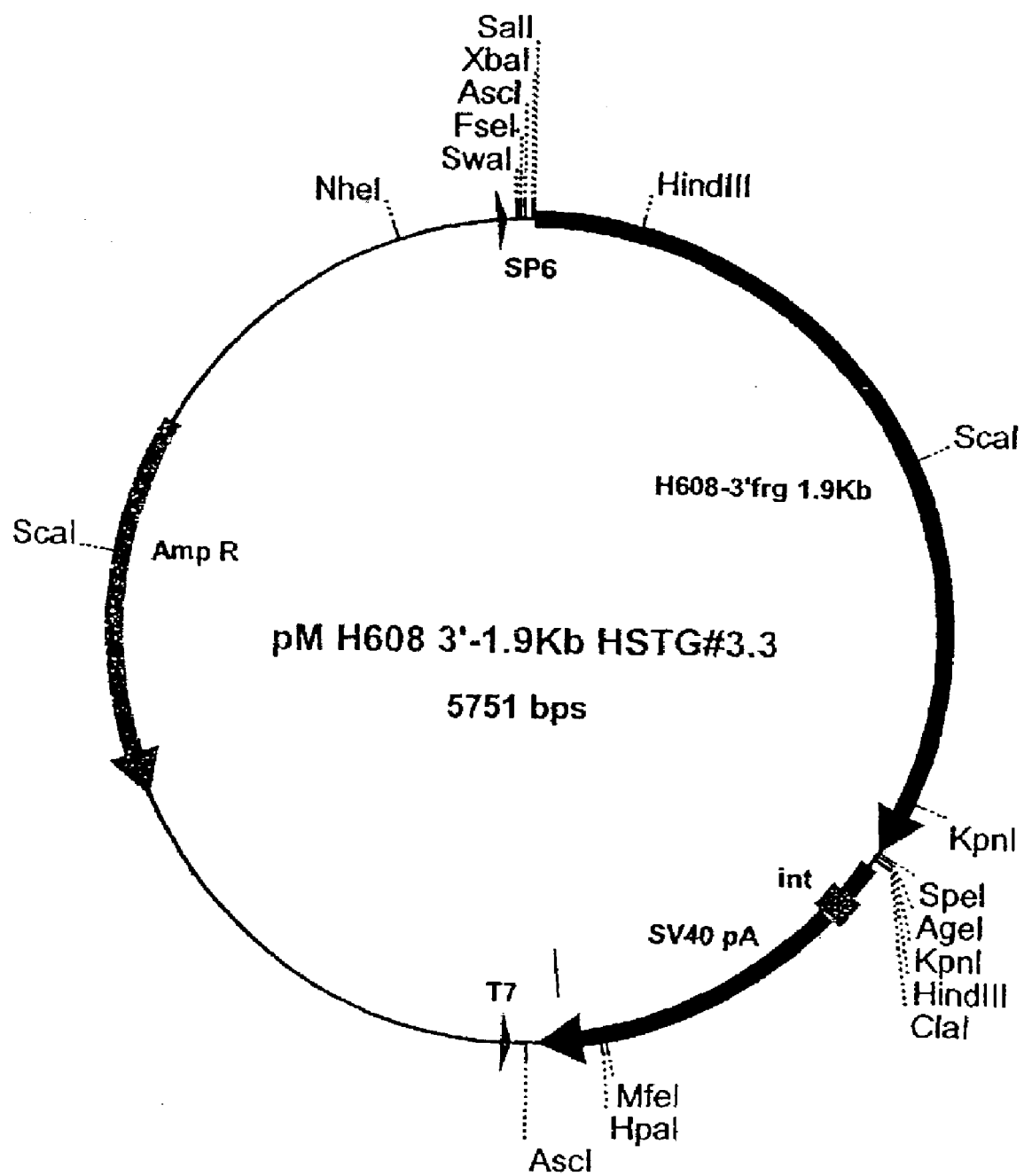
FIG. 37 shows the structure of the pM H608 3'-1.9Kb HSTG#3.3 construct (deposited on Nov. 21, 2001 under the terms of the Budapest Treaty with the American Type Culture Collection (ATCC), P.O. Box 1549, Manassas, Va. 20108, USA, under ATCC accession number PTA-3877).

The ultimate test for the role of OCP as a crucial factor that induces osteoblast-related genes is its ability to up-regulate these genes in pre-osteoblastic and osteoblastic cells. Stable transfection of OCP to ROS 17/2.8 (differentiating osteoblast cell line) cells upregulated ALP and BSP expression.FIG. 24 In addition, marked increase in osteoblastic proliferation was observed; see FIG. 25

C3H10T1/2 cells were transfected with the following constructs containing the CMV promoter:
1. 608-663 a.a—Construct containing 5' untranslated region of β-actin, the OCP coding region from ATG at position 1 to the amino acid at position 663 of FIG. 3 (SEQ ID NO:2) and 3' Flag Tag. The functional portion of the mammalian OCP expressed using this construct contains the first 663 amino acids of the OCP polypeptide sequence, plus several additional amino acids of the 3° Flag tag An additional construct was made, designated pCm-H608-663Nterm, which has the 5' untranslated region of β-actin, the human OCP coding region from which encodes polypeptide from the ATG at position 1 to the amino acid at position 663 of FIG. 30 (SEQ ID NO:24) but no Flag Tag; this construct was deposited in the ATCC on Aug. 14, 2001 under ATCC Number PTA-3638.
2. pCMV-neo—as negative control. This is the empty plasmid into which the 608-663aa was cloned to create vector #1 above. It serves as negative control to show that the effects are not caused by any other part of the #1 construct but by expression of the 608-663aa.

Example 15

Creation of a Readout System

A readout system is created to identify small molecules that can either activate or inactivate the OCP bone-precursor-specific promoter Example 16

Bioinformatic Analysis of Human 608

A DNA sequence encoding a fragment of human OCP named AC024886 is found in htgs database but not in nt. There is no genomic DNA corresponding to the rat cDNA. Alignment of AC024886 against the rat cDNA using BLAST shows two areas of long alignment (and several shorter areas):
   1. cDNA: 6462-8186
   Genomic: 89228-90952
   plus/plus orientation: 81% identity
   2. cDNA: 5581-6451
   Genomic: 107710-106840
   Plus/minus orientation: 80% identity Thus AC024886 was wrongly assembled in the region upstream of position 6462 (according to the rat cDNA), it was in the incorrect orientation. Using the incorrect orientation provided incorrect coding sequence and does not yield the human OCP protein.

The Genbank report on AC024886 was as follows:
LOCUS AC024886 175319 bp DNA
HTG 06-SEP-2000
DEFINITION Homo sapiens chromosome 3 clone RP11-25K24, WORKING DRAFT
SEQUENCE, 9 unordered pieces.
ACCESSION AC024886
VERSION AC024886.10 GI:9438330
KEYWORDS HTG; HTGS_PHASE1; HTGS_DRAFT.
SOURCE human.

NOTE: This was a 'working draft' sequence. It consisted of 9 contigs. The true order of the pieces was not known and their order in this sequence record was arbitrary. Gaps between the contigs are represented as runs of N, but the exact sizes of the gaps was unknown.
* 1 62523: contig of 62523 bp in length
* 62524 62623: gap of unknown length
* 62624 85445: contig of 22822 bp in length
* 85446 85545: gap of unknown length
* 85546 106059: contig of 20514 bp in length
* 106060 106159: gap of unknown length
* 106160 127908: contig of 21749 bp in length
* 127909 128008: gap of unknown length
* 128009 143068: contig of 15060 bp in length

* 143069 143168: gap of unknown length
* 143169 158734: contig of 15566 bp in length
* 158735 158834: gap of unknown length
* 158835 170042: contig of 11208 bp in length
* 170043 170142: gap of unknown length
* 170143 173715: contig of 3573 bp in length
* 173716 173815: gap of unknown length
* 173816 175319: contig of 1504 bp in length.

a. Mapping Human Genomic 608 Exons

Ten exons were mapped on the rat cDNA sequence from base 107 to 6451. Thus the first exon on the human genomic piece may be lacking. The human genomic piece (AC024886) upstream (19090 bases) of base 6462 of cDNA (reverse complement from base of AC024886 92001 to 111090) was compared with the rat cDNA using the program ExonMapper of Genomatix. In the Table, base 1 is actually 1131 in the genomic piece used so that the actual genomic location starts at 91870.

Two additional exons were mapped on the rat cDNA sequence from base 6462 to 8883. Thus bases 6452-6461 are lacking. The human genomic piece used is from base 165,337 to 17,5667 (10,331 bases). The same type of program was used to compare this sequence to the genomic mouse 608 sequence deduced as described above.

Connecting the exon/intron borders from the genomic sequences yielded the predicted human and mouse cDNAs. The mouse and human predicted cDNAs were modified in order to allow frame shifts that allow a good multiple alignment of the human, mouse and rat proteins. Alignment was done using CLUSTALX and Pretty.

The cDNA modifications after the alignment of human cDNA to rat cDNA by GeneWise were as follows. In the following two tables, −x indicates a deletion of nucleotide x in the cDNA sequence; +x indicates an insertion of nucleotide x in the cDNA sequence; and all changed positions are in to the original sequence

| Position | Change |
|---|---|
| 1111 | −g |
| 4154 | −c |
| 4538 | +g |
| 4730 | −a |
| 4744-5 | −aa |
| 4830 | +c |
| 4852 | −g |
| 4902 | +t |
| 4942 | +c |
| 5370 | +t |
| 5387 | −a |
| 5395 | +c |

The corrections of frame-shifts in mouse 608 were as follows:

| Position | Change |
|---|---|
| 678 | −c |
| 1106 | −a |

Chromosomal Location on the Human Chromosome:
Two different types of data exist.
a. Genomic piece AC024886 has identity to the fragment identified as ACCESSION D14436 as described by Fukui et al. (1994) Biochem. Biophys. Res. Commun. 201:894-901.
Alignment information:
Identities=315/335 (94%),
hrh1: 4-338
AC024886: 41662-41328
Hrh1 is mapped to chromosome 3 and to 3p25; and
b. Identity to STS at 3q. STS: 20-432 is identified as ACCESSION G54370 and described by Joensuu et al. (2000) Genomics 63:409-416.

Example 17

Polyclonal Antibody Preparation

Polyclonal antibodies specific to the whole 608 putative protein are prepared by methods well-known in the art (the structure of 608 resembles that of growth factor precursors). Polyclonal antibodies are identified and the recombinant active form of 608 is prepared. The activities of the polyclonal antibodies are tested in vivo in mice. The antibodies can be used for the identification of the active form of this protein which is likely to constitute a fraction of the 608 protein.

Example 18

Stretch of Basic Amino Acids Found at the Boundary of the Rat and Human 608 Proteins, and its Implications The homology between the rat and human N-terminal portions of the 608 protein is especially significant within the first 250 amino acids. At the boundary of this conserved region there is a completely conserved stretch of basic amino acids: KCKKDR (aa 242-247 and 240-245, in rat and human proteins, respectively). Stretches of basic amino acids frequently serve as protease cleavage sites. The fact that such a stretch is found on the boundary of more or less conserved sequences and the fact that it occurs within the C-terminal LRR, a generally conserved domain, suggests an underlying biological significance.

Accordingly, the 608 protein may undergo post-translational processing through the cleavage of its highly conserved N-terminal portion and this portion may be an active part of the 608 protein or possess at least part of its biological activities. Since the resulting ~25 kD protein preserves the signal peptide, it would be secreted.

The biologically active 25 kD N-terminal cleavage product of 608 can thus be used for treatment and/or prevention of osteoporosis, fracture healing, bone elongation and periodontosis. As an indirect product (inhibition by either chemicals or by neutralizing mAbs), the fragment can be used for treatment and/or prevention of osteoarthritis, osteopetrosis, and osteosclerosis.

Example 19

The Adlican Protein and Gene

Adlican is a recently described protein. Crowl and Luk (2000) Arthritis Biol. Res. Adlican, a proteoglycan, was derived from placenta. The full amino acid sequence of Adlican is disclosed and identified as AF245505.1:1.8487, and is hereby incorporated by reference into this application; see FIG. 27.

The structure of Adlican was analyzed using methods described herein and found to have leucine-rich repeats and immunoglobulin regions similar to those of the OCP protein. The overall homology found between the amino acid residues of the indicated regions in the two proteins, is as follows:

| OCP | Adlican | % |
|---|---|---|
| 1-661 | 1-669 | 38.4 |
| 662-1629 | 670-1865 | 19.7 |
| 1630-2587 | 1866-2828 | 46.5 |
| 1-2587 | 1-2828 | 33.2 |

The invention therefor encompasses the use of Adlican in any manner described herein for the OCP protein. These functions and uses have not been disclosed previously for Adlican. They include use of Adlican, or a functional portion thereof, for preventing, treating or controlling osteoporosis, or for fracture healing, bone elongation or treatment of osteopenia, periodontosis, bone fractures or low bone density or other factors causing or contributing to osteoporosis or symptoms thereof or other conditions involving mechanical stress or lack thereof in a subject.

The Adlican gene, or functional portions thereof, can likewise be used for any purpose described herein for an OCP gene. Compositions comprising the Adlican gene, Adlican or antibodies specific for Adlican and physiologically acceptable excipients are likewise encompassed by the invention. Such excipients are known in the art and include saline, phosphate buffered saline and Ringer's solutions.

Example 20

Sequencing of the N-terminal of the OCP Gene

Sequencing of the N-terminal fragment of the OCP gene using the 663 amino acid human construct (Example 14) added six additional nucleotides to the DNA sequence as shown in FIG. 29 (SEQ ID NO:23), where these 6 additional nucleotides are underlined.

The corresponding amino acid sequence of the encoded OCP protein thus has an additional two amino acids, as shown in FIG. 30,(SEQ ID NO:24) where these 2 additional amino acids are underlined.

Example 21

Preparation of a Recombinant Functional Portion of OCP

The 663 amino acid construct described in Example 14 was expressed in 293T cells. Western blot analysis of the medium, using antibody to the Flag tag, showed the presence of the 663 amino acid polypeptide. This polypeptide was purified from the medium, using a column of anti-Flag tag antibodies.

Our objective was to determine if the 1-663 amino acid polypeptide fragment of the 608 protein could induce proliferation in bone-related cell lines. Proliferation activity was tested by $^3$[H] thymidine incorporation assay on 4 bone related cell lines, with IGF1 or PTH as standards. (Pre-osteoblastic and osteoblastic proliferation is an activity that characterizes bone formation inducing factors such as IGF1 and PTH.)

In this key series of experiments, the purified 663 polypeptide showed a proliferative effect on W-20-17, a mouse bone marrow stromal cell line. This effect was reproduced with two 663- polypeptide batches in 5 independent experiments.

The activity of proliferation of bone marrow stromal cells demonstrated in the above experiments could be indicative of pre-osteoblastic proliferation activity induced by the 663 amino acid polypeptide. The 663 polypeptide activity could be mimicing the complete 608 protein in vivo activity. Alternatively, the 663 polypeptide activity could have a dominant negative effect, i.e. an effect that inhibits the whole 608 protein in vivo activity. Regardless of the mechanism, the 663 polypeptide could be used to induce proliferation of pre-osteoblastic stromal cells. This activity could help restore the pre-osteoblastic cell population that is known to be depleted in old-age or senile osteoporosis.

Example 22

Identification of RGD and Subtilisin-like Proprotein Convertase (SPC) Motifs in Rat OCP SEQ ID NO: 2 and SEQ ID NO: 34 depict the amino acid sequence of the rat 608 polypeptide. There is an RGD sequence at positions 729-731, and there is a putative cleavage motif subtilisin-like proprotein convertase (SPC) consensus sequence at positions 735-741.

The 608 protein was partially cleaved by SPC, in 293HEK cells. This putative peptide also contained the RGD sequence. Many adhesive proteins, present in extracellular matrices and in the blood, contain this tripeptide as their cell recognition site. Therefore, the 608 peptide comprising 1-741 amino acids, or a shorter fragment of the 608 protein containing the RGD sequence, may be a much more effective drug than the 663 amino acid fragment. The RGD and RxxRxxR (viz. R-aa1-aa2-R-aa3-aa4-R, i.e., SPC cleavage site) sequences are present in the human 608 protein sequence but are not present in Adlican or in Adlican-2.

Example 23

Natural Cleavage of Rat OCP

A polyclonal antibody against the rat 608 fragment comprising amino acid residues 1-312 was prepared by methods well-known in the art. This antibody was used to identify 608 peptides on Western blots. Several 608 sequences were expressed in cells derived from the transiently transfected 293T kidney cell line. The sequences were rat full length 608 polypeptide, rat 608 polypeptide fragment comprising amino acid residues 1-1634, and rat 608 polypeptide fragment comprising amino acid residues 1-663. The antibody identified a peptide of about 90 kDa in all three constructs produced. This peptide was detected by the anti-608 antibody in the conditioned medium of the cells, and not in cell extracts.

TABLE

Western blot analysis using polyclonal antibody to rat 608 fragment comprising 1-312 amino acid residues:

| 608 amino acid sequence | Expected size | Detected size |
|---|---|---|
| 1-663 | 80 kDa | 75-100 kDa |
| 1-1634 | 196 kDa | 75-100 kDa (larger than 1-663 aa peptide) |
| 1-2597 (full length) | 311 kDa | 75-100 kDa (larger than 1-663 aa peptide) |
| 1-741 | 89 kDa | |

The 608 full length and the 608 1-1634 aa proteins produced in 293T cells were cleaved and secreted into the medium. The cleaved products appeared to be of identical size. The 608 1-663 aa protein was also secreted into the medium, but appeared to be slightly smaller than the cleaved full length and 1-1634 aa proteins. The expected size of the 608 fragment from 1-741 aa, that is, the putative SPC cleavage product, was approximately 89 kDa.

In further experiments, mouse calvaria cells cultured in vitro were analyzed by western blotting with the antibody to the 608 fragment 1-312aa. No 608 specific band was detected in cell extracts. In the conditioned medium from the cells a band of approximately 350 kDa was detected by the anti 608 1-312aa. The size of this band correlates with the protein size expected from the full length 608 protein. This analysis probably indicates that the 608 full-length protein is secreted.

To summarize, in human embryonic kidney cells, which do not normally express the 608 gene, overexpression of 608 protein results in secretion of a cleaved part of the 608 protein. In mouse calvaria cells, which normally express the 608 gene, the naturally expressed 608 protein is probably secreted uncleaved. One possible explanation of this data is that 608 activity is regulated by proteases that are selectively expressed.

Example 24

Human Adlican as a Candidate for Osteoblast Proliferation and Differentiation As discussed in Example 19, Adlican is a recently described protein. The Adlican protein has LRR (Leucine-rich-repeats) and immunoglobulin regions highly similar to those of the OCP protein. The overall homology found between the amino acid residues of the indicated regions in the two human proteins is as shown in Example 19.

The deduced Adlican protein comprises the following features:

a. A cleavable, well-defined N-terminal signal peptide at 1-26 aa, b. A LRR region (26-205 aa). This region can be divided into N-terminal and C-terminal domains of LRR (aa 26-59 and 217-276, respectively). Between them, there are six LRR (aa 55-77, 78-101, 102-125, 126-149, 150-173, 182-205).

c. Twelve immunoglobulin C-2 type repeats at amino acid positions 492-562, 590 658, 1866-1935, 1963-2032, 2060-2129, 2159-2228, 2256-2331, 2359-2425, 2457-2525, 2555-2623, 2650-2718, 2746-2817. Thus, two Ig-like repeats are found immediately downstream of a LRR region, while the remaining 10 repeats are clustered at the protein's C-terminus, as in OCP.

d. 4 nuclear putative localization domains (NLS) at amino acids: 676-682, 1146-1165, 1230-1236, and 1747-1763.

Therefore, we have determined that Adlican is a good candidate as an inducer of osteoblast proliferation and differentiation.

In order to determine if human Adlican expression causes proliferation and differentiation of osteoblasts and chondrocytes, the expression product of Adlican, or cells or vectors expressing Adlican are monitored to determine if they cause cells to selectively proliferate and differentiate and thereby increase or alter bone density. Detecting levels of Adlican mRNA or expression and comparing it to "normal" non-osteopathic levels will allow screening and detection of individuals who may be at risk for developing osteoporosis or lower levels of osteoblasts and chondrocytes.

Example 25

The Deduced Adlican-2 Protein

The deduced Adlican-2 protein (Genomic location: Yq11.21) was generated following the alignment (shown in FIG. 41) comparing Adlican-2 predicted sequences (FIGS. 39 and 40) and the equivalent human Adlican amino acid sequences (FIG. 27). This DNA molecule and the encoded polypeptide are novel molecules and constitute an integral part of this invention.

A Y chromosome BAC clone (gi 8748884) shows 93% homology to Human Adlican. Two mRNA sequences 100% homologous to this BAC clone were submitted to the gene bank (gi 14719942, and gi 14719940). However, the sequence of these clones is not based on cDNA sequences, but on human genomic data and they cover a short stretch of the nucleotide sequence in the C-terminal Ig region. We performed upstream nucleotide and deduced amino acid sequencing. The sequence alignment of Adlican and Adlican-2 exists along the entire Adlican sequence with one possible exception. Alignment along aa 66-215 of Adlican may be missing from the Adlican-2 molecule. This is the area of the 6 LRR (leucine-rich repeats). Although the encoding nt's for the 6 LRR region have not yet been observed, their existence has not been definitely ruled out.

The invention therefore encompasses the use of Adlican-2 in any manner described herein for the OCP protein. No functions or uses have been disclosed previously for Adlican-2. The proposed uses include use of Adlican-2, or a functional portion thereof, for preventing, treating or controlling osteoporosis, or of fracture healing, bone elongation or treatment of osteopenia, periodontosis, bone fractures or low bone density or other factors causing or contributing to osteoporosis or symptoms thereof or other conditions involving mechanical stress or lack thereof in a subject. As an indirect product (inhibition by either chemicals or by neutralizing mAbs), Adlican-2 can be used for treatment and/or prevention of osteoarthritis, osteopetrosis, and osteosclerosis. The Adlican-2 gene, or functional portions thereof, can likewise be used for any purpose described herein for an OCP gene. Compositions comprising the Adlican-2 gene, Adlican-2 or antibodies specific for Adlican-2 and physiologically acceptable excipients are likewise encompassed by the invention. Such excipients are known in the art and include saline, phosphate buffered saline and Ringer's solutions.

Example 26

The Physical Sequence of the Human OCP

Obtaining the sequence of human OCP was a difficult task. Initially several attempts were made to do amplification via RT-PCR using rat primers from the rat OCP coding sequence, in order to obtain human OCP cDNA, but these efforts failed. Thereafter, a predicted sequence was created as described in Examples 5 and 16 by bioinformatic analysis of the human genome. Then primers specifically designed according to the predicted sequence were used to amplify human cDNA. This proved difficult, due to the large size of the gene and also to the problem of the low abundancy of OCP mRNA in human tissue and the unavailabilty of such tissue. Eventually, cell line U2OS (human osteosarcoma cell line) was found to be a suitable source for OCP mRNA. It was also decide to clone the DNA in fragments.

The first section of the gene to be cloned was a small fragment corresponding to the first 663 amino acids, creating the plasmid described in Example 14 (ATCC Number PTA-3638), and giving a corrected predicted sequence.

Since the complete human OCP gene could not be amplified and cloned as one entity, three large overlapping fragments were amplified, spanning the complete ORF. These PCR fragments were sequenced and the physical sequence of the human OCP was determined accordingly. The physical sequence was found to contain inserts relative to the predicted sequence. The overlapping PCR fragments were subsequently cloned in three separate plasmids (described below) as continous clones (overlapping regions were removed).

FIG. 42 shows the physical DNA sequence of the coding region-ORF of human OCP (SEQ ID NO: 31) having 7872 base pairs, including the stop codon. The sequence contains a silent mutation (C>T transition) at position 6729 compared to the predicted sequence of human OCP ORF. This transition does not change the identity of the encoded amino acid residue.

FIG. 43 shows the predicted amino acid sequence corresponding to the physical DNA sequence of the coding region-ORF of human OCP (SEQ ID NO:32), having 2623 amino acids.

The three plasmids harboring the 5' fragment (A), middle fragment (B) and 3' fragment (C) are depicted in FIGS. 34, 36 and 38 respectively, and were deposited on Nov. 21, 2001 under the terms of the Budapest Treaty with the American Type Culture Collection (ATCC), P.O. Box 1549, Manassas, Va. 20108, USA, under ATCC accession numbers PTA-3878, PTA-3876 and PTA-3877 respectively.

FIG. 34 shows the physical sequence of the 5' fragment (A) cloned into pBluescript KS to NotI (5') and HindIII (3') sites. Fragment A is comprised of the 5' region (2440bp) of the complete human OCP sequence and includes, in addition, at the 5' end, 21 nucleotides of the β-actin "Kozak" region (nucleotides 9-29) followed by the ATG initiation coNotI (5') and HindIII (3') sites are located at nucleotides 1-8 and 2464-2469 respectively (SEQ ID NO:26).

FIG. 36 shows the physical sequence of the middle fragment (B) cloned into pBluescript KS to HindIII (5') and SalI (3') sites. Fragment B is comprised of the central region (3518 bp) of the complete human OCP sequence; the HindIII (5') and SalI (3') sites are located at nucleotides 1-6 and 3513-3518 respectively (SEQ ID NO:27).

FIG. 38 shows the physical sequence of the 3' fragment (C) cloned into pMCS SV(A) to SalI (5') and SpeI (3') sites. Fragment C is comprised of the 3' region (1923 bp, not including the 3 bp stop codon) of the complete human OCP sequence and includes at the 3' end, 18 nucleotides coding for 6 Histidine residues, nucleotides 1924-1941, followed by the TGA stop codon.; the SalI (5') and SpeI (3') sites are located at nucleotides 1-6 and 1945-1950 respectively (SEQ ID NO:28).

Additionally, as discussed above, cloned fragment C contains a silent mutation (C>T transition) at nucleotide 783 compared to the predicted sequence of human OCP ORF; this transition does not change the identity of the encoded amino acid residue.

Note that if the number of OCP-encoding nucleotides in the three separate clones is added (viz., 2440+3518+1923), nine (9) more nucleotides are obtained than in the single complete sequence (7881 nucleotides vs 7872 nucleotides). This discrepancy is due to three reasons:

1. The restriction site that appears at the 3' end of fragment A and at the 5' end of fragment B is counted twice, once in each fragment, giving an extra 6 nucleotides 2. The restriction site that appears at the 3' end of fragment B and at the 5' end of fragment C is counted twice, once in each fragment, giving an extra 6 nucleotides 3. The sequence of fragment C does not include the 3 nucleotide stop codon at the 3' end, since it is interrupted by 18 nucleotides coding for 6 Histidine residues.

Therefore the difference is 6+6−3=9, which exactly explains the discrepancy mentioned above.

Example 27

608 Knockout Bone Phenotypes in Females With and Without Ovariectomy Introduction Knockout (KO) mice deleted of the 608 gene were prepared by the method of Wattler et. al. BioTechniques 26:1150-1160, 1999. Comparison of 608 knockout (KO) mice to age, sex, and treatment matched wild type (WT) mice was performed to test the effect of 608 absence on bone parameters. Bone parameters of KO and WT were compared in untreated 3 and 4 months old females. KO and WT bone parameters were also compared in 3 months old female mice 5 weeks post ovariectomy (post-menopausal osteoporosis model).

The bone-related phenotypes were evaluated using two analyses: Peripheral Quantitative Computed Tomography (pQCT) of femur and tibia Rosen H N et. Al. Calcif. Tissue Int. 57:35-39, 1995) and serum Alkaline phosphatase (ALP) (Farley J R et. al. J Bone Miner Res 9:497-508, 1994. pQCT scanning is a 2D X-ray analysis that measures bone mineral density (BMD), bone mineral content (BMC), and bone geometric parameters. Serum ALP is a biochemical marker of bone formation.

Results

A Untreated KO females

Figure 46:
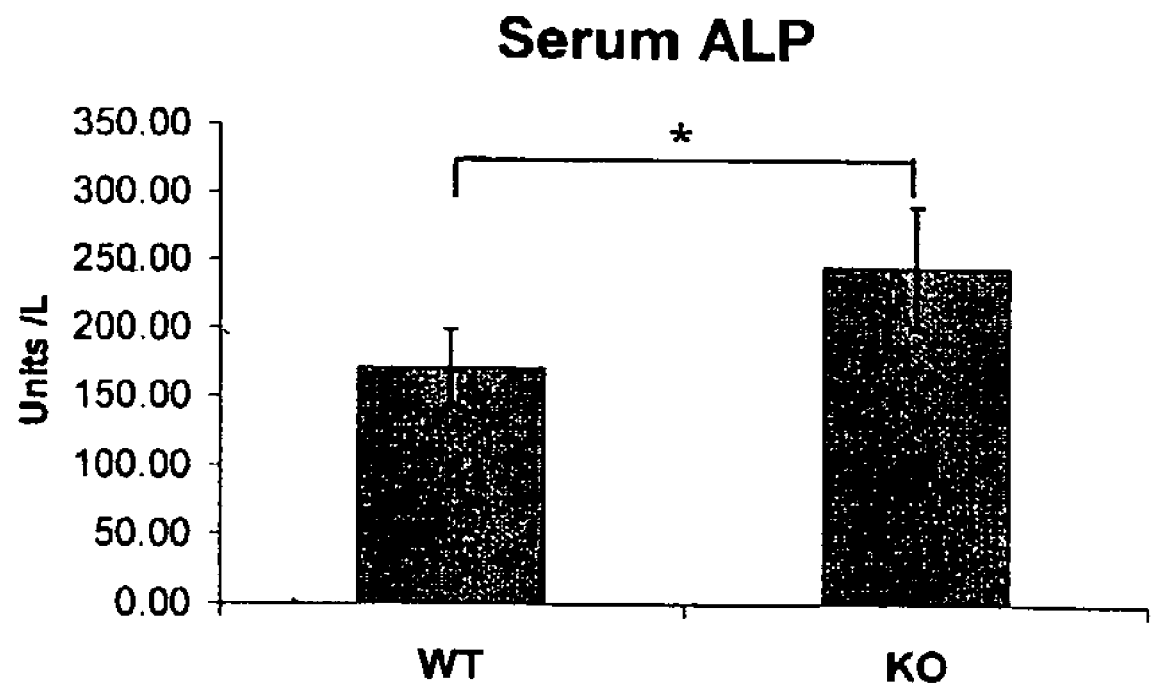
FIG. 46 shows that ALP, which is a biochemical serum marker of bone formation, is significantly increased in 3 month old 608 KO mice.

It was found that the serum marker (serum ALP) of bone formation was significantly increased in 3 month old 608 KO mice. These results are depicted in FIG. 46.

-pQCT scanning was performed for two groups of mice. pQCT of 3 months old untreated (sham operated) female mice gave parameters that were significantly different between WT and KO by two-way ANOVA analysis (pvalue<0.05), as shown in the Table below.

| pQCT Parameter | WT Average | KO Average | P value | % Increase |
|---|---|---|---|---|
| Femur Metaphysis Total Area | 3.572 | 4.070 | P < 0.05 | 14 |
| Tibia Diaphysis Cortical Thickness | 0.296 | 0.314 | P < 0.05 | 6.1 |
| Femur Diaphysis Cortical Area | 0.990 | 1.114 | P < 0.05 | 12.5 |

Similarly, pQCT of 4 months old untreated female mice also gave parameters that were significantly different between WT and KO by one-way ANOVA analysis (pvalue<0.05), as shown in the following Table.

| pQCT Parameter | WT Average | KO Average | P value | % Increase |
|---|---|---|---|---|
| Tibia metaphysis cortical BMD | 833.4 | 911.6 | 0.001803 | 9.4 |
| Femur Metaphysis Total Area | 3.38 | 3.8 | 0.004296 | 12.4 |
| Tibia Diaphysis Cortical BMD | 1150.4 | 1192 | 0.015211 | 3.6 |
| Femur Diaphysis Cortical BMD | 1202.4 | 1241.5 | 0.015951 | 3.3 |

In summary, the bone related phenotype of untreated 608 KO females is as follows:

At 3 months old, serum ALP is significantly increased in 608 KO mice. This may indicate that bone metabolism is different due to lack of the 608 gene. At this age, the significant increases are in bone geometric parameters. Slightly larger bone diameter and increased cortical thickness could affect bone strength.

At 4 months old, there is also a significant increase in cortical BMD of both femur and tibia. The incidence of fracture is closely related to BMD. Patients who sustain fractures have significantly decreased BMD.

In all parameters that showed a significant difference, the 608KO values were higher compared to WT. This may implicate an inhibitory role for the 608 gene in bone metabolism.

B. Ovariectomized KO females

None of the parameters that were significantly increased in untreated females showed differences in ovariectomized females. Loss of tibia metaphysis total BMD due to ovariectomy may be smaller in 608KO mice. However, this difference was not found significant. Increasing the number of animals in each group could improve the statistical results.

Conclusions

The bones of KO mice appeared to have some basic anatomical differences compared to the bones of WT mice. This observation is based on trends seen in parameters reflecting bone geometry, such as total slice area, periosteal circumference, cortical area and thickness. Compared to untreated WT mice, an increase in the femur metaphysis area was observed in KO animals, both in 4 month-old and 3 month-old mice. Distal femur total BMD was notably unaffected by genotype despite the differences in bone size. Similar increases in geometric parameters were noted in KO mice compared to WT at the femur diaphysis (cortical area) and at the tibia diaphysis (cortical thickness) in 3 month-old mice. At 4 months old there is also a significant increase in cortical BMD of both femur and tibia.

Consistent with these effects on bone mass, biochemical markers of bone turnover were increased in KO mice, relative to the WT controls, suggesting that bone metabolism is different. Parameters that could affect bone strength, such as a slightly larger bone diameter and increased cortical thickness, could contribute to bone strength.

The effects on bone mass and biochemical markers of bone turnover noted in the KO mice appear to be indicative of a protective effect of the KO phenotype on bone loss following ovariectomy, although the effects were small. A trend to a genotype-related prevention of bone loss in the distal femur metaphysis relative to the ovariectomized controls was observed in KO animals. A slight partial prevention of bone loss relative to the ovariectomized control group was observed in KO mice at the endocortical surface of femur and tibia metaphysis, although the effects were not marked.

In conclusion, the effects on bone mass and biochemical markers of bone turnover noted in the KO mice appear to be indicative of a protective effect of the KO genotype on bone loss following ovariectomy. Bone metabolism and bone geometry could be different in KO mice.

The following hypothesis may correlate the in vitro data in the previous Examples with this in vivo data from the KO mice analyses:

The function of the 608 protein could be to promote proliferation of the undifferentiated osteoprogenitor cell population. This hypothesis is based on the proliferative effect of the 608 1-663aa polypeptide on mouse bone marrow cell line, as shown in Example 21. In the absence of this protein the balance between proliferation and differentiation of osteoprogenitors is changed in favor of differentiation and therefore the increased bone parameters are obtained at a young age. It could be that in aged mice this change in balance causes a decrease in bone parameters due to the normal decrease in osteoprogenitors that occures with aging. If this hypothesis is correct an intermittent administration of the 608 protein or fragments of it could be used as a treatment for osteoporosis. Administration of the 608 polypeptide would cause proliferation of osteoprogenitors. When 608 level is allowed to decrease to normal levels, differentiation could take place.

An example of timing of intermittent treatment may be daily e.g. daily administration, preferably by injection, preferably subcutaneous, as opposed to continuous administration e.g. by infusion. Other examples may be administration every other day, or every few days, or even once a week or once a month In the case of parathyroid hormone (1-34 amino acid), daily subcutaneous injections of 20-40 µg were considered intermittent administration as opposed to continuous infusions; see Neer R. M. et. al. 2001, The New England Journal of Medicine. 344: 1434-1441, Effect of parathyroid hormone (1-34) on fractures and bone mineral density in postmenopausal women with osteoporosis.

Alternatively the 663aa fragment may act as an inhibitor of 608 function, as discussed in Example 21.

The invention claimed is:

1. An isolated nucleic acid molecule consisting of (a) a sequence that encodes the polypeptide encoded by the sequence of SEQ ID NO:31, or (b) a fragment of at least 50 contiguous nucleotides of (a).

2. An isolated nucleic acid molecule in accordance with claim 1, comprising consisting of a sequence that encodes the polypeptide encoded by the sequence of SEQ ID NO:31.

3. An isolated nucleic acid molecule in accordance with claim 1, consisting of a fragment of at least 50 contiguous nucleotides of a sequence that encodes the polypeptide encoded by the sequence of SEQ ID NO:31.

4. An isolated nucleic acid molecule in accordance with claim 1, consisting of SEQ ID NO:31.

5. An isolated nucleic acid molecule in accordance with claim 1, consisting of a sequence encoding a 10 kD to 100 kD N-terminal cleavage product of the polypeptide encoded by the nucleotide sequence of SEQ ID NO:31.

6. An isolated nucleic acid molecule in accordance with claim 5, wherein said N-terminal cleavage product comprises a polypeptide of about 25 kD to about 80 kD.

7. A vector comprising (a) a sequence that encodes the polypeptide encoded by the sequence of SEQ ID NO:31, or (b) a fragment of at least 50 contiguous nucleotides of (a).

8. A vector in accordance with claim 7, comprising a sequence that encodes the polypeptide encoded by the sequence of SEQ ID NO:3.

9. A vector in accordance with claim 7, comprising a fragment of at least 50 contiguous nucleotides of a sequence that encodes the polypeptide encoded by the sequence of SEQ ID NO:31.

10. A vector in accordance with claim 7, comprising SEQ ID NO:31.

11. A vector in accordance with claim 7, comprising a sequence encoding a 10 kD to 100 kD N-terminal cleavage product of the polypeptide encoded by the nucleotide sequence of SEQ ID NO:31.

12. A method for preparing a polypeptide comprising expressing the nucleic acid molecule in accordance with claim 1, and isolating the polypeptide.

13. A method for preparing a polypeptide comprising expressing the nucleic acid molecule in accordance with claim 2, and isolating the polypeptide.

14. A method for preparing a polypeptide comprising expressing the nucleic acid molecule in accordance with claim 5, and isolating the polypeptide.

15. A method for preparing a polypeptide comprising expressing the nucleic acid molecule in accordance with claim 3, and isolating the polypeptide.

16. A method for preparing a polypeptide comprising expressing the nucleic acid molecule in accordance with claim 4, and isolating the polypeptide.

17. A vector in accordance with claim 7, consisting of an expression plasmid selected from pCm-H608-663Nterm, pKS H608 5'-2.4Kb bAc#1, pKS H608 m.FRG.3.5Kb#34 and pM H608 3'-1.9Kb HSTG#3.3, corresponding to plasmids deposited under ATCC Accession Nos. PTA-738, PTA-3878, PTA-3876 and PTA-3877, respectively.

18. An isolated nucleic acid molecule consisting of a fragment of at least 15 contiguous nucleotides of a sequence that encodes the polypeptide encoded by SEQ ID NO:31, or the complement thereof.

* * * * *

SEQUENCE LISTING

<160> NUMBER OF SEQ ID NOS: 37

<210> SEQ ID NO 1
<211> LENGTH: 8883
<212> TYPE: DNA
<213> ORGANISM: Rattus species
<220> FEATURE:
<221> NAME/KEY: misc_feature
<222> LOCATION: (1)..(8883)
<223> OTHER INFORMATION: 'n' can be any nucleotide 'a', 'c', 'g' or 't'.

<400> SEQUENCE: 1

```
cgagagacga cagaaggtta cggctgcgag aagacgacag aagggtccag aaaaaggaaa      60
gtgctggagg ggagtgggga caaaagcagc gaccaagtga atgtcacttc agtgactgag     120
gccaggcaaa acgcgcggga aggattttgt gtagcttggg acccttttcat agacactgat    180
gacacgttta cgcaaaatag aaatttgagg agaaacgcct gggccttcgg aaaggagtga    240
ttgattagta cttgcaagtt taggtgactt taaggagaac taactaatgt atactattga    300
gggaggagga agagcattac agagtttcca gcagcagcag gaaagctttg gttaatttgg    360
aaatggatga tagcattaaa ataacagaag cgcctccagg tctctgaagc ttcagtcccc    420
cagctgaaag ccagaaaaga ctaagcccac taagcctttt gatccctttg gaagcaaaga    480
actttccttc cctggggtga agactctcct cagaagattt cctgtctctg cctatgttac    540
aagaggaatc aaaaccaaga cagaagagct caggatgcag gtgagaggca gggaagtcag    600
cggcttgttg atctccctca ctgctgtctg cctggtggtc acccctggga gcagggcctg    660
tcctcgccgc tgtgcctgct atgtgcccac agaggtgcac tgtacatttc ggtacctgac    720
ctccatccca gatggcatcc cggccaatgt ggaacgaata aatttaggat ataacagcct    780
tactagattg acagaaaacg actttgatgg cctgagcaaa ctggagttac tcatgctgca    840
cagtaatggc attcacagag tcagtgacaa gaccttctcg ggcttgcagt ccttgcaggt    900
cttaaaaatg agctataaca aagtccaaat cattcggaag gatactttct acggactcgg    960
gagcttggtc cggttgcacc tggatcacaa caacattgaa ttcatcaacc ctgaggcctt   1020
ttatggactt acctcgctcc gcttggtaca tttagaagga aaccggctca caaagctcca   1080
tccagacaca tttgtctcat taagctatct ccagatattt aaaacctctt tcattaagta   1140
cctgttcttg tctgataact tcctgacctc cctcccaaaa gaaatggtct cctacatgcc   1200
aaacctagaa agcctgtatt tgcatggaaa cccatggacc tgtgactgcc atttaaagtg   1260
gttgtctgag tggatgcagg gaaacccaga tataataaaa tgcaagaaag acagaagctc   1320
ttccagtcct cagcaatgtc ccctttgcat gaacccccagg atctctaaag gcagacccttt   1380
tgctatggta ccatctggag cttctcctatg tacaaagcca accattgatc catcactgaa   1440
gtcaaagagc ctggttactc aggaggacaa tggatctgcc tccacctcac ctcaagattt   1500
catagaaccc tttggctcct tgtctttgaa catgacanan ntntctggaa ataaggccga   1560
catggtctgt agtatccaaa agccatcaag gacatcacca actgcattca ctgaagaaaa   1620
tgactacatc atgctaaatg cgtcattttc cacaaatctt gtgtgcagtg tagattataa   1680
tcacatccag ccagtgtggc aacttctggc tttatacagt gactctcctc tgatactaga   1740
aaggaagccc cagcttaccg agactccttc actgtcttct agatataaac aggtggctct   1800
taggcctgaa gacattttta ccagcataga ggctgatgtc agagcagacc cttttttggtt   1860
ccaacaagaa aaaattgtct tgcagctgaa cagaactgcc accacactta gcacattaca   1920
```

```
gatccagttt tccactgatg ctcaaatcgc tttaccaagg gcggagatga gagcggagag    1980
actcaaatgg accatgatcc tgatgatgaa caatcccaaa ctggaacgca ctgtcctggt    2040
tggcggcact attgccctga gctgtccagg caaaggcgac ccttcacctc acttggaatg    2100
gcttctagct gatgggagta aagtgagagc cccttacgtt agcgaggatg gcgaatcct     2160 aatagacaaa aatgggaagt tggaactgca gatggctgac agctttgatg caggtcttta    2220
ccactgcata agcaccaatg atgcagatgc ggatgttctc acatacagga taactgtggt    2280
agagccctat ggagaaagca cacatgacag tggagtccag cacacagtgg ttacgggtga    2340
gacgctcgac cttccatgcc tttccacggg tgttccagat gcttctatta gctggattct    2400
tccagggaac actgtgttct ctcagccatc aagagacagg caaattctta caatgggac     2460 cttaagaata ttacaggtta cgccaaaaga tcaaggtcat taccaatgtg tggctgccaa    2520
cccatcaggg gccgactttt ccagttttaa agtttcagtt caaaagaaag gccaaaggat    2580
ggttgagcat gacagggagg caggtggatc tggacttgga gaacccaact ccagtgtttc    2640
ccttaagcag ccagcatctt tgaaactctc tgcatcagct ttgacagggt cagaggctgg    2700
aaaacaagtc tccggtgtac ataggaagaa caaacataga gacttaatac atcggcggcg    2760
tggggattcc acgctccggc gattcaggga gcataggagg cagctccctc tctctgctcg    2820
gagaattgac ccgcaacgct gggcagcact tctagaaaaa gccaaaaaga attctgtgcc    2880
aaaaaagcaa gaaatacca cagtaaagcc agtgccactg ctgttcccc tcgtggaact     2940 cactgacgag gaaaaggatg cctctggcat gattcctcca gatgaagaat tcatggttct    3000
gaaaactaag gcttctggtg tcccaggaag gtcaccaact gctgactctg gaccagtaaa    3060
tcatggtttt atgacgagta tagcttctgg cacagaagtc tcaactgtga atccacaaac    3120
actacaatct gagcaccttc ctgatttcaa attatttagt gtaacaaacg gtacagctgt    3180
gacaaagagt atgaacccat ccatagcaag caaaatagaa gatacaacca accaaaaccc    3240
aatcattatc tttccatcag tagctgaaat tcgagattct gctcaggcag aagagcatc     3300 ttcccaaagt gcacaccctg taacagggggg aaacatggct acctatggcc ataccaacac    3360
atatagtagc tttaccagca aagccagtac agtcttgcag ccaataaatc caacagaaag    3420 ttatggaccct cagataccta ttacaggagt cagcagacct agcagtagtg acatctcttc    3480
tcacactact gcagacccta gcttctccag tcacccttca ggttcacaca ccactgcctc    3540
gtctttattt cacattccta gaaacaacaa tacaggtaac ttccccttgt ccaggcactt    3600
gggaagagag aggacaattt ggagcagagg gagagttaaa aacccacata gaaccccagt    3660
tctccgacgg catagacaca ggactgtgag gccagcaatc aagggacctg ctaacaaaaa    3720
tgtgagccaa gttccagcca cagagtaccc tgggatgtgc cacacatgtc cttccgcaga    3780
ggggctcaca gtggctactg cagcactgtc agttccaagt tcatcccaca gtgccctccc    3840
caaaactaat aatgttgggg tcatagcaga agagtctacc actgtggtca agaaaccact    3900
gttactattt aaggacaaac aaaatgtaga tattgagata ataacaacca ctacaaata     3960 ttccggaggg gaaagtaacc acgtgattcc tacggaagca agcatgactt ctgctccaac    4020
atctgtatcc ctggggaaat ctcctgtaga caatagtggt cacctgagca tgcctgggac    4080
catccaaact gggaaagatt cagtggaaac aacaccactt cccagccccc tcagcacacc    4140
ctcaatacca caagcacaa aattctcaaa ggagaaaact cccttgcacc agatctttgt     4200
aaataaccag aagaaggagg ggatgttaaa gaatccatat caattcggtt acaaaagaa     4260
```

```
cccagccgca aagcttccca aaatagctcc tcttttaccc acaggtcaga gttccccctc    4320
agattctaca actctcttga caagtccgcc accagctctg tctacaacaa tggctgccac    4380
tcagaacaag ggcactgaag tagtatcagg tgccagaagt ctctcagcag ggaagaagca    4440
gcccttcacc aactcctctc cagtgcttcc tagcaccata agcaagagat ctaatacatt    4500
aaacttcttg tcaacggaaa cccccacagt gacaagtcct actgctactg catctgtcat    4560
tatgtctgaa acccaacgaa caagatccaa agaagcaaaa gaccaaataa aggggcctcg    4620
gaagaacaga aacaacgcaa acaccacccc caggcaggtt tctggctata gtgcatactc    4680
agctctaaca acagctgata cccccttggc tttcagtcat tccccacgac aagatgatgg    4740
tggaaatgta agtgcagttg cttatcactc aacaacctct cttctggcca taactgaact    4800
gtttgagaag tacacccaga ctttgggaaa tacaacagct ttggaaacaa cgttgttgag    4860
caaatcacag gagagtacca cagtgaaaag agcctcagac acaccaccac cactcctcag    4920
cagtggggcg ccccccagtg ccactccttc cccacctcct tttactaagg gtgtggttac    4980
agacagcaaa gtcacatcag ctttccagat gacgtcaaat agagtggtca ccatatatga    5040
atcttcaagg cacaatacag atctgcagca accctcagca gaggctagcc ccaatcctga    5100
gatcataact ggaaccactg actctccctc taatctgttt ccatccactt ctgtgccagc    5160
actaagggta gataaaccac agaattctaa atggaagccc tctccctggc cagaacacaa    5220
atatcagctc aagtcatact ccgaaaccat tgagaagggc aaaaggccag cagtaagcat    5280 gtcccccac ctcagccttc cagaggccag cactcatgcc tcacactgga atacacagaa    5340
gcatgcagaa aagagtgttt ttgataagaa acctggtcaa aacccaactt ccaaacatct    5400
gccttacgtc tctctaccta agactctatt gaaaaagcca agaataattg gaggaaaggc    5460
tgcaagcttt acagttccag ctaattcaga cgtttttctt ccttgtgagg ctgttggaga    5520
cccactgccc atcatccact ggaccagagt ttcatcagga nttgaaatat cccaagggac    5580
acagaaaagc cggttccacg tgcttcccaa tggcaccttg tccatccaga gggtcagtat    5640
tcaggaccgt ggacagtacc tgtgctctgc atttaatcca ctgggcgtag accattttca    5700
tgtctctttg tctgtggttt tttacccggc aaggattttg gacagacatg tcaaggagat    5760
cacagttcac tttggaagta ctgtggaact aaagtgcaga gtggagggta tgccgaggcc    5820 tacggttttcc tggatacttg caaaccaaac ggtggtctca gaaacggcca agggaagcag    5880
aaaggtctgg gtaacacctg atggaacatt gatcatctat aatctgagtc tttatgatcg    5940 tggttttttac aagtgtgtgg ccagcaaccc atctggccag gattcactgt tggttaagat    6000
acaagtcatc acagctcccc ctgtcattat agagcaaaag aggcaagcca tcgttgggggt    6060 tttaggtgga agtttgaaac tgccctgcac tgcaaaagga actccccagc ctagtgttca    6120
ctgggtcctt tatgatggga ctgaactaaa accattgcag ttgactcatt ccagattttt    6180
cttgtatcca aatggaactc tgtatataag aagcatcgct ccttcagtga ggggcactta    6240
tgagtgcatt gccaccagct cctcaggctc agagagaagg gtagtgattc ttactgtgga    6300
agagggagag acaatcccca ggatagaaac tgcctctcag aaatggactg aggtgaattt    6360
gggtgagaaa ttactactga actgctcagc tactggggat ccaaagccta gaataatctg    6420
gaggctgcca tccaaggctg tcatcgacca gtggcacaga atgggcagcc gaatccacgt    6480
ctacccaaat ggatccttgg tggttgggtc agtgacggaa aaagacgctg gtgactactt    6540
atgtgtggca agaaacaaaa tgggagatga cctagtcctg atgcatgtcc gcctgagatt    6600
gacacctgcc aaaattgaac agaagcagta ttttaagaag caagtgctcc atgggaaaga    6660
```

```
tttccaagtt gactgcaagg cctctggctc ccctgtgcct gaggtatcct ggagtttgcc   6720
tgatgggaca gtgctcaaca atgtagccca agctgatgac agtggctata ggaccaagag   6780
gtacacccct ttccacaatg gaaccttgta tttcaacaac gttgggatgg cagaggaagg   6840
agattatatc tgctctgccc agaacacctt agggaaagat gagatgaaag tccacctaac   6900
agttctaaca gccatcccac ggataaggca aagctacaag accaccatga ggctcagggc   6960
tggagaaaca gctgtccttg actgcgaggt cactgggaa ccgaagccca atgtattttg   7020
gttgctgcct tccaacaatg tcatttcatt ctccaatgac aggttcacat tcatgccaa    7080 tagaactttg tccatccata aagtgaaacc acttgactct ggggactatg tgtgcgtagc   7140
tcagaatcct agtggggatg acactaagac atacaaactg acattgtct ctaaacctcc    7200 attaatcaat ggcctgtatg caaacaagac tgttattaaa gccacagcca ttcggcactc   7260
caaaaaatac tttgactgca gagcagatgg gatcccatct tcccaggtca cgtggattat   7320
gccaggcaat atttcctcc cagctccata ctttggaagc agagtcacgg tccatccaaa    7380
tggaaccttg gagatgagga acatccggct ttctgactct gcggacttca cctgtgtggt   7440
tcggagcgag ggaggagaga gtgtgttggt agtgcagtta gaagtcctag aaatgctgag   7500
aagaccaaca ttcagaaacc cattcaacga aaaagtcatc gcccaagctg caagcccgt    7560 agcactgaac tgctctgtgg atgggaaccc cccacctgaa attacctgga tcttacctga   7620
cggcacacag tttgctaaca gaccacacaa ttccccgtat ctgatggcag caatggctc    7680 tctcatcctt tacaaagcaa ctcggaacaa gtcaggaag tatcgctgtg cagccaggaa    7740
taaggttggc tacatcgaga aactcatcct gttagagatt gggcagaagc cagtcattct   7800
gacatacgaa ccagggatgg tgaagagcgt cagtggggaa ccgttatcac tgcattgtgt   7860
gtctgatggg atccccaagc caaatgtcaa gtggactaca ccgggtggcc atgtaatcga   7920
caggcctcaa gtgatggaa atacatact gcatgaaaat ggcacgctgg tcatcaaagc    7980
aacaacagct cacgaccaag gaaattatat ctgtagggct caaaacagtg ttggccaggc   8040
agttattagc gtgtcagtga tggttgtggc ctaccctccc cgaatcataa actacctacc   8100
caggaacatg ctcaggagga caggggaagc catgcagctc cactgtgtgg ccttgggaat   8160 cccccaagcca aaagtcacct gggagacgcc aagacactcc ctgctctcaa agcaacagc   8220 aagaaaaccc catagaagtg agatgcttca cccacaaggt acgctggtca ttcagaatct   8280
ccaaacctcg gattccggag tctataagtg cagagctcag aacctacttg ggactgatta   8340
cgcaacaact tacatccagg tactctgaca ggaaggggga gactaaaatt caacagaagt   8400
ccacatccac agggtttatt ttttggaaga gtttaatca aggcagcca taggcatgta    8460 aatgagtctg aatacatta cagtattaaa tttacaatgg acatgcgatg agacttgtaa   8520
atgaaagcat tgtgaactga aaccgagtct ctgtggatct caaagcaaac tcttaactta   8580 aggcacttg atttgccaa caataataa caaacattaa gagaaaaaa tgatccacta     8640 cgaaataaca aacggctaat gcacctgaat tctcagtaaa aagacctttc tctcgctaac   8700
agttgccagc tgcctcgtgt ctgtttccta ccaatgtcac aaacatcgca cacagggtga   8760
atggagtcaa cggaaagat taagtttgcg gtctgtgtaa atctcaatgt acaaatattc   8820
tgtcnctggt ttataaacat tttgataaaa ccgaaaaaaa aaaaaaaaa aaaaaaaaa   8880 aaa                                                                8883
```

<210> SEQ ID NO 2

```
<211> LENGTH: 2597
<212> TYPE: PRT
<213> ORGANISM: Rattus species
<220> FEATURE:
<221> NAME/KEY: misc_feature
<222> LOCATION: (1)..(2597)
<223> OTHER INFORMATION: 'x' can be any amino acid

<400> SEQUENCE: 2
```

| Met | Gln | Val | Arg | Gly | Arg | Glu | Val | Ser | Gly | Leu | Leu | Ile | Ser | Leu | Thr |
|---|---|---|---|---|---|---|---|---|---|---|---|---|---|---|---|
| 1 | | | | 5 | | | | | 10 | | | | | 15 | |

| Ala | Val | Cys | Leu | Val | Val | Thr | Pro | Gly | Ser | Arg | Ala | Cys | Pro | Arg | Arg |
|---|---|---|---|---|---|---|---|---|---|---|---|---|---|---|---|
| | | | 20 | | | | | 25 | | | | | 30 | | |

| Cys | Ala | Cys | Tyr | Val | Pro | Thr | Glu | Val | His | Cys | Thr | Phe | Arg | Tyr | Leu |
|---|---|---|---|---|---|---|---|---|---|---|---|---|---|---|---|
| | | | 35 | | | | | 40 | | | | | 45 | | |

| Thr | Ser | Ile | Pro | Asp | Gly | Ile | Pro | Ala | Asn | Val | Glu | Arg | Ile | Asn | Leu |
|---|---|---|---|---|---|---|---|---|---|---|---|---|---|---|---|
| | 50 | | | | | 55 | | | | | 60 | | | | |

| Gly | Tyr | Asn | Ser | Leu | Thr | Arg | Leu | Thr | Glu | Asn | Asp | Phe | Asp | Gly | Leu |
|---|---|---|---|---|---|---|---|---|---|---|---|---|---|---|---|
| 65 | | | | | 70 | | | | | 75 | | | | | 80 |

| Ser | Lys | Leu | Glu | Leu | Leu | Met | Leu | His | Ser | Asn | Gly | Ile | His | Arg | Val |
|---|---|---|---|---|---|---|---|---|---|---|---|---|---|---|---|
| | | | | 85 | | | | | 90 | | | | | 95 | |

| Ser | Asp | Lys | Thr | Phe | Ser | Gly | Leu | Gln | Ser | Leu | Gln | Val | Leu | Lys | Met |
|---|---|---|---|---|---|---|---|---|---|---|---|---|---|---|---|
| | | | 100 | | | | | 105 | | | | | 110 | | |

| Ser | Tyr | Asn | Lys | Val | Gln | Ile | Ile | Arg | Lys | Asp | Thr | Phe | Tyr | Gly | Leu |
|---|---|---|---|---|---|---|---|---|---|---|---|---|---|---|---|
| | | | 115 | | | | | 120 | | | | | 125 | | |

| Gly | Ser | Leu | Val | Arg | Leu | His | Leu | Asp | His | Asn | Asn | Ile | Glu | Phe | Ile |
|---|---|---|---|---|---|---|---|---|---|---|---|---|---|---|---|
| | 130 | | | | | 135 | | | | | 140 | | | | |

| Asn | Pro | Glu | Ala | Phe | Tyr | Gly | Leu | Thr | Ser | Leu | Arg | Leu | Val | His | Leu |
|---|---|---|---|---|---|---|---|---|---|---|---|---|---|---|---|
| 145 | | | | | 150 | | | | | 155 | | | | | 160 |

| Glu | Gly | Asn | Arg | Leu | Thr | Lys | Leu | His | Pro | Asp | Thr | Phe | Val | Ser | Leu |
|---|---|---|---|---|---|---|---|---|---|---|---|---|---|---|---|
| | | | | 165 | | | | | 170 | | | | | 175 | |

| Ser | Tyr | Leu | Gln | Ile | Phe | Lys | Thr | Ser | Phe | Ile | Lys | Tyr | Leu | Phe | Leu |
|---|---|---|---|---|---|---|---|---|---|---|---|---|---|---|---|
| | | | 180 | | | | | 185 | | | | | 190 | | |

| Ser | Asp | Asn | Phe | Leu | Thr | Ser | Leu | Pro | Lys | Glu | Met | Val | Ser | Tyr | Met |
|---|---|---|---|---|---|---|---|---|---|---|---|---|---|---|---|
| | | | 195 | | | | | 200 | | | | | 205 | | |

| Pro | Asn | Leu | Glu | Ser | Leu | Tyr | Leu | His | Gly | Asn | Pro | Trp | Thr | Cys | Asp |
|---|---|---|---|---|---|---|---|---|---|---|---|---|---|---|---|
| | 210 | | | | | 215 | | | | | 220 | | | | |

| Cys | His | Leu | Lys | Trp | Leu | Ser | Glu | Trp | Met | Gln | Gly | Asn | Pro | Asp | Ile |
|---|---|---|---|---|---|---|---|---|---|---|---|---|---|---|---|
| 225 | | | | | 230 | | | | | 235 | | | | | 240 |

| Ile | Lys | Cys | Lys | Lys | Asp | Arg | Ser | Ser | Ser | Pro | Gln | Gln | Cys | Pro |
|---|---|---|---|---|---|---|---|---|---|---|---|---|---|---|
| | | | | 245 | | | | | 250 | | | | | 255 |

| Leu | Cys | Met | Asn | Pro | Arg | Ile | Ser | Lys | Gly | Arg | Pro | Phe | Ala | Met | Val |
|---|---|---|---|---|---|---|---|---|---|---|---|---|---|---|---|
| | | | | 260 | | | | | 265 | | | | | 270 | |

| Pro | Ser | Gly | Ala | Phe | Leu | Cys | Thr | Lys | Pro | Thr | Ile | Asp | Pro | Ser | Leu |
|---|---|---|---|---|---|---|---|---|---|---|---|---|---|---|---|
| | | 275 | | | | | 280 | | | | | 285 | | | |

| Lys | Ser | Lys | Ser | Leu | Val | Thr | Gln | Glu | Asp | Asn | Gly | Ser | Ala | Ser | Thr |
|---|---|---|---|---|---|---|---|---|---|---|---|---|---|---|---|
| | 290 | | | | | 295 | | | | | 300 | | | | |

| Ser | Pro | Gln | Asp | Phe | Ile | Glu | Pro | Phe | Gly | Ser | Leu | Ser | Leu | Asn | Met |
|---|---|---|---|---|---|---|---|---|---|---|---|---|---|---|---|
| 305 | | | | | 310 | | | | | 315 | | | | | 320 |

| Thr | Xaa | Xaa | Ser | Gly | Asn | Lys | Ala | Asp | Met | Val | Cys | Ser | Ile | Gln | Lys |
|---|---|---|---|---|---|---|---|---|---|---|---|---|---|---|---|
| | | | | 325 | | | | | 330 | | | | | 335 | |

| Pro | Ser | Arg | Thr | Ser | Pro | Thr | Ala | Phe | Thr | Glu | Glu | Asn | Asp | Tyr | Ile |
|---|---|---|---|---|---|---|---|---|---|---|---|---|---|---|---|
| | | | 340 | | | | | 345 | | | | | 350 | | |

| Met | Leu | Asn | Ala | Ser | Phe | Ser | Thr | Asn | Leu | Val | Cys | Ser | Val | Asp | Tyr |
|---|---|---|---|---|---|---|---|---|---|---|---|---|---|---|---|
| | | | 355 | | | | | 360 | | | | | 365 | | |

```
Asn His Ile Gln Pro Val Trp Gln Leu Leu Ala Leu Tyr Ser Asp Ser
370                 375                 380

Pro Leu Ile Leu Glu Arg Lys Pro Gln Leu Thr Glu Thr Pro Ser Leu
385                 390                 395                 400

Ser Ser Arg Tyr Lys Gln Val Ala Leu Arg Pro Glu Asp Ile Phe Thr
            405                 410                 415

Ser Ile Glu Ala Asp Val Arg Ala Asp Pro Phe Trp Phe Gln Gln Glu
        420                 425                 430

Lys Ile Val Leu Gln Leu Asn Arg Thr Ala Thr Thr Leu Ser Thr Leu
        435                 440                 445

Gln Ile Gln Phe Ser Thr Asp Ala Gln Ile Ala Leu Pro Arg Ala Glu
    450                 455                 460

Met Arg Ala Glu Arg Leu Lys Trp Thr Met Ile Leu Met Met Asn Asn
465                 470                 475                 480

Pro Lys Leu Glu Arg Thr Val Leu Val Gly Gly Thr Ile Ala Leu Ser
                485                 490                 495

Cys Pro Gly Lys Gly Asp Pro Ser Pro His Leu Glu Trp Leu Leu Ala
            500                 505                 510

Asp Gly Ser Lys Val Arg Ala Pro Tyr Val Ser Glu Asp Gly Arg Ile
        515                 520                 525

Leu Ile Asp Lys Asn Gly Lys Leu Glu Leu Gln Met Ala Asp Ser Phe
    530                 535                 540

Asp Ala Gly Leu Tyr His Cys Ile Ser Thr Asn Asp Ala Asp Ala Asp
545                 550                 555                 560

Val Leu Thr Tyr Arg Ile Thr Val Val Glu Pro Tyr Gly Glu Ser Thr
                565                 570                 575

His Asp Ser Gly Val Gln His Thr Val Val Thr Gly Glu Thr Leu Asp
            580                 585                 590

Leu Pro Cys Leu Ser Thr Gly Val Pro Asp Ala Ser Ile Ser Trp Ile
        595                 600                 605

Leu Pro Gly Asn Thr Val Phe Ser Gln Pro Ser Arg Asp Arg Gln Ile
    610                 615                 620

Leu Asn Asn Gly Thr Leu Arg Ile Leu Gln Val Thr Pro Lys Asp Gln
625                 630                 635                 640

Gly His Tyr Gln Cys Val Ala Ala Asn Pro Ser Gly Ala Asp Phe Ser
                645                 650                 655

Ser Phe Lys Val Ser Val Gln Lys Lys Gly Gln Arg Met Val Glu His
            660                 665                 670

Asp Arg Glu Ala Gly Gly Ser Gly Leu Gly Glu Pro Asn Ser Ser Val
        675                 680                 685

Ser Leu Lys Gln Pro Ala Ser Leu Lys Leu Ser Ala Ser Ala Leu Thr
    690                 695                 700

Gly Ser Glu Ala Gly Lys Gln Val Ser Gly Val His Arg Lys Asn Lys
705                 710                 715                 720

His Arg Asp Leu Ile His Arg Arg Gly Asp Ser Thr Leu Arg Arg
                725                 730                 735

Phe Arg Glu His Arg Arg Gln Leu Pro Leu Ser Ala Arg Arg Ile Asp
            740                 745                 750

Pro Gln Arg Trp Ala Ala Leu Leu Glu Lys Ala Lys Lys Asn Ser Val
        755                 760                 765

Pro Lys Lys Gln Glu Asn Thr Thr Val Lys Pro Val Pro Leu Ala Val
    770                 775                 780

Pro Leu Val Glu Leu Thr Asp Glu Glu Lys Asp Ala Ser Gly Met Ile
```

-continued

```
                785                 790                 795                 800
Pro Pro Asp Glu Glu Phe Met Val Leu Lys Thr Lys Ala Ser Gly Val
                    805                 810                 815

Pro Gly Arg Ser Pro Thr Ala Asp Ser Gly Pro Val Asn His Gly Phe
                820                 825                 830

Met Thr Ser Ile Ala Ser Gly Thr Glu Val Ser Thr Val Asn Pro Gln
                835                 840                 845

Thr Leu Gln Ser Glu His Leu Pro Asp Phe Lys Leu Phe Ser Val Thr
        850                 855                 860

Asn Gly Thr Ala Val Thr Lys Ser Met Asn Pro Ser Ile Ala Ser Lys
865                 870                 875                 880

Ile Glu Asp Thr Thr Asn Gln Asn Pro Ile Ile Phe Pro Ser Val
            885                 890                 895

Ala Glu Ile Arg Asp Ser Ala Gln Ala Gly Arg Ala Ser Ser Gln Ser
            900                 905                 910

Ala His Pro Val Thr Gly Gly Asn Met Ala Thr Tyr Gly His Thr Asn
            915                 920                 925

Thr Tyr Ser Ser Phe Thr Ser Lys Ala Ser Thr Val Leu Gln Pro Ile
        930                 935                 940

Asn Pro Thr Glu Ser Tyr Gly Pro Gln Ile Pro Ile Thr Gly Val Ser
945                 950                 955                 960

Arg Pro Ser Ser Ser Asp Ile Ser Ser His Thr Thr Ala Asp Pro Ser
                965                 970                 975

Phe Ser His Pro Ser Gly Ser His Thr Thr Ala Ser Ser Leu Phe
            980                 985                 990

His Ile Pro Arg Asn Asn Asn Thr  Gly Asn Phe Pro Leu  Ser Arg His
            995                1000                1005

Leu Gly  Arg Glu Arg Thr Ile  Trp Ser Arg Gly Arg  Val Lys Asn
    1010                1015                1020

Pro His  Arg Thr Pro Val Leu  Arg Arg His Arg His  Arg Thr Val
    1025                1030                1035

Arg Pro  Ala Ile Lys Gly Pro  Ala Asn Lys Asn Val  Ser Gln Val
    1040                1045                1050

Pro Ala  Thr Glu Tyr Pro Gly  Met Cys His Thr Cys  Pro Ser Ala
    1055                1060                1065

Glu Gly  Leu Thr Val Ala Thr  Ala Ala Leu Ser Val  Pro Ser Ser
    1070                1075                1080

Ser His  Ser Ala Leu Pro Lys  Thr Asn Asn Val Gly  Val Ile Ala
    1085                1090                1095

Glu Glu  Ser Thr Thr Val Val  Lys Lys Pro Leu Leu  Leu Phe Lys
    1100                1105                1110

Asp Lys  Gln Asn Val Asp Ile  Glu Ile Ile Thr Thr  Thr Thr Lys
    1115                1120                1125

Tyr Ser  Gly Gly Glu Ser Asn  His Val Ile Pro Thr  Glu Ala Ser
    1130                1135                1140

Met Thr  Ser Ala Pro Thr Ser  Val Ser Leu Gly Lys  Ser Pro Val
    1145                1150                1155

Asp Asn  Ser Gly His Leu Ser  Met Pro Gly Thr Ile  Gln Thr Gly
    1160                1165                1170

Lys Asp  Ser Val Glu Thr Thr  Pro Leu Pro Ser Pro  Leu Ser Thr
    1175                1180                1185

Pro Ser  Ile Pro Thr Ser Thr  Lys Phe Ser Lys Arg  Lys Thr Pro
    1190                1195                1200
```

-continued

| | | | | | | | | | | | |
|---|---|---|---|---|---|---|---|---|---|---|---|
|Leu|His|Gln|Ile|Phe|Val|Asn|Asn|Gln|Lys|Lys|Glu Gly Met Leu|
| |1205| | | |1210| | | |1215| | |
|Lys|Asn|Pro|Tyr|Gln|Phe|Gly|Leu|Gln|Lys|Asn|Pro Ala Ala Lys|
| |1220| | | |1225| | | |1230| | |
|Leu|Pro|Lys|Ile|Ala|Pro|Leu|Leu|Pro|Thr|Gly|Gln Ser Ser Pro|
| |1235| | | |1240| | | |1245| | |
|Ser|Asp|Ser|Thr|Thr|Leu|Leu|Thr|Ser|Pro|Pro|Ala Leu Ser|
| |1250| | | |1255| | | |1260| | |
|Thr|Thr|Met|Ala|Ala|Thr|Gln|Asn|Lys|Gly|Thr|Glu Val Val Ser|
| |1265| | | |1270| | | |1275| | |
|Gly|Ala|Arg|Ser|Leu|Ser|Ala|Gly|Lys|Lys|Gln|Pro Phe Thr Asn|
| |1280| | | |1285| | | |1290| | |
|Ser|Ser|Pro|Val|Leu|Pro|Ser|Thr|Ile|Ser|Lys|Arg Ser Asn Thr|
| |1295| | | |1300| | | |1305| | |
|Leu|Asn|Phe|Leu|Ser|Thr|Glu|Thr|Pro|Thr|Val|Thr Ser Pro Thr|
| |1310| | | |1315| | | |1320| | |
|Ala|Thr|Ala|Ser|Val|Ile|Met|Ser|Glu|Thr|Gln|Arg Thr Arg Ser|
| |1325| | | |1330| | | |1335| | |
|Lys|Glu|Ala|Lys|Asp|Gln|Ile|Lys|Gly|Pro|Arg|Lys Asn Arg Asn|
| |1340| | | |1345| | | |1350| | |
|Asn|Ala|Asn|Thr|Thr|Pro|Arg|Gln|Val|Ser|Gly|Tyr Ser Ala Tyr|
| |1355| | | |1360| | | |1365| | |
|Ser|Ala|Leu|Thr|Thr|Ala|Asp|Thr|Pro|Leu|Ala|Phe Ser His Ser|
| |1370| | | |1375| | | |1380| | |
|Pro|Arg|Gln|Asp|Asp|Gly|Gly|Asn|Val|Ser|Ala|Val Ala Tyr His|
| |1385| | | |1390| | | |1395| | |
|Ser|Thr|Thr|Ser|Leu|Leu|Ala|Ile|Thr|Glu|Leu|Phe Glu Lys Tyr|
| |1400| | | |1405| | | |1410| | |
|Thr|Gln|Thr|Leu|Gly|Asn|Thr|Thr|Ala|Leu|Glu|Thr Thr Leu Leu|
| |1415| | | |1420| | | |1425| | |
|Ser|Lys|Ser|Gln|Glu|Ser|Thr|Thr|Val|Lys|Arg|Ala Ser Asp Thr|
| |1430| | | |1435| | | |1440| | |
|Pro|Pro|Pro|Leu|Leu|Ser|Ser|Gly|Ala|Pro|Pro|Val Pro Thr Pro|
| |1445| | | |1450| | | |1455| | |
|Ser|Pro|Pro|Pro|Phe|Thr|Lys|Gly|Val|Val|Thr|Asp Ser Lys Val|
| |1460| | | |1465| | | |1470| | |
|Thr|Ser|Ala|Phe|Gln|Met|Thr|Ser|Asn|Arg|Val|Val Thr Ile Tyr|
| |1475| | | |1480| | | |1485| | |
|Glu|Ser|Ser|Arg|His|Asn|Thr|Asp|Leu|Gln|Gln|Pro Ser Ala Glu|
| |1490| | | |1495| | | |1500| | |
|Ala|Ser|Pro|Asn|Pro|Glu|Ile|Ile|Thr|Gly|Thr|Thr Asp Ser Pro|
| |1505| | | |1510| | | |1515| | |
|Ser|Asn|Leu|Phe|Pro|Ser|Thr|Ser|Val|Pro|Ala|Leu Arg Val Asp|
| |1520| | | |1525| | | |1530| | |
|Lys|Pro|Gln|Asn|Ser|Lys|Trp|Lys|Pro|Ser|Pro|Trp Pro Glu His|
| |1535| | | |1540| | | |1545| | |
|Lys|Tyr|Gln|Leu|Lys|Ser|Tyr|Ser|Glu|Thr|Ile|Glu Lys Gly Lys|
| |1550| | | |1555| | | |1560| | |
|Arg|Pro|Ala|Val|Ser|Met|Ser|Pro|His|Leu|Ser|Leu Pro Glu Ala|
| |1565| | | |1570| | | |1575| | |
|Ser|Thr|His|Ala|Ser|His|Trp|Asn|Thr|Gln|Lys|His Ala Glu Lys|
| |1580| | | |1585| | | |1590| | |

```
Ser Val Phe Asp Lys Lys Pro Gly Gln Asn Pro Thr Ser Lys His
1595                1600                1605

Leu Pro Tyr Val Ser Leu Pro Lys Thr Leu Leu Lys Lys Pro Arg
1610                1615                1620

Ile Ile Gly Gly Lys Ala Ala Ser Phe Thr Val Pro Ala Asn Ser
1625                1630                1635

Asp Val Phe Leu Pro Cys Glu Ala Val Gly Asp Pro Leu Pro Ile
1640                1645                1650

Ile His Trp Thr Arg Val Ser Ser Gly Xaa Glu Ile Ser Gln Gly
1655                1660                1665

Thr Gln Lys Ser Arg Phe His Val Leu Pro Asn Gly Thr Leu Ser
1670                1675                1680

Ile Gln Arg Val Ser Ile Gln Asp Arg Gly Gln Tyr Leu Cys Ser
1685                1690                1695

Ala Phe Asn Pro Leu Gly Val Asp His Phe His Val Ser Leu Ser
1700                1705                1710

Val Val Phe Tyr Pro Ala Arg Ile Leu Asp Arg His Val Lys Glu
1715                1720                1725

Ile Thr Val His Phe Gly Ser Thr Val Glu Leu Lys Cys Arg Val
1730                1735                1740

Glu Gly Met Pro Arg Pro Thr Val Ser Trp Ile Leu Ala Asn Gln
1745                1750                1755

Thr Val Val Ser Glu Thr Ala Lys Gly Ser Arg Lys Val Trp Val
1760                1765                1770

Thr Pro Asp Gly Thr Leu Ile Ile Tyr Asn Leu Ser Leu Tyr Asp
1775                1780                1785

Arg Gly Phe Tyr Lys Cys Val Ala Ser Asn Pro Ser Gly Gln Asp
1790                1795                1800

Ser Leu Leu Val Lys Ile Gln Val Ile Thr Ala Pro Pro Val Ile
1805                1810                1815

Ile Glu Gln Lys Arg Gln Ala Ile Val Gly Val Leu Gly Gly Ser
1820                1825                1830

Leu Lys Leu Pro Cys Thr Ala Lys Gly Thr Pro Gln Pro Ser Val
1835                1840                1845

His Trp Val Leu Tyr Asp Gly Thr Glu Leu Lys Pro Leu Gln Leu
1850                1855                1860

Thr His Ser Arg Phe Phe Leu Tyr Pro Asn Gly Thr Leu Tyr Ile
1865                1870                1875

Arg Ser Ile Ala Pro Ser Val Arg Gly Thr Tyr Glu Cys Ile Ala
1880                1885                1890

Thr Ser Ser Ser Gly Ser Glu Arg Arg Val Val Ile Leu Thr Val
1895                1900                1905

Glu Glu Gly Glu Thr Ile Pro Arg Ile Glu Thr Ala Ser Gln Lys
1910                1915                1920

Trp Thr Glu Val Asn Leu Gly Glu Lys Leu Leu Leu Asn Cys Ser
1925                1930                1935

Ala Thr Gly Asp Pro Lys Pro Arg Ile Ile Trp Arg Leu Pro Ser
1940                1945                1950

Lys Ala Val Ile Asp Gln Trp His Arg Met Gly Ser Arg Ile His
1955                1960                1965

Val Tyr Pro Asn Gly Ser Leu Val Val Gly Ser Val Thr Glu Lys
1970                1975                1980

Asp Ala Gly Asp Tyr Leu Cys Val Ala Arg Asn Lys Met Gly Asp
```

-continued

```
         1985                1990                1995

Asp Leu  Val Leu Met His Val  Arg Leu Arg Leu  Thr Pro Ala Lys
         2000                2005                2010

Ile Glu  Gln Lys Gln Tyr Phe  Lys Lys Gln Val  Leu His Gly Lys
         2015                2020                2025

Asp Phe  Gln Val Asp Cys Lys  Ala Ser Gly Ser  Pro Val Pro Glu
         2030                2035                2040

Val Ser  Trp Ser Leu Pro Asp  Gly Thr Val Leu  Asn Asn Val Ala
         2045                2050                2055

Gln Ala  Asp Asp Ser Gly Tyr  Arg Thr Lys Arg  Tyr Thr Leu Phe
         2060                2065                2070

His Asn  Gly Thr Leu Tyr Phe  Asn Asn Val Gly  Met Ala Glu Glu
         2075                2080                2085

Gly Asp  Tyr Ile Cys Ser Ala  Gln Asn Thr Leu  Gly Lys Asp Glu
         2090                2095                2100

Met Lys  Val His Leu Thr Val  Leu Thr Ala Ile  Pro Arg Ile Arg
         2105                2110                2115

Gln Ser  Tyr Lys Thr Thr Met  Arg Leu Arg Ala  Gly Glu Thr Ala
         2120                2125                2130

Val Leu  Asp Cys Glu Val Thr  Gly Glu Pro Lys  Pro Asn Val Phe
         2135                2140                2145

Trp Leu  Leu Pro Ser Asn Asn  Val Ile Ser Phe  Ser Asn Asp Arg
         2150                2155                2160

Phe Thr  Phe His Ala Asn Arg  Thr Leu Ser Ile  His Lys Val Lys
         2165                2170                2175

Pro Leu  Asp Ser Gly Asp Tyr  Val Cys Val Ala  Gln Asn Pro Ser
         2180                2185                2190

Gly Asp  Asp Thr Lys Thr Tyr  Lys Leu Asp Ile  Val Ser Lys Pro
         2195                2200                2205

Pro Leu  Ile Asn Gly Leu Tyr  Ala Asn Lys Thr  Val Ile Lys Ala
         2210                2215                2220

Thr Ala  Ile Arg His Ser Lys  Lys Tyr Phe Asp  Cys Arg Ala Asp
         2225                2230                2235

Gly Ile  Pro Ser Ser Gln Val  Thr Trp Ile Met  Pro Gly Asn Ile
         2240                2245                2250

Phe Leu  Pro Ala Pro Tyr Phe  Gly Ser Arg Val  Thr Val His Pro
         2255                2260                2265

Asn Gly  Thr Leu Glu Met Arg  Asn Ile Arg Leu  Ser Asp Ser Ala
         2270                2275                2280

Asp Phe  Thr Cys Val Val Arg  Ser Glu Gly Glu  Ser Val Leu
         2285                2290                2295

Val Val  Gln Leu Glu Val Leu  Glu Met Leu Arg  Arg Pro Thr Phe
         2300                2305                2310

Arg Asn  Pro Phe Asn Glu Lys  Val Ile Ala Gln  Ala Gly Lys Pro
         2315                2320                2325

Val Ala  Leu Asn Cys Ser Val  Asp Gly Asn Pro  Pro Pro Glu Ile
         2330                2335                2340

Thr Trp  Ile Leu Pro Asp Gly  Thr Gln Phe Ala  Asn Arg Pro His
         2345                2350                2355

Asn Ser  Pro Tyr Leu Met Ala  Gly Asn Gly Ser  Leu Ile Leu Tyr
         2360                2365                2370

Lys Ala  Thr Arg Asn Lys Ser  Gly Lys Tyr Arg  Cys Ala Ala Arg
         2375                2380                2385
```

-continued

```
Asn Lys Val Gly Tyr Ile Glu Lys Leu Ile Leu Glu Ile Gly
    2390            2395                2400

Gln Lys Pro Val Ile Leu Thr Tyr Glu Pro Gly Met Val Lys Ser
    2405                2410                2415

Val Ser Gly Glu Pro Leu Ser Leu His Cys Val Ser Asp Gly Ile
    2420                2425                2430

Pro Lys Pro Asn Val Lys Trp Thr Thr Pro Gly Gly His Val Ile
    2435                2440                2445

Asp Arg Pro Gln Val Asp Gly Lys Tyr Ile Leu His Glu Asn Gly
    2450                2455                2460

Thr Leu Val Ile Lys Ala Thr Thr Ala His Asp Gln Gly Asn Tyr
    2465                2470                2475

Ile Cys Arg Ala Gln Asn Ser Val Gly Gln Ala Val Ile Ser Val
    2480                2485                2490

Ser Val Met Val Ala Tyr Pro Pro Arg Ile Ile Asn Tyr Leu
    2495                2500                2505

Pro Arg Asn Met Leu Arg Arg Thr Gly Glu Ala Met Gln Leu His
    2510                2515                2520

Cys Val Ala Leu Gly Ile Pro Lys Pro Lys Val Thr Trp Glu Thr
    2525                2530                2535

Pro Arg His Ser Leu Leu Ser Lys Ala Thr Ala Arg Lys Pro His
    2540                2545                2550

Arg Ser Glu Met Leu His Pro Gln Gly Thr Leu Val Ile Gln Asn
    2555                2560                2565

Leu Gln Thr Ser Asp Ser Gly Val Tyr Lys Cys Arg Ala Gln Asn
    2570                2575                2580

Leu Leu Gly Thr Asp Tyr Ala Thr Thr Tyr Ile Gln Val Leu
    2585                2590                2595

<210> SEQ ID NO 3
<211> LENGTH: 11967
<212> TYPE: DNA
<213> ORGANISM: mouse sp
<220> FEATURE:
<221> NAME/KEY: misc_feature
<222> LOCATION: (1)..(11967)
<223> OTHER INFORMATION: 'n' can be any nucleotide 'a', 'c', 'g' or 't'.

<400> SEQUENCE: 3
tttggaacca acccagatgc ccctcaacag agaaatgggc cagaaaatgt ggtccattta      60
tccaatggaa tactactcaa cttattaaaa acaacgactt tcataaaatt tttaggcaaa     120
tgnatggtct gnaggatctt gagtgaggta acccaatcac aaaagaacac tcatggtatg     180
cactcactga taagtggcta tttgtctatg gagtgattta aagggaaga agacacatag      240 cttttttgtgt gtataatatt aagatggaaa tttgccagtg ctgtttggct tatgagtgaa     300
tcttgtttca gtggattacc ggaagaaaat aataagtgaa ctgtaggaag aagtagttaa     360
tcaaggtgac aaagtatcct gacacattgg gaaaagacca cagtccagga aactgagtct     420
taaggattca tattaactcc agttccccat gtgcagctct gagactttgg cagatcagac     480
acttaacttc accagcttcc tacacagagc agttactatc cttgcacttc acacatggag     540
tgtgaccatt aagctgcact gaaacatgag tctgacttgt taataatctt aaaatacaaa     600
ttgtgttgta agtatgtgca ccaaagagca tggtcatgct attaaccttt gatgttctat     660
ggactcttaa ttttatggta gaaatgtcaa caagcttgtg gaggctggaa gatacaaggc     720
```

```
ttaagaggat ggcctttcag ttttgaaagt aattcagtat gtgttctggc atcccttttc      780
ctaaagcaat ttaacccccc aagtaggcat aattttaatg cttacttcat cagaatatgt      840
ctaattgact cttctaaaaa gactttggta tgcataggat ctaaatgtaa atgtgattta      900
ctgacataat aaataggaga aactgagcta gaataggtat aaaatatgtg ctggctttct      960
aataggtctt ataggttata taagaggtgg gaaaggaata tttgaaacat ctagaagtaa     1020
aatgatcctg agtagcgatc ctgggaaaat acgtactcta acacactgca atcatctctc     1080
tgtggtttgc tggagctgag gtctggaagg ctcgaccttg gttagaaata acctaccgaa     1140
tacagagcta tgacgttagt ctggaaggag ctttggaaga atgacaagct gtagctgccc     1200
agaacatact agatgccata tttccaaggc aagtgtccac atgcggacat cttaagaata     1260
tggttgtctc tgcagtgcta aggaccttgt tcgtgccaca caggtctcca gggttagtgc     1320
taactctgac tgcttgactc tttaattcta ccttgatcat taatgactag aaatcacttg     1380
gtgattagca actggatatg gaatattact aatttgtacc caagccaggc cacctcagct     1440
ttggcagctc cattcattct gtggagccca gtcacgtggg tttgaatcaa ctgtactgtt     1500
tctacttaca agacgcatta cctgagatga gtcattttc  ttcacaagtc ttttagaag      1560 agtcaattag acatattctg atgaagtaag catataaagt gagagcagca tgaatgtgtt     1620
ccatgtatgc tcatggatgc tattataatg tggaaataaa ctgactttaa aaaaaaagc      1680 ttatgatact tgtcacagag taaatcttcc ataaatatca tctgcattta taaattattt     1740
tcataatcca tcaattaaaa acctttagaa attttgttaa cacaaagatc cctaggcccc     1800
tgccctagga tggtctgtat ggtgggcctg agagatggag cttaagaact tacttgctcc     1860
aggagcacat cttcagaaca tctgcctcaa aacatttatc ccaaatgctc atcaaaggct     1920
cactcacatg tgcttcaacc acagggatta aacagtcatt ttagtcacat ttctcaaacg     1980
gtggaagcct gctagaggaa caggatgtat caggataaca tccaacctta caaaaggatg     2040
tcataaccct caccacaaca acaacaacg  acaacaaacc cataaaaatt atcacggcaa     2100
atgaactaag ccatatgcag aaaaagtatt atatgttctc attgtggggt gttttcctt     2160 aatagtcaaa tatgcagaat atagacaaag atggtttatg caagtgggga tggcgaagga     2220
tacttgtaga ttagaggaca caaagcaaca actacagagt gaagtaatcc agagacttaa     2280
tgtataatat gaggactgta tttaataatt ctatttaaga tacacagcaa acgagtgtat     2340
cttactaaca cacacactta catagagaga ataaagtgat agatacgttt gtttatctt     2400 catgtagctg ataatttcat attgtacacc tcaaacatag ataaccaaca aagaggaaga     2460
ggataggtgc ctctcccagg gcggaagagt acattcgaaa gtcagacacc attgtgtaga     2520
tgtaccacat ggaggagcta gagaaagtag ccaaggagct aaagggatct gcaaccctat     2580
aggtggaaca acattatgag ctaaccagta ccccggagct cttgactcta gctgcatata     2640
tatcaaaaga tggcctaatc ggccatcact ggaaagagag gcccattgga cttgcaaact     2700
ttatatgccc cagtacaggg gaataccagg gccaaaaagg gggagtgggt gggcagggga     2760 gtggggggtgg gtggatatgg gggacttttg gtatagcatt ggaaatgtaa atgagttaaa     2820
tacctaataa aaaatggaaa aaaaaaaaa  aaaaaaaaa  aaggaaggtc agacacctca     2880
cttcactgct atctcaactt gcaaacagaa ggggagtcac aaacccagga caaaccacag     2940
tgattgaagc gtctttgaat gttattgctg ttgttgttac caccatcatt agcatatatt     3000
cattgtgaaa acttacgggg tctatgacat gttttttttat tcaagtatat cacatgctgt     3060
cagcatattt ggcaccacta ccagccccag cccccttgc  cccgccccca acacacacac     3120
```

```
acacacacac acacacacac acacacacac acacacacac acacacacct ttaccttctc     3180
ctgggcatca tctgctcact cacccaccca agcttaatcc ttttccttcc ctgcaatagt     3240
acctctccta ttttttatgtc taggttcccc ctcccctgt taggagatgg gagaggtcac    3300
gaaaggaaag aatttgtagc ccctgagcca gcccgggcca cagagcctgc caccagacag     3360
gaaaagccca gggcttacca gcacaggagg agcaaactcg caggcgagcc tgggttggcg     3420
ctggtggtcc cgggtcgatg gcccgcccat tcccagaagc cgaggctata gctgcgtcac     3480
ctgccccgcc ctcctcccga gtgaagaccc tagaggctg agcagacccc aaaggcggtg     3540
caattccatt ggcccaaggc agaggtgagc ggctgctaat cccctcggga agtgaaggga     3600
cccagagagt ctggtagatg tgggagctgg ggttcagggc gagacagagg gtgggatggg     3660
cagaagggtc caggaaaagg aaagtactgg aggggagttg ggacaaaagc agcgaccaag     3720
ggaacatcgc ttcagtgact gaagccaggc aaaaggagcg ggaaggatta tatgtagcct     3780
gggacgcttt cataaacact gatgacgtgt ttgtgcaaag caagcaattt gaggagaaac     3840
gcctgggacg tcggaaagaa ggagtgatcg attagtactt gtaagtttag gtgagtttga     3900
gaactaacta acctatacta ttgagggaga aggaagagca ttccagcagc agcagcagca     3960
gcagcaatca gataaaggaa agctttggtt agtttggaaa tgtatgatac cattaaaata     4020
acagaagcgc ctccagttct ctgaagagtc agtcccccag ctagtgaaga ctaagcctac     4080
taagcctttt gctcccgttg gaagcaaaga acgttccttc aatcaggtga aggctctcct     4140
cagaagattt cctgtctctg cttatgttac aagaggattc aaaagcaaga cagaagagct     4200
caggtattgc caactctttt gttaaataca gtttgaggct taagtgtacg ggaactcatg     4260
tggtattcat ttacggctct cttctcttat aactaactct taaggtgcat atagtctctt     4320
ctgtttccca gctaccttgt accatctttg tttatctaat aatagcaagc tcatctgctt     4380
tttaatcatc acgcagagag tattcaaaaa tattcagtga tgtaacagtg acagtgtagg     4440
catagaagta atcattagta aatcttaatt tgggttaaac tcattcataa cagctccagg     4500
ttgggaggga tcactgagcc ttcgccacgt gcgggttaaa gatatttcct aacaagagaa     4560
gcagaattct tccttggcca tgctccccat cactgtgtca gtaagcagag gggtgtttcc     4620
aagcagagaa agagcagaca gtgttatgcc tgcaaagtca gagactcagc cctcccagct     4680
ggtcagttta ctgtcctccc ggtcattagt tggctctgaa aaggcccatg tgtccttatt     4740
ggcaaggact tgcagacatg ctagaaagaa atttgacctt tttttctagt gggttattac     4800
agctgtaaaa gtattttgga aggttaagcc aaataaataa aacacatatt aaataataca     4860
atgttacaaa aattgatcat ataaagaagt acattcataa atgcaatgtg aaaaatatat     4920
ataatttta tctatttact ggtgcaaagt tttctaaatt gcacatgtac tattttata      4980
tttataaaaa tattttttaaa atgtatataa aagtgtaaaa ggctcttggt caaacaagag    5040
agttaaattt acaaacttta attgtcccga taacattatt atgatctcta atgacaggga    5100
tcctgctttt cattgggaaa tgagaagcta tgaagatatg tttacaataa taagcccatt    5160
tagtgataaa gtccaatggg aagctagcac acactggttt ataaagagaa cagtttcctg    5220
agtctatgca agtttacact ctagggaata agagttcctc tttctccaga tttcactagc    5280
atttgttgtc atcatttatc ttcttgatga tgagcattat aagtggaata agataggatc    5340
tcaaaggaat gtcaatttgg atgccctgaa caatctttca ggtctttctt tcagttcact    5400
agtctattca tttattggat aattggggga tggtgttaat tttttttgcag ttcttatgga   5460
```

```
attccaaaaa acaaaaaaca aacaaacaaa caaaaaacct ctgaaactag aactaccaat   5520
ccattactgg gtatgtaaca aagagaaatc tgcacagaat ttattgctac attgttcatt   5580
attcacgaca gccaagaatg tggaaccaac ttacgtagcc gtcaaaatat gaacggataa   5640
agaaaatgtg gaaatgtgta caacagagtc ccatgtggcc ataaaagagt gaaatcatga   5700
catatgcagg aaatggatgc aactggaaat caattgggct aatcaaaaca agacagactc   5760
aaaaaggaaa caccgtgtag cttctctgac aaacagaagc tagatttaca cttgtacgtg   5820
cgcatgtgtg tttagaattt tatttagtta tacactattc taatctgtga gtgtgtataa   5880
aggcatgcat gtaaagcaaa aacaagctag ctggggtggg taggagagaa agcaatgaga   5940
ggagttaata agaacgaagc atagtaacat aggtgccagg atgaaatgca ttaatttgta   6000
tgctaactaa accacagaca ggaggcacac gttcaaacca gggtgaaatc ccagcacaga   6060 gaagggaag tagacacaaa gtttcgccac taaccaagaa gccatttgca gttgctgcct    6120
gctgggaggg gcgttccagt tttctccagt ctgacactgt gtataacaac cagttgacaa   6180
tacaaagttg gcatgatgga tggttttgt gctattttc attttttttc ttactgtttt      6240
gttgttgtgg tggttgttgt ggtggtggct gtggttttca tttgtttctt ttgagagaga   6300
gaaggaacat gaaattgggt gggtaggaag ctggaaacga tctggaagaa gttggggaaa   6360
gagaaaaatt gtatggagca tatttaaaca aacaaacaaa caaacaaaag gttcattttg   6420
ccacaaaaag gtgtgaatta aattaaccag ttacgactct taaagaaaat attcccaatt   6480
attcccagag ttgctatgta tgctgtgcct aggactttgc ttgaactggc cctataactc   6540
tggtgtggtg tcttttcagg atgcagaaga gaggcaggga agtcagctgc ttgctgatct   6600
ccctcactgc catctgcctg gtggtcaccc ctgggagcag ggtctgtcct cgccgatgtg   6660
cctgctatgt gcccacagag gtgcactgta catttcggga cctgacctcc atcccagacg   6720
ggcatcccag ccaatgtgga acgagtcaat ttagggtgtg tggaccttgc ctgatctcct   6780
tctcagagag ggaccactga ttttcctggt actttgcccc ccaaacacct gtgattactt    6840
ttaatagttt tcttctaaaa tgggttcata caaaccttat attgtggaga caatgaacat   6900
tttatcccaa tagtctttta ctagaacttg aagcccctct tagttgtttg ggagcctcat   6960
aattatgggg cagctttatt ctgaatgaat tttaaatgaa aaagatacag tttctgttaa   7020
caatcattat gataccaagg aagaggaatt gtcattgaat attttaaaaa agcatttctt   7080
ttgcaattta taaatacccca ttacaaaatg gcttacttaa aatacttgcc ttactaaatc   7140
tgacaaatta tggtgatatt ttgaaggttt atgaaaattt gtttatgtgt ataaatgcac   7200
aagaaatggg atatgccatc acctatgtgc cattagtgag catgtacagt atgccaaaca   7260
ctattgttca cgtttggagg aagtaatggg ggtggggag caacaagggt tataaccgta     7320
tacccagtgc cttggaagcg attgcaaaca gtaaagactg acattgtgtt ctccctatga   7380 gggagggcc ttgggctgag cactttgcaa tgagcatttg ctcattgtgc tggcaggttt     7440
tatgataact tgacccaagc tagagtcact ggagaggaag gaacttcaac tgagaacatg   7500
cctgaagaag atcagattat aggcaggcct gtggggcatt tcttaattag tgattcatg    7560 gggcagggcc cagtccattg ttcgtggtac catttctcag gcactattaa aaaaaaaaa   7620 acaggctgag caagtgtcaa ggagcaagtc agtgagcagc agccctaatg atctctgcat   7680
cagctcctgc ctccaggttc ctaccctatt tgagttcctg tcctagctcc ctacagtgat   7740
gaacaatgat gtgaagtat aagccaaata aatccttctt tccccaactt gctgttggtc    7800
atgatgtttc atcacagtga taatagtcct catgaagatg ctggtgttta taacaccttt   7860
```

```
ggactaaatt ctgttatcta tagctgagga aaatggagca tagaaagtct ccagactaca    7920
ccagagtgta atctgggcct gagcttagaa tcacacccac gtgcactcca ctgccggggc    7980
ttcttaaccg gaacacagtt gtaaaaggga attttctgtt tgtttccatt ttgacatgtg    8040
gactttaatt gacgattcat ctgaagctga aatgatttt ttttccaggt ataacagcct    8100
cactagattg acagaaaatg acttttctgg cctgagcaga ctggagttac tcatgctgca    8160
cagcaatggc attcacagag tcagtgacaa gaccttctcg ggcttgcagt ccttgcaggt    8220
gagataggta gagggtgatg gaggctgaga agagaggtgc aactgtgggt tatacccaaa    8280
agctgctgat tcccgtggga gacattctat aagcattcta taaactagag gcagatatca    8340
aggaaggatt tcaattgtaa tgcaattta tgagaaaatt tgaatattaa gaaaatgctg    8400
gggaaaatgc ttacacaatt gcgaggacct aatttaggat ctccaatagc cacataaaaa    8460
gcacagcatg gcggcagaca cctgcaattc ctgtccctgg aagcacctgt tcagaatccc    8520
agagactcat tggccaaaca ctctattcaa tcaatgaagt ccatattcag tgacaaaact    8580
tgactcagaa actaatgtgg aaagcatcag gaagacagcc aacatctggt ctctactcat    8640
gcatgaataa gggatcccag agagaaggga agaaaaagga aggaaggaag gaaggaagga    8700
aggaaggaag gaaggaagga aggaaggaag agagggagga aaggagggag ggaaggaagg    8760
aaagggaaag gaaaaagag atggggaggg agggaaggaa aggaaagggg gagaaagaag    8820
agaagaaagg aaaataaata aattttcagg gattattaca cctttaaatt ttatccataa    8880
aaggtcattt ccacctgttt gtctggaagt agagtgggat ccttatata agggcagtct    8940 ttaacatagt agcatttat aaaccattac aaatttgag ttttctctac ttttatcct    9000 ctaccatctt caaactgaaa ctacaattat tcccacaaat gaagaaatg ctgtaagagt    9060 tttcacacac cgaagtggga aacttaagga ttagacaagt ctaacaatga gaatggggag    9120
aacaaaaaga gactgcacag ggagcccttt ctctgcttat aatcttgaca cttgagaagc    9180
taattgacgc tgcatgacta ctcaactctt taagcaaaca atgctgttgt tcatgaaaag    9240
cacaataaag tacatatgtc ccataatatt catcaaaatt tgcatgcagc acataatagc    9300
aatcaaagca ataacaccca ctgttcacag agactttaaa catgaaactg gaactatgtc    9360
tagtgttttg acttagggta catagtatgc tgtgtctgta tgtaccaatg ttgatttagg    9420
tcatcagaca gcatttggaa catgtatctt caggaggaat cattcatgta tcctgcatga    9480
aattctccac ctatgtttat tctcttagcc aggttttttct ctgatggaga acattgggt    9540 ttgaggtttt actcccaggt aacatttagg gaaaagctgt ctatgttctc agtttggctt    9600
ttatttatga gggatgttgg tattccagaa aattctcttt tgaagagatt acaatttagg    9660
tcaaaacaga aaatatgta aaagttatt gttttatta gtatttcatg ttcttttctt    9720
ttttaaaaat ggtatgctta gaactaatta agattagatt agattagatt agaaaataat    9780
cagagaggga tttgatgaat gctaaagcat catgaaaaat tcaaattttt ttgcttctaa    9840
ttcagaatca attaaattca tattactata aagacagca cgccagatgt gtgccagctg    9900
aggagtggat aaactgtgta acgtgagtgc tatgtagaaa cagaaggag tgaagggttg    9960 atgtgcgctg caacatcttg aaaacattcg gctacatgat ggaagccagg cacaaaaagc   10020
cacatattgc atggttatgt ttatatgaaa tgtttaaaat acatggattc ttagcaaaca   10080
gagtaagatg ttacttaggg tcaggaaaag attaaaaaaa aaaaaactat tgatgtggaa   10140
tgatcttaat ttggggaaaa gacaatttcc taagacgaaa tagttgaggt agatatagtt   10200
```

-continued

```
atatccctgt ggatattgta ataaaccagc atgctgtgct ctgagaaggg cctaatgaag    10260
gggcaggagg aagtgaaatg agatggtaga aaggaaagtc atataccatg gcttctctcg    10320
tgggtggaat ctagatatgt taatatattg acataaagga aggaattgtt tagggaagga    10380
tcaaaaccaa caggagtgag ggagacaata ggaaccaatg agaggcaaag ttcatggtca    10440
atgtgtgtgg agacaccata ataaaactcc ttttttgttt gctaactaaa accactaaaa    10500
tctaaaaaca aacatttttt gcacaagaat tatttattat tcaataaaga tgtttaaatg    10560
ggggaagttg aagttcattg atagtctcat aaatcttaaa tgtatttaaa ctgcttttta    10620
cgttttttat tattaattac tcttgctgtc attattatca tcatcattat cgtcatcatc    10680
atcactaatg cttttcacca tacacaaatg taggcagaag agtgtaatcc acttagtgag    10740
gcaatcttgg agagggaaag gaagcggatg cggggcagag gcacacagga ggacagtgag    10800
agggaaatga acaagaaaaa atgtggacac atgcacaaaa attccatagt ccactacatt    10860
actttgtatt ctaatattaa gaaaataata aacccatttc tgtgcactta tcacccaggc    10920
tcaacagtta tcttggccac agatcctgtc tcactgcatc ctgtccacct gagtccactt    10980
agcgttctga atccaatcca gggcatgatg cttactccta cacagaacta aagattaaag    11040
agagtttaaa agtaaccatg acatctctct gttcctttag cgataagttc ttaatattta    11100
tggctgcttg tgtatgttct aatttctcta atattgtcac atttagttgg caactacttt    11160
gtttgaattg agttggagtt aaggtcccat aggattaatc tcaacatatt tctatattta    11220
taaacttttc tctctttgtg aaagttcctt tgagaaaaca aatatgccca tatctttctt    11280
tacaggtctt aaaaatgagc tataacaaag tccaaataat tgagaaggat actttgtatg    11340
gactcaggag cttgacccgg ttgcacctgg atcacaacaa cattgagttt atcaaccccg    11400
aggcgtttta cggactcacc ttgctccgct tggtacatct agaaggaaac cggctgacaa    11460
agctccatcc agacacattt gtctctttga gctatctcca gatatttaaa acctccttca    11520
ttaagnacct gtacttgtat gataacttca ttgacctccc tcccaaaaga aatggtctcc    11580
tctatgccaa acctagaaag cctttacttg catggaaacc catggacctg tgactgccat    11640
ttaaagtggt tgtccgagtg gatgcaggga aacccaggta actatcttgt ttgtttgttt    11700 cttttttttat arkacgtatt ttcctcaatt tcatttagaa tgatatccca aaagtccccc    11760
ataacctccc ccccacttcc ctacctaccc attcccattt tttggccctg gcattcccct    11820 gtactgggc atataaagtt tgcgtgtcca atgaccctct ctttccagtg atggccaact    11880
aggccatctt ttgatacata tgcagctaga gtcaagagct ctggggtact ggttagttca    11940
taatgttgtt gcacctacag ggttgaa                                        11967
```

<210> SEQ ID NO 4
<211> LENGTH: 2404
<212> TYPE: DNA
<213> ORGANISM: homo sapiens

<400> SEQUENCE: 4

```
tgggcagctg gatccacgtc taccctaatg gatccctgtt tattggatca gtaacagaaa      60
aagacagtgg tgtctacttg tgtgtggcaa gaaacaaaat gggggatgat ctgatactga     120
tgcatgttag cctaagactg aaacctgcca aaattgacca caagcagtat tttagaaagc     180
aagtgctcca tgggaaagat ttccaagtag attgcaaagc ttccggctcc ccagtgccag     240
agatatcttg gagtttgcct gatggaacca tgatcaacaa tgcaatgcaa gccgatgaca     300
gtggccacag gactaggaga tataccctttt tcaacaatgg aactttatac ttcaacaaag     360
```

```
ttggggtagc ggaggaagga gattatactt gctatgccca gaacacccta gggaaagatg       420
aaatgaaggt ccacttaaca gttataacag ctgctccccg gataaggcag agtaacaaaa       480
ccaacaagag aatcaaagct ggagacacag ctgtccttga ctgtgaggtc actggggatc       540
ccaaaccaaa aatattttgg ttgctgcctt ccaatgacat gatttccttc tccattgata       600
ggtacacatt tcatgccaat gggtctttga ccatcaacaa agtgaaactg ctcgattctg       660
gagagtacgt atgtgtagcc cgaaatccca gtggggatga caccaaaatg tacaaactgg       720
atgtggtctc taaacctcca ttaatcaatg gtctgtatac aaacagaact gttattaaag       780
ccacagctgt gagacattcc aaaaaacact ttgactgcag agctgaaggg acaccatctc       840
ctgaagtcat gtggatcatg ccagacaata ttttcctcac agccccatac tatggaagca       900
gaatcacagt ccataaaaat ggaaccttgg aaattaggaa tgtgaggctt tcagattcag       960
ccgactttat ctgtgtggcc cgaaatgaag gtggagagag cgtgttggta gtacagttag      1020
aagtactgga aatgctgaga agaccgacat ttagaaatcc atttaatgaa aaaatagttg      1080
cccagctggg aaagtccaca gcattgaatt gctctgttga tggtaaccca ccacctgaaa      1140
taatctggat tttaccaaat ggcacacgat tttccaatgg accacaaagt tatcagtatc      1200
tgatagcaag caatggttct tttatcattt ctaaaacaac tcgggaggat gcaggaaaat      1260
atcgctgtgc agctaggaat aaagttggct atattgagaa attagtcata ttagaaattg      1320
gccagaagcc agttattctt acctatgcac cagggacagt aaaaggcatc agtggagaat      1380
ctctatcact gcattgtgtg tctgatggaa tccctaagcc aaatatcaaa tggactatgc      1440
caagtggtta tgtagtagac aggcctcaaa ttaatgggaa atacatattg catgacaatg      1500
gcaccttagt cattaaagaa gcaacagctt atgacagagg aaactatatc tgtaaggctc      1560
aaaatagtgt tggtcataca ctgattactg ttccagtaat gattgtagcc taccctcccc      1620
gaattacaaa tcgtccaccc aggagtattg tcaccaggac aggggcagcc tttcagctcc      1680
actgtgtggc cttgggagtt cccaagccag aaatcacatg ggagatgcct gaccactccc      1740
ttctctcaac ggcaagtaaa gagaggacac atggaagtga gcagcttcac ttacaaggta      1800
ccctagtcat tcagaatccc caaacctccg attctggat atacaaatgc acagcaaaga      1860
acccacttgg tagtgattat gcagcaacgt atattcaagt aatctgacat gaaataataa      1920
agtcaacaac atctgggcag aatttatttt ttggaagaag tttaatcaaa ggcagccata      1980
ggcatgtaaa tgaatttgaa tacatttaca gtattaaatt tacaatgaac atgcaaaata      2040
aaaggacttg taaataaatg cattatgaac tgatgataag tctctgtgga tctcaaagca      2100
aactcttaac ttaaggcact ttgctgattt atttaatgga tctcaaaaca aactttaac       2160 ttaaggcact tttattttgc caacaaataa caataaacaa acattgaaac ggttcactat      2220
aaaataacaa atggctaatg tacctgaatt tttcagtaaa aaaatgaact tctaatacca      2280
gttgcctagt gtccacctcc tatcaatgtt acaagcatgg cactcagaac agagacaatg      2340
gaaaatatta aatctgcaat ctttatgatg taaatttacc atcctgatgt ataaatattt      2400
tgtg                                                                   2404

<210> SEQ ID NO 5
<211> LENGTH: 8883
<212> TYPE: DNA
<213> ORGANISM: Rattus species
<220> FEATURE:
<221> NAME/KEY: misc_feature
<222> LOCATION: (1)..(8916)
```

<223> OTHER INFORMATION: n can be any amino acid

<400> SEQUENCE: 5

```
cgagagacga cagaaggtta cggctgcgag aagacgacag aagggtccag aaaaaggaaa      60
gtgctggagg ggagtgggga caaaagcagc gaccaagtga atgtcacttc agtgactgag     120
gccaggcaaa acgcgcggga aggattttgt gtagcttggg acccttcat agacactgat      180
gacacgttta cgcaaaatag aaatttgagg agaaacgcct gggccttcgg aaaggagtga     240
ttgattagta cttgcaagtt taggtgactt taaggagaac taactaatgt atactattga     300
gggaggagga agagcattac agagtttcca gcagcagcag gaaagctttg gttaatttgg     360
aaatggatga tagcattaaa ataacagaag cgcctccagg tctctgaagc ttcagtcccc     420
cagctgaaag ccagaaaaga ctaagcccac taagcctttt gatcccttg gaagcaaaga      480
actttccttc cctggggtga agactctcct cagaagattt cctgtctctg cctatgttac     540
aagaggaatc aaaccaaga cagaagagct caggatgcag gtgagaggca gggaagtcag      600
cggcttgttg atctccctca ctgctgtctg cctggtggtc acccctggga gcagggcctg     660
tcctcgccgc tgtgcctgct atgtgcccac agaggtgcac tgtacatttc ggtacctgac     720
ctccatccca gatggcatcc cggccaatgt ggaacgaata aatttaggat ataacagcct     780
tactagatta acagaaaacg actttgatgg cctgagcaaa ctggagttac tcatgctgca     840
cagtaatggc attcacagag tcagtgacaa gaccttctcg ggcttgcagt ccttgcaggt     900
cttaaaaatg agctataaca aagtccaaat cattcggaag gatactttct acggactcgg     960
gagcttggtc cggttgcacc tggatcacaa caacattgaa ttcatcaacc ctgaggcctt    1020
ttatggactt acctcgctcc gcttggtaca tttagaagga aaccggctca caaagctcca    1080
tccagacaca tttgtctcat taagctatct ccagatattt aaaacctctt tcattaagta    1140
cctgttcttg tctgataact tcctgacctc cctcccaaaa gaaatggtct cctacatgcc    1200
aaacctagaa agcctgtatt tgcatggaaa cccatggacc tgtgactgcc atttaaagtg    1260
gttgtctgag tggatgcagg gaaacccaga tataataaaa tgcaagaaag acagaagctc    1320
ttccagtcct cagcaatgtc ccctttgcat gaaccccagg atctctaaag gcagacctt     1380
tgctatggta ccatctggag ctttcctatg tacaaagcca accattgatc catcactgaa    1440
gtcaaagagc ctggttactc aggaggacaa tggatctgcc tccacctcac ctcaagattt    1500
catagaaccc tttggctcct tgtctttgaa catgacanan ntntctggaa ataaggccga    1560
catggtctgt agtatccaaa agccatcaag gacatcacca actgcattca ctgaagaaaa    1620
tgactacatc atgctaaatg cgtcattttc cacaaatctt gtgtgcagtg tagattataa    1680
tcacatccag ccagtgtggc aacttctggc tttatacagt gactctcctc tgatactaga    1740
aaggaagccc cagcttaccg agactccttc actgtcttct agatataaac aggtggctct    1800
taggcctgaa gacattttta ccagcataga ggctgatgtc agagcagacc cttttttggtt    1860
ccaacaagaa aaaattgtct tgcagctgaa cagaactgcc accacactta gcacattaca    1920
gatccagttt tccactgatg ctcaaatcgc tttaccaagg gcggagatga gagcggagag    1980
actcaaatgg accatgatcc tgatgatgaa caatcccaaa ctggaacgca ctgtcctggt    2040
tggcggcact attgccctga gctgtccagg caaaggcgac ccttcacctc acttggaatg    2100
gcttctagct gatgggagta aagtgagagc cccttacgtt agcgaggatg ggcgaatcct    2160
aatagacaaa aatgggaagt tggaactgca gatggctgac agctttgatg caggtctttta    2220
ccactgcata agcaccaatg atgcagatgc ggatgttctc acatacagga taactgtggt    2280
```

```
agagccctat ggagaaagca cacatgacag tggagtccag cacacagtgg ttacgggtga    2340
gacgctcgac cttccatgcc tttccacggg tgttccagat gcttctatta gctggattct    2400
tccagggaac actgtgttct ctcagccatc aagagacagg caaattctta caatgggac     2460 cttaagaata ttacaggtta cgccaaaaga tcaaggtcat taccaatgtg tggctgccaa    2520
cccatcaggg gccgactttt ccagttttaa agtttcagtt caaaagaaag gccaaaggat    2580
ggttgagcat gacagggagg caggtggatc tggacttgga gaacccaact ccagtgtttc    2640
ccttaagcag ccagcatctt tgaaactctc tgcatcagct ttgacagggt cagaggctgg    2700
aaaacaagtc tccggtgtac ataggaagaa caaacataga gacttaatac atcggcggcg    2760
tggggattcc acgctccggc gattcaggga gcataggagg cagctccctc tctctgctcg    2820
gagaattgac ccgcaacgct gggcagcact tctagaaaaa gccaaaaaga attctgtgcc    2880
aaaaaagcaa gaaatacca cagtaaagcc agtgccactg gctgttcccc tcgtggaact    2940
cactgacgag gaaaaggatg cctctggcat gattcctcca gatgaagaat tcatggttct    3000
gaaaactaag gcttctggtg tcccaggaag gtcaccaact gctgactctg gaccagtaaa    3060
tcatggtttt atgacgagta tagcttctgg cacagaagtc tcaactgtga atccacaaac    3120
actacaatct gagcaccttc ctgatttcaa attatttagt gtaacaaacg gtacagctgt    3180
gacaaagagt atgaacccat ccatagcaag caaaatagaa gatacaacca accaaaaccc    3240
aatcattatc tttccatcag tagctgaaat tcgagattct gctcaggcag gaagagcatc    3300
ttcccaaagt gcacaccctg taacaggggg aaacatggct acctatggcc ataccaacac    3360
atatagtagc tttaccagca aagccagtac agtcttgcag ccaataaatc aacagaaag    3420 ttatggacct cagataccta ttacaggagt cagcagacct agcagtagtg acatctcttc    3480
tcacactact gcagacccta gcttctccag tcacccttca ggttcacaca ccactgcctc    3540
gtctttattt cacattccta gaaacaacaa tacaggtaac ttccccttgt ccaggcactt    3600
gggaagagag aggacaattt ggagcagagg gagagttaaa aacccacata gaaccccagt    3660
tctccgacgg catagacaca ggactgtgag gccagcaatc aagggacctg ctaacaaaaa    3720
tgtgagccaa gttccagcca cagagtaccc tgggatgtgc cacacatgtc cttccgcaga    3780
ggggctcaca gtggctactg cagcactgtc agttccaagt tcatcccaca gtgccctccc    3840
caaaactaat aatgttgggg tcatagcaga agagtctacc actgtggtca agaaaccact    3900
gttactattt aaggacaaac aaaatgtaga tattgagata ataacaacca ctacaaaata    3960
ttccggaggg gaaagtaacc acgtgattcc tacggaagca agcatgactt ctgctccaac    4020
atctgtatcc ctggggaaat ctcctgtaga caatagtggt cacctgagca tgcctgggac    4080
catccaaact gggaaagatt cagtggaaac aacaccactt cccagccccc tcagcacacc    4140
ctcaatacca acaagcacaa aattctcaaa gaggaaaact cccttgcacc agatctttgt    4200
aaataaccag aagaaggagg ggatgttaaa gaatccatat caattcggtt tacaaaagaa    4260
cccagccgca aagcttccca aaatagctcc tcttttaccc acaggtcaga gttccccctc    4320
agattctaca actctcttga caagtccgcc accagctctg tctacaacaa tggctgccac    4380
tcagaacaag ggcactgaag tagtatcagg tgccagaagt ctctcagcag ggaagaagca    4440
gcccttcacc aactcctctc cagtgcttcc tagcaccata agcaagagat ctaatacatt    4500
aaacttcttg tcaacggaaa cccccacagt gacaagtcct actgctactg catctgtcat    4560
tatgtctgaa acccaacgaa caagatccaa agaagcaaaa gaccaaataa aggggcctcg    4620
```

```
gaagaacaga aacaacgcaa acaccacccc caggcaggtt tctggctata gtgcatactc    4680
agctctaaca acagctgata cccccttggc tttcagtcat tccccacgac aagatgatgg    4740
tggaaatgta agtgcagttg cttatcactc aacaacctct cttctggcca taactgaact    4800
gtttgagaag tacacccaga ctttgggaaa tacaacagct ttggaaacaa cgttgttgag    4860
caaatcacag gagagtacca cagtgaaaag agcctcagac acaccaccac cactcctcag    4920
cagtggggcg ccccagtgc ccactccttc cccacctcct tttactaagg gtgtggttac    4980
agacagcaaa gtcacatcag ctttccagat gacgtcaaat agagtggtca ccatatatga    5040
atcttcaagg cacaatacag atctgcagca accctcagca gaggctagcc ccaatcctga    5100
gatcataact ggaaccactg actctccctc taatctgttt ccatccactt ctgtgccagc    5160
actaagggta gataaaccac agaattctaa atggaagccc tctccctggc cagaacacaa    5220
atatcagctc aagtcatact ccgaaaccat tgagaagggc aaaaggccag cagtaagcat    5280 gtcccccccac ctcagccttc cagaggccag cactcatgcc tcacactgga atacacagaa    5340
gcatgcagaa aagagtgttt ttgataagaa acctggtcaa aacccaactt ccaaacatct    5400
gccttacgtc tctctaccta agactctatt gaaaaagcca agaataattg gaggaaaggc    5460
tgcaagcttt acagttccag ctaattcaga cgttttctt ccttgtgagg ctgttggaga    5520
cccactgccc atcatccact ggaccagagt ttcatcagga nttgaaatat cccaagggac    5580
acagaaaagc cggttccacg tgcttcccaa tggcaccttg tccatccaga gggtcagtat    5640
tcaggaccgt ggacagtacc tgtgctctgc atttaatcca ctgggcgtag accattttca    5700
tgtctctttg tctgtggttt tttacccggc aaggattttg gacagacatg tcaaggagat    5760
cacagttcac tttggaagta ctgtggaact aaagtgcaga gtggagggta tgccgaggcc    5820
tacggtttcc tggatacttg caaccaaac ggtggtctca gaaacggcca agggaagcag    5880
aaaggtctgg gtaacacctg atggaacatt gatcatctat aatctgagtc tttatgatcg    5940 tggttttac aagtgtgtgg ccagcaaccc atctggccag gattcactgt tggttaagat    6000
acaagtcatc acagctcccc ctgtcattat agagcaaaag aggcaagcca tcgttggggt    6060
tttaggtgga agtttgaaac tgccctgcac tgcaaaagga actccccagc ctagtgttca    6120
ctgggtcctt tatgatggga ctgaactaaa accattgcag ttgactcatt ccagattttt    6180
cttgtatcca aatggaactc tgtatataag aagcatcgct ccttcagtga ggggcactta    6240
tgagtgcatt gccaccagct cctcaggctc agagagaagg gtagtgattc ttactgtgga    6300
agagggagag acaatcccca ggatagaaac tgcctctcag aaatggactg aggtgaattt    6360
gggtgagaaa ttactactga actgctcagc tactggggat ccaaagccta gaataatctg    6420
gaggctgcca tccaaggctg tcatcgacca gtggcacaga atgggcagcc gaatccacgt    6480
ctacccaaat ggatccttgg tggttgggtc agtgacggaa aaagacgctg gtgactactt    6540
atgtgtggca agaaacaaaa tgggagatga cctagtcctg atgcatgtcc gcctgagatt    6600
gacacctgcc aaaattgaac agaagcagta ttttaagaag caagtgctcc atgggaaaga    6660
tttccaagtt gactgcaagg cctctggctc ccctgtgcct gaggtatcct ggagtttgcc    6720
tgatgggaca gtgctcaaca atgtagccca agctgatgac agtggctata ggaccaagag    6780 gtacacccctt tccacaatg gaaccttgta tttcaacaac gttgggatgg cagaggaagg    6840
agattatatc tgctctgccc agaacacctt agggaaagat gagatgaaag tccacctaac    6900
agttctaaca gccatcccac ggataaggca aagctacaag accaccatga ggctcagggc    6960
tggagaaaca gctgtccttg actgcgaggt cactggggaa ccgaagccca atgtattttg    7020
```

```
gttgctgcct tccaacaatg tcatttcatt ctccaatgac aggttcacat ttcatgccaa      7080
tagaactttg tccatccata aagtgaaacc acttgactct ggggactatg tgtgcgtagc      7140
tcagaatcct agtggggatg acactaagac atacaaactg acattgtct ctaaacctcc       7200 attaatcaat ggcctgtatg caaacaagac tgttattaaa gccacagcca ttcggcactc      7260
caaaaaatac tttgactgca gagcagatgg gatcccatct tcccaggtca cgtggattat      7320
gccaggcaat attttcctcc cagctccata ctttggaagc agagtcacgg tccatccaaa     7380
tggaaccttg gagatgagga acatccggct ttctgactct gcggacttca cctgtgtggt     7440
tcggagcgag ggaggagaga gtgtgttggt agtgcagtta gaagtcctag aaatgctgag      7500
aagaccaaca ttcagaaacc cattcaacga aaaagtcatc gcccaagctg caagcccgt       7560 agcactgaac tgctctgtgg atgggaaccc cccacctgaa attacctgga tcttacctga     7620
cggcacacag tttgctaaca gaccacacaa ttccccgtat ctgatggcag gcaatggctc      7680
tctcatcctt tacaaagcaa ctcggaacaa gtcagggaag tatcgctgtg cagccaggaa     7740
taaggttggc tacatcgaga aactcatcct gttagagatt gggcagaagc cagtcattct     7800
gacatacgaa ccagggatgg tgaagagcgt cagtggggaa ccgttatcac tgcattgtgt     7860
gtctgatggg atccccaagc caaatgtcaa gtggactaca ccgggtggcc atgtaatcga     7920
caggcctcaa gtggatggaa atacatact gcatgaaaat ggcacgctgg tcatcaaagc      7980
aacaacagct cacgaccaag gaattatat ctgtagggct caaaacagtg ttggccaggc      8040
agttattagc gtgtcagtga tggttgtggc ctaccctccc cgaatcataa actacctacc     8100
caggaacatg ctcaggagga caggggaagc catgcagctc cactgtgtgg ccttgggaat     8160
ccccaagcca aaagtcacct gggagacgcc aagcacactcc ctgctctcaa agcaacagc     8220 aagaaaaccc catagaagtg agatgcttca cccacaaggt acgctggtca ttcagaatct     8280
ccaaacctcg gattccggag tctataagtg cagagctcag aacctacttg ggactgatta    8340
cgcaacaact tacatccagg tactctgaca ggaagggga gactaaaatt caacagaagt      8400
ccacatccac agggtttatt ttttggaaga agtttaatca aaggcagcca taggcatgta    8460
aatgagtctg aatacattta cagtattaaa tttacaatgg acatgcgatg agacttgtaa    8520
atgaaagcat tgtgaactga aaccgagtct ctgtggatct caaagcaaac tcttaactta    8580
aggcactttg attttgccaa caaataataa caaacattaa gagaaaaaaa tgatccacta    8640
cgaaataaca aacggctaat gcacctgaat tctcagtaaa aagacctttc tctcgctaac    8700
agttgccagc tgcctcgtgt ctgtttccta ccaatgtcac aaacatcgca cacagggtga    8760
atggagtcaa cgggaaagat taagtttgcg gtctgtgtaa atctcaatgt acaaatattc    8820
tgtcnctggt ttataaacat tttgataaaa ccgaaaaaaa aaaaaaaaaa aaaaaaaaa     8880 aaa                                                                  8883
```

<210> SEQ ID NO 6
<211> LENGTH: 8262
<212> TYPE: DNA
<213> ORGANISM: homo sapiens
<220> FEATURE:
<221> NAME/KEY: misc_feature
<222> LOCATION: (1)..(8262)
<223> OTHER INFORMATION: 'n' can be any nucleotide 'a', 'c', 'g' or 't'.

<400> SEQUENCE: 6

```
atgaaggtaa aaggcagagg aatcaccctgc ttgctggtct cctttgctgt gatctgcctg      60
```

```
gtcgccaccc ctgggggcaa ggcctgtcct cgccgctgtg cctgttatat gcctacggag    120
gtacactgca catttcggta cctgacttcc atcccagaca gcatcccgcc caatgtggaa    180
cgcatcaatt taggatacaa cagcttggtt agattgatgg aaacagattt ttctggcctg    240
accaaactgg agttactcat gcttcacagc aatggcattc acacaatccc tgacaagacc    300
ttctcagatt tgcaggcctt gcaggtctta aaaatgagct ataataaagt ccgaaaactt    360
cagaaagata cttttatgg cctcaggagc ttgacacgat gcacatgga ccacaacaat     420 attgagttta taaacccaga ggttttttat gggctcaact ttctccgcct ggtgcacttg    480
gaaggaaatc agctcactaa gctccaccca gatacatttg tctctttgag ctacctccag    540
atatttaaaa tctctttcat taagttccta tacttgtctg ataacttcct gacctccctc    600
cctcaagaga tggtctccta tatgcctgac ctagacagcc tttacctgca tggaaaccca    660
tggacctgtg attgccattt aaagtggttg tctgactgga tacaggnnnn nccagatgta    720
ataaaatgca aaaagatag aagtccctct agtgctcagc agtgtccact ttgcatgaac     780
cctaggactt ctaaaggcaa gccgttagct atggtctcag ctgcagcttt ccagtgtgcc    840
aagccaacca ttgactcatc cctgaaatca aagagcctga ctattctgga agacagtagt    900
tctgctttca tctctcccca aggtttcatg gcacccttg gctccctcac tttgaatatg      960
acagatcagt ctgaaaatga agctaacatg gtctgcagta ttcaaaagcc tcaaggaca    1020 tcacccattg cattcactga agaaaatgac tacatcgtgc taaatacttc attttcaaca    1080
tttttggtgt gcaacataga ttacggtcac attcagccag tgtggcaaat tttggctttg    1140
tacagtgatt ctcctctgat actagaaagg agccacttgc ttagtgaaac accgcagctc    1200
tattacaaat ataaacaggt ggctcctaag cctgaagaca ttttaccaa catagaggca     1260 gatctcagag cagatccctc ttggttaatg caagaccaaa tttccttgca gctgaacaga    1320
actgccacca cattcagtac attacagatc cagtactcca gtgatgctca aatcacttta    1380
ccaagagcag agatgaggcc agtgaaacac aaatggacta tgatttcaag ggataacaat    1440
actaagctgg aacatactgt cttggtaggt ggaaccgttg gcctgaactg cccaggccaa    1500
ggagacccca ccccacacgt ggattggctt ctagctgatg aagtaaagt gagagcccct    1560 tatgtcagtg aggatggacg gatcctaata gacaaaagtg gaaaattgga actccagatg    1620
gctgatagtt ttgacacagg cgtatatcac tgtataagca gcaattatga tgatgcagat    1680
attctcacct ataggataac tgtggtagaa cctttggtcg aagcctatca ggaaaatggg    1740
attcatcaca cagttttcat tggtgaaaca cttgatcttc catgccattc tactggtatc    1800
ccagatgcct ctattagctg ggttattcca ggaaacaatg tgctctatca gtcatcaaga    1860
gacaagaaag ttctaaacaa tggcacatta agaatattac aggtcaccc gaaagaccaa     1920 ggttattatc gctgtgtggc agccaaccca tcaggggttg attttttgat tttccaagtt    1980
tcagtcaaga tgaaaggaca aaggcccttg gagcatgatg agaaacaga gggatctgga    2040 cttgatgagt ccaatcctat tgctcatctt aaggagccac caggtgcaca actccgtaca    2100
tctgctctga tggaggctga ggttggaaaa cacacctcaa gcacaagtaa gaggcacaac    2160
tatcgggaat taacactcca gcgacgtgga gattcaacac atcgacgttt tagggagaat    2220
aggaggcatt tccctccctc tgctaggaga attgacccac aacattgggc ggcactgttg    2280
gagaaagcta aaagaatgc tatgccagac aagcgagaaa ataccacagt gagcccaccc    2340
ccagtggtca cccaactccc aaacataccc ggtgaagaag acgattcctc aggcatgctc    2400
gctctacatg aggaatttat ggtcccggcc actaaagctt tgaaccttcc agcaaggaca    2460
```

-continued

```
gtgactgctg actccagaac aatatctgat agtcctatga caaacataaa ttatggcaca    2520
gaactctccg ttgtgaattc acaaatacta ccacctgaag aacccacaga tttcaaactg    2580
tctactgcta ttaaaactac agccatgtca aagaatataa acccaaccat gtcaagccaa    2640
atacaaggca caaccaatca acattcatcc actgtctttc cactgctact tggagcaact    2700
gaatttcagg actctgacag agggaagagg aagagagcat ttccagtaac ccccaataac    2760
agtaaggact atgatcaaag atgntcaatg tcaaanatgc ttagtagcac caccaacaaa    2820
ctattattag agtcagtaaa taccacaaat agtcatcaga catctgtaag agaagtgagt    2880
gaacccaggc acaatcactt ctattctcac actactcaaa tacttagcac ctccacgttc    2940
ccttcagatc cacacacagc tgctcattct cagtttccga tccctagann naatagtaca    3000
gttaacatcc cgctgttcag acgctttggg aggcagagga aaattggcgg aaggggcgg    3060 attatcagcc catatagaac tccagttctg cgacggcata gatacagcat tttcaggtca    3120
acaaccagag gttcttctga aaaagcact actgcattct cagccacagt gctcaatgtg    3180
acatgtctgt cctgtcttcc cagggagagg ctcaccactg ccacagcagc attgtctttt    3240
ccaagtgctg ctcccatcac cttccccaaa gctgacattg ctagagtccc atcagaagag    3300
tctacaactc tagtccagaa tccactatta ctacttgaga acaaacccag tgtagannnn    3360
gaaannacaa cacccacaat aaaatattca ggactngaaa tttcccaagt gactccaact    3420
ggtgcagtca tgacatatgc tccaacatcc atcccatgg aaaaaactca caaagtaaac    3480
gccagttacc cacgtgtgtc tagcaccaat gaagctaaaa gagattcagt gattacatcg    3540
tcactttcag gtgctatcac caagccacca atgactatta tagccattac aaggttttca    3600
agaaggaaaa ttccctggca acagaacttt gtaaataacc ataacccaaa aggcagatta    3660
aggaatcaac ataaagttag tttacaaaaa agcacagctg tgatgcttcc taaaacatct    3720
cctgctttac cacagagaca aagttcccct ttccatttca ccacacttc aacaagtgtg    3780 atgcaaattc catctaatac cttgactacc gctcaccaca ctacgaccaa acacacaat    3840 cctggaagtc ttccaacaaa gaaggagctt cccttcccac cccttaaccc tatgcttcct    3900
agtattataa gcaaagactc aagtacaaaa agcatcatat caacgcaaac agcaaccgca    3960
acaactccta ccttccctgc atctgtcatc acttatgaaa cccaaacaga gagatctaga    4020
gcacaaacaa tacaaagaga aggacctcaa aagaagaaca ggactgaccc aaacatctct    4080
ccagaccaga gttctggctt cactacaccc actgctatga cnacctcctn ngctctnnnn    4140
gcattcactc attccccacc agaaaacaca actgggattt caagcacaat cagttttcat    4200
tcaagaactc ttaatctgac agatgtgatt gaagaactag cccaagcaag tactcagact    4260
ttgaagagca caattgcttc tgaaacaact ttgtccagca atcacacca gagtaccaca    4320 actaggaaag catcattaga cactcaacca ccaccattct tgagcagcag tgctactcta    4380
atgccagttc ccatctcccc tcccttact cagagagcag ttactgacaa cgtggcgact    4440
cccatttccg ggcttatgac aaatacagtg gtcaagctgc acgaatcctc aaggcacaat    4500
ccnnnnnnnc aaatgccaag ttcacnnaat tgngaaccnn nnactcnnnn nacttcatct    4560
acntctaatc tgttacattc tactcccatg ccagcactaa caacagttaa atcacagaat    4620
tccaaattaa ctccatctcc ctgggcagaa taccaatttt ggcacaaacc atactcagac    4680
attgctgaaa aggcaaaaaa gccagaagta agcatgttgg ctactacagg cctgtccgag    4740
gccaccactc ttgtttcaga ttgggatgga cagaagaaca caaagaagag tgactttgat    4800
```

```
aagaaaccag ttcaagaagc aacaacttcc aaactccttc cctttgactc tttgtctagg   4860
tatatatttg aaaagcccag gatagttgga ggaaaagctg caagttttac tattccagct   4920
aactcagatg cctttcttcc ctgtgaagct gttggaaatc ccctgcccac cattcattgg   4980
accagagtnn nntcaggact tgatttatct aagaggaaac agaatagcag ggtccaggtt   5040
ctccccaatg gtaccctgtc catccagagg gtggaaattc aggaccgcgg acagtacttg   5100
tgttccgcat ccaatctgtt tggcacagac caccttcatg tcaccttgtc tgtggtttcc   5160
tatcctccca ggatcctgga gagacgtacc aaagagatca cagttcattc cggaagcact   5220
gtggaactga agtgcagagc agaaggtagg ccaagcccta cagttacctg gattcttgca   5280
aaccaaacag ttgtctcaga atcatcccag ggaagtaggc aggctgtggt gacggttgac   5340
ggaacattgg tcctccacaa tctcagtatt tatgaccgtg gcttttacaa atgtgtggcc   5400
agcaacccag gtggccagga ttcactgctg gttaaaatac aagtcattgc agcaccacct   5460
gttattctag agcaaaggag gcaagtcatt gtaggcactt ggggtgaaag tttaaaactg   5520
ccctgtactg caaaaggaac tcctcagccc agcgtttact gggtcctctc tgatggcact   5580
gaagtgaaac cattacagtt taccaattcc aagttgttct tattttcaaa tgggactttg   5640
tatataagaa acctagcctc ttcagacagg ggcacttatg aatgcattgc taccagttcc   5700
actggttcgg agcgaagagt agtaatgctt acaatggaag agcgagtgac cagccccagg   5760
atagaagctg catcccagaa aaggactgaa gtgaattttg gggacaaatt actactgaac   5820
tgctcagcca ctggggagcc caaacccaa ataatgtgga ggttaccatc caaggctgtg   5880
gtcgaccagt gggcagctgg atccacgtct accctaatgg atccctgttt attggatcag   5940
taacagaaaa agacagtggt gtctacttgt gtgtggcaag aaacaaaatg ggggatgatc   6000
tgatactgat gcatgttagc ctaagactga aacctgccaa aattgaccac aagcagtatt   6060
ttagaaagca agtgctccat gggaaagatt tccaagtaga ttgcaaagct tccggctccc   6120
cagtgccaga gatatcttgg agtttgcctg atggaaccat gatcaacaat gcaatgcaag   6180
ccgatgacag tggccacagg actaggagat ataccctttt caacaatgga actttatact   6240
tcaacaaagt tgggtagcg gaggaaggag attatacttg ctatgcccag aacaccctag   6300
ggaaagatga aatgaaggtc cacttaacag ttataacagc tgctccccgg ataaggcaga   6360
gtaacaaaac caacaagaga atcaaagctg gagacacagc tgtccttgac tgtgaggtca   6420
ctggggatcc caaaccaaaa atattttggt tgctgccttc caatgacatg atttccttct   6480
ccattgatag gtacacattt catgccaatg ggtctttgac catcaacaaa gtgaaactgc   6540
tcgattctgg agagtacgta tgtgtagccc gaaatccag tggggatgac accaaaatgt   6600
acaaactgga tgtggtctct aaacctccat taatcaatgg tctgtataca aacagaactg   6660
ttattaaagc cacagctgtg agacattcca aaaacactt tgactgcaga gctgaaggga   6720
caccatctcc tgaagtcatg tggatcatgc agacaatat tttcctcaca gccccatact   6780
atggaagcag aatcacagtc cataaaaatg gaaccttgga aattaggaat gtgaggcttt   6840
cagattcagc cgactttatc tgtgtggccc gaaatgaagg tggagagagc gtgttggtag   6900
tacagttaga agtactggaa atgctgagaa gaccgacatt tagaaatcca tttaatgaaa   6960
aaatagttgc ccagctggga aagtccacag cattgaattg ctctgttgat ggtaacccac   7020
cacctgaaat aatctggatt ttaccaaatg gcacacgatt ttccaatgga ccacaaagtt   7080
atcagtatct gatagcaagc aatggttctt ttatcatttc taaaacaact cgggaggatg   7140
caggaaaata tcgctgtgca gctaggaata agttggcta tattgagaaa ttagtcatat   7200
```

-continued

| | |
|---|---|
| tagaaattgg ccagaagcca gttattctta cctatgcacc agggacagta aaaggcatca | 7260 |
| gtggagaatc tctatcactg cattgtgtgt ctgatggaat ccctaagcca aatatcaaat | 7320 |
| ggactatgcc aagtggttat gtagtagaca ggcctcaaat taatgggaaa tacatattgc | 7380 |
| atgacaatgg caccttagtc attaaagaag caacagctta tgacagagga aactatatct | 7440 |
| gtaaggctca aaatagtgtt ggtcatacac tgattactgt tccagtaatg attgtagcct | 7500 |
| accctccccg aattacaaat cgtccaccca ggagtattgt caccaggaca ggggcagcct | 7560 |
| ttcagctcca ctgtgtggcc ttgggagttc ccaagccaga atcacatgg gagatgcctg | 7620 |
| accactccct tctctcaacg gcaagtaaag agaggacaca tggaagtgag cagcttcact | 7680 |
| tacaaggtac cctagtcatt cagaatcccc aaacctccga ttctgggata tacaaatgca | 7740 |
| cagcaaagaa cccacttggt agtgattatg cagcaacgta tattcaagta atctgacatg | 7800 |
| aaataataaa gtcaacaaca tctgggcaga atttatttt tggaagaagt ttaatcaaag | 7860 |
| gcagccatag gcatgtaaat gaatttgaat acatttacag tattaaattt acaatgaaca | 7920 |
| tgcaaaataa aaggacttgt aaataaatgc attatgaact gatgtactg atttatttaa | 7980 |
| tggatctcaa aacaaacttt taacttaagg cactttatt ttgccaacaa ataacaataa | 8040 |
| acaaacattg aaacggttca ctataaaata acaaatggct aatgtacctg aattttcag | 8100 |
| taaaaaaatg aacttctaat accagttgcc tagtgtccac ctcctatcaa tgttacaagc | 8160 |
| atggcactca gaacagagac aatgaaaat attaaatctg caatctatgt ataaatattt | 8220 |
| tgtggtttat aaatttttt gctaaaacct acagaaaata ag | 8262 |

<210> SEQ ID NO 7
<211> LENGTH: 8883
<212> TYPE: DNA
<213> ORGANISM: Rattus species
<220> FEATURE:
<221> NAME/KEY: misc_feature
<222> LOCATION: (1)..(8916)
<223> OTHER INFORMATION: 'n' can be any nucleotide 'a', 'c', 'g' or 't'.

<400> SEQUENCE: 7

| | |
|---|---|
| cgagagacga cagaaggtta cggctgcgag aagacgacag aagggtccag aaaaaggaaa | 60 |
| gtgctggagg ggagtgggga caaaagcagc gaccaagtga atgtcacttc agtgactgag | 120 |
| gccaggcaaa acgcgcggga aggattttgt gtagcttggg accctttcat agacactgat | 180 |
| gacacgttta cgcaaaatag aaatttgagg agaaacgcct gggccttcgg aaaggagtga | 240 |
| ttgattagta cttgcaagtt taggtgactt taaggagaac taactaatgt atactattga | 300 |
| gggaggagga agagcattac agagtttcca gcagcagcag gaaagctttg gttaatttgg | 360 |
| aaatggatga tagcattaaa ataacagaag cgcctccagg tctctgaagc ttcagtcccc | 420 |
| cagctgaaag ccagaaaaga ctaagcccac taagcctttt gatccctttg aagcaaaga | 480 |
| actttccttc cctggggtga agactctcct cagaagattt cctgtctctg cctatgttac | 540 |
| aagaggaatc aaaaccaaga cagaagagct caggatgcag gtgagaggca gggaagtcag | 600 |
| cggcttgttg atctccctca ctgctgtctg cctggtggtc acccctggga gcagggcctg | 660 |
| tcctcgccgc tgtgcctgct atgtgcccac agaggtgcac tgtacatttc ggtacctgac | 720 |
| ctccatccca gatggcatcc cggccaatgt ggaacgaata aatttaggat ataacagcct | 780 |
| tactagattg acagaaaacg actttgatgg cctgagcaaa ctggagttac tcatgctgca | 840 |
| cagtaatggc attcacagag tcagtgacaa gaccttctcg ggcttgcagt ccttgcaggt | 900 |

```
cttaaaaatg agctataaca aagtccaaat cattcggaag gatactttct acggactcgg      960
gagcttggtc cggttgcacc tggatcacaa caacattgaa ttcatcaacc ctgaggcctt     1020
ttatggactt acctcgctcc gcttggtaca tttagaagga aaccggctca caaagctcca     1080
tccagacaca tttgtctcat taagctatct ccagatattt aaaacctctt tcattaagta     1140
cctgttcttg tctgataact tcctgacctc cctcccaaaa gaaatggtct cctacatgcc     1200
aaacctagaa agcctgtatt tgcatggaaa cccatggacc tgtgactgcc atttaaagtg     1260
gttgtctgag tggatgcagg gaaacccaga tataataaaa tgcaagaaag acagaagctc     1320
ttccagtcct cagcaatgtc cccttttgcat gaacccccagg atctctaaag gcagacccctt     1380 tgctatggta ccatctggag ctttcctatg tacaaagcca accattgatc catcactgaa     1440
gtcaaagagc ctggttactc aggaggacaa tggatctgcc tccacctcac ctcaagattt     1500
catagaaccc tttggctcct tgtctttgaa catgacanan ntntctggaa ataaggccga     1560
catggtctgt agtatccaaa agccatcaag gacatcacca actgcattca ctgaagaaaa     1620
tgactacatc atgctaaatg cgtcattttc cacaaatctt gtgtgcagtg tagattataa     1680
tcacatccag ccagtgtggc aacttctggc tttatacagt gactctcctc tgatactaga     1740
aaggaagccc cagcttaccg agactccttc actgtcttct agatataaac aggtggctct     1800
taggcctgaa gacattttta ccagcataga ggctgatgtc agagcagacc ctttttggtt     1860
ccaacaagaa aaaattgtct tgcagctgaa cagaactgcc accacactta gcacattaca     1920
gatccagttt tccactgatg ctcaaatcgc tttaccaagg gcggagatga gagcggagag     1980
actcaaatgg accatgatcc tgatgatgaa caatcccaaa ctggaacgca ctgtcctggt     2040
tggcggcact attgccctga gctgtccagg caaaggcgac ccttcacctc acttggaatg     2100
gcttctagct gatgggagta aagtgagagc cccttacgtt agcgaggatg ggcgaatcct     2160
aatagacaaa aatgggaagt tggaactgca gatggctgac agctttgatg caggtctttta     2220 ccactgcata agcaccaatg atgcagatgc ggatgttctc acatacagga taactgtggt     2280
agagccctat ggagaaagca cacatgacag tggagtccag cacacagtgg ttacgggtga     2340
gacgctcgac cttccatgcc tttccacggg tgttccagat gcttctatta gctggattct     2400
tccagggaac actgtgttct ctcagccatc aagagacagg caaattctta acaatgggac     2460
cttaagaata ttacaggtta cgccaaaaga tcaaggtcat taccaatgtg tggctgccaa     2520
cccatcaggg gccgactttt ccagttttaa agtttcagtt caaaagaaag gccaaaggat     2580
ggttgagcat gacagggagg caggtggatc tggacttgga gaacccaact ccagtgtttc     2640
ccttaagcag ccagcatctt tgaaactctc tgcatcagct ttgacagggt cagaggctgg     2700
aaaacaagtc tccggtgtac ataggaagaa caaacataga gacttaatac atcggcggcg     2760
tggggattcc acgctccggc gattcaggga gcataggagg cagctcccctc tctctgctcg     2820 gagaattgac ccgcaacgct gggcagcact tctagaaaaa gccaaaaaga attctgtgcc     2880
aaaaaagcaa gaaatacca cagtaaagcc agtgccactg gctgttcccc tcgtggaact     2940
cactgacgag gaaaaggatg cctctggcat gattcctcca gatgaagaat tcatggttct     3000
gaaaactaag gcttctggtg tcccaggaag gtcaccaact gctgactctg gaccagtaaa     3060
tcatggtttt atgacgagta tagcttctgg cacagaagtc tcaactgtga atccacaaac     3120
actacaatct gagcaccttc ctgatttcaa attatttagt gtaacaaacg gtacagctgt     3180
gacaaagagt atgaacccat ccatagcaag caaaatagaa gatacaacca accaaaaccc     3240
aatcattatc tttccatcag tagctgaaat tcgagattct gctcaggcag gaagagcatc     3300
```

```
ttcccaaagt gcacaccctg taacagggg aaacatggct acctatggcc ataccaacac      3360
atatagtagc tttaccagca aagccagtac agtcttgcag ccaataaatc aacagaaag      3420
ttatggacct cagataccta ttacaggagt cagcagacct agcagtagtg acatctcttc     3480
tcacactact gcagacccta gcttctccag tcacccttca ggttcacaca ccactgcctc     3540
gtctttattt cacattccta gaaacaacaa tacaggtaac ttcccttgt ccaggcactt      3600
gggaagagag aggacaattt ggagcagagg gagagttaaa aacccacata gaaccccagt    3660
tctccgacgg catagacaca ggactgtgag gccagcaatc aagggacctg ctaacaaaaa     3720
tgtgagccaa gttccagcca cagagtaccc tgggatgtgc cacacatgtc cttccgcaga     3780
ggggctcaca gtggctactg cagcactgtc agttccaagt tcatcccaca gtgccctccc    3840
caaaactaat aatgttgggg tcatagcaga agagtctacc actgtggtca agaaaccact     3900
gttactattt aaggacaaac aaaatgtaga tattgagata ataacaacca ctacaaaata    3960
ttccggaggg gaaagtaacc acgtgattcc tacggaagca agcatgactt ctgctccaac    4020
atctgtatcc ctgggggaaat ctcctgtaga caatagtggt cacctgagca tgcctgggac    4080
catccaaact gggaaagatt cagtggaaac aacaccactt cccagccccc tcagcacacc    4140
ctcaatacca acaagcacaa aattctcaaa gaggaaaact cccttgcacc agatctttgt    4200
aaataaccag aagaaggagg ggatgttaaa gaatccatat caattcggtt tacaaaagaa    4260
cccagccgca aagcttccca aaatagctcc tcttttaccc acaggtcaga gttcccctc     4320
agattctaca actctcttga caagtccgcc accagctctg tctacaacaa tggctgccac    4380
tcagaacaag ggcactgaag tagtatcagg tgccagaagt ctctcagcag gaagaagca    4440
gcccttcacc aactcctctc cagtgcttcc tagcaccata agcaagagat ctaatacatt    4500
aaacttcttg tcaacggaaa cccccacagt gacaagtcct actgctactg catctgtcat    4560
tatgtctgaa acccaacgaa caagatccaa agaagcaaaa gaccaaataa agggcctcg    4620
gaagaacaga aacaacgcaa acaccacccc caggcaggtt tctggctata gtgcatactc    4680
agctctaaca acagctgata ccccttggc tttcagtcat tccccacgac aagatgatgg   4740
tggaaatgta agtgcagttg cttatcactc aacaacctct cttctggcca taactgaact   4800
gtttgagaag tacacccaga ctttgggaaa tacaacagct ttggaaacaa cgttgttgag   4860
caaatcacag gagagtacca cagtgaaaag agcctcagac acaccaccac cactcctcag   4920
cagtgggggcg ccccccagtgc ccactccttc cccacctcct tttactaagg gtgtggttac   4980
agacagcaaa gtcacatcag cttttccagat gacgtcaaat agagtggtca ccatatatga   5040
atcttcaagg cacaatacag atctgcagca ccctcagca gaggctagcc ccaatcctga    5100
gatcataact ggaaccactg actctccctc taatctgttt ccatccactt ctgtgccagc   5160
actaagggta gataaaccac agaattctaa atggaagccc tctccctggc cagaacacaa    5220
atatcagctc aagtcatact ccgaaaccat tgagaagggc aaaaggccag cagtaagcat    5280
gtccccccac ctcagccttc cagaggccag cactcatgcc tcacactgga atacacagaa    5340
gcatgcagaa aagagtgttt ttgataagaa acctggtcaa aacccaactt ccaaacatct    5400
gccttacgtc tctctaccta agactctatt gaaaaagcca agaataattg gaggaaaggc   5460
tgcaagcttt acagttccag ctaattcaga cgttttttct ccttgtgagg ctgttggaga    5520
cccactgccc atcatccact ggaccagagt ttcatcagga nttgaaatat cccaagggac   5580
acagaaaagc cggttccacg tgcttcccaa tggcaccttg tccatccaga gggtcagtat   5640
```

```
tcaggaccgt ggacagtacc tgtgctctgc atttaatcca ctgggcgtag accatttca      5700 tgtctctttg tctgtggttt tttacccggc aaggattttg acagacatg tcaaggagat       5760 cacagttcac tttggaagta ctgtggaact aaagtgcaga gtggagggta tgccgaggcc      5820
tacggtttcc tggatacttg caaaccaaac ggtggtctca gaaacggcca agggaagcag      5880
aaaggtctgg gtaacacctg atggaacatt gatcatctat aatctgagtc tttatgatcg      5940
tggtttttac aagtgtgtgg ccagcaaccc atctggccag gattcactgt tggttaagat      6000
acaagtcatc acagctcccc ctgtcattat agagcaaaag aggcaagcca tcgttgggt       6060 tttaggtgga agtttgaaac tgccctgcac tgcaaaagga actccccagc ctagtgttca      6120
ctgggtcctt tatgatggga ctgaactaaa accattgcag ttgactcatt ccagattttt      6180
cttgtatcca aatggaactc tgtatataag aagcatcgct ccttcagtga ggggcactta     6240
tgagtgcatt gccaccagct cctcaggctc agagagaagg gtagtgattc ttactgtgga     6300
agagggagag acaatcccca ggatagaaac tgcctctcag aaatgactg aggtgaattt      6360 gggtgagaaa ttactactga actgctcagc tactggggat ccaaagccta gaataatctg     6420
gaggctgcca tccaaggctg tcatcgacca gtggcacaga atgggcagcc gaatccacgt     6480
ctacccaaat ggatccttgg tggttgggtc agtgacggaa aaagacgctg gtgactactt     6540
atgtgtggca agaaacaaaa tgggagatga cctagtcctg atgcatgtcc gcctgagatt    6600
gacacctgcc aaaattgaac agaagcagta ttttaagaag caagtgctcc atgggaaaga     6660
tttccaagtt gactgcaagg cctctggctc ccctgtgcct gaggtatcct ggagtttgcc      6720
tgatgggaca gtgctcaaca atgtagccca agctgatgac agtggctata ggaccaagag     6780 gtacacccttt tccacaatg gaaccttgta tttcaacaac gttgggatgg cagaggaagg     6840
agattatatc tgctctgccc agaacacctt agggaaagat gagatgaaag tccacctaac     6900
agttctaaca gccatcccac ggataaggca aagctacaag accaccatga ggctcagggc     6960
tggagaaaca gctgtccttg actgcgaggt cactgggaa ccgaagccca atgtattttg     7020
gttgctgcct tccaacaatg tcatttcatt ctccaatgac aggttcacat tcatgccaa      7080 tagaactttg tccatccata aagtgaaacc acttgactct gggactatg tgtgcgtagc      7140 tcagaatcct agtggggatg acactaagac atacaaactg gacattgtct ctaaacctcc    7200
attaatcaat ggcctgtatg caaacaagac tgttattaaa gccacagcca ttcggcactc    7260
caaaaaatac tttgactgca gagcagatgg gatcccatct tcccaggtca cgtggattat     7320
gccaggcaat attttcctcc cagctccata ctttggaagc agagtcacgg tccatccaaa     7380
tggaaccttg gagatgagga acatccggct ttctgactct gcggacttca cctgtgtggt     7440
tcggagcgag ggaggagaga gtgtgttggt agtgcagtta gaagtcctag aaatgctgag     7500
aagaccaaca ttcagaaacc cattcaacga aaaagtcatc gcccaagctg gcaagcccgt    7560
agcactgaac tgctctgtgg atgggaaccc cccacctgaa attacctgga tcttacctga     7620
cggcacacag tttgctaaca gaccacacaa ttccccgtat ctgatggcag gcaatggctc    7680
tctcatcctt tacaaagcaa ctcggaacaa gtcaggaaag tatcgctgtg cagccaggaa    7740
taaggttggc tacatcgaga aactcatcct gttagagatt gggcagaagc cagtcattct     7800
gacatacgaa ccaggatgg tgaagagcgt cagtggggaa ccgttatcac tgcattgtgt    7860
gtctgatggg atccccaagc caaatgtcaa gtggactaca ccgggtggcc atgtaatcga    7920
caggcctcaa gtggatggaa aatacatact gcatgaaaat ggcacgctgg tcatcaaagc    7980
aacaacagct cacgaccaag gaaattatat ctgtagggct caaaacagtg ttggccaggc    8040
```

```
agttattagc gtgtcagtga tggttgtggc ctaccctccc cgaatcataa actacctacc      8100
caggaacatg ctcaggagga caggggaagc catgcagctc cactgtgtgg ccttgggaat      8160
ccccaagcca aaagtcacct gggagacgcc aagacactcc ctgctctcaa aagcaacagc      8220
aagaaaaccc catagaagtg agatgcttca cccacaaggt acgctggtca ttcagaatct      8280
ccaaacctcg gattccggag tctataagtg cagagctcag aacctacttg ggactgatta      8340
cgcaacaact tacatccagg tactctgaca ggaaggggga gactaaaatt caacagaagt      8400
ccacatccac agggtttatt ttttggaaga agtttaatca aaggcagcca taggcatgta      8460
aatgagtctg aatacattta cagtattaaa tttacaatgg acatgcgatg agacttgtaa      8520
atgaaagcat tgtgaactga aaccgagtct ctgtggatct caaagcaaac tcttaactta      8580
aggcactttg attttgccaa caaataataa caaacattaa gagaaaaaaa tgatccacta      8640
cgaaataaca aacggctaat gcacctgaat tctcagtaaa aagacctttc tctcgctaac      8700
agttgccagc tgcctcgtgt ctgtttccta ccaatgtcac aaacatcgca cacagggtga      8760
atggagtcaa cggaaagat taagtttgcg gtctgtgtaa atctcaatgt acaaatattc       8820
tgtcnctggt ttataaacat tttgataaaa ccgaaaaaaa aaaaaaaaaa aaaaaaaaa       8880 aaa                                                                    8883

<210> SEQ ID NO 8
<211> LENGTH: 8180
<212> TYPE: DNA
<213> ORGANISM: homo sapiens
<220> FEATURE:
<221> NAME/KEY: misc_feature
<222> LOCATION: (1)..(8180)
<223> OTHER INFORMATION: 'n' can be any nucleotide 'a', 'c', 'g' or 't'.

<400> SEQUENCE: 8
tcacctgctt gctggtctcc tttgctgtga tctgcctggt cgccacccct gggggcaagg        60
cctgtcctcg ccgctgtgcc tgttatatgc ctacggaggt acactgcaca tttcggtacc       120
tgacttccat cccagacagc atcccgccca atgtggaacg catcaattta ggatacaaca       180
gcttggttag attgatggaa acagattttt ctggcctgac caaactggag ttactcatgc       240
ttcacagcaa tggcattcac acaatccctg acaagacctt ctcagatttg caggccttgc       300
aggtcttaaa aatgagctat aataaagtcc gaaaacttca gaaagatact ttttatggcc       360
tcaggagctt gacacgattg cacatggacc acaacaatat tgagtttata aacccagagg       420 tttttttatgg gctcaacttt ctccgcctgg tgcacttgga aggaaatcag ctcactaagc       480
tccacccaga tacatttgtc tctttgagct acctccagat attaaaatc tctttcatta        540 agttcctata cttgtctgat aacttcctga cctccctccc tcaagagatg gtctcctata       600
tgcctgacct agacagcctt tacctgcatg gaaacccatg gacctgtgat tgccatttaa       660
agtggttgtc tgactggata caggnnnnnc cagatgtaat aaaatgcaaa aagatagaa        720 gtccctctag tgctcagcag tgtccacttt gcatgaaccc taggacttct aaaggcaagc       780
cgttagctat ggtctcagct gcagctttcc agtgtgccaa gccaaccatt gactcatccc       840
tgaaatcaaa gagcctgact attctggaag acagtagttc tgctttcatc tctcccaag        900 gtttcatggc acccttggcc tccctcactt tgaatatgac agatcagtct ggaaatgaag       960
ctaacatggt ctgcagtatt caaaagcccc caaggcacatc acccattgca ttcactgaag      1020
aaaatgacta catcgtgcta aatacttcat tttcaacatt tttggtgtgc aacatagatt      1080
```

```
acggtcacat tcagccagtg tggcaaattt tggctttgta cagtgattct cctctgatac    1140
tagaaaggag ccacttgctt agtgaaacac cgcagctcta ttacaaatat aaacaggctt    1200
ggttaatgca agaccaaatt tccttgcagc tgaacagaac tgccaccaca ttcagtacat    1260
tacagatcca gtactccagt gatgctcaaa tcactttacc aagagcagag atgaggccag    1320
tgaaacacaa atggactatg atttcaaggg ataacaatac taagctggaa catactgtct    1380
tggtaggtgg aaccgttggc ctgaactgcc caggccaagg agaccccacc ccacacgtgg    1440
attggcttct agctgatgga agtaaagtga gagcccctta tgtcagtgag gatggacgga    1500
tcctaataga caaaagtgga aaattggaac tccagatggc tgatagtttt gacacaggcg    1560
tatatcactg tataagcagc aattatgatg atgcagatat tctcacctat aggataactg    1620
tggtagaacc tttggtcgaa gcctatcagg aaaatgggat tcatcacaca gttttcattg    1680
gtgaaacact tgatcttcca tgccattcta ctggtatccc agatgcctct attagctggg    1740
ttattccagg aaacaatgtg ctctatcagt catcaagaga caagaaagtt ctaaacaatg    1800
gcacattaag aatattacag gtcaccccga agaccaagg ttattatcgc tgtgtggcag     1860
ccaacccatc aggggttgat tttttgattt tccaagtttc agtcaagatg aaaggacaaa    1920
ggcccttgga gcatgatgga gaaacagagg atctggact tgatgagtcc aatcctattg      1980
ctcatcttaa ggagccacca ggtgcacaac tccgtacatc tgctctgatg gaggctgagg    2040
ttggaaaaca cacctcaagc acaagtaaga ggcacaacta tcgggaatta acactccagc    2100
gacgtggaga ttcaacacat cgacgtttta gggagaatag gaggcatttc cctccctctg    2160
ctaggagaat tgacccacaa cattgggcgg cactgttgga gaaagctaaa aagaatgcta    2220
tgccagacaa gcgagaaaat accacagtga gcccacccc agtggtcacc caactcccaa     2280
acatacctgg tgaagaagac gattcctcag gcatgctcgc tctacatgag gaatttatgg    2340
tcccggccac taaagctttg aaccttccag caaggacagt gactgctgac tccagaacaa    2400
tatctgatag tcctatgaca aacataaatt atggcacaga actctccgtt gtgaattcac    2460
aaatactacc acctgaagaa cccacagatt caaactgtc tactgctatt aaaactacag     2520
ccatgtcaaa gaatataaac ccaaccatgt caagccaaat acaaggcaca accaatcaac    2580
attcatccac tgtctttcca ctgctacttg gagcaactga atttcaggac tctgacagag    2640
ggaagaggaa gagagcattt ccagtaaccc ccaataacag taaggactat gatcaaagat    2700
gntcaatgtc aaanatgctt agtagcacca ccaacaaact attattagag tcagtaaata    2760
ccacaaatag tcatcagaca tctgtaagag aagtgagtga acccaggcac aatcacttct    2820
attctcacac tactcaaata cttagcacct ccacgttccc ttcagatcca cacacagctg    2880
ctcattctca gtttccgatc cctagannna atagtacagt taacatcccg ctgttcagac    2940
gctttgggag gcagaggaaa attggcggaa ggggcggat tatcagccca tatagaactc     3000
cagttctgcg acggcataga tacagcattt tcaggtcaac aaccagaggt tcttctgaaa    3060
aaagcactac tgcattctca gccacagtgc tcaatgtgac atgtctgtcc tgtcttccca    3120
gggagaggct caccactgcc acagcagcat tgtcttttcc aagtgctgct cccatcacct    3180
tccccaaagc tgacattgct agagtcccat cagaagagtc tacaactcta gtccagaatc    3240
cactattact acttgagaac aaacccagtg tagannnnga aannacaaca cccacaataa    3300
aatattcagg actngaaatt tcccaagtga ctccaactgg tgcagtcatg acatatgctc    3360
caacatccat acccatggaa aaaactcaca agtaaacgc cagttaccca cgtgtgtcta     3420
gcaccaatga agctaaaaga gattcagtga ttacatcgtc actttcaggt gctatcacca    3480
```

```
agccaccaat gactattata gccattacaa ggttttcaag aaggaaaatt ccctggcaac    3540
agaactttgt aaataaccat aacccaaaag gcagattaag gaatcaacat aaagttagtt    3600
tacaaaaaag cacagctgtg atgcttccta aaacatctcc tgctttacca cagagacaaa    3660
gttccccttt ccatttcacc acactttcaa caagtgtgat gcaaattcca tctaatacct    3720
tgactaccgc tcaccacact acgaccaaaa cacacaatcc tggaagtctt ccaacaaaga    3780
aggagcttcc cttcccaccc cttaaccta tgcttcctag tattataagc aaagactcaa    3840
gtacaaaaag catcatatca acgcaaacag caaccgcaac aactcctacc ttccctgcat    3900
ctgtcatcac ttatgaaacc caaacagaga gatctagagc acaaacaata caaagagaag    3960
gacctcaaaa gaagaacagg actgaccaa acatctctcc agaccagagt tctggcttca    4020
ctacacccac tgctatgacn acctcctnng ctctnnnngc attcactcat tccccaccag    4080
aaaacacaac tgggatttca agcacaatca gttttcattc aagaactctt aatctgacag    4140
atgtgattga agaactagcc caagcaagta ctcagacttt gaagagcaca attgcttctg    4200
aaacaacttt gtccagcaaa tcacaccaga gtaccacaac taggaaagca tcattagaca    4260
ctcaaccacc accattcttg agcagcagtg ctactctaat gccagttccc atctcccctc    4320
cctttactca gagagcagtt actgacaacg tggcgactcc catttccggg cttatgacaa    4380
atacagtggt caagctgcac gaatcctcaa ggcacaatcc nnnnnnncaa atgccaagtt    4440
cacnnaattg ngaaccnnnn actcnnnnna cttcatctac ntctaatctg ttacattcta    4500
ctcccatgcc agcactaaca acagttaaat cacagaattc caaattaact ccatctccct    4560
gggcagaata ccaattttgg cacaaaccat actcagacat tgctgaaaaa ggcaaaaagc    4620
cagaagtaag catgttggct actacaggcc tgtccgaggc caccactctt gtttcagatt    4680
gggatggaca aagaacaca aagaagagtg actttgataa gaaaccagtt caagaagcaa    4740
caacttccaa actccttccc tttgactctt tgtctaggta tatatttgaa aagcccagga    4800
tagttggagg aaaagctgca agttttacta ttccagctaa ctcagatgcc tttcttccct    4860
gtgaagctgt tggaaatccc ctgcccacca ttcattggac cagagtnnnn tcaggacttg    4920
atttatctaa gaggaaacag aatagcaggg tccaggttct ccccaatggt accctgtcca    4980
tccagagggt ggaaattcag gaccgcggac agtacttgtg ttccgcatcc aatctgtttg    5040
gcacagacca ccttcatgtc accttgtctg tggtttccta tcctcccagg atcctggaga    5100
gacgtaccaa agagatcaca gttcattccg gaagcactgt ggaactgaag tgcagagcag    5160
aaggtaggcc aagccctaca gttacctgga ttcttgcaaa ccaaacagtt gtctcagaat    5220
catcccaggg aagtaggcag gctgtggtga cggttgacgg aacattggtc tccacaatc    5280 tcagtattta tgaccgtggc ttttacaaat gtgtggccag caacccaggt ggccaggatt    5340
cactgctggt aaaatacaa gtcattgcag caccacctgt tattctagag caaaggaggc    5400
aagtcattgt aggcacttgg ggtgaaagtt taaaactgcc ctgtactgca aaaggaactc    5460
ctcagcccag cgtttactgg gtcctctctg atggcactga agtgaaacca ttacagttta    5520
ccaattccaa gttgttctta ttttcaaatg ggactttgta tataagaaac ctagcctctt    5580
cagacagggg cacttatgaa tgcattgcta ccagttccac tggttcggag cgaagagtag    5640
taatgcttac aatggaagag cgagtgacca gccccaggat agaagctgca tcccagaaaa    5700
ggactgaagt gaattttggg gacaaattac tactgaactg ctcagccact ggggagccca    5760
aaccccaaat aatgtggagg ttaccatcca aggctgtggt cgaccagtgg gcagctggat    5820
```

-continued

```
ccacgtctac cctaatggat ccctgtttat tggatcagta acagaaaaag acagtggtgt      5880
ctacttgtgt gtggcaagaa acaaaatggg ggatgatctg atactgatgc atgttagcct      5940
aagactgaaa cctgccaaaa ttgaccacaa gcagtatttt agaaagcaag tgctccatgg      6000
gaaagatttc caagtagatt gcaaagcttc cggctcccca gtgccagaga tatcttggag      6060
tttgcctgat ggaaccatga tcaacaatgc aatgcaagcc gatgacagtg gccacaggac      6120
taggagatat accctttcca caatggaac tttatacttc aacaaagttg gggtagcgga       6180
ggaaggagat tatacttgct atgcccagaa caccctaggg aaagatgaaa tgaaggtcca      6240
cttaacagtt ataacagctg ctccccggat aaggcagagt aacaaaacca acaagagaat      6300
caaagctgga gacacagctg tccttgactg tgaggtcact ggggatccca accaaaaat      6360 attttggttg ctgccttcca atgacatgat ttccttctcc attgataggt acacatttca      6420
tgccaatggg tctttgacca tcaacaaagt gaaactgctc gattctggag agtacgtatg      6480
tgtagcccga aatcccagtg gggatgacac caaaatgtac aaactggatg tggtctctaa      6540
acctccatta atcaatggtc tgtatacaaa cagaactgtt attaaagcca cagctgtgag      6600
acattccaaa aaacactttg actgcagagc tgaagggaca ccatctcctg aagtcatgtg      6660
gatcatgcca gacaatattt tcctcacagc cccatactat ggaagcagaa tcacagtcca      6720
taaaaatgga accttggaaa ttaggaatgt gaggctttca gattcagccg actttatctg      6780
tgtggcccga aatgaaggtg gagagagcgt gttggtagta cagttagaag tactggaaat      6840
gctgagaaga ccgacattta gaaatccatt taatgaaaaa atagttgccc agctgggaaa      6900
gtccacagca ttgaattgct ctgttgatgg taaccccacca cctgaaataa tctggatttt      6960
accaaatggc acacgatttt ccaatggacc acaaagttat cagtatctga tagcaagcaa      7020
tggttctttt atcatttcta aaacaactcg ggaggatgca ggaaaatatc gctgtgcagc      7080
taggaataaa gttggctata ttgagaaatt agtcatatta gaaattggcc agaagccagt      7140
tattcttacc tatgcaccag ggacagtaaa aggcatcagt ggagaatctc tatcactgca      7200
ttgtgtgtct gatggaatcc ctaagccaaa tatcaaatgg actatgccaa gtggttatgt      7260
agtagacagg cctcaaatta atgggaaata catattgcat gacaatggca ccttagtcat      7320
taaagaagca acagcttatg acagaggaaa ctatatctgt aaggctcaaa atagtgttgg      7380
tcatacactg attactgttc cagtaatgat tgtagcctac cctccccgaa ttacaaatcg      7440
tccacccagg agtattgtca ccaggacagg ggcagccttt cagctccact gtgtggcctt      7500
gggagttccc aagccagaaa tcacatggga gatgcctgac cactcccttc tctcaacggc      7560
aagtaaagag aggacacatg gaagtgagca gcttcactta caaggtaccc tagtcattca      7620
gaatccccaa acctccgatt ctgggatata caaatgcaca gcaagaacc cacttggtag      7680 tgattatgca gcaacgtata ttcaagtaat ctgacatgaa ataataaagt caacaacatc      7740
tgggcagaat ttattttttg gaagaagttt aatcaaaggc agccataggc atgtaaatga      7800
atttgaatac atttacagta ttaaatttac aatgaacatg caaaataaaa ggacttgtaa      7860
ataaatgcat tatgaactga tgatactgat ttatttaatg gatctcaaaa caaacttta      7920 acttaaggca ctttattttt gccaacaaat aacaataaac aaacattgaa acggttcact      7980
ataaaataac aaatggctaa tgtacctgaa tttttcagta aaaaaatgaa cttctaatac      8040
cagttgccta gtgtccacct cctatcaatg ttacaagcat ggcactcaga acagagacaa      8100
tggaaaatat taaatctgca atctatgtat aaatattttg tggtttataa atttttttgc      8160
taaaacctac agaaaataag                                                  8180
```

<210> SEQ ID NO 9
<211> LENGTH: 897
<212> TYPE: DNA
<213> ORGANISM: Mus musculus
<220> FEATURE:
<221> NAME/KEY: misc_feature
<222> LOCATION: (1)..(897)
<223> OTHER INFORMATION: 'n' can be any nucleotide 'a', 'c', 'g' or 't'.

<400> SEQUENCE: 9

```
aagaacgttc cttcaatcag gtgaaggctc tcctcagaag atttcctgtc tctgcttatg      60
tcagctgctt gctgatctcc ctcactgcca tctgcctggt ggtcacccct gggagcaggg     120
tctgtcctcg ccgatgtgcc tgctatgtgc ccacagaggt gcactgtaca tttcgggacc     180
tgacctccat cccagacggg catcccagcc aatgtggaac gagtcaattt agggtataac     240
agcctcacta gattgacaga aaatgacttt tctggcctga gcagactgga gttactcatg     300
ctgcacagca atggcattca cagagtcagt gacaagacct tctcgggctt gcagtccttg     360
caggtcttaa aaatgagcta taacaaagtc caaataattg agaaggatac tttgtatgga     420
ctcaggagct tgacccggtt gcacctggat cacaacaaca ttgagtttat caaccccgag     480
gcgttttacg gactcacctt gctccgcttg gtacatctag aaggaaaccg gctgacaaag     540
ctccatccag acacatttgt ctctttgagc tatctccaga tatttaaaac ctccttcatt     600
aagnacctgt acttgtatga taacttcatt gacctccctc ccaaaagaaa tggtctcctc     660
tatgccaaac ctagaaagcc tttacttgca tggaaaccca tggacctgtg actgccattt     720
aaagtggttg tccgagtgga tgcagggaaa cccaggtaac tatcttgttt gtttgtttct     780
ttttttatar kacgtatttt cctcaatttc atttagaatg atatcccaaa agtcccccat     840
aacctccccc ccacttccct acctacccat tcccattttt tggccctggc attcccc       897
```

<210> SEQ ID NO 10
<211> LENGTH: 2597
<212> TYPE: PRT
<213> ORGANISM: Rattus species
<220> FEATURE:
<221> NAME/KEY: misc_feature
<222> LOCATION: (1)..(2597)
<223> OTHER INFORMATION: 'x' can be any amino acid

<400> SEQUENCE: 10

```
Met Gln Val Arg Gly Arg Glu Val Ser Gly Leu Leu Ile Ser Leu Thr
1               5                   10                  15

Ala Val Cys Leu Val Val Thr Pro Gly Ser Arg Ala Cys Pro Arg Arg
            20                  25                  30

Cys Ala Cys Tyr Val Pro Thr Glu Val His Cys Thr Phe Arg Tyr Leu
        35                  40                  45

Thr Ser Ile Pro Asp Gly Ile Pro Ala Asn Val Glu Arg Ile Asn Leu
    50                  55                  60

Gly Tyr Asn Ser Leu Thr Arg Leu Thr Glu Asn Asp Phe Asp Gly Leu
65                  70                  75                  80

Ser Lys Leu Glu Leu Leu Met Leu His Ser Asn Gly Ile His Arg Val
                85                  90                  95

Ser Asp Lys Thr Phe Ser Gly Leu Gln Ser Leu Gln Val Leu Lys Met
            100                 105                 110

Ser Tyr Asn Lys Val Gln Ile Ile Arg Lys Asp Thr Phe Tyr Gly Leu
        115                 120                 125
```

-continued

```
Gly Ser Leu Val Arg Leu His Leu Asp His Asn Asn Ile Glu Phe Ile
130                 135                 140
Asn Pro Glu Ala Phe Tyr Gly Leu Thr Ser Leu Arg Leu Val His Leu
145                 150                 155                 160
Glu Gly Asn Arg Leu Thr Lys Leu His Pro Asp Thr Phe Val Ser Leu
                165                 170                 175
Ser Tyr Leu Gln Ile Phe Lys Thr Ser Phe Ile Lys Tyr Leu Phe Leu
                180                 185                 190
Ser Asp Asn Phe Leu Thr Ser Leu Pro Lys Glu Met Val Ser Tyr Met
            195                 200                 205
Pro Asn Leu Glu Ser Leu Tyr Leu His Gly Asn Pro Trp Thr Cys Asp
210                 215                 220
Cys His Leu Lys Trp Leu Ser Glu Trp Met Gln Gly Asn Pro Asp Ile
225                 230                 235                 240
Ile Lys Cys Lys Lys Asp Arg Ser Ser Ser Pro Gln Gln Cys Pro
                245                 250                 255
Leu Cys Met Asn Pro Arg Ile Ser Lys Gly Arg Pro Phe Ala Met Val
            260                 265                 270
Pro Ser Gly Ala Phe Leu Cys Thr Lys Pro Thr Ile Asp Pro Ser Leu
        275                 280                 285
Lys Ser Lys Ser Leu Val Thr Gln Glu Asp Asn Gly Ser Ala Ser Thr
290                 295                 300
Ser Pro Gln Asp Phe Ile Glu Pro Phe Gly Ser Leu Ser Leu Asn Met
305                 310                 315                 320
Thr Xaa Xaa Ser Gly Asn Lys Ala Asp Met Val Cys Ser Ile Gln Lys
                325                 330                 335
Pro Ser Arg Thr Ser Pro Thr Ala Phe Thr Glu Glu Asn Asp Tyr Ile
            340                 345                 350
Met Leu Asn Ala Ser Phe Ser Thr Asn Leu Val Cys Ser Val Asp Tyr
            355                 360                 365
Asn His Ile Gln Pro Val Trp Gln Leu Leu Ala Leu Tyr Ser Asp Ser
        370                 375                 380
Pro Leu Ile Leu Glu Arg Lys Pro Gln Leu Thr Glu Thr Pro Ser Leu
385                 390                 395                 400
Ser Ser Arg Tyr Lys Gln Val Ala Leu Arg Pro Glu Asp Ile Phe Thr
                405                 410                 415
Ser Ile Glu Ala Asp Val Arg Ala Asp Pro Phe Trp Phe Gln Gln Glu
            420                 425                 430
Lys Ile Val Leu Gln Leu Asn Arg Thr Ala Thr Thr Leu Ser Thr Leu
        435                 440                 445
Gln Ile Gln Phe Ser Thr Asp Ala Gln Ile Ala Leu Pro Arg Ala Glu
    450                 455                 460
Met Arg Ala Glu Arg Leu Lys Trp Thr Met Ile Leu Met Met Asn Asn
465                 470                 475                 480
Pro Lys Leu Glu Arg Thr Val Leu Val Gly Gly Thr Ile Ala Leu Ser
                485                 490                 495
Cys Pro Gly Lys Gly Asp Pro Ser Pro His Leu Glu Trp Leu Leu Ala
            500                 505                 510
Asp Gly Ser Lys Val Arg Ala Pro Tyr Val Ser Glu Asp Gly Arg Ile
        515                 520                 525
Leu Ile Asp Lys Asn Gly Lys Leu Glu Leu Gln Met Ala Asp Ser Phe
    530                 535                 540
Asp Ala Gly Leu Tyr His Cys Ile Ser Thr Asn Asp Ala Asp Ala Asp
```

-continued

```
        545                 550                 555                 560
    Val Leu Thr Tyr Arg Ile Thr Val Val Glu Pro Tyr Gly Glu Ser Thr
                        565                 570                 575

His Asp Ser Gly Val Gln His Thr Val Thr Gly Glu Thr Leu Asp
                    580                 585                 590

Leu Pro Cys Leu Ser Thr Gly Val Pro Asp Ala Ser Ile Ser Trp Ile
                    595                 600                 605

Leu Pro Gly Asn Thr Val Phe Ser Gln Pro Ser Arg Asp Arg Gln Ile
                610                 615                 620

Leu Asn Asn Gly Thr Leu Arg Ile Leu Gln Val Thr Pro Lys Asp Gln
    625                 630                 635                 640

Gly His Tyr Gln Cys Val Ala Ala Asn Pro Ser Gly Ala Asp Phe Ser
                        645                 650                 655

Ser Phe Lys Val Ser Val Gln Lys Lys Gly Gln Arg Met Val Glu His
                    660                 665                 670

Asp Arg Glu Ala Gly Gly Ser Gly Leu Gly Glu Pro Asn Ser Ser Val
                675                 680                 685

Ser Leu Lys Gln Pro Ala Ser Leu Lys Leu Ser Ala Ser Ala Leu Thr
                690                 695                 700

Gly Ser Glu Ala Gly Lys Gln Val Ser Gly Val His Arg Lys Asn Lys
    705                 710                 715                 720

His Arg Asp Leu Ile His Arg Arg Gly Asp Ser Thr Leu Arg Arg
                        725                 730                 735

Phe Arg Glu His Arg Arg Gln Leu Pro Leu Ser Ala Arg Arg Ile Asp
                    740                 745                 750

Pro Gln Arg Trp Ala Ala Leu Leu Glu Lys Ala Lys Lys Asn Ser Val
                755                 760                 765

Pro Lys Lys Gln Glu Asn Thr Thr Val Lys Pro Val Pro Leu Ala Val
                770                 775                 780

Pro Leu Val Glu Leu Thr Asp Glu Glu Lys Asp Ala Ser Gly Met Ile
    785                 790                 795                 800

Pro Pro Asp Glu Glu Phe Met Val Leu Lys Thr Lys Ala Ser Gly Val
                        805                 810                 815

Pro Gly Arg Ser Pro Thr Ala Asp Ser Gly Pro Val Asn His Gly Phe
                    820                 825                 830

Met Thr Ser Ile Ala Ser Gly Thr Glu Val Ser Thr Val Asn Pro Gln
                835                 840                 845

Thr Leu Gln Ser Glu His Leu Pro Asp Phe Lys Leu Phe Ser Val Thr
                850                 855                 860

Asn Gly Thr Ala Val Thr Lys Ser Met Asn Pro Ser Ile Ala Ser Lys
    865                 870                 875                 880

Ile Glu Asp Thr Thr Asn Gln Asn Pro Ile Ile Phe Pro Ser Val
                        885                 890                 895

Ala Glu Ile Arg Asp Ser Ala Gln Ala Gly Arg Ala Ser Ser Gln Ser
                    900                 905                 910

Ala His Pro Val Thr Gly Gly Asn Met Ala Thr Tyr Gly His Thr Asn
                915                 920                 925

Thr Tyr Ser Ser Phe Thr Ser Lys Ala Ser Thr Val Leu Gln Pro Ile
                930                 935                 940

Asn Pro Thr Glu Ser Tyr Gly Pro Gln Ile Pro Ile Thr Gly Val Ser
    945                 950                 955                 960

Arg Pro Ser Ser Ser Asp Ile Ser His Thr Thr Ala Asp Pro Ser
                        965                 970                 975
```

-continued

```
Phe Ser Ser His Pro Ser Gly Ser His Thr Thr Ala Ser Ser Leu Phe
        980                 985                 990

His Ile Pro Arg Asn Asn Thr  Gly Asn Phe Pro Leu  Ser Arg His
        995                 1000                1005

Leu Gly Arg Glu Arg Thr Ile Trp Ser Arg Gly Arg  Val Lys Asn
        1010                1015                1020

Pro His Arg Thr Pro Val Leu Arg Arg His Arg His  Arg Thr Val
        1025                1030                1035

Arg Pro Ala Ile Lys Gly Pro Ala Asn Lys Asn Val  Ser Gln Val
        1040                1045                1050

Pro Ala Thr Glu Tyr Pro Gly Met Cys His Thr Cys  Pro Ser Ala
        1055                1060                1065

Glu Gly Leu Thr Val Ala Thr Ala Ala Leu Ser Val  Pro Ser Ser
        1070                1075                1080

Ser His Ser Ala Leu Pro Lys Thr Asn Asn Val Gly  Val Ile Ala
        1085                1090                1095

Glu Glu Ser Thr Thr Val Val Lys Lys Pro Leu Leu  Leu Phe Lys
        1100                1105                1110

Asp Lys Gln Asn Val Asp Ile Glu Ile Ile Thr Thr  Thr Thr Lys
        1115                1120                1125

Tyr Ser Gly Gly Glu Ser Asn His Val Ile Pro Thr  Glu Ala Ser
        1130                1135                1140

Met Thr Ser Ala Pro Thr Ser Val Ser Leu Gly Lys  Ser Pro Val
        1145                1150                1155

Asp Asn Ser Gly His Leu Ser Met Pro Gly Thr Ile  Gln Thr Gly
        1160                1165                1170

Lys Asp Ser Val Glu Thr Thr Pro Leu Pro Ser Pro  Leu Ser Thr
        1175                1180                1185

Pro Ser Ile Pro Thr Ser Thr Lys Phe Ser Lys Arg  Lys Thr Pro
        1190                1195                1200

Leu His Gln Ile Phe Val Asn Asn Gln Lys Lys Glu  Gly Met Leu
        1205                1210                1215

Lys Asn Pro Tyr Gln Phe Gly Leu Gln Lys Asn Pro  Ala Ala Lys
        1220                1225                1230

Leu Pro Lys Ile Ala Pro Leu Leu Pro Thr Gly Gln  Ser Ser Pro
        1235                1240                1245

Ser Asp Ser Thr Thr Leu Leu Thr Ser Pro Pro Pro  Ala Leu Ser
        1250                1255                1260

Thr Thr Met Ala Ala Thr Gln Asn Lys Gly Thr Glu  Val Val Ser
        1265                1270                1275

Gly Ala Arg Ser Leu Ser Ala Gly Lys Lys Gln Pro  Phe Thr Asn
        1280                1285                1290

Ser Ser Pro Val Leu Pro Ser Thr Ile Ser Lys Arg  Ser Asn Thr
        1295                1300                1305

Leu Asn Phe Leu Ser Thr Glu Thr Pro Thr Val Thr  Ser Pro Thr
        1310                1315                1320

Ala Thr Ala Ser Val Ile Met Ser Glu Thr Gln Arg  Thr Arg Ser
        1325                1330                1335

Lys Glu Ala Lys Asp Gln Ile Lys Gly Pro Arg Lys  Asn Arg Asn
        1340                1345                1350

Asn Ala Asn Thr Thr Pro Arg Gln Val Ser Gly Tyr  Ser Ala Tyr
        1355                1360                1365
```

-continued

| | | | | | | | | | | | | |
|---|---|---|---|---|---|---|---|---|---|---|---|---|
| Ser | Ala | Leu | Thr | Thr | Ala | Asp | Thr | Pro | Leu | Ala | Phe | Ser His Ser |
| 1370 | | | | | 1375 | | | | 1380 | | | |
| Pro | Arg | Gln | Asp | Asp | Gly | Gly | Asn | Val | Ser | Ala | Val | Ala Tyr His |
| 1385 | | | | | 1390 | | | | 1395 | | | |
| Ser | Thr | Thr | Ser | Leu | Leu | Ala | Ile | Thr | Glu | Leu | Phe | Glu Lys Tyr |
| 1400 | | | | | 1405 | | | | 1410 | | | |
| Thr | Gln | Thr | Leu | Gly | Asn | Thr | Thr | Ala | Leu | Glu | Thr | Thr Leu Leu |
| 1415 | | | | | 1420 | | | | 1425 | | | |
| Ser | Lys | Ser | Gln | Glu | Ser | Thr | Thr | Val | Lys | Arg | Ala | Ser Asp Thr |
| 1430 | | | | | 1435 | | | | 1440 | | | |
| Pro | Pro | Pro | Leu | Leu | Ser | Ser | Gly | Ala | Pro | Pro | Val | Pro Thr Pro |
| 1445 | | | | | 1450 | | | | 1455 | | | |
| Ser | Pro | Pro | Pro | Phe | Thr | Lys | Gly | Val | Val | Thr | Asp | Ser Lys Val |
| 1460 | | | | | 1465 | | | | 1470 | | | |
| Thr | Ser | Ala | Phe | Gln | Met | Thr | Ser | Asn | Arg | Val | Val | Thr Ile Tyr |
| 1475 | | | | | 1480 | | | | 1485 | | | |
| Glu | Ser | Ser | Arg | His | Asn | Thr | Asp | Leu | Gln | Gln | Pro | Ser Ala Glu |
| 1490 | | | | | 1495 | | | | 1500 | | | |
| Ala | Ser | Pro | Asn | Pro | Glu | Ile | Ile | Thr | Gly | Thr | Thr | Asp Ser Pro |
| 1505 | | | | | 1510 | | | | 1515 | | | |
| Ser | Asn | Leu | Phe | Pro | Ser | Thr | Ser | Val | Pro | Ala | Leu | Arg Val Asp |
| 1520 | | | | | 1525 | | | | 1530 | | | |
| Lys | Pro | Gln | Asn | Ser | Lys | Trp | Lys | Pro | Ser | Pro | Trp | Pro Glu His |
| 1535 | | | | | 1540 | | | | 1545 | | | |
| Lys | Tyr | Gln | Leu | Lys | Ser | Tyr | Ser | Glu | Thr | Ile | Glu | Lys Gly Lys |
| 1550 | | | | | 1555 | | | | 1560 | | | |
| Arg | Pro | Ala | Val | Ser | Met | Ser | Pro | His | Leu | Ser | Leu | Pro Glu Ala |
| 1565 | | | | | 1570 | | | | 1575 | | | |
| Ser | Thr | His | Ala | Ser | His | Trp | Asn | Thr | Gln | Lys | His | Ala Glu Lys |
| 1580 | | | | | 1585 | | | | 1590 | | | |
| Ser | Val | Phe | Asp | Lys | Lys | Pro | Gly | Gln | Asn | Pro | Thr | Ser Lys His |
| 1595 | | | | | 1600 | | | | 1605 | | | |
| Leu | Pro | Tyr | Val | Ser | Leu | Pro | Lys | Thr | Leu | Leu | Lys | Lys Pro Arg |
| 1610 | | | | | 1615 | | | | 1620 | | | |
| Ile | Ile | Gly | Gly | Lys | Ala | Ala | Ser | Phe | Thr | Val | Pro | Ala Asn Ser |
| 1625 | | | | | 1630 | | | | 1635 | | | |
| Asp | Val | Phe | Leu | Pro | Cys | Glu | Ala | Val | Gly | Asp | Pro | Leu Pro Ile |
| 1640 | | | | | 1645 | | | | 1650 | | | |
| Ile | His | Trp | Thr | Arg | Val | Ser | Ser | Gly | Xaa | Glu | Ile | Ser Gln Gly |
| 1655 | | | | | 1660 | | | | 1665 | | | |
| Thr | Gln | Lys | Ser | Arg | Phe | His | Val | Leu | Pro | Asn | Gly | Thr Leu Ser |
| 1670 | | | | | 1675 | | | | 1680 | | | |
| Ile | Gln | Arg | Val | Ser | Ile | Gln | Asp | Arg | Gly | Gln | Tyr | Leu Cys Ser |
| 1685 | | | | | 1690 | | | | 1695 | | | |
| Ala | Phe | Asn | Pro | Leu | Gly | Val | Asp | His | Phe | His | Val | Ser Leu Ser |
| 1700 | | | | | 1705 | | | | 1710 | | | |
| Val | Val | Phe | Tyr | Pro | Ala | Arg | Ile | Leu | Asp | Arg | His | Val Lys Glu |
| 1715 | | | | | 1720 | | | | 1725 | | | |
| Ile | Thr | Val | His | Phe | Gly | Ser | Thr | Val | Glu | Leu | Lys | Cys Arg Val |
| 1730 | | | | | 1735 | | | | 1740 | | | |
| Glu | Gly | Met | Pro | Arg | Pro | Thr | Val | Ser | Trp | Ile | Leu | Ala Asn Gln |
| 1745 | | | | | 1750 | | | | 1755 | | | |
| Thr | Val | Val | Ser | Glu | Thr | Ala | Lys | Gly | Ser | Arg | Lys | Val Trp Val |

-continued

```
                1760                1765                1770
Thr Pro Asp Gly Thr Leu Ile Ile Tyr Asn Leu Ser Leu Tyr Asp
    1775                1780                1785
Arg Gly Phe Tyr Lys Cys Val Ala Ser Asn Pro Ser Gly Gln Asp
    1790                1795                1800
Ser Leu Leu Val Lys Ile Gln Val Ile Thr Ala Pro Pro Val Ile
    1805                1810                1815
Ile Glu Gln Lys Arg Gln Ala Ile Val Gly Val Leu Gly Gly Ser
    1820                1825                1830
Leu Lys Leu Pro Cys Thr Ala Lys Gly Thr Pro Gln Pro Ser Val
    1835                1840                1845
His Trp Val Leu Tyr Asp Gly Thr Glu Leu Lys Pro Leu Gln Leu
    1850                1855                1860
Thr His Ser Arg Phe Phe Leu Tyr Pro Asn Gly Thr Leu Tyr Ile
    1865                1870                1875
Arg Ser Ile Ala Pro Ser Val Arg Gly Thr Tyr Glu Cys Ile Ala
    1880                1885                1890
Thr Ser Ser Ser Gly Ser Glu Arg Arg Val Val Ile Leu Thr Val
    1895                1900                1905
Glu Glu Gly Glu Thr Ile Pro Arg Ile Glu Thr Ala Ser Gln Lys
    1910                1915                1920
Trp Thr Glu Val Asn Leu Gly Glu Lys Leu Leu Leu Asn Cys Ser
    1925                1930                1935
Ala Thr Gly Asp Pro Lys Pro Arg Ile Ile Trp Arg Leu Pro Ser
    1940                1945                1950
Lys Ala Val Ile Asp Gln Trp His Arg Met Gly Ser Arg Ile His
    1955                1960                1965
Val Tyr Pro Asn Gly Ser Leu Val Val Gly Ser Val Thr Glu Lys
    1970                1975                1980
Asp Ala Gly Asp Tyr Leu Cys Val Ala Arg Asn Lys Met Gly Asp
    1985                1990                1995
Asp Leu Val Leu Met His Val Arg Leu Arg Leu Thr Pro Ala Lys
    2000                2005                2010
Ile Glu Gln Lys Gln Tyr Phe Lys Lys Gln Val Leu His Gly Lys
    2015                2020                2025
Asp Phe Gln Val Asp Cys Lys Ala Ser Gly Ser Pro Val Pro Glu
    2030                2035                2040
Val Ser Trp Ser Leu Pro Asp Gly Thr Val Leu Asn Asn Val Ala
    2045                2050                2055
Gln Ala Asp Asp Ser Gly Tyr Arg Thr Lys Arg Tyr Thr Leu Phe
    2060                2065                2070
His Asn Gly Thr Leu Tyr Phe Asn Asn Val Gly Met Ala Glu Glu
    2075                2080                2085
Gly Asp Tyr Ile Cys Ser Ala Gln Asn Thr Leu Gly Lys Asp Glu
    2090                2095                2100
Met Lys Val His Leu Thr Val Leu Thr Ala Ile Pro Arg Ile Arg
    2105                2110                2115
Gln Ser Tyr Lys Thr Thr Met Arg Leu Arg Ala Gly Glu Thr Ala
    2120                2125                2130
Val Leu Asp Cys Glu Val Thr Gly Glu Pro Lys Pro Asn Val Phe
    2135                2140                2145
Trp Leu Leu Pro Ser Asn Asn Val Ile Ser Phe Ser Asn Asp Arg
    2150                2155                2160
```

```
Phe Thr Phe His Ala Asn Arg Thr Leu Ser Ile His Lys Val Lys
2165                2170                2175

Pro Leu Asp Ser Gly Asp Tyr Val Cys Val Ala Gln Asn Pro Ser
2180                2185                2190

Gly Asp Asp Thr Lys Thr Tyr Lys Leu Asp Ile Val Ser Lys Pro
2195                2200                2205

Pro Leu Ile Asn Gly Leu Tyr Ala Asn Lys Thr Val Ile Lys Ala
2210                2215                2220

Thr Ala Ile Arg His Ser Lys Lys Tyr Phe Asp Cys Arg Ala Asp
2225                2230                2235

Gly Ile Pro Ser Ser Gln Val Thr Trp Ile Met Pro Gly Asn Ile
2240                2245                2250

Phe Leu Pro Ala Pro Tyr Phe Gly Ser Arg Val Thr Val His Pro
2255                2260                2265

Asn Gly Thr Leu Glu Met Arg Asn Ile Arg Leu Ser Asp Ser Ala
2270                2275                2280

Asp Phe Thr Cys Val Val Arg Ser Glu Gly Gly Glu Ser Val Leu
2285                2290                2295

Val Val Gln Leu Glu Val Leu Glu Met Leu Arg Arg Pro Thr Phe
2300                2305                2310

Arg Asn Pro Phe Asn Glu Lys Val Ile Ala Gln Ala Gly Lys Pro
2315                2320                2325

Val Ala Leu Asn Cys Ser Val Asp Gly Asn Pro Pro Pro Glu Ile
2330                2335                2340

Thr Trp Ile Leu Pro Asp Gly Thr Gln Phe Ala Asn Arg Pro His
2345                2350                2355

Asn Ser Pro Tyr Leu Met Ala Gly Asn Gly Ser Leu Ile Leu Tyr
2360                2365                2370

Lys Ala Thr Arg Asn Lys Ser Gly Lys Tyr Arg Cys Ala Ala Arg
2375                2380                2385

Asn Lys Val Gly Tyr Ile Glu Lys Leu Ile Leu Leu Glu Ile Gly
2390                2395                2400

Gln Lys Pro Val Ile Leu Thr Tyr Glu Pro Gly Met Val Lys Ser
2405                2410                2415

Val Ser Gly Glu Pro Leu Ser Leu His Cys Val Ser Asp Gly Ile
2420                2425                2430

Pro Lys Pro Asn Val Lys Trp Thr Thr Pro Gly Gly His Val Ile
2435                2440                2445

Asp Arg Pro Gln Val Asp Gly Lys Tyr Ile Leu His Glu Asn Gly
2450                2455                2460

Thr Leu Val Ile Lys Ala Thr Thr Ala His Asp Gln Gly Asn Tyr
2465                2470                2475

Ile Cys Arg Ala Gln Asn Ser Val Gly Gln Ala Val Ile Ser Val
2480                2485                2490

Ser Val Met Val Val Ala Tyr Pro Pro Arg Ile Ile Asn Tyr Leu
2495                2500                2505

Pro Arg Asn Met Leu Arg Arg Thr Gly Glu Ala Met Gln Leu His
2510                2515                2520

Cys Val Ala Leu Gly Ile Pro Lys Pro Lys Val Thr Trp Glu Thr
2525                2530                2535

Pro Arg His Ser Leu Leu Ser Lys Ala Thr Ala Arg Lys Pro His
2540                2545                2550
```

-continued

```
Arg Ser Glu Met Leu His Pro Gln Gly Thr Leu Val Ile Gln Asn
    2555            2560                2565

Leu Gln Thr Ser Asp Ser Gly Val Tyr Lys Cys Arg Ala Gln Asn
2570            2575                2580

Leu Leu Gly Thr Asp Tyr Ala Thr Thr Tyr Ile Gln Val Leu
    2585            2590                2595

<210> SEQ ID NO 11
<211> LENGTH: 2586
<212> TYPE: PRT
<213> ORGANISM: Homo sapiens
<220> FEATURE:
<221> NAME/KEY: misc_feature
<222> LOCATION: (1)..(2586)
<223> OTHER INFORMATION: 'x' can be any amino acid

<400> SEQUENCE: 11

Met Lys Val Lys Gly Arg Gly Ile Thr Cys Leu Leu Val Ser Phe Ala
1               5                   10                  15

Val Ile Cys Leu Val Ala Thr Pro Gly Gly Lys Ala Cys Pro Arg Arg
            20                  25                  30

Cys Ala Cys Tyr Met Pro Thr Val His Cys Thr Phe Arg Tyr Leu
        35                  40                  45

Thr Ser Ile Pro Asp Ser Ile Pro Pro Asn Val Glu Arg Ile Asn Leu
    50                  55                  60

Gly Tyr Asn Ser Leu Val Arg Leu Met Glu Thr Asp Phe Ser Gly Leu
65                  70                  75                  80

Thr Lys Leu Glu Leu Leu Met Leu His Ser Asn Gly Ile His Thr Ile
                85                  90                  95

Pro Asp Lys Thr Phe Ser Asp Leu Gln Ala Leu Gln Val Leu Lys Met
            100                 105                 110

Ser Tyr Asn Lys Val Arg Lys Leu Gln Lys Asp Thr Phe Tyr Gly Leu
        115                 120                 125

Arg Ser Leu Thr Arg Leu His Met Asp His Asn Asn Ile Glu Phe Ile
    130                 135                 140

Asn Pro Glu Val Phe Tyr Gly Leu Asn Phe Leu Arg Leu Val His Leu
145                 150                 155                 160

Glu Gly Asn Gln Leu Thr Lys Leu His Pro Asp Thr Phe Val Ser Leu
                165                 170                 175

Ser Tyr Leu Gln Ile Phe Lys Ile Ser Phe Ile Lys Phe Leu Tyr Leu
            180                 185                 190

Ser Asp Asn Phe Leu Thr Ser Leu Pro Gln Glu Met Val Ser Tyr Met
        195                 200                 205

Pro Asp Leu Asp Ser Leu Tyr Leu His Gly Asn Pro Trp Thr Cys Asp
    210                 215                 220

Cys His Leu Lys Trp Leu Ser Asp Trp Ile Gln Pro Asp Val Ile Lys
225                 230                 235                 240

Cys Lys Lys Asp Arg Ser Pro Ser Ser Ala Gln Gln Cys Pro Leu Cys
                245                 250                 255

Met Asn Pro Arg Thr Ser Lys Gly Lys Pro Leu Ala Met Val Ser Ala
            260                 265                 270

Ala Ala Phe Gln Cys Ala Lys Pro Thr Ile Asp Ser Ser Leu Lys Ser
        275                 280                 285

Lys Ser Leu Thr Ile Leu Glu Asp Ser Ser Ala Phe Ile Ser Pro
    290                 295                 300

Gln Gly Phe Met Ala Pro Phe Gly Ser Leu Thr Leu Asn Met Thr Asp
```

-continued

```
            305                 310                 315                 320
Gln Ser Gly Asn Glu Ala Asn Met Val Cys Ser Ile Gln Lys Pro Ser
                325                 330                 335
Arg Thr Ser Pro Ile Ala Phe Thr Glu Glu Asn Asp Tyr Ile Val Leu
                340                 345                 350
Asn Thr Ser Phe Ser Thr Phe Leu Val Cys Asn Ile Asp Tyr Gly His
                355                 360                 365
Ile Gln Pro Val Trp Gln Ile Leu Ala Leu Tyr Ser Asp Ser Pro Leu
                370                 375                 380
Ile Leu Glu Arg Ser His Leu Leu Ser Glu Thr Pro Gln Leu Tyr Tyr
385                 390                 395                 400
Lys Tyr Lys Gln Val Ala Pro Lys Pro Glu Asp Ile Phe Thr Asn Ile
                405                 410                 415
Glu Ala Asp Leu Arg Ala Asp Pro Ser Trp Leu Met Gln Asp Gln Ile
                420                 425                 430
Ser Leu Gln Leu Asn Arg Thr Ala Thr Phe Ser Thr Leu Gln Ile
                435                 440                 445
Gln Tyr Ser Ser Asp Ala Gln Ile Thr Leu Pro Arg Ala Glu Met Arg
450                 455                 460
Pro Val Lys His Lys Trp Thr Met Ile Ser Arg Asp Asn Asn Thr Lys
465                 470                 475                 480
Leu Glu His Thr Val Leu Val Gly Gly Thr Val Gly Leu Asn Cys Pro
                485                 490                 495
Gly Gln Gly Asp Pro Thr Pro His Val Asp Trp Leu Leu Ala Asp Gly
                500                 505                 510
Ser Lys Val Arg Ala Pro Tyr Val Ser Glu Asp Gly Arg Ile Leu Ile
                515                 520                 525
Asp Lys Ser Gly Lys Leu Glu Leu Gln Met Ala Asp Ser Phe Asp Thr
                530                 535                 540
Gly Val Tyr His Cys Ile Ser Ser Asn Tyr Asp Ala Asp Ile Leu
545                 550                 555                 560
Thr Tyr Arg Ile Thr Val Val Glu Pro Leu Val Glu Ala Tyr Gln Glu
                565                 570                 575
Asn Gly Ile His His Thr Val Phe Ile Gly Glu Thr Leu Asp Leu Pro
                580                 585                 590
Cys His Ser Thr Gly Ile Pro Asp Ala Ser Ile Ser Trp Val Ile Pro
                595                 600                 605
Gly Asn Asn Val Leu Tyr Gln Ser Ser Arg Asp Lys Lys Val Leu Asn
                610                 615                 620
Asn Gly Thr Leu Arg Ile Leu Gln Val Thr Pro Lys Asp Gln Gly Tyr
625                 630                 635                 640
Tyr Arg Cys Val Ala Ala Asn Pro Ser Gly Val Asp Phe Leu Ile Phe
                645                 650                 655
Gln Val Ser Val Lys Met Lys Gly Gln Arg Pro Leu Glu His Asp Gly
                660                 665                 670
Glu Thr Glu Gly Ser Gly Leu Asp Glu Ser Asn Pro Ile Ala His Leu
                675                 680                 685
Lys Glu Pro Pro Gly Ala Gln Leu Arg Thr Ser Ala Leu Met Glu Ala
                690                 695                 700
Glu Val Gly Lys His Thr Ser Ser Thr Ser Lys Arg His Asn Tyr Arg
705                 710                 715                 720
Glu Leu Thr Leu Gln Arg Arg Gly Asp Ser Thr His Arg Arg Phe Arg
                725                 730                 735
```

-continued

```
Glu Asn Arg Arg His Phe Pro Pro Ser Ala Arg Arg Ile Asp Pro Gln
            740                 745                 750

His Trp Ala Ala Leu Leu Glu Lys Ala Lys Lys Asn Ala Met Pro Asp
            755                 760                 765

Lys Arg Glu Asn Thr Thr Val Ser Pro Pro Val Val Thr Gln Leu
            770                 775                 780

Pro Asn Ile Pro Gly Glu Glu Asp Asp Ser Ser Gly Met Leu Ala Leu
785                 790                 795                 800

His Glu Glu Phe Met Val Pro Ala Thr Lys Ala Leu Asn Leu Pro Ala
                    805                 810                 815

Arg Thr Val Thr Ala Asp Ser Arg Thr Ile Ser Asp Ser Pro Met Thr
                820                 825                 830

Asn Ile Asn Tyr Gly Thr Glu Phe Ser Pro Val Val Asn Ser Gln Ile
                835                 840                 845

Leu Pro Pro Glu Glu Pro Thr Asp Phe Lys Leu Ser Thr Ala Ile Lys
850                 855                 860

Thr Thr Ala Met Ser Lys Asn Ile Asn Pro Thr Met Ser Ser Gln Ile
865                 870                 875                 880

Gln Gly Thr Thr Asn Gln His Ser Ser Thr Val Phe Pro Leu Leu Leu
                    885                 890                 895

Gly Ala Thr Glu Phe Gln Asp Ser Asp Gln Met Gly Arg Gly Arg Glu
                900                 905                 910

His Phe Gln Ser Arg Pro Pro Ile Thr Val Arg Thr Met Ile Lys Asp
                915                 920                 925

Val Asn Val Lys Met Leu Ser Ser Thr Thr Asn Lys Leu Leu Leu Glu
                930                 935                 940

Ser Val Asn Thr Thr Asn Ser His Gln Thr Ser Val Arg Glu Val Ser
945                 950                 955                 960

Glu Pro Arg His Asn His Phe Tyr Ser His Thr Thr Gln Ile Leu Ser
                965                 970                 975

Thr Ser Thr Phe Pro Ser Asp Pro His Thr Ala Ala His Ser Gln Phe
                980                 985                 990

Pro Ile Pro Arg Asn Ser Thr Val  Asn Ile Pro Leu Phe  Arg Arg Phe
            995                 1000                1005

Gly Arg  Gln Arg Lys Ile Gly  Gly Arg Gly Arg Ile  Ile Ser Pro
    1010                1015                1020

Tyr Arg  Thr Pro Val Leu Arg  Arg His Arg Tyr Ser  Ile Phe Arg
    1025                1030                1035

Ser Thr  Thr Arg Gly Ser Ser  Glu Lys Ser Thr Thr  Ala Phe Ser
    1040                1045                1050

Ala Thr  Val Leu Asn Val Thr  Cys Leu Ser Cys Leu  Pro Arg Glu
    1055                1060                1065

Arg Leu  Thr Thr Ala Thr Ala  Ala Leu Ser Phe Pro  Ser Ala Ala
    1070                1075                1080

Pro Ile  Thr Phe Pro Lys Ala  Asp Ile Ala Arg Val  Pro Ser Glu
    1085                1090                1095

Glu Ser  Thr Thr Leu Val Gln  Asn Pro Leu Leu Leu  Leu Glu Asn
    1100                1105                1110

Lys Pro  Ser Val Glu Lys Thr  Thr Pro Thr Ile Lys  Tyr Phe Arg
    1115                1120                1125

Thr Glu  Ile Ser Gln Val Thr  Pro Thr Gly Ala Val  Met Thr Tyr
    1130                1135                1140
```

-continued

```
Ala Pro Thr Ser Ile Pro Met Glu Lys Thr His Lys Val Asn Ala
1145                1150                1155

Ser Tyr Pro Arg Val Ser Ser Thr Asn Glu Ala Lys Arg Asp Ser
    1160                1165                1170

Val Ile Thr Ser Ser Leu Ser Gly Ala Ile Thr Lys Pro Pro Met
    1175                1180                1185

Thr Ile Ile Ala Ile Thr Arg Phe Ser Arg Arg Lys Ile Pro Trp
    1190                1195                1200

Gln Gln Asn Phe Val Asn Asn His Asn Pro Lys Gly Arg Leu Arg
1205                1210                1215

Asn Gln His Lys Val Ser Leu Gln Lys Ser Thr Ala Val Met Leu
1220                1225                1230

Pro Lys Thr Ser Pro Ala Leu Pro Gln Arg Gln Ser Ser Pro Phe
1235                1240                1245

His Phe Thr Thr Leu Ser Thr Ser Val Met Gln Ile Pro Ser Asn
1250                1255                1260

Thr Leu Thr Thr Ala His His Thr Thr Thr Lys Thr His Asn Pro
1265                1270                1275

Gly Ser Leu Pro Thr Lys Lys Glu Leu Pro Phe Pro Pro Leu Asn
1280                1285                1290

Pro Met Leu Pro Ser Ile Ile Ser Lys Asp Ser Ser Thr Lys Ser
1295                1300                1305

Ile Ile Ser Thr Gln Thr Ala Ile Pro Ala Thr Thr Pro Thr Phe
1310                1315                1320

Pro Ala Ser Val Ile Thr Tyr Glu Thr Gln Thr Glu Arg Ser Arg
1325                1330                1335

Ala Gln Thr Ile Gln Arg Glu Gln Glu Pro Gln Lys Lys Asn Arg
1340                1345                1350

Thr Asp Pro Asn Ile Ser Pro Asp Gln Ser Ser Gly Phe Thr Thr
1355                1360                1365

Pro Thr Ala Met Thr Pro Pro Ala Leu Ala Phe Thr His Ser Pro
1370                1375                1380

Pro Glu Asn Thr Thr Gly Ile Ser Ser Thr Ile Ser Phe His Ser
1385                1390                1395

Arg Thr Leu Asn Leu Thr Asp Val Ile Glu Glu Leu Ala Gln Ala
1400                1405                1410

Ser Thr Gln Thr Leu Lys Ser Thr Ile Ala Ser Glu Thr Thr Leu
1415                1420                1425

Ser Ser Lys Ser His Gln Ser Thr Thr Thr Arg Lys Ala Ser Leu
1430                1435                1440

Asp Thr Pro Ile Pro Pro Phe Leu Ser Ser Ser Ala Thr Leu Met
1445                1450                1455

Pro Val Pro Ile Ser Pro Pro Phe Thr Gln Arg Ala Val Thr Asp
1460                1465                1470

Thr Arg Gly Asp Ser His Phe Arg Leu Met Thr Asn Thr Val Val
1475                1480                1485

Lys Leu His Glu Ser Ser Arg His Asn Leu Gln Met Pro Ser Ser
1490                1495                1500

Gln Leu Glu Pro Leu Thr Ser Ser Thr Ser Asn Leu Leu His Ser
1505                1510                1515

Thr Pro Met Pro Ala Leu Thr Val Lys Ser Gln Asn Ser Lys
1520                1525                1530

Leu Thr Pro Ser Pro Trp Ala Glu Tyr Gln Phe Trp His Lys Pro
```

-continued

|  |  |  |  |  |  |  |  |  |  |
|---|---|---|---|---|---|---|---|---|---|
|  | 1535 |  |  | 1540 |  |  | 1545 |  |  |
| Tyr | Ser | Asp | Ile | Ala | Glu | Lys | Gly | Lys | Lys | Pro | Glu | Val | Ser | Met |
| 1550 |  |  |  |  | 1555 |  |  |  |  | 1560 |

Tyr Ser Asp Ile Ala Glu Lys Gly Lys Lys Pro Glu Val Ser Met
1550                1555                1560

Leu Ala Thr Thr Gly Leu Ser Glu Ala Thr Thr Leu Val Ser Asp
1565                1570                1575

Trp Asp Gly Gln Lys Asn Thr Lys Lys Ser Asp Phe Asp Lys Lys
1580                1585                1590

Pro Val Gln Glu Ala Thr Thr Ser Lys Leu Leu Pro Phe Asp Ser
1595                1600                1605

Leu Ser Arg Tyr Ile Phe Glu Lys Pro Arg Ile Val Gly Gly Lys
1610                1615                1620

Ala Ala Ser Phe Thr Ile Pro Ala Asn Ser Asp Ala Phe Leu Pro
1625                1630                1635

Cys Glu Ala Val Gly Asn Pro Leu Pro Thr Ile His Trp Thr Arg
1640                1645                1650

Val Ser Gly Leu Asp Leu Ser Arg Gly Asn Gln Asn Ser Arg Val
1655                1660                1665

Gln Val Leu Pro Asn Gly Thr Leu Ser Ile Gln Arg Val Glu Ile
1670                1675                1680

Gln Asp Arg Gly Gln Tyr Leu Cys Ser Ala Ser Asn Leu Phe Gly
1685                1690                1695

Thr Asp His Leu His Val Thr Leu Ser Val Val Ser Tyr Pro Pro
1700                1705                1710

Arg Ile Leu Glu Arg Arg Thr Lys Glu Ile Thr Val His Ser Gly
1715                1720                1725

Ser Thr Val Glu Leu Lys Cys Arg Ala Glu Gly Arg Pro Ser Pro
1730                1735                1740

Thr Val Thr Trp Ile Leu Ala Asn Gln Thr Val Val Ser Glu Ser
1745                1750                1755

Ser Gln Gly Ser Arg Gln Ala Val Val Thr Val Asp Gly Thr Leu
1760                1765                1770

Val Leu His Asn Leu Ser Ile Tyr Asp Arg Gly Phe Tyr Lys Cys
1775                1780                1785

Val Ala Ser Asn Pro Gly Gly Gln Asp Ser Leu Leu Val Lys Ile
1790                1795                1800

Gln Val Ile Ala Ala Pro Pro Val Ile Leu Glu Gln Arg Arg Gln
1805                1810                1815

Val Ile Val Gly Thr Trp Gly Glu Ser Leu Lys Leu Pro Cys Thr
1820                1825                1830

Ala Lys Gly Thr Pro Gln Pro Ser Val Tyr Trp Val Leu Ser Asp
1835                1840                1845

Gly Thr Glu Val Lys Pro Leu Gln Phe Thr Asn Ser Lys Leu Phe
1850                1855                1860

Leu Phe Ser Asn Gly Thr Leu Tyr Ile Arg Asn Leu Ala Ser Ser
1865                1870                1875

Asp Arg Gly Thr Tyr Glu Cys Ile Ala Thr Ser Ser Thr Gly Ser
1880                1885                1890

Glu Arg Arg Val Val Met Leu Thr Met Glu Glu Arg Val Thr Ser
1895                1900                1905

Pro Arg Ile Glu Ala Ala Ser Gln Lys Arg Thr Glu Val Asn Phe
1910                1915                1920

Gly Asp Lys Leu Leu Leu Asn Cys Ser Ala Thr Gly Glu Pro Lys
1925                1930                1935

```
Pro Gln Ile Met Trp Arg Leu Pro Ser Lys Ala Val Val Asp Gln
    1940                1945                1950

Gly Ser Trp Ile His Val Tyr Pro Asn Gly Ser Leu Phe Ile Gly
    1955                1960                1965

Ser Val Thr Glu Lys Asp Ser Gly Val Tyr Leu Cys Val Ala Arg
    1970                1975                1980

Asn Lys Met Gly Asp Leu Ile Leu Met His Val Ser Leu Arg
    1985                1990                1995

Leu Lys Pro Ala Lys Ile Asp His Lys Gln Tyr Phe Arg Lys Gln
    2000                2005                2010

Val Leu His Gly Lys Asp Phe Gln Val Asp Cys Lys Ala Ser Gly
    2015                2020                2025

Ser Pro Val Pro Glu Ile Ser Trp Ser Leu Pro Asp Gly Thr Met
    2030                2035                2040

Ile Asn Asn Ala Met Gln Ala Asp Asp Ser Gly His Arg Thr Arg
    2045                2050                2055

Arg Tyr Thr Leu Phe Asn Asn Gly Thr Leu Tyr Phe Asn Lys Val
    2060                2065                2070

Gly Val Ala Glu Glu Gly Asp Tyr Thr Cys Tyr Ala Gln Asn Thr
    2075                2080                2085

Leu Gly Lys Asp Glu Met Lys Val His Leu Thr Val Ile Thr Ala
    2090                2095                2100

Ala Pro Arg Ile Arg Gln Ser Asn Lys Thr Asn Lys Arg Ile Lys
    2105                2110                2115

Ala Gly Asp Thr Ala Val Leu Asp Cys Glu Val Thr Gly Asp Pro
    2120                2125                2130

Lys Pro Lys Ile Phe Trp Leu Leu Pro Ser Asn Asp Met Ile Ser
    2135                2140                2145

Phe Ser Ile Asp Arg Tyr Thr Phe His Ala Asn Gly Ser Leu Thr
    2150                2155                2160

Ile Asn Lys Val Lys Leu Leu Asp Ser Gly Glu Tyr Val Cys Val
    2165                2170                2175

Ala Arg Asn Pro Ser Gly Asp Asp Thr Lys Met Tyr Lys Leu Asp
    2180                2185                2190

Val Val Ser Lys Pro Pro Leu Ile Asn Gly Leu Tyr Thr Asn Arg
    2195                2200                2205

Thr Val Ile Lys Ala Thr Ala Val Arg His Ser Lys Lys His Phe
    2210                2215                2220

Asp Cys Arg Ala Glu Gly Thr Pro Ser Pro Glu Val Met Trp Ile
    2225                2230                2235

Met Pro Asp Asn Ile Phe Leu Thr Ala Pro Tyr Tyr Gly Ser Arg
    2240                2245                2250

Ile Thr Val His Lys Asn Gly Thr Leu Glu Ile Arg Asn Val Arg
    2255                2260                2265

Leu Ser Asp Ser Ala Asp Phe Ile Cys Val Ala Arg Asn Glu Gly
    2270                2275                2280

Gly Glu Ser Val Leu Val Val Gln Leu Glu Val Leu Glu Met Leu
    2285                2290                2295

Arg Arg Pro Thr Phe Arg Asn Pro Phe Asn Glu Lys Ile Val Ala
    2300                2305                2310

Gln Leu Gly Lys Ser Thr Ala Leu Asn Cys Ser Val Asp Gly Asn
    2315                2320                2325
```

Pro Pro Pro Glu Ile Ile Trp Ile Leu Pro Asn Gly Thr Arg Phe
    2330                2335                2340

Ser Asn Gly Pro Gln Ser Tyr Gln Tyr Leu Ile Ala Ser Asn Gly
    2345                2350                2355

Ser Phe Ile Ile Ser Lys Thr Thr Arg Glu Asp Ala Gly Lys Tyr
    2360                2365                2370

Arg Cys Ala Ala Arg Asn Lys Val Gly Tyr Ile Glu Lys Leu Val
    2375                2380                2385

Ile Leu Glu Ile Gly Gln Lys Pro Val Ile Leu Thr Tyr Ala Pro
    2390                2395                2400

Gly Thr Val Lys Gly Ile Ser Gly Glu Ser Leu Ser Leu His Cys
    2405                2410                2415

Val Ser Asp Gly Ile Pro Lys Pro Asn Ile Lys Trp Thr Met Pro
    2420                2425                2430

Ser Gly Tyr Val Val Asp Arg Pro Gln Ile Asn Gly Lys Tyr Ile
    2435                2440                2445

Leu His Asp Asn Gly Thr Leu Val Ile Lys Glu Ala Thr Ala Tyr
    2450                2455                2460

Asp Arg Gly Asn Tyr Ile Cys Lys Ala Gln Asn Ser Val Gly His
    2465                2470                2475

Thr Leu Ile Thr Val Pro Val Met Ile Val Ala Tyr Pro Pro Arg
    2480                2485                2490

Ile Thr Asn Arg Pro Pro Arg Ser Ile Val Thr Arg Thr Gly Ala
    2495                2500                2505

Ala Phe Gln Leu His Cys Val Ala Leu Gly Val Pro Lys Pro Glu
    2510                2515                2520

Ile Thr Trp Glu Met Pro Asp His Ser Leu Leu Ser Thr Ala Ser
    2525                2530                2535

Lys Glu Arg Thr His Gly Ser Glu Gln Leu His Leu Gln Gly Thr
    2540                2545                2550

Leu Val Ile Gln Asn Pro Gln Thr Ser Asp Ser Gly Ile Tyr Lys
    2555                2560                2565

Cys Thr Ala Lys Asn Pro Leu Gly Ser Asp Tyr Ala Ala Thr Tyr
    2570                2575                2580

Ile Gln Val
    2585

<210> SEQ ID NO 12
<211> LENGTH: 236
<212> TYPE: PRT
<213> ORGANISM: Mus musculus
<220> FEATURE:
<221> NAME/KEY: misc_feature
<222> LOCATION: (1)..(236)
<223> OTHER INFORMATION: 'x' can be any amino acid

<400> SEQUENCE: 12

Met Gln Lys Arg Gly Arg Glu Val Ser Cys Leu Leu Ile Ser Leu Thr
1               5                   10                  15

Ala Ile Cys Leu Val Val Thr Pro Gly Ser Arg Val Cys Pro Arg Arg
                20                  25                  30

Cys Ala Cys Tyr Val Pro Thr Glu Val His Cys Thr Phe Arg Asp Leu
            35                  40                  45

Thr Ser Ile Pro Asp Gly Pro Ala Asn Val Glu Arg Val Asn Leu Gly
        50                  55                  60

Tyr Asn Ser Leu Thr Arg Leu Thr Glu Asn Asp Phe Ser Gly Leu Ser

-continued

```
                65                  70                  75                  80
Arg Leu Glu Leu Leu Met Leu His Ser Asn Gly Ile His Arg Val Ser
                    85                  90                  95
Asp Lys Thr Phe Ser Gly Leu Gln Ser Leu Gln Val Leu Lys Met Ser
                100                 105                 110
Tyr Asn Lys Val Gln Ile Ile Glu Lys Asp Thr Leu Tyr Gly Leu Arg
                115                 120                 125
Ser Leu Thr Arg Leu His Leu Asp His Asn Asn Ile Glu Phe Ile Asn
            130                 135                 140
Pro Glu Ala Phe Tyr Gly Leu Thr Leu Leu Arg Leu Val His Leu Glu
145                 150                 155                 160
Gly Asn Arg Leu Thr Lys Leu His Pro Asp Thr Phe Val Ser Leu Ser
                165                 170                 175
Tyr Leu Gln Ile Phe Lys Thr Ser Phe Ile Lys Xaa Leu Tyr Leu Tyr
                180                 185                 190
Asp Asn Phe Thr Ser Leu Pro Lys Glu Met Val Ser Ser Met Pro Asn
                195                 200                 205
Leu Glu Ser Leu Tyr Leu His Gly Asn Pro Trp Thr Cys Asp Cys His
            210                 215                 220
Leu Lys Trp Leu Ser Glu Trp Met Gln Gly Asn Pro
225                 230                 235

<210> SEQ ID NO 13
<211> LENGTH: 2597
<212> TYPE: PRT
<213> ORGANISM: Rattus species
<220> FEATURE:
<221> NAME/KEY: misc_feature
<222> LOCATION: (1)..(2597)
<223> OTHER INFORMATION: 'x' can be any amino acid

<400> SEQUENCE: 13

Met Gln Val Arg Gly Arg Glu Val Ser Gly Leu Leu Ile Ser Leu Thr
1               5                   10                  15
Ala Val Cys Leu Val Val Thr Pro Gly Ser Arg Ala Cys Pro Arg Arg
                20                  25                  30
Cys Ala Cys Tyr Val Pro Thr Glu Val His Cys Thr Phe Arg Tyr Leu
            35                  40                  45
Thr Ser Ile Pro Asp Gly Ile Pro Ala Asn Val Glu Arg Ile Asn Leu
        50                  55                  60
Gly Tyr Asn Ser Leu Thr Arg Leu Thr Glu Asn Asp Phe Asp Gly Leu
65                  70                  75                  80
Ser Lys Leu Glu Leu Leu Met Leu His Ser Asn Gly Ile His Arg Val
                85                  90                  95
Ser Asp Lys Thr Phe Ser Gly Leu Gln Ser Leu Gln Val Leu Lys Met
                100                 105                 110
Ser Tyr Asn Lys Val Gln Ile Ile Arg Lys Asp Thr Phe Tyr Gly Leu
            115                 120                 125
Gly Ser Leu Val Arg Leu His Leu Asp His Asn Asn Ile Glu Phe Ile
        130                 135                 140
Asn Pro Glu Ala Phe Tyr Gly Leu Thr Ser Leu Arg Leu Val His Leu
145                 150                 155                 160
Glu Gly Asn Arg Leu Thr Lys Leu His Pro Asp Thr Phe Val Ser Leu
                165                 170                 175
Ser Tyr Leu Gln Ile Phe Lys Thr Ser Phe Ile Lys Tyr Leu Phe Leu
                180                 185                 190
```

```
Ser Asp Asn Phe Leu Thr Ser Leu Pro Lys Glu Met Val Ser Tyr Met
            195                 200                 205

Pro Asn Leu Glu Ser Leu Tyr Leu His Gly Asn Pro Trp Thr Cys Asp
        210                 215                 220

Cys His Leu Lys Trp Leu Ser Glu Trp Met Gln Gly Asn Pro Asp Ile
225                 230                 235                 240

Ile Lys Cys Lys Lys Asp Arg Ser Ser Ser Pro Gln Gln Cys Pro
                245                 250                 255

Leu Cys Met Asn Pro Arg Ile Ser Lys Gly Arg Pro Phe Ala Met Val
            260                 265                 270

Pro Ser Gly Ala Phe Leu Cys Thr Lys Pro Thr Ile Asp Pro Ser Leu
        275                 280                 285

Lys Ser Lys Ser Leu Val Thr Gln Glu Asp Asn Gly Ser Ala Ser Thr
        290                 295                 300

Ser Pro Gln Asp Phe Ile Glu Pro Phe Gly Ser Leu Ser Leu Asn Met
305                 310                 315                 320

Thr Xaa Xaa Ser Gly Asn Lys Ala Asp Met Val Cys Ser Ile Gln Lys
                325                 330                 335

Pro Ser Arg Thr Ser Pro Thr Ala Phe Thr Glu Glu Asn Asp Tyr Ile
            340                 345                 350

Met Leu Asn Ala Ser Phe Ser Thr Asn Leu Val Cys Ser Val Asp Tyr
            355                 360                 365

Asn His Ile Gln Pro Val Trp Gln Leu Leu Ala Leu Tyr Ser Asp Ser
        370                 375                 380

Pro Leu Ile Leu Glu Arg Lys Pro Gln Leu Thr Glu Thr Pro Ser Leu
385                 390                 395                 400

Ser Ser Arg Tyr Lys Gln Val Ala Leu Arg Pro Glu Asp Ile Phe Thr
                405                 410                 415

Ser Ile Glu Ala Asp Val Arg Ala Asp Pro Phe Trp Phe Gln Gln Glu
            420                 425                 430

Lys Ile Val Leu Gln Leu Asn Arg Thr Ala Thr Thr Leu Ser Thr Leu
        435                 440                 445

Gln Ile Gln Phe Ser Thr Asp Ala Gln Ile Ala Leu Pro Arg Ala Glu
    450                 455                 460

Met Arg Ala Glu Arg Leu Lys Trp Thr Met Ile Leu Met Met Asn Asn
465                 470                 475                 480

Pro Lys Leu Glu Arg Thr Val Leu Val Gly Gly Thr Ile Ala Leu Ser
            485                 490                 495

Cys Pro Gly Lys Gly Asp Pro Ser Pro His Leu Glu Trp Leu Leu Ala
                500                 505                 510

Asp Gly Ser Lys Val Arg Ala Pro Tyr Val Ser Glu Asp Gly Arg Ile
        515                 520                 525

Leu Ile Asp Lys Asn Gly Lys Leu Glu Leu Gln Met Ala Asp Ser Phe
        530                 535                 540

Asp Ala Gly Leu Tyr His Cys Ile Ser Thr Asn Asp Ala Asp Ala Asp
545                 550                 555                 560

Val Leu Thr Tyr Arg Ile Thr Val Val Glu Pro Tyr Gly Glu Ser Thr
                565                 570                 575

His Asp Ser Gly Val Gln His Thr Val Thr Gly Glu Thr Leu Asp
            580                 585                 590

Leu Pro Cys Leu Ser Thr Gly Val Pro Asp Ala Ser Ile Ser Trp Ile
        595                 600                 605
```

-continued

Leu Pro Gly Asn Thr Val Phe Ser Gln Pro Ser Arg Asp Arg Gln Ile
    610                 615                 620

Leu Asn Asn Gly Thr Leu Arg Ile Leu Gln Val Thr Pro Lys Asp Gln
625                 630                 635                 640

Gly His Tyr Gln Cys Val Ala Ala Asn Pro Ser Gly Ala Asp Phe Ser
                645                 650                 655

Ser Phe Lys Val Ser Val Gln Lys Lys Gly Gln Arg Met Val Glu His
                660                 665                 670

Asp Arg Glu Ala Gly Gly Ser Gly Leu Gly Glu Pro Asn Ser Ser Val
            675                 680                 685

Ser Leu Lys Gln Pro Ala Ser Leu Lys Leu Ser Ala Ser Ala Leu Thr
    690                 695                 700

Gly Ser Glu Ala Gly Lys Gln Val Ser Gly Val His Arg Lys Asn Lys
705                 710                 715                 720

His Arg Asp Leu Ile His Arg Arg Gly Asp Ser Thr Leu Arg Arg
                725                 730                 735

Phe Arg Glu His Arg Arg Gln Leu Pro Leu Ser Ala Arg Arg Ile Asp
                740                 745                 750

Pro Gln Arg Trp Ala Ala Leu Leu Glu Lys Ala Lys Lys Asn Ser Val
    755                 760                 765

Pro Lys Lys Gln Glu Asn Thr Thr Val Lys Pro Val Pro Leu Ala Val
770                 775                 780

Pro Leu Val Glu Leu Thr Asp Glu Glu Lys Asp Ala Ser Gly Met Ile
785                 790                 795                 800

Pro Pro Asp Glu Glu Phe Met Val Leu Lys Thr Lys Ala Ser Gly Val
                805                 810                 815

Pro Gly Arg Ser Pro Thr Ala Asp Ser Gly Pro Val Asn His Gly Phe
            820                 825                 830

Met Thr Ser Ile Ala Ser Gly Thr Glu Val Ser Thr Val Asn Pro Gln
                835                 840                 845

Thr Leu Gln Ser Glu His Leu Pro Asp Phe Lys Leu Phe Ser Val Thr
    850                 855                 860

Asn Gly Thr Ala Val Thr Lys Ser Met Asn Pro Ser Ile Ala Ser Lys
865                 870                 875                 880

Ile Glu Asp Thr Thr Asn Gln Asn Pro Ile Ile Phe Pro Ser Val
                885                 890                 895

Ala Glu Ile Arg Asp Ser Ala Gln Ala Gly Arg Ala Ser Ser Gln Ser
            900                 905                 910

Ala His Pro Val Thr Gly Gly Asn Met Ala Thr Tyr Gly His Thr Asn
    915                 920                 925

Thr Tyr Ser Ser Phe Thr Ser Lys Ala Ser Thr Val Leu Gln Pro Ile
    930                 935                 940

Asn Pro Thr Glu Ser Tyr Gly Pro Gln Ile Pro Ile Thr Gly Val Ser
945                 950                 955                 960

Arg Pro Ser Ser Ser Asp Ile Ser Ser His Thr Thr Ala Asp Pro Ser
                965                 970                 975

Phe Ser His Pro Ser Gly Ser His Thr Thr Ala Ser Ser Leu Phe
            980                 985                 990

His Ile Pro Arg Asn Asn Asn Thr Gly Asn Phe Pro Leu Ser Arg His
    995                 1000                1005

Leu Gly Arg Glu Arg Thr Ile Trp Ser Arg Gly Arg Val Lys Asn
    1010                1015                1020

Pro His Arg Thr Pro Val Leu Arg Arg His Arg His Arg Thr Val

-continued

```
            1025              1030              1035
Arg Pro Ala Ile Lys Gly Pro Ala Asn Lys Asn Val Ser Gln Val
        1040              1045              1050
Pro Ala Thr Glu Tyr Pro Gly Met Cys His Thr Cys Pro Ser Ala
        1055              1060              1065
Glu Gly Leu Thr Val Ala Thr Ala Ala Leu Ser Val Pro Ser Ser
        1070              1075              1080
Ser His Ser Ala Leu Pro Lys Thr Asn Asn Val Gly Val Ile Ala
        1085              1090              1095
Glu Glu Ser Thr Thr Val Val Lys Lys Pro Leu Leu Leu Phe Lys
        1100              1105              1110
Asp Lys Gln Asn Val Asp Ile Glu Ile Ile Thr Thr Thr Thr Lys
        1115              1120              1125
Tyr Ser Gly Gly Glu Ser Asn His Val Ile Pro Thr Glu Ala Ser
        1130              1135              1140
Met Thr Ser Ala Pro Thr Ser Val Ser Leu Gly Lys Ser Pro Val
        1145              1150              1155
Asp Asn Ser Gly His Leu Ser Met Pro Gly Thr Ile Gln Thr Gly
        1160              1165              1170
Lys Asp Ser Val Glu Thr Thr Pro Leu Pro Ser Pro Leu Ser Thr
        1175              1180              1185
Pro Ser Ile Pro Thr Ser Thr Lys Phe Ser Lys Arg Lys Thr Pro
        1190              1195              1200
Leu His Gln Ile Phe Val Asn Asn Gln Lys Lys Glu Gly Met Leu
        1205              1210              1215
Lys Asn Pro Tyr Gln Phe Gly Leu Gln Lys Asn Pro Ala Ala Lys
        1220              1225              1230
Leu Pro Lys Ile Ala Pro Leu Leu Pro Thr Gly Gln Ser Ser Pro
        1235              1240              1245
Ser Asp Ser Thr Thr Leu Leu Thr Ser Pro Pro Pro Ala Leu Ser
        1250              1255              1260
Thr Thr Met Ala Ala Thr Gln Asn Lys Gly Thr Glu Val Val Ser
        1265              1270              1275
Gly Ala Arg Ser Leu Ser Ala Gly Lys Lys Gln Pro Phe Thr Asn
        1280              1285              1290
Ser Ser Pro Val Leu Pro Ser Thr Ile Ser Lys Arg Ser Asn Thr
        1295              1300              1305
Leu Asn Phe Leu Ser Thr Glu Thr Pro Thr Val Thr Ser Pro Thr
        1310              1315              1320
Ala Thr Ala Ser Val Ile Met Ser Glu Thr Gln Arg Thr Arg Ser
        1325              1330              1335
Lys Glu Ala Lys Asp Gln Ile Lys Gly Pro Arg Lys Asn Arg Asn
        1340              1345              1350
Asn Ala Asn Thr Thr Pro Arg Gln Val Ser Gly Tyr Ser Ala Tyr
        1355              1360              1365
Ser Ala Leu Thr Thr Ala Asp Thr Pro Leu Ala Phe Ser His Ser
        1370              1375              1380
Pro Arg Gln Asp Asp Gly Gly Asn Val Ser Ala Val Ala Tyr His
        1385              1390              1395
Ser Thr Thr Ser Leu Leu Ala Ile Thr Glu Leu Phe Glu Lys Tyr
        1400              1405              1410
Thr Gln Thr Leu Gly Asn Thr Thr Ala Leu Glu Thr Thr Leu Leu
        1415              1420              1425
```

```
Ser Lys Ser Gln Glu Ser Thr Thr Val Lys Arg Ala Ser Asp Thr
    1430                1435                1440
Pro Pro Pro Leu Leu Ser Ser Gly Ala Pro Val Pro Thr Pro
1445                1450                1455
Ser Pro Pro Pro Phe Thr Lys Gly Val Val Thr Asp Ser Lys Val
    1460                1465                1470
Thr Ser Ala Phe Gln Met Thr Ser Asn Arg Val Val Thr Ile Tyr
    1475                1480                1485
Glu Ser Ser Arg His Asn Thr Asp Leu Gln Gln Pro Ser Ala Glu
    1490                1495                1500
Ala Ser Pro Asn Pro Glu Ile Ile Thr Gly Thr Thr Asp Ser Pro
    1505                1510                1515
Ser Asn Leu Phe Pro Ser Thr Ser Val Pro Ala Leu Arg Val Asp
    1520                1525                1530
Lys Pro Gln Asn Ser Lys Trp Lys Pro Ser Pro Trp Pro Glu His
    1535                1540                1545
Lys Tyr Gln Leu Lys Ser Tyr Ser Glu Thr Ile Glu Lys Gly Lys
    1550                1555                1560
Arg Pro Ala Val Ser Met Ser Pro His Leu Ser Leu Pro Glu Ala
    1565                1570                1575
Ser Thr His Ala Ser His Trp Asn Thr Gln Lys His Ala Glu Lys
    1580                1585                1590
Ser Val Phe Asp Lys Lys Pro Gly Gln Asn Pro Thr Ser Lys His
    1595                1600                1605
Leu Pro Tyr Val Ser Leu Pro Lys Thr Leu Leu Lys Lys Pro Arg
    1610                1615                1620
Ile Ile Gly Gly Lys Ala Ala Ser Phe Thr Val Pro Ala Asn Ser
    1625                1630                1635
Asp Val Phe Leu Pro Cys Glu Ala Val Gly Asp Pro Leu Pro Ile
    1640                1645                1650
Ile His Trp Thr Arg Val Ser Ser Gly Xaa Glu Ile Ser Gln Gly
    1655                1660                1665
Thr Gln Lys Ser Arg Phe His Val Leu Pro Asn Gly Thr Leu Ser
    1670                1675                1680
Ile Gln Arg Val Ser Ile Gln Asp Arg Gly Gln Tyr Leu Cys Ser
    1685                1690                1695
Ala Phe Asn Pro Leu Gly Val Asp His Phe His Val Ser Leu Ser
    1700                1705                1710
Val Val Phe Tyr Pro Ala Arg Ile Leu Asp Arg His Val Lys Glu
    1715                1720                1725
Ile Thr Val His Phe Gly Ser Thr Val Glu Leu Lys Cys Arg Val
    1730                1735                1740
Glu Gly Met Pro Arg Pro Thr Val Ser Trp Ile Leu Ala Asn Gln
    1745                1750                1755
Thr Val Val Ser Glu Thr Ala Lys Gly Ser Arg Lys Val Trp Val
    1760                1765                1770
Thr Pro Asp Gly Thr Leu Ile Ile Tyr Asn Leu Ser Leu Tyr Asp
    1775                1780                1785
Arg Gly Phe Tyr Lys Cys Val Ala Ser Asn Pro Ser Gly Gln Asp
    1790                1795                1800
Ser Leu Leu Val Lys Ile Gln Val Ile Thr Ala Pro Pro Val Ile
    1805                1810                1815
```

-continued

| | | | | | | | | | | |
|---|---|---|---|---|---|---|---|---|---|---|
| Ile | Glu | Gln | Lys | Arg | Gln | Ala | Ile | Val | Gly | Val | Leu | Gly | Gly | Ser |
| | 1820 | | | | 1825 | | | | 1830 | |
| Leu | Lys | Leu | Pro | Cys | Thr | Ala | Lys | Gly | Thr | Pro | Gln | Pro | Ser | Val |
| | 1835 | | | | 1840 | | | | 1845 | |
| His | Trp | Val | Leu | Tyr | Asp | Gly | Thr | Glu | Leu | Lys | Pro | Leu | Gln | Leu |
| | 1850 | | | | 1855 | | | | 1860 | |
| Thr | His | Ser | Arg | Phe | Phe | Leu | Tyr | Pro | Asn | Gly | Thr | Leu | Tyr | Ile |
| | 1865 | | | | 1870 | | | | 1875 | |
| Arg | Ser | Ile | Ala | Pro | Ser | Val | Arg | Gly | Thr | Tyr | Glu | Cys | Ile | Ala |
| | 1880 | | | | 1885 | | | | 1890 | |
| Thr | Ser | Ser | Ser | Gly | Ser | Glu | Arg | Arg | Val | Val | Ile | Leu | Thr | Val |
| | 1895 | | | | 1900 | | | | 1905 | |
| Glu | Glu | Gly | Glu | Thr | Ile | Pro | Arg | Ile | Glu | Thr | Ala | Ser | Gln | Lys |
| | 1910 | | | | 1915 | | | | 1920 | |
| Trp | Thr | Glu | Val | Asn | Leu | Gly | Glu | Lys | Leu | Leu | Leu | Asn | Cys | Ser |
| | 1925 | | | | 1930 | | | | 1935 | |
| Ala | Thr | Gly | Asp | Pro | Lys | Pro | Arg | Ile | Ile | Trp | Arg | Leu | Pro | Ser |
| | 1940 | | | | 1945 | | | | 1950 | |
| Lys | Ala | Val | Ile | Asp | Gln | Trp | His | Arg | Met | Gly | Ser | Arg | Ile | His |
| | 1955 | | | | 1960 | | | | 1965 | |
| Val | Tyr | Pro | Asn | Gly | Ser | Leu | Val | Val | Gly | Ser | Val | Thr | Glu | Lys |
| | 1970 | | | | 1975 | | | | 1980 | |
| Asp | Ala | Gly | Asp | Tyr | Leu | Cys | Val | Ala | Arg | Asn | Lys | Met | Gly | Asp |
| | 1985 | | | | 1990 | | | | 1995 | |
| Asp | Leu | Val | Leu | Met | His | Val | Arg | Leu | Arg | Leu | Thr | Pro | Ala | Lys |
| | 2000 | | | | 2005 | | | | 2010 | |
| Ile | Glu | Gln | Lys | Gln | Tyr | Phe | Lys | Lys | Gln | Val | Leu | His | Gly | Lys |
| | 2015 | | | | 2020 | | | | 2025 | |
| Asp | Phe | Gln | Val | Asp | Cys | Lys | Ala | Ser | Gly | Ser | Pro | Val | Pro | Glu |
| | 2030 | | | | 2035 | | | | 2040 | |
| Val | Ser | Trp | Ser | Leu | Pro | Asp | Gly | Thr | Val | Leu | Asn | Asn | Val | Ala |
| | 2045 | | | | 2050 | | | | 2055 | |
| Gln | Ala | Asp | Asp | Ser | Gly | Tyr | Arg | Thr | Lys | Arg | Tyr | Thr | Leu | Phe |
| | 2060 | | | | 2065 | | | | 2070 | |
| His | Asn | Gly | Thr | Leu | Tyr | Phe | Asn | Asn | Val | Gly | Met | Ala | Glu | Glu |
| | 2075 | | | | 2080 | | | | 2085 | |
| Gly | Asp | Tyr | Ile | Cys | Ser | Ala | Gln | Asn | Thr | Leu | Gly | Lys | Asp | Glu |
| | 2090 | | | | 2095 | | | | 2100 | |
| Met | Lys | Val | His | Leu | Thr | Val | Leu | Thr | Ala | Ile | Pro | Arg | Ile | Arg |
| | 2105 | | | | 2110 | | | | 2115 | |
| Gln | Ser | Tyr | Lys | Thr | Thr | Met | Arg | Leu | Arg | Ala | Gly | Glu | Thr | Ala |
| | 2120 | | | | 2125 | | | | 2130 | |
| Val | Leu | Asp | Cys | Glu | Val | Thr | Gly | Glu | Pro | Lys | Pro | Asn | Val | Phe |
| | 2135 | | | | 2140 | | | | 2145 | |
| Trp | Leu | Leu | Pro | Ser | Asn | Asn | Val | Ile | Ser | Phe | Ser | Asn | Asp | Arg |
| | 2150 | | | | 2155 | | | | 2160 | |
| Phe | Thr | Phe | His | Ala | Asn | Arg | Thr | Leu | Ser | Ile | His | Lys | Val | Lys |
| | 2165 | | | | 2170 | | | | 2175 | |
| Pro | Leu | Asp | Ser | Gly | Asp | Tyr | Val | Cys | Val | Ala | Gln | Asn | Pro | Ser |
| | 2180 | | | | 2185 | | | | 2190 | |
| Gly | Asp | Asp | Thr | Lys | Thr | Tyr | Lys | Leu | Asp | Ile | Val | Ser | Lys | Pro |
| | 2195 | | | | 2200 | | | | 2205 | |
| Pro | Leu | Ile | Asn | Gly | Leu | Tyr | Ala | Asn | Lys | Thr | Val | Ile | Lys | Ala |

-continued

```
            2210                2215                2220

Thr Ala Ile Arg His Ser Lys Lys Tyr Phe Asp Cys Arg Ala Asp
            2225                2230                2235

Gly Ile Pro Ser Ser Gln Val Thr Trp Ile Met Pro Gly Asn Ile
            2240                2245                2250

Phe Leu Pro Ala Pro Tyr Phe Gly Ser Arg Val Thr Val His Pro
            2255                2260                2265

Asn Gly Thr Leu Glu Met Arg Asn Ile Arg Leu Ser Asp Ser Ala
            2270                2275                2280

Asp Phe Thr Cys Val Val Arg Ser Glu Gly Gly Glu Ser Val Leu
            2285                2290                2295

Val Val Gln Leu Glu Val Leu Glu Met Leu Arg Arg Pro Thr Phe
            2300                2305                2310

Arg Asn Pro Phe Asn Glu Lys Val Ile Ala Gln Ala Gly Lys Pro
            2315                2320                2325

Val Ala Leu Asn Cys Ser Val Asp Gly Asn Pro Pro Pro Glu Ile
            2330                2335                2340

Thr Trp Ile Leu Pro Asp Gly Thr Gln Phe Ala Asn Arg Pro His
            2345                2350                2355

Asn Ser Pro Tyr Leu Met Ala Gly Asn Gly Ser Leu Ile Leu Tyr
            2360                2365                2370

Lys Ala Thr Arg Asn Lys Ser Gly Lys Tyr Arg Cys Ala Ala Arg
            2375                2380                2385

Asn Lys Val Gly Tyr Ile Glu Lys Leu Ile Leu Leu Glu Ile Gly
            2390                2395                2400

Gln Lys Pro Val Ile Leu Thr Tyr Glu Pro Gly Met Val Lys Ser
            2405                2410                2415

Val Ser Gly Glu Pro Leu Ser Leu His Cys Val Ser Asp Gly Ile
            2420                2425                2430

Pro Lys Pro Asn Val Lys Trp Thr Thr Pro Gly Gly His Val Ile
            2435                2440                2445

Asp Arg Pro Gln Val Asp Gly Lys Tyr Ile Leu His Glu Asn Gly
            2450                2455                2460

Thr Leu Val Ile Lys Ala Thr Thr Ala His Asp Gln Gly Asn Tyr
            2465                2470                2475

Ile Cys Arg Ala Gln Asn Ser Val Gly Gln Ala Val Ile Ser Val
            2480                2485                2490

Ser Val Met Val Val Ala Tyr Pro Pro Arg Ile Ile Asn Tyr Leu
            2495                2500                2505

Pro Arg Asn Met Leu Arg Arg Thr Gly Glu Ala Met Gln Leu His
            2510                2515                2520

Cys Val Ala Leu Gly Ile Pro Lys Pro Lys Val Thr Trp Glu Thr
            2525                2530                2535

Pro Arg His Ser Leu Leu Ser Lys Ala Thr Ala Arg Lys Pro His
            2540                2545                2550

Arg Ser Glu Met Leu His Pro Gln Gly Thr Leu Val Ile Gln Asn
            2555                2560                2565

Leu Gln Thr Ser Asp Ser Gly Val Tyr Lys Cys Arg Ala Gln Asn
            2570                2575                2580

Leu Leu Gly Thr Asp Tyr Ala Thr Thr Tyr Ile Gln Val Leu
            2585                2590                2595
```

<210> SEQ ID NO 14

-continued

```
<211> LENGTH: 2586
<212> TYPE: PRT
<213> ORGANISM: Homo sapiens

<400> SEQUENCE: 14

Met Lys Val Lys Gly Arg Gly Ile Thr Cys Leu Leu Val Ser Phe Ala
1               5                   10                  15

Val Ile Cys Leu Val Ala Thr Pro Gly Gly Lys Ala Cys Pro Arg Arg
            20                  25                  30

Cys Ala Cys Tyr Met Pro Thr Glu Val His Cys Thr Phe Arg Tyr Leu
        35                  40                  45

Thr Ser Ile Pro Asp Ser Ile Pro Pro Asn Val Glu Arg Ile Asn Leu
    50                  55                  60

Gly Tyr Asn Ser Leu Val Arg Leu Met Glu Thr Asp Phe Ser Gly Leu
65                  70                  75                  80

Thr Lys Leu Glu Leu Leu Met Leu His Ser Asn Gly Ile His Thr Ile
                85                  90                  95

Pro Asp Lys Thr Phe Ser Asp Leu Gln Ala Leu Gln Val Leu Lys Met
            100                 105                 110

Ser Tyr Asn Lys Val Arg Lys Leu Gln Lys Asp Thr Phe Tyr Gly Leu
        115                 120                 125

Arg Ser Leu Thr Arg Leu His Met Asp His Asn Asn Ile Glu Phe Ile
130                 135                 140

Asn Pro Glu Val Phe Tyr Gly Leu Asn Phe Leu Arg Leu Val His Leu
145                 150                 155                 160

Glu Gly Asn Gln Leu Thr Lys Leu His Pro Asp Thr Phe Val Ser Leu
                165                 170                 175

Ser Tyr Leu Gln Ile Phe Lys Ile Ser Phe Ile Lys Phe Leu Tyr Leu
            180                 185                 190

Ser Asp Asn Phe Leu Thr Ser Leu Pro Gln Glu Met Val Ser Tyr Met
        195                 200                 205

Pro Asp Leu Asp Ser Leu Tyr Leu His Gly Asn Pro Trp Thr Cys Asp
    210                 215                 220

Cys His Leu Lys Trp Leu Ser Asp Trp Ile Gln Pro Asp Val Ile Lys
225                 230                 235                 240

Cys Lys Lys Asp Arg Ser Pro Ser Ser Ala Gln Gln Cys Pro Leu Cys
                245                 250                 255

Met Asn Pro Arg Thr Ser Lys Gly Lys Pro Leu Ala Met Val Ser Ala
            260                 265                 270

Ala Ala Phe Gln Cys Ala Lys Pro Thr Ile Asp Ser Ser Leu Lys Ser
        275                 280                 285

Lys Ser Leu Thr Ile Leu Glu Asp Ser Ser Ala Phe Ile Ser Pro
    290                 295                 300

Gln Gly Phe Met Ala Pro Phe Gly Ser Leu Thr Leu Asn Met Thr Asp
305                 310                 315                 320

Gln Ser Gly Asn Glu Ala Asn Met Val Cys Ser Ile Gln Lys Pro Ser
                325                 330                 335

Arg Thr Ser Pro Ile Ala Phe Thr Glu Asn Asp Tyr Ile Val Leu
            340                 345                 350

Asn Thr Ser Phe Ser Thr Phe Leu Val Cys Asn Ile Asp Tyr Gly His
        355                 360                 365

Ile Gln Pro Val Trp Gln Ile Leu Ala Leu Tyr Ser Asp Ser Pro Leu
    370                 375                 380

Ile Leu Glu Arg Ser His Leu Leu Ser Glu Thr Pro Gln Leu Tyr Tyr
```

```
                385                 390                 395                 400
Lys Tyr Lys Gln Val Ala Pro Lys Pro Glu Asp Ile Phe Thr Asn Ile
                    405                 410                 415
Glu Ala Asp Leu Arg Ala Asp Pro Ser Trp Leu Met Gln Asp Gln Ile
            420                 425                 430
Ser Leu Gln Leu Asn Arg Thr Ala Thr Thr Phe Ser Thr Leu Gln Ile
            435                 440                 445
Gln Tyr Ser Ser Asp Ala Gln Ile Thr Leu Pro Arg Ala Glu Met Arg
        450                 455                 460
Pro Val Lys His Lys Trp Thr Met Ile Ser Arg Asp Asn Asn Thr Lys
465                 470                 475                 480
Leu Glu His Thr Val Leu Val Gly Gly Thr Val Gly Leu Asn Cys Pro
                485                 490                 495
Gly Gln Gly Asp Pro Thr Pro His Val Asp Trp Leu Leu Ala Asp Gly
                500                 505                 510
Ser Lys Val Arg Ala Pro Tyr Val Ser Glu Asp Gly Arg Ile Leu Ile
            515                 520                 525
Asp Lys Ser Gly Lys Leu Glu Leu Gln Met Ala Asp Ser Phe Asp Thr
        530                 535                 540
Gly Val Tyr His Cys Ile Ser Ser Asn Tyr Asp Asp Ala Asp Ile Leu
545                 550                 555                 560
Thr Tyr Arg Ile Thr Val Val Glu Pro Leu Val Glu Ala Tyr Gln Glu
                565                 570                 575
Asn Gly Ile His His Thr Val Phe Ile Gly Glu Thr Leu Asp Leu Pro
                580                 585                 590
Cys His Ser Thr Gly Ile Pro Asp Ala Ser Ile Ser Trp Val Ile Pro
            595                 600                 605
Gly Asn Asn Val Leu Tyr Gln Ser Ser Arg Asp Lys Lys Val Leu Asn
        610                 615                 620
Asn Gly Thr Leu Arg Ile Leu Gln Val Thr Pro Lys Asp Gln Gly Tyr
625                 630                 635                 640
Tyr Arg Cys Val Ala Ala Asn Pro Ser Gly Val Asp Phe Leu Ile Phe
                645                 650                 655
Gln Val Ser Val Lys Met Lys Gly Gln Arg Pro Leu Glu His Asp Gly
                660                 665                 670
Glu Thr Glu Gly Ser Gly Leu Asp Glu Ser Asn Pro Ile Ala His Leu
            675                 680                 685
Lys Glu Pro Pro Gly Ala Gln Leu Arg Thr Ser Ala Leu Met Glu Ala
        690                 695                 700
Glu Val Gly Lys His Thr Ser Ser Thr Ser Lys Arg His Asn Tyr Arg
705                 710                 715                 720
Glu Leu Thr Leu Gln Arg Arg Gly Asp Ser Thr His Arg Arg Phe Arg
                725                 730                 735
Glu Asn Arg Arg His Phe Pro Pro Ser Ala Arg Ile Asp Pro Gln
                740                 745                 750
His Trp Ala Ala Leu Leu Glu Lys Ala Lys Asn Ala Met Pro Asp
            755                 760                 765
Lys Arg Glu Asn Thr Thr Val Ser Pro Pro Val Val Thr Gln Leu
        770                 775                 780
Pro Asn Ile Pro Gly Glu Asp Asp Ser Ser Gly Met Leu Ala Leu
785                 790                 795                 800
His Glu Glu Phe Met Val Pro Ala Thr Lys Ala Leu Asn Leu Pro Ala
                805                 810                 815
```

```
Arg Thr Val Thr Ala Asp Ser Arg Thr Ile Ser Asp Ser Pro Met Thr
            820                 825                 830

Asn Ile Asn Tyr Gly Thr Glu Phe Ser Pro Val Val Asn Ser Gln Ile
            835                 840                 845

Leu Pro Pro Glu Glu Pro Thr Asp Phe Lys Leu Ser Thr Ala Ile Lys
            850                 855                 860

Thr Thr Ala Met Ser Lys Asn Ile Asn Pro Thr Met Ser Ser Gln Ile
865                 870                 875                 880

Gln Gly Thr Thr Asn Gln His Ser Ser Thr Val Phe Pro Leu Leu Leu
                885                 890                 895

Gly Ala Thr Glu Phe Gln Asp Ser Asp Gln Met Gly Arg Gly Arg Glu
            900                 905                 910

His Phe Gln Ser Arg Pro Pro Ile Thr Val Arg Thr Met Ile Lys Asp
            915                 920                 925

Val Asn Val Lys Met Leu Ser Ser Thr Thr Asn Lys Leu Leu Leu Glu
            930                 935                 940

Ser Val Asn Thr Thr Asn Ser His Gln Thr Ser Val Arg Glu Val Ser
945                 950                 955                 960

Glu Pro Arg His Asn His Phe Tyr Ser His Thr Thr Gln Ile Leu Ser
                965                 970                 975

Thr Ser Thr Phe Pro Ser Asp Pro His Thr Ala Ala His Ser Gln Phe
                980                 985                 990

Pro Ile Pro Arg Asn Ser Thr Val  Asn Ile Pro Leu Phe  Arg Arg Phe
            995                 1000                1005

Gly Arg  Gln Arg Lys Ile Gly  Gly Arg Gly Arg Ile  Ile Ser Pro
1010                 1015                 1020

Tyr Arg  Thr Pro Val Leu Arg  Arg His Arg Tyr Ser  Ile Phe Arg
1025                 1030                 1035

Ser Thr  Thr Arg Gly Ser Ser  Glu Lys Ser Thr Thr  Ala Phe Ser
1040                 1045                 1050

Ala Thr  Val Leu Asn Val Thr  Cys Leu Ser Cys Leu  Pro Arg Glu
1055                 1060                 1065

Arg Leu  Thr Thr Ala Thr Ala  Ala Leu Ser Phe Pro  Ser Ala Ala
1070                 1075                 1080

Pro Ile  Thr Phe Pro Lys Ala  Asp Ile Ala Arg Val  Pro Ser Glu
1085                 1090                 1095

Glu Ser  Thr Thr Leu Val Gln  Asn Pro Leu Leu Leu  Leu Glu Asn
1100                 1105                 1110

Lys Pro  Ser Val Glu Lys Thr  Thr Pro Thr Ile Lys  Tyr Phe Arg
1115                 1120                 1125

Thr Glu  Ile Ser Gln Val Thr  Pro Thr Gly Ala Val  Met Thr Tyr
1130                 1135                 1140

Ala Pro  Thr Ser Ile Pro Met  Glu Lys Thr His Lys  Val Asn Ala
1145                 1150                 1155

Ser Tyr  Pro Arg Val Ser Ser  Thr Asn Glu Ala Lys  Arg Asp Ser
1160                 1165                 1170

Val Ile  Thr Ser Ser Leu Ser  Gly Ala Ile Thr Lys  Pro Pro Met
1175                 1180                 1185

Thr Ile  Ile Ala Ile Thr Arg  Phe Ser Arg Arg Lys  Ile Pro Trp
1190                 1195                 1200

Gln Gln  Asn Phe Val Asn Asn  His Asn Pro Lys Gly  Arg Leu Arg
1205                 1210                 1215
```

```
Asn Gln His Lys Val Ser Leu Gln Lys Ser Thr Ala Val Met Leu
    1220            1225            1230

Pro Lys Thr Ser Pro Ala Leu Pro Gln Arg Gln Ser Ser Pro Phe
    1235            1240            1245

His Phe Thr Thr Leu Ser Thr Ser Val Met Gln Ile Pro Ser Asn
    1250            1255            1260

Thr Leu Thr Thr Ala His His Thr Thr Thr Lys Thr His Asn Pro
    1265            1270            1275

Gly Ser Leu Pro Thr Lys Lys Glu Leu Pro Phe Pro Pro Leu Asn
    1280            1285            1290

Pro Met Leu Pro Ser Ile Ile Ser Lys Asp Ser Ser Thr Lys Ser
    1295            1300            1305

Ile Ile Ser Thr Gln Thr Ala Ile Pro Ala Thr Thr Pro Thr Phe
    1310            1315            1320

Pro Ala Ser Val Ile Thr Tyr Glu Thr Gln Thr Glu Arg Ser Arg
    1325            1330            1335

Ala Gln Thr Ile Gln Arg Glu Gln Glu Pro Gln Lys Lys Asn Arg
    1340            1345            1350

Thr Asp Pro Asn Ile Ser Pro Asp Gln Ser Ser Gly Phe Thr Thr
    1355            1360            1365

Pro Thr Ala Met Thr Pro Pro Ala Leu Ala Phe Thr His Ser Pro
    1370            1375            1380

Pro Glu Asn Thr Thr Gly Ile Ser Ser Thr Ile Ser Phe His Ser
    1385            1390            1395

Arg Thr Leu Asn Leu Thr Asp Val Ile Glu Glu Leu Ala Gln Ala
    1400            1405            1410

Ser Thr Gln Thr Leu Lys Ser Thr Ile Ala Ser Glu Thr Thr Leu
    1415            1420            1425

Ser Ser Lys Ser His Gln Ser Thr Thr Thr Arg Lys Ala Ser Leu
    1430            1435            1440

Asp Thr Pro Ile Pro Pro Phe Leu Ser Ser Ala Thr Leu Met
    1445            1450            1455

Pro Val Pro Ile Ser Pro Pro Phe Thr Gln Arg Ala Val Thr Asp
    1460            1465            1470

Thr Arg Gly Asp Ser His Phe Arg Leu Met Thr Asn Thr Val Val
    1475            1480            1485

Lys Leu His Glu Ser Ser Arg His Asn Leu Gln Met Pro Ser Ser
    1490            1495            1500

Gln Leu Glu Pro Leu Thr Ser Ser Thr Ser Asn Leu Leu His Ser
    1505            1510            1515

Thr Pro Met Pro Ala Leu Thr Thr Val Lys Ser Gln Asn Ser Lys
    1520            1525            1530

Leu Thr Pro Ser Pro Trp Ala Glu Tyr Gln Phe Trp His Lys Pro
    1535            1540            1545

Tyr Ser Asp Ile Ala Glu Lys Gly Lys Lys Pro Glu Val Ser Met
    1550            1555            1560

Leu Ala Thr Thr Gly Leu Ser Glu Ala Thr Thr Leu Val Ser Asp
    1565            1570            1575

Trp Asp Gly Gln Lys Asn Thr Lys Lys Ser Asp Phe Asp Lys Lys
    1580            1585            1590

Pro Val Gln Glu Ala Thr Thr Ser Lys Leu Leu Pro Phe Asp Ser
    1595            1600            1605

Leu Ser Arg Tyr Ile Phe Glu Lys Pro Arg Ile Val Gly Gly Lys
```

-continued

```
             1610                1615                1620
Ala Ala Ser Phe Thr Ile Pro Ala Asn Ser Asp Ala Phe Leu Pro
        1625                1630                1635
Cys Glu Ala Val Gly Asn Pro Leu Pro Thr Ile His Trp Thr Arg
        1640                1645                1650
Val Ser Gly Leu Asp Leu Ser Arg Gly Asn Gln Asn Ser Arg Val
        1655                1660                1665
Gln Val Leu Pro Asn Gly Thr Leu Ser Ile Gln Arg Val Glu Ile
        1670                1675                1680
Gln Asp Arg Gly Gln Tyr Leu Cys Ser Ala Ser Asn Leu Phe Gly
        1685                1690                1695
Thr Asp His Leu His Val Thr Leu Ser Val Val Ser Tyr Pro Pro
        1700                1705                1710
Arg Ile Leu Glu Arg Arg Thr Lys Glu Ile Thr Val His Ser Gly
        1715                1720                1725
Ser Thr Val Glu Leu Lys Cys Arg Ala Glu Gly Arg Pro Ser Pro
        1730                1735                1740
Thr Val Thr Trp Ile Leu Ala Asn Gln Thr Val Val Ser Glu Ser
        1745                1750                1755
Ser Gln Gly Ser Arg Gln Ala Val Val Thr Val Asp Gly Thr Leu
        1760                1765                1770
Val Leu His Asn Leu Ser Ile Tyr Asp Arg Gly Phe Tyr Lys Cys
        1775                1780                1785
Val Ala Ser Asn Pro Gly Gly Gln Asp Ser Leu Leu Val Lys Ile
        1790                1795                1800
Gln Val Ile Ala Ala Pro Pro Val Ile Leu Glu Gln Arg Arg Gln
        1805                1810                1815
Val Ile Val Gly Thr Trp Gly Glu Ser Leu Lys Leu Pro Cys Thr
        1820                1825                1830
Ala Lys Gly Thr Pro Gln Pro Ser Val Tyr Trp Val Leu Ser Asp
        1835                1840                1845
Gly Thr Glu Val Lys Pro Leu Gln Phe Thr Asn Ser Lys Leu Phe
        1850                1855                1860
Leu Phe Ser Asn Gly Thr Leu Tyr Ile Arg Asn Leu Ala Ser Ser
        1865                1870                1875
Asp Arg Gly Thr Tyr Glu Cys Ile Ala Thr Ser Ser Thr Gly Ser
        1880                1885                1890
Glu Arg Arg Val Val Met Leu Thr Met Glu Glu Arg Val Thr Ser
        1895                1900                1905
Pro Arg Ile Glu Ala Ala Ser Gln Lys Arg Thr Glu Val Asn Phe
        1910                1915                1920
Gly Asp Lys Leu Leu Leu Asn Cys Ser Ala Thr Gly Glu Pro Lys
        1925                1930                1935
Pro Gln Ile Met Trp Arg Leu Pro Ser Lys Ala Val Val Asp Gln
        1940                1945                1950
Gly Ser Trp Ile His Val Tyr Pro Asn Gly Ser Leu Phe Ile Gly
        1955                1960                1965
Ser Val Thr Glu Lys Asp Ser Gly Val Tyr Leu Cys Val Ala Arg
        1970                1975                1980
Asn Lys Met Gly Asp Asp Leu Ile Leu Met His Val Ser Leu Arg
        1985                1990                1995
Leu Lys Pro Ala Lys Ile Asp His Lys Gln Tyr Phe Arg Lys Gln
        2000                2005                2010
```

-continued

```
Val Leu His Gly Lys Asp Phe Gln Val Asp Cys Lys Ala Ser Gly
    2015                2020                2025

Ser Pro Val Pro Glu Ile Ser Trp Ser Leu Pro Asp Gly Thr Met
    2030                2035                2040

Ile Asn Asn Ala Met Gln Ala Asp Asp Ser Gly His Arg Thr Arg
    2045                2050                2055

Arg Tyr Thr Leu Phe Asn Asn Gly Thr Leu Tyr Phe Asn Lys Val
    2060                2065                2070

Gly Val Ala Glu Gly Asp Tyr Thr Cys Tyr Ala Gln Asn Thr
    2075                2080                2085

Leu Gly Lys Asp Glu Met Lys Val His Leu Thr Val Ile Thr Ala
    2090                2095                2100

Ala Pro Arg Ile Arg Gln Ser Asn Lys Thr Asn Lys Arg Ile Lys
    2105                2110                2115

Ala Gly Asp Thr Ala Val Leu Asp Cys Glu Val Thr Gly Asp Pro
    2120                2125                2130

Lys Pro Lys Ile Phe Trp Leu Leu Pro Ser Asn Asp Met Ile Ser
    2135                2140                2145

Phe Ser Ile Asp Arg Tyr Thr Phe His Ala Asn Gly Ser Leu Thr
    2150                2155                2160

Ile Asn Lys Val Lys Leu Leu Asp Ser Gly Glu Tyr Val Cys Val
    2165                2170                2175

Ala Arg Asn Pro Ser Gly Asp Asp Thr Lys Met Tyr Lys Leu Asp
    2180                2185                2190

Val Val Ser Lys Pro Pro Leu Ile Asn Gly Leu Tyr Thr Asn Arg
    2195                2200                2205

Thr Val Ile Lys Ala Thr Ala Val Arg His Ser Lys Lys His Phe
    2210                2215                2220

Asp Cys Arg Ala Glu Gly Thr Pro Ser Pro Glu Val Met Trp Ile
    2225                2230                2235

Met Pro Asp Asn Ile Phe Leu Thr Ala Pro Tyr Tyr Gly Ser Arg
    2240                2245                2250

Ile Thr Val His Lys Asn Gly Thr Leu Glu Ile Arg Asn Val Arg
    2255                2260                2265

Leu Ser Asp Ser Ala Asp Phe Ile Cys Val Ala Arg Asn Glu Gly
    2270                2275                2280

Gly Glu Ser Val Leu Val Val Gln Leu Glu Val Leu Glu Met Leu
    2285                2290                2295

Arg Arg Pro Thr Phe Arg Asn Pro Phe Asn Glu Lys Ile Val Ala
    2300                2305                2310

Gln Leu Gly Lys Ser Thr Ala Leu Asn Cys Ser Val Asp Gly Asn
    2315                2320                2325

Pro Pro Pro Glu Ile Ile Trp Ile Leu Pro Asn Gly Thr Arg Phe
    2330                2335                2340

Ser Asn Gly Pro Gln Ser Tyr Gln Tyr Leu Ile Ala Ser Asn Gly
    2345                2350                2355

Ser Phe Ile Ile Ser Lys Thr Thr Arg Glu Asp Ala Gly Lys Tyr
    2360                2365                2370

Arg Cys Ala Ala Arg Asn Lys Val Gly Tyr Ile Glu Lys Leu Val
    2375                2380                2385

Ile Leu Glu Ile Gly Gln Lys Pro Val Ile Leu Thr Tyr Ala Pro
    2390                2395                2400
```

```
Gly Thr Val Lys Gly Ile Ser Gly Glu Ser Leu Ser Leu His Cys
    2405                2410                2415

Val Ser Asp Gly Ile Pro Lys Pro Asn Ile Lys Trp Thr Met Pro
    2420                2425                2430

Ser Gly Tyr Val Val Asp Arg Pro Gln Ile Asn Gly Lys Tyr Ile
    2435                2440                2445

Leu His Asp Asn Gly Thr Leu Val Ile Lys Glu Ala Thr Ala Tyr
    2450                2455                2460

Asp Arg Gly Asn Tyr Ile Cys Lys Ala Gln Asn Ser Val Gly His
    2465                2470                2475

Thr Leu Ile Thr Val Pro Val Met Ile Val Ala Tyr Pro Pro Arg
    2480                2485                2490

Ile Thr Asn Arg Pro Pro Arg Ser Ile Val Thr Arg Thr Gly Ala
    2495                2500                2505

Ala Phe Gln Leu His Cys Val Ala Leu Gly Val Pro Lys Pro Glu
    2510                2515                2520

Ile Thr Trp Glu Met Pro Asp His Ser Leu Leu Ser Thr Ala Ser
    2525                2530                2535

Lys Glu Arg Thr His Gly Ser Glu Gln Leu His Leu Gln Gly Thr
    2540                2545                2550

Leu Val Ile Gln Asn Pro Gln Thr Ser Asp Ser Gly Ile Tyr Lys
    2555                2560                2565

Cys Thr Ala Lys Asn Pro Leu Gly Ser Asp Tyr Ala Ala Thr Tyr
    2570                2575                2580

Ile Gln Val
    2585

<210> SEQ ID NO 15
<211> LENGTH: 236
<212> TYPE: PRT
<213> ORGANISM: Mus musculus
<220> FEATURE:
<221> NAME/KEY: misc_feature
<222> LOCATION: (1)..(236)
<223> OTHER INFORMATION: 'x' can be any amino acid

<400> SEQUENCE: 15

Met Gln Lys Arg Gly Arg Glu Val Ser Cys Leu Leu Ile Ser Leu Thr
1               5                   10                  15

Ala Ile Cys Leu Val Val Thr Pro Gly Ser Arg Val Cys Pro Arg Arg
            20                  25                  30

Cys Ala Cys Tyr Val Pro Thr Glu Val His Cys Thr Phe Arg Asp Leu
        35                  40                  45

Thr Ser Ile Pro Asp Gly Pro Ala Asn Val Glu Arg Val Asn Leu Gly
    50                  55                  60

Tyr Asn Ser Leu Thr Arg Leu Thr Glu Asn Asp Phe Ser Gly Leu Ser
65                  70                  75                  80

Arg Leu Glu Leu Leu Met Leu His Ser Asn Gly Ile His Arg Val Ser
                85                  90                  95

Asp Lys Thr Phe Ser Gly Leu Gln Ser Leu Gln Val Leu Lys Met Ser
            100                 105                 110

Tyr Asn Lys Val Gln Ile Ile Glu Lys Asp Thr Leu Tyr Gly Leu Arg
        115                 120                 125

Ser Leu Thr Arg Leu His Leu Asp His Asn Asn Ile Glu Phe Ile Asn
    130                 135                 140

Pro Glu Ala Phe Tyr Gly Leu Thr Leu Leu Arg Leu Val His Leu Glu
```

```
                145                 150                 155                 160
Gly Asn Arg Leu Thr Lys Leu His Pro Asp Thr Phe Val Ser Leu Ser
                165                 170                 175

Tyr Leu Gln Ile Phe Lys Thr Ser Phe Ile Lys Xaa Leu Tyr Leu Tyr
                180                 185                 190

Asp Asn Phe Thr Ser Leu Pro Lys Glu Met Val Ser Met Pro Asn
                195                 200             205

Leu Glu Ser Leu Tyr Leu His Gly Asn Pro Trp Thr Cys Asp Cys His
    210                 215                 220

Leu Lys Trp Leu Ser Glu Trp Met Gln Gly Asn Pro
225                 230                 235

<210> SEQ ID NO 16
<211> LENGTH: 2587
<212> TYPE: PRT
<213> ORGANISM: homo sapiens

<400> SEQUENCE: 16

Met Lys Val Lys Gly Arg Gly Ile Thr Cys Leu Leu Val Ser Phe Ala
1               5                   10                  15

Val Ile Cys Leu Val Ala Thr Pro Gly Gly Lys Ala Cys Pro Arg Arg
                20                  25                  30

Cys Ala Cys Tyr Met Pro Thr Glu Val His Cys Thr Phe Arg Tyr Leu
            35                  40                  45

Thr Ser Ile Pro Asp Ser Ile Pro Pro Asn Val Glu Arg Ile Asn Leu
    50                  55                  60

Gly Tyr Asn Ser Leu Val Arg Leu Met Glu Thr Asp Phe Ser Gly Leu
65                  70                  75                  80

Thr Lys Leu Glu Leu Leu Met Leu His Ser Asn Gly Ile His Thr Ile
                85                  90                  95

Pro Asp Lys Thr Phe Ser Asp Leu Gln Ala Leu Gln Val Leu Lys Met
                100                 105                 110

Ser Tyr Asn Lys Val Arg Lys Leu Gln Lys Asp Thr Phe Tyr Gly Leu
            115                 120                 125

Arg Ser Leu Thr Arg Leu His Met Asp His Asn Asn Ile Glu Phe Ile
    130                 135                 140

Asn Pro Glu Val Phe Tyr Gly Leu Asn Phe Leu Arg Leu Val His Leu
145                 150                 155                 160

Glu Gly Asn Gln Leu Thr Lys Leu His Pro Asp Thr Phe Val Ser Leu
                165                 170                 175

Ser Tyr Leu Gln Ile Phe Lys Ile Ser Phe Ile Lys Phe Leu Tyr Leu
            180                 185                 190

Ser Asp Asn Phe Leu Thr Ser Leu Pro Gln Glu Met Val Ser Tyr Met
            195                 200                 205

Pro Asp Leu Asp Ser Leu Tyr Leu His Gly Asn Pro Trp Thr Cys Asp
    210                 215                 220

Cys His Leu Lys Trp Leu Ser Asp Trp Ile Gln Pro Asp Val Ile Lys
225                 230                 235                 240

Cys Lys Lys Asp Arg Ser Pro Ser Ser Ala Gln Gln Cys Pro Leu Cys
            245                 250                 255

Met Asn Pro Arg Thr Ser Lys Gly Lys Pro Leu Ala Met Val Ser Ala
                260                 265                 270

Ala Ala Phe Gln Cys Ala Lys Pro Thr Ile Asp Ser Ser Leu Lys Ser
            275                 280                 285
```

```
Lys Ser Leu Thr Ile Leu Glu Asp Ser Ser Ala Phe Ile Ser Pro
290                 295                 300

Gln Gly Phe Met Ala Pro Phe Gly Ser Leu Thr Leu Asn Met Thr Asp
305                 310                 315                 320

Gln Ser Gly Asn Glu Ala Asn Met Val Cys Ser Ile Gln Lys Pro Ser
                325                 330                 335

Arg Thr Ser Pro Ile Ala Phe Thr Glu Glu Asn Asp Tyr Ile Val Leu
            340                 345                 350

Asn Thr Ser Phe Ser Thr Phe Leu Val Cys Asn Ile Asp Tyr Gly His
        355                 360                 365

Ile Gln Pro Val Trp Gln Ile Leu Ala Leu Tyr Ser Asp Ser Pro Leu
370                 375                 380

Ile Leu Glu Arg Ser His Leu Leu Ser Glu Thr Pro Gln Leu Tyr Tyr
385                 390                 395                 400

Lys Tyr Lys Gln Val Ala Pro Lys Pro Glu Asp Ile Phe Thr Asn Ile
                405                 410                 415

Glu Ala Asp Leu Arg Ala Asp Pro Ser Trp Leu Met Gln Asp Gln Ile
            420                 425                 430

Ser Leu Gln Leu Asn Arg Thr Ala Thr Thr Phe Ser Thr Leu Gln Ile
        435                 440                 445

Gln Tyr Ser Ser Asp Ala Gln Ile Thr Leu Pro Arg Ala Glu Met Arg
450                 455                 460

Pro Val Lys His Lys Trp Thr Met Ile Ser Arg Asp Asn Asn Thr Lys
465                 470                 475                 480

Leu Glu His Thr Val Leu Val Gly Gly Thr Val Gly Leu Asn Cys Pro
                485                 490                 495

Gly Gln Gly Asp Pro Thr Pro His Val Asp Trp Leu Leu Ala Asp Gly
            500                 505                 510

Ser Lys Val Arg Ala Pro Tyr Val Ser Glu Asp Gly Arg Ile Leu Ile
        515                 520                 525

Asp Lys Ser Gly Lys Leu Glu Leu Gln Met Ala Asp Ser Phe Asp Thr
530                 535                 540

Gly Val Tyr His Cys Ile Ser Ser Asn Tyr Asp Asp Ala Asp Ile Leu
545                 550                 555                 560

Thr Tyr Arg Ile Thr Val Val Glu Pro Leu Val Glu Ala Tyr Gln Glu
                565                 570                 575

Asn Gly Ile His His Thr Val Phe Ile Gly Glu Thr Leu Asp Leu Pro
            580                 585                 590

Cys His Ser Thr Gly Ile Pro Asp Ala Ser Ile Ser Trp Val Ile Pro
        595                 600                 605

Gly Asn Asn Val Leu Tyr Gln Ser Ser Arg Asp Lys Lys Val Leu Asn
610                 615                 620

Asn Gly Thr Leu Arg Ile Leu Gln Val Thr Pro Lys Asp Gln Gly Tyr
625                 630                 635                 640

Tyr Arg Cys Val Ala Ala Asn Pro Ser Gly Val Asp Phe Leu Ile Phe
                645                 650                 655

Gln Val Ser Val Lys Met Lys Gly Gln Arg Pro Leu Glu His Asp Gly
            660                 665                 670

Glu Thr Glu Gly Ser Gly Leu Asp Glu Ser Asn Pro Ile Ala His Leu
        675                 680                 685

Lys Glu Pro Pro Gly Ala Gln Leu Arg Thr Ser Ala Leu Met Glu Ala
690                 695                 700

Glu Val Gly Lys His Thr Ser Ser Thr Ser Lys Arg His Asn Tyr Arg
```

```
                705                 710                 715                 720
        Glu Leu Thr Leu Gln Arg Arg Gly Asp Ser Thr His Arg Arg Phe Arg
                        725                 730                 735
        Glu Asn Arg Arg His Phe Pro Pro Ser Ala Arg Arg Ile Asp Pro Gln
                        740                 745                 750
        His Trp Ala Ala Leu Leu Glu Lys Ala Lys Lys Asn Ala Met Pro Asp
                        755                 760                 765
        Lys Arg Glu Asn Thr Thr Val Ser Pro Pro Val Val Thr Gln Leu
                    770                 775                 780
        Pro Asn Ile Pro Gly Glu Glu Asp Asp Ser Ser Gly Met Leu Ala Leu
        785                 790                 795                 800
        His Glu Glu Phe Met Val Pro Ala Thr Lys Ala Leu Asn Leu Pro Ala
                                805                 810                 815
        Arg Thr Val Thr Ala Asp Ser Arg Thr Ile Ser Asp Ser Pro Met Thr
                        820                 825                 830
        Asn Ile Asn Tyr Gly Thr Glu Phe Ser Pro Val Val Asn Ser Gln Ile
                        835                 840                 845
        Leu Pro Pro Glu Glu Pro Thr Asp Phe Lys Leu Ser Thr Ala Ile Lys
        850                 855                 860
        Thr Thr Ala Met Ser Lys Asn Ile Asn Pro Thr Met Ser Ser Gln Ile
        865                 870                 875                 880
        Gln Gly Thr Thr Asn Gln His Ser Ser Thr Val Phe Pro Leu Leu Leu
                        885                 890                 895
        Gly Ala Thr Glu Phe Gln Asp Ser Asp Gln Met Gly Arg Gly Arg Glu
                        900                 905                 910
        His Phe Gln Ser Arg Pro Pro Ile Thr Val Arg Thr Met Ile Lys Asp
                        915                 920                 925
        Val Asn Val Lys Met Leu Ser Ser Thr Thr Asn Lys Leu Leu Leu Glu
                930                 935                 940
        Ser Val Asn Thr Thr Asn Ser His Gln Thr Ser Val Arg Glu Val Ser
        945                 950                 955                 960
        Glu Pro Arg His Asn His Phe Tyr Ser His Thr Thr Gln Ile Leu Ser
                        965                 970                 975
        Thr Ser Thr Phe Pro Ser Asp Pro His Thr Ala Ala His Ser Gln Phe
                        980                 985                 990
        Pro Ile Pro Arg Asn Ser Thr Val  Asn Ile Pro Leu Phe  Arg Arg Phe
                        995                 1000                1005
        Gly Arg  Gln Arg Lys Ile Gly  Gly Arg Gly Arg Ile  Ile Ser Pro
            1010                1015                1020
        Tyr Arg  Thr Pro Val Leu Arg  Arg His Arg Tyr Ser  Ile Phe Arg
            1025                1030                1035
        Ser Thr  Thr Arg Gly Ser Ser  Glu Lys Ser Thr Thr  Ala Phe Ser
            1040                1045                1050
        Ala Thr  Val Leu Asn Val Thr  Cys Leu Ser Cys Leu  Pro Arg Glu
            1055                1060                1065
        Arg Leu  Thr Thr Ala Thr Ala  Ala Leu Ser Phe Pro  Ser Ala Ala
            1070                1075                1080
        Pro Ile  Thr Phe Pro Lys Ala  Asp Ile Ala Arg Val  Pro Ser Glu
            1085                1090                1095
        Glu Ser  Thr Thr Leu Val Gln  Asn Pro Leu Leu Leu  Leu Glu Asn
            1100                1105                1110
        Lys Pro  Ser Val Glu Lys Thr  Thr Pro Thr Ile Lys  Tyr Phe Arg
            1115                1120                1125
```

-continued

| | | | | | | | | | | | | | |
|---|---|---|---|---|---|---|---|---|---|---|---|---|---|
|Thr|Glu|Ile|Ser|Gln|Val|Thr|Pro|Thr|Gly|Ala|Val|Met|Thr|Tyr|
| |1130| | | |1135| | | |1140| | | | | |
|Ala|Pro|Thr|Ser|Ile|Pro|Met|Glu|Lys|Thr|His|Lys|Val|Asn|Ala|
| |1145| | | |1150| | | |1155| | | | | |
|Ser|Tyr|Pro|Arg|Val|Ser|Ser|Thr|Asn|Glu|Ala|Lys|Arg|Asp|Ser|
| |1160| | | |1165| | | |1170| | | | | |
|Val|Ile|Thr|Ser|Ser|Leu|Ser|Gly|Ala|Ile|Thr|Lys|Pro|Pro|Met|
| |1175| | | |1180| | | |1185| | | | | |
|Thr|Ile|Ile|Ala|Ile|Thr|Arg|Phe|Ser|Arg|Arg|Lys|Ile|Pro|Trp|
| |1190| | | |1195| | | |1200| | | | | |
|Gln|Gln|Asn|Phe|Val|Asn|Asn|His|Asn|Pro|Lys|Gly|Arg|Leu|Arg|
| |1205| | | |1210| | | |1215| | | | | |
|Asn|Gln|His|Lys|Val|Ser|Leu|Gln|Lys|Ser|Thr|Ala|Val|Met|Leu|
| |1220| | | |1225| | | |1230| | | | | |
|Pro|Lys|Thr|Ser|Pro|Ala|Leu|Pro|Gln|Arg|Gln|Ser|Ser|Pro|Phe|
| |1235| | | |1240| | | |1245| | | | | |
|His|Phe|Thr|Thr|Leu|Ser|Thr|Ser|Val|Met|Gln|Ile|Pro|Ser|Asn|
| |1250| | | |1255| | | |1260| | | | | |
|Thr|Leu|Thr|Thr|Ala|His|His|Thr|Thr|Lys|Thr|His|Asn|Pro|
| |1265| | | |1270| | | |1275| | | | | |
|Gly|Ser|Leu|Pro|Thr|Lys|Lys|Glu|Leu|Pro|Phe|Pro|Pro|Leu|Asn|
| |1280| | | |1285| | | |1290| | | | | |
|Pro|Met|Leu|Pro|Ser|Ile|Ile|Ser|Lys|Asp|Ser|Ser|Thr|Lys|Ser|
| |1295| | | |1300| | | |1305| | | | | |
|Ile|Ile|Ser|Thr|Gln|Thr|Ala|Ile|Pro|Ala|Thr|Thr|Pro|Thr|Phe|
| |1310| | | |1315| | | |1320| | | | | |
|Pro|Ala|Ser|Val|Ile|Thr|Tyr|Glu|Thr|Gln|Thr|Glu|Arg|Ser|Arg|
| |1325| | | |1330| | | |1335| | | | | |
|Ala|Gln|Thr|Ile|Gln|Arg|Glu|Gln|Glu|Pro|Gln|Lys|Lys|Asn|Arg|
| |1340| | | |1345| | | |1350| | | | | |
|Thr|Asp|Pro|Asn|Ile|Ser|Pro|Asp|Gln|Ser|Ser|Gly|Phe|Thr|Thr|
| |1355| | | |1360| | | |1365| | | | | |
|Pro|Thr|Ala|Met|Thr|Pro|Pro|Ala|Leu|Ala|Phe|Thr|His|Ser|Pro|
| |1370| | | |1375| | | |1380| | | | | |
|Pro|Glu|Asn|Thr|Thr|Gly|Ile|Ser|Ser|Thr|Ile|Ser|Phe|His|Ser|
| |1385| | | |1390| | | |1395| | | | | |
|Arg|Thr|Leu|Asn|Leu|Thr|Asp|Val|Ile|Glu|Glu|Leu|Ala|Gln|Ala|
| |1400| | | |1405| | | |1410| | | | | |
|Ser|Thr|Gln|Thr|Leu|Lys|Ser|Thr|Ile|Ala|Ser|Glu|Thr|Thr|Leu|
| |1415| | | |1420| | | |1425| | | | | |
|Ser|Ser|Lys|Ser|His|Gln|Ser|Thr|Thr|Thr|Arg|Lys|Ala|Ser|Leu|
| |1430| | | |1435| | | |1440| | | | | |
|Asp|Thr|Pro|Ile|Pro|Pro|Phe|Leu|Ser|Ser|Ser|Ala|Thr|Leu|Met|
| |1445| | | |1450| | | |1455| | | | | |
|Pro|Val|Pro|Ile|Ser|Pro|Pro|Phe|Thr|Gln|Arg|Ala|Val|Thr|Asp|
| |1460| | | |1465| | | |1470| | | | | |
|Thr|Arg|Gly|Asp|Ser|His|Phe|Arg|Leu|Met|Thr|Asn|Thr|Val|Val|
| |1475| | | |1480| | | |1485| | | | | |
|Lys|Leu|His|Glu|Ser|Ser|Arg|His|Asn|Leu|Gln|Met|Pro|Ser|Ser|
| |1490| | | |1495| | | |1500| | | | | |
|Gln|Leu|Glu|Pro|Leu|Thr|Ser|Ser|Thr|Ser|Asn|Leu|Leu|His|Ser|
| |1505| | | |1510| | | |1515| | | | | |

-continued

```
Thr Pro Met Pro Ala Leu Thr  Thr Val Lys Ser Gln  Asn Ser Lys
    1520             1525              1530

Leu Thr Pro Ser Pro Trp Ala  Glu Tyr Gln Phe Trp  His Lys Pro
    1535             1540              1545

Tyr Ser Asp Ile Ala Glu Lys  Gly Lys Lys Pro Glu  Val Ser Met
    1550             1555              1560

Leu Ala Thr Thr Gly Leu Ser  Glu Ala Thr Thr Leu  Val Ser Asp
    1565             1570              1575

Trp Asp Gly Gln Lys Asn Thr  Lys Lys Ser Asp Phe  Asp Lys Lys
    1580             1585              1590

Pro Val Gln Glu Ala Thr Thr  Ser Lys Leu Leu Pro  Phe Asp Ser
    1595             1600              1605

Leu Ser Arg Tyr Ile Phe Glu  Lys Pro Arg Ile Val  Gly Gly Lys
    1610             1615              1620

Ala Ala Ser Phe Thr Ile Pro  Ala Asn Ser Asp Ala  Phe Leu Pro
    1625             1630              1635

Cys Glu Ala Val Gly Asn Pro  Leu Pro Thr Ile His  Trp Thr Arg
    1640             1645              1650

Val Ser Gly Leu Asp Leu Ser  Arg Gly Asn Gln Asn  Ser Arg Val
    1655             1660              1665

Gln Val Leu Pro Asn Gly Thr  Leu Ser Ile Gln Arg  Val Glu Ile
    1670             1675              1680

Gln Asp Arg Gly Gln Tyr Leu  Cys Ser Ala Ser Asn  Leu Phe Gly
    1685             1690              1695

Thr Asp His Leu His Val Thr  Leu Ser Val Val Ser  Tyr Pro Pro
    1700             1705              1710

Arg Ile Leu Glu Arg Arg Thr  Lys Glu Ile Thr Val  His Ser Gly
    1715             1720              1725

Ser Thr Val Glu Leu Lys Cys  Arg Ala Glu Gly Arg  Pro Ser Pro
    1730             1735              1740

Thr Val Thr Trp Ile Leu Ala  Asn Gln Thr Val Val  Ser Glu Ser
    1745             1750              1755

Ser Gln Gly Ser Arg Gln Ala  Val Val Thr Val Asp  Gly Thr Leu
    1760             1765              1770

Val Leu His Asn Leu Ser Ile  Tyr Asp Arg Gly Phe  Tyr Lys Cys
    1775             1780              1785

Val Ala Ser Asn Pro Gly Gly  Gln Asp Ser Leu Leu  Val Lys Ile
    1790             1795              1800

Gln Val Ile Ala Ala Pro Pro  Val Ile Leu Glu Gln  Arg Arg Gln
    1805             1810              1815

Val Ile Val Gly Thr Trp Gly  Glu Ser Leu Lys Leu  Pro Cys Thr
    1820             1825              1830

Ala Lys Gly Thr Pro Gln Pro  Ser Val Tyr Trp Val  Leu Ser Asp
    1835             1840              1845

Gly Thr Glu Val Lys Pro Leu  Gln Phe Thr Asn Ser  Lys Leu Phe
    1850             1855              1860

Leu Phe Ser Asn Gly Thr Leu  Tyr Ile Arg Asn Leu  Ala Ser Ser
    1865             1870              1875

Asp Arg Gly Thr Tyr Glu Cys  Ile Ala Thr Ser Ser  Thr Gly Ser
    1880             1885              1890

Glu Arg Arg Val Val Met Leu  Thr Met Glu Glu Arg  Val Thr Ser
    1895             1900              1905

Pro Arg Ile Glu Ala Ala Ser  Gln Lys Arg Thr Glu  Val Asn Phe
```

-continued

```
                1910                1915                1920

Gly Asp Lys Leu Leu Asn Cys Ser Ala Thr Gly Glu Pro Lys
    1925                1930                1935

Pro Gln Ile Met Trp Arg Leu Pro Ser Lys Ala Val Val Asp Gln
    1940                1945                1950

Gly Ser Trp Ile His Val Tyr Pro Asn Gly Ser Leu Phe Ile Gly
    1955                1960                1965

Ser Val Thr Glu Lys Asp Ser Gly Val Tyr Leu Cys Val Ala Arg
    1970                1975                1980

Asn Lys Met Gly Asp Asp Leu Ile Leu Met His Val Ser Leu Arg
    1985                1990                1995

Leu Lys Pro Ala Lys Ile Asp His Lys Gln Tyr Phe Arg Lys Gln
    2000                2005                2010

Val Leu His Gly Lys Asp Phe Gln Val Asp Cys Lys Ala Ser Gly
    2015                2020                2025

Ser Pro Val Pro Glu Ile Ser Trp Ser Leu Pro Asp Gly Thr Met
    2030                2035                2040

Ile Asn Asn Ala Met Gln Ala Asp Asp Ser Gly His Arg Thr Arg
    2045                2050                2055

Arg Tyr Thr Leu Phe Asn Asn Gly Thr Leu Tyr Phe Asn Lys Val
    2060                2065                2070

Gly Val Ala Glu Glu Gly Asp Tyr Thr Cys Tyr Ala Gln Asn Thr
    2075                2080                2085

Leu Gly Lys Asp Glu Met Lys Val His Leu Thr Val Ile Thr Ala
    2090                2095                2100

Ala Pro Arg Ile Arg Gln Ser Asn Lys Thr Asn Lys Arg Ile Lys
    2105                2110                2115

Ala Gly Asp Thr Ala Val Leu Asp Cys Glu Val Thr Gly Asp Pro
    2120                2125                2130

Lys Pro Lys Ile Phe Trp Leu Leu Pro Ser Asn Asp Met Ile Ser
    2135                2140                2145

Phe Ser Ile Asp Arg Tyr Thr Phe His Ala Asn Gly Ser Leu Thr
    2150                2155                2160

Ile Asn Lys Val Lys Leu Leu Asp Ser Gly Glu Tyr Val Cys Val
    2165                2170                2175

Ala Arg Asn Pro Ser Gly Asp Asp Thr Lys Met Tyr Lys Leu Asp
    2180                2185                2190

Val Val Ser Lys Pro Pro Leu Ile Asn Gly Leu Tyr Thr Asn Arg
    2195                2200                2205

Thr Val Ile Lys Ala Thr Ala Val Arg His Ser Lys Lys His Phe
    2210                2215                2220

Asp Cys Arg Ala Glu Gly Thr Pro Ser Pro Glu Val Met Trp Ile
    2225                2230                2235

Met Pro Asp Asn Ile Phe Leu Thr Ala Pro Tyr Tyr Gly Ser Arg
    2240                2245                2250

Ile Thr Val His Lys Asn Gly Thr Leu Glu Ile Arg Asn Val Arg
    2255                2260                2265

Leu Ser Asp Ser Ala Asp Phe Ile Cys Val Ala Arg Asn Glu Gly
    2270                2275                2280

Gly Glu Ser Val Leu Val Val Gln Leu Glu Val Leu Glu Met Leu
    2285                2290                2295

Arg Arg Pro Thr Phe Arg Asn Pro Phe Asn Glu Lys Ile Val Ala
    2300                2305                2310
```

```
Gln Leu Gly Lys Ser Thr Ala Leu Asn Cys Ser Val Asp Gly Asn
    2315                2320                2325

Pro Pro Pro Glu Ile Ile Trp Ile Leu Pro Asn Gly Thr Arg Phe
    2330                2335                2340

Ser Asn Gly Pro Gln Ser Tyr Gln Tyr Leu Ile Ala Ser Asn Gly
    2345                2350                2355

Ser Phe Ile Ile Ser Lys Thr Thr Arg Glu Asp Ala Gly Lys Tyr
    2360                2365                2370

Arg Cys Ala Ala Arg Asn Lys Val Gly Tyr Ile Glu Lys Leu Val
    2375                2380                2385

Ile Leu Glu Ile Gly Gln Lys Pro Val Ile Leu Thr Tyr Ala Pro
    2390                2395                2400

Gly Thr Val Lys Gly Ile Ser Gly Glu Ser Leu Ser Leu His Cys
    2405                2410                2415

Val Ser Asp Gly Ile Pro Lys Pro Asn Ile Lys Trp Thr Met Pro
    2420                2425                2430

Ser Gly Tyr Val Val Asp Arg Pro Gln Ile Asn Gly Lys Tyr Ile
    2435                2440                2445

Leu His Asp Asn Gly Thr Leu Val Ile Lys Glu Ala Thr Ala Tyr
    2450                2455                2460

Asp Arg Gly Asn Tyr Ile Cys Lys Ala Gln Asn Ser Val Gly His
    2465                2470                2475

Thr Leu Ile Thr Val Pro Val Met Ile Val Ala Tyr Pro Pro Arg
    2480                2485                2490

Ile Thr Asn Arg Pro Pro Arg Ser Ile Val Thr Arg Thr Gly Ala
    2495                2500                2505

Ala Phe Gln Leu His Cys Val Ala Leu Gly Val Pro Lys Pro Glu
    2510                2515                2520

Ile Thr Trp Glu Met Pro Asp His Ser Leu Leu Ser Thr Ala Ser
    2525                2530                2535

Lys Glu Arg Thr His Gly Ser Glu Gln Leu His Leu Gln Gly Thr
    2540                2545                2550

Leu Val Ile Gln Asn Pro Gln Thr Ser Asp Ser Gly Ile Tyr Lys
    2555                2560                2565

Cys Thr Ala Lys Asn Pro Leu Gly Ser Asp Tyr Ala Ala Thr Tyr
    2570                2575                2580

Ile Gln Val Ile
    2585

<210> SEQ ID NO 17
<211> LENGTH: 5551
<212> TYPE: DNA
<213> ORGANISM: Mus musculus

<400> SEQUENCE: 17
tctagaagta aaatgatcct gagtagcgat cctgggaaaa tacgtactct aacacactgc      60
aatcatctct ctgtggtttg ctggagctga ggtctggaag gctcgacctt ggttagaaat     120
aacctaccga atacagagct atgacgttag tctggaagga gctttggaag aatgacaagc     180
tgtagctgcc cagaacatac tagatgccat atttccaagg caagtgtcca catgcggaca     240
tcttaagaat atggttgtct ctgcagtgct aaggaccttg ttcgtgccac acaggtctcc     300
agggttagtg ctaactctga ctgcttgact ctttaattct accttgatca ttaatgacta     360
gaaatcactt ggtgattagc aactggatat ggaatattac taatttgtac ccaagccagg     420
```

```
ccacctcagc tttggcagct ccattcattc tgtggagccc agtcacgtgg gtttgaatca    480
actgtactgt ttctacttac aagacgcatt acctgagatg agtcattttt cttcacaagt    540 cttttagaa gagtcaatta gacatattct gatgaagtaa gcatataaag tgagagcagc    600
atgaatgtgt tccatgtatg ctcatggatg ctattataat gtggaaataa actgacttta    660 aaaaaaaag cttatgatac ttgtcacaga gtaaatcttc cataaatatc atctgcattt    720
ataaattatt ttcataatcc atcaattaaa aacctttaga aattttgtta acacaaagat    780
ccctaggccc ctgccctagg atggtctgta tggtgggcct gagagatgga gcttaagaac    840
ttacttgctc caggagcaca tcttcagaac atctgcctca aaacatttat cccaaatgct    900
catcaaaggc tcactcacat gtgcttcaac cacaggggatt aaacagtcat tttagtcaca    960
tttctcaaac ggtggaagcc tgctagagga acaggatgta tcaggataac atccaacctt   1020
acaaaaggat gtcataaccc tcaccacaac aaacaacaac gacaacaaac ccataaaaat   1080
tatcacggca aatgaactaa gccatatgca gaaaagtat tatatgttct cattgtgggg    1140 tgttttcct taatagtcaa atatgcagaa tatagacaaa gatggtttat gcaagtgggg   1200
atggcgaagg atacttgtag attagaggac acaaagcaac aactacagag tgaagtaatc   1260
cagagactta atgtataata tgaggactgt atttaataat tctatttaag atacacagca   1320
aacgagtgta tcttactaac acacacactt acatagagag aataaagtga tagatacgtt   1380
tgttttatct tcatgtagct gataattca tattgtacac ctcaaacata gataaccaac   1440
aaagaggaag aggataggtg cctctcccag ggcggaagag tacattcgaa agtcagacac   1500
cattgtgtag atgtaccaca tggaggagct agagaaagta gccaaggagc taaagggatc   1560
tgcaacccta taggtggaac aacattatga gctaaccagt accccggagc tcttgactct   1620
agctgcatat atatcaaaag atggcctaat cggccatcac tggaaagaga ggcccattgg   1680
acttgcaaac tttatatgcc ccagtacagg ggaataccag ggccaaaaag ggggagtggg   1740
tgggcagggg agtgggggtg ggtggatatg ggggactttt ggtatagcat tggaaatgta   1800
aatgagttaa atacctaata aaaatggaaa aaaaaaaa aaaaaaaaa aaggaaggt    1860 cagacacctc acttcactgc tatctcaact tgcaaacaga agggagtca caaacccagg   1920 acaaaccaca gtgattgaag cgtctttgaa tgttattgct gttgttgtta ccaccatcat   1980
tagcatatat tcattgtgaa aacttacggg gtctatgaca tgttttttta ttcaagtata   2040
tcacatgctg tcagcatatt tggcaccact accagcccca gccccctttg ccccgccccc   2100
aacacacaca cacacacaca cacacacaca cacacacaca cacacacaca cacacacacc   2160
tttaccttct cctgggcatc atctgctcac tcacccaccc aagcttaatc ctttttccttc   2220 cctgcaatag tacctctcct attttttatgt ctaggttccc cctcccctg ttaggagatg    2280 ggagaggtca cgaaaggaaa gaatttgtag cccctgagcc agcccgggcc acagagcctg   2340
ccaccagaca ggaaaagccc agggcttacc agcacaggag gagcaaactc gcaggcgagc   2400
ctgggttggc gctggtggtc ccgggtcgat ggcccgccca ttcccagaag ccgaggctat   2460
agctgcgtca cctgccccgc cctcctcccg agtgaagacc cctagaggct gagcagaccc   2520
caaaggcggt gcaattccat tggcccaagg cagaggtgag cggctgctaa tcccctcggg   2580
aagtgaaggg acccagagag tctggtagat gtgggagctg gggttcaggg cgagacagag   2640
ggtgggatgg gcagaagggt ccaggaaaag gaaagtactg gagggagtt gggacaaaag    2700 cagcgaccaa gggaacatcg cttcagtgac tgaagccagg caaaaggagc gggaaggatt   2760
```

```
atatgtagcc tgggacgctt tcataaacac tgatgacgtg tttgtgcaaa gcaagcaatt    2820
tgaggagaaa cgcctgggac gtcggaaaga aggagtgatc gattagtact tgtaagttta    2880
ggtgagtttg agaactaact aacctatact attgagggag aaggaagagc attccagcag    2940
cagcagcagc agcagcaatc agataaagga aagctttggt tagtttggaa atgtatgata    3000
ccattaaaat aacagaagcg cctccagttc tctgaagagt cagtccccca gctagtgaag    3060
actaagccta ctaagccttt tgctcccgtt ggaagcaaag aacgttcctt caatcaggtg    3120
aaggctctcc tcagaagatt tcctgtctct gcttatgtta caagaggatt caaaagcaag    3180
acagaagagc tcaggtattg ccaactcttt tgttaaatac agtttgaggc ttaagtgtac    3240
gggaactcat gtggtattca tttacggctc tcttctctta taactaactc ttaaggtgca    3300
tatagtctct tctgtttccc agctaccttg taccatcttt gttatctaa taatagcaag    3360
ctcatctgct ttttaatcat cacgcagaga gtattcaaaa atattcagtg atgtaacagt    3420
gacagtgtag gcatagaagt aatcattagt aaatcttaat ttgggttaaa ctcattcata    3480
acagctccag gttgggaggg atcactgagc cttcgccacg tgcgggttaa agatattttc    3540
taacaagaga agcagaattc ttccttggcc atgctcccca tcactgtgtc agtaagcaga    3600
ggggtgtttc caagcagaga aagagcagac agtgttatgc ctgcaaagtc agagactcag    3660
ccctcccagc tggtcagttt actgtcctcc cggtcattag ttggctctga aaaggcccat    3720
gtgtccttat tggcaaggac ttgcagacat gctagaaaga aatttgacct ttttttctag    3780
tgggttatta cagctgtaaa agtattttgg aaggttaagc caaataaata aaacacatat    3840
taaataatac aatgttacaa aaattgatca tataaagaag tacattcata aatgcaatgt    3900
gaaaaatata tataattttt atctatttac tggtgcaaag ttttctaaat tgcacatgta    3960
ctattttat atttataaaa atattttaa aatgtatata aaagtgtaaa aggctcttgg    4020
tcaaacaaga gagttaaatt tacaaacttt aattgtcccg ataacattat tatgatctct    4080
aatgacaggg atcctgcttt tcattgggaa atgagaagct atgaagatat gtttacaata    4140
ataagcccat ttagtgataa agtccaatgg gaagctagca cacactggtt tataaagaga    4200
acagtttcct gagtctatgc aagtttacac tctagggaat aagagttcct ctttctccag    4260
atttcactag catttgttgt catcatttat cttcttgatg atgagcatta taagtggaat    4320
aagataggat ctcaaaggaa tgtcaatttg gatgccctga acaatctttc aggtctttct    4380
ttcagttcac tagtctattc atttattgga taattggggg atggtgttaa ttttttttgca    4440
gttcttatgg aattccaaaa aacaaaaaac aaacaaacaa acaaaaaacc tctgaaacta    4500
gaactaccaa tccattactg ggtatgtaac aaagagaaat ctgcacagaa tttattgcta    4560
cattgttcat tattcacgac agccaagaat gtggaaccaa cttacgtagc cgtcaaaata    4620
tgaacggata aagaaaatgt ggaaatgtgt acaacagagt cccatgtggc cataaaagag    4680
tgaaatcatg acatatgcag gaaatggatg caactggaaa tcaattgggc taatcaaaac    4740
aagacagact caaaaggaa acaccgtgta gcttctctga caaacagaag ctagatttac    4800
acttgtacgt gcgcatgtgt gtttagaatt ttatttagtt atacactatt ctaatctgtg    4860
agtgtgtata aaggcatgca tgtaaagcaa aaacaagcta gctgggggtgg gtaggagaga    4920
aagcaatgag aggagttaat aagaacgaag catagtaaca taggtgccag gatgaaatgc    4980
attaatttgt atgctaacta aaccacagac aggaggcaca cgttcaaacc agggtgaaat    5040
cccagcacag agaaggggaa gtagacacaa agtttcgcca ctaaccaaga agccatttgc    5100
agttgctgcc tgctgggagg ggcgttccag ttttctccag tctgacactg tgtataacaa    5160
```

-continued

```
ccagttgaca atacaaagtt ggcatgatgg atggttttg tgctatttt cattttttt    5220 cttactgttt tgttgttgtg gtggttgttg tggtggtggc tgtggttttc atttgtttct    5280
tttgagagag agaaggaaca tgaaattggg tgggtaggaa gctggaaacg atctggaaga    5340
agttggggaa agagaaaaat tgtatggagc atatttaaac aaacaaacaa acaaacaaaa    5400
ggttcatttt gccacaaaaa ggtgtgaatt aaattaacca gttacgactc ttaaagaaaa    5460
tattcccaat tattcccaga gttgctatgt atgctgtgcc taggactttg cttgaactgg    5520
ccctataact ctggtgtggt gtcttttcag g                                   5551
```

<210> SEQ ID NO 18
<211> LENGTH: 4610
<212> TYPE: DNA
<213> ORGANISM: Mus musculus

<400> SEQUENCE: 18

```
cacagacctt cctcttctaa cctctctccc ccatcttgtt gcttcatccc agacttcaac      60
accagcaagc acactctgct aatgcaaggg ctgctcctgt caggacaaca aggaggctga     120
aggcagaccc acacgtttcc aactgctcct gagagtcaat cccctagac tcatctatag      180 caggaaacct gctgtgatct ccatttcttc tctgaccaca tccccaagtt atcacaagga     240
gtttttcctc aaacctttcc tctccagcaa acccttcag ctccttgggt actttctcta      300
gccccttcat tgggaaccct gtgctccatc caatggatgg ctgtgagcat ccacttctgt     360
atagaatctt ggtcagtgca gtcttttgta tcctcaagaa cactgggtct gaaaatttta     420
acccaaagaa ctgttttttg ttatgattgc tgcaatctct ttcaattcca ataaagagta     480
agcatctcat tcctttgtct cctcctttca gtaccaccct gcctttgctg cctttctcaa     540
agaatcaata aaaccaaagt gatatagatt catggcattc ctctaactgc tacatccact     600
ccagtagtat ctcacttggc aggtgtaaaa gcctggaagc agtcacgagg cagtttcaca     660
gaaacttagc ctcctggaac cttggcattc ccatagctag aatgccccag atttgtccct     720
gagatattgt ggtgggtctt gcatgctttc ttgcagtatt ttactggata agagttagaa     780
atctcagggc gagcttagca aaagtatacc tagaatcttc atgacagtca ggtattgcaa     840
actacattgc atattagaag aaagttggta aattcttctg acaaatggag attccctaca     900
gataacttaa agaacagct aagtcacact catatgcaag aatttaccaa ggcctaggaa      960
aggggggggg ggtactgctt tattcatgat aaggtctgct agagcagaac ccctggtgc     1020 tagctttcac aaggttcaaa ggtgtagcat aaattgtgac tagagtgtga atctttacc     1080 tgtcattagc tgactctagg cagagctgtt ttatctttac tgtaaacatt acctggttcc    1140
tgtcagtcct ttgaaggcat cctctgtttt tgtgacagat acttctatgt acctcgcctg    1200
ctgtgacacc ctactccttt gttttctgta ttatataagc ctggtgttcc ctttgtgaaa    1260
aattacatcc agatacagca ctcccttgtg tctgtgtcct tttgtcattt ctggccaact    1320
ccatgcccac ctgccagaac ccctagtctt ttccacagat tgagggaggc cgactgagcc    1380
tggtccatgg catctaacca ctgtcagctc actgttggtg actacctcaa ggtacaagct    1440
ccattactaa tgaaacaaaa ttagataagt gtgggtccag gaagcaggtt gtacaccctg    1500
tctgaatgaa cattatgaaa tgactgaaat aagttaaccc atctcttcct cgtttgctaa    1560
tatagcaaat aaaccgagtt tctgagctgc tgctggtgtg tctccatcag agggcagagc    1620
cagtctgatc ctagctttcc tgtatgtgtg tccattgttt cttcagttcc tgttgcccca    1680
```

```
ttaggaaatc ctaagccatg aaagccatga atctgggaat gacttttcta agaaatgcca      1740
cgtgaacctt gcgtttcaac gttttgcctg taaacaagat atatggtgcg cagtttataa      1800
tcataataag ctttgaaata atatataact ccattctcat tctgcttcca cgctgagcat      1860
cctgtttccc cagggaccac aagagcattt gaaaagtagt gatttatgac ctgctttgtt      1920
ctgttactat aaaagcttca tgaaagggca gccatgttga acatggaac ttggggtgac       1980
ctgtatctgt gttcctgggt cgtgctcact catatttgtc tccagaataa atgagtttat      2040
caacttcgag gaaaagttg tgtgtttgta tagcacgccc gtggagtccc accattctac        2100
ttcctgtaat ctgtatatgg tagaaaaagt taatttatgt gattcttcca actccaaata      2160
tttcaaatct tttagcccct cagcctggga tttctttgac taagtctatt gatttggaag      2220
atctcagtgg ttaggatttg cagtcatgat gttcatacgt caggctaagc tgaaaaatat      2280
gacaaatgaa atgtcaaatg tcatgtgcct gggaatgtga gtgttagggg gttttaaaga      2340
aacaaatacc tactctaaat agttaataag tcccatggtt ctattctagt tttgaataat      2400
gttccctagt atacagcaat ttaatttgaa atgaatagct tcttatcttg accaatctca      2460
gtgacttcat ccgtcccaag tcatgttttc atattcataa ggataggtct cattcaacca      2520
catgtttatc atttgggatc tgcatttttc tgatgcaaaa tgatttattc ttccagagca      2580
ctggaattgg gttgaatcat cttataacgg ccaaaactaa atgcttctgt gctaaacaga      2640
gagttacaag acctttttat gtggatggca gcattttagt catccttatg acagaatgtc      2700
agagtggagc tcccactggg ggaggggctg gtccttggca ggattctctt ggaacatcac      2760
acaaagaaat tccaaattat gaaatgcaca tgatccatcc agaatgtgac ttttgactct      2820
tgaacatgag cttttaaagt acgtttggct gttcagacct tgactttgag gtgaaggaaa      2880
gctcgccaac tcctttttat atgtaacaca atatatcaag atctaatgtg agacagtatg      2940
ccagtcccaa gatctgtcaa tatgactgaa gacacattgc gatgttatca ctaaggcagg      3000
agaaggcaag ctacagtgaa gcccagttca ctataaagct ttatgagaaa ttagataaga      3060
agggtttcta atttttaaat ttttttttatt agatattttc ttcatttaca tttcaaatgc      3120
tatcccaaaa gtcccctata ctccccccctc accctgctcc cctacccacc cactcccatt      3180
tcttggccct ggttacttgt gatagtggtc atatgatcca ccaagcttta catgctcact      3240
atctggtcta ttgcaagaat ggctgccgag ctgatgcagt cagatacaga cacctacagc      3300
caaacagtgg aaggaacttg gggactctta tggaagaaaa ggaggaaggg ttatgggccc      3360
cggatgggga aaggaactcc acaggaagac caacatactt ggtcaactaa cctggaccct      3420
tggggctctc agagtctgaa ccaccaacca tagaacattc atgggctgta cccaggcctc      3480
tccactcata tgtaacagat atgtggcttg gccttcatct gggtcctgaa caactagatg      3540
ggggttaggg gtggggatgg gggttatctc aaaagctgtt gcctgtatgt gggatatgtt      3600
cttactgagc tgcctagtct ggcctcagtg ggagaggaag cacctagctt tagccttgta      3660
aagacttgaa gttctgaggt gtcggtggag ggtatactca gggaggccct cacctgctag      3720
gaagagaaga ggaggggggaa gacttggggg agggggcagt gagcaggttg gtaaaatgaa      3780
taagaaaaaa aaaataaaaa taattaaaaa aaaaaagaa tggctgctga gccctactct      3840
aaaaccattg catcccccccc ccccaatcat tcagtgacta cgaattaaaa tcattgatac      3900
taacaataga tgtaggaaac tattgttaac ttctttgtga ccacgagtgg tatttggaac      3960
ctttttttatt gaagctttca cacagagcct tgttctttca tttccctgta catgcatgta      4020
gcttaatgat gttcagtgaa ttaaaaataa caatgaagaa taaagacaac tgtatttttaa     4080
```

```
ggattcttcg tatatattta aaaatctaag gtggtcacct ggaagaaatg tcttcagttt    4140
ttctatatat gtttactcta tcgtatgtta attaattata tgcaataatt cataaaatct    4200
acaacatagt atgtaactta taagaaagta aaacattcat gaaattgtga aggttacttt    4260
tccttaccct cagaaacact gggtttgaat aattcttatt ttggtatcag tgaagaattt    4320
gaaagaatgt aataacctac taaggcaaac atagaagttg aaattaaaaa gagtagacag    4380
gagaagtaat aaggcaaata atgaatattt gctttaaata gttcttaatg tatcatctaa    4440
ctagggtgtg attctccaga cttgactcca tccaaaatat ccaaaatgac tctaaccaca    4500
gtcattgaaa caatgtgttg aaaataataa acatttccta cttgaaaatt cagatttctc    4560
ctactttgct ttttattgct gtgataagca ccatgaccaa agcagcttat                4610

<210> SEQ ID NO 19
<211> LENGTH: 424
<212> TYPE: DNA
<213> ORGANISM: Artificial Sequence
<220> FEATURE:
<223> OTHER INFORMATION: primer

<400> SEQUENCE: 19 taagccttt tgctcccgttg gaagcaaaga acgttccttc aatcaggtga aggctctcct      60
cagaagattt catgtctcag cttatgttac aagaggattc aaaagcaaga cagaagagct     120
caggtatagc caactctttt gttaaataca gtatgaggct taagtgtacg gcaactcatg     180
tggtattcat ttgcggctct cttctcttat aactaactct taaggtgcat atagtctctt     240
ctgtttccca gctaccttgc accatctttg tttatctaat aatagcaagc tcatctgctt     300
tttaatcatc acgcagagag tattcaaaaa tattcagtga tgtaacagtg acagtgtagg     360
catagaagta atcattagta aatcttaata tgggttaaac tcattcataa cagctccagg     420
ttgg                                                                  424

<210> SEQ ID NO 20
<211> LENGTH: 11962
<212> TYPE: DNA
<213> ORGANISM: Mus musculus
<220> FEATURE:
<221> NAME/KEY: misc_feature
<222> LOCATION: (1)..(11962)
<223> OTHER INFORMATION: 'n' can be any nucleotide 'a', 'c', 'g' or 't'.

<400> SEQUENCE: 20
tttggaacca acccagatgc ccctcaacag agaaatgggc cagaaaatgt ggtccattta     60
tccaatggaa tactactcaa cttattaaaa acaacgactt tcataaaatt tttaggcaaa    120
tgnatggtct gnaggatctt gagtgaggta acccaatcac aaaagaacac tcatggtatg    180
cactcactga taagtggcta tttgtctatg gagtgattta aaagggaaga agacacatag    240 cttttttgtgt gtataatatt aagatggaaa tttgccagtg ctgtttggct tatgagtgaa    300
tcttgtttca gtggattacc ggaagaaaat aataagtgaa ctgtaggaag aagtagttaa    360
tcaaggtgac aaagtatcct gacacattgg gaaaagacca cagtccagga aactgagtct    420
taaggattca tattaactcc agttccccat gtgcagctct gagactttgg cagatcagac    480
acttaacttc accagcttcc tacacagagc agttactatc cttgccttca cacatggagt    540
gtgccattaa gtgcctgaac atgagtctga cttgttaata atctttaaaa tccaattgtg    600
tgtaaagtat gtgaccaaag agcatggtca tgctattaac ctttgatgtt ctatggactc    660
```

-continued

```
ttaattttat ggtagaaatg tcaacaagct tgtggaggct ggaagataca aggcttaaga      720
ggatggcctt tcagttttga agtaattca gtatgtgttc tggcatccct tttcctaaag      780
caatttaacc ccccaagtag gcataatttt aatgcttact tcatcagaat atatctaatt      840
gactcttcta aaaagacttt ggtatgcata ggatctaaat gtaaatgtga tttactgaca      900
taataaatag gagaaactga gctagaatag gtataaaata tgtgctggct ttctaatagg      960
tcttataggt tatataagag gtgggaaagg aatatttgaa acatctagaa gtaaaatgat     1020
cctgagtagc gatcctggga aaatacgtac tctaacacac tgcaatcatc tctctgtggt     1080
ttgctggagc tgaggtctgg aaggctcgac cttggttaga aataacctac cgaatacaga     1140
gctatgacgt tagtctggaa ggagctttgg aagaatgaca agctgtagct gcccagaaca     1200
tactagatgc catatttcca aggcaagtgt ccacatgcgg acatcttaag aatatggttg     1260
tctctgcagt gctaaggacc ttgttcgtgc cacacaggtc tccagggtta gtgctaactc     1320
tgactgcttg actctttaat tctcccttga tcattaatga ctagaaatca cttggtgatt     1380
agcaactgga tatggaatat tacttaattt gtacccaagc caggccacct cagctttggc     1440
agctccattc attctgtgga gcccagtcac gtgggtttga atcaactgta ctgtttctac     1500
ttacaagacg cattacctga gatgagtcat ttttcttcac aagtctttt agaagagtca      1560 attagacata ttctgatgaa gtaagcatat aaagtgagag cagcatgaat gtgttccatg     1620
tatgctcatg gatgctatta taatgtggaa ataaactgac tttaaaaaaa aaagcttatg     1680
atacttgtca cagagtaaat cttccataaa tatcatctgc atttataaat tattttcata     1740
atccatcaat taaaaacctt tagaaatttt gttaacacaa agatccctag gcccctgccc     1800
taggatggtc tgtatggtgg gcctgagaga tggagcttaa gaacttactt gctccaggag     1860
cacatcttca gaacatctgc ctcaaaacat ttatcccaaa tgctcatcaa aggctcactc     1920
acatgtgctt caaccacagg gattaaacag tcattttagt cacatttctc aaacggtgga     1980
agcctgctag aggaacagga tgtatcagga taacatccaa ccttacaaaa ggatgtcata     2040
accctcacca caacaaacaa caacgacaac aaacccataa aaattatcac ggcaaatgaa     2100
ctaagccata tgcagaaaaa gtattatatg ttctcattgt ggggtgtttt tccttaatag     2160
tcaaatatgc agaatataga caaagatggt ttatgcaagt ggggatggcg aaggatactt     2220
gtagattaga ggacacaaag caacaactac agagtgaagt aatccagaga cttaatgtat     2280
aatatgagga ctgtatttaa taattctatt taagatacac agcaaacgag tgtatcttac     2340
taacacacac acttacatag agagaataaa gtgatagata cgtttgtttt atcttcatgt     2400
agctgataat ttcatattgt acacctcaaa catagataac caacaaagag gaagaggata     2460
ggtgcctctc ccagggcgga agagtacatt cgaaagtcag acaccattgt gtagatgtac     2520
cacatggagg agctagagaa agtagccaag gagctaaagg gatctgcaac cctataggtg     2580
gaacaacatt atgagctaac cagtaccccg gagctcttga ctctagctgc atatatatca     2640
aaagatggcc taatcggcca tcactggaaa gagaggccat ggacttgca aactttatat      2700 gccccagtac aggggaatac cagggccaaa aaggggagt gggtgggcag gggagtgggg      2760
gtgggtggat atgggggact tttggtatag cattggaaat gtaaatgagt taaataccta     2820
ataaaaaatg gaaaaaaaa aaaaaaaaa aaaaaggaa ggtcagacac ctcacttcac        2880
tgctatctca acttgcaaac agaagggag tcacaaaccc aggacaaacc acagtgattg      2940
aagcgtcttt gaatgttatt gctgttgttg ttaccaccat cattagcata tattcattgt     3000
gaaaacttac ggggtctatg acatgttttt ttattcaagt atatcacatg ctgtcagcat     3060
```

```
atttggcacc actaccagcc ccagccccct tgccccgcc cccaacacac acacacacac    3120
acacacacac acacacacac acacacacac acacacacac acctttacct tctcctgggc    3180
atcatctgct cactcaccca cccaagctta atccttttcc ttccctgcaa tagtacctct    3240 cctatttta tgtctaggtt cccctcccc ctgttaggag atgggagagg tcacgaaaga     3300
aaggaatttg tagcccttga gccagcccgg gccacagagc ctgccaccag acaggaaaag    3360
cccagggctt accagcacag gaggagcaaa ctcgcaggcg agcctgggtt ggcgctggtg    3420
gtcccgggtc gatggcccgc ccattccag aagccgaggc tatagctgcg tcacctgccc     3480
cgccctcctc ccgagtgaag acccctagag gctgagcaga ccccaaaggc ggtgcaattc    3540
cattggccca aggcagaggt gagcggctgc taatcccctc gggaagtgaa gggacccaga    3600
gagtctggta gatgtgggag ctggggttca gggcgagaca gagggtggga tgggcagaag    3660
ggtccaggaa aggaaagtac tggaggggag ttgggacaaa agcagcgacc aagggaacat    3720
cgcttcagtg actgaagcca ggcaaaagga gcgggaagga ttatatgtag cctgggacgc    3780
tttcataaac actgatgacg tgtttgtgca aagcaagcaa tttgaggaga aacgcctggg    3840
acgtcggaaa gaaggagtga tcgattagta cttgtaagtt taggtgagtt tgagaactaa    3900
ctaacctata ctattgaggg agaaggaaga gcattccagc agcagcagca gcagcagcaa    3960
tcagataaag gaaagctttg gttagtttgg aaatgtatga taccattaaa ataacagaag    4020
cgcctccagt tctctgaaga gtcagtcccc cagctagtga agactaagcc tactaagcct    4080
tttgctcccg ttggaagcaa agaacgttcc ttcaatcagg tgaaggctct cctcagaaga    4140
tttcctgtct ctgcttatgt tacaagagga ttcaaaagca agacagaaga gctcaggtat    4200
tgccaactct tttgttaaat acagtttgag gcttaagtgt acgggaactc atgtggtatt    4260
catttacggc tctcttctct tataactaac tcttaaggtg catatagtct cttctgtttc    4320
ccagctacct tgtaccatct tgtttatct aataatagca agctcatctg ctttttaatc     4380
atcacgcaga gagtattcaa aaatattcag tgatgtaaca gtgacagtgt aggcatagaa    4440
gtaatcatta gtaaatctta atttgggtta aactcattca taacagctcc aggttgggag    4500
ggatcactga gccttcgcca cgtgcgggtt aaagatattt tctaacaaga gaagcagaat    4560
tcttccttgg ccatgctccc catcactgtg tcagtaagca gagggtgtt tccaagcaga     4620 gaaagagcag acagtgttat gcctgcaaag tcagagactc agccctccca gctggtcagt    4680
ttactgtcct cccggtcatt agttggctct gaaaaggccc atgtgtcctt attggcaagg    4740
acttgcagac atgctagaaa gaaatttgac cttttttct agtgggttat tacagctgta     4800
aaagtatttt ggaaggttaa gccaaataaa taaaacacat attaaataat acaatgttac    4860
aaaaattgat catataaaga agtacattca taaatgcaat gtgaaaaata tatataattt    4920 ttatctatt actggtgcaa agttttctaa attgcacatg tactatttt atatttataa      4980 aaatatttt aaaatgtata taaagtgta aaaggctctt ggtcaaacaa gagagttaaa      5040
tttacaaact ttaattgtcc cgataacatt attatgatct ctaatgacag ggatcctgct    5100
tttcattggg aaatgagaag ctatgaagat atgtttacaa taataagccc atttagtgat    5160
aaagtccaat gggaagctag cacacactgg tttataaaga gaacagtttc ctgagtctat    5220
gcaagtttac actctaggga ataagagttc ctctttctcc agatttcact agcatttgtt    5280
gtcatcattt atcttcttga tgatgagcat tataagtgga ataagatagg atctcaaagg    5340
aatgtcaatt tggatgccct gaacaatctt tcaggtcttt ctttcagttc actagtctat    5400
```

-continued

```
tcatttattg gataattggg gggatggtgg taatttttt gcagttctta tggaattcca      5460
aaaaacaaaa aacaaaccaa ccaaccaaaa acctctgaaa ctagaactac caatccatta      5520
ctgggtatgt aacaaagaga aatctgcaca gaatttattg ctacattgtt cattattcac      5580
gacagccaag aatgtggaac caacttacgt agccgtcaaa atatgaacgg ataaagaaaa      5640
tgtggaaatg tgtacaacag agtcccatgt ggccataaaa gagtgaaatc atgacatatg      5700
caggaaatgg atgcaactgg aaatcaattg ggctaatcaa acaagacag actcaaaaag       5760
gaaacaccgt gtagcttctc tgacaaacag aagctagatt tacacttgta cgtgcgcatg      5820
tgtgtttaga attttattta gttatacact attctaatct gtgagtgtgt ataaaggcat      5880
gcatgtaaag caaaaacaag ctagctgggg tgggtaggag agaaagcaat gagaggagtt      5940
aataagaacg aagcatagta acataggtgc caggatgaaa tgcattaatt tgtatgctaa      6000
ctaaaccaca gacaggaggc acacgttcaa accagggtga atcccagca cagagaaggg       6060
gaagtagaca caaagtttcg ccactaacca agaagccatt tgcagttgct gcctgctggg      6120
aagggcgtt ccagttttct ccagtctgac actgtgtata acaaccagtt gacaatacaa       6180
agttggcatg atggatggtt tttgtgctat ttttcatttt ttttcttact gttttgttgt      6240
tgtggtggtt gttgtggtgg tggctgtggt tttcatttgt ttcttttgag agagagaagg     6300
aacatgaaat tgggtgggta ggaagctgga aacgatctgg aagaagttgg ggaaagagaa      6360
aaattgtatg gagcatattt aaacaaacaa acaaacaaac aaaggttca ttttgccaca       6420
aaaggtgtg aattaaatta accagttacg actcttaaag aaaatattcc caattattcc       6480
cagagttgct atgtatgctg tgcctaggac tttgcttgaa ctggccctat aactctggtg      6540
tggtgtcttt tcaggatgca gaagagaggc agggaagtca gctgcttgct gatctccctc      6600
actgccatct gcctggtggt caccctgggg agcagggtct gtcctcgccg atgtgcctgc      6660
tatgtgccca cagaggtgca ctgtacattt cgggacctga cctccatccc agacgggcat      6720
cccagccaat gtggaacgag tcaatttagg gtgtgtggac cttgcctgat ctccttctca      6780
gagagggacc actgatttc ctggtacttt gcccccaaa cacctgtgat tactttaat         6840
agttttcttc taaaatgggt tcatacaaac cttatattgt ggagacaatg aacattttat      6900
cccaatagtc ttttactaga acttgaagcc cctcttagtt gtttgggagc ctcataatta      6960
tggggcagct ttattctgaa tgaattttaa atgaaaaaga tacagtttct gttaacaatc      7020
attatgatac caaggaagag gaattgtcat tgaatatttt aaaaaagcat ttcttttgca      7080
atttataaat acccattaca aaatggctta cttaaaatac ttgccttact aaatctgaca      7140
aattatggtg atattttgaa ggtttatgaa aatttgttta tgtgtataaa tgcacaagaa      7200
atgggatatg ccatcaccta tgtgccatta gtgagcatgt acagtatgcc aaacactatt      7260
gttcacgttt ggaggaagta atgggggtgg gggagcaaca agggttataa ccgtataccc     7320
agtgccttgg aagcgattgc aaacagtaaa gactgacatt gtgttctccc tatgagggag      7380
gggccttggg ctgagcactt tgcaatgagc atttgctcat tgtgctggca ggttttatga      7440
taacttgacc caagctagag tcactggaga ggaaggaact tcaactgaga acatgcctga      7500
agaagatcag attataggca ggcctgtggg gcattttctt aattagtgat tcatggggca      7560
gggcccagtc cattgttcgt ggtaccattt ctcaggcact attaaaaaaa aaaaacagg       7620
ctgagcaagt gtcaaggagc aagtcagtga gcagcagccc taatgatctc tgcatcagct      7680
cctgcctcca ggttcctacc ctattgagt tcctgtccta gctccctaca gtgatgaaca       7740
atgatgtgga agtataagcc aaataaatcc tttcttcccc aacttgctgt tggtcatgat      7800
```

-continued

```
gtttcatcac agtgataata gtcctcatga agatgctggt gtttataaca cctttggact   7860
aaattctgtt atctatagct gaggaaaatg gagcatagaa agtctccaga ctacaccaga   7920
gtgtaatctg ggcctgagct tagaatcaca cccacgtgca ctccactgcc ggggcttctt   7980
aaccggaaca cagttgtaaa aggaattttt ctgtttgttt ccattttgac atgtggactt   8040
taattgacga ttcatctgaa gctgaaaatg atttttttc caggtataac agcctcacta   8100
gattgacaga aaatgacttt tctggcctga gcagactgga gttactcatg ctgcacagca   8160
atggcattca cagagtcagt gacaagacct tctcgggctt gcagtccttg caggtgagat   8220
aggtagaggg tgatggaggc tgagaagaga ggtgcaactg tgggttatac ccaaaagctg   8280
ctgattcccg tgggagacat tctataagca ttctataaac tagaggcaga tatcaaggaa   8340
ggatttcaat tgtaatgcaa ttttatgaga aaatttgaat attaagaaaa tgctggggaa   8400
aatgcttaca caattgcgag gacctaattt aggatctcca atagccacat aaaaagcaca   8460
gcatggcggc agacacctgc aattcctgtc cctggaagca cctgttcaga atcccagaga   8520
ctcattggcc aaaacactcta ttcaatcaat gaagtccata ttcagtgaca aaacttgact   8580
cagaaactaa tgtggaaagc atcaggaaga cagccaacat ctggtctcta ctcatgcatg   8640
aataagggat cccagagaga agggaagaaa aaggaaggaa ggaaggaagg aaggaaggaa   8700
ggaaggaagg aaggaaggaa ggagagaggg aggaaaagga gggagggaag gaaggaaagg   8760
gaaaggaaaa aagagatggg gagggaggga aggaaaggaa aggggggagaa agaagagaag   8820
aaaggaaaat aaataaattt tcagggatta ttacaccttt aaattttatc cataaaaggt   8880
catttccacc tgtttgtctg gaagtagagt gggatccctt atataagggc agtctttaac   8940
atagtagcat tttataaacc attacaaatt ttgagttttc tctactttt atcctctacc   9000
atcttcaaac tgaaactaca attattccca caaatgaaga aaatgctgta agagttttca   9060
cacaccgaag tgggaaactt aaggattaga caagtctaac aatgagaatg gggagaacaa   9120
aaagagactg cacagggagc cctttctctg cttataatct tgacacttga gaagctaatt   9180
gacgctgcat gactactcaa ctctttaagc aaacaatgct gttgttcatg aaaagcacaa   9240
taaagtacat atgtcccata atattcatca aaatttgcat gcagcacata atagcaatca   9300
aagcaataac acccactgtt cacagagact ttaaacatga aactgaaact atgtctagtg   9360
ttttgactta gggtacatag tatgctgtgt ctgtatgtac caatgttgat ttaggtcatc   9420
agacagcatt tggaacatgt atcttcagga ggaatcattc atgtatcctg catgaaattc   9480
tccacctatg tttattctct tagccaggtt tttctctgat ggagaaacat tgggtttgag   9540
gttttactcc caggtaacat ttagggaaaa gctgtctatg ttctcagttt ggcttttatt   9600
tatgagggat gttggtattc cagaaaattc tcttttgaag agattacaat ttaggtcaaa   9660
acagaaaaat atgtaaaaag ttattgtttt tattagtatt tcatgttctt ttcttttta   9720
aaaatggtat gcttagaact aattaagatt agattagatt agattagaaa ataatcagag   9780
agggatttga tgaatgctaa agcatcatga aaaattcaaa attttttgct tctaattcag   9840
aatcaattaa attcatatta ctataaaaga cagcacgcca gatgtgtgcc agctgaggag   9900
tggataaact gtgtaacgtg agtgctatgt agaaacagaa aggagtgaag ggttgatgtg   9960
cgctgcaaca tcttgaaaac attcggctac atgatggaag ccaggcacaa aaagccacat  10020
attgcatggt tatgtttata tgaaatgttt aaaatacatg gattcttagc aaacagagta  10080
agatgttact tagggtcagg aaaagattaa aaaaaaaaaa actattgatg tggaatgatc  10140
```

-continued

| | |
|---|---|
| ttaatttggg gaaaagacaa tttcctaaga cgaaatagtt gaggtagata tagttatatc | 10200 |
| cctgtggata ttgtaataaa ccagcatgct gtgctctgag aagggcctaa tgaaggggca | 10260 |
| ggaggaagtg aaatgagatg gtagaaagga aagtcatata ccatggcttc tctcgtgggt | 10320 |
| ggaatctaga tatgttaata tattgacata aggaaggaa ttgtttaggg aaggatcaaa | 10380 |
| accaacagga gtgagggaga caataggaac caatgagagg caaagttcat ggtcaatgtg | 10440 |
| tgtggagaca ccataataaa actccttttt tgtttgctaa ctaaaaccac taaaatctaa | 10500 |
| aaacaaaaca tttttgcaca agaattattt attattcaat aaagatgttt aaatggggga | 10560 |
| agttgaagtt cattgatagt ctcataaatc ttaaatgtat ttaaactgct ttttacgttt | 10620 |
| tttattatta attactcttg ctgtcattat tatcatcatc attatcgtca tcatcatcac | 10680 |
| taatgctttt caccatacac aaatgtaggc agaagagtg aatccactta gtgaggcaat | 10740 |
| cttggagagg gaaaggaagc ggatgcgggg cagaggcaca caggaggaca gtgagaggga | 10800 |
| aatgaacaag aaaaaatgtg gacacatgca caaaaattcc atagtccact acattacttt | 10860 |
| gtattctaat attaagaaaa taataaaccc atttctgtgc acttatcacc caggctcaac | 10920 |
| agttatcttg gccacagatc ctgtctcact gcatcctgtc cacctgagtc cacttagcgt | 10980 |
| tctgaatcca atccagggca tgatgcttac tcctacacag aactaaagat taaagagagt | 11040 |
| ttaaaagtaa ccatgacatc tctctgttcc tttagcgata agttcttaat atttatggct | 11100 |
| gcttgtgtat gttctaattt ctctaatatt gtcacattta gttggcaact actttgtttg | 11160 |
| aattgagttg gagttaaggt cccataggat taatctcaac atatttctat atttataaac | 11220 |
| ttttctctct ttgtgaaagt tccttgaga aaacaaatat gcccatatct ttctttacag | 11280 |
| gtcttaaaaa tgagctataa caaagtccaa ataattgaga aggatacttt gtatggactc | 11340 |
| aggagcttga cccggttgca cctggatcac aacaacattg agtttatcaa ccccgaggcg | 11400 |
| ttttacggac tcaccttgct ccgcttggta catctagaag gaaaccggct gacaaagctc | 11460 |
| catccagaca catttgtctc tttgagctat ctccagatat ttaaaacctc cttcattaag | 11520 |
| nacctgtact tgtatgataa cttcattgac ctccctccca aaagaaatgg tctcctctat | 11580 |
| gccaaaccta gaaagccttt acttgcatgg aaacccatgg acctgtgact gccatttaaa | 11640 |
| gtggttgtcc gagtggatgc agggaaaccc aggtaactat cttgtttgtt tgtttctttt | 11700 |
| tttatarkac gtatttcct caatttcatt tagaatgata tcccaaaagt cccccataac | 11760 |
| ctccccccca cttccctacc tacccattcc cattttttgg ccctggcatt ccctgtact | 11820 |
| ggggcatata aagtttgcgt gtccaatgga cctctctttc cagtgatggc caactaggcc | 11880 |
| atcttttgat acatatgcag ctagagtcaa gagctctggg gtactggtta gttcataatg | 11940 |
| ttgttgcacc tacagggttg aa | 11962 |

<210> SEQ ID NO 21
<211> LENGTH: 2828
<212> TYPE: PRT
<213> ORGANISM: homo sapiens

<400> SEQUENCE: 21

Met Pro Lys Arg Ala His Trp Gly Ala Leu Ser Val Val Leu Ile Leu
1               5                   10                  15

Leu Trp Gly His Pro Arg Val Ala Leu Ala Cys Pro His Pro Cys Ala
                20                  25                  30

Cys Tyr Val Pro Ser Glu Val His Cys Thr Phe Arg Ser Leu Ala Ser
            35                  40                  45

-continued

```
Val Pro Ala Gly Ile Ala Arg His Val Glu Arg Ile Asn Leu Gly Phe
 50                  55                  60

Asn Ser Ile Gln Ala Leu Ser Glu Thr Ser Phe Ala Gly Leu Thr Lys
 65                  70                  75                  80

Leu Glu Leu Leu Met Ile His Gly Asn Glu Ile Pro Ser Ile Pro Asp
                 85                  90                  95

Gly Ala Leu Arg Asp Leu Ser Ser Leu Gln Val Phe Lys Phe Ser Tyr
                100                 105                 110

Asn Lys Leu Arg Val Ile Thr Gly Gln Thr Leu Gln Gly Leu Ser Asn
            115                 120                 125

Leu Met Arg Leu His Ile Asp His Asn Lys Ile Glu Phe Ile His Pro
130                 135                 140

Gln Ala Phe Asn Gly Leu Thr Ser Leu Arg Leu Leu His Leu Glu Gly
145                 150                 155                 160

Asn Leu Leu His Gln Leu His Pro Ser Thr Phe Ser Thr Phe Thr Phe
                165                 170                 175

Leu Asp Tyr Phe Arg Leu Ser Thr Ile Arg His Leu Tyr Leu Ala Glu
                180                 185                 190

Asn Met Val Arg Thr Leu Pro Ala Ser Met Leu Arg Asn Met Pro Leu
            195                 200                 205

Leu Glu Asn Leu Tyr Leu Gln Gly Asn Pro Trp Thr Cys Asp Cys Glu
210                 215                 220

Met Arg Trp Phe Leu Glu Trp Asp Ala Lys Ser Arg Gly Ile Leu Lys
225                 230                 235                 240

Cys Lys Lys Asp Lys Ala Tyr Glu Gly Gly Gln Leu Cys Ala Met Cys
                245                 250                 255

Phe Ser Pro Lys Lys Leu Tyr Lys His Glu Ile His Lys Leu Lys Asp
                260                 265                 270

Met Thr Cys Leu Lys Pro Ser Ile Glu Ser Pro Leu Arg Gln Asn Arg
            275                 280                 285

Ser Arg Ser Ile Glu Glu Glu Gln Glu Gln Glu Glu Asp Gly Gly Ser
290                 295                 300

Gln Leu Ile Leu Glu Lys Phe Gln Leu Pro Gln Trp Ser Ile Ser Leu
305                 310                 315                 320

Asn Met Thr Asp Glu His Gly Asn Met Val Asn Leu Val Cys Asp Ile
                325                 330                 335

Lys Lys Pro Met Asp Val Tyr Lys Ile His Leu Asn Gln Thr Asp Pro
                340                 345                 350

Pro Asp Ile Asp Ile Asn Ala Thr Val Ala Leu Asp Phe Glu Cys Pro
            355                 360                 365

Met Thr Arg Glu Asn Tyr Glu Lys Leu Trp Lys Leu Ile Ala Tyr Tyr
370                 375                 380

Ser Glu Val Pro Val Lys Leu His Arg Glu Leu Met Leu Ser Lys Asp
385                 390                 395                 400

Pro Arg Val Ser Tyr Gln Tyr Arg Gln Asp Ala Asp Glu Glu Ala Leu
                405                 410                 415

Tyr Tyr Thr Gly Val Arg Ala Gln Ile Leu Ala Glu Pro Glu Trp Val
                420                 425                 430

Met Gln Pro Ser Ile Asp Ile Gln Leu Asn Arg Arg Gln Ser Thr Ala
            435                 440                 445

Lys Lys Val Leu Leu Ser Tyr Tyr Thr Gln Tyr Ser Gln Thr Ile Ser
450                 455                 460

Thr Lys Asp Thr Arg Gln Ala Arg Gly Arg Ser Trp Val Met Ile Glu
```

```
               465                 470                 475                 480
          Pro Ser Gly Ala Val Gln Arg Asp Gln Thr Val Leu Glu Gly Gly Pro
                          485                 490                 495
          Cys Gln Leu Ser Cys Asn Val Lys Ala Ser Glu Ser Pro Ser Ile Phe
                          500                 505                 510
          Trp Val Leu Pro Asp Gly Ser Ile Leu Lys Ala Pro Met Asp Asp Pro
                          515                 520                 525
          Asp Ser Lys Phe Ser Ile Leu Ser Ser Gly Trp Leu Arg Ile Lys Ser
                          530                 535                 540
          Met Glu Pro Ser Asp Ser Gly Leu Tyr Gln Cys Ile Ala Gln Val Arg
          545                 550                 555                 560
          Asp Glu Met Asp Arg Met Val Tyr Arg Val Leu Val Gln Ser Pro Ser
                              565                 570                 575
          Thr Gln Pro Ala Glu Lys Asp Thr Val Thr Ile Gly Lys Asn Pro Gly
                          580                 585                 590
          Glu Ser Val Thr Leu Pro Cys Asn Ala Leu Ala Ile Pro Glu Ala His
                          595                 600                 605
          Leu Ser Trp Ile Leu Pro Asn Arg Arg Ile Ile Asn Asp Leu Ala Asn
                          610                 615                 620
          Thr Ser His Val Tyr Met Leu Pro Asn Gly Thr Leu Ser Ile Pro Lys
          625                 630                 635                 640
          Val Gln Val Ser Asp Ser Gly Tyr Tyr Arg Cys Val Ala Val Asn Gln
                              645                 650                 655
          Gln Gly Ala Asp His Phe Thr Val Gly Ile Thr Val Thr Lys Lys Gly
                          660                 665                 670
          Ser Gly Leu Pro Ser Lys Arg Gly Arg Pro Gly Ala Lys Ala Leu
                          675                 680                 685
          Ser Arg Val Arg Glu Asp Ile Val Glu Asp Glu Gly Ser Gly Met
          690                 695                 700
          Gly Asp Glu Glu Asn Thr Ser Arg Arg Leu Leu His Pro Lys Asp Gln
          705                 710                 715                 720
          Glu Val Phe Leu Lys Thr Lys Asp Asp Ala Ile Asn Gly Asp Lys Lys
                          725                 730                 735
          Ala Lys Lys Gly Arg Arg Lys Leu Lys Leu Trp Lys His Ser Glu Lys
                          740                 745                 750
          Glu Pro Glu Thr Asn Val Ala Glu Gly Arg Arg Val Phe Glu Ser Arg
                          755                 760                 765
          Arg Arg Ile Asn Met Ala Asn Lys Gln Ile Asn Pro Glu Arg Trp Ala
                          770                 775                 780
          Asp Ile Leu Ala Lys Val Arg Gly Lys Asn Leu Pro Lys Gly Thr Glu
          785                 790                 795                 800
          Val Pro Pro Leu Ile Lys Thr Thr Ser Pro Pro Ser Leu Ser Leu Glu
                          805                 810                 815
          Val Thr Pro Pro Phe Pro Ala Val Ser Pro Pro Ser Ala Ser Pro Val
                          820                 825                 830
          Gln Thr Val Thr Ser Ala Glu Glu Ser Ser Ala Asp Val Pro Leu Leu
                          835                 840                 845
          Gly Glu Glu Glu His Val Leu Gly Thr Ile Ser Ser Ala Ser Met Gly
                          850                 855                 860
          Leu Glu His Asn His Asn Gly Val Ile Leu Val Glu Pro Glu Val Thr
          865                 870                 875                 880
          Ser Thr Pro Leu Glu Glu Val Val Asp Asp Leu Ser Glu Lys Thr Glu
                          885                 890                 895
```

-continued

```
Glu Ile Thr Ser Thr Glu Gly Asp Leu Lys Gly Thr Ala Ala Pro Thr
            900                 905                 910
Leu Ile Ser Glu Pro Tyr Glu Pro Ser Pro Thr Leu His Thr Leu Asp
        915                 920                 925
Thr Val Tyr Glu Lys Pro Thr His Glu Glu Thr Ala Thr Glu Gly Trp
    930                 935                 940
Ser Ala Ala Asp Val Gly Ser Ser Pro Glu Pro Thr Ser Ser Glu Tyr
945                 950                 955                 960
Glu Pro Pro Leu Asp Ala Val Ser Leu Ala Glu Ser Glu Pro Met Gln
                965                 970                 975
Tyr Phe Asp Pro Asp Leu Glu Thr Lys Ser Gln Pro Asp Glu Asp Lys
            980                 985                 990
Met Lys Glu Asp Thr Phe Ala His Leu Thr Pro Thr Pro Thr Ile Trp
            995                 1000                1005
Val Asn Asp Ser Ser Thr Ser Gln Leu Phe Glu Asp Ser Thr Ile
    1010                1015                1020
Gly Glu Pro Gly Val Pro Gly Gln Ser His Leu Gln Gly Leu Thr
    1025                1030                1035
Asp Asn Ile His Leu Val Lys Ser Ser Leu Ser Thr Gln Asp Thr
    1040                1045                1050
Leu Leu Ile Lys Lys Gly Met Lys Glu Met Ser Gln Thr Leu Gln
    1055                1060                1065
Gly Gly Asn Met Leu Glu Gly Asp Pro Thr His Ser Arg Ser Ser
    1070                1075                1080
Glu Ser Glu Gly Gln Glu Ser Lys Ser Ile Thr Leu Pro Asp Ser
    1085                1090                1095
Thr Leu Gly Ile Met Ser Ser Met Ser Pro Val Lys Lys Pro Ala
    1100                1105                1110
Glu Thr Thr Val Gly Thr Leu Leu Asp Lys Asp Thr Thr Thr Val
    1115                1120                1125
Thr Thr Thr Pro Arg Gln Lys Val Ala Pro Ser Ser Thr Met Ser
    1130                1135                1140
Thr His Pro Ser Arg Arg Arg Pro Asn Gly Arg Arg Arg Leu Arg
    1145                1150                1155
Pro Asn Lys Phe Arg His Arg His Lys Gln Thr Pro Pro Thr Thr
    1160                1165                1170
Phe Ala Pro Ser Glu Thr Phe Ser Thr Gln Pro Thr Gln Ala Pro
    1175                1180                1185
Asp Ile Lys Ile Ser Ser Gln Val Glu Ser Ser Leu Val Pro Thr
    1190                1195                1200
Ala Trp Val Asp Asn Thr Val Asn Thr Pro Lys Gln Leu Glu Met
    1205                1210                1215
Glu Lys Asn Ala Glu Pro Thr Ser Lys Gly Thr Pro Arg Arg Lys
    1220                1225                1230
His Gly Lys Arg Pro Asn Lys His Arg Tyr Thr Pro Ser Thr Val
    1235                1240                1245
Ser Ser Arg Ala Ser Gly Ser Lys Pro Ser Pro Ser Pro Glu Asn
    1250                1255                1260
Lys His Arg Asn Ile Val Thr Pro Ser Ser Glu Thr Ile Leu Leu
    1265                1270                1275
Pro Arg Thr Val Ser Leu Lys Thr Glu Gly Pro Tyr Asp Ser Leu
    1280                1285                1290
```

-continued

```
Asp Tyr Met Thr Thr Thr Arg Lys Ile Tyr Ser Ser Tyr Pro Lys
    1295                1300                1305

Val Gln Glu Thr Leu Pro Val Thr Tyr Lys Pro Thr Ser Asp Gly
    1310                1315                1320

Lys Glu Ile Lys Asp Asp Val Ala Thr Asn Val Asp Lys His Lys
    1325                1330                1335

Ser Asp Ile Leu Val Thr Gly Glu Ser Ile Thr Asn Ala Ile Pro
    1340                1345                1350

Thr Ser Arg Ser Leu Val Ser Thr Met Gly Glu Phe Lys Glu Glu
    1355                1360                1365

Ser Ser Pro Val Gly Phe Pro Gly Thr Pro Thr Trp Asn Pro Ser
    1370                1375                1380

Arg Thr Ala Gln Pro Gly Arg Leu Gln Thr Asp Ile Pro Val Thr
    1385                1390                1395

Thr Ser Gly Glu Asn Leu Thr Asp Pro Pro Leu Leu Lys Glu Leu
    1400                1405                1410

Glu Asp Val Asp Phe Thr Ser Glu Phe Leu Ser Leu Thr Val
    1415                1420                1425

Ser Thr Pro Phe His Gln Glu Ala Gly Ser Ser Thr Thr Leu
    1430                1435                1440

Ser Ser Ile Lys Val Glu Val Ala Ser Ser Gln Ala Glu Thr Thr
    1445                1450                1455

Thr Leu Asp Gln Asp His Leu Glu Thr Thr Val Ala Ile Leu Leu
    1460                1465                1470

Ser Glu Thr Arg Pro Gln Asn His Thr Pro Thr Ala Ala Arg Met
    1475                1480                1485

Lys Glu Pro Ala Ser Ser Pro Ser Thr Ile Leu Met Ser Leu
    1490                1495                1500

Gly Gln Thr Thr Thr Thr Lys Pro Ala Leu Pro Ser Pro Arg Ile
    1505                1510                1515

Ser Gln Ala Ser Arg Asp Ser Lys Glu Asn Val Phe Leu Asn Tyr
    1520                1525                1530

Val Gly Asn Pro Glu Thr Glu Ala Thr Pro Val Asn Asn Glu Gly
    1535                1540                1545

Thr Gln His Met Ser Gly Pro Asn Glu Leu Ser Thr Pro Ser Ser
    1550                1555                1560

Asp Arg Asp Ala Phe Asn Leu Ser Thr Lys Leu Glu Leu Glu Lys
    1565                1570                1575

Gln Val Phe Gly Ser Arg Ser Leu Pro Arg Gly Pro Asp Ser Gln
    1580                1585                1590

Arg Gln Asp Gly Arg Val His Ala Ser His Gln Leu Thr Arg Val
    1595                1600                1605

Pro Ala Lys Pro Ile Leu Pro Thr Ala Thr Val Arg Leu Pro Glu
    1610                1615                1620

Met Ser Thr Gln Ser Ala Ser Arg Tyr Phe Val Thr Ser Gln Ser
    1625                1630                1635

Pro Arg His Trp Thr Asn Lys Pro Glu Ile Thr Thr Tyr Pro Ser
    1640                1645                1650

Gly Ala Leu Pro Glu Asn Lys Gln Phe Thr Thr Pro Arg Leu Ser
    1655                1660                1665

Ser Thr Thr Ile Pro Leu Pro Leu His Met Ser Lys Pro Ser Ile
    1670                1675                1680

Pro Ser Lys Phe Thr Asp Arg Arg Thr Asp Gln Phe Asn Gly Tyr
```

-continued

```
            1685                1690                1695

Ser Lys Val Phe Gly Asn Asn Ile Pro Glu Ala Arg Asn Pro
    1700                1705                1710

Val Gly Lys Pro Pro Ser Pro Arg Ile Pro His Tyr Ser Asn Gly
    1715                1720                1725

Arg Leu Pro Phe Phe Thr Asn Lys Thr Leu Ser Phe Pro Gln Leu
    1730                1735                1740

Gly Val Thr Arg Arg Pro Gln Ile Pro Thr Ser Pro Ala Pro Val
    1745                1750                1755

Met Arg Glu Arg Lys Val Ile Pro Gly Ser Tyr Asn Arg Ile His
    1760                1765                1770

Ser His Ser Thr Phe His Leu Asp Phe Gly Pro Pro Ala Pro Pro
    1775                1780                1785

Leu Leu His Thr Pro Gln Thr Thr Gly Ser Pro Ser Thr Asn Leu
    1790                1795                1800

Gln Asn Ile Pro Met Val Ser Ser Thr Gln Ser Ser Ile Ser Phe
    1805                1810                1815

Ile Thr Ser Ser Val Gln Ser Ser Gly Ser Phe His Gln Ser Ser
    1820                1825                1830

Ser Lys Phe Phe Ala Gly Gly Pro Pro Ala Ser Lys Phe Trp Ser
    1835                1840                1845

Leu Gly Glu Lys Pro Gln Ile Leu Thr Lys Ser Pro Gln Thr Val
    1850                1855                1860

Ser Val Thr Ala Glu Thr Asp Thr Val Phe Pro Cys Glu Ala Thr
    1865                1870                1875

Gly Lys Pro Lys Pro Phe Val Thr Trp Thr Lys Val Ser Thr Gly
    1880                1885                1890

Ala Leu Met Thr Pro Asn Thr Arg Ile Gln Arg Phe Glu Val Leu
    1895                1900                1905

Lys Asn Gly Thr Leu Val Ile Arg Lys Val Gln Val Gln Asp Arg
    1910                1915                1920

Gly Gln Tyr Met Cys Thr Ala Ser Asn Leu His Gly Leu Asp Arg
    1925                1930                1935

Met Val Val Leu Leu Ser Val Thr Val Gln Gln Pro Gln Ile Leu
    1940                1945                1950

Ala Ser His Tyr Gln Asp Val Thr Val Tyr Leu Gly Asp Thr Ile
    1955                1960                1965

Ala Met Glu Cys Leu Ala Lys Gly Thr Pro Ala Pro Gln Ile Ser
    1970                1975                1980

Trp Ile Phe Pro Asp Arg Arg Val Trp Gln Thr Val Ser Pro Val
    1985                1990                1995

Glu Ser Arg Ile Thr Leu His Glu Asn Arg Thr Leu Ser Ile Lys
    2000                2005                2010

Glu Ala Ser Phe Ser Asp Arg Gly Val Tyr Lys Cys Val Ala Ser
    2015                2020                2025

Asn Ala Ala Gly Ala Asp Ser Leu Ala Ile Arg Leu His Val Ala
    2030                2035                2040

Ala Leu Pro Pro Val Ile His Gln Glu Lys Leu Glu Asn Ile Ser
    2045                2050                2055

Leu Pro Pro Gly Leu Ser Ile His Ile His Cys Thr Ala Lys Ala
    2060                2065                2070

Ala Pro Leu Pro Ser Val Arg Trp Val Leu Gly Asp Gly Thr Gln
    2075                2080                2085
```

-continued

```
Ile Arg Pro Ser Gln Phe Leu His Gly Asn Leu Phe Val Phe Pro
2090                2095                2100

Asn Gly Thr Leu Tyr Ile Arg Asn Leu Ala Pro Lys Asp Ser Gly
2105                2110                2115

Arg Tyr Glu Cys Val Ala Ala Asn Leu Val Gly Ser Ala Arg Arg
2120                2125                2130

Thr Val Gln Leu Asn Val Gln Arg Ala Ala Ala Asn Ala Arg Ile
2135                2140                2145

Thr Gly Thr Ser Pro Arg Arg Thr Asp Val Arg Tyr Gly Gly Thr
2150                2155                2160

Leu Lys Leu Asp Cys Ser Ala Ser Gly Asp Pro Trp Pro Arg Ile
2165                2170                2175

Leu Trp Arg Leu Pro Ser Lys Arg Met Ile Asp Ala Leu Phe Ser
2180                2185                2190

Phe Asp Ser Arg Ile Lys Val Phe Ala Asn Gly Thr Leu Val Val
2195                2200                2205

Lys Ser Val Thr Asp Lys Asp Ala Gly Asp Tyr Leu Cys Val Ala
2210                2215                2220

Arg Asn Lys Val Gly Asp Asp Tyr Val Leu Lys Val Asp Val
2225                2230                2235

Val Met Lys Pro Ala Lys Ile Glu His Lys Glu Asn Asp His
2240                2245                2250

Lys Val Phe Tyr Gly Gly Asp Leu Lys Val Asp Cys Val Ala Thr
2255                2260                2265

Gly Leu Pro Asn Pro Glu Ile Ser Trp Ser Leu Pro Asp Gly Ser
2270                2275                2280

Leu Val Asn Ser Phe Met Gln Ser Asp Asp Ser Gly Gly Arg Thr
2285                2290                2295

Lys Arg Tyr Val Val Phe Asn Asn Gly Thr Leu Tyr Phe Asn Glu
2300                2305                2310

Val Gly Met Arg Glu Glu Gly Asp Tyr Thr Cys Phe Ala Glu Asn
2315                2320                2325

Gln Val Gly Lys Asp Glu Met Arg Val Arg Val Lys Val Val Thr
2330                2335                2340

Ala Pro Ala Thr Ile Arg Asn Lys Thr Tyr Leu Ala Val Gln Val
2345                2350                2355

Pro Tyr Gly Asp Val Val Thr Val Ala Cys Glu Ala Lys Gly Glu
2360                2365                2370

Pro Met Pro Lys Val Thr Trp Leu Ser Pro Thr Asn Lys Val Ile
2375                2380                2385

Pro Thr Ser Ser Glu Lys Tyr Gln Ile Tyr Gln Asp Gly Thr Leu
2390                2395                2400

Leu Ile Gln Lys Ala Gln Arg Ser Asp Ser Gly Asn Tyr Thr Cys
2405                2410                2415

Leu Val Arg Asn Ser Ala Gly Glu Asp Arg Lys Thr Val Trp Ile
2420                2425                2430

His Val Asn Val Gln Pro Pro Lys Ile Asn Gly Asn Pro Asn Pro
2435                2440                2445

Ile Thr Thr Val Arg Glu Ile Ala Ala Gly Gly Ser Arg Lys Leu
2450                2455                2460

Ile Asp Cys Lys Ala Glu Gly Ile Pro Thr Pro Arg Val Leu Trp
2465                2470                2475
```

| | | | | | | | | | |
|---|---|---|---|---|---|---|---|---|---|
| Ala | Phe 2480 | Pro | Glu | Gly | Val 2485 | Val | Leu | Pro | Ala Pro 2490 | Tyr | Tyr | Gly | Asn |
| Arg | Ile 2495 | Thr | Val | His | Gly 2500 | Asn | Gly | Ser | Leu Asp 2505 | Ile | Arg | Ser | Leu |
| Arg | Lys 2510 | Ser | Asp | Ser | Val 2515 | Gln | Leu | Val | Cys Met 2520 | Ala | Arg | Asn | Glu |
| Gly | Gly 2525 | Glu | Ala | Arg | Leu 2530 | Ile | Val | Gln | Leu Thr 2535 | Val | Leu | Glu | Pro |
| Met | Glu 2540 | Lys | Pro | Ile | Phe 2545 | His | Asp | Pro | Ile Ser 2550 | Glu | Lys | Ile | Thr |
| Ala | Met 2555 | Ala | Gly | His | Thr 2560 | Ile | Ser | Leu | Asn Cys 2565 | Ser | Ala | Ala | Gly |
| Thr | Pro 2570 | Thr | Pro | Ser | Leu 2575 | Val | Trp | Val | Leu Pro 2580 | Asn | Gly | Thr | Asp |
| Leu | Gln 2585 | Ser | Gly | Gln | Gln 2590 | Leu | Gln | Arg | Phe Tyr 2595 | His | Lys | Ala | Asp |
| Gly | Met 2600 | Leu | His | Ile | Ser 2605 | Gly | Leu | Ser | Ser Val 2610 | Asp | Ala | Gly | Ala |
| Tyr | Arg 2615 | Cys | Val | Ala | Arg 2620 | Asn | Ala | Ala | Gly His 2625 | Thr | Glu | Arg | Leu |
| Val | Ser 2630 | Leu | Lys | Val | Gly 2635 | Leu | Lys | Pro | Glu Ala 2640 | Asn | Lys | Gln | Tyr |
| His | Asn 2645 | Leu | Val | Ser | Ile 2650 | Ile | Asn | Gly | Glu Thr 2655 | Leu | Lys | Leu | Pro |
| Cys | Thr 2660 | Pro | Pro | Gly | Ala 2665 | Gly | Gln | Gly | Arg Phe 2670 | Ser | Trp | Thr | Leu |
| Pro | Asn 2675 | Gly | Met | His | Leu 2680 | Glu | Gly | Pro | Gln Thr 2685 | Leu | Gly | Arg | Val |
| Ser | Leu 2690 | Leu | Asp | Asn | Gly 2695 | Thr | Leu | Thr | Val Arg 2700 | Glu | Ala | Ser | Val |
| Phe | Asp 2705 | Arg | Gly | Thr | Tyr 2710 | Val | Cys | Arg | Met Glu 2715 | Thr | Glu | Tyr | Gly |
| Pro | Ser 2720 | Val | Thr | Ser | Ile 2725 | Pro | Val | Ile | Val Ile 2730 | Ala | Tyr | Pro | Pro |
| Arg | Ile 2735 | Thr | Ser | Glu | Pro 2740 | Thr | Pro | Val | Ile Tyr 2745 | Thr | Arg | Pro | Gly |
| Asn | Thr 2750 | Val | Lys | Leu | Asn 2755 | Cys | Met | Ala | Met Gly 2760 | Ile | Pro | Lys | Ala |
| Asp | Ile 2765 | Thr | Trp | Glu | Leu 2770 | Pro | Asp | Lys | Ser His 2775 | Leu | Lys | Ala | Gly |
| Val | Gln 2780 | Ala | Arg | Leu | Tyr 2785 | Gly | Asn | Arg | Phe Leu 2790 | His | Pro | Gln | Gly |
| Ser | Leu 2795 | Thr | Ile | Gln | His 2800 | Ala | Thr | Gln | Arg Asp 2805 | Ala | Gly | Phe | Tyr |
| Lys | Cys 2810 | Met | Ala | Lys | Asn 2815 | Ile | Leu | Gly | Ser Asp 2820 | Ser | Lys | Thr | Thr |
| Tyr | Ile 2825 | His | Val | Phe | | | | | | | | | |

```
<210> SEQ ID NO 22
<211> LENGTH: 9645
<212> TYPE: DNA
<213> ORGANISM: homo sapiens
<220> FEATURE:
<221> NAME/KEY: misc_feature
```

-continued

<222> LOCATION: (1)..(9645)
<223> OTHER INFORMATION: 'n' can be any nucleotide 'a', 'c', 'g' or 't'.

<400> SEQUENCE: 22

| | | | | |
|---|---|---|---|---|
| atgcccaagc | gcgcgcactg | gggggccctc | tccgtggtgc | tgatcctgct ttggggccat | 60 |
| ccgcgagtgg | cgctggcctg | cccgcatcct | tgtgcctgct | acgtccccag cgaggtccac | 120 |
| tgcacgttcc | gatccctggc | ttccgtgccc | gctggcattg | ctagacacgt ggaaagaatc | 180 |
| aatttggggt | taatagcat | acaggccctg | tcagaaacct | catttgcagg actgaccaag | 240 |
| ttggagctac | ttatgattca | cggcaatgag | atcccaagca | tccccgatgg agctttaaga | 300 |
| gacctcagct | ctcttcaggt | tttcaagttc | agctacaaca | agctgagagt gatcacagga | 360 |
| cagaccctcc | agggtctctc | taacttaatg | aggctgcaca | ttgaccacaa caagatcgag | 420 |
| tttatccacc | ctcaagcttt | caacggctta | acgtctctga | ggctactcca tttggaagga | 480 |
| aatctcctcc | accagctgca | ccccagcacc | ttctccacgt | tcacatttt ggattatttc | 540 |
| agactctcca | ccataaggca | cctctactta | gcagagaaca | tggttagaac tcttcctgcc | 600 |
| agcatgcttc | ggaacatgcc | gcttctggag | aatctttact | gcagggaaa tccgtggacc | 660 |
| tgcgattgtg | agatgagatg | gttttggaa | tgggatgcaa | aatccagagg aattctgaag | 720 |
| tgtaaaaagg | acaaagctta | tgaaggcggt | cagttgtgtg | caatgtgctt cagtccaaag | 780 |
| aagttgtaca | aacatgagat | acacaagctg | aaggacatga | cttgtctgaa gccttcaata | 840 |
| gagtccctc | tgagacagaa | caggagcagg | agtattgagg | aggagcaaga acaggaagag | 900 |
| gatggtggca | gccagctcat | cctggagaaa | ttccaactgc | cccagtggag catctctttg | 960 |
| aatatgaccg | acgagcacgg | gaacatggtg | aacttggtct | gtgacatcaa gaaaccaatg | 1020 |
| gatgtgtaca | agattcactt | gaaccaaacg | gatcctccag | atattgacat aaatgcaaca | 1080 |
| gttgccttgg | actttgagtg | tccaatgacc | cgagaaaact | atgaaaagct atggaaattg | 1140 |
| atagcatact | acagtgaagt | tcccgtgaag | ctacacagag | agctcatgct cagcaaagac | 1200 |
| cccagagtca | gctaccagta | caggcaggat | gctgatgagg | aagctctta ctacacaggt | 1260 |
| gtgagagccc | agattcttgc | agaaccagaa | tgggtcatgc | agccatccat agatatccag | 1320 |
| ctgaaccgac | gtcagagtac | ggccaagaag | gtgctacttt | cctactacac ccagtattct | 1380 |
| caaacaatat | ccaccaaaga | tacaaggcag | gctcggggca | aagctgggt aatgattgag | 1440 |
| cctagtggag | ctgtgcaaag | agatcagact | gtcctggaag | ggggtccatg ccagttgagc | 1500 |
| tgcaacgtga | aagcttctga | gagtccatct | atcttctggg | tgcttccaga tggctccatc | 1560 |
| ctgaaagcgc | ccatggatga | cccagacagc | aagttctcca | ttctcagcag tggctggctg | 1620 |
| aggatcaagt | ccatggagcc | atctgactca | ggcttgtacc | agtgcattgc tcaagtgagg | 1680 |
| gatgaaatgg | accgcatggt | atatagggta | cttgtgcagt | ctccctccac tcagccagcc | 1740 |
| gagaaagaca | cagtgacaat | tggcaagaac | ccaggggagt | cggtgacatt gccttgcaat | 1800 |
| gctttagcaa | tacccgaagc | ccaccttagc | tggattcttc | aaacagaag gataattaat | 1860 |
| gatttggcta | acacatcaca | tgtatacatg | ttgccaaatg | gaactctttc catcccaaag | 1920 |
| gtccaagtca | gtgatagtgg | ttactacaga | tgtgtggctg | tcaaccagca aggggcagac | 1980 |
| cattttacgg | tgggaatcac | agtgaccaag | aaagggtctg | gcttgccatc caaaagaggc | 2040 |
| agacgcccag | gtgcaaaggc | tctttccaga | gtcagagaag | acatcgtgga ggatgaaggg | 2100 |
| ggctcgggca | tggagatga | agagaacact | tcaaggagac | ttctgcatcc aaaggaccaa | 2160 |
| gaggtgttcc | tcaaaacaaa | ggatgatgcc | atcaatggag | acaagaaagc caagaaaggg | 2220 |

```
agaagaaagc tgaaactctg gaagcattcg gaaaaagaac cagagaccaa tgttgcagaa    2280
ggtcgcagag tgtttgaatc tagacgaagg ataaacatgg caaacaaaca gattaatccg    2340
gagcgctggg ctgatatttt agccaaagtc cgtgggaaaa atctccctaa gggcacagaa    2400 gtaccccgt tgattaaaac cacaagtcct ccatccttga gcctagaagt cacaccacct     2460
tttcctgctg tttctccccc ctcagcatcc cctgtgcaga cagtaaccag tgctgaagaa    2520
tcctcagcag atgtacctct acttggtgaa gaagagcacg ttttgggtac catttcctca    2580
gccagcatgg ggctagaaca caaccacaat ggagttattc ttgttgaacc tgaagtaaca    2640
agcacacctc tggaggaagt tgttgatgac ctttctgaga agactgagga gataacttcc    2700
actgaaggag acctgaaggg gacagcagcc cctacactta tatctgagcc ttatgaacca    2760
tctcctactc tgcacacatt agacacagtc tatgaaaagc ccacccatga agagacggca    2820
acagagggtt ggtctgcagc agatgttgga tcgtcaccag agcccacatc cagtgagtat    2880
gagcctccat tggatgctgt ctccttggct gagtctgagc ccatgcaata ctttgaccca    2940
gatttggaga ctaagtcaca accagatgag gataagatga agaagacac ctttgcacac     3000 cttactccaa cccccaccat ctgggttaat gactccagta catcacagtt atttgaggat    3060
tctactatag gggaaccagg tgtcccaggc caatcacatc tacaaggact gacagacaac    3120
atccaccttg tgaaaagtag tctaagcact caagacacct tactgattaa aaagggtatg    3180
aaagagatgt ctcagacact acagggagga aatatgctag agggagaccc cacacactcc    3240
agaagttctg agagtgaggg ccaagagagc aaatccatca ctttgcctga ctccacactg    3300
ggtataatga gcagtatgtc tccagttaag aagcctgcgg aaaccacagt tggtaccctc    3360
ctagacaaag acaccacaac agtaacaaca acaccaaggc aaaaagttgc tccgtcatcc    3420
accatgagca ctcacccttc tcgaaggaga cccaacggga gaggagatt acgccccaac     3480 aaattccgcc accggcacaa gcaaacccca cccacaactt tgccccatc agagactttt      3540 tctactcaac caactcaagc acctgacatt aagatttcaa gtcaagtgga gagttctctg    3600
gttcctacag cttgggtgga taacacagtt aatacccca aacagttgga aatggagaag      3660
aatgcagaac ccacatccaa gggaacacca cggagaaaac acgggaagag gccaaacaaa    3720
catcgatata cccttctac agtgagctca agagcgtccg gatccaagcc cagcccttct      3780
ccagaaaata acatagaaa cattgttact cccagttcag aaactatact tttgcctaga     3840
actgtttctc tgaaaactga gggcccttat gattccttag attacatgac aaccaccaga    3900
aaaatatatt catcttaccc taaagtccaa gagacacttc cagtcacata taaacccaca    3960
tcagatggaa aagaaattaa ggatgatgtt gccacaaatg ttgacaaaca taaaagtgac    4020
attttagtca ctggtgaatc aattactaat gccataccaa cttctcgctc cttggtctcc    4080
actatgggag aatttaagga agaatcctct cctgtaggct ttccaggaac tccaacctgg    4140
aatccctcaa ggacggccca gcctgggagg ctacagacag acatacctgt taccacttct    4200
ggggaaaatc ttacagaccc tccccttctt aaagagcttg aggatgtgga tttcacttcc    4260
gagtttttgt cctctttgac agtctccaca ccatttcacc aggaagaagc tggttcttcc    4320
acaactctct caagcataaa agtggaggtg gcttcaagtc aggcagaaac caccaccctt    4380
gatcaagatc atcttgaaac cactgtggct attctccttt ctgaaactag accacagaat    4440
cacaccccta ctgctgcccg gatgaaggag ccagcatcct cgtccccatc cacaattctc    4500
atgtctttgg gacaaaccac caccactaag ccagcacttc ccagtccaag aatatctcaa    4560
gcatctagag attccaagga aaatgttttc ttgaattatg tggggaatcc agaaacagaa    4620
```

```
gcaaccccag tcaacaatga aggaacacag catatgtcag ggccaaatga attatcaaca    4680
ccctcttccg accgggatgc atttaacttg tctacaaagc tggaattgga aaagcaagta    4740
tttggtagta ggagtctacc acgtggccca gatagccaac gccaggatgg aagagttcat    4800
gcttctcatc aactaaccag agtccctgcc aaacccatcc taccaacagc aacagtgagg    4860
ctacctgaaa tgtccacaca aagcgcttcc agatactttg taacttccca gtcacctcgt    4920
cactggacca acaaaccgga ataactaca tatccttctg gggctttgcc agagaacaaa     4980
cagtttacaa ctccaagatt atcaagtaca acaattcctc tcccattgca catgtccaaa    5040
cccagcattc ctagtaagtt tactgaccga agaactgacc aattcaatgg ttactccaaa    5100
gtgtttggaa ataacaacat ccctgaggca agaaacccag ttggaaagcc tcccagtcca    5160
agaattcctc attattccaa tggaagactc cctttcttta ccaacaagac tctttctttt    5220
ccacagttgg gagtcacccg agacccccag atacccactt ctcctgcccc agtaatgaga    5280
gagagaaaag ttattccagg ttcctacaac aggatacatt cccatagcac cttccatctg    5340
gactttggcc ctccggcacc tccgttgttg cacactccgc agaccacggg atcccctca    5400 actaacttac agaatatccc tatggtctct tccacccaga gttctatctc ctttataaca    5460
tcttctgtcc agtcctcagg aagcttccac cagagcagct caaagttctt tgcaggagga    5520
cctcctgcat ccaaattctg gtctcttggg gaaaagcccc aaatcctcac caagtcccca    5580
cagactgtgt ccgtcaccgc tgagacagac actgtgttcc cctgtgaggc aacaggaaaa    5640
ccaaagcctt tcgttacttg gacaaaggtt ccacaggag ctcttatgac tccgaatacc     5700
aggatacaac ggtttgaggt tctcaagaac ggtaccttag tgatacggaa ggttcaagta    5760
caagatcgag gccagtatat gtgcaccgcc agcaacctgc acggcctgga caggatggtg    5820
gtcttgcttt cggtcaccgt gcagcaacct caaatcctag cctcccacta ccaggacgtc    5880
actgtctacc tgggagacac cattgcaatg gagtgtctgg ccaaagggac cccagccccc    5940
caaatttcct ggatcttccc tgacaggagg gtgtggcaaa ctgtgtcccc cgtggagagc    6000
cgcatcaccc tgcacgaaaa ccggacccct tccatcaagg aggcgtcctt ctcagacaga    6060
ggcgtctata agtgcgtggc cagcaatgca gccggggcgg acagcctggc catccgcctg    6120
cacgtggcgg cactgccccc cgttatccac caggagaagc tggagaacat ctcgctgccc    6180
ccggggctca gcattcacat tcactgcact gccaaggctg cgccctgcc cagcgtgcgc     6240 tgggtgctcg gggacggtac ccagatccgc ccctcgcagt tcctccacgg gaacttgttt    6300
gttttcccca acgggacgct ctacatccgc aacctcgcgc caaggacag cgggcgctat     6360 gagtgcgtgg ccgccaacct ggtaggctcc gcgcgcagga cggtgcagct gaacgtgcag    6420
cgtgcagcag ccaacgcgcg catcacgggc acctccccgc ggaggacgga cgtcaggtac    6480
ggaggaaccc tcaagctgga ctgcagcgcc tcggggacc cctggccgcg catcctctgg    6540
aggctgccgt ccaagaggat gatcgacgcg ctcttcagtt ttgatagcag aatcaaggtg    6600
tttgccaatg ggaccctggt ggtgaaatca gtgacggaca agatgccgg agattacctg    6660 tgcgtagctc gaaataaggt tggtgatgac tacgtggtgc tcaaagtgga tgtggtgatg    6720
aaaccggcca agattgaaca caggaggag aacgaccaca aagtcttcta cggggtgac     6780 ctgaaagtgg actgtgtggc caccgggctt cccaatcccg agatctcctg gagcctccca    6840
gacgggagtc tggtgaactc cttcatgcag tcggatgaca cgcgtggacg caccaagcgc    6900
tatgtcgtct tcaacaatgg gacactctac tttaacgaag tggggatgag ggaggaagga    6960
```

```
gactacacct gctttgctga aaatcaggtc gggaaggacg agatgagagt cagagtcaag      7020
gtggtgacag cgcccgccac catccggaac aagacttact tggcggttca ggtgccctat      7080
ggagacgtgg tcactgtagc ctgtgaggcc aaaggagaac ccatgcccaa ggtgacttgg      7140
ttgtccccaa ccaacaaggt gatccccacc tcctctgaga agtatcagat ataccaagat      7200
ggcactctcc ttattcagaa agcccagcgt tctgacagcg gcaactacac ctgcctggtc      7260
aggaacagcg cgggagagga taggaagacg gtgtggattc acgtcaacgt ccagccaccc      7320
aagatcaacg gtaaccccaa ccccatcacc accgtgcggg agatagcagc cggggggcagt      7380 cggaaactga ttgactgcaa agctgaaggc atccccaccc cgagggtgtt atgggctttt      7440
cccgagggtg tggttctgcc agctccatac tatggaaacc ggatcactgt ccatggcaac      7500
ggttccctgg acatcaggag tttgaggaag agcgactccg tccagctggt atgcatggca      7560
cgcaacgagg gagggaggc gaggttgatc gtgcagctca ctgtcctgga gcccatggag      7620
aaacccatct tccacgaccc gatcagcgag aagatcacgg ccatggcggg ccacaccatc      7680
agcctcaact gctctgccgc ggggacccg acacccagcc tggtgtgggt ccttcccaat      7740
ggcaccgatc tgcagagtgg acagcagctg cagcgcttct accacaaggc tgacggcatg      7800
ctacacatta gcggtctctc ctcggtggac gctggggcct accgctgcgt ggcccgcaat      7860
gccgctggcc acacggagag gctggtctcc ctgaaggtgg gactgaagcc agaagcaaac      7920
aagcagtatc ataacctggt cagcatcatc aatggtgaga ccctgaagct cccctgcacc      7980
cctcccgggg ctgggcaggg acgtttctcc tggacgctcc ccaatggcat gcatctggag      8040 ggccccaaa ccctgggacg cgtttctctt ctggacaatg gcaccctcac ggttcgtgag      8100
gcctcggtgt ttgacagggg tacctatgta tgcaggatgg agacggagta cggcccttcg      8160
gtcaccagca tccccgtgat tgtgatcgcc tatcctcccc ggatcaccag cgagcccacc      8220
ccggtcatct acacccggcc cgggaacacc gtgaaactga actgcatggc tatggggatt      8280
cccaaagctg acatcacgtg ggagttaccg gataagtcgc atctgaaggc aggggttcag      8340
gctcgtctgt atggaaacag atttcttcac ccccagggat cactgaccat ccagcatgcc      8400
acacagagag atgccggctt ctacaagtgc atggcaaaaa acattctcgg cagtgactcc      8460
aaaacaactt catccacgt cttctgaaat gtggattcca gaatgattgc ttaggaactg      8520
acaacaaagc ggggtttgta agggaagcca ggttggggaa taggagctct taaataatgt      8580
gtcacagtgc atggtggcct ctggtggggtt tcaagttgag gttgatcttg atctacaatt      8640
gttgggaaaa ggaagcaatg cagacacgag aaggagggct cagccttgct gagacacttt      8700
cttttgtgtt tacatcatgc caggggcttc attcagggtg tctgtgctct gactgcaatt      8760
tttcttcttt tgcaaatgcc actcgactgc cttcataagc gtccatagga tatctgagga      8820
acattcatca aaaataagcc atagacatga caacacctc actacccat gaagacgca      8880 tcacctagtt aacctgctgc agtttttaca tgatagactt tgttccagat tgacaagtca      8940
tctttcagtt atttcctctg tcacttcaaa actccagctt gcccaataag gatttagaac      9000
cagagtgact gatatatata tatatatttt aattcagagt tacatacata cagctaccat      9060
tttatatgaa aaagaaaaa catttcttcc tggaactcac tttttatata atgtttata       9120 tatatatttt ttcctttcaa atcagacgat gagactagaa ggagaaatac tttctgtctt      9180
attaaaatta ataaattatt ggtctttaca agacttggat acattacagc agacatggaa      9240 atataattt aaaaaatttc tctccaacct ccttcaaatt cagtcaccac tgttatatta      9300
ccttctccag gaaccctcca gtggggaagg ctgcgatatt agattttcctt gtatgcaaag      9360
```

-continued

| | |
|---|---|
| tttttgttga aagctgtgct cagaggaggt gagaggagag gaaggagaaa actgcatcat | 9420 |
| aactttacag aattgaatct agagtcttcc ccgaaaagcc cagaaacttc tctgcagtat | 9480 |
| ctggcttgtc catctggtct aaggtggctg cttcttcccc agccatgagt cagtttgtgc | 9540 |
| ccatgaataa tacacgacct gttatttcca tgactgcttt actgtatttt taaggtcaat | 9600 |
| atactgtaca tttgataata aaataatatt ctcccaaaaa aaaaa | 9645 |

<210> SEQ ID NO 23
<211> LENGTH: 7770
<212> TYPE: DNA
<213> ORGANISM: homo sapien

<400> SEQUENCE: 23

| | |
|---|---|
| atgaaggtaa aaggcagagg aatcacctgc ttgctggtct cctttgctgt gatctgcctg | 60 |
| gtcgccaccc ctgggggcaa ggcctgtcct cgccgctgtg cctgttatat gcctacggag | 120 |
| gtacactgca catttcggta cctgacttcc atcccagaca gcatcccgcc caatgtggaa | 180 |
| cgcatcaatt taggatacaa cagcttggtt agattgatgg aaacagattt ttctggcctg | 240 |
| accaaactgg agttactcat gcttcacagc aatggcattc acacaatccc tgacaagacc | 300 |
| ttctcagatt tgcaggcctt gcaggtctta aaaatgagct ataataaagt ccgaaaactt | 360 |
| cagaaagata cttttttatgg cctcaggagc ttgacacgat gcacatggga ccacaacaat | 420 |
| attgagttta taaacccaga ggttttttat gggctcaact ttctccgcct ggtgcacttg | 480 |
| gaaggaaatc agctcactaa gctccaccca gatacatttg tctctttgag ctacctccag | 540 |
| atatttaaaa tctcttttcat taagttccta tacttgtctg ataacttcct gacctccctc | 600 |
| cctcaagaga tggtctccta tatgcctgac ctagacagcc tttacctgca tggaaaccca | 660 |
| tggacctgtg attgccattt aaagtggttg tctgactgga tacaggagaa gccagatgta | 720 |
| ataaaatgca aaaagatag aagtccctct agtgctcagc agtgtccact ttgcatgaac | 780 |
| cctaggactt ctaaaggcaa gccgttagct atggtctcag ctgcagcttt ccagtgtgcc | 840 |
| aagccaacca ttgactcatc cctgaaatca aagagcctga ctattctgga agacagtagt | 900 |
| tctgctttca tctctcccca aggtttcatg gcacccttttg gctccctcac tttgaatatg | 960 |
| acagatcagt ctgaaaatga agctaacatg gtctgcagta ttcaaaagcc tcaaggaca | 1020 |
| tcacccattg cattcactga gaaaatgac tacatcgtgc taaatacttc attttcaaca | 1080 |
| tttttggtgt gcaacataga ttacggtcac attcagccag tgtggcaaat tttggctttg | 1140 |
| tacagtgatt ctcctctgat actagaaagg agccacttgc ttagtgaaac accgcagctc | 1200 |
| tattacaaat ataaacaggt ggctcctaag cctgaagaca tttttaccaa catagaggca | 1260 |
| gatctcagag cagatccctc ttggttaatg caagaccaaa tttccttgca gctgaacaga | 1320 |
| actgccacca cattcagtac attacagatc cagtactcca gtgatgctca aatcacttta | 1380 |
| ccaagagcag agatgaggcc agtgaaacac aaatggacta tgatttcaag ggataacaat | 1440 |
| actaagctgg aacatactgt cttggtaggt ggaaccgttg gcctgaactg cccaggccaa | 1500 |
| ggagaccccca ccccacacgt ggattggctt ctagctgatg aagtaaagt gagagcccct | 1560 |
| tatgtcagtg aggatggacg gatcctaata gacaaaagtg aaaattgga actccagatg | 1620 |
| gctgatagtt ttgacacagg cgtatatcac tgtataagca gcaattatga tgatgcagat | 1680 |
| attctcacct ataggataac tgtggtagaa ccttttggtcg aagcctatca ggaaaatggg | 1740 |
| attcatcaca cagttttcat tggtgaaaca cttgatcttc catgccattc tactggtatc | 1800 |

-continued

```
ccagatgcct ctattagctg ggttattcca ggaaacaatg tgctctatca gtcatcaaga      1860
gacaagaaag ttctaaacaa tggcacatta agaatattac aggtcacccc gaaagaccaa      1920
ggttattatc gctgtgtggc agccaaccca tcagggttg attttttgat tttccaagtt       1980
tcagtcaaga tgaaaggaca aaggcccttg gagcatgatg gagaaacaga gggatctgga     2040
cttgatgagt ccaatcctat tgctcatctt aaggagccac caggtgcaca actccgtaca     2100
tctgctctga tggaggctga ggttggaaaa cacacctcaa gcacaagtaa gaggcacaac     2160
tatcgggaat taacactcca gcgacgtgga gattcaacac atcgacgttt tagggagaat     2220
aggaggcatt tccctccctc tgctaggaga attgacccac aacattgggc ggcactgttg     2280
gagaaagcta aaagaatgc tatgccagac aagcgagaaa ataccacagt gagcccaccc     2340
ccagtggtca cccaactccc aaacatacct ggtgaagaag acgattcctc aggcatgctc     2400
gctctacatg aggaatttat ggtcccggcc actaaagctt tgaaccttcc agcaaggaca     2460
gtgactgctg actccagaac aatatctgat agtcctatga caaacataaa ttatggcaca     2520
gaattctctc ctgttgtgaa ttcacaaata ctaccacctg aagaacccac agatttcaaa     2580
ctgtctactc ctattaaaac tacagccatg tcaaagaata taaacccaac catgtcaagc     2640
caaatacaag gcacaaccaa tcaacattca tccactgtct ttccactgct acttggagca     2700
actgaatttc aggactctga ccagatggga agaggaagag agcatttcca aagtagaccc     2760
ccaataacag taaggactat gatcaaagat gtcaatgtca aaatgcttag tagcaccacc     2820
aacaaactat tattagagtc agtaaatacc acaaatagtc atcagacatc tgtaagagaa     2880
gtgagtgaac ccaggcacaa tcacttctat tctcacacta ctcaaatact tagcacctcc     2940
acgttccctt cagatccaca cacagctgct cattctcagt ttccgatccc tagaaatagt     3000
acagttaaca tcccgctgtt cagacgcttt gggaggcaga ggaaaattgg cggaagggg      3060 cggattatca gcccatatag aactccagtt ctgcgacggc atagatacag cattttcagg     3120
tcaacaacca gaggttcttc tgaaaaaagc actactgcat tctcagccac agtgctcaat     3180
gtgacatgtc tgtcctgtct tcccagggag aggctcacca ctgccacagc agcattgtct     3240
tttccaagtg ctgctcccat caccttcccc aaagctgaca ttgctagagt cccatcagaa     3300
gagtctacaa ctctagtcca gaatccacta ttactacttg agaacaaacc cagtgtagag     3360
aaaacaacac ccacaataaa atatttcagg actgaaattt cccaagtgac tccaactggt     3420
gcagtcatga catatgctcc aacatccata cccatggaaa aaactcacaa agtaaacgcc     3480
agttacccac gtgtgtctag caccaatgaa gctaaaagag attcagtgat tacatcgtca     3540
ctttcaggtg ctatcaccaa gccaccaatg actattatag ccattacaag gtttttcaaga    3600 aggaaaattc cctggcaaca gaactttgta ataaccata acccaaaagg cagattaagg      3660
aatcaacata aagttagttt acaaaaaagc acagctgtga tgcttcctaa acatctcct      3720 gctttaccac agagacaaag ttcccctttc catttcacca cacttcaac aagtgtgatg     3780 caaattccat ctaataccctt gactaccgct caccacacta cgaccaaaac acacaatcct    3840
ggaagtcttc caacaaagaa ggagcttccc ttcccacccc ttaaccctat gcttcctagt     3900
attataagca aagactcaag tacaaaaagc atcatatcaa cgcaaacagc aataccagca     3960
acaactccta ccttccctgc atctgtcatc acttatgaaa cccaaacaga gagatctaga     4020
gcacaaacaa tacaaagaga acaggagcct caaaagaaga acaggactga cccaaacatc     4080
tctccagacc agagttctgg cttcactaca cccactgcta tgcacctcc tgctctggca     4140 ttcactcatt ccccaccaga aaacacaact gggatttcaa gcacaatcag ttttcattca     4200
```

```
agaactctta atctgacaga tgtgattgaa gaactagccc aagcaagtac tcagactttg   4260
aagagcacaa ttgcttctga acaactttg  tccagcaaat cacaccagag taccacaact   4320
aggaaagcat cattagacac tcccatacca ccattcttga gcagcagtgc tactctaatg   4380
ccagttccca tctcccctcc ctttactcag agagcagtta ctgacacacg tggcgactcc   4440
catttccggc ttatgacaaa tacagtggtc aagctgcacg aatcctcaag gcacaatctc   4500
caaatgccaa gttcacaatt ggaaccactc acttcatcta cctctaatct gttacattct   4560
actcccatgc cagcactaac aacagttaaa tcacagaatt ccaaattaac tccatctccc   4620
tgggcagaat accaattttg gcacaaacca tactcagaca ttgctgaaaa aggcaaaaag   4680
ccagaagtaa gcatgttggc tactacaggc ctgtccgagg ccaccactct tgtttcagat   4740
tgggatggac agaagaacac aaagaagagt gactttgata agaaaccagt tcaagaagca   4800
acaacttcca aactccttcc ctttgactct ttgtctaggt atatatttga aaagcccagg   4860
atagttggag gaaaagctgc aagttttact attccagcta actcagatgc ctttcttccc   4920
tgtgaagctg ttggaaatcc cctgcccacc attcattgga ccagagtttc aggacttgat   4980
ttatctagag gaaaccagaa tagcagggtc caggttctcc ccaatggtac cctgtccatc   5040
cagagggtgg aaaattcagga ccgcggacag tacttgtgtt ccgcatccaa tctgtttggc   5100
acagaccacc ttcatgtcac cttgtctgtg gtttcctatc ctcccaggat cctggagaga   5160
cgtaccaaag agatcacagt tcattccgga agcactgtgg aactgaagtg cagagcagaa   5220
ggtaggccaa gccctacagt tacctggatt cttgcaaacc aaacagttgt ctcagaatca   5280
tcccagggaa gtaggcaggc tgtggtgacg gttgacggaa cattggtcct ccacaatctc   5340
agtatttatg accgtggctt ttacaaatgt gtggccagca acccaggtgg ccaggattca   5400
ctgctggtta aaatacaagt cattgcagca ccacctgtta ttctagagca aaggaggcaa   5460
gtcattgtag gcacttgggg tgaaagttta aaactgccct gtactgcaaa aggaactcct   5520
cagcccagcg tttactgggt cctctctgat ggcactgaag tgaaaccatt acagtttacc   5580
aattccaagt tgttcttatt ttcaaatggg actttgtata taagaaacct agcctcttca   5640
gacaggggca cttatgaatg cattgctacc agttccactg gttcggagcg aagagtagta   5700
atgcttacaa tggaagagcg agtgaccagc cccaggatag aagctgcatc ccagaaaagg   5760
actgaagtga attttgggga caaattacta ctgaactgct cagccactgg ggagcccaaa   5820
ccccaaataa tgtggaggtt accatccaag gctgtggtcg accagtggag ctggatccac   5880
gtctacccta atggatccct gtttattgga tcagtaacag aaaaagacag tggtgtctac   5940
ttgtgtgtgg caagaaacaa aatgggggat gatctgatac tgatgcatgt tagcctaaga   6000
ctgaaacctg ccaaaattga ccacaagcag tattttagaa agcaagtgct ccatgggaaa   6060
gatttccaag tagattgcaa agcttccggc tccccagtgc cagagatatc ttggagtttg   6120
cctgatggaa ccatgatcaa caatgcaatg caagccgatg acagtggcca caggactagg   6180
agatataccc ttttcaacaa tggaactttt acttcaaca  aagttggggt agcggaggaa   6240
ggagattata cttgctatgc ccagaacacc ctagggaaag atgaaatgaa ggtccactta   6300
acagttataa cagctgctcc ccggataagg cagagtaaca aaaccaacaa gagaatcaaa   6360
gctggagaca cagctgtcct tgactgtgag gtcactgggg atcccaaacc aaaaatattt   6420
tggttgctgc cttccaatga catgattccc ttctccattg ataggtacac atttcatgcc   6480
aatgggtctt tgaccatcaa caaagtgaaa ctgctcgatt ctggagagta cgtatgtgta   6540
```

-continued

```
gcccgaaatc ccagtgggga tgacaccaaa atgtacaaac tggatgtggt ctctaaacct      6600
ccattaatca atggtctgta tacaaacaga actgttatta aagccacagc tgtgagacat      6660
tccaaaaaac actttgactg cagagctgaa gggacaccat ctcctgaagt catgtggatc      6720
atgccagaca atattttcct cacagcccca tactatggaa gcagaatcac agtccataaa      6780
aatgaaccct tggaaattag gaatgtgagg ctttcagatt cagccgactt tatctgtgtg      6840
gcccgaaatg aaggtggaga gagcgtgttg gtagtacagt tagaagtact ggaaatgctg      6900
agaagaccga catttagaaa tccatttaat gaaaaaatag ttgcccagct gggaaagtcc      6960
acagcattga attgctctgt tgatggtaac ccaccacctg aaataatctg gattttacca      7020
aatggcacac gattttccaa tggaccacaa agttatcagt atctgatagc aagcaatggt      7080
tcttttatca tttctaaaac aactcggag gatgcaggaa atatcgctg tgcagctagg       7140 aataaagttg gctatattga gaaattagtc atattagaaa ttggccagaa gccagttatt      7200
cttacctatg caccagggac agtaaaaggc atcagtggga atctctatc actgcattgt       7260 gtgtctgatg gaatccctaa gccaaatatc aaatggacta tgccaagtgg ttatgtagta      7320
gacaggcctc aaattaatgg gaaatacata ttgcatgaca atggcacctt agtcattaaa      7380
gaagcaacag cttatgacag aggaaactat atctgtaagg ctcaaaatag tgttggtcat      7440
acactgatta ctgttccagt aatgattgta gcctaccctc cccgaattac aaatcgtcca      7500
cccaggagta ttgtcaccag gacaggggca gcctttcagc tccactgtgt ggccttggga      7560
gttcccaagc cagaaatcac atgggagatg cctgaccact cccttctctc aacggcaagt      7620
aaagagagga cacatggaag tgagcagctt cacttacaag gtaccctagt cattcagaat      7680
ccccaaacct ccgattctgg gatatacaaa tgcacagcaa agaacccact tggtagtgat      7740
tatgcagcaa cgtatattca agtaatctga                                      7770
```

<210> SEQ ID NO 24
<211> LENGTH: 2589
<212> TYPE: PRT
<213> ORGANISM: homo sapien

<400> SEQUENCE: 24

```
Met Lys Val Lys Gly Arg Gly Ile Thr Cys Leu Leu Val Ser Phe Ala
1               5                   10                  15

Val Ile Cys Leu Val Ala Thr Pro Gly Gly Lys Ala Cys Pro Arg Arg
            20                  25                  30

Cys Ala Cys Tyr Met Pro Thr Glu Val His Cys Thr Phe Arg Tyr Leu
        35                  40                  45

Thr Ser Ile Pro Asp Ser Ile Pro Pro Asn Val Glu Arg Ile Asn Leu
    50                  55                  60

Gly Tyr Asn Ser Leu Val Arg Leu Met Glu Thr Asp Phe Ser Gly Leu
65                  70                  75                  80

Thr Lys Leu Glu Leu Leu Met Leu His Ser Asn Gly Ile His Thr Ile
                85                  90                  95

Pro Asp Lys Thr Phe Ser Asp Leu Gln Ala Leu Gln Val Leu Lys Met
            100                 105                 110

Ser Tyr Asn Lys Val Arg Lys Leu Gln Lys Asp Thr Phe Tyr Gly Leu
        115                 120                 125

Arg Ser Leu Thr Arg Leu His Met Asp His Asn Asn Ile Glu Phe Ile
    130                 135                 140

Asn Pro Glu Val Phe Tyr Gly Leu Asn Phe Leu Arg Leu Val His Leu
145                 150                 155                 160
```

-continued

```
Glu Gly Asn Gln Leu Thr Lys Leu His Pro Asp Thr Phe Val Ser Leu
                165                 170                 175

Ser Tyr Leu Gln Ile Phe Lys Ile Ser Phe Ile Lys Phe Leu Tyr Leu
            180                 185                 190

Ser Asp Asn Phe Leu Thr Ser Leu Pro Gln Glu Met Val Ser Tyr Met
        195                 200                 205

Pro Asp Leu Asp Ser Leu Tyr Leu His Gly Asn Pro Trp Thr Cys Asp
    210                 215                 220

Cys His Leu Lys Trp Leu Ser Asp Trp Ile Gln Glu Lys Pro Asp Val
225                 230                 235                 240

Ile Lys Cys Lys Lys Asp Arg Ser Pro Ser Ala Gln Gln Cys Pro
                245                 250                 255

Leu Cys Met Asn Pro Arg Thr Ser Lys Gly Lys Pro Leu Ala Met Val
            260                 265                 270

Ser Ala Ala Ala Phe Gln Cys Ala Lys Pro Thr Ile Asp Ser Ser Leu
        275                 280                 285

Lys Ser Lys Ser Leu Thr Ile Leu Glu Asp Ser Ser Ser Ala Phe Ile
290                 295                 300

Ser Pro Gln Gly Phe Met Ala Pro Phe Gly Ser Leu Thr Leu Asn Met
305                 310                 315                 320

Thr Asp Gln Ser Gly Asn Glu Ala Asn Met Val Cys Ser Ile Gln Lys
                325                 330                 335

Pro Ser Arg Thr Ser Pro Ile Ala Phe Thr Glu Glu Asn Asp Tyr Ile
            340                 345                 350

Val Leu Asn Thr Ser Phe Ser Thr Phe Leu Val Cys Asn Ile Asp Tyr
        355                 360                 365

Gly His Ile Gln Pro Val Trp Gln Ile Leu Ala Leu Tyr Ser Asp Ser
    370                 375                 380

Pro Leu Ile Leu Glu Arg Ser His Leu Ser Glu Thr Pro Gln Leu
385                 390                 395                 400

Tyr Tyr Lys Tyr Lys Gln Val Ala Pro Lys Pro Glu Asp Ile Phe Thr
                405                 410                 415

Asn Ile Glu Ala Asp Leu Arg Ala Asp Pro Ser Trp Leu Met Gln Asp
            420                 425                 430

Gln Ile Ser Leu Gln Leu Asn Arg Thr Ala Thr Thr Phe Ser Thr Leu
        435                 440                 445

Gln Ile Gln Tyr Ser Ser Asp Ala Gln Ile Thr Leu Pro Arg Ala Glu
    450                 455                 460

Met Arg Pro Val Lys His Lys Trp Thr Met Ile Ser Arg Asp Asn Asn
465                 470                 475                 480

Thr Lys Leu Glu His Thr Val Leu Val Gly Thr Val Gly Leu Asn
                485                 490                 495

Cys Pro Gly Gln Gly Asp Pro Thr Pro His Val Asp Trp Leu Leu Ala
            500                 505                 510

Asp Gly Ser Lys Val Arg Ala Pro Tyr Val Ser Glu Asp Gly Arg Ile
        515                 520                 525

Leu Ile Asp Lys Ser Gly Lys Leu Glu Leu Gln Met Ala Asp Ser Phe
    530                 535                 540

Asp Thr Gly Val Tyr His Cys Ile Ser Ser Asn Tyr Asp Asp Ala Asp
545                 550                 555                 560

Ile Leu Thr Tyr Arg Ile Thr Val Val Glu Pro Leu Val Glu Ala Tyr
                565                 570                 575
```

```
Gln Glu Asn Gly Ile His His Thr Val Phe Ile Gly Glu Thr Leu Asp
            580                 585                 590

Leu Pro Cys His Ser Thr Gly Ile Pro Asp Ala Ser Ile Ser Trp Val
        595                 600                 605

Ile Pro Gly Asn Asn Val Leu Tyr Gln Ser Ser Arg Asp Lys Lys Val
610                 615                 620

Leu Asn Asn Gly Thr Leu Arg Ile Leu Gln Val Thr Pro Lys Asp Gln
625                 630                 635                 640

Gly Tyr Tyr Arg Cys Val Ala Ala Asn Pro Ser Gly Val Asp Phe Leu
                645                 650                 655

Ile Phe Gln Val Ser Val Lys Met Lys Gly Gln Arg Pro Leu Glu His
            660                 665                 670

Asp Gly Glu Thr Glu Gly Ser Gly Leu Asp Glu Ser Asn Pro Ile Ala
            675                 680                 685

His Leu Lys Glu Pro Pro Gly Ala Gln Leu Arg Thr Ser Ala Leu Met
    690                 695                 700

Glu Ala Glu Val Gly Lys His Thr Ser Ser Thr Ser Lys Arg His Asn
705                 710                 715                 720

Tyr Arg Glu Leu Thr Leu Gln Arg Arg Gly Asp Ser Thr His Arg Arg
                725                 730                 735

Phe Arg Glu Asn Arg Arg His Phe Pro Pro Ser Ala Arg Arg Ile Asp
            740                 745                 750

Pro Gln His Trp Ala Ala Leu Leu Glu Lys Ala Lys Lys Asn Ala Met
        755                 760                 765

Pro Asp Lys Arg Glu Asn Thr Thr Val Ser Pro Pro Val Val Thr
770                 775                 780

Gln Leu Pro Asn Ile Pro Gly Glu Glu Asp Ser Ser Gly Met Leu
785                 790                 795                 800

Ala Leu His Glu Glu Phe Met Val Pro Ala Thr Lys Ala Leu Asn Leu
                805                 810                 815

Pro Ala Arg Thr Val Thr Ala Asp Ser Arg Thr Ile Ser Asp Ser Pro
            820                 825                 830

Met Thr Asn Ile Asn Tyr Gly Thr Glu Phe Ser Pro Val Val Asn Ser
            835                 840                 845

Gln Ile Leu Pro Pro Glu Glu Pro Thr Asp Phe Lys Leu Ser Thr Ala
850                 855                 860

Ile Lys Thr Thr Ala Met Ser Lys Asn Ile Asn Pro Thr Met Ser Ser
865                 870                 875                 880

Gln Ile Gln Gly Thr Thr Asn Gln His Ser Ser Thr Val Phe Pro Leu
                885                 890                 895

Leu Leu Gly Ala Thr Glu Phe Gln Asp Ser Asp Gln Met Gly Arg Gly
                900                 905                 910

Arg Glu His Phe Gln Ser Arg Pro Pro Ile Thr Val Arg Thr Met Ile
            915                 920                 925

Lys Asp Val Asn Val Lys Met Leu Ser Ser Thr Thr Asn Lys Leu Leu
        930                 935                 940

Leu Glu Ser Val Asn Thr Thr Asn Ser His Gln Thr Ser Val Arg Glu
945                 950                 955                 960

Val Ser Glu Pro Arg His Asn His Phe Tyr Ser His Thr Thr Gln Ile
                965                 970                 975

Leu Ser Thr Ser Thr Phe Pro Ser Asp Pro His Thr Ala Ala His Ser
            980                 985                 990

Gln Phe Pro Ile Pro Arg Asn Ser  Thr Val Asn Ile Pro  Leu Phe Arg
```

-continued

```
             995                 1000                1005
Arg Phe Gly Arg Gln Arg Lys Ile Gly Gly Arg Gly Arg Ile Ile
        1010            1015            1020

Ser Pro Tyr Arg Thr Pro Val Leu Arg Arg His Arg Tyr Ser Ile
        1025            1030            1035

Phe Arg Ser Thr Thr Arg Gly Ser Ser Glu Lys Ser Thr Thr Ala
        1040            1045            1050

Phe Ser Ala Thr Val Leu Asn Val Thr Cys Leu Ser Cys Leu Pro
        1055            1060            1065

Arg Glu Arg Leu Thr Thr Ala Thr Ala Ala Leu Ser Phe Pro Ser
        1070            1075            1080

Ala Ala Pro Ile Thr Phe Pro Lys Ala Asp Ile Ala Arg Val Pro
        1085            1090            1095

Ser Glu Glu Ser Thr Thr Leu Val Gln Asn Pro Leu Leu Leu Leu
        1100            1105            1110

Glu Asn Lys Pro Ser Val Glu Lys Thr Thr Pro Thr Ile Lys Tyr
        1115            1120            1125

Phe Arg Thr Glu Ile Ser Gln Val Thr Pro Thr Gly Ala Val Met
        1130            1135            1140

Thr Tyr Ala Pro Thr Ser Ile Pro Met Glu Lys Thr His Lys Val
        1145            1150            1155

Asn Ala Ser Tyr Pro Arg Val Ser Ser Thr Asn Glu Ala Lys Arg
        1160            1165            1170

Asp Ser Val Ile Thr Ser Ser Leu Ser Gly Ala Ile Thr Lys Pro
        1175            1180            1185

Pro Met Thr Ile Ile Ala Ile Thr Arg Phe Ser Arg Arg Lys Ile
        1190            1195            1200

Pro Trp Gln Gln Asn Phe Val Asn Asn His Asn Pro Lys Gly Arg
        1205            1210            1215

Leu Arg Asn Gln His Lys Val Ser Leu Gln Lys Ser Thr Ala Val
        1220            1225            1230

Met Leu Pro Lys Thr Ser Pro Ala Leu Pro Gln Arg Gln Ser Ser
        1235            1240            1245

Pro Phe His Phe Thr Thr Leu Ser Thr Ser Val Met Gln Ile Pro
        1250            1255            1260

Ser Asn Thr Leu Thr Thr Ala His His Thr Thr Thr Lys Thr His
        1265            1270            1275

Asn Pro Gly Ser Leu Pro Thr Lys Lys Glu Leu Pro Phe Pro Pro
        1280            1285            1290

Leu Asn Pro Met Leu Pro Ser Ile Ile Ser Lys Asp Ser Ser Thr
        1295            1300            1305

Lys Ser Ile Ile Ser Thr Gln Thr Ala Ile Pro Ala Thr Thr Pro
        1310            1315            1320

Thr Phe Pro Ala Ser Val Ile Thr Tyr Glu Thr Gln Thr Glu Arg
        1325            1330            1335

Ser Arg Ala Gln Thr Ile Gln Arg Glu Gln Glu Pro Gln Lys Lys
        1340            1345            1350

Asn Arg Thr Asp Pro Asn Ile Ser Pro Asp Gln Ser Ser Gly Phe
        1355            1360            1365

Thr Thr Pro Thr Ala Met Thr Pro Pro Ala Leu Ala Phe Thr His
        1370            1375            1380

Ser Pro Pro Glu Asn Thr Thr Gly Ile Ser Ser Thr Ile Ser Phe
        1385            1390            1395
```

-continued

```
His Ser Arg Thr Leu Asn Leu Thr Asp Val Ile Glu Glu Leu Ala
    1400            1405                1410

Gln Ala Ser Thr Gln Thr Leu Lys Ser Thr Ile Ala Ser Glu Thr
    1415            1420                1425

Thr Leu Ser Ser Lys Ser His Gln Ser Thr Thr Thr Arg Lys Ala
    1430            1435                1440

Ser Leu Asp Thr Pro Ile Pro Pro Phe Leu Ser Ser Ser Ala Thr
    1445            1450                1455

Leu Met Pro Val Pro Ile Ser Pro Pro Phe Thr Gln Arg Ala Val
    1460            1465                1470

Thr Asp Thr Arg Gly Asp Ser His Phe Arg Leu Met Thr Asn Thr
    1475            1480                1485

Val Val Lys Leu His Glu Ser Ser Arg His Asn Leu Gln Met Pro
    1490            1495                1500

Ser Ser Gln Leu Glu Pro Leu Thr Ser Ser Thr Ser Asn Leu Leu
    1505            1510                1515

His Ser Thr Pro Met Pro Ala Leu Thr Thr Val Lys Ser Gln Asn
    1520            1525                1530

Ser Lys Leu Thr Pro Ser Pro Trp Ala Glu Tyr Gln Phe Trp His
    1535            1540                1545

Lys Pro Tyr Ser Asp Ile Ala Glu Lys Gly Lys Lys Pro Glu Val
    1550            1555                1560

Ser Met Leu Ala Thr Thr Gly Leu Ser Glu Ala Thr Thr Leu Val
    1565            1570                1575

Ser Asp Trp Asp Gly Gln Lys Asn Thr Lys Lys Ser Asp Phe Asp
    1580            1585                1590

Lys Lys Pro Val Gln Glu Ala Thr Thr Ser Lys Leu Leu Pro Phe
    1595            1600                1605

Asp Ser Leu Ser Arg Tyr Ile Phe Glu Lys Pro Arg Ile Val Gly
    1610            1615                1620

Gly Lys Ala Ala Ser Phe Thr Ile Pro Ala Asn Ser Asp Ala Phe
    1625            1630                1635

Leu Pro Cys Glu Ala Val Gly Asn Pro Leu Pro Thr Ile His Trp
    1640            1645                1650

Thr Arg Val Ser Gly Leu Asp Leu Ser Arg Gly Asn Gln Asn Ser
    1655            1660                1665

Arg Val Gln Val Leu Pro Asn Gly Thr Leu Ser Ile Gln Arg Val
    1670            1675                1680

Glu Ile Gln Asp Arg Gly Gln Tyr Leu Cys Ser Ala Ser Asn Leu
    1685            1690                1695

Phe Gly Thr Asp His Leu His Val Thr Leu Ser Val Val Ser Tyr
    1700            1705                1710

Pro Pro Arg Ile Leu Glu Arg Thr Lys Glu Ile Thr Val His
    1715            1720                1725

Ser Gly Ser Thr Val Glu Leu Lys Cys Arg Ala Glu Gly Arg Pro
    1730            1735                1740

Ser Pro Thr Val Thr Trp Ile Leu Ala Asn Gln Thr Val Val Ser
    1745            1750                1755

Glu Ser Ser Gln Gly Ser Arg Gln Ala Val Val Thr Val Asp Gly
    1760            1765                1770

Thr Leu Val Leu His Asn Leu Ser Ile Tyr Asp Arg Gly Phe Tyr
    1775            1780                1785
```

-continued

| | | | | | | | | | | | |
|---|---|---|---|---|---|---|---|---|---|---|---|
| Lys | Cys | Val | Ala | Ser | Asn | Pro | Gly | Gly | Gln | Asp | Ser | Leu | Leu | Val |
| 1790 | | | | 1795 | | | | | 1800 | | |
| Lys | Ile | Gln | Val | Ile | Ala | Ala | Pro | Pro | Val | Ile | Leu | Glu | Gln | Arg |
| 1805 | | | | 1810 | | | | | 1815 | | |
| Arg | Gln | Val | Ile | Val | Gly | Thr | Trp | Gly | Glu | Ser | Leu | Lys | Leu | Pro |
| 1820 | | | | 1825 | | | | | 1830 | | |
| Cys | Thr | Ala | Lys | Gly | Thr | Pro | Gln | Pro | Ser | Val | Tyr | Trp | Val | Leu |
| 1835 | | | | 1840 | | | | | 1845 | | |
| Ser | Asp | Gly | Thr | Glu | Val | Lys | Pro | Leu | Gln | Phe | Thr | Asn | Ser | Lys |
| 1850 | | | | 1855 | | | | | 1860 | | |
| Leu | Phe | Leu | Phe | Ser | Asn | Gly | Thr | Leu | Tyr | Ile | Arg | Asn | Leu | Ala |
| 1865 | | | | 1870 | | | | | 1875 | | |
| Ser | Ser | Asp | Arg | Gly | Thr | Tyr | Glu | Cys | Ile | Ala | Thr | Ser | Ser | Thr |
| 1880 | | | | 1885 | | | | | 1890 | | |
| Gly | Ser | Glu | Arg | Arg | Val | Val | Met | Leu | Thr | Met | Glu | Glu | Arg | Val |
| 1895 | | | | 1900 | | | | | 1905 | | |
| Thr | Ser | Pro | Arg | Ile | Glu | Ala | Ala | Ser | Gln | Lys | Arg | Thr | Glu | Val |
| 1910 | | | | 1915 | | | | | 1920 | | |
| Asn | Phe | Gly | Asp | Lys | Leu | Leu | Leu | Asn | Cys | Ser | Ala | Thr | Gly | Glu |
| 1925 | | | | 1930 | | | | | 1935 | | |
| Pro | Lys | Pro | Gln | Ile | Met | Trp | Arg | Leu | Pro | Ser | Lys | Ala | Val | Val |
| 1940 | | | | 1945 | | | | | 1950 | | |
| Asp | Gln | Trp | Ser | Trp | Ile | His | Val | Tyr | Pro | Asn | Gly | Ser | Leu | Phe |
| 1955 | | | | 1960 | | | | | 1965 | | |
| Ile | Gly | Ser | Val | Thr | Glu | Lys | Asp | Ser | Gly | Val | Tyr | Leu | Cys | Val |
| 1970 | | | | 1975 | | | | | 1980 | | |
| Ala | Arg | Asn | Lys | Met | Gly | Asp | Asp | Leu | Ile | Leu | Met | His | Val | Ser |
| 1985 | | | | 1990 | | | | | 1995 | | |
| Leu | Arg | Leu | Lys | Pro | Ala | Lys | Ile | Asp | His | Lys | Gln | Tyr | Phe | Arg |
| 2000 | | | | 2005 | | | | | 2010 | | |
| Lys | Gln | Val | Leu | His | Gly | Lys | Asp | Phe | Gln | Val | Asp | Cys | Lys | Ala |
| 2015 | | | | 2020 | | | | | 2025 | | |
| Ser | Gly | Ser | Pro | Val | Pro | Glu | Ile | Ser | Trp | Ser | Leu | Pro | Asp | Gly |
| 2030 | | | | 2035 | | | | | 2040 | | |
| Thr | Met | Ile | Asn | Asn | Ala | Met | Gln | Ala | Asp | Asp | Ser | Gly | His | Arg |
| 2045 | | | | 2050 | | | | | 2055 | | |
| Thr | Arg | Arg | Tyr | Thr | Leu | Phe | Asn | Asn | Gly | Thr | Leu | Tyr | Phe | Asn |
| 2060 | | | | 2065 | | | | | 2070 | | |
| Lys | Val | Gly | Val | Ala | Glu | Glu | Gly | Asp | Tyr | Thr | Cys | Tyr | Ala | Gln |
| 2075 | | | | 2080 | | | | | 2085 | | |
| Asn | Thr | Leu | Gly | Lys | Asp | Glu | Met | Lys | Val | His | Leu | Thr | Val | Ile |
| 2090 | | | | 2095 | | | | | 2100 | | |
| Thr | Ala | Ala | Pro | Arg | Ile | Arg | Gln | Ser | Asn | Lys | Thr | Asn | Lys | Arg |
| 2105 | | | | 2110 | | | | | 2115 | | |
| Ile | Lys | Ala | Gly | Asp | Thr | Ala | Val | Leu | Asp | Cys | Glu | Val | Thr | Gly |
| 2120 | | | | 2125 | | | | | 2130 | | |
| Asp | Pro | Lys | Pro | Lys | Ile | Phe | Trp | Leu | Leu | Pro | Ser | Asn | Asp | Met |
| 2135 | | | | 2140 | | | | | 2145 | | |
| Ile | Ser | Phe | Ser | Ile | Asp | Arg | Tyr | Thr | Phe | His | Ala | Asn | Gly | Ser |
| 2150 | | | | 2155 | | | | | 2160 | | |
| Leu | Thr | Ile | Asn | Lys | Val | Lys | Leu | Leu | Asp | Ser | Gly | Glu | Tyr | Val |
| 2165 | | | | 2170 | | | | | 2175 | | |
| Cys | Val | Ala | Arg | Asn | Pro | Ser | Gly | Asp | Asp | Thr | Lys | Met | Tyr | Lys |

```
                2180              2185              2190
Leu Asp Val Val Ser Lys Pro Pro Leu Ile Asn Gly Leu Tyr Thr
    2195              2200              2205
Asn Arg Thr Val Ile Lys Ala Thr Ala Val Arg His Ser Lys Lys
    2210              2215              2220
His Phe Asp Cys Arg Ala Glu Gly Thr Pro Ser Pro Glu Val Met
    2225              2230              2235
Trp Ile Met Pro Asp Asn Ile Phe Leu Thr Ala Pro Tyr Tyr Gly
    2240              2245              2250
Ser Arg Ile Thr Val His Lys Asn Gly Thr Leu Glu Ile Arg Asn
    2255              2260              2265
Val Arg Leu Ser Asp Ser Ala Asp Phe Ile Cys Val Ala Arg Asn
    2270              2275              2280
Glu Gly Gly Glu Ser Val Leu Val Val Gln Leu Glu Val Leu Glu
    2285              2290              2295
Met Leu Arg Arg Pro Thr Phe Arg Asn Pro Phe Asn Glu Lys Ile
    2300              2305              2310
Val Ala Gln Leu Gly Lys Ser Thr Ala Leu Asn Cys Ser Val Asp
    2315              2320              2325
Gly Asn Pro Pro Pro Glu Ile Ile Trp Ile Leu Pro Val Gly Thr
    2330              2335              2340
Arg Phe Ser Asn Gly Pro Gln Ser Tyr Gln Tyr Leu Ile Ala Ser
    2345              2350              2355
Asn Gly Ser Phe Ile Ile Ser Lys Thr Thr Arg Glu Asp Ala Gly
    2360              2365              2370
Lys Tyr Arg Cys Ala Ala Arg Asn Lys Val Gly Tyr Ile Glu Lys
    2375              2380              2385
Leu Val Ile Leu Glu Ile Gly Gln Lys Pro Val Ile Leu Thr Tyr
    2390              2395              2400
Ala Pro Gly Thr Val Lys Gly Ile Ser Gly Glu Ser Leu Ser Leu
    2405              2410              2415
His Cys Val Ser Asp Gly Ile Pro Lys Pro Asn Ile Lys Trp Thr
    2420              2425              2430
Met Pro Ser Gly Tyr Val Val Asp Arg Pro Gln Ile Asn Gly Lys
    2435              2440              2445
Tyr Ile Leu His Asp Asn Gly Thr Leu Val Ile Lys Glu Ala Thr
    2450              2455              2460
Ala Tyr Asp Arg Gly Asn Tyr Ile Cys Lys Ala Gln Asn Ser Val
    2465              2470              2475
Gly His Thr Leu Ile Thr Val Pro Val Met Ile Val Ala Tyr Pro
    2480              2485              2490
Pro Arg Ile Thr Asn Arg Pro Pro Arg Ser Ile Val Thr Arg Thr
    2495              2500              2505
Gly Ala Ala Phe Gln Leu His Cys Val Ala Leu Gly Val Pro Lys
    2510              2515              2520
Pro Glu Ile Thr Trp Glu Met Pro Asp His Ser Leu Leu Ser Thr
    2525              2530              2535
Ala Ser Lys Glu Arg Thr His Gly Ser Glu Gln Leu His Leu Gln
    2540              2545              2550
Gly Thr Leu Val Ile Gln Asn Pro Gln Thr Ser Asp Ser Gly Ile
    2555              2560              2565
Tyr Lys Cys Thr Ala Lys Asn Pro Leu Gly Ser Asp Tyr Ala Ala
    2570              2575              2580
```

-continued

```
Thr Tyr  Ile Gln Val Ile
    2585

<210> SEQ ID NO 25
<211> LENGTH: 663
<212> TYPE: PRT
<213> ORGANISM: Rattus Species
<220> FEATURE:
<221> NAME/KEY: misc_feature
<222> LOCATION: (322)..(322)
<223> OTHER INFORMATION: "x" can be any amino acid
<220> FEATURE:
<221> NAME/KEY: misc_feature
<222> LOCATION: (323)..(323)
<223> OTHER INFORMATION: "x" can be any amino acid

<400> SEQUENCE: 25

Met Gln Val Arg Gly Arg Glu Val Ser Gly Leu Leu Ile Ser Leu Thr
1               5                   10                  15

Ala Val Cys Leu Val Val Thr Pro Gly Ser Arg Ala Cys Pro Arg Arg
            20                  25                  30

Cys Ala Cys Tyr Val Pro Thr Glu Val His Cys Thr Phe Arg Tyr Leu
        35                  40                  45

Thr Ser Ile Pro Asp Gly Ile Pro Ala Asn Val Glu Arg Ile Asn Leu
    50                  55                  60

Gly Tyr Asn Ser Leu Thr Arg Leu Thr Glu Asn Asp Phe Asp Gly Leu
65                  70                  75                  80

Ser Lys Leu Glu Leu Leu Met Leu His Ser Asn Gly Ile His Arg Val
                85                  90                  95

Ser Asp Lys Thr Phe Ser Gly Leu Gln Ser Leu Gln Val Leu Lys Met
            100                 105                 110

Ser Tyr Asn Lys Val Gln Ile Ile Arg Lys Asp Thr Phe Tyr Gly Leu
        115                 120                 125

Gly Ser Leu Val Arg Leu His Leu Asp His Asn Asn Ile Glu Phe Ile
    130                 135                 140

Asn Pro Glu Ala Phe Tyr Gly Leu Thr Ser Leu Arg Leu Val His Leu
145                 150                 155                 160

Glu Gly Asn Arg Leu Thr Lys Leu His Pro Asp Thr Phe Val Ser Leu
                165                 170                 175

Ser Tyr Leu Gln Ile Phe Lys Thr Ser Phe Ile Lys Tyr Leu Phe Leu
            180                 185                 190

Ser Asp Asn Phe Leu Thr Ser Leu Pro Lys Glu Met Val Ser Tyr Met
        195                 200                 205

Pro Asn Leu Glu Ser Leu Tyr Leu His Gly Asn Pro Trp Thr Cys Asp
    210                 215                 220

Cys His Leu Lys Trp Leu Ser Glu Trp Met Gln Gly Asn Pro Asp Ile
225                 230                 235                 240

Ile Lys Cys Lys Lys Asp Arg Ser Ser Ser Pro Gln Gln Cys Pro
                245                 250                 255

Leu Cys Met Asn Pro Arg Ile Ser Lys Gly Arg Pro Phe Ala Met Val
            260                 265                 270

Pro Ser Gly Ala Phe Leu Cys Thr Lys Pro Thr Ile Asp Pro Ser Leu
        275                 280                 285

Lys Ser Lys Ser Leu Val Thr Gln Glu Asp Asn Gly Ser Ala Ser Thr
    290                 295                 300

Ser Pro Gln Asp Phe Ile Glu Pro Phe Gly Ser Leu Ser Leu Asn Met
305                 310                 315                 320
```

```
Thr Xaa Xaa Ser Gly Asn Lys Ala Asp Met Val Cys Ser Ile Gln Lys
            325                 330                 335

Pro Ser Arg Thr Ser Pro Thr Ala Phe Thr Glu Glu Asn Asp Tyr Ile
            340                 345                 350

Met Leu Asn Ala Ser Phe Ser Thr Asn Leu Val Cys Ser Val Asp Tyr
            355                 360                 365

Asn His Ile Gln Pro Val Trp Gln Leu Leu Ala Leu Tyr Ser Asp Ser
    370                 375                 380

Pro Leu Ile Leu Glu Arg Lys Pro Gln Leu Thr Glu Thr Pro Ser Leu
385                 390                 395                 400

Ser Ser Arg Tyr Lys Gln Val Ala Leu Arg Pro Glu Asp Ile Phe Thr
                405                 410                 415

Ser Ile Glu Ala Asp Val Arg Ala Asp Pro Phe Trp Phe Gln Gln Glu
            420                 425                 430

Lys Ile Val Leu Gln Leu Asn Arg Thr Ala Thr Thr Leu Ser Thr Leu
                435                 440                 445

Gln Ile Gln Phe Ser Thr Asp Ala Gln Ile Ala Leu Pro Arg Ala Glu
    450                 455                 460

Met Arg Ala Glu Arg Leu Lys Trp Thr Met Ile Leu Met Met Asn Asn
465                 470                 475                 480

Pro Lys Leu Glu Arg Thr Val Leu Val Gly Gly Thr Ile Ala Leu Ser
                485                 490                 495

Cys Pro Gly Lys Gly Asp Pro Ser Pro His Leu Glu Trp Leu Leu Ala
            500                 505                 510

Asp Gly Ser Lys Val Arg Ala Pro Tyr Val Ser Glu Asp Gly Arg Ile
            515                 520                 525

Leu Ile Asp Lys Asn Gly Lys Leu Glu Leu Gln Met Ala Asp Ser Phe
    530                 535                 540

Asp Ala Gly Leu Tyr His Cys Ile Ser Thr Asn Asp Ala Asp Ala Asp
545                 550                 555                 560

Val Leu Thr Tyr Arg Ile Thr Val Val Glu Pro Tyr Gly Glu Ser Thr
                565                 570                 575

His Asp Ser Gly Val Gln His Thr Val Val Thr Gly Glu Thr Leu Asp
            580                 585                 590

Leu Pro Cys Leu Ser Thr Gly Val Pro Asp Ala Ser Ile Ser Trp Ile
    595                 600                 605

Leu Pro Gly Asn Thr Val Phe Ser Gln Pro Ser Arg Asp Arg Gln Ile
    610                 615                 620

Leu Asn Asn Gly Thr Leu Arg Ile Leu Gln Val Thr Pro Lys Asp Gln
625                 630                 635                 640

Gly His Tyr Gln Cys Val Ala Ala Asn Pro Ser Gly Ala Asp Phe Ser
                645                 650                 655

Ser Phe Lys Val Ser Val Gln
            660

<210> SEQ ID NO 26
<211> LENGTH: 2469
<212> TYPE: DNA
<213> ORGANISM: Homo sapiens

<400> SEQUENCE: 26
gcggccgcca cacccgccac cagttcgcca tgaaggtaaa aggcagagga atcacctgct      60
tgctggtctc ctttgctgtg atctgcctgg tcgccacccc tggggggcaag gcctgtcctc     120
```

-continued

```
gccgctgtgc ctgttatatg cctacggagg tacactgcac atttcggtac ctgacttcca    180
tcccagacag catcccgccc aatgtggaac gcatcaattt aggatacaac agcttggtta    240
gattgatgga acagatttt tctggcctga ccaaactgga gttactcatg cttcacagca     300
atggcattca cacaatccct gacaagacct tctcagattt gcaggccttg caggtcttaa    360
aaatgagcta taataaagtc cgaaaacttc agaaagatac ttttttatggc ctcaggagct    420
tgacacgatt gcacatggac cacaacaata ttgagtttat aaacccagag gttttttatg    480
ggctcaactt tctccgcctg gtgcacttgg aaggaaatca gctcactaag ctccacccag    540
atacatttgt ctctttgagc tacctccaga tatttaaaat ctctttcatt aagttcctat    600
acttgtctga taacttcctg acctccctcc ctcaagagat ggtctcctat atgcctgacc    660
tagacagcct ttacctgcat ggaaacccat ggacctgtga ttgccattta agtggttgt     720
ctgactggat acaggagaag ccagatgtaa taaaatgcaa aaagataga agtccctcta     780
gtgctcagca gtgtccactt tgcatgaacc ctaggacttc taaaggcaag ccgttagcta    840
tggtctcagc tgcagctttc cagtgtgcca agccaaccat tgactcatcc ctgaaatcaa    900
agagcctgac tattctggaa gacagtagtt ctgctttcat ctctcccaa ggtttcatgg      960
cacccttggg ctccctcact ttgaatatga cagatcagtc tggaaatgaa gctaacatgg   1020
tctgcagtat tcaaaagccc tcaaggacat cacccattgc attcactgaa gaaaatgact   1080
acatcgtgct aaatacttca ttttcaacat ttttggtgtg caacatagat tacggtcaca   1140
ttcagccagt gtggcaaatt ttggctttgt acagtgattc tcctctgata ctagaaagga   1200
gccacttgct tagtgaaaca ccgcagctct attacaaata taaacaggtg gctcctaagc   1260
ctgaagacat ttttaccaac atagaggcag atctcagagc agatccctct tggttaatgc   1320
aagaccaaat ttccttgcag ctgaacagaa ctgccaccac attcagtaca ttacagatcc   1380
agtactccag tgatgctcaa atcactttac caagagcaga gatgaggcca gtgaaacaca   1440
aatggactat gatttcaagg gataacaata ctaagctgga acatactgtc ttggtaggtg   1500
gaaccgttgg cctgaactgc ccaggccaag gagaccccac cccacacgtg gattggcttc   1560
tagctgatgg aagtaaagtg agagcccctt atgtcagtga ggatggacgg atcctaatag   1620
acaaaagtgg aaaattggaa ctccagatgg ctgatagttt tgacacaggc gtatatcact   1680
gtataagcag caattatgat gatgcagata ttctcaccta taggataact gtggtagaac   1740
ctttggtcga agcctatcag gaaaatggga ttcatcacac agttttcatt ggtgaaacac   1800
ttgatcttcc atgccattct actggtatcc cagatgcctc tattagctgg gttattccag   1860
gaaacaatgt gctctatcag tcatcaagag acaagaaagt tctaaacaat ggcacattaa   1920
gaatattaca ggtcacccg aaagaccaag gttattatcg ctgtgtggca gccaacccat    1980
caggggttga tttttttgatt ttccaagttt cagtcaagat gaaaggacaa aggcccttgg   2040
agcatgatgg agaaacagag ggatctggac ttgatgagtc caatcctatt gctcatctta   2100
aggagccacc aggtgcacaa ctccgtacat ctgctctgat ggaggctgag gttggaaaac   2160
acacctcaag cacaagtaag aggcacaact atcgggaatt aacactccag cgacgtggag   2220
attcaacaca tcgacgtttt agggagaata ggaggcattt ccctccctct gctaggagaa   2280
ttgacccaca acattgggcg gcactgttgg agaaagctaa aaagaatgct atgccagaca   2340
agcgagaaaa taccacagtg agcccacccc cagtggtcac ccaactccca aacatacctg   2400
gtgaagaaga cgattcctca ggcatgctcg ctctacatga ggaatttatg gtcccggcca   2460
ctaaagctt                                                           2469
```

-continued

<210> SEQ ID NO 27
<211> LENGTH: 3518
<212> TYPE: DNA
<213> ORGANISM: Homo sapiens

<400> SEQUENCE: 27

| | | | | | |
|---|---|---|---|---|---|
| aagctttgaa | ccttccagca | aggacagtga | ctgctgactc | cagaacaata | tctgatagtc | 60 |
| ctatgacaaa | cataaattat | ggcacagaat | tctctcctgt | tgtgaattca | caaatactac | 120 |
| cacctgaaga | acccacagat | ttcaaactgt | ctactgctat | taaaactaca | gccatgtcaa | 180 |
| agaatataaa | cccaaccatg | tcaagccaaa | tacaaggcac | aaccaatcaa | cattcatcca | 240 |
| ctgtctttcc | actgctactt | ggagcaactg | aatttcagga | ctctgaccag | atgggaagag | 300 |
| gaagagagca | tttccaaagt | agaccoccaa | taacagtaag | gactatgatc | aaagatgtca | 360 |
| atgtcaaaat | gcttagtagc | accaccaaca | aactattatt | agagtcagta | ataccacaa | 420 |
| atagtcatca | gacatctgta | agagaagtga | gtgaacccag | gcacaatcac | ttctattctc | 480 |
| acactactca | aatacttagc | acctccacgt | tcccttcaga | tccacacaca | gctgctcatt | 540 |
| ctcagtttcc | gatccctaga | aatagtacag | ttaacatccc | gctgttcaga | cgctttggga | 600 |
| ggcagaggaa | aattggcgga | aggggcgga | ttatcagccc | atatagaact | ccagttctgc | 660 |
| gacggcatag | atacagcatt | ttcaggtcaa | caaccagagg | ttcttctgaa | aaaagcacta | 720 |
| ctgcattctc | agccacagtg | ctcaatgtga | catgtctgtc | ctgtcttccc | agggagaggc | 780 |
| tcaccactgc | cacagcagca | ttgtcttttc | caagtgctgc | tcccatcacc | ttccccaaag | 840 |
| ctgacattgc | tagagtccca | tcagaagagt | ctacaactct | agtccagaat | ccactattac | 900 |
| tacttgagaa | caaacccagt | gtagagaaaa | caacacccac | aataaaatat | ttcaggactg | 960 |
| aaatttccca | agtgactcca | actggtgcag | tcatgacata | tgctccaaca | tccatacccc | 1020 |
| tggaaaaaac | tcacaaagta | aacgccagtt | acccacgtgt | gtctagcacc | aatgaagcta | 1080 |
| aaagagattc | agtgattaca | tcgtcacttt | caggtgctat | caccaagcca | ccaatgacta | 1140 |
| ttatagccat | tacaaggttt | tcaagaagga | aaattccctg | gcaacagaac | tttgtaaata | 1200 |
| accataaccc | aaaaggcaga | ttaaggaatc | aacataaagt | tagtttacaa | aaaagcacag | 1260 |
| ctgtgatgct | tcctaaaaca | tctcctgctt | tacccagaga | caaagtctcc | cctttccatt | 1320 |
| tcaccacact | ttcaacaagt | gtgatgcaaa | ttccatctaa | taccttgact | accgctcacc | 1380 |
| acactacgac | caaaacacac | aatcctggaa | gtcttccaac | aaagaaggag | cttcccttcc | 1440 |
| caccccttaa | ccctatgctt | cctagtatta | taagcaaaga | ctcaagtaca | aaaagcatca | 1500 |
| tatcaacgca | aacagcaata | ccagcaacaa | ctcctacctt | ccctgcatct | gtcatcactt | 1560 |
| atgaaaccca | aacagagaga | tctagagcac | aaacaataca | aagagaacag | gagcctcaaa | 1620 |
| agaagaacag | gactgaccca | aacatctctc | cagaccagag | ttctggcttc | actacaccca | 1680 |
| ctgctatgac | acctcctgtt | ctaaccacag | ccgaaacttc | agtcaagccc | agtgtctctg | 1740 |
| cattcactca | ttcccacca | gaaaacacaa | ctgggatttc | aagcacaatc | agttttcatt | 1800 |
| caagaactct | taatctgaca | gatgtgattg | aagaactagc | ccaagcaagt | actcagactt | 1860 |
| tgaagagcac | aattgcttct | gaaacaactt | tgtccagcaa | atcacaccag | agtaccacaa | 1920 |
| ctaggaaagc | aatcattaga | cactcaacca | taccaccatt | cttgagcagc | agtgctactc | 1980 |
| taatgccagt | tccatctcc | cctcccttta | ctcagagagc | agttactgac | aacgtggcga | 2040 |
| ctcccatttc | cgggcttatg | acaaatacag | tggtcaagct | gcacgaatcc | tcaaggcaca | 2100 |

-continued

```
atgctaaacc acagcaatta gtagcagagg ttgcaacatc ccccaaggtt cacccaaatg    2160
ccaagttcac aattggaacc actcacttca tctactctaa tctgttacat tctactccca    2220
tgccagcact aacaacagtt aaatcacaga attctaaatt aactccatct ccctgggcag    2280
aaaaccaatt ttggcacaaa ccatactcag aaattgctga aaaaggcaaa aagccagaag    2340
taagcatgtt ggctactaca ggcctgtccg aggccaccac tcttgtttca gattgggatg    2400
gacagaagaa cacaaagaag agtgactttg ataagaaacc agttcaagaa gcaacaactt    2460
ccaaactcct tccctttgac tctttgtcta ggtatatatt tgaaaagccc aggatagttg    2520
gaggaaaagc tgcaagtttt actattccag ctaactcaga tgcctttctt ccctgtgaag    2580
ctgttggaaa tccctgccc accattcatt ggaccagagt cccatcagga cttgatttat    2640
ctaagaggaa acagaatagc agggtccagg ttctccccaa tggtaccctg tccatccaga    2700
gggtggaaat tcaggaccgc ggacagtact tgtgttccgc atccaatctg tttggcacag    2760
accaccttca tgtcaccttg tctgtggttt cctatcctcc caggatcctg gagagacgta    2820
ccaaagagat cacagttcat tccggaagca ctgtggaact gaagtgcaga gcagaaggta    2880
ggccaagccc tacagttacc tggattcttg caaaccaaac agttgtctca gaatcatccc    2940
agggaagtag gcaggctgtg gtgacggttg acggaacatt ggtcctccac aatctcagta    3000
tttatgaccg tggcttttac aaatgtgtgg ccagcaaccc aggtggccag gattcactgc    3060
tggttaaaat acaagtcatt gcagcaccac ctgttattct agagcaaagg aggcaagtca    3120
ttgtaggcac ttggggtgaa agtttaaaac tgccctgtac tgcaaaagga actcctcagc    3180
ccagcgttta ctgggtcctc tctgatggca ctgaagtgaa accattacag tttaccaatt    3240
ccaagttgtt cttatttca atgggactt tgtatataag aaacctagcc tcttcagaca    3300
ggggcactta tgaatgcatt gctaccagtt ccactggttc ggagcgaaga gtagtaatgc    3360
ttacaatgga agagcgagtg accagcccca ggatagaagc tgcatcccag aaaaggactg    3420
aagtgaattt tggggacaaa ttactactga actgctcagc cactggggag cccaaacccc    3480
aaataatgtg gaggttacca tccaaggctg tggtcgac                            3518
```

<210> SEQ ID NO 28
<211> LENGTH: 1950
<212> TYPE: DNA
<213> ORGANISM: Homo sapiens

<400> SEQUENCE: 28

```
gtcgaccagc agcatagagt gggcagctgg atccacgtct accctaatgg atccctgttt     60
attggatcag taacagaaaa agacagtggt gtctacttgt gtgtggcaag aaacaaaatg    120
ggggatgatc tgatactgat gcatgttagc ctaagactga aacctgccaa aattgaccac    180
aagcagtatt ttagaaagca agtgctccat gggaaagatt tccaagtaga ttgcaaagct    240
tccggctccc cagtgccaga gatatcttgg agtttgcctg atggaaccat gatcaacaat    300
gcaatgcaag ccgatgacag tggccacagg actaggagat ataccctttt caacaatgga    360
actttatact tcaacaaagt tggggtagcg gaggaaggag attatacttg ctatgcccag    420
aacaccctag ggaaagatga aatgaaggtc cacttaacag ttataacagc tgctccccgg    480
ataaggcaga gtaacaaaac caacaagaga tcaaagctg agacacagc tgtccttgac    540 tgtgaggtca ctgggatcc caaaccaaaa atatttggt tgctgccttc caatgacatg    600
atttccttct ccattgatag gtacacattt catgccaatg ggtctttgac catcaacaaa    660
gtgaaactgc tcgattctgg agagtacgta tgtgtagccc gaaatccag tggggatgac    720
```

| | |
|---|---|
| accaaaatgt acaaactgga tgtggtctct aaacctccat taatcaatgg tctgtataca | 780 |
| aatagaactg ttattaaagc cacagctgtg agacattcca aaaaacactt tgactgcaga | 840 |
| gctgaaggga caccatctcc tgaagtcatg tggatcatgc cagacaatat tttcctcaca | 900 |
| gccccatact atggaagcag aatcacagtc cataaaaatg gaaccttgga aattaggaat | 960 |
| gtgaggcttt cagattcagc cgactttatc tgtgtggccc gaaatgaagg tggagagagc | 1020 |
| gtgttggtag tacagttaga agtactggaa atgctgagaa gaccgacatt tagaaatcca | 1080 |
| tttaatgaaa aaatagttgc ccagctggga aagtccacag cattgaattg ctctgttgat | 1140 |
| ggtaacccac cacctgaaat aatctggatt ttaccaaatg gcacacgatt tccaatggga | 1200 |
| ccacaaagtt atcagtatct gatagcaagc aatggttctt ttatcatttc taaaacaact | 1260 |
| cgggaggatg caggaaaata tcgctgtgca gctaggaata agttggcta tattgagaaa | 1320 |
| ttagtcatat tagaaattgg ccagaagcca gttattctta cctatgcacc agggacagta | 1380 |
| aaaggcatca gtggagaatc tctatcactg cattgtgtgt ctgatggaat ccctaagcca | 1440 |
| aatatcaaat ggactatgcc aagtggttat gtagtagaca ggcctcaaat taatgggaaa | 1500 |
| tacatattgc atgacaatgg caccttagtc attaaagaag caacagctta tgacagagga | 1560 |
| aactatatct gtaaggctca aaatagtgtt ggtcatacac tgattactgt tccagtaatg | 1620 |
| attgtagcct accctcccg aattacaaat cgtccaccca ggagtattgt caccaggaca | 1680 |
| ggggcagcct ttcagctcca ctgtgtggcc ttgggagttc ccaagccaga aatcacatgg | 1740 |
| gagatgcctg accactccct tctctcaacg gcaagtaaag agaggacaca tggaagtgag | 1800 |
| cagcttcact tacaaggtac cctagtcatt cagaatcccc aaacctccga ttctgggata | 1860 |
| tacaaatgca cagcaaagaa cccacttggt agtgattatg cagcaacgta tattcaagta | 1920 |
| atccaccacc accaccacca ttgaactagt | 1950 |

<210> SEQ ID NO 29
<211> LENGTH: 9109
<212> TYPE: DNA
<213> ORGANISM: Homo sapiens

<400> SEQUENCE: 29

| | |
|---|---|
| atgcccaagc gcgcgcactg gggggccctc tctgtggtgc tgatcctgct ttggggtcat | 60 |
| ccgcgagtgg cgctggcctg ccctcatcct tgtgcctgct acgtccccag cgaggtccac | 120 |
| tgcacgttcc gatccctggc ttctgtgccc gctggcattg ctaaacatgt ggaaagaatc | 180 |
| aatttggggt ttggaattct gaagtgtaaa aaggacaaag cttatgaagg cggtcagttg | 240 |
| tgtgcaatgt gcttcagtcc aaagaagttg tacaaacatg agattcacaa gctgaaggac | 300 |
| ctgacttgtc tgaagccttc catagagtct cctctgagac agaacaggag caggagtatt | 360 |
| gaggaggagc aaaaacaaga agagaatggt gacagccagc tcatcctgga gaaaatccaa | 420 |
| cttccccagt ggagcatctc tttgaatatg actgatgagc acgggaacct ggtgaacttg | 480 |
| gtgtgtgaca tcaagaaacc aatggatgtg tacaaaattc acttgaacca aacagatcct | 540 |
| ccagatattg acataaatgc aatggttgcc ttggactttg agtatccaat gacccaggaa | 600 |
| aactatgaaa atctatggaa attgatagca tactacagtg aagttcccat gaagctacac | 660 |
| agagagctca tgctcagcaa acaccccaga gtcagctacc agtacaggca agatgccgat | 720 |
| gaagaagctc tttactacac aggtgtgaga gcccagattc ttgcagaacc agaatggatc | 780 |
| atgcagccat ccatagatat ccagctgaac cgacctcaga gtacgccaa gaaggtgcta | 840 |

```
ctttcctact acaaccagta ttctcaaaca atagccacca aagatacaag gcaggctcgg      900
ggcagaagct gggtaatgat tgagcctagt agagctgtgc aaaaagatca gactgtcctg      960
gaagggggtc gatgccagtt gagctgcaat gtgaaagctt ctgagagtcc atctatcttc     1020
tgggtgcttc cagatggctc catcctgaaa gtgcctgtgg atgacccaga cagcaagttc     1080
tccattctca gcagtggctg gctgaggatc aagtccatgg agccatctga ctcgggcttg     1140
taccagtgca ttgctcaagt gagggatgaa atggaccgca tggtatatag ggtacttgtg     1200
cagtctccct ccactcagcc agccgagaaa gacacagtga caattggcaa gaacccaggg     1260
gagccagtga tgttgccttg caatgcttta gctatacccg aagcccacct tagctggatt     1320
cttccaaaca gaaggataat taatgatttg gctaacacat cacatgtata catgctgcca     1380
aatggaactc tttccatccc aaaggtccaa gtcagtgaca gtggttacca cagatgtgtg     1440
gctgtcaacc agcatggggc agaccatatc acggtgggaa tcacagtgac caagaaaggt     1500
tctggctcgc catccaaaag aggcagatgg ccaggtccaa aggctctttc cagagtgaga     1560
gaagacatcg tggaggatga aggggtctca ggcacgggag atgaagagaa cacttcaagg     1620
agacttctac atccaaagca ccaagaggcg ttcctcaaaa caaaggatga tgccatcaat     1680
ggagataaga aagccaagaa agggagaaga aagctgaaac tctggaagca ttcagaaaaa     1740
gaaccagaga ccagtgttgc agaagatctc agagtgtttg aatcaagacg aaggataaac     1800
gtggcaaaca aacagattaa tccggagcac tgggctgata ttttagccaa agtctttggg     1860
aaaaatctcc ctacaggcac agaagtatcc ccaattatta aaccacaag ttctccattc      1920 ttgagcctag tagtcacacc acctttgcct gctgtttctc ccccttggc atctccaata      1980 cagacagcaa caagtgctga agaatcctca gcagatgtac ctctactcag cgaaggaaag     2040
cacattttga gtaccatttc ctcagccagc atgggactag aacaccacaa caatggagtt     2100
attcttgttg aacctgaagt aacaagcaca cctctggaag aagttgttga tgagtattcc     2160
aagaagactg aggagatgac ttccactgaa ggcgacctga aggggactgc agcctctaca     2220
cttatatctg agccttatga acaatctcct actctacaca ccttagacac agtctatgaa     2280
gagcccaccc atgaagagac ggaaacagag ggttggtctg cagcagatgt tggatcctca     2340
ccagatccca catccagtga gtatgagctt ccattggttg ttgtctcctt ggctgagtct     2400
aagcctgtgc aatactttga cccagatttg gagactaatt cacaaccaca tgaggataac     2460
ataaaagaat acagttttgc acaccttact ccaaccgcca tcatctggtt taatgactct     2520
agtacatcac tgtcatttga ggattctact gtaggggaac aaggtgtccc aggcaaatca     2580
catctacaag gaccgacaga gaacatccag cttgtgaaaa gtagttttag cactcaagac     2640
accttattga ttaaaaaagg tatgaaagag atgtctcaga cactcagggg aggaaatatg     2700
ctagagggag accctacaca ctccagaagt tctgagaatg agggccaaga gagcaaatcc     2760
atcactttac ctgactccac actgggtata acgagcagta cgtctccagt taagaagcct     2820
gcggaaacca cagttgtcac cctgctacac aaagacacca aacagaaac aactccaagg     2880 caaaaagtgg cttcatcatc caccatgagc actcaccctt ctcgaaggag acccaatggg     2940
agaaaattac accctcacaa attccaccac cggcacaagc aaaccccacc cacaactttt     3000
gctccattag agacttttc tactcaacca actcaagcaa ctgacattaa gatttcaaat     3060
caaatggaga gttctctggt tcctacatct tgggagatta acacagttaa taccccaaa      3120 cagctggaaa tggagaagaa tgtagagctc atatcaaagg gaactccacg gagaaaacac     3180
gggaagaggc caaacaaaca tcgatatacc ccttctacag tgagttcaag agcatctgca     3240
```

```
tccaagccca gcccttctcc agaaaataaa catagaaaca ttgttactcc cagttcagaa    3300
actacacttt tgcctagaaa tgtttctctg aaaactgagg gcgtttatga ttccttagat    3360
tacacgacaa ccaccagaaa aatacattca tctcaccata aagtccaaga cacacttcca    3420
gtcatgtata aacccacatc agatggaaaa gaaattcagg atgatgttgc cacaaatgtt    3480
gacaaacata aaagtgacat tttagtccct ggtgagtcaa ttacaaatgt cacacaaact    3540
tctcgctcct tggtctccac tatgggagaa tttaaggaag aatcctctcc tgtgggcttt    3600
ccaggaattc caacctggaa tccctcaagg aaagctcagc ctgggaggct acagacagac    3660
atacatgtta ccacttctgg ggaaacccct acagaccctc cccttgttaa cgagcttgag    3720
gatgtggatt ttacttctga gttttttgtcc tctgtgacag tctccacacc atttcaccag    3780
gaagaagctg gttttttccac aattctctca agcataaaag tggagatggc ttcaagtcag    3840
gtagaaacta ccacccttgg tcaagatcat catgaaacca ctgtggctat tctccactct    3900
gaaactagac cacagaatca catccttact gctgcctgga tgaaggagcc agcatctttg    3960 tccctccca tgattctcct gtctttggga caaaccacca ccactaagcc agaacttctc    4020
agtccaagaa catctcaaat atgtaaagat tccaaggaaa atgttttctt gaattacatg    4080
gggaatccag aaacagaagc aaccccagtg aaaaatgaag gaacacagcg tatgtcaggg    4140
ccaaatgaat tatcaacacc atcttctgac cacgatgcat ttaacttgtc tacaaagcta    4200
gaattggaaa agcaagtatt tgatagtagg agtctaacac gtgggcccaga tagccaccac    4260 caggatggaa gagttcatgc ttctcatcaa ctaaccagaa tccctgccaa acccatccta    4320
ccaacaggaa cagtgaggct gcctgaaatg tccacacaaa gcacttccag atactttgta    4380
actttccagc cacctcatca cgggaccaac aaaccagaaa taactacata tccttctagg    4440
gctttgccag agagcaaaca gtttacaact ccaagagtag caagtacaac tcctctccta    4500
tcacacatgt ccaaacccag catttctagt aagtttgctg acctaagaac tgaccaatcc    4560
aatggctcct acaaagtgtt tggaaatagc aacatccctg aggcaagaaa ctcagttgga    4620
aagcctctca gtccaagaat ttatcattat tccaatggaa gactccctt ctttaccaac    4680 aggactcttt cttttttcaca gttgggagtc acccggagac cccagatacc ctcttctcct    4740
gtcccagtaa tgagagagag aaaagttaat ccaggttcct acaataggat atattcccat    4800
agcaccttcc atctggactt tggccttcca gcacctccac tgttgcacac tccatggacc    4860
atggtatcac ccccaactaa cttacagaat atccctatgg tctcatccac ccagagttct    4920
gtctccttta taacatcttc tgtccagtcc tcaggaagca tccaccaaag cggctcaaag    4980
ttctttgcag gaggaccgcc tgcatccaaa ttctggcctc ttggggaaaa gccccaaatc    5040
ctcaccaagt ccccacagac tgtgtctgtc actgctgaaa cggacgctgt gttcccgtgt    5100
gaggcaatag gaaaaccaaa gcctttcgtt acttggacaa agtttccac aggagttctt    5160 atgactccga ataccaggat acaacggttt gaggttctca gaacggtac cttagtgata    5220 aggaagtttc aagtgcaaga tcgaggccag tatatgtgca ccgccagcaa cctgtacggc    5280
ctggacagga tggtggtctt tctctgggtc accgtgcagc aacctcaaat cctagcctcc    5340
cactaccagg acgtcaccgt ctacctggga gacaccatta caatggagtg tctggcgaaa    5400 gggacccag cccccccaaat ttcctggatc ttccgtgaca ggagggtgtg gcaaactctg    5460
tcctccgtgg agggcggat cacccctgcac caaaaccgga cccttttccat caaggaggcg    5520 tccttctcag acagaggcgt ctataagtgc gtggccagca acgcaacccg ggcggacagc    5580
```

```
gtgtccatcc gcctacacgt ggcggcactg ccccccatta tccaccagga gaagctggag    5640
aacatctcgc tgcccccggg gctcagcatt cacattcact gcactgccaa agctgcgccc    5700
ctgcccagcg tgctctgggt gctcggggat ggtacccaaa tccgcccctc gcatttcctc    5760
caccggaact tgtttgtttt ccccaacggg acgctctaca tctgcaacct cgcgcccaag    5820
gacagcgggc gctatgagtg cgtggccgcc aacctgatcg gctccgcgcg cagtacggtg    5880
cagctgaacg tgcagcgcgc agcagcgaac gcgcgcatca cgggcacctc ctcgcagagg    5940
acggacgtca ggtacggagg gaccctcaag ctggactgca gcgcctcggg ggatccctgg    6000
ccgcgcatcc tctggaggct gccgtccaag aggacgatcg acgcgctttt cagttttgat    6060
agtagaatca aggtgtttgc caacaggacc ctggtggtga aatcaatgac agacaaagac    6120
gccggagatt acctgtgtgt agctcgaaat aaggttggtg atgactgcgt ggtgctcaag    6180
gtggatgtga tgatgaaacc ggccaagatt gaacacaagg aggagaacga ccacaaagtc    6240
ttctacaggg tgtgacctga agtggactgt gtggccactg gacttcccaa tcccgagatc    6300
tcctggagcc tcctggatgg gagtctggtg aactccttca tgcagtcaga tgacagtggt    6360
ggacgcacca agcactatgt ggtcttcaac aatgggacac tctacttcag tgaagtgggg    6420
atgagggagg aaggagacta cacctgcttt gctgaaaatc aggttgggaa ggatgagatg    6480
agagtcagag tcaagatggt gacacctgcc accatctgga acaagactta cttggcagtt    6540
caggtacccct atggagatgt ggtcactgta acctgtgagg ccaaaggaga acccatgccc    6600
aaggtgactt ggttgtcccc agccaacagg gtgatcccca cctcctctga aagtatcag    6660
atataccaat atggcactct ccttattcag aaagcccagt gctctgacag cggcaactac    6720
acctgcctgg tcaggaacag tgccggagag gataggaaga cagtgtggat tcacgtcaac    6780
ctccagccac ccaagatcaa tggtaacccc aaccccatca ccaccgtgtg ggagatagca    6840
gccgggggca gtcggaaact gattgactgc aaagctgaag gcatccccac cccgagggtg    6900
ttatgggctt ttcccgaggg tgtggttctg ccagatccat actatggaaa ccggatcact    6960
gtccatggca acggttccct ggacatcagg agtttgagga gagcgactc cgtccagctg    7020
gtatgcatgg cacgcaacga gggaggggag gcgaggttga tcgtgcagct cactgtcctg    7080
gagcccatgg agaaacccat cttccacgac ccgatcagcg agaagatcac ggccatggcg    7140
ggccacacca tcagcctcaa ctgctctgcc gcggggaccc tgacacccag cctggtgtgg    7200
gtccttccca tggcaccga tctgcagagt ggacagcagc tgcagcgctt ctaccacaag    7260
gctgacggca tgctacacat tagcggtctc tcctcggtgg acgccgggggc ctaccgctgc    7320
gtggcccgca atgccgcggg ccacacggag aggctggtct ccctgaaggt gggactgaag    7380
ccagaagcaa acaagcagta tcataacctg gtcagcatca tcaatggtga ccctgaag    7440
ctcccctgca cccctcctgc agctgggcag ggacatttct cctggacact ccccaatggc    7500
atgcatctgg agggccccca aaccctggga cgcgtttctc ttctggacaa tggcacctc    7560
acggttcgtg aggcctcggt gtttgacagg ggtacctatg tatgcaggat ggagacggcg    7620
tacgcccctt cggtcaccag catccccgtg attgtgatcg cctatcctcc ccggatcacc    7680
agcgagccta ccccagtcat ctacacccgt cccgggaaca ccgtgaaact gaactgcatg    7740
gctatgggga ttcccaaagg tgacatcacg tgggagttac cggataagtt gcatctgaag    7800
gcagggggttc aggctcgtct gtatggaaac agatttcttc accccagggg atcactgacc    7860
atccagcagg ccagacggag agacgctggc ttctacaagt gcacggcaaa aaacattctc    7920
agcagtgact ccaaaacaac ttatatccat gtcttctgaa atgtggattc cagaatgatt    7980
```

-continued

```
gctcaggaac tgacaacaaa gcggggtttg taagggaagc caggctgggg aatcagagct    8040
cttaaataat gtgtcacagt gcatggtggc ccccggtggg attcaagttg aggttgatct    8100
tgatctacaa ttgttgggaa aaggaagcaa tacagacatg agtaaaaggg ctcagcctca    8160
ctgagaactt tcttttgtgt ttacatcatg ccaggggctt cattcagggt gtctgtgctc    8220
tgactgtaat ttttattttt ttgcaaatgt cattcgactg cctgcgtaag tgtccatagg    8280
atatctgagg aacattcacc gaaaataagc catagacatg aacaacacct cactccccca    8340
ttgaagatgc atcgtctagt taacctgctg cagtttttac atgatagact ttgttccaga    8400
ttgacaagtc atctttcagt tatttcctct atcacttcaa aactccagct tgcccaataa    8460
ggatttagaa ctagagtgat tgttatatat ataatatata tattttaatt cagagttaca    8520
tacatacagc taccatttta tatgaaaaaa acatttcttc ctggaaccca cttttatgt     8580 aattttttta tataaatatt tttcctttca aatcagatga tgagactaga aggagaaata    8640
ctttctgtct cattaaaatt aataaatgat tggtctttac aagacttgga tacattacag    8700
cagacatgga aatagaattt taaacaattc ctctccaacc tccttcaaat tcagtcgcta    8760
ctgttatgtt actttctcca gcaaccctgc actggggaag gctgtgatat tagatttcct    8820
tgtatgcaaa gttttgttg aaagctgtgc tcagcggagg tgagaggaga ggaggagaaa     8880
actgcatcat atctttccag aattgaatct agagtcttcc ctggaaagcc cagaaacttc    8940
tctgcagtat ctgacttgtc catctggtct aaggtggctg cttcttccgc aaccatgagt    9000
tagtctgtgt ccatgaataa tacaagatct gttatttcca tgactgcttt actgtaattt    9060
tagggtcaat atactgtaca tttgataata aaatatattc tcccaaaaa               9109
```

<210> SEQ ID NO 30
<211> LENGTH: 2652
<212> TYPE: PRT
<213> ORGANISM: Homo sapiens

<400> SEQUENCE: 30

Met Pro Lys Arg Ala His Trp Gly Ala Leu Ser Val Val Leu Ile Leu
1               5                   10                  15

Leu Trp Gly His Pro Arg Val Ala Leu Ala Cys Pro His Pro Cys Ala
            20                  25                  30

Cys Tyr Val Pro Ser Glu Val His Cys Thr Phe Arg Ser Leu Ala Ser
        35                  40                  45

Val Pro Ala Gly Ile Ala Lys His Val Glu Arg Ile Asn Leu Gly Phe
    50                  55                  60

Gly Ile Leu Lys Cys Lys Lys Asp Lys Ala Tyr Glu Gly Gly Gln Leu
65                  70                  75                  80

Cys Ala Met Cys Phe Ser Pro Lys Lys Leu Tyr Lys His Glu Ile His
                85                  90                  95

Lys Leu Lys Asp Leu Thr Cys Leu Lys Pro Ser Ile Glu Ser Pro Leu
            100                 105                 110

Arg Gln Asn Arg Ser Arg Ser Ile Glu Glu Gln Lys Gln Glu Glu
        115                 120                 125

Asn Gly Asp Ser Gln Leu Ile Leu Glu Lys Ile Gln Leu Pro Gln Trp
    130                 135                 140

Ser Ile Ser Leu Asn Met Thr Asp Glu His Gly Asn Leu Val Asn Leu
145                 150                 155                 160

Val Cys Asp Ile Lys Lys Pro Met Asp Val Tyr Lys Ile His Leu Asn
                165                 170                 175

```
Gln Thr Asp Pro Pro Asp Ile Asp Ile Asn Ala Met Val Ala Leu Asp
            180                 185                 190

Phe Glu Tyr Pro Met Thr Gln Glu Asn Tyr Glu Asn Leu Trp Lys Leu
            195                 200                 205

Ile Ala Tyr Tyr Ser Glu Val Pro Met Lys Leu His Arg Glu Leu Met
            210                 215                 220

Leu Ser Lys His Pro Arg Val Ser Tyr Gln Tyr Arg Gln Asp Ala Asp
225                 230                 235                 240

Glu Glu Ala Leu Tyr Tyr Thr Gly Val Arg Ala Gln Ile Leu Ala Glu
                245                 250                 255

Pro Glu Trp Ile Met Gln Pro Ser Ile Asp Ile Gln Leu Asn Arg Pro
            260                 265                 270

Gln Ser Thr Ala Lys Lys Val Leu Leu Ser Tyr Tyr Asn Gln Tyr Ser
            275                 280                 285

Gln Thr Ile Ala Thr Lys Asp Thr Arg Gln Ala Arg Gly Arg Ser Trp
            290                 295                 300

Val Met Ile Glu Pro Ser Arg Ala Val Gln Lys Asp Gln Thr Val Leu
305                 310                 315                 320

Glu Gly Gly Arg Cys Gln Leu Ser Cys Asn Val Lys Ala Ser Glu Ser
                325                 330                 335

Pro Ser Ile Phe Trp Val Leu Pro Asp Gly Ser Ile Leu Lys Val Pro
            340                 345                 350

Val Asp Asp Pro Asp Ser Lys Phe Ser Ile Leu Ser Ser Gly Trp Leu
            355                 360                 365

Arg Ile Lys Ser Met Glu Pro Ser Asp Ser Gly Leu Tyr Gln Cys Ile
370                 375                 380

Ala Gln Val Arg Asp Glu Met Asp Arg Met Val Tyr Arg Val Leu Val
385                 390                 395                 400

Gln Ser Pro Ser Thr Gln Pro Ala Glu Lys Asp Thr Val Thr Ile Gly
            405                 410                 415

Lys Asn Pro Gly Glu Pro Val Met Leu Pro Cys Asn Ala Leu Ala Ile
            420                 425                 430

Pro Glu Ala His Leu Ser Trp Ile Leu Pro Asn Arg Arg Ile Ile Asn
            435                 440                 445

Asp Leu Ala Asn Thr Ser His Val Tyr Met Leu Pro Asn Gly Thr Leu
450                 455                 460

Ser Ile Pro Lys Val Gln Val Ser Asp Ser Gly Tyr His Arg Cys Val
465                 470                 475                 480

Ala Val Asn Gln His Gly Ala Asp His Ile Thr Val Gly Ile Thr Val
            485                 490                 495

Thr Lys Lys Gly Ser Gly Ser Pro Ser Lys Arg Gly Arg Trp Pro Gly
            500                 505                 510

Pro Lys Ala Leu Ser Arg Val Arg Glu Asp Ile Val Glu Asp Glu Gly
            515                 520                 525

Val Ser Gly Thr Gly Asp Glu Glu Asn Thr Ser Arg Arg Leu Leu His
530                 535                 540

Pro Lys His Gln Glu Ala Phe Leu Lys Thr Lys Asp Ala Ile Asn
545                 550                 555                 560

Gly Asp Lys Lys Ala Lys Lys Gly Arg Arg Lys Leu Lys Leu Trp Lys
                565                 570                 575

His Ser Glu Lys Glu Pro Glu Thr Ser Val Ala Glu Asp Leu Arg Val
            580                 585                 590
```

-continued

```
Phe Glu Ser Arg Arg Ile Asn Val Ala Asn Lys Gln Ile Asn Pro
            595                 600                 605
Glu His Trp Ala Asp Ile Leu Ala Lys Val Phe Gly Lys Asn Leu Pro
610                 615                 620
Thr Gly Thr Glu Val Ser Pro Ile Ile Lys Thr Thr Ser Ser Pro Phe
625                 630                 635                 640
Leu Ser Leu Val Val Thr Pro Pro Leu Pro Ala Val Ser Pro Pro Leu
                645                 650                 655
Ala Ser Pro Ile Gln Thr Ala Thr Ser Ala Glu Glu Ser Ser Ala Asp
                660                 665                 670
Val Pro Leu Leu Ser Glu Gly Lys His Ile Leu Ser Thr Ile Ser Ser
                675                 680                 685
Ala Ser Met Gly Leu Glu His His Asn Asn Gly Val Ile Leu Val Glu
                690                 695                 700
Pro Glu Val Thr Ser Thr Pro Leu Glu Glu Val Val Asp Glu Tyr Ser
705                 710                 715                 720
Lys Lys Thr Glu Glu Met Thr Ser Thr Glu Gly Asp Leu Lys Gly Thr
                725                 730                 735
Ala Ala Ser Thr Leu Ile Ser Glu Pro Tyr Glu Gln Ser Pro Thr Leu
                740                 745                 750
His Thr Leu Asp Thr Val Tyr Glu Glu Pro Thr His Glu Glu Thr Glu
                755                 760                 765
Thr Glu Gly Trp Ser Ala Ala Asp Val Gly Ser Ser Pro Asp Pro Thr
770                 775                 780
Ser Ser Glu Tyr Glu Leu Pro Leu Val Val Val Ser Leu Ala Glu Ser
785                 790                 795                 800
Lys Pro Val Gln Tyr Phe Asp Pro Asp Leu Glu Thr Asn Ser Gln Pro
                805                 810                 815
His Glu Asp Asn Ile Lys Glu Tyr Ser Phe Ala His Leu Thr Pro Thr
                820                 825                 830
Ala Ile Ile Trp Phe Asn Asp Ser Ser Thr Ser Leu Ser Phe Glu Asp
                835                 840                 845
Ser Thr Val Gly Glu Gln Gly Val Pro Gly Lys Ser His Leu Gln Gly
                850                 855                 860
Pro Thr Glu Asn Ile Gln Leu Val Lys Ser Ser Phe Ser Thr Gln Asp
865                 870                 875                 880
Thr Leu Leu Ile Lys Lys Gly Met Lys Glu Met Ser Gln Thr Leu Gln
                885                 890                 895
Gly Gly Asn Met Leu Glu Gly Asp Pro Thr His Ser Arg Ser Ser Glu
                900                 905                 910
Asn Glu Gly Gln Glu Ser Lys Ser Ile Thr Leu Pro Asp Ser Thr Leu
                915                 920                 925
Gly Ile Thr Ser Ser Thr Ser Pro Val Lys Lys Pro Ala Glu Thr Thr
                930                 935                 940
Val Val Thr Leu Leu His Lys Asp Thr Thr Glu Thr Thr Pro Arg
945                 950                 955                 960
Gln Lys Val Ala Ser Ser Ser Thr Met Ser Thr His Pro Ser Arg Arg
                965                 970                 975
Arg Pro Asn Gly Arg Lys Leu His Pro His Lys Phe His His Arg His
                980                 985                 990
Lys Gln Thr Pro Pro Thr Thr Phe  Ala Pro Leu Glu Thr  Phe Ser Thr
                995                 1000                1005
Gln Pro  Thr Gln Ala Thr Asp  Ile Lys Ile Ser Asn  Gln Met Glu
```

-continued

```
                1010                1015                1020
Ser  Ser  Leu  Val  Pro  Thr  Ser  Trp  Glu  Ile  Asn  Thr  Val  Asn  Thr
     1025                1030                1035
Pro  Lys  Gln  Leu  Glu  Met  Glu  Lys  Asn  Val  Glu  Leu  Ile  Ser  Lys
     1040                1045                1050
Gly  Thr  Pro  Arg  Arg  Lys  His  Gly  Lys  Arg  Pro  Asn  Lys  His  Arg
     1055                1060                1065
Tyr  Thr  Pro  Ser  Thr  Val  Ser  Ser  Arg  Ala  Ser  Ala  Ser  Lys  Pro
     1070                1075                1080
Ser  Pro  Ser  Pro  Glu  Asn  Lys  His  Arg  Asn  Ile  Val  Thr  Pro  Ser
     1085                1090                1095
Ser  Glu  Thr  Thr  Leu  Leu  Pro  Arg  Asn  Val  Ser  Leu  Lys  Thr  Glu
     1100                1105                1110
Gly  Val  Tyr  Asp  Ser  Leu  Asp  Tyr  Thr  Thr  Thr  Arg  Lys  Ile
     1115                1120                1125
His  Ser  Ser  His  His  Lys  Val  Gln  Asp  Thr  Leu  Pro  Val  Met  Tyr
     1130                1135                1140
Lys  Pro  Thr  Ser  Asp  Gly  Lys  Glu  Ile  Gln  Asp  Val  Ala  Thr
     1145                1150                1155
Asn  Val  Asp  Lys  His  Lys  Ser  Asp  Ile  Leu  Val  Pro  Gly  Glu  Ser
     1160                1165                1170
Ile  Thr  Asn  Val  Thr  Gln  Thr  Ser  Arg  Ser  Leu  Val  Ser  Thr  Met
     1175                1180                1185
Gly  Glu  Phe  Lys  Glu  Glu  Ser  Ser  Pro  Val  Gly  Phe  Pro  Gly  Ile
     1190                1195                1200
Pro  Thr  Trp  Asn  Pro  Ser  Arg  Lys  Ala  Gln  Pro  Gly  Arg  Leu  Gln
     1205                1210                1215
Thr  Asp  Ile  His  Val  Thr  Thr  Ser  Gly  Glu  Thr  Pro  Thr  Asp  Pro
     1220                1225                1230
Pro  Leu  Val  Asn  Glu  Leu  Glu  Asp  Val  Asp  Phe  Thr  Ser  Glu  Phe
     1235                1240                1245
Leu  Ser  Ser  Val  Thr  Val  Ser  Thr  Pro  Phe  His  Gln  Glu  Glu  Ala
     1250                1255                1260
Gly  Phe  Ser  Thr  Ile  Leu  Ser  Ser  Ile  Lys  Val  Glu  Met  Ala  Ser
     1265                1270                1275
Ser  Gln  Val  Glu  Thr  Thr  Thr  Leu  Gly  Gln  Asp  His  His  Glu  Thr
     1280                1285                1290
Thr  Val  Ala  Ile  Leu  His  Ser  Glu  Thr  Arg  Pro  Gln  Asn  His  Ile
     1295                1300                1305
Leu  Thr  Ala  Ala  Trp  Met  Lys  Glu  Pro  Ala  Ser  Leu  Ser  Pro  Pro
     1310                1315                1320
Met  Ile  Leu  Leu  Ser  Leu  Gly  Gln  Thr  Thr  Thr  Lys  Pro  Glu
     1325                1330                1335
Leu  Leu  Ser  Pro  Arg  Thr  Ser  Gln  Ile  Cys  Lys  Asp  Ser  Lys  Glu
     1340                1345                1350
Asn  Val  Phe  Leu  Asn  Tyr  Met  Gly  Asn  Pro  Glu  Thr  Glu  Ala  Thr
     1355                1360                1365
Pro  Val  Lys  Asn  Glu  Gly  Thr  Gln  Arg  Met  Ser  Gly  Pro  Asn  Glu
     1370                1375                1380
Leu  Ser  Thr  Pro  Ser  Ser  Asp  His  Asp  Ala  Phe  Asn  Leu  Ser  Thr
     1385                1390                1395
Lys  Leu  Glu  Leu  Glu  Lys  Gln  Val  Phe  Asp  Ser  Arg  Ser  Leu  Thr
     1400                1405                1410
```

-continued

Arg Gly Pro Asp Ser His His Gln Asp Gly Arg Val His Ala Ser
    1415            1420                1425

His Gln Leu Thr Arg Ile Pro Ala Lys Pro Ile Leu Pro Thr Gly
1430            1435                1440

Thr Val Arg Leu Pro Glu Met Ser Thr Gln Ser Thr Ser Arg Tyr
1445            1450                1455

Phe Val Thr Phe Gln Pro Pro His His Gly Thr Asn Lys Pro Glu
1460            1465                1470

Ile Thr Thr Tyr Pro Ser Arg Ala Leu Pro Glu Ser Lys Gln Phe
1475            1480                1485

Thr Thr Pro Arg Val Ala Ser Thr Thr Pro Leu Leu Ser His Met
1490            1495                1500

Ser Lys Pro Ser Ile Ser Ser Lys Phe Ala Asp Leu Arg Thr Asp
1505            1510                1515

Gln Ser Asn Gly Ser Tyr Lys Val Phe Gly Asn Ser Asn Ile Pro
1520            1525                1530

Glu Ala Arg Asn Ser Val Gly Lys Pro Leu Ser Pro Arg Ile Tyr
1535            1540                1545

His Tyr Ser Asn Gly Arg Leu Pro Phe Phe Thr Asn Arg Thr Leu
1550            1555                1560

Ser Phe Ser Gln Leu Gly Val Thr Arg Arg Pro Gln Ile Pro Ser
1565            1570                1575

Ser Pro Val Pro Val Met Arg Glu Arg Lys Val Asn Pro Gly Ser
1580            1585                1590

Tyr Asn Arg Ile Tyr Ser His Ser Thr Phe His Leu Asp Phe Gly
1595            1600                1605

Leu Pro Ala Pro Pro Leu Leu His Thr Pro Trp Thr Met Val Ser
1610            1615                1620

Pro Pro Thr Asn Leu Gln Asn Ile Pro Met Val Ser Ser Thr Gln
1625            1630                1635

Ser Ser Val Ser Phe Ile Thr Ser Ser Val Gln Ser Ser Gly Ser
1640            1645                1650

Ile His Gln Ser Gly Ser Lys Phe Phe Ala Gly Gly Pro Pro Ala
1655            1660                1665

Ser Lys Phe Trp Pro Leu Gly Glu Lys Pro Gln Ile Leu Thr Lys
1670            1675                1680

Ser Pro Gln Thr Val Ser Val Thr Ala Glu Thr Asp Ala Val Phe
1685            1690                1695

Pro Cys Glu Ala Ile Gly Lys Pro Lys Pro Phe Val Thr Trp Thr
1700            1705                1710

Lys Val Ser Thr Gly Val Leu Met Thr Pro Asn Thr Arg Ile Gln
1715            1720                1725

Arg Phe Glu Val Leu Lys Asn Gly Thr Leu Val Ile Arg Lys Phe
1730            1735                1740

Gln Val Gln Asp Arg Gly Gln Tyr Met Cys Thr Ala Ser Asn Leu
1745            1750                1755

Tyr Gly Leu Asp Arg Met Val Val Phe Leu Trp Val Thr Val Gln
1760            1765                1770

Gln Pro Gln Ile Leu Ala Ser His Tyr Gln Asp Val Thr Val Tyr
1775            1780                1785

Leu Gly Asp Thr Ile Thr Met Glu Cys Leu Ala Lys Gly Thr Pro
1790            1795                1800

-continued

```
Ala Pro Gln Ile Ser Trp Ile Phe Arg Asp Arg Val Trp Gln
1805            1810            1815

Thr Leu Ser Ser Val Glu Gly Arg Ile Thr Leu His Gln Asn Arg
1820            1825            1830

Thr Leu Ser Ile Lys Glu Ala Ser Phe Ser Asp Arg Gly Val Tyr
1835            1840            1845

Lys Cys Val Ala Ser Asn Ala Thr Arg Ala Asp Ser Val Ser Ile
1850            1855            1860

Arg Leu His Val Ala Ala Leu Pro Pro Ile Ile His Gln Glu Lys
1865            1870            1875

Leu Glu Asn Ile Ser Leu Pro Pro Gly Leu Ser Ile His Ile His
1880            1885            1890

Cys Thr Ala Lys Ala Ala Pro Leu Pro Ser Val Leu Trp Val Leu
1895            1900            1905

Gly Asp Gly Thr Gln Ile Arg Pro Ser His Phe Leu His Arg Asn
1910            1915            1920

Leu Phe Val Phe Pro Asn Gly Thr Leu Tyr Ile Cys Asn Leu Ala
1925            1930            1935

Pro Lys Asp Ser Gly Arg Tyr Glu Cys Val Ala Ala Asn Leu Ile
1940            1945            1950

Gly Ser Ala Arg Ser Thr Val Gln Leu Asn Val Gln Arg Ala Ala
1955            1960            1965

Ala Asn Ala Arg Ile Thr Gly Thr Ser Ser Gln Arg Thr Asp Val
1970            1975            1980

Arg Tyr Gly Gly Thr Leu Lys Leu Asp Cys Ser Ala Ser Gly Asp
1985            1990            1995

Pro Trp Pro Arg Ile Leu Trp Arg Leu Pro Ser Lys Arg Thr Ile
2000            2005            2010

Asp Ala Leu Phe Ser Phe Asp Ser Arg Ile Lys Val Phe Ala Asn
2015            2020            2025

Arg Thr Leu Val Val Lys Ser Met Thr Asp Lys Asp Ala Gly Asp
2030            2035            2040

Tyr Leu Cys Val Ala Arg Asn Lys Val Gly Asp Asp Cys Val Val
2045            2050            2055

Leu Lys Val Asp Val Met Met Lys Pro Ala Lys Ile Glu His Lys
2060            2065            2070

Glu Glu Asn Asp His Lys Val Phe Tyr Arg Gly Asp Leu Lys Val
2075            2080            2085

Asp Cys Val Ala Thr Gly Leu Pro Asn Pro Glu Ile Ser Trp Ser
2090            2095            2100

Leu Leu Asp Gly Ser Leu Val Asn Ser Phe Met Gln Ser Asp Asp
2105            2110            2115

Ser Gly Gly Arg Thr Lys His Tyr Val Val Phe Asn Asn Gly Thr
2120            2125            2130

Leu Tyr Phe Ser Glu Val Gly Met Arg Glu Gly Asp Tyr Thr
2135            2140            2145

Cys Phe Ala Glu Asn Gln Val Gly Lys Asp Glu Met Arg Val Arg
2150            2155            2160

Val Lys Met Val Thr Pro Ala Thr Ile Trp Asn Lys Thr Tyr Leu
2165            2170            2175

Ala Val Gln Val Pro Tyr Gly Asp Val Val Thr Val Thr Cys Glu
2180            2185            2190

Ala Lys Gly Glu Pro Met Pro Lys Val Thr Trp Leu Ser Pro Ala
```

```
                    2195                2200                2205

Asn Arg Val Ile Pro Thr Ser Ser Glu Lys Tyr Gln Ile Tyr Gln
2210                2215                2220

Tyr Gly Thr Leu Leu Ile Gln Lys Ala Gln Cys Ser Asp Ser Gly
2225                2230                2235

Asn Tyr Thr Cys Leu Val Arg Asn Ser Ala Gly Glu Asp Arg Lys
2240                2245                2250

Thr Val Trp Ile His Val Asn Leu Gln Pro Pro Lys Ile Asn Gly
2255                2260                2265

Asn Pro Asn Pro Ile Thr Thr Val Trp Glu Ile Ala Ala Gly Gly
2270                2275                2280

Ser Arg Lys Leu Ile Asp Cys Lys Ala Glu Gly Ile Pro Thr Pro
2285                2290                2295

Arg Val Leu Trp Ala Phe Pro Glu Gly Val Val Leu Pro Asp Pro
2300                2305                2310

Tyr Tyr Gly Asn Arg Ile Thr Val His Gly Asn Gly Ser Leu Asp
2315                2320                2325

Ile Arg Ser Leu Arg Lys Ser Asp Ser Val Gln Leu Val Cys Met
2330                2335                2340

Ala Arg Asn Glu Gly Gly Glu Ala Arg Leu Ile Val Gln Leu Thr
2345                2350                2355

Val Leu Glu Pro Met Glu Lys Pro Ile Phe His Asp Pro Ile Ser
2360                2365                2370

Glu Lys Ile Thr Ala Met Ala Gly His Thr Ile Ser Leu Asn Cys
2375                2380                2385

Ser Ala Ala Gly Thr Leu Thr Pro Ser Leu Val Trp Val Leu Pro
2390                2395                2400

Asn Gly Thr Asp Leu Gln Ser Gly Gln Gln Leu Gln Arg Phe Tyr
2405                2410                2415

His Lys Ala Asp Gly Met Leu His Ile Ser Gly Leu Ser Ser Val
2420                2425                2430

Asp Ala Gly Ala Tyr Arg Cys Val Ala Arg Asn Ala Ala Gly His
2435                2440                2445

Thr Glu Arg Leu Val Ser Leu Lys Val Gly Leu Lys Pro Glu Ala
2450                2455                2460

Asn Lys Gln Tyr His Asn Leu Val Ser Ile Ile Asn Gly Glu Thr
2465                2470                2475

Leu Lys Leu Pro Cys Thr Pro Pro Ala Ala Gly Gln Gly His Phe
2480                2485                2490

Ser Trp Thr Leu Pro Asn Gly Met His Leu Glu Gly Pro Gln Thr
2495                2500                2505

Leu Gly Arg Val Ser Leu Leu Asp Asn Gly Thr Leu Thr Val Arg
2510                2515                2520

Glu Ala Ser Val Phe Asp Arg Gly Thr Tyr Val Cys Arg Met Glu
2525                2530                2535

Thr Ala Tyr Gly Pro Ser Val Thr Ser Ile Pro Val Ile Val Ile
2540                2545                2550

Ala Tyr Pro Pro Arg Ile Thr Ser Glu Pro Thr Pro Val Ile Tyr
2555                2560                2565

Thr Arg Pro Gly Asn Thr Val Lys Leu Asn Cys Met Ala Met Gly
2570                2575                2580

Ile Pro Lys Gly Asp Ile Thr Trp Glu Leu Pro Asp Lys Leu His
2585                2590                2595
```

```
Leu Lys Ala Gly Val Gln Ala Arg Leu Tyr Gly Asn Arg Phe Leu
    2600            2605                2610

His Pro Gln Gly Ser Leu Thr Ile Gln Gln Ala Arg Arg Arg Asp
    2615            2620                2625

Ala Gly Phe Tyr Lys Cys Thr Ala Lys Asn Ile Leu Ser Ser Asp
    2630            2635                2640

Ser Lys Thr Thr Tyr Ile His Val Phe
    2645            2650

<210> SEQ ID NO 31
<211> LENGTH: 7872
<212> TYPE: DNA
<213> ORGANISM: Homo sapiens

<400> SEQUENCE: 31
atgaaggtaa aaggcagagg aatcacctgc ttgctggtct cctttgctgt gatctgcctg      60
gtcgccaccc ctgggggcaa ggcctgtcct cgccgctgtg cctgttatat gcctacggag     120
gtacactgca catttcggta cctgacttcc atcccagaca gcatcccgcc caatgtggaa     180
cgcatcaatt taggatacaa cagcttggtt agattgatgg aaacagattt ttctggcctg     240
accaaactgg agttactcat gcttcacagc aatggcattc acacaatccc tgacaagacc     300
ttctcagatt gcaggcctt gcaggtctta aaaatgagct ataataaagt ccgaaaactt     360
cagaaagata cttttatgg cctcaggagc ttgacacgat gcacatgga ccacaacaat     420 attgagttta taaacccaga ggttttttat gggctcaact ttctccgcct ggtgcacttg     480
gaaggaaatc agctcactaa gctccacccca gatacatttg tctctttgag ctacctccag     540
atatttaaaa tctctttcat taagttccta tacttgtctg ataacttcct gacctccctc     600
cctcaagaga tggtctccta tatgcctgac ctagacagcc tttacctgca tggaaaccca     660
tggacctgtg attgccattt aaagtggttg tctgactgga tacaggagaa gccagatgta     720
ataaaatgca aaaaagatag aagtccctct agtgctcagc agtgtccact ttgcatgaac     780
cctaggactt ctaaaggcaa gccgttagct atggtctcag ctgcagcttt ccagtgtgcc     840
aagccaacca ttgactcatc cctgaaatca agagcctga ctattctgga agacagtagt     900
tctgctttca tctctccca aggtttcatg gcacccttg ctccctcac tttgaatatg     960 acagatcagt ctggaaatga agctaacatg gtctgcagta ttcaaaagcc ctcaaggaca    1020
tcacccattg cattcactga gaaaaatgac tacatcgtgc taaatacttc attttcaaca    1080 ttttttggtgt gcaacataga ttacggtcac attcagccag tgtggcaaat tttggctttg    1140
tacagtgatt ctcctctgat actagaaagg agccacttgc ttagtgaaac accgcagctc    1200
tattacaaat ataaacaggt ggctcctaag cctgaagaca ttttttaccaa catagaggca    1260 gatctcagag cagatccctc ttggttaatg caagaccaaa tttccttgca gctgaacaga    1320
actgccacca cattcagtac attacagatc cagtactcca gtgatgctca aatcacttta    1380
ccaagagcag agatgaggcc agtgaaacac aaatggacta tgatttcaag ggataacaat    1440
actaagctgg aacatactgt cttggtaggt ggaaccgttg gcctgaactg cccaggccaa    1500 ggagaccccca ccccacacgt ggattggctt ctagctgatg aagtaaagt gagagccct    1560 tatgtcagtg aggatggacg gatcctaata gacaaaagtg gaaaattgga actccagatg    1620
gctgatagtt ttgacacagg cgtatatcac tgtataagca gcaattatga tgatgcagat    1680
attctcacct ataggataac tgtggtagaa cctttggtcg aagcctatca ggaaaatggg    1740
```

```
attcatcaca cagttttcat tggtgaaaca cttgatcttc catgccattc tactggtatc    1800
ccagatgcct ctattagctg ggttattcca ggaaacaatg tgctctatca gtcatcaaga    1860
gacaagaaag ttctaaacaa tggcacatta agaatattac aggtcacccc gaaagaccaa    1920
ggttattatc gctgtgtggc agccaaccca tcaggggttg attttttgat tttccaagtt    1980
tcagtcaaga tgaaaggaca aaggcccttg gagcatgatg gagaaacaga gggatctgga    2040
cttgatgagt ccaatcctat tgctcatctt aaggagccac caggtgcaca actccgtaca    2100
tctgctctga tggaggctga ggttggaaaa cacacctcaa gcacaagtaa gaggcacaac    2160
tatcgggaat taacactcca gcgacgtgga gattcaacac atcgacgttt tagggagaat    2220
aggaggcatt tccctccctc tgctaggaga attgacccac aacattgggc ggcactgttg    2280
gagaaagcta aaaagaatgc tatgccagac aagcgagaaa ataccacagt gagcccaccc    2340
ccagtggtca cccaactccc aaacatacct ggtgaagaag acgattcctc aggcatgctc    2400
gctctacatg aggaatttat ggtcccggcc actaaagctt tgaaccttcc agcaaggaca    2460
gtgactgctg actccagaac aatatctgat agtcctatga caaacataaa ttatggcaca    2520
gaattctctc ctgttgtgaa ttcacaaata ctaccacctg aagaacccac agatttcaaa    2580
ctgtctactg ctattaaaac tacagccatg tcaaagaata taaacccaac catgtcaagc    2640
caaatacaag gcacaaccaa tcaacattca tccactgtct ttccactgct acttggagca    2700
actgaatttc aggactctga ccagatggga agaggaagag agcatttcca agtagaccc     2760
ccaataacag taaggactat gatcaaagat gtcaatgtca aaatgcttag tagcaccacc    2820
aacaaactat tattagagtc agtaaatacc acaaatagtc atcagacatc tgtaagagaa    2880
gtgagtgaac ccaggcacaa tcacttctat tctcacacta ctcaaatact tagcacctcc    2940
acgttccctt cagatccaca cacagctgct cattctcagt ttccgatccc tagaaatagt    3000
acagttaaca tcccgctgtt cagacgcttt gggaggcaga ggaaaattgg cggaaggggg    3060
cggattatca gcccatatag aactccagtt ctgcgacggc atagatacag cattttcagg    3120
tcaacaacca gaggttcttc tgaaaaaagc actactgcat tctcagccac agtgctcaat    3180
gtgacatgtc tgtcctgtct tcccagggag aggctcacca ctgccacagc agcattgtct    3240
tttccaagtg ctgctcccat caccttcccc aaagctgaca ttgctagagt cccatcagaa    3300
gagtctacaa ctctagtcca gaatccacta ttactacttg agaacaaacc cagtgtagag    3360
aaaacaacac ccacaataaa atatttcagg actgaaattt cccaagtgac tccaactggt    3420
gcagtcatga catatgctcc aacatccata cccatggaaa aaactcacaa agtaaacgcc    3480
agttacccac gtgtgtctag caccaatgaa gctaaaagag attcagtgat tacatcgtca    3540
cttttcaggtg ctatcaccaa gccaccaatg actattatag ccattacaag gttttcaaga    3600
aggaaaattc cctggcaaca gaactttgta aataaccata acccaaaagg cagattaagg    3660
aatcaacata aagttagttt acaaaaaagc acagctgtga tgcttcctaa aacatctcct    3720
gctttaccca gagacaaagt ctccccttc catttcacca cactttcaac aagtgtgatg    3780
caaattccat ctaataccct tgactaccgct caccacacta cgaccaaaac acacaatcct    3840
ggaagtcttc caacaaagaa ggagcttccc ttcccacccc ttaaccctat gcttcctagt    3900
attataagca aagactcaag tacaaaaagc atcatatcaa cgcaaacagc aataccagca    3960
acaactccta ccttccctgc atctgtcatc acttatgaaa cccaaacaga gagatctaga    4020
gcacaaacaa tacaaagaga acaggagcct caaaagaaga acaggactga cccaaacatc    4080
tctccagacc agagttctgg cttcactaca cccactgcta tgacacctcc tgttctaacc    4140
```

-continued

```
acagccgaaa cttcagtcaa gcccagtgtc tctgcattca ctcattcccc accagaaaac    4200
acaactggga tttcaagcac aatcagtttt cattcaagaa ctcttaatct gacagatgtg    4260
attgaagaac tagcccaagc aagtactcag actttgaaga gcacaattgc ttctgaaaca    4320
actttgtcca gcaaatcaca ccagagtacc acaactagga aagcaatcat tagacactca    4380
accataccac cattcttgag cagcagtgct actctaatgc cagttcccat ctcccctccc    4440
tttactcaga gagcagttac tgacaacgtg gcgactccca tttccgggct tatgacaaat    4500
acagtggtca agctgcacga atcctcaagg cacaatgcta aaccacagca attagtagca    4560
gaggttgcaa catcccccaa ggttcaccca aatgccaagt tcacaattgg aaccactcac    4620
ttcatctact ctaatctgtt acattctact cccatgccag cactaacaac agttaaatca    4680
cagaattcta aattaactcc atctccctgg gcagaaaacc aattttggca caaccatac    4740 tcagaaattg ctgaaaaagg caaaaagcca gaagtaagca tgttggctac tacaggcctg    4800
tccgaggcca ccactcttgt ttcagattgg gatggacaga agaacacaaa gaagagtgac    4860
tttgataaga aaccagttca agaagcaaca acttccaaac tccttccctt tgactctttg    4920
tctaggtata tatttgaaaa gcccaggata gttggaggaa aagctgcaag ttttactatt    4980
ccagctaact cagatgcctt tcttccctgt gaagctgttg gaaatcccct gcccaccatt    5040
cattggacca gagtcccatc aggacttgat ttatctaaga ggaaacagaa tagcagggtc    5100
caggttctcc ccaatggtac cctgtccatc cagagggtgg aaattcagga ccgcggacag    5160
tacttgtgtt ccgcatccaa tctgtttggc acagaccacc ttcatgtcac cttgtctgtg    5220
gtttcctatc ctcccaggat cctggagaga cgtaccaaag agatcacagt tcattccgga    5280
agcactgtgg aactgaagtg cagagcagaa ggtaggccaa gccctacagt tacctggatt    5340
cttgcaaacc aaacagttgt ctcagaatca tcccagggaa gtaggcaggc tgtggtgacg    5400
gttgacggaa cattggtcct ccacaatctc agtatttatg accgtggctt ttacaaatgt    5460
gtggccagca acccaggtgg ccaggattca ctgctggtta aaatacaagt cattgcagca    5520
ccacctgtta ttctagagca aaggaggcaa gtcattgtag gcacttgggg tgaaagttta    5580
aaactgccct gtactgcaaa aggaactcct cagcccagcg tttactgggt cctctctgat    5640
ggcactgaag tgaaaccatt acagtttacc aattccaagt tgttcttatt ttcaaatggg    5700
actttgtata taagaaacct agcctcttca gacagggca cttatgaatg cattgctacc    5760
agttccactg gttcggagcg aagagtagta atgcttacaa tggaagagcg agtgaccagc    5820
cccaggatag aagctgcatc ccagaaaagg actgaagtga attttgggga caaattacta    5880
ctgaactgct cagccactgg ggagcccaaa ccccaaataa tgtggaggtt accatccaag    5940
gctgtggtcg accagcagca tagagtgggc agctggatcc acgtctaccc taatggatcc    6000
ctgtttattg gatcagtaac agaaaaagac agtggtgtct acttgtgtgt ggcaagaaac    6060
aaaatggggg atgatctgat actgatgcat gttagcctaa gactgaaacc tgccaaaatt    6120
gaccacaagc agtattttag aaagcaagtg ctccatggga aagatttcca gtagattgc    6180 aaagcttccg gctccccagt gccagagata tcttggagtt tgcctgatgg aaccatgatc    6240
aacaatgcaa tgcaagccga tgacagtggc cacaggacta ggagatatac ccttttcaac    6300
aatggaactt tatacttcaa caagttgggg gtagcggagg aaggagatta tacttgctat    6360
gcccagaaca ccctagggaa agatgaaatg aaggtccact aacagttat aacagctgct    6420 ccccggataa ggcagagtaa caaaaccaac aagagaatca aagctggaga cacagctgtc    6480
```

```
                                                     -continued cttgactgtg aggtcactgg ggatcccaaa ccaaaaatat tttggttgct gccttccaat   6540
gacatgattt ccttctccat tgataggtac acatttcatg ccaatgggtc tttgaccatc   6600
aacaaagtga aactgctcga ttctggagag tacgtatgtg tagcccgaaa tcccagtggg   6660
gatgacacca aaatgtacaa actggatgtg gtctctaaac ctccattaat caatggtctg   6720
tatacaaaca gaactgttat taaagccaca gctgtgagac attccaaaaa acactttgac   6780
tgcagagctg aagggacacc atctcctgaa gtcatgtgga tcatgccaga caatattttc   6840
ctcacagccc catactatgg aagcagaatc acagtccata aaaatggaac cttggaaatt   6900
aggaatgtga ggctttcaga ttcagccgac tttatctgtg tggcccgaaa tgaaggtgga   6960
gagagcgtgt tggtagtaca gttagaagta ctggaaatgc tgagaagacc gacatttaga   7020
aatccattta atgaaaaaat agttgcccag ctgggaaagt ccacagcatt gaattgctct   7080
gttgatggta acccaccacc tgaaataatc tggattttac caaatggcac acgatttttcc   7140 aatggaccac aaagttatca gtatctgata gcaagcaatg gttcttttat catttctaaa   7200
acaactcggg aggatgcagg aaaatatcgc tgtgcagcta ggaataaagt tggctatatt   7260
gagaaattag tcatattaga aattggccag aagccagtta ttcttaccta tgcaccaggg   7320
acagtaaaag gcatcagtgg agaatctcta tcactgcatt gtgtgtctga tggaatccct   7380
aagccaaata tcaaatggac tatgccaagt ggttatgtag tagacaggcc tcaaattaat   7440
gggaaataca tattgcatga caatggcacc ttagtcatta agaagcaac agcttatgac   7500 agaggaaact atatctgtaa ggctcaaaat agtgttggtc atacactgat tactgttcca   7560
gtaatgattg tagcctaccc tccccgaatt acaaatcgtc cacccaggag tattgtcacc   7620
aggacagggg cagcctttca gctccactgt gtggccttgg gagttcccaa gccagaaatc   7680
acatgggaga tgcctgacca ctcccttctc tcaacggcaa gtaaagagag gacacatgga   7740
agtgagcagc ttcacttaca aggtaccccta gtcattcaga atcccaaaac ctccgattct   7800
gggatataca aatgcacagc aaagaaccca cttggtagtg attatgcagc aacgtatatt   7860
caagtaatct ga                                                      7872
```

<210> SEQ ID NO 32
<211> LENGTH: 2623
<212> TYPE: PRT
<213> ORGANISM: Homo sapiens

<400> SEQUENCE: 32

```
Met Lys Val Lys Gly Arg Gly Ile Thr Cys Leu Leu Val Ser Phe Ala
1               5                   10                  15

Val Ile Cys Leu Val Ala Thr Pro Gly Gly Lys Ala Cys Pro Arg Arg
            20                  25                  30

Cys Ala Cys Tyr Met Pro Thr Glu Val His Cys Thr Phe Arg Tyr Leu
        35                  40                  45

Thr Ser Ile Pro Asp Ser Ile Pro Pro Asn Val Glu Arg Ile Asn Leu
    50                  55                  60

Gly Tyr Asn Ser Leu Val Arg Leu Met Glu Thr Asp Phe Ser Gly Leu
65                  70                  75                  80

Thr Lys Leu Glu Leu Leu Met Leu His Ser Asn Gly Ile His Thr Ile
                85                  90                  95

Pro Asp Lys Thr Phe Ser Asp Leu Gln Ala Leu Gln Val Leu Lys Met
            100                 105                 110

Ser Tyr Asn Lys Val Arg Lys Leu Gln Lys Asp Thr Phe Tyr Gly Leu
        115                 120                 125
```

```
Arg Ser Leu Thr Arg Leu His Met Asp His Asn Asn Ile Glu Phe Ile
        130                 135                 140
Asn Pro Glu Val Phe Tyr Gly Leu Asn Phe Leu Arg Leu Val His Leu
145                 150                 155                 160
Glu Gly Asn Gln Leu Thr Lys Leu His Pro Asp Thr Phe Val Ser Leu
                    165                 170                 175
Ser Tyr Leu Gln Ile Phe Lys Ile Ser Phe Ile Lys Phe Leu Tyr Leu
                180                 185                 190
Ser Asp Asn Phe Leu Thr Ser Leu Pro Gln Glu Met Val Ser Tyr Met
            195                 200                 205
Pro Asp Leu Asp Ser Leu Tyr Leu His Gly Asn Pro Trp Thr Cys Asp
        210                 215                 220
Cys His Leu Lys Trp Leu Ser Asp Trp Ile Gln Glu Lys Pro Asp Val
225                 230                 235                 240
Ile Lys Cys Lys Lys Asp Arg Ser Pro Ser Ala Gln Gln Cys Pro
                    245                 250                 255
Leu Cys Met Asn Pro Arg Thr Ser Lys Gly Lys Pro Leu Ala Met Val
                260                 265                 270
Ser Ala Ala Phe Gln Cys Ala Lys Pro Thr Ile Asp Ser Ser Leu
            275                 280                 285
Lys Ser Lys Ser Leu Thr Ile Leu Glu Asp Ser Ser Ala Phe Ile
290                 295                 300
Ser Pro Gln Gly Phe Met Ala Pro Phe Gly Ser Leu Thr Leu Asn Met
305                 310                 315                 320
Thr Asp Gln Ser Gly Asn Glu Ala Asn Met Val Cys Ser Ile Gln Lys
                325                 330                 335
Pro Ser Arg Thr Ser Pro Ile Ala Phe Thr Glu Glu Asn Asp Tyr Ile
            340                 345                 350
Val Leu Asn Thr Ser Phe Ser Thr Phe Leu Val Cys Asn Ile Asp Tyr
        355                 360                 365
Gly His Ile Gln Pro Val Trp Gln Ile Leu Ala Leu Tyr Ser Asp Ser
    370                 375                 380
Pro Leu Ile Leu Glu Arg Ser His Leu Leu Ser Glu Thr Pro Gln Leu
385                 390                 395                 400
Tyr Tyr Lys Tyr Lys Gln Val Ala Pro Lys Pro Glu Asp Ile Phe Thr
                405                 410                 415
Asn Ile Glu Ala Asp Leu Arg Ala Asp Pro Ser Trp Leu Met Gln Asp
            420                 425                 430
Gln Ile Ser Leu Gln Leu Asn Arg Thr Ala Thr Thr Phe Ser Thr Leu
        435                 440                 445
Gln Ile Gln Tyr Ser Ser Asp Ala Gln Ile Thr Leu Pro Arg Ala Glu
    450                 455                 460
Met Arg Pro Val Lys His Lys Trp Thr Met Ile Ser Arg Asp Asn Asn
465                 470                 475                 480
Thr Lys Leu Glu His Thr Val Leu Val Gly Thr Val Gly Leu Asn
                485                 490                 495
Cys Pro Gly Gln Gly Asp Pro Thr Pro His Val Asp Trp Leu Leu Ala
                500                 505                 510
Asp Gly Ser Lys Val Arg Ala Pro Tyr Val Ser Glu Asp Gly Arg Ile
            515                 520                 525
Leu Ile Asp Lys Ser Gly Lys Leu Glu Leu Gln Met Ala Asp Ser Phe
        530                 535                 540
```

-continued

```
Asp Thr Gly Val Tyr His Cys Ile Ser Ser Asn Tyr Asp Asp Ala Asp
545                 550                 555                 560

Ile Leu Thr Tyr Arg Ile Thr Val Val Glu Pro Leu Val Glu Ala Tyr
                565                 570                 575

Gln Glu Asn Gly Ile His His Thr Val Phe Ile Gly Glu Thr Leu Asp
            580                 585                 590

Leu Pro Cys His Ser Thr Gly Ile Pro Asp Ala Ser Ile Ser Trp Val
        595                 600                 605

Ile Pro Gly Asn Asn Val Leu Tyr Gln Ser Ser Arg Asp Lys Lys Val
    610                 615                 620

Leu Asn Asn Gly Thr Leu Arg Ile Leu Gln Val Thr Pro Lys Asp Gln
625                 630                 635                 640

Gly Tyr Tyr Arg Cys Val Ala Ala Asn Pro Ser Gly Val Asp Phe Leu
                645                 650                 655

Ile Phe Gln Val Ser Val Lys Met Lys Gly Gln Arg Pro Leu Glu His
            660                 665                 670

Asp Gly Glu Thr Glu Gly Ser Gly Leu Asp Glu Ser Asn Pro Ile Ala
        675                 680                 685

His Leu Lys Glu Pro Pro Gly Ala Gln Leu Arg Thr Ser Ala Leu Met
    690                 695                 700

Glu Ala Glu Val Gly Lys His Thr Ser Ser Thr Ser Lys Arg His Asn
705                 710                 715                 720

Tyr Arg Glu Leu Thr Leu Gln Arg Arg Gly Asp Ser Thr His Arg Arg
                725                 730                 735

Phe Arg Glu Asn Arg Arg His Phe Pro Pro Ser Ala Arg Arg Ile Asp
            740                 745                 750

Pro Gln His Trp Ala Ala Leu Leu Glu Lys Ala Lys Lys Asn Ala Met
        755                 760                 765

Pro Asp Lys Arg Glu Asn Thr Thr Val Ser Pro Pro Val Val Thr
    770                 775                 780

Gln Leu Pro Asn Ile Pro Gly Glu Glu Asp Asp Ser Ser Gly Met Leu
785                 790                 795                 800

Ala Leu His Glu Glu Phe Met Val Pro Ala Thr Lys Ala Leu Asn Leu
                805                 810                 815

Pro Ala Arg Thr Val Thr Ala Asp Ser Arg Thr Ile Ser Asp Ser Pro
            820                 825                 830

Met Thr Asn Ile Asn Tyr Gly Thr Glu Phe Ser Pro Val Val Asn Ser
        835                 840                 845

Gln Ile Leu Pro Pro Glu Glu Pro Thr Asp Phe Lys Leu Ser Thr Ala
    850                 855                 860

Ile Lys Thr Thr Ala Met Ser Lys Asn Ile Asn Pro Thr Met Ser Ser
865                 870                 875                 880

Gln Ile Gln Gly Thr Thr Asn Gln His Ser Ser Thr Val Phe Pro Leu
                885                 890                 895

Leu Leu Gly Ala Thr Glu Phe Gln Asp Ser Asp Gln Met Gly Arg Gly
            900                 905                 910

Arg Glu His Phe Gln Ser Arg Pro Pro Ile Thr Val Arg Thr Met Ile
        915                 920                 925

Lys Asp Val Asn Val Lys Met Leu Ser Ser Thr Asn Lys Leu Leu
    930                 935                 940

Leu Glu Ser Val Asn Thr Thr Asn Ser His Gln Thr Ser Val Arg Glu
945                 950                 955                 960

Val Ser Glu Pro Arg His Asn His Phe Tyr Ser His Thr Thr Gln Ile
```

-continued

```
                965                 970                 975
Leu Ser Thr Ser Thr Phe Pro Ser Asp Pro His Thr Ala Ala His Ser
        980                 985                 990
Gln Phe Pro Ile Pro Arg Asn Ser Thr Val Asn Ile Pro Leu Phe Arg
        995                 1000                1005
Arg Phe Gly Arg Gln Arg Lys Ile Gly Gly Arg Gly Arg Ile Ile
    1010                1015                1020
Ser Pro Tyr Arg Thr Pro Val Leu Arg Arg His Arg Tyr Ser Ile
    1025                1030                1035
Phe Arg Ser Thr Thr Arg Gly Ser Ser Glu Lys Ser Thr Thr Ala
    1040                1045                1050
Phe Ser Ala Thr Val Leu Asn Val Thr Cys Leu Ser Cys Leu Pro
    1055                1060                1065
Arg Glu Arg Leu Thr Thr Ala Thr Ala Ala Leu Ser Phe Pro Ser
    1070                1075                1080
Ala Ala Pro Ile Thr Phe Pro Lys Ala Asp Ile Ala Arg Val Pro
    1085                1090                1095
Ser Glu Glu Ser Thr Thr Leu Val Gln Asn Pro Leu Leu Leu Leu
    1100                1105                1110
Glu Asn Lys Pro Ser Val Glu Lys Thr Thr Pro Thr Ile Lys Tyr
    1115                1120                1125
Phe Arg Thr Glu Ile Ser Gln Val Thr Pro Thr Gly Ala Val Met
    1130                1135                1140
Thr Tyr Ala Pro Thr Ser Ile Pro Met Glu Lys Thr His Lys Val
    1145                1150                1155
Asn Ala Ser Tyr Pro Arg Val Ser Ser Thr Asn Glu Ala Lys Arg
    1160                1165                1170
Asp Ser Val Ile Thr Ser Ser Leu Ser Gly Ala Ile Thr Lys Pro
    1175                1180                1185
Pro Met Thr Ile Ile Ala Ile Thr Arg Phe Ser Arg Arg Lys Ile
    1190                1195                1200
Pro Trp Gln Gln Asn Phe Val Asn Asn His Asn Pro Lys Gly Arg
    1205                1210                1215
Leu Arg Asn Gln His Lys Val Ser Leu Gln Lys Ser Thr Ala Val
    1220                1225                1230
Met Leu Pro Lys Thr Ser Pro Ala Leu Pro Arg Asp Lys Val Ser
    1235                1240                1245
Pro Phe His Phe Thr Thr Leu Ser Thr Ser Val Met Gln Ile Pro
    1250                1255                1260
Ser Asn Thr Leu Thr Thr Ala His His Thr Thr Thr Lys Thr His
    1265                1270                1275
Asn Pro Gly Ser Leu Pro Thr Lys Lys Glu Leu Pro Phe Pro Pro
    1280                1285                1290
Leu Asn Pro Met Leu Pro Ser Ile Ile Ser Lys Asp Ser Ser Thr
    1295                1300                1305
Lys Ser Ile Ile Ser Thr Gln Thr Ala Ile Pro Ala Thr Thr Pro
    1310                1315                1320
Thr Phe Pro Ala Ser Val Ile Thr Tyr Glu Thr Gln Thr Glu Arg
    1325                1330                1335
Ser Arg Ala Gln Thr Ile Gln Arg Glu Gln Glu Pro Gln Lys Lys
    1340                1345                1350
Asn Arg Thr Asp Pro Asn Ile Ser Pro Asp Gln Ser Ser Gly Phe
    1355                1360                1365
```

-continued

Thr Thr Pro Thr Ala Met Thr Pro Pro Val Leu Thr Thr Ala Glu
1370                1375                1380

Thr Ser Val Lys Pro Ser Val Ser Ala Phe Thr His Ser Pro Pro
1385                1390                1395

Glu Asn Thr Thr Gly Ile Ser Ser Thr Ile Ser Phe His Ser Arg
1400                1405                1410

Thr Leu Asn Leu Thr Asp Val Ile Glu Glu Leu Ala Gln Ala Ser
1415                1420                1425

Thr Gln Thr Leu Lys Ser Thr Ile Ala Ser Glu Thr Thr Leu Ser
1430                1435                1440

Ser Lys Ser His Gln Ser Thr Thr Thr Arg Lys Ala Ile Ile Arg
1445                1450                1455

His Ser Thr Ile Pro Pro Phe Leu Ser Ser Ser Ala Thr Leu Met
1460                1465                1470

Pro Val Pro Ile Ser Pro Pro Phe Thr Gln Arg Ala Val Thr Asp
1475                1480                1485

Asn Val Ala Thr Pro Ile Ser Gly Leu Met Thr Asn Thr Val Val
1490                1495                1500

Lys Leu His Glu Ser Ser Arg His Asn Ala Lys Pro Gln Gln Leu
1505                1510                1515

Val Ala Glu Val Ala Thr Ser Pro Lys Val His Pro Asn Ala Lys
1520                1525                1530

Phe Thr Ile Gly Thr Thr His Phe Ile Tyr Ser Asn Leu Leu His
1535                1540                1545

Ser Thr Pro Met Pro Ala Leu Thr Thr Val Lys Ser Gln Asn Ser
1550                1555                1560

Lys Leu Thr Pro Ser Pro Trp Ala Glu Asn Gln Phe Trp His Lys
1565                1570                1575

Pro Tyr Ser Glu Ile Ala Glu Lys Gly Lys Lys Pro Glu Val Ser
1580                1585                1590

Met Leu Ala Thr Thr Gly Leu Ser Glu Ala Thr Thr Leu Val Ser
1595                1600                1605

Asp Trp Asp Gly Gln Lys Asn Thr Lys Lys Ser Asp Phe Asp Lys
1610                1615                1620

Lys Pro Val Gln Glu Ala Thr Thr Ser Lys Leu Leu Pro Phe Asp
1625                1630                1635

Ser Leu Ser Arg Tyr Ile Phe Glu Lys Pro Arg Ile Val Gly Gly
1640                1645                1650

Lys Ala Ala Ser Phe Thr Ile Pro Ala Asn Ser Asp Ala Phe Leu
1655                1660                1665

Pro Cys Glu Ala Val Gly Asn Pro Leu Pro Thr Ile His Trp Thr
1670                1675                1680

Arg Val Pro Ser Gly Leu Asp Leu Ser Lys Arg Lys Gln Asn Ser
1685                1690                1695

Arg Val Gln Val Leu Pro Asn Gly Thr Leu Ser Ile Gln Arg Val
1700                1705                1710

Glu Ile Gln Asp Arg Gly Gln Tyr Leu Cys Ser Ala Ser Asn Leu
1715                1720                1725

Phe Gly Thr Asp His Leu His Val Thr Leu Ser Val Val Ser Tyr
1730                1735                1740

Pro Pro Arg Ile Leu Glu Arg Arg Thr Lys Glu Ile Thr Val His
1745                1750                1755

```
Ser Gly Ser Thr Val Glu Leu Lys Cys Arg Ala Glu Gly Arg Pro
    1760            1765                1770
Ser Pro Thr Val Thr Trp Ile Leu Ala Asn Gln Thr Val Val Ser
    1775            1780                1785
Glu Ser Ser Gln Gly Ser Arg Gln Ala Val Val Thr Val Asp Gly
    1790            1795                1800
Thr Leu Val Leu His Asn Leu Ser Ile Tyr Asp Arg Gly Phe Tyr
    1805            1810                1815
Lys Cys Val Ala Ser Asn Pro Gly Gly Gln Asp Ser Leu Leu Val
    1820            1825                1830
Lys Ile Gln Val Ile Ala Ala Pro Pro Val Ile Leu Glu Gln Arg
    1835            1840                1845
Arg Gln Val Ile Val Gly Thr Trp Gly Glu Ser Leu Lys Leu Pro
    1850            1855                1860
Cys Thr Ala Lys Gly Thr Pro Gln Pro Ser Val Tyr Trp Val Leu
    1865            1870                1875
Ser Asp Gly Thr Glu Val Lys Pro Leu Gln Phe Thr Asn Ser Lys
    1880            1885                1890
Leu Phe Leu Phe Ser Asn Gly Thr Leu Tyr Ile Arg Asn Leu Ala
    1895            1900                1905
Ser Ser Asp Arg Gly Thr Tyr Glu Cys Ile Ala Thr Ser Ser Thr
    1910            1915                1920
Gly Ser Glu Arg Arg Val Val Met Leu Thr Met Glu Glu Arg Val
    1925            1930                1935
Thr Ser Pro Arg Ile Glu Ala Ala Ser Gln Lys Arg Thr Glu Val
    1940            1945                1950
Asn Phe Gly Asp Lys Leu Leu Leu Asn Cys Ser Ala Thr Gly Glu
    1955            1960                1965
Pro Lys Pro Gln Ile Met Trp Arg Leu Pro Ser Lys Ala Val Val
    1970            1975                1980
Asp Gln Gln His Arg Val Gly Ser Trp Ile His Val Tyr Pro Asn
    1985            1990                1995
Gly Ser Leu Phe Ile Gly Ser Val Thr Glu Lys Asp Ser Gly Val
    2000            2005                2010
Tyr Leu Cys Val Ala Arg Asn Lys Met Gly Asp Asp Leu Ile Leu
    2015            2020                2025
Met His Val Ser Leu Arg Leu Lys Pro Ala Lys Ile Asp His Lys
    2030            2035                2040
Gln Tyr Phe Arg Lys Gln Val Leu His Gly Lys Asp Phe Gln Val
    2045            2050                2055
Asp Cys Lys Ala Ser Gly Ser Pro Val Pro Glu Ile Ser Trp Ser
    2060            2065                2070
Leu Pro Asp Gly Thr Met Ile Asn Asn Ala Met Gln Ala Asp Asp
    2075            2080                2085
Ser Gly His Arg Thr Arg Arg Tyr Thr Leu Phe Asn Asn Gly Thr
    2090            2095                2100
Leu Tyr Phe Asn Lys Val Gly Val Ala Glu Glu Gly Asp Tyr Thr
    2105            2110                2115
Cys Tyr Ala Gln Asn Thr Leu Gly Lys Asp Glu Met Lys Val His
    2120            2125                2130
Leu Thr Val Ile Thr Ala Ala Pro Arg Ile Arg Gln Ser Asn Lys
    2135            2140                2145
Thr Asn Lys Arg Ile Lys Ala Gly Asp Thr Ala Val Leu Asp Cys
```

-continued

```
            2150                  2155                  2160
Glu Val Thr Gly Asp Pro Lys Pro Lys Ile Phe Trp Leu Leu Pro
    2165                  2170                  2175
Ser Asn Asp Met Ile Ser Phe Ser Ile Asp Arg Tyr Thr Phe His
    2180                  2185                  2190
Ala Asn Gly Ser Leu Thr Ile Asn Lys Val Lys Leu Leu Asp Ser
    2195                  2200                  2205
Gly Glu Tyr Val Cys Val Ala Arg Asn Pro Ser Gly Asp Asp Thr
    2210                  2215                  2220
Lys Met Tyr Lys Leu Asp Val Val Ser Lys Pro Pro Leu Ile Asn
    2225                  2230                  2235
Gly Leu Tyr Thr Asn Arg Thr Val Ile Lys Ala Thr Ala Val Arg
    2240                  2245                  2250
His Ser Lys Lys His Phe Asp Cys Arg Ala Glu Gly Thr Pro Ser
    2255                  2260                  2265
Pro Glu Val Met Trp Ile Met Pro Asp Asn Ile Phe Leu Thr Ala
    2270                  2275                  2280
Pro Tyr Tyr Gly Ser Arg Ile Thr Val His Lys Asn Gly Thr Leu
    2285                  2290                  2295
Glu Ile Arg Asn Val Arg Leu Ser Asp Ser Ala Asp Phe Ile Cys
    2300                  2305                  2310
Val Ala Arg Asn Glu Gly Gly Glu Ser Val Leu Val Val Gln Leu
    2315                  2320                  2325
Glu Val Leu Glu Met Leu Arg Arg Pro Thr Phe Arg Asn Pro Phe
    2330                  2335                  2340
Asn Glu Lys Ile Val Ala Gln Leu Gly Lys Ser Thr Ala Leu Asn
    2345                  2350                  2355
Cys Ser Val Asp Gly Asn Pro Pro Glu Ile Trp Ile Leu
    2360                  2365                  2370
Pro Asn Gly Thr Arg Phe Ser Asn Gly Pro Gln Ser Tyr Gln Tyr
    2375                  2380                  2385
Leu Ile Ala Ser Asn Gly Ser Phe Ile Ile Ser Lys Thr Thr Arg
    2390                  2395                  2400
Glu Asp Ala Gly Lys Tyr Arg Cys Ala Ala Arg Asn Lys Val Gly
    2405                  2410                  2415
Tyr Ile Glu Lys Leu Val Ile Leu Glu Ile Gly Gln Lys Pro Val
    2420                  2425                  2430
Ile Leu Thr Tyr Ala Pro Gly Thr Val Lys Gly Ile Ser Gly Glu
    2435                  2440                  2445
Ser Leu Ser Leu His Cys Val Ser Asp Gly Ile Pro Lys Pro Asn
    2450                  2455                  2460
Ile Lys Trp Thr Met Pro Ser Gly Tyr Val Val Asp Arg Pro Gln
    2465                  2470                  2475
Ile Asn Gly Lys Tyr Ile Leu His Asp Asn Gly Thr Leu Val Ile
    2480                  2485                  2490
Lys Glu Ala Thr Ala Tyr Asp Arg Gly Asn Tyr Ile Cys Lys Ala
    2495                  2500                  2505
Gln Asn Ser Val Gly His Thr Leu Ile Thr Val Pro Val Met Ile
    2510                  2515                  2520
Val Ala Tyr Pro Pro Arg Ile Thr Asn Arg Pro Pro Arg Ser Ile
    2525                  2530                  2535
Val Thr Arg Thr Gly Ala Ala Phe Gln Leu His Cys Val Ala Leu
    2540                  2545                  2550
```

```
Gly Val Pro Lys Pro Glu Ile Thr Trp Glu Met Pro Asp His Ser
    2555                2560                2565

Leu Leu Ser Thr Ala Ser Lys Glu Arg Thr His Gly Ser Glu Gln
    2570                2575                2580

Leu His Leu Gln Gly Thr Leu Val Ile Gln Asn Pro Gln Thr Ser
    2585                2590                2595

Asp Ser Gly Ile Tyr Lys Cys Thr Ala Lys Asn Pro Leu Gly Ser
    2600                2605                2610

Asp Tyr Ala Ala Thr Tyr Ile Gln Val Ile
    2615                2620

<210> SEQ ID NO 33
<211> LENGTH: 8883
<212> TYPE: DNA
<213> ORGANISM: Rattus rattus
<220> FEATURE:
<221> NAME/KEY: misc_feature
<222> LOCATION: (8825)..(8825)
<223> OTHER INFORMATION: n is a, c, g, or t

<400> SEQUENCE: 33
cgagagacga cagaaggtta cggctgcgag aagacgacag aagggtccag aaaaaggaaa      60
gtgctggagg ggagtgggga caaaagcagc gaccaagtga atgtcacttc agtgactgag     120
gccaggcaaa acgcgcggga aggatttttgt gtagcttggg accctttcat agacactgat   180
gacacgtttta cgcaaaatag aaatttgagg agaaacgcct gggccttcgg aaaggagtga    240
ttgattagta cttgcaagtt taggtgactt taaggagaac taactaatgt atactattga     300
gggaggagga agagcattac agagtttcca gcagcagcag gaaagctttg gttaatttgg     360
aaatggatga tagcattaaa ataacagaag cgcctccagg tctctgaagc ttcagtcccc     420
cagctgaaag ccagaaaaga ctaagcccac taagcctttt gatcccttttg gaagcaaaga    480
actttccttc cctggggtga agactctcct cagaagattt cctgtctctg cctatgttac     540
aagaggaatc aaaaccaaga cagaagagct caggatgcag gtgagaggca gggaagtcag     600
cggcttgttg atctccctca ctgctgtctg cctggtggtc acccctggga gcagggcctg     660
tcctcgccgc tgtgcctgct atgtgcccac agaggtgcac tgtacatttc ggtacctgac     720
ctccatccca gatggcatcc cggccaatgt ggaacgaata aatttaggat ataacagcct     780
tactagattg acagaaaacg actttgatgg cctgagcaaa ctggagttac tcatgctgca     840
cagtaatggc attcacagag tcagtgacaa gaccttctcg ggcttgcagt ccttgcaggt     900
cttaaaaatg agctataaca aagtccaaat cattcggaag gatactttct acggactcgg     960
gagcttggtc cggttgcacc tggatcacaa caacattgaa ttcatcaacc ctgaggcctt    1020
ttatggactt acctcgctcc gcttggtaca tttagaagga accggctcca caaagctcca    1080
tccagacaca tttgtctcat taagctatct ccagatattt aaaaacctctt tcattaagta   1140
cctgttcttg tctgataact tcctgacctc cctcccaaaa gaaatggtct cctacatgcc    1200
aaacctagaa agcctgtatt tgcatggaaa cccatggacc tgtgactgcc atttaaagtg    1260
gttgtctgag tggatgcagg gaaacccaga tataataaaa tgcaagaaag acagaagctc    1320
ttccagtcct cagcaatgtc cccttttgcat gaaccccagg atctctaaag gcagacccctt  1380
tgctatggta ccatctggag ctttcctatg tacaaagcca accattgatc catcactgaa    1440
gtcaaagagc ctggttactc aggaggacaa tggatctgcc tccacctcac ctcaagattt    1500
catagaaccc tttggctcct gtctctttgaa catgacagac ctgtctggaa ataaggccga   1560
```

-continued

```
catggtctgt agtatccaaa agccatcaag gacatcacca actgcattca ctgaagaaaa      1620
tgactacatc atgctaaatg cgtcattttc cacaaatctt gtgtgcagtg tagattataa      1680
tcacatccag ccagtgtggc aacttctggc tttatacagt gactctcctc tgatactaga      1740
aaggaagccc cagcttaccg agactccttc actgtcttct agatataaac aggtggctct      1800
taggcctgaa gacatttttta ccagcataga ggctgatgtc agagcagacc cttttttggtt     1860
ccaacaagaa aaaattgtct tgcagctgaa cagaactgcc accacactta gcacattaca      1920
gatccagttt tccactgatg ctcaaatcgc tttaccaagg gcggagatga gagcggagag      1980
actcaaatgg accatgatcc tgatgatgaa caatcccaaa ctggaacgca ctgtcctggt      2040
tggcggcact attgccctga gctgtccagg caaaggcgac ccttcacctc acttggaatg      2100
gcttctagct gatgggagta agtgagagc cccttacgtt agcgaggatg ggcgaatcct       2160
aatagacaaa aatgggaagt tggaactgca gatggctgac agctttgatg caggtctttta    2220
ccactgcata agcaccaatg atgcagatgc ggatgttctc acatacagga taactgtggt     2280
agagccctat ggagaaagca cacatgacag tggagtccag cacacagtgg ttacgggtga     2340
gacgctcgac cttccatgcc tttccacggg tgttccagat gcttctatta gctggattct    2400
tccagggaac actgtgttct ctcagccatc aagagacagg caaattctta caatgggac      2460
cttaagaata ttacaggtta cgccaaaaga tcaaggtcat taccaatgtg tggctgccaa    2520
cccatcaggg gccgactttt ccagtttttaa agtttcagtt caaaagaaag gccaaaggat   2580
ggttgagcat gacagggagg caggtggatc tggacttgga gaacccaact ccagtgtttc    2640
ccttaagcag ccagcatctt tgaaactctc tgcatcagct ttgacagggt cagaggctgg    2700
aaaacaagtc tccggtgtac ataggaagaa caaacataga gacttaatac atcggcggcg    2760
tggggattcc acgctccggc gattcaggga gcataggagg cagctccctc tctctgctcg    2820
gagaattgac ccgcaacgct gggcagcact tctagaaaaa gccaaaaaga attctgtgcc    2880
aaaaaagcaa gaaaatacca cagtaaagcc agtgccactg gctgttcccc tcgtggaact    2940
cactgacgag gaaaaggatg cctctggcat gattcctcca gatgaagaat tcatggttct    3000
gaaaactaag gcttctggtg tcccaggaag gtcaccaact gctgactctg gaccagtaaa    3060
tcatggtttt atgacgagta tagccttctgg cacagaagtc tcaactgtga atccacaaac   3120
actacaatct gagcaccttc ctgatttcaa attatttagt gtaacaaacg gtacagctgt   3180
gacaaagagt atgaacccat ccatagcaag caaaatagaa gatacaacca accaaaaccc    3240
aatcattatc tttccatcag tagctgaaat tcgagattct gctcaggcag aagagcatc     3300
ttcccaaagt gcacaccctg taacagggggg aaacatggct acctatggcc ataccaacac   3360
atatagtagc tttaccagca aagccagtac agtcttgcag ccaataaatc caacagaaag   3420
ttatggacct cagataccta ttacaggagt cagcagacct agcagtagtg acatctcttc    3480
tcacactact gcagaccccta gcttctccag tcacccttca ggttcacaca ccactgcctc    3540
gtctttatt cacattccta gaaacaacaa tacaggtaac ttccccttgt ccaggcactt    3600
gggaagagag aggacaattt ggagcagagg gagagttaaa aacccacata gaaccccagt     3660
tctccgacgg catagacaca ggactgtgag gccagcaatc aagggacctg ctaacaaaaa    3720
tgtgagccaa gttccagcca cagagtaccc tgggatgtgc cacacatgtc cttccgcaga    3780
ggggctcaca gtggctactg cagcactgtc agtccaagt tcatcccaca gtgccctccc     3840
caaaactaat aatgttgggg tcatagcaga agagtctacc actgtggtca agaaaccact   3900
```

```
gttactattt aaggacaaac aaaatgtaga tattgagata taacaacca ctacaaaata    3960 ttccggaggg gaaagtaacc acgtgattcc tacggaagca agcatgactt ctgctccaac    4020
atctgtatcc ctgggaaat ctcctgtaga caatagtggt cacctgagca tgcctgggac    4080
catccaaact gggaaagatt cagtggaaac aacaccactt cccagccccc tcagcacacc    4140
ctcaatacca acaagcacaa aattctcaaa gaggaaaact cccttgcacc agatctttgt    4200
aaataaccag aagaaggagg ggatgttaaa gaatccatat caattcggtt tacaaaagaa    4260
cccagccgca aagcttccca aaatagctcc tcttttaccc acaggtcaga gttccccctc    4320
agattctaca actctcttga caagtccgcc accagctctg tctacaacaa tggctgccac    4380
tcagaacaag ggcactgaag tagtatcagg tgccagaagt ctctcagcag ggaagaagca    4440
gcccttcacc aactcctctc cagtgcttcc tagcaccata agcaagagat ctaatacatt    4500
aaacttcttg tcaacggaaa ccccacagt gacaagtcct actgctactg catctgtcat    4560
tatgtctgaa acccaacgaa caagatccaa agaagcaaaa gaccaaataa agggcctcg    4620 gaagaacaga aacaacgcaa acaccacccc caggcaggtt tctggctata gtgcatactc    4680
agctctaaca acagctgata ccccttggc tttcagtcat tccccacgac aagatgatgg    4740
tggaaatgta agtgcagttg cttatcactc aacaacctct cttctggcca taactgaact    4800
gtttgagaag tacacccaga cttttgggaaa tacaacagct ttggaaacaa cgttgttgag    4860
caaatcacag gagagtacca cagtgaaaag agcctcagac acaccaccac cactcctcag    4920 cagtgggcg ccccccagtgc ccactccttc cccacctcct tttactaagg gtgtggttac    4980
agacagcaaa gtcacatcag ctttccagat gacgtcaaat agagtggtca ccatatatga    5040
atcttcaagg cacaatacag atctgcagca accctcagca gaggctagcc ccaatcctga    5100
gatcataact ggaaccactg actctccctc taatctgtttt ccatccactt ctgtgccagc    5160
actaagggta gataaaccac agaattctaa atggaagccc tctccctggc cagaacacaa    5220
atatcagctc aagtcatact ccgaaaccat tgagaagggc aaaaggccag cagtaagcat    5280 gtcccccac ctcagccttc cagaggccag cactcatgcc tcacactgga atacacagaa    5340
gcatgcagaa aagagtgttt ttgataagaa acctggtcaa aacccaactt ccaaacatct    5400
gccttacgtc tctctaccta agactctatt gaaaaagcca agaataattg gaggaaaggc    5460
tgcaagcttt acagttccag ctaattcaga cgttttttctt ccttgtgagg ctgttggaga    5520
cccactgccc atcatccact ggaccagagt ttcatcagga cttgaaatat cccaagggac    5580
acagaaaagc cggttccacg tgcttcccaa tggcaccttg tccatccaga gggtcagtat    5640
tcaggaccgt ggacagtacc tgtgctctgc atttaatcca ctgggcgtag accattttca    5700
tgtctctttg tctgtggttt tttacccggc aaggattttg gacagacatg tcaaggagat    5760
cacagttcac tttggaagta ctgtggaact aaagtgcaga gtggagggta tgccgaggcc    5820 tacggttttcc tggatacttg caaaccaaac ggtggtctca gaaacggcca agggaagcag    5880
aaaggtctgg gtaacacctg atggaacatt gatcatctat aatctgagtc tttatgatcg    5940 tggttttttac aagtgtgtgg ccagcaaccc atctggccag gattcactgt ggttaagat    6000 acaagtcatc acagctcccc ctgtcattat agagcaaaag aggcaagcca tcgttgggt    6060 tttaggtgga agtttgaaac tgccctgcac tgcaaaagga actccccagc ctagtgttca    6120
ctgggtcctt tatgatggga ctgaactaaa accattgcag ttgactcatt ccagattttt    6180
cttgtatcca aatggaactc tgtatataag aagcatcgct ccttcagtga ggggcactta    6240
tgagtgcatt gccaccagct cctcaggctc agagagaagg gtagtgattc ttactgtgga    6300
```

```
agagggagag acaatcccca ggatagaaac tgcctctcag aaatggactg aggtgaattt    6360
gggtgagaaa ttactactga actgctcagc tactggggat ccaaagccta gaataatctg    6420
gaggctgcca tccaaggctg tcatcgacca gtggcacaga atgggcagcc gaatccacgt    6480
ctacccaaat ggatccttgg tggttgggtc agtgacgaaa aagacgctg gtgactactt     6540 atgtgtggca agaaacaaaa tgggagatga cctagtcctg atgcatgtcc gcctgagatt    6600
gacacctgcc aaaattgaac agaagcagta ttttaagaag caagtgctcc atgggaaaga    6660
tttccaagtt gactgcaagg cctctggctc ccctgtgcct gaggtatcct ggagtttgcc    6720
tgatgggaca gtgctcaaca atgtagccca agctgatgac agtggctata ggaccaagag    6780 gtacacccctt ttccacaatg gaaccttgta tttcaacaac gttgggatgg cagaggaagg   6840
agattatatc tgctctgccc agaacacctt agggaaagat gagatgaaag tccacctaac    6900
agttctaaca gccatcccac ggataaggca aagctacaag accaccatga ggctcagggc    6960
tggagaaaca gctgtccttg actgcgaggt cactgggaa ccgaagccca atgtatttg      7020 gttgctgcct tccaacaatg tcatttcatt ctccaatgac aggttcacat ttcatgccaa    7080
tagaactttg tccatccata aagtgaaacc acttgactct ggggactatg tgtgcgtagc    7140
tcagaatcct agtggggatg acactaagac atacaaactg acattgtct ctaaaccctcc    7200 attaatcaat ggcctgtatg caaacaagac tgttattaaa gccacagcca ttcggcactc    7260
caaaaaatac tttgactgca gagcagatgg gatcccatct tcccaggtca cgtggattat    7320
gccaggcaat atttcctcc cagctccata ctttggaagc agagtcacgg tccatccaaa     7380
tggaaccttg gagatgagga acatccggct ttctgactct gcggacttca cctgtgtggt    7440
tcggagcgag ggaggagaga gtgtgttggt agtgcagtta gaagtcctag aaatgctgag    7500
aagaccaaca ttcagaaacc cattcaacga aaaagtcatc gcccaagctg gcaagcccgt    7560
agcactgaac tgctctgtgg atgggaaccc cccaccgtga attacctgga tcttacctga    7620
cggcacacag tttgctaaca gaccacacaa ttccccgtat ctgatggcag gcaatggctc    7680 tctcatccttt tacaaagcaa ctcggaacaa gtcaggaag tatcgctgtg cagccaggaa    7740
taaggttggc tacatcgaga aactcatcct gttagagatt gggcagaagc cagtcattct    7800
gacatacgaa ccaggatgg tgaagagcgt cagtggggaa ccgttatcac tgcattgtgt     7860
gtctgatggg atccccaagc caaatgtcaa gtggactaca ccgggtggcc atgtaatcga    7920
caggcctcaa gtggatggaa atacatact gcatgaaaat ggcacgctgg tcatcaaagc     7980
aacaacagct cacgaccaag gaaattatat ctgtagggct caaaacagtg ttggccaggc    8040
agttattagc gtgtcagtga tggttgtggc ctaccctccc cgaatcataa actacctacc    8100
caggaacatg ctcaggagga caggggaagc catgcagctc cactgtgtgg ccttgggaat    8160
ccccaagcca aaagtcacct gggagacgcc aagacactcc ctgctctcaa aagcaacagc    8220
aagaaaaccc catagaagtg agatgcttca cccacaaggt acgctggtca ttcagaatct    8280
ccaaacctcg gattccggag tctataagtg cagagctcag aacctacttg ggactgatta    8340
cgcaacaact tacatccagg tactctgaca ggaaggggga gactaaaatt caacagaagt    8400
ccacatccac agggtttat ttttggaaga agttttaatca aaggcagcca taggcatgta    8460
aatgagtctg aatacatttta cagtattaaa tttacaatgg acatgcgatg agacttgtaa    8520
atgaaagcat tgtgaactga aaccgagtct ctgtggatct caaagcaaac tcttaactta    8580
aggcactttg attttgccaa caaataataa caaacattaa gagaaaaaaa tgatccacta    8640
```

```
cgaaataaca aacggctaat gcacctgaat tctcagtaaa aagacctttc tctcgctaac    8700
agttgccagc tgcctcgtgt ctgtttccta ccaatgtcac aaacatcgca cacagggtga    8760
atggagtcaa cgggaaagat taagtttgcg gtctgtgtaa atctcaatgt acaaatattc    8820
tgtcnctggt ttataaacat tttgataaaa ccgaaaaaaa aaaaaaaaa aaaaaaaaa      8880 aaa                                                                  8883
```

<210> SEQ ID NO 34
<211> LENGTH: 2597
<212> TYPE: PRT
<213> ORGANISM: Rattus rattus

<400> SEQUENCE: 34

```
Met Gln Val Arg Gly Arg Glu Val Ser Gly Leu Leu Ile Ser Leu Thr
1               5                   10                  15

Ala Val Cys Leu Val Val Thr Pro Gly Ser Arg Ala Cys Pro Arg Arg
            20                  25                  30

Cys Ala Cys Tyr Val Pro Thr Glu Val His Cys Thr Phe Arg Tyr Leu
        35                  40                  45

Thr Ser Ile Pro Asp Gly Ile Pro Ala Asn Val Glu Arg Ile Asn Leu
    50                  55                  60

Gly Tyr Asn Ser Leu Thr Arg Leu Thr Glu Asn Asp Phe Asp Gly Leu
65                  70                  75                  80

Ser Lys Leu Glu Leu Leu Met Leu His Ser Asn Gly Ile His Arg Val
                85                  90                  95

Ser Asp Lys Thr Phe Ser Gly Leu Gln Ser Leu Gln Val Leu Lys Met
            100                 105                 110

Ser Tyr Asn Lys Val Gln Ile Ile Arg Lys Asp Thr Phe Tyr Gly Leu
        115                 120                 125

Gly Ser Leu Val Arg Leu His Leu Asp His Asn Asn Ile Glu Phe Ile
    130                 135                 140

Asn Pro Glu Ala Phe Tyr Gly Leu Thr Ser Leu Arg Leu Val His Leu
145                 150                 155                 160

Glu Gly Asn Arg Leu Thr Lys Leu His Pro Asp Thr Phe Val Ser Leu
                165                 170                 175

Ser Tyr Leu Gln Ile Phe Lys Thr Ser Phe Ile Lys Tyr Leu Phe Leu
            180                 185                 190

Ser Asp Asn Phe Leu Thr Ser Leu Pro Lys Glu Met Val Ser Tyr Met
        195                 200                 205

Pro Asn Leu Glu Ser Leu Tyr Leu His Gly Asn Pro Trp Thr Cys Asp
    210                 215                 220

Cys His Leu Lys Trp Leu Ser Glu Trp Met Gln Gly Asn Pro Asp Ile
225                 230                 235                 240

Ile Lys Cys Lys Lys Asp Arg Ser Ser Ser Pro Gln Gln Cys Pro
                245                 250                 255

Leu Cys Met Asn Pro Arg Ile Ser Lys Gly Arg Pro Phe Ala Met Val
            260                 265                 270

Pro Ser Gly Ala Phe Leu Cys Thr Lys Pro Thr Ile Asp Pro Ser Leu
        275                 280                 285

Lys Ser Lys Ser Leu Val Thr Gln Glu Asp Asn Gly Ser Ala Ser Thr
    290                 295                 300

Ser Pro Gln Asp Phe Ile Glu Pro Phe Gly Leu Ser Leu Asn Met
305                 310                 315                 320

Thr Asp Leu Ser Gly Asn Lys Ala Asp Met Val Cys Ser Ile Gln Lys
```

```
                    325                 330                 335
Pro Ser Arg Thr Ser Pro Thr Ala Phe Thr Glu Glu Asn Asp Tyr Ile
                340                 345                 350
Met Leu Asn Ala Ser Phe Ser Thr Asn Leu Val Cys Ser Val Asp Tyr
                355                 360                 365
Asn His Ile Gln Pro Val Trp Gln Leu Leu Ala Leu Tyr Ser Asp Ser
            370                 375                 380
Pro Leu Ile Leu Glu Arg Lys Pro Gln Leu Thr Glu Thr Pro Ser Leu
385                 390                 395                 400
Ser Ser Arg Tyr Lys Gln Val Ala Leu Arg Pro Glu Asp Ile Phe Thr
                405                 410                 415
Ser Ile Glu Ala Asp Val Arg Ala Asp Pro Phe Trp Phe Gln Gln Glu
                420                 425                 430
Lys Ile Val Leu Gln Leu Asn Arg Thr Ala Thr Thr Leu Ser Thr Leu
                435                 440                 445
Gln Ile Gln Phe Ser Thr Asp Ala Gln Ile Ala Leu Pro Arg Ala Glu
            450                 455                 460
Met Arg Ala Glu Arg Leu Lys Trp Thr Met Ile Leu Met Met Asn Asn
465                 470                 475                 480
Pro Lys Leu Glu Arg Thr Val Leu Val Gly Thr Ile Ala Leu Ser
                485                 490                 495
Cys Pro Gly Lys Gly Asp Pro Ser Pro His Leu Glu Trp Leu Leu Ala
                500                 505                 510
Asp Gly Ser Lys Val Arg Ala Pro Tyr Val Ser Glu Asp Gly Arg Ile
            515                 520                 525
Leu Ile Asp Lys Asn Gly Lys Leu Glu Leu Gln Met Ala Asp Ser Phe
            530                 535                 540
Asp Ala Gly Leu Tyr His Cys Ile Ser Thr Asn Asp Ala Asp Ala Asp
545                 550                 555                 560
Val Leu Thr Tyr Arg Ile Thr Val Val Glu Pro Tyr Gly Glu Ser Thr
                565                 570                 575
His Asp Ser Gly Val Gln His Thr Val Val Thr Gly Glu Thr Leu Asp
            580                 585                 590
Leu Pro Cys Leu Ser Thr Gly Val Pro Asp Ala Ser Ile Ser Trp Ile
            595                 600                 605
Leu Pro Gly Asn Thr Val Phe Ser Gln Pro Ser Arg Asp Arg Gln Ile
            610                 615                 620
Leu Asn Asn Gly Thr Leu Arg Ile Leu Gln Val Thr Pro Lys Asp Gln
625                 630                 635                 640
Gly His Tyr Gln Cys Val Ala Ala Asn Pro Ser Gly Ala Asp Phe Ser
                645                 650                 655
Ser Phe Lys Val Ser Val Gln Lys Lys Gly Gln Arg Met Val Glu His
                660                 665                 670
Asp Arg Glu Ala Gly Gly Ser Gly Leu Gly Glu Pro Asn Ser Ser Val
            675                 680                 685
Ser Leu Lys Gln Pro Ala Ser Leu Lys Leu Ser Ala Ser Ala Leu Thr
            690                 695                 700
Gly Ser Glu Ala Gly Lys Gln Val Ser Gly Val His Arg Lys Asn Lys
705                 710                 715                 720
His Arg Asp Leu Ile His Arg Arg Gly Asp Ser Thr Leu Arg Arg
                725                 730                 735
Phe Arg Glu His Arg Arg Gln Leu Pro Leu Ser Ala Arg Arg Ile Asp
                740                 745                 750
```

-continued

```
Pro Gln Arg Trp Ala Ala Leu Leu Glu Lys Ala Lys Lys Asn Ser Val
        755                 760                 765
Pro Lys Lys Gln Glu Asn Thr Thr Val Lys Pro Val Pro Leu Ala Val
        770                 775                 780
Pro Leu Val Glu Leu Thr Asp Glu Glu Lys Asp Ala Ser Gly Met Ile
785                 790                 795                 800
Pro Pro Asp Glu Glu Phe Met Val Leu Lys Thr Lys Ala Ser Gly Val
                    805                 810                 815
Pro Gly Arg Ser Pro Thr Ala Asp Ser Gly Pro Val Asn His Gly Phe
            820                 825                 830
Met Thr Ser Ile Ala Ser Gly Thr Glu Val Ser Thr Val Asn Pro Gln
            835                 840                 845
Thr Leu Gln Ser Glu His Leu Pro Asp Phe Lys Leu Phe Ser Val Thr
        850                 855                 860
Asn Gly Thr Ala Val Thr Lys Ser Met Asn Pro Ser Ile Ala Ser Lys
865                 870                 875                 880
Ile Glu Asp Thr Thr Asn Gln Asn Pro Ile Ile Phe Pro Ser Val
                    885                 890                 895
Ala Glu Ile Arg Asp Ser Ala Gln Ala Gly Arg Ala Ser Ser Gln Ser
                900                 905                 910
Ala His Pro Val Thr Gly Gly Asn Met Ala Thr Tyr Gly His Thr Asn
            915                 920                 925
Thr Tyr Ser Ser Phe Thr Ser Lys Ala Ser Thr Val Leu Gln Pro Ile
        930                 935                 940
Asn Pro Thr Glu Ser Tyr Gly Pro Gln Ile Pro Ile Thr Gly Val Ser
945                 950                 955                 960
Arg Pro Ser Ser Ser Asp Ile Ser Ser His Thr Thr Ala Asp Pro Ser
                    965                 970                 975
Phe Ser Ser His Pro Ser Gly Ser His Thr Thr Ala Ser Ser Leu Phe
                980                 985                 990
His Ile Pro Arg Asn Asn Asn Thr Gly Asn Phe Pro Leu Ser Arg His
        995                 1000                1005
Leu Gly Arg Glu Arg Thr Ile Trp Ser Arg Gly Arg Val Lys Asn
    1010                1015                1020
Pro His Arg Thr Pro Val Leu Arg Arg His Arg His Arg Thr Val
    1025                1030                1035
Arg Pro Ala Ile Lys Gly Pro Ala Asn Lys Asn Val Ser Gln Val
    1040                1045                1050
Pro Ala Thr Glu Tyr Pro Gly Met Cys His Thr Cys Pro Ser Ala
    1055                1060                1065
Glu Gly Leu Thr Val Ala Thr Ala Ala Leu Ser Val Pro Ser Ser
    1070                1075                1080
Ser His Ser Ala Leu Pro Lys Thr Asn Asn Val Gly Val Ile Ala
    1085                1090                1095
Glu Glu Ser Thr Thr Val Val Lys Lys Pro Leu Leu Leu Phe Lys
    1100                1105                1110
Asp Lys Gln Asn Val Asp Ile Glu Ile Ile Thr Thr Thr Thr Lys
    1115                1120                1125
Tyr Ser Gly Gly Glu Ser Asn His Val Ile Pro Thr Glu Ala Ser
    1130                1135                1140
Met Thr Ser Ala Pro Thr Ser Val Ser Leu Gly Lys Ser Pro Val
    1145                1150                1155
```

-continued

```
Asp Asn Ser Gly His Leu Ser Met Pro Gly Thr Ile Gln Thr Gly
    1160                1165                1170

Lys Asp Ser Val Glu Thr Thr Pro Leu Pro Ser Pro Leu Ser Thr
    1175                1180                1185

Pro Ser Ile Pro Thr Ser Thr Lys Phe Ser Lys Arg Lys Thr Pro
    1190                1195                1200

Leu His Gln Ile Phe Val Asn Asn Gln Lys Lys Glu Gly Met Leu
    1205                1210                1215

Lys Asn Pro Tyr Gln Phe Gly Leu Gln Lys Asn Pro Ala Ala Lys
    1220                1225                1230

Leu Pro Lys Ile Ala Pro Leu Leu Pro Thr Gly Gln Ser Ser Pro
    1235                1240                1245

Ser Asp Ser Thr Thr Leu Leu Thr Ser Pro Pro Ala Leu Ser
    1250                1255                1260

Thr Thr Met Ala Ala Thr Gln Asn Lys Gly Thr Glu Val Val Ser
    1265                1270                1275

Gly Ala Arg Ser Leu Ser Ala Gly Lys Lys Gln Pro Phe Thr Asn
    1280                1285                1290

Ser Ser Pro Val Leu Pro Ser Thr Ile Ser Lys Arg Ser Asn Thr
    1295                1300                1305

Leu Asn Phe Leu Ser Thr Glu Thr Pro Thr Val Thr Ser Pro Thr
    1310                1315                1320

Ala Thr Ala Ser Val Ile Met Ser Glu Thr Gln Arg Thr Arg Ser
    1325                1330                1335

Lys Glu Ala Lys Asp Gln Ile Lys Gly Pro Arg Lys Asn Arg Asn
    1340                1345                1350

Asn Ala Asn Thr Thr Pro Arg Gln Val Ser Gly Tyr Ser Ala Tyr
    1355                1360                1365

Ser Ala Leu Thr Thr Ala Asp Thr Pro Leu Ala Phe Ser His Ser
    1370                1375                1380

Pro Arg Gln Asp Asp Gly Gly Asn Val Ser Ala Val Ala Tyr His
    1385                1390                1395

Ser Thr Thr Ser Leu Leu Ala Ile Thr Glu Leu Phe Glu Lys Tyr
    1400                1405                1410

Thr Gln Thr Leu Gly Asn Thr Thr Ala Leu Glu Thr Thr Leu Leu
    1415                1420                1425

Ser Lys Ser Gln Glu Ser Thr Thr Val Lys Arg Ala Ser Asp Thr
    1430                1435                1440

Pro Pro Pro Leu Leu Ser Ser Gly Ala Pro Pro Val Pro Thr Pro
    1445                1450                1455

Ser Pro Pro Phe Thr Lys Gly Val Val Thr Asp Ser Lys Val
    1460                1465                1470

Thr Ser Ala Phe Gln Met Thr Ser Asn Arg Val Val Thr Ile Tyr
    1475                1480                1485

Glu Ser Ser Arg His Asn Thr Asp Leu Gln Gln Pro Ser Ala Glu
    1490                1495                1500

Ala Ser Pro Asn Pro Glu Ile Ile Thr Gly Thr Thr Asp Ser Pro
    1505                1510                1515

Ser Asn Leu Phe Pro Ser Thr Ser Val Pro Ala Leu Arg Val Asp
    1520                1525                1530

Lys Pro Gln Asn Ser Lys Trp Lys Pro Ser Pro Trp Pro Glu His
    1535                1540                1545

Lys Tyr Gln Leu Lys Ser Tyr Ser Glu Thr Ile Glu Lys Gly Lys
```

-continued

```
              1550                 1555                 1560

Arg Pro  Ala Val Ser Met Ser  Pro His Leu Ser Leu  Pro Glu Ala
    1565                 1570                 1575

Ser Thr  His Ala Ser His Trp  Asn Thr Gln Lys His  Ala Glu Lys
    1580                 1585                 1590

Ser Val  Phe Asp Lys Lys Pro  Gly Gln Asn Pro Thr  Ser Lys His
    1595                 1600                 1605

Leu Pro  Tyr Val Ser Leu Pro  Lys Thr Leu Leu Lys  Lys Pro Arg
    1610                 1615                 1620

Ile Ile  Gly Gly Lys Ala Ala  Ser Phe Thr Val Pro  Ala Asn Ser
    1625                 1630                 1635

Asp Val  Phe Leu Pro Cys Glu  Ala Val Gly Asp Pro  Leu Pro Ile
    1640                 1645                 1650

Ile His  Trp Thr Arg Val Ser  Ser Gly Leu Glu Ile  Ser Gln Gly
    1655                 1660                 1665

Thr Gln  Lys Ser Arg Phe His  Val Leu Pro Asn Gly  Thr Leu Ser
    1670                 1675                 1680

Ile Gln  Arg Val Ser Ile Gln  Asp Arg Gly Gln Tyr  Leu Cys Ser
    1685                 1690                 1695

Ala Phe  Asn Pro Leu Gly Val  Asp His Phe His Val  Ser Leu Ser
    1700                 1705                 1710

Val Val  Phe Tyr Pro Ala Arg  Ile Leu Asp Arg His  Val Lys Glu
    1715                 1720                 1725

Ile Thr  Val His Phe Gly Ser  Thr Val Glu Leu Lys  Cys Arg Val
    1730                 1735                 1740

Glu Gly  Met Pro Arg Pro Thr  Val Ser Trp Ile Leu  Ala Asn Gln
    1745                 1750                 1755

Thr Val  Val Ser Glu Thr Ala  Lys Gly Ser Arg Lys  Val Trp Val
    1760                 1765                 1770

Thr Pro  Asp Gly Thr Leu Ile  Ile Tyr Asn Leu Ser  Leu Tyr Asp
    1775                 1780                 1785

Arg Gly  Phe Tyr Lys Cys Val  Ala Ser Asn Pro Ser  Gly Gln Asp
    1790                 1795                 1800

Ser Leu  Leu Val Lys Ile Gln  Val Ile Thr Ala Pro  Pro Val Ile
    1805                 1810                 1815

Ile Glu  Gln Lys Arg Gln Ala  Ile Val Gly Val Leu  Gly Gly Ser
    1820                 1825                 1830

Leu Lys  Leu Pro Cys Thr Ala  Lys Gly Thr Pro Gln  Pro Ser Val
    1835                 1840                 1845

His Trp  Val Leu Tyr Asp Gly  Thr Glu Leu Lys Pro  Leu Gln Leu
    1850                 1855                 1860

Thr His  Ser Arg Phe Phe Leu  Tyr Pro Asn Gly Thr  Leu Tyr Ile
    1865                 1870                 1875

Arg Ser  Ile Ala Pro Ser Val  Arg Gly Thr Tyr Glu  Cys Ile Ala
    1880                 1885                 1890

Thr Ser  Ser Ser Gly Ser Glu  Arg Arg Val Val Ile  Leu Thr Val
    1895                 1900                 1905

Glu Glu  Gly Glu Thr Ile Pro  Arg Ile Glu Thr Ala  Ser Gln Lys
    1910                 1915                 1920

Trp Thr  Glu Val Asn Leu Gly  Glu Lys Leu Leu Leu  Asn Cys Ser
    1925                 1930                 1935

Ala Thr  Gly Asp Pro Lys Pro  Arg Ile Ile Trp Arg  Leu Pro Ser
    1940                 1945                 1950
```

```
Lys Ala Val Ile Asp Gln Trp His Arg Met Gly Ser Arg Ile His
1955                1960                1965

Val Tyr Pro Asn Gly Ser Leu Val Val Gly Ser Val Thr Glu Lys
1970                1975                1980

Asp Ala Gly Asp Tyr Leu Cys Val Ala Arg Asn Lys Met Gly Asp
1985                1990                1995

Asp Leu Val Leu Met His Val Arg Leu Arg Leu Thr Pro Ala Lys
2000                2005                2010

Ile Glu Gln Lys Gln Tyr Phe Lys Lys Gln Val Leu His Gly Lys
2015                2020                2025

Asp Phe Gln Val Asp Cys Lys Ala Ser Gly Ser Pro Val Pro Glu
2030                2035                2040

Val Ser Trp Ser Leu Pro Asp Gly Thr Val Leu Asn Asn Val Ala
2045                2050                2055

Gln Ala Asp Asp Ser Gly Tyr Arg Thr Lys Arg Tyr Thr Leu Phe
2060                2065                2070

His Asn Gly Thr Leu Tyr Phe Asn Asn Val Gly Met Ala Glu Glu
2075                2080                2085

Gly Asp Tyr Ile Cys Ser Ala Gln Asn Thr Leu Gly Lys Asp Glu
2090                2095                2100

Met Lys Val His Leu Thr Val Leu Thr Ala Ile Pro Arg Ile Arg
2105                2110                2115

Gln Ser Tyr Lys Thr Thr Met Arg Leu Arg Ala Gly Glu Thr Ala
2120                2125                2130

Val Leu Asp Cys Glu Val Thr Gly Glu Pro Lys Pro Asn Val Phe
2135                2140                2145

Trp Leu Leu Pro Ser Asn Asn Val Ile Ser Phe Ser Asn Asp Arg
2150                2155                2160

Phe Thr Phe His Ala Asn Arg Thr Leu Ser Ile His Lys Val Lys
2165                2170                2175

Pro Leu Asp Ser Gly Asp Tyr Val Cys Val Ala Gln Asn Pro Ser
2180                2185                2190

Gly Asp Asp Thr Lys Thr Tyr Lys Leu Asp Ile Val Ser Lys Pro
2195                2200                2205

Pro Leu Ile Asn Gly Leu Tyr Ala Asn Lys Thr Val Ile Lys Ala
2210                2215                2220

Thr Ala Ile Arg His Ser Lys Lys Tyr Phe Asp Cys Arg Ala Asp
2225                2230                2235

Gly Ile Pro Ser Ser Gln Val Thr Trp Ile Met Pro Gly Asn Ile
2240                2245                2250

Phe Leu Pro Ala Pro Tyr Phe Gly Ser Arg Val Thr Val His Pro
2255                2260                2265

Asn Gly Thr Leu Glu Met Arg Asn Ile Arg Leu Ser Asp Ser Ala
2270                2275                2280

Asp Phe Thr Cys Val Val Arg Ser Glu Gly Gly Glu Ser Val Leu
2285                2290                2295

Val Val Gln Leu Glu Val Leu Glu Met Leu Arg Arg Pro Thr Phe
2300                2305                2310

Arg Asn Pro Phe Asn Glu Lys Val Ile Ala Gln Ala Gly Lys Pro
2315                2320                2325

Val Ala Leu Asn Cys Ser Val Asp Gly Asn Pro Pro Pro Glu Ile
2330                2335                2340
```

-continued

Thr Trp Ile Leu Pro Asp Gly Thr Gln Phe Ala Asn Arg Pro His
    2345                2350                2355

Asn Ser Pro Tyr Leu Met Ala Gly Asn Gly Ser Leu Ile Leu Tyr
    2360                2365                2370

Lys Ala Thr Arg Asn Lys Ser Gly Lys Tyr Arg Cys Ala Ala Arg
    2375                2380                2385

Asn Lys Val Gly Tyr Ile Glu Lys Leu Ile Leu Leu Glu Ile Gly
    2390                2395                2400

Gln Lys Pro Val Ile Leu Thr Tyr Glu Pro Gly Met Val Lys Ser
    2405                2410                2415

Val Ser Gly Glu Pro Leu Ser Leu His Cys Val Ser Asp Gly Ile
    2420                2425                2430

Pro Lys Pro Asn Val Lys Trp Thr Thr Pro Gly Gly His Val Ile
    2435                2440                2445

Asp Arg Pro Gln Val Asp Gly Lys Tyr Ile Leu His Glu Asn Gly
    2450                2455                2460

Thr Leu Val Ile Lys Ala Thr Thr Ala His Asp Gln Gly Asn Tyr
    2465                2470                2475

Ile Cys Arg Ala Gln Asn Ser Val Gly Gln Ala Val Ile Ser Val
    2480                2485                2490

Ser Val Met Val Val Ala Tyr Pro Pro Arg Ile Ile Asn Tyr Leu
    2495                2500                2505

Pro Arg Asn Met Leu Arg Arg Thr Gly Glu Ala Met Gln Leu His
    2510                2515                2520

Cys Val Ala Leu Gly Ile Pro Lys Pro Lys Val Thr Trp Glu Thr
    2525                2530                2535

Pro Arg His Ser Leu Leu Ser Lys Ala Thr Ala Arg Lys Pro His
    2540                2545                2550

Arg Ser Glu Met Leu His Pro Gln Gly Thr Leu Val Ile Gln Asn
    2555                2560                2565

Leu Gln Thr Ser Asp Ser Gly Val Tyr Lys Cys Arg Ala Gln Asn
    2570                2575                2580

Leu Leu Gly Thr Asp Tyr Ala Thr Thr Tyr Ile Gln Val Leu
    2585                2590                2595

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
gcactgaact gctctgtggat                                      21

<210> SEQ ID NO 36
<211> LENGTH: 23
<212> TYPE: DNA
<213> ORGANISM: Artificial Sequence
<220> FEATURE:
<223> OTHER INFORMATION: primer

<400> SEQUENCE: 36
ccacagaagt aaggttcctt cac                                   23

<210> SEQ ID NO 37
<211> LENGTH: 6
<212> TYPE: PRT

```
<213> ORGANISM: homo sapiens

<400> SEQUENCE: 37

Lys Cys Lys Lys Asp Arg
1               5
```